(12) United States Patent
Callahan et al.

(10) Patent No.: US 11,078,216 B2
(45) Date of Patent: Aug. 3, 2021

(54) BISARYL AMIDES AS NRF2 ACTIVATORS

(71) Applicant: GLAXOSMITHKLINE INTELLECTUAL PROPERTY DEVELOPMENT LIMITED, Brentford (GB)

(72) Inventors: James Francis Callahan, King of Prussia, PA (US); Vincent J. Colandrea, King of Prussia, PA (US); Anthony William James Cooper, Stevenage (GB); Nicole Cathleen Goodwin, King of Prussia, PA (US); Chelsea Ariane Huff, King of Prussia, PA (US); Joel Karpiak, King of Prussia, PA (US); Jeffrey K. Kerns, King of Prussia, PA (US); Hong Nie, King of Prussia, PA (US)

(73) Assignee: GLAXOSMITHKLINE INTELLECTUAL PROPERTY DEVELOPMENT LIMITED, Brentford (GB)

(*) Notice: Subject to any disclaimer, the term of this patent is extended or adjusted under 35 U.S.C. 154(b) by 0 days.

(21) Appl. No.: 16/467,538

(22) PCT Filed: Dec. 11, 2017

(86) PCT No.: PCT/IB2017/057805
§ 371 (c)(1),
(2) Date: Jun. 7, 2019

(87) PCT Pub. No.: WO2018/109647
PCT Pub. Date: Jun. 21, 2018

(65) Prior Publication Data
US 2019/0330238 A1   Oct. 31, 2019

Related U.S. Application Data

(60) Provisional application No. 62/433,954, filed on Dec. 14, 2016.

(51) Int. Cl.
| | | |
|---|---|---|
| *A61K 31/554* | (2006.01) | |
| *A61K 31/553* | (2006.01) | |
| *A61P 1/16* | (2006.01) | |
| *A61P 9/00* | (2006.01) | |
| *A61P 11/00* | (2006.01) | |
| *A61P 11/06* | (2006.01) | |
| *A61P 13/12* | (2006.01) | |
| *A61P 17/06* | (2006.01) | |
| *A61P 35/00* | (2006.01) | |
| *C07D 281/02* | (2006.01) | |
| *C07D 417/06* | (2006.01) | |
| *C07D 417/12* | (2006.01) | |
| *C07D 417/14* | (2006.01) | |
| *C07D 419/06* | (2006.01) | |
| *C07D 419/12* | (2006.01) | |
| *C07D 419/14* | (2006.01) | |
| *C07D 513/04* | (2006.01) | |
| *C07D 515/04* | (2006.01) | |
| *C07D 401/14* | (2006.01) | |

(52) U.S. Cl.
CPC ......... *C07D 515/04* (2013.01); *C07D 401/14* (2013.01); *C07D 417/12* (2013.01); *C07D 417/14* (2013.01); *C07D 513/04* (2013.01)

(58) Field of Classification Search
CPC ....... A61K 31/554; A61K 31/553; A61P 1/16; A61P 9/00; A61P 11/00; A61P 11/06; A61P 13/12; A61P 17/06; A61P 35/00; C07D 281/02; C07D 417/06; C07D 417/12; C07D 417/14; C07D 419/06; C07D 419/12; C07D 419/14; C07D 513/04; C07D 515/04
See application file for complete search history.

(56) References Cited

FOREIGN PATENT DOCUMENTS

| WO | WO 2015/092713 A1 | 6/2015 |
|---|---|---|
| WO | WO 2016/202253 A1 | 12/2016 |
| WO | WO 2016/203400 A1 | 12/2016 |

OTHER PUBLICATIONS

Davies, et al. Journal of Medicinal Chemistry, 59(8): 3991-4006 (Mar. 31, 2016).
Heightman, et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAP1/NRF2) Protein-Protein Interaction", Journal of Medicinal Chemistry, 62; 4683-4702; 2019.

*Primary Examiner* — Brenda L Coleman
(74) *Attorney, Agent, or Firm* — Nora L. Stein; Fang Qian; Duke M. Fitch

(57) ABSTRACT

The present invention relates to bisaryl amide analogs, pharmaceutical compositions containing them and their use as NRF2 activators. In particular, the invention relates to bisaryl heterocycles of Formula (I),

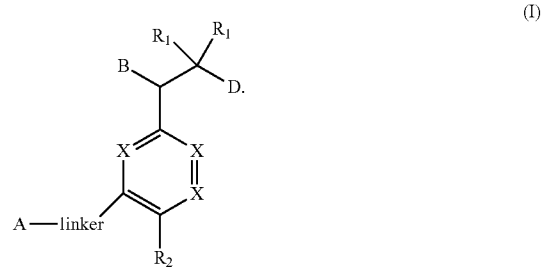

18 Claims, No Drawings

US 11,078,216 B2

BISARYL AMIDES AS NRF2 ACTIVATORS

This application is a § 371 national phase entry of International Application No. PCT/IB2017/057805, filed 11 Dec. 2017, which claims the benefit of U.S. Provisional Application No. 62/433,954, filed 14 Dec. 2016.

FIELD OF THE INVENTION

The present invention relates to bisaryl amide analogs, pharmaceutical compositions containing them and their use as NRF2 activators.

BACKGROUND OF THE INVENTION

NRF2 (NF-E2 related factor 2) is a member of the cap-n-collar family of transcription factors containing a characteristic basic-leucine zipper motif. Under basal conditions, NRF2 levels are tightly controlled by the cytosolic actin-bound repressor, KEAP1 (Kelch-like ECH associating protein 1), which binds to NRF2 and targets it for ubiquitylation and proteasomal degradation via the Cul3-based E3-ubiquitin ligase complex. Under conditions of oxidative stress, DJ1 (PARK7) is activated and stabilizes NRF2 protein by preventing NRF2 from interacting with KEAP1. Also, modification of reactive cysteines on KEAP1 can cause a conformational change in KEAP1 that alters NRF2 binding and promotes NRF2 stabilization. Thus, the levels of NRF2 in the cell are usually kept low in normal conditions but the system is designed to respond quickly to environmental stress by increasing NRF2 levels and thus downstream NRF2 activity.

Inappropriately low NRF2 activity in the face of on-going oxidative stress appears to be a pathological mechanism underlying chronic obstructive pulmonary disease (COPD). Yamada, K., et al. *BMC Pulmonary Medicine*, 2016, 16: 27. This may be a result of an altered equilibrium between NRF2 activators with both inappropriate lack of positive activators such as DJ1, and overabundance of negative activators such as Keap1 and Bach1. Therefore, restoration of NRF2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, NRF2 activators may treat COPD (Boutten, A., et al. 2011. *Trends Mol. Med.* 17:363-371) and other respiratory diseases, including asthma, Acute Lung Injury (ALI) (Cho, H. Y., and Kleeberger, S. R., 2015, *Arch Toxicol.* 89:1931-1957; Zhao, H. et al., 2017, *Am J Physiol Lung Clee Mol Physiol* 312:L155-L162, first published Nov. 18, 2016; doi:10.1152/ajplung.00449.2016), Acute Respiratory Distress Syndrome (ARDS) and pulmonary fibrosis (Cho, H. Y., and Kleeberger, S. R. 2010. *Toxicol. Appl. Pharmacol.* 244:43-56).

The therapeutic potential of an NRF2 activator is exemplified in pulmonary macrophages from COPD patients where NRF2 pathway appears maladaptive. These cells have impaired bacterial phagocytosis compared with similar cells from control patients, and this effect is reversed by the addition of NRF2 activators in vitro. Therefore, in addition to the effects mentioned above, restoration of appropriate NRF2 activity could also rescue COPD exacerbations by reducing lung infection.

This is demonstrated by the NRF2 activator, Sulforaphane, which increases the expression of Macrophage Receptor with Collagenous structure (MARCO) by COPD macrophages and alveolar macrophages from cigarette smoke-exposed mice, thereby improving in these cells bacterial phagocytosis (*Pseudomonas aeruginosa*, non-typable *Haemophilus influenzae*) and bacterial clearance both ex vivo and in vivo. (Harvey, C. J., et al. 2011. *Sci. Transl. Med.* 3:78ra32).

The therapeutic potential of targeting NRF2 in the lung is not limited to COPD. Rather, targeting the NRF2 pathway could provide treatments for other human lung and respiratory diseases that exhibit oxidative stress components such as chronic asthma and acute asthma, lung disease secondary to environmental exposures including but not limited to ozone, diesel exhaust and occupational exposures, fibrosis, acute lung infection (e.g., viral (Noah, T. L. et al. 2014. *PLoS ONE* 9(6): e98671), bacterial or fungal), chronic lung infection, α1 antitrypsin disease, ALI, ARDS and cystic fibrosis (C F, Chen, J. et al. 2008. *PLoS One.* 2008; 3(10): e3367).

A therapy that targets the NRF2 pathway also has many potential uses outside the lung and respiratory system. Many of the diseases for which an NRF2 activator may be useful are autoimmune diseases (psoriasis, IBD, MS), suggesting that an NRF2 activator may be useful in autoimmune diseases in general.

In the clinic, a drug targeting the NRF2 pathway (bardoxolone methyl) has shown efficacy in diabetic patients with diabetic nephropathy/chronic kidney disease (CKD) (Aleksunes, L. M., et al. 2010. *J. Pharmacol. Exp. Ther.* 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. *Kidney International.* June 19. doi: 10.1038/ki.2013.248.), and kidney disease or malfunction seen during kidney transplantation.

In the cardiac area, bardoxolone methyl is currently under investigation in patients 30 with Pulmonary Arterial Hypertension and so a drug targeting NRF2 by other mechanisms may also be useful in this disease area. Oxidative stress is increased in the diseased myocardium, resulting in accumulation of reactive oxygen species (ROS) which impairs cardiac function [*Circ* (1987) 76(2); 458-468] and increases susceptibility to arrhythmia [*J of Mol & Cell Cardio* (1991) 23(8); 899-918] by a direct toxic effect of increased necrosis and apoptosis [*Circ Res* (2000) 87(12); 1172-1179]. In a mouse model of pressure overload (TAC), NRF2 gene and protein expression is increased during the early stage of cardiac adaptive hypertrophy, but decreased in the later stage of maladaptive cardiac remodeling associated with systolic dysfunction [*Arterioscler Thromb Vasc Biol* (2009) 29(11); 1843-5 1850; *PLOS ONE* (2012) 7(9); e44899]. In addition, NRF2 activation has been shown to suppress myocardial oxidative stress as well as cardiac apoptosis, fibrosis, hypertrophy, and dysfunction in mouse models of pressure overload [*Arterioscler Thromb Vasc Biol* (2009) 29(11); *J of Mol & Cell Cardio* (2014) 72; 305-315; and 1843-1850; *PLOS ONE* (2012) 7(9); e44899]. NRF2 activation has also been shown to protect against cardiac I/R injury in mice 10 [*Circ Res* (2009) 105(4); 365-374; *J of Mol & Cell Cardio* (2010) 49(4); 576-586] and reduce myocardial oxidative damage following cardiac I/R injury in rat. Therefore, a drug targeting NRF2 by other mechanisms may be useful in a variety of cardiovascular diseases including but not limited to atherosclerosis, hypertension, and heart failure (Oxidative Medicine and Cellular Longevity Volume 2013 (2013), Article ID 104308, 10 pages), acute coronary 15 syndrome, myocardial infarction, myocardial repair, cardiac remodeling, cardiac arrhythmias, heart failure with preserved ejection fraction, heart failure with reduced ejection fraction and diabetic cardiomyopathy.

A drug activating the NRF2 pathway could also be useful for treatment of several neurodegenerative diseases including Parkinson's disease (PD), Alzheimer's disease (AD), amyotrophic lateral sclerosis (ALS) (Brain Res. 2012 Mar. 29; 1446:109-18. 2011.12.064. Epub 2012 Jan. 12) and multiple sclerosis (MS). Multiple in vivo models have shown that NRF2 KO mice are more sensitive to neurotoxic insults than their wild-type counterparts. Treatment of rats with the NRF2 activator tert-butylhydroquinone (tBHQ) reduced cortical damage in rats in a cerebral ischemia-reperfusion model, and cortical glutathione levels were increased in NRF2 wild-type but not KO mice after administration of tBHQ (Shih, A. Y., et al. 2005. *J. Neurosci.* 25: 10321-10335). Tecfidera™ (dimethyl fumarate), which activates NRF2 among other targets, is approved in the U.S. to treat relapsing-remitting multiple sclerosis (MS). Activation of NRF2 may also help treat cases of Friedreich's Ataxia, where increased sensitivity to oxidative stress and impaired NRF2 activation has been reported (Paupe V., et al, 2009. PLoS One; 4(1):e4253. Omaveloxolone (RTA-408) is also in clinical trials for Friedreich's Ataxia.

There is preclinical evidence of the specific protective role of the NRF2 pathway in models of inflammatory bowel disease (IBD, Crohn's Disease and Ulcerative Colitis) and/or colon cancer (Khor, T. O., et al 2008. *Cancer Prev. Res. (Phila)* 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the NRF2 pathway is involved in the anti-oxidant response of retinal epithelial cells and modulation of inflammation in pre-clinical models of eye injury (Schimel, et al. 2011. *Am. J. Pathol.* 178:2032-2043). Fuchs Endothelial Corneal Dystrophy (FECD) is a progressive, blinding disease characterized by corneal endothelial cells apoptosis. It is a disease of aging and increased oxidative stress related to low levels of NRF2 expression and/or function (Bitar, M. S., et al. 2012. *Invest Ophthalmol. Vis. Sci.* Aug. 24, 2012 vol. 53 no. 9 5806-5813). In addition, an NRF2 activator may be useful in uveitis or other inflammatory eye conditions.

Non-alcoholic steatohepatitis (NASH) is a disease of fat deposition, inflammation, and damage in the liver that occurs in patients who drink little or no alcohol. In preclinical models, development of NASH is greatly accelerated in KO mice lacking NRF2 when challenged with a methionine- and choline-deficient diet (Chowdhry S., et al. 2010. *Free Rad. Biol. & Med.* 48:357-371). Administration of the NRF2 activators oltipraz and NK-252 in rats on a choline-deficient L-amino acid-defined diet significantly attenuated progression of histologic abnormalities, especially hepatic fibrosis (Shimozono R. et al. 2012. *Molecular Pharmacology*. 84:62-70). Other liver diseases that may be amenable to NRF2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. Indian J Clin Biochem. 2010 October; 25(4): 388-392). Also, an NRF2 activator may be useful in treating the dermatitis/topical effects of radiation (Schäfer, M. et al. 2010. *Genes & Devl.* 24:1045-1058), and the immunosuppression due to radiation exposure (Kim, J. H. et al., J. Clin. Invest. 2014 Feb. 3; 124(2): 730-41).

There is also data suggesting that an NRF2 activator may be beneficial in preeclampsia, a disease that occurs in 2-5% of pregnancies and involves hypertension and proteinuria (*Annals of Anatomy-Anatomischer Anzeiger* Volume 196, Issue 5, September 2014, Pages 268-277).

Preclinical data has shown that compounds with NRF2 activating activity are better at reversing high altitude-induced damage than compounds without NRF2 activity, using animal and cellular models of Acute Mountain Sickness (Lisk C. et al, 2013, Free Radic Biol Med. October 2013; 63: 264-273.)

SUMMARY OF THE INVENTION

In one aspect, this invention provides for bisaryl amide analogs, pharmaceutically acceptable salts thereof, and pharmaceutical compositions containing them. In particular, the compounds of this invention include a compound of Formula (I)

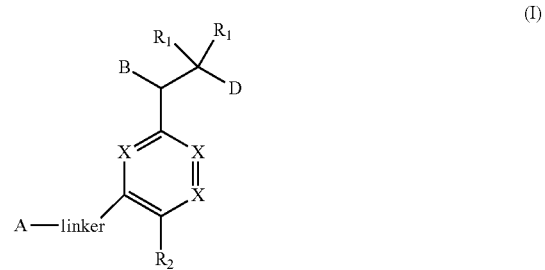

wherein:
B is benzotriazolyl, phenyl, triazolopyridinyl, —O—($CH_2$)-triazolyl, or —($CH_2$)$_2$-triazolyl wherein each of benzotriazolyl, phenyl, triazolopyridinyl, —O—($CH_2$)-triazolyl, or —($CH_2$)$_2$-triazolyl is unsubstituted or substituted by 1, 2, or 3 substituents independently selected from —$C_{1-3}$ alkyl, —$C_{3-7}$cycloalkyl, —O—$C_{1-3}$alkyl, —CN, —($CH_2$)$_2$—O—($CH_2$)$_2$—O$R_3$ and halo;
D is —C(O)—N$R_4R_5$, —$NR_4$—C(O)—$R_5$, —$NR_3$—C(O)—N$R_4R_5$; —$NR_4$—C(O)—O—$R_5$;
$R_1$ is hydrogen, —$C_{1-3}$alkyl, F, —$C_{3-6}$spirocycloalkyl, oxetane, or the two $R_1$ groups together with the carbon to which they are attached form a cyclopropyl group;
$R_2$ is hydrogen, methyl, —$CF_3$, or halo;
$R_3$ is hydrogen or —$C_{1-5}$alkyl;
$R_4$ is hydrogen or —$C_{1-5}$alkyl;
$R_5$ is hydrogen, —$C_{1-5}$alkyl, —$C_{3-7}$cycloalkyl, —$C_{4-8}$heterocycloalkyl, —$C_{1-5}$alkoxy, —$C_{1-3}$ alkyl-O–$C_{1-3}$alkyl, —$C_{1-3}$ alkyl-NH—$C_{1-3}$ alkyl, —$C_{1-3}$ alkyl-NH—C(O)$R_3$, —$C_{1-3}$ alkyl-$SO_2C_{1-3}$ alkyl, $C_{4-8}$heterocycloalkyl, —$C_{1-3}$ alkyl-C(O)N$R_3R_4$, aryl, —$C_{1-5}$alkylheteroaryl, or heteroaryl, wherein each of —C$_{1-5}$alkyl, —C$_{3-7}$ cycloalkyl, —C$_{4-7}$ heterocycloalkyl, —C$_{1-5}$alkoxy, —C$_{1-3}$alkyl-O—C$_{1-3}$alkyl, —C$_{1-3}$alkyl-NH—C$_{1-3}$ alkyl, —C$_{1-3}$ alkyl-C(O)NR$_3$R$_4$, aryl, —C$_{1-5}$alkylheteroaryl, or heteroaryl is unsubstituted or substituted by one or two substituents independently selected from —C$_{1-3}$ alkyl, —C$_{1-3}$alkylaryl, —C$_{1-3}$alkylheteroaryl, aryl, —C$_{1-3}$alkylC(O)R$_3$, —C$_{1-3}$alkylC(O)OH, —C$_{1-3}$alkylNC(O)OR$_4$, —C$_{1-3}$alkylOSi(R$_3$)$_3$, —C$_{1-3}$ alkylOH, —C$_{1-3}$ alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —N—C(O)—C$_{1-3}$ alkyl, F, Cl, —CN, —CH—F$_2$, —CF$_3$, —(CH$_2$)$_n$—O—(CH$_2$)$_m$—CH$_3$, —O(CH$_2$)$_n$—O—(CH$_2$)$_m$, —O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S.

or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

and wherein each of the tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CF$_3$, —CH$_2$—O—CH$_3$, and —OH;

and wherein the piperidinyl is further unsubstituted or substituted independently by pyrazolyl, —CH$_2$pyrazolyl, or oxadiazolyl, and wherein each of the pyrazolyl, —CH$_2$pyrazolyl, or oxadiazolyl is further unsubstituted or substituted independently by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;

and wherein the oxazepane is further unsubstituted or substituted independently by 1 or 2 of —C$_{1-3}$alkyl or —C$_{3-7}$ cycloalkyl;

and wherein the morpholinyl is further unsubstituted or substituted by a phenyl which itself is optionally substituted independently by —C$_{1-3}$ alkyl or —O—C$_{1-3}$ alkyl;

and wherein the pyrrolidinyl is further unsubstituted or substituted by a triazolyl group which itself is optionally substituted by —C$_{1-3}$alkyl;

and wherein each of the imidazolyl, triazolyl, pyrazolyl, and tetrazolyl groups are further unsubstituted or substituted independently by —CH$_2$—C$_{4-7}$cycloalkyl, —CH$_2$—C$_{5-7}$ heterocycloalkyl, —CH$_2$-azabicycloheptanyl, —CH$_2$-oxepane, or —CH$_2$-azabicyclohexanyl, all of which, including the —CH$_2$—, is optionally further substituted independently by 1 or 2 of —C$_{1-3}$alkyl or F;

or A is

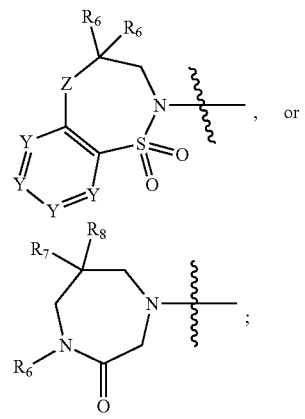

Y is independently selected from N or CH;
Z is O, CH$_2$, NR$_5$, S, S(O) or S(O)$_2$;
R$_6$ is independently hydrogen or —C$_{1-4}$alkyl;
R$_7$ is hydrogen, —C$_{1-5}$alkyl or —(CH$_2$), —C$_{3-5}$cycloalkyl;
R$_8$ is hydrogen or —C$_{1-4}$alkyl;
or R$_7$ and R$_8$, together with the carbon to which they are attached form a C$_3$-C$_5$-membered cycloalkyl ring;
and, wherein when A is

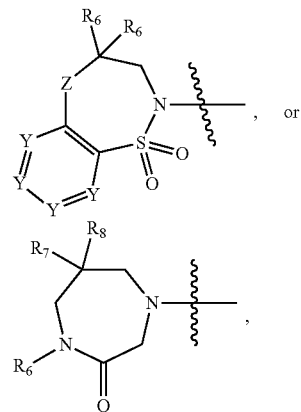

it is unsubstituted or substituted with one, two or three substituents independently selected from halo, —CF$_3$, —CN, —OMe, —C(O)NH$_2$, —OCF$_3$, —C$_{1-4}$alkylNR$_8$R$_9$;

$R_9$ is —$C_{1-3}$alkyl, aryl, heteroaryl, —C(O)$C_{1-3}$alkyl, —SO$_2$$C_{1-3}$alkyl, —C(O)aryl, —C(O)heteroaryl, —SO$_2$aryl, —SO$_2$heteroaryl, —$C_{3-7}$cycloalkyl, —$C_{1-3}$alkyl$C_{3-7}$cycloalkyl, —$C_{1-3}$alkyl$C_{3-7}$heterocycloalkyl, —$C_{1-3}$alkylheteroaryl or —$C_{1-3}$alkylaryl, wherein each of —$C_{1-3}$alkyl, aryl, heteroaryl, —C(O)$C_{1-3}$alkyl, —SO$_2$$C_{1-3}$ alkyl, —C(O)aryl, —C(O)heteroaryl, —SO$_2$aryl, —SO$_2$heteroaryl, —$C_{3-7}$cycloalkyl, —$C_{1-3}$alkyl$C_{3-7}$cycloalkyl, —$C_{1-3}$alkyl$C_{3-7}$heterocycloalkyl, —$C_{1-3}$alkylheteroaryl or —$C_{1-3}$alkylaryl is unsubstituted or substituted by 1, 2 or 3 substituents independently selected from halo, —CN, —CF$_3$, —OCF$_3$, —OCH$_3$, —$C_{1-3}$alkyl, —O$C_{1-3}$alkyl, —O$C_{3-7}$cycloalkyl, —O$C_{3-7}$hetercycloalkyl, —O-aryl and —O-heteroaryl;

X is independently CH or N;

m is 1, 2 or 3; and n is 1, 2 or 3;

or a pharmaceutically acceptable salt thereof.

In a second aspect, this invention provides for the use of a compound of Formula (I) as NRF2 activators.

In another aspect, this invention provides for the use of a compound of Formula (I) for treating and preventing conditions associated with NRF2 imbalance.

In one aspect, the invention provides a pharmaceutical composition comprising a compound of the invention according to Formula (I), or a pharmaceutically acceptable salt thereof, and a pharmaceutically acceptable excipient. Particularly, this invention is directed to a pharmaceutical composition for the treatment of an NRF2 regulated disease or disorder, wherein the composition comprises a compound according to Formula (I), or a pharmaceutically acceptable salt thereof, and a pharmaceutically acceptable excipient.

In a further aspect, this invention provides for a method of treating respiratory and non-respiratory disorders, including COPD, asthma, ALI, ARDS, fibrosis, chronic asthma, acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, which comprises administering to a human in need thereof, a compound of Formula (I).

In yet another aspect, this invention provides for the use of a compound of Formula (I) for the treatment of respiratory and non-respiratory disorders, including COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to use of a compound of Formula (I) or a pharmaceutically acceptable salt thereof in the manufacture of a medicament for the treatment of respiratory and non-respiratory disorders, including COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to a compound of Formula (I) or a pharmaceutically acceptable salt thereof, for use in medical therapy.

In a further aspect, this invention relates to a compound of Formula (I) or a pharmaceutically acceptable salt thereof, for use in the treatment of respiratory and non-respiratory disorders, including COPD, asthma, ALI, ARDS, fibrosis, chronic asthma and acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

In a further aspect, this invention relates to the use of a compound of Formula (I) for the treatment of COPD.

In a further aspect, this invention relates to use of a compound of Formula (I) or a pharmaceutically acceptable salt thereof in the manufacture of a medicament for the treatment of COPD.

In a further aspect, this invention relates to a compound of Formula (I) or a pharmaceutically acceptable salt thereof, for use in the treatment COPD.

In a further aspect, this invention relates to a method of treating COPD which comprises administering to a human in need thereof, a compound of Formula (I).

In a further aspect, this invention relates to the use of a compound of Formula (I) for the treatment of heart failure.

In a further aspect, this invention relates to use of a compound of Formula (I) or a pharmaceutically acceptable salt thereof in the manufacture of a medicament for the treatment of heart failure.

In a further aspect, this invention relates to a method of treating heart failure which comprises administering to a human in need thereof, a compound of Formula (I).

In a further aspect, this invention relates to a compound of Formula (I) or a pharmaceutically acceptable salt thereof, for use in the treatment of heart failure.

In one embodiment, the invention is directed to the use of a compound of Formula (I), or a pharmaceutically acceptable salt thereof, as an active therapeutic substance. More specifically, this invention provides for the use of the compounds described herein for the treatment of a respiratory and non-respiratory disorder, specifically, a disease or disorder recited herein. Accordingly, the invention provides for the use of a compound of Formula (I), or a pharmaceutically acceptable salt thereof, as an active therapeutic substance in the treatment of a human in need thereof with a respiratory and non-respiratory disorder, specifically, a disease or disorder recited herein. Specifically, the invention provides for the use of a compound of Formula (I), or a pharmaceutically acceptable salt thereof, as an active therapeutic substance in the treatment of COPD. Specifically, the invention provides for the use of a compound of Formula (I), or a pharmaceutically acceptable salt thereof, as an active therapeutic substance in the treatment of heart failure.

Other aspects and advantages of the present invention are described further in the following detailed description of the preferred embodiments thereof.

DETAILED DESCRIPTION OF THE INVENTION

The present invention provides for compounds of Formula (I):

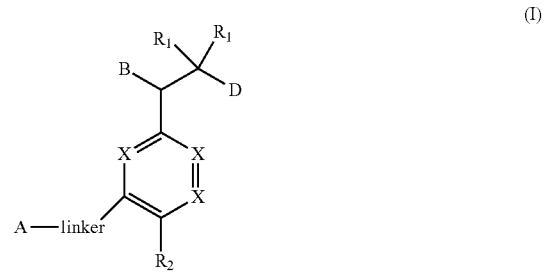

wherein:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$ alkyl, —C$_{3-7}$cycloalkyl, —O—C$_{1-3}$alkyl, —CN, —(CH$_2$)$_2$—O—(CH$_2$)$_2$—OR$_3$ and halo;
D is —C(O)—NR$_4$R$_5$, —NR$_4$—C(O)—R$_5$, —NR$_3$—C(O)—NR$_4$R$_5$; —NR$_4$—C(O)—O—R$_5$;
R$_1$ is hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-5}$alkyl;
R$_4$ is hydrogen or —C$_{1-5}$alkyl;
R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$ alkyl-O—C$_{1-3}$alkyl, —C$_{1-3}$ alkyl-NH—C$_{1-3}$ alkyl, —C$_{1-3}$ alkyl-NH—C(O)R$_3$, —C$_{1-3}$ alkyl-SO$_2$C$_{1-3}$ alkyl, —C$_{1-3}$ alkyl-C$_{4-8}$heterocycloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$ cycloalkyl, —C$_{4-7}$heterocycloalkyl, —C$_{1-5}$alkoxy, —C$_{1-3}$alkyl-O—C$_{1-3}$alkyl, —C$_{1-3}$alkyl-NH—C$_{1-3}$ alkyl, —C$_{1-3}$ alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$ alkylaryl, —C$_{1-3}$ alkylheteroaryl, aryl, —C$_{1-3}$ alkylC(O)R$_3$, —C$_{1-3}$ alkylC(O)OH, —C$_{1-3}$alkylNC(O)OR$_4$, —C$_{1-3}$ alkylOSi(R$_3$)$_3$, —C$_{1-3}$ alkylOH, —C$_{1-3}$ alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —N—C(O)—C$_{1-3}$alkyl, F, Cl, —CN, —CH—F$_2$, —CF$_3$, —(CH$_2$)$_n$—O—(CH$_2$)$_m$—CH$_3$, —O(CH$_2$)$_n$—O—(CH$_2$)$_m$, —O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S;
or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$alkyl, —$C_{3-7}$cycloalkyl, —$C_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

and wherein each of the tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —$C_{1-3}$alkyl, —$C_{3-6}$spirocycloalkyl, halo, —CN, —O—$C_{1-3}$alkyl, —CF$_3$, —CH$_2$—O—CH$_3$, and —OH;

and wherein the piperidinyl is further unsubstituted or substituted independently by pyrazolyl, —CH$_2$pyrazolyl, or oxadiazolyl, and wherein each of the pyrazolyl, —CH$_2$pyrazolyl, or oxadiazolyl is further unsubstituted or substituted independently by —$C_{1-3}$alkyl, or, when A is piperidinyl, it is unsubstituted or substituted by —SO$_2$R, wherein R is —$C_{1-3}$alkyl, phenyl or —$C_{3-7}$cycloalkyl;

and wherein the oxazepane is further unsubstituted or substituted independently by 1 or 2 of —$C_{1-3}$alkyl or —$C_{3-7}$ cycloalkyl;

and wherein the morpholinyl is further unsubstituted or substituted by a phenyl which itself is optionally substituted independently by —$C_{1-3}$alkyl or —O—$C_{1-3}$alkyl;

and wherein the pyrrolidinyl is further unsubstituted or substituted by a triazolyl group which itself is optionally substituted by —$C_{1-3}$alkyl;

and wherein each of the imidazolyl, triazolyl, pyrazolyl, and tetrazolyl groups are further unsubstituted or substituted independently by —CH$_2$—$C_{4-7}$cycloalkyl, —CH$_2$—$C_{5-7}$heterocycloalkyl, —CH$_2$-azabicycloheptanyl, —CH$_2$-oxepane, or —CH$_2$-azabicyclohexanyl, all of which, including the —CH$_2$—, is optionally further substituted independently by 1 or 2 of —$C_{1-3}$ alkyl or F;

or A is

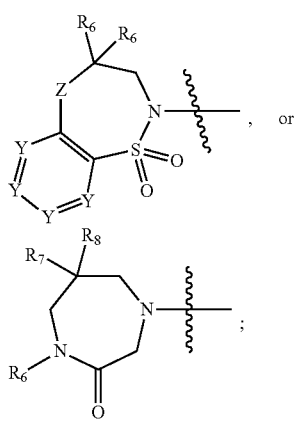

Y is independently selected from N or CH;
Z is O, CH$_2$, NR$_5$, S, S(O) or S(O)$_2$;
R$_6$ is independently hydrogen or —$C_{1-4}$alkyl;
R$_7$ is hydrogen, —$C_{1-5}$alkyl or —(CH$_2$), —$C_{3-5}$cycloalkyl;
R$_8$ is hydrogen or —$C_{1-4}$alkyl;
or R$_7$ and R$_8$, together with the carbon to which they are attached form a C$_3$-C$_5$-membered cycloalkyl ring;
and, wherein when A is

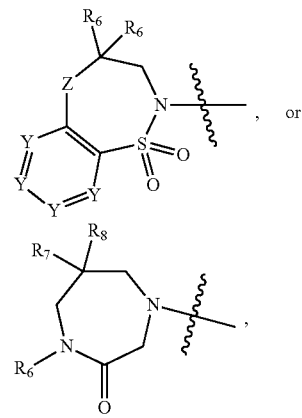

it is unsubstituted or substituted with one, two or three substituents independently selected from halo, —CF$_3$, —$C_{1-4}$alkyl, —CN, —OMe, —C(O)NH$_2$, —OCF$_3$, —$C_{1-4}$alkylNR$_8$R$_9$;

R$_9$ is —$C_{1-3}$alkyl, aryl, heteroaryl, —C(O)$C_{1-3}$alkyl, —SO$_2$$C_{1-3}$alkyl, —C(O)aryl, —C(O)heteroaryl, —SO$_2$aryl, —SO$_2$heteroaryl, —$C_{3-7}$cycloalkyl, —$C_{1-3}$ alkyl$C_{3-7}$ cycloalkyl, —$C_{1-3}$ alkyl$C_{3-7}$heterocycloalkyl, —$C_{1-3}$alkylheteroaryl or —$C_{1-3}$alkylaryl, wherein each of —$C_{1-3}$alkyl, aryl, heteroaryl, —C(O)$C_{1-3}$alkyl, —SO$_2$$C_{1-3}$alkyl, —C(O)aryl, —C(O)heteroaryl, —SO$_2$aryl, —SO$_2$heteroaryl, —$C_{3-7}$cycloalkyl, —$C_{1-3}$ alkyl$C_{3-7}$ cycloalkyl, —$C_{1-3}$alkyl$C_{3-7}$heterocycloalkyl, —$C_{1-3}$alkylheteroaryl or —$C_{1-3}$alkylaryl is unsubstituted or substituted by 1, 2 or 3 substituents independently selected from halo, —CN, —CF$_3$, —OCF$_3$, —OCH$_3$, —$C_{1-3}$alkyl, —OC$_{1-3}$alkyl, —OC$_{3-7}$cycloalkyl, —OC$_{3-7}$hetercycloalkyl, —O-aryl and —O-heteroaryl;

X is independently CH or N;
m is 1, 2 or 3; and
n is 1, 2 or 3;
or a pharmaceutically acceptable salt thereof.

"Alkyl" refers to a monovalent saturated hydrocarbon chain having the specified number of carbon member atoms. For example, $C_{1-4}$alkyl refers to an alkyl group having from 1 to 4 carbon member atoms. Alkyl groups may be straight or branched. Representative branched alkyl groups have one, two, or three branches. Alkyl includes methyl, ethyl, propyl, (n-propyl and isopropyl), and butyl (n-butyl, isobutyl, s-butyl, and t-butyl).

"Alkoxy" refers to an "alkyl-oxy-" group, containing an alkyl moiety attached through an oxygen linking atom. For example, the term "(C$_1$-C$_4$)alkoxy" represents a saturated, straight or branched hydrocarbon moiety having at least 1 and up to 4 carbon atoms attached through an oxygen linking atom. Exemplary "(C$_1$-C$_4$)alkoxy" groups include, but are not limited to, methoxy, ethoxy, n-propoxy, isopropoxy, n-butoxy, s-butoxy, and t-butoxy.

"Aryl" refers to a group or moiety comprising an aromatic, monocyclic or bicyclic hydrocarbon radical containing from 5 to 10 carbon ring atoms and having at least one aromatic ring. Examples of "aryl" groups are phenyl, naphthyl, indenyl, and dihydroindenyl (indanyl).

"Cycloalkyl" refers to a non-aromatic, saturated, cyclic hydrocarbon group containing the specified number of carbon atoms. For example, $C_{3-6}$cycloalkyl refers to a cycloalkyl group having from 3 to 6 carbon member atoms. Cycloalkyl includes cyclopropyl, cyclopropenyl, cyclobutyl, cyclobutenyl, cyclopentyl, cyclopentenyl, cyclohexyl, and cyclohexenyl.

A heterocyclic group is a cyclic group having, as ring members, atoms of at least two different elements, which cyclic group may be saturated, partially unsaturated (non aromatic) or fully unsaturated (aromatic). The terms "heterocyclic" or "heterocyclyl" includes heterocycloalkyl and heteroaryl groups. It is to be understood that the terms heterocyclic, heterocyclyl, heteroaryl, and heterocycloalkyl, are intended to encompass stable groups where a ring nitrogen heteroatom is optionally oxidized (e.g., heteroaryl groups containing an N oxide, such as oxo-pyridyl (pyridyl N oxide) and oxo-oxadiazolyl (oxo-4,5-dihydro-1,3,4-oxadiazolyl) or where a ring sulfur heteroatom is optionally oxidized (e.g., heterocycloalkyl groups containing sulfones or sulfoxide moieties, such as tetrahydrothienyl 1 oxide (tetrahydrothienyl sulfoxide, tetrahydrothiophenyl sulfoxide) and tetrahydrothienyl 1,1 dioxide (tetrahydrothienyl sulfone)).

"$C_{4-8}$heterocycloalkyl" refers to a saturated, non-aromatic, monocyclic or bicyclic group containing 4-8 ring atoms, unless otherwise limited in size, containing one or more (generally one or two) heteroatom substitutions independently selected from oxygen, sulfur, and nitrogen. Non-limited examples include, pyrrolidine, piperidine, morpholine, azepane, 1,4-oxazepane, 1,4-thiazepane, 1,4-thiazepane 1-oxide, 1,4-thiazepane 1,1-dioxide, thiomorpholine, thiomorpholine 1-oxide, and thiomorpholine 1,1-dioxide.

When used herein, the terms 'halogen' and 'halo' include fluorine, chlorine, bromine and iodine, and fluoro, chloro, bromo, and iodo, respectively.

"Heteroaryl" represents a group or moiety comprising an aromatic monocyclic radical, containing 5 to 6 ring atoms unless otherwise limited in size, including 1 to 4 heteroatoms independently selected from nitrogen, oxygen and sulfur. This term also encompasses 9- to 10-membered bicyclic heterocyclic-aryl groups containing either an aryl ring moiety fused to a heterocycloalkyl ring moiety or a heteroaryl ring moiety fused to a cycloalkyl ring moiety. This term also encompasses 9- to 10-membered fused bicyclic heteroaryl-aryl groups.

Illustrative examples of heteroaryls include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl (pyridyl), oxopyridyl (pyridyl-N-oxide), pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, indolizinyl, indolyl, isoindolyl, dihydroindolyl, benzimidazolyl, dihydrobenzimidazolyl, benzoxazolyl, dihydrobenzoxazolyl, benzothiazolyl, benzoisothiazolyl, dihydrobenzoisothiazolyl, indazolyl, imidazopyridinyl, pyrazolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

Bicyclic heteroaryl groups include 6,5-fused heteroaryl (9-membered heteroaryl) and 6,6-fused heteroaryl (10-membered heteroaryl) groups. Examples of 6,5-fused heteroaryl (9-membered heteroaryl) groups include benzothienyl, benzofuranyl, indolyl, indolinyl, isoindolyl, isoindolinyl, indazolyl, indolizinyl, isobenzofuryl, 2,3-dihydrobenzofuryl, benzoxazolyl, benzthiazolyl, benzimidazolyl, benzoxadiazolyl, benzthiadiazolyl, benzotriazolyl, 1,3-benzoxathiol-2-on-yl(2-oxo-1,3-benzoxathiolyl), purinyl and imidazopyridinyl.

Examples of 6,6-fused heteroaryl (10-membered heteroaryl) groups include quinolyl, isoquinolyl, phthalazinyl, naphthridinyl (1,5-naphthyridinyl, 1,6-naphthyridinyl, 1,7-naphthyridinyl, 1,8-naphthyridinyl), quinazolinyl, quinoxalinyl, 4H-quinolizinyl, tetrahydroquinolinyl, cinnolinyl, and pteridinyl.

"Oxo" represents a double-bonded oxygen moiety; for example, if attached directly to a carbon atom forms a carbonyl moiety (C=O). "Hydroxy" or "hydroxyl" is intended to mean the radical —OH. As used herein, the term "cyano" refers to the group —CN.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

The term "independently" means that where more than one substituent is selected from a number of possible substituents, those substituents may be the same or different. That is, each substituent is separately selected from the entire group of recited possible substituents.

The invention also includes various isomers of the compounds of Formula (I) and mixtures thereof. "Isomer" refers to compounds that have the same composition and molecular weight but differ in physical and/or chemical properties. The structural difference may be in constitution (geometric isomers) or in the ability to rotate the plane of polarized light (stereoisomers). The compounds according to Formula (I) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formula (I), or in any chemical structure illustrated herein, is not specified the structure is intended to encompass any stereoisomer and all mixtures thereof. Thus, compounds according to Formula (I) containing one or more chiral centers may be used as racemic mixtures, enantiomerically enriched mixtures, or as enantiomerically pure individual stereoisomers.

Individual stereoisomers of a compound according to Formula (I) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

It is to be understood that the references herein to a compound of Formula (I) or a salt thereof includes a compound of Formula (I) as a free base [or acid, as appropriate], or as a salt thereof, for example as a pharmaceutically acceptable salt thereof. Thus, in one embodiment, the invention is directed to a compound of Formula (I). In another embodiment, the invention is directed to a salt of a compound of Formula (I). In a further embodiment, the invention is directed to a pharmaceutically acceptable salt of a compound of Formula (I). In another embodiment, the invention is directed to a compound of Formula (I) or a salt thereof. In a further embodiment, the invention is directed to a compound of Formula (I) or a pharmaceutically acceptable salt thereof.

Compounds of Formula (I) have both a basic amine group and a carboxylic acid group and can consequently be in the form of a zwitterion, also known as an inner salt. Therefore, in an embodiment the compound of Formula (I) is in a zwitterion form.

As used herein, "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: Wiley-VCH/VHCA, 2011 (see http://www.wiley.com/WileyCDA/WileyTitle/productCd-3906390519.html).

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively.

It will be understood that if a compound of Formula (I) contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of Formula (I) are included within the scope of the invention, including sub-stoichiometric salts, for example where a counterion contains more than one acidic proton.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

Representative Embodiments

In one embodiment, the invention is a compound of Formula (I):

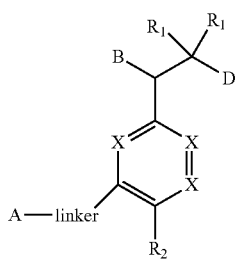

(I)

wherein:
B is benzotriazolyl, phenyl, triazolopyridinyl, —O—(CH$_2$)-triazolyl, or —(CH$_2$)$_2$-triazolyl wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$ alkyl, —C$_{3-7}$cycloalkyl, —O—C$_{1-3}$alkyl, —CN, —(CH$_2$)$_2$—O—(CH$_2$)$_2$—OR$_3$ and halo;
D is —C(O)—NR$_4$R$_5$, —NR$_4$—C(O)—R$_5$, —NR$_3$—C(O)—NR$_4$R$_5$; —NR$_4$—C(O)—O—R$_5$;
R$_1$ is independently selected from hydrogen, —C$_{1-3}$alkyl, F, —C$_{3-6}$spirocycloalkyl, oxetane, or the two R$_1$ groups together with the carbon to which they are attached form a cyclopropyl group;
R$_2$ is hydrogen, methyl, —CF$_3$, or halo;
R$_3$ is hydrogen or —C$_{1-5}$alkyl;
R$_4$ is hydrogen or —C$_{1-5}$alkyl;
R$_5$ is hydrogen, —C$_{1-5}$alkyl, —C$_{3-7}$ cycloalkyl, —C$_{4-8}$ heterocycloalkyl, —C$_{1-5}$alkoxy, —C$_{1-3}$ alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{1-8}$heterocycloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$ cycloalkyl, —C$_{4-7}$ heterocycloalkyl, —C$_{1-5}$ alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_3$R$_4$, aryl, —C$_{1-5}$alkylheteroaryl, or heteroaryl is unsubstituted or substituted by one or two substituents independently selected from —C$_{1-3}$ alkyl, —C$_{1-3}$alkylaryl, —C$_{1-3}$alkylheteroaryl, aryl, —C$_{1-3}$alkylC(O)R$_3$, —C$_{1-3}$alkylC(O)OH, —C$_{1-3}$alkylNC(O)OR$_4$, —C$_{1-3}$ alkylOSi(R$_3$)$_3$, —C$_{1-3}$ alkylOH, —C$_{1-3}$ alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —N—C(O)—C$_{1-3}$ alkyl, F, Cl, —CN, —CH—F$_2$, —CF$_3$, —(CH$_2$)$_n$—O—(CH$_2$)$_m$—CH$_3$, —O(CH$_2$)$_n$—O—(CH$_2$)$_m$, —O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S.
or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

and wherein each of the tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —$C_{1-3}$alkyl, —$C_{3-6}$spirocycloalkyl, halo, —CN, —O—$C_{1-3}$alkyl, —$CF_3$, —$CH_2$—O—$CH_3$, and —OH;

and wherein the piperidinyl is further unsubstituted or substituted independently by pyrazolyl, —$CH_2$pyrazolyl, or oxadiazolyl, and wherein each of the pyrazolyl, —$CH_2$pyrazolyl, or oxadiazolyl is further unsubstituted or substituted independently by —$C_{1-3}$alkyl, or, when A is piperidinyl, it is unsubstituted or substituted by —$SO_2R$, wherein R is —$C_{1-3}$alkyl, phenyl or —$C_{3-7}$cycloalkyl;

and wherein the oxazepane is further unsubstituted or substituted independently by 1 or 2 of —$C_{1-3}$alkyl or —$C_{3-7}$cycloalkyl;

and wherein the morpholinyl is further unsubstituted or substituted by a phenyl which itself is optionally substituted independently by —$C_{1-3}$alkyl or —O—$C_{1-3}$alkyl;

and wherein the pyrrolidinyl is further unsubstituted or substituted by a triazolyl group which itself is optionally substituted by —$C_{1-3}$alkyl;

and wherein each of the imidazolyl, triazolyl, pyrazolyl, and tetrazolyl groups are further unsubstituted or substituted independently by —$CH_2$—$C_{4-7}$cycloalkyl, —$CH_2$—$C_{5-7}$heterocycloalkyl, —$CH_2$-azabicycloheptanyl, —$CH_2$-oxepane, or —$CH_2$-azabicyclohexanyl, all of which, including the —$CH_2$—, is optionally further substituted independently by 1 or 2 of —$C_{1-3}$ alkyl or F;

or A is

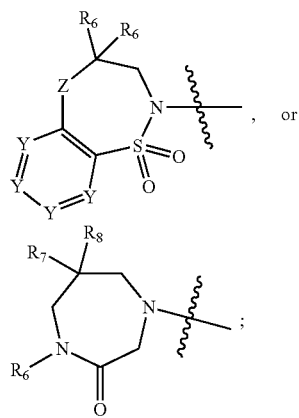

Y is independently selected from N or CH;
Z is O, $CH_2$, $NR_5$, S, S(O) or $S(O)_2$;
$R_6$ is independently hydrogen or —$C_{1-4}$alkyl;
$R_7$ is hydrogen, —$C_{1-5}$alkyl or —$(CH_2)$, —$C_{3-5}$cycloalkyl;
$R_9$ is hydrogen or —$C_{1-4}$alkyl;
or $R_7$ and $R_8$, together with the carbon to which they are attached form a $C_3$-$C_5$-membered cycloalkyl ring;

and, wherein when A is

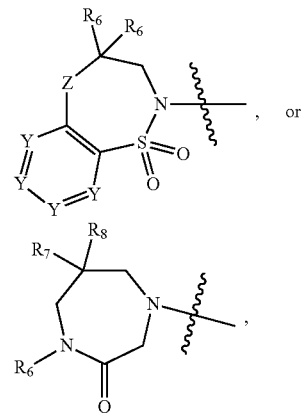

it is unsubstituted or substituted with one, two or three substituents independently selected from halo, —$CF_3$, —$C_{1-4}$alkyl, —CN, —OMe, —$C(O)NH_2$, —$OCF_3$, —$C_{1-4}$ alkyl$NR_8R_9$;

$R_9$ is —$C_{1-3}$alkyl, aryl, heteroaryl, —$C(O)C_{1-3}$alkyl, —$SO_2C_{1-3}$alkyl, —$C(O)$aryl, —$C(O)$heteroaryl, —$SO_2$aryl, —$SO_2$heteroaryl, —$C_{3-7}$cycloalkyl, —$C_{1-3}$ alkyl$C_{3-7}$ cycloalkyl, —$C_{1-3}$ alkyl$C_{3-7}$heterocycloalkyl, —$C_{1-3}$alkylheteroaryl or —$C_{1-3}$alkylaryl, wherein each of —$C_{1-3}$alkyl, aryl, heteroaryl, —$C(O)C_{1-3}$alkyl, —$SO_2C_{1-3}$ alkyl, —$C(O)$aryl, —$C(O)$heteroaryl, —$SO_2$aryl, —$SO_2$heteroaryl, —$C_{3-7}$cycloalkyl, —$C_{1-3}$ alkyl$C_{3-7}$ cycloalkyl, —$C_{1-3}$alkyl$C_{3-7}$heterocycloalkyl, —$C_{1-3}$alkylheteroaryl or —$C_{1-3}$alkylaryl is unsubstituted or substituted by 1, 2 or 3 substituents independently selected from halo, —CN, —$CF_3$, —$OCF_3$, —$OCH_3$, —$C_{1-3}$alkyl, —$OC_{1-3}$alkyl, —$OC_{3-7}$cycloalkyl, —$OC_{3-7}$ hetercycloalkyl, —O-aryl and —O-heteroaryl;

X is independently CH or N;
m is 1, 2 or 3; and
n is 1, 2 or 3;
or a pharmaceutically acceptable salt thereof.

In another embodiment, the compound of Formula (I) is substituted as follows:
B is benzotriazolyl, phenyl, triazolopyridinyl, —O—$(CH_2)$-triazolyl, or —$(CH_2)_2$-triazolyl wherein each of benzotriazolyl, phenyl, triazolopyridinyl, —O—$(CH_2)$-triazolyl, or —$(CH_2)_2$-triazolyl is unsubstituted or substituted by 1, 2, or 3 substituents independently selected from —$C_{1-3}$ alkyl, —O—$C_{1-3}$alkyl, —CN, —$(CH_2)_2$—O—$(CH_2)_2$—$OR_3$ and halo;
D is —C(O)—$NR_4R_5$;
$R_1$ is independently selected from hydrogen, —$C_{1-3}$alkyl, F, —$C_{3-6}$spirocycloalkyl, oxetane, or the two $R_1$ groups together with the carbon to which they are attached form a cyclopropyl group;
$R_2$ is hydrogen, methyl, $CF_3$, or halo;
$R_3$ is hydrogen or —$C_{1-5}$alkyl;
$R_4$ is hydrogen or —$C_{1-5}$alkyl;
$R_5$ is hydrogen, —$C_{1-5}$alkyl, —$C_{3-7}$cycloalkyl, —$C_{4-8}$heterocycloalkyl, —$C_{1-5}$alkoxy, —$C_{1-3}$ alkyl-O—$C_{1-3}$alkyl, —$C_{1-3}$alkyl-NH—$C_{1-3}$alkyl, —$C_{1-3}$alkyl-$SO_2C_{1-3}$alkyl, —$C_{1-3}$alkyl-$C_{4-8}$heterocycloalkyl, —$C_{1-3}$alkyl-C(O)$NR_3R_4$, or heteroaryl, wherein each of —$C_{1-6}$ alkyl, —$C_{3-7}$ cycloalkyl, —$C_{4-7}$ heterocycloalkyl, —$C_{1-5}$ alkoxy, —$C_{1-3}$ alkyl-O—$C_{1-3}$ alkyl, —$C_{1-3}$ alkyl-NH—$C_{1-3}$ alkyl, —$C_{1-3}$alkyl-C(O)$NR_3R_4$, or heteroaryl is unsubstituted or substituted by one or two substituents selected from —OH, —C(O), —N═C(O)—C$_{1-3}$alkyl, F, CN, —CH—F$_2$, —CF$_3$, —(CH$_2$)$_n$—O—(CH$_2$)$_m$—CH$_3$, and —C$_{3-7}$cycloalkyl;

or, R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

And wherein each of the tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, C$_{3-6}$spirocycloalkyl, halo, CN, —O—C$_{1-3}$alkyl, —CH$_2$—O—CH$_3$, and OH;

And wherein the piperidinyl is further optionally substituted independently by pyrazolyl, —CH$_2$pyrazolyl, or oxadiazolyl, and wherein each of the pyrazolyl, —CH$_2$pyrazolyl, or oxadiazolyl is further optionally substituted independently by —C$_{1-3}$alkyl, or, when A is piperidinyl, it is optionally substituted by —SO$_2$R, wherein R is —C$_{1-3}$alkyl, phenyl or —C$_{3-7}$cycloalkyl;

And wherein the oxazepane is further optionally substituted independently by 1 or 2 of —C$_{1-3}$alkyl or —C$_{3-7}$cycloalkyl;

And wherein the morpholinyl is further optionally substituted by a phenyl which itself is optionally substituted independently by —C$_{1-3}$alkyl or —O—C$_{1-3}$alkyl;

And wherein the pyrrolidinyl is further optionally substituted by a triazolyl group which itself is optionally substituted by —C$_{1-3}$alkyl;

And wherein the imidazolyl, triazolyl, pyrazolyl, and tetrazolyl groups are further optionally substituted independently by —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, all of which, including the —CH$_2$—, is optionally further substituted independently by 1 or 2 of —C$_{1-3}$alkyl or F;

X is independently CH or N;

m is 1, 2 or 3; and n is 1, 2 or 3;

or a pharmaceutically acceptable salt thereof.

In another embodiment, the compound of Formula (I) is substituted as follows:

B is benzotriazolyl, phenyl, triazolopyridinyl, —O—(CH$_2$)$_2$ triazolyl, or —(CH$_2$)$_2$ triazolyl wherein each of benzotriazolyl, phenyl, triazolopyridinyl, —O—(CH$_2$)$_2$triazolyl, or —(CH$_2$)$_2$ triazolyl is unsubstituted or substituted by 1, 2, or 3 substituents independently selected from —C$_{1-3}$ alkyl, —O—C$_{1-3}$alkyl, —CN, —(CH$_2$)$_2$—O—(CH$_2$)$_2$—OR$_3$ and halo;

D is —C(O)—NR$_4$R$_5$;

R$_1$ is independently selected from hydrogen, —C$_{1-3}$ alkyl, F, —C$_{3-6}$ spirocycloalkyl, oxetane, or the two R$_1$ groups together with the carbon to which they are attached form a cyclopropyl group;

R$_2$ is hydrogen, methyl, CF$_3$, or halo;

R$_3$ is hydrogen or —C$_{1-5}$alkyl;

R$_4$ is hydrogen or —C$_{1-5}$alkyl;

R$_5$ is hydrogen, —C$_{1-5}$ alkyl, —C$_{3-7}$cycloalkyl, —C$_{4-8}$heterocycloalkyl, —C$_{1-5}$ alkoxy, —C$_{1-3}$ alkyl-O—C$_{1-3}$alkyl, —C$_{1-3}$alkyl-NH—C$_{1-3}$alkyl, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_3$R$_4$, or heteroaryl, wherein each of —C$_{1-5}$ alkyl, —C$_{3-7}$ cycloalkyl, —C$_{4-7}$ heterocycloalkyl, —C$_{1-5}$ alkoxy, —C$_{1-3}$ alkyl-O—C$_{1-3}$ alkyl, —C$_{1-3}$ alkyl-NH—C$_{1-3}$ alkyl, —C$_{1-3}$ alkyl-C(O)NR$_3$R$_4$, or heteroaryl is unsubstituted or substituted by one or two substituents selected from —OH, —C(O), —N═C(O)—C$_{1-3}$alkyl, F, CN, —CH—F$_2$, —CF$_3$, —(CH$_2$)$_n$—O—(CH$_2$)$_m$—CH$_3$, and —C$_{3-7}$cycloalkyl;

or, R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

And wherein each of the tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —$C_{1-3}$alkyl, $C_{3-6}$spirocycloalkyl, halo, CN, —O—$C_{1-3}$alkyl, —$CH_2$—O—$CH_3$, and OH;

And wherein the piperidinyl is further optionally substituted independently by pyrazolyl, —$CH_2$pyrazolyl, or oxadiazolyl, and wherein each of the pyrazolyl, —$CH_2$pyrazolyl, or oxadiazolyl is further optionally substituted independently by —$C_{1-3}$alkyl, or, when A is piperidinyl, it is optionally substituted by —$SO_2R$, wherein R is —$C_{1-3}$ alkyl, phenyl or —$C_{3-7}$cycloalkyl;

And wherein the oxazepane is further optionally substituted independently by 1 or 2 of —$C_{1-3}$alkyl or —$C_{3-7}$cycloalkyl;

And wherein the morpholinyl is further optionally substituted by a phenyl which itself is optionally substituted independently by —$C_{1-3}$alkyl or —O—$C_{1-3}$alkyl;

And wherein the pyrrolidinyl is further optionally substituted by a triazolyl group which itself is optionally substituted by —$C_{1-3}$alkyl;

And wherein the imidazolyl, triazolyl, pyrazolyl, and tetrazolyl groups are further optionally substituted independently by —$CH_2$—$C_{4-7}$cycloalkyl, —$CH_2$—$C_{5-7}$heterocycloalkyl, —$CH_2$-azabicycloheptanyl, —$CH_2$-oxepane, or —$CH_2$-azabicyclohexanyl, all of which, including the —$CH_2$—, is optionally further substituted independently by 1 or 2 of —$C_{1-3}$alkyl or F;

X is independently CH or N;

m is 1, 2 or 3; and n is 1, 2 or 3;

or a pharmaceutically acceptable salt thereof.

In a further embodiment, the compound of Formula (I) is substituted as follows:

B is benzotriazolyl or —$(CH_2)_2$ triazolyl wherein each of benzotriazolyl or —$(CH_2)_2$ triazolyl is unsubstituted or substituted by 1, 2, or 3 substituents independently selected from —$C_{1-3}$alkyl and halo;

D is —C(O)—$NR_4R_5$;

$R_1$ is hydrogen;

$R_2$ is methyl or halo;

$R_3$ is hydrogen, ethyl or methyl;

$R_4$ is hydrogen;

$R_5$ is —$C_{1-5}$alkyl, —$C_{3-7}$ cycloalkyl, —$C_{4-8}$heterocycloalkyl, —$C_{1-5}$ alkoxy, —$C_{1-3}$alkyl-O—$C_{1-3}$alkyl, —$C_{1-3}$alkyl-NH—$C_{1-3}$ alkyl, —$C_{1-3}$alkyl-C(O)$NR_3R_4$, or —$C_{5-8}$ heteroaryl, wherein each of —$C_{1-5}$alkyl, —$C_{3-7}$ cycloalkyl, —$C_{4-7}$heterocycloalkyl, —$C_{1-5}$alkoxy, —$C_{1-3}$ alkyl-O—$C_{1-3}$ alkyl, —$C_{1-3}$ alkyl-NH—$C_{1-3}$ alkyl, —$C_{1-3}$alkyl-C(O)$NR_3R_4$, or —$C_{5-7}$ heteroaryl is unsubstituted or substituted by one or two substituents selected from F, CN, —CH—$F_2$, —$CF_3$, —$(CH_2)_n$—O—$(CH_2)_m$—$CH_3$, and —$C_{3-7}$cycloalkyl;

Linker is —$CH_2$—;

A is tetrahydrobenzoxazepinyl, tetrahydro-pyrido-oxazepinyl, piperidinyl, tetrahydrobenzazepinyl, pyrazolyl, imidazolyl, triazolyl, tetrazolyl, or tetrahydrobenzodiazepinyl;

And wherein each of the tetrahydrobenzoxazepinyl, tetrahydro-pyrido-oxazepinyl, piperidinyl, tetrahydrobenzazepinyl, pyrazolyl, imidazolyl, triazolyl, tetrazolyl, or tetrahydrobenzodiazepinyl groups is unsubstituted or substituted by 1, 2, or 3 substituents independently selected from —$C_{1-3}$alkyl, halo, CN, and —$OC_{1-3}$alkyl;

And the piperidinyl is further optionally substituted independently by pyrazolyl or oxadiazolyl and wherein each of the pyrazolyl or oxadiazolyl is unsubstituted or substituted by —$C_{1-3}$alkyl or, when A is piperidinyl, it is optionally substituted by —$SO_2R$, wherein R is —$C_{1-3}$ alkyl, phenyl or —$C_{3-7}$cycloalkyl;

And wherein each of the imidazolyl, triazolyl, pyrazolyl, and tetrazolyl groups is further optionally substituted independently by —$CH_2$—$C_{4-7}$ cycloalkyl, —$CH_2$-oxepane or —$CH_2$—$C_{5-7}$; and X is independently CH or N;

or a pharmaceutically acceptable salt thereof.

In another embodiment, the compound of Formula (I) is substituted as follows:

B is benzotriazolyl or —$(CH_2)_2$-triazolyl wherein each of benzotriazolyl or —$(CH_2)_2$-triazolyl is unsubstituted or substituted by 1, 2, or 3 substituents independently selected from —$C_{1-3}$alkyl and halo;

D is —C(O)—$NR_4R_5$, —$NR_4$—C(O)—$R_5$, —$NR_3$—C(O)—$NR_4R_5$; —$NR_4$—C(O)—O—$R_5$;

$R_1$ is independently selected from hydrogen, —$C_{1-3}$alkyl, F, —$C_{3-6}$spirocycloalkyl, oxetane, or the two $R_1$ groups together with the carbon to which they are attached form a cyclopropyl group;

$R_2$ is hydrogen, methyl, —$CF_3$, or halo;

$R_3$ is hydrogen or —$C_{1-5}$alkyl;

$R_4$ is hydrogen or —$C_{1-5}$alkyl;

$R_5$ is hydrogen, —$C_{1-5}$alkyl, —$C_{3-7}$cycloalkyl, —$C_{4-8}$heterocycloalkyl, —$C_{1-5}$alkoxy, —$C_{1-3}$ alkyl-O—$C_{1-3}$alkyl, —$C_{1-3}$alkyl-NH—$C_{1-3}$alkyl, —$C_{1-3}$alkyl-NH—C(O)$R_3$, —$C_{1-3}$alkyl-$SO_2C_{1-3}$alkyl, —$C_{1-3}$alkyl-$C_{1-8}$heterocycloalkyl, —$C_{1-3}$alkyl-C(O)$NR_3R_4$, aryl, —$C_{1-5}$alkylheteroaryl, or heteroaryl, wherein each of —$C_{1-5}$alkyl, —$C_{3-7}$cycloalkyl, —$C_{4-7}$heterocycloalkyl, —$C_{1-5}$alkoxy, —$C_{1-3}$alkyl-O—$C_{1-3}$alkyl, —$C_{1-3}$alkyl-NH—$C_{1-3}$ alkyl, —$C_{1-3}$ alkyl-C(O)$NR_3R_4$, aryl, —$C_{1-5}$alkylheteroaryl, or heteroaryl is unsubstituted or substituted by one or two substituents independently selected from —$C_{1-3}$alkyl, —$C_{1-3}$alkylaryl, —$C_{1-3}$alkylheteroaryl, aryl, —$C_{1-3}$alkylC(O)$R_3$, —$C_{1-3}$alkylC(O)OH, —$C_{1-3}$alkylNC(O)$OR_4$, —$C_{1-3}$ alkylOSi$(R_3)_3$, —$C_{1-3}$ alkylOH, —$C_{1-3}$ alkyl$NH_2$, —$SCH_3$, —$OCH_3$, —$C_{4-8}$heterocycloalkyl (optionally substituted with $R_3$), —NH—CH—$(CH_2)_n(OH)_2$, —O—$CH_2$—CH—$(NH_2)$—$CH_2$—OH, —$SO_2R_3$, —$SO_2NR_3R_4$, —OH, —$C_{1-3}$alkoxy, oxo, —$CO_2H$, —C(O)$NR_3R_4$, —C(O)$OR_3$, —N—C(O)—$C_{1-3}$alkyl, F, Cl, —CN, —CH—$F_2$, —$CF_3$, —$(CH_2)_n$—O—$(CH_2)$, —$CH_3$, —O$(CH_2)_n$—O—$(CH_2)_m$—O$(CH_2)_n$—OH, —O$(CH_2)_n$C(O)$OR_3$, —O$(CH_2)_n OR_3$, —O$(CH_2)_n$NC(O) $OR_3$, —O$(CH_2)_n NH_2$, —$C_{3-7}$cycloalkyl, and a 5-6-membered heteroaryl ring containing 1, 2 or 3 heteroatoms selected from O, N and S;

or $R_4$ and $R_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$alkyl, —$C_{3-7}$cycloalkyl, —$C_{4-7}$heterocycloalkyl, —$(CH_2)$phenyl, halogen, —$NR_3R_4$, —$CHF_2$, —$CF_3$, and —$(CH_2)_n$—O—$(CH_2)_m$—$CH_3$;

Linker is —CH₂—, —CH₂—N(-cyclopropyl)-CH₂—, —CH₂—N(CH₃)—CH₂— or —N—(CH₃)—CH₂—;
A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;
and wherein each of the tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —$C_{1-3}$ alkyl, —$C_{3-6}$spirocycloalkyl, halo, —CN, —O—$C_{1-3}$alkyl, —$CF_3$, —$CH_2$—O—$CH_3$, and —OH;
and wherein the piperidinyl is further unsubstituted or substituted independently by pyrazolyl, —$CH_2$pyrazolyl, or oxadiazolyl, and wherein each of the pyrazolyl, —$CH_2$pyrazolyl, or oxadiazolyl is further unsubstituted or substituted independently by —$C_{1-3}$alkyl, or, when A is piperidinyl, it is unsubstituted or substituted by —$SO_2R$, wherein R is —$C_{1-3}$alkyl, phenyl or —$C_{3-7}$cycloalkyl;
and wherein the oxazepane is further unsubstituted or substituted independently by 1 or 2 of —$C_{1-3}$alkyl or —$C_{3-7}$cycloalkyl;
and wherein the morpholinyl is further unsubstituted or substituted by a phenyl which itself is optionally substituted independently by —$C_{1-3}$alkyl or —O—$C_{1-3}$alkyl;
and wherein the pyrrolidinyl is further unsubstituted or substituted by a triazolyl group which itself is optionally substituted by —$C_{1-3}$alkyl;
and wherein each of the imidazolyl, triazolyl, pyrazolyl, and tetrazolyl groups are further unsubstituted or substituted independently by —$CH_2$—$C_{4-7}$cycloalkyl, —$CH_2$—$C_{5-7}$heterocycloalkyl, —$CH_2$-azabicycloheptanyl, —$CH_2$-oxepane, or —$CH_2$-azabicyclohexanyl, all of which, including the —$CH_2$—, is optionally further substituted independently by 1 or 2 of —$C_{1-3}$alkyl or F;
or A is

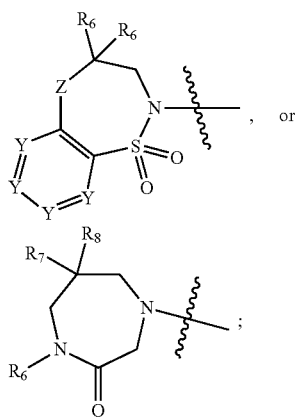

Y is independently selected from N or CH;
Z is O, $CH_2$, $NR_5$, S, S(O) or $S(O)_2$;
$R_6$ is independently hydrogen or —$C_{1-4}$alkyl;
$R_7$ is hydrogen, —$C_{1-5}$alkyl or —$(CH_2)_n$—$C_{3-5}$cycloalkyl;

$R_8$ is hydrogen or —$C_{1-4}$alkyl;
or $R_7$ and $R_8$, together with the carbon to which they are attached form a $C_3$-$C_5$-membered cycloalkyl ring;
and, wherein when A is

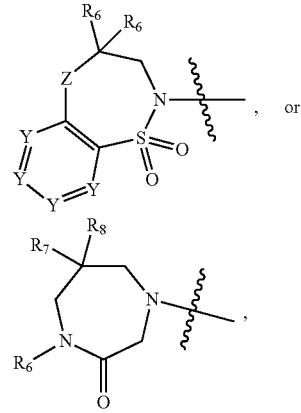

it is unsubstituted or substituted with one, two or three substituents independently selected from halo, —$CF_3$, —CN, —OMe, —$C(O)NH_2$, —$OCF_3$, —$C_{1-4}$alkyl$NR_8R_9$;
$R_9$ is —$C_{1-3}$alkyl, aryl, heteroaryl, —$C(O)C_{1-3}$alkyl, —$SO_2C_{1-3}$alkyl, —C(O)aryl, —C(O)heteroaryl, —$SO_2$aryl, —$SO_2$heteroaryl, —$C_{3-7}$cycloalkyl, —$C_{1-3}$alkyl$C_{3-7}$cycloalkyl, —$C_{1-3}$alkyl$C_{3-7}$heterocycloalkyl, —$C_{1-3}$alkylheteroaryl or —$C_{1-3}$alkylaryl, wherein each of —$C_{1-3}$alkyl, aryl, heteroaryl, —$C(O)C_{1-3}$alkyl, —$SO_2$ $C_{1-3}$alkyl, —C(O)aryl, —C(O)heteroaryl, —$SO_2$aryl, —$SO_2$heteroaryl, —$C_{3-7}$cycloalkyl, —$C_{1-3}$ alkyl$C_{3-7}$cycloalkyl, —$C_{1-3}$alkyl$C_{3-7}$heterocycloalkyl, —$C_1$-3alkylheteroaryl or —$C_{1-3}$ alkylaryl is unsubstituted or substituted by 1, 2 or 3 substituents independently selected from halo, —CN, —$CF_3$, —$OCF_3$, —$OCH_3$, —$C_{1-3}$alkyl, —$OC_{1-3}$alkyl, —$OC_{3-7}$cycloalkyl, —$OC_{3-7}$hetercycloalkyl, —O-aryl and —O-heteroaryl;
X is independently CH or N;
m is 1, 2 or 3; and
n is 1, 2 or 3;
or a pharmaceutically acceptable salt thereof.
In another embodiment, the compound of Formula (I) is substituted as follows:
B is benzotriazolyl wherein benzotriazolyl is unsubstituted or substituted by 1, 2, or 3 substituents independently selected from —$C_{1-3}$alkyl and halo;
D is —C(O)—$NR_4R_5$, —$NR_4$—C(O)—$R_5$, —$NR_3$—C(O)—$NR_4R_5$; —$NR_4$—C(O)—O—$R_5$;
$R_1$ is independently selected from hydrogen, —$C_{1-3}$ alkyl, F, —$C_{3-6}$ spirocycloalkyl, oxetane, or the two $R_1$ groups together with the carbon to which they are attached form a cyclopropyl group;
$R_2$ is hydrogen, methyl, —$CF_3$, or halo;
$R_3$ is hydrogen or —$C_{1-5}$alkyl;
$R_4$ is hydrogen or —$C_{1-5}$alkyl;
$R_5$ is hydrogen, —$C_{1-5}$alkyl, —$C_{3-7}$cycloalkyl, —$C_{4-8}$heterocycloalkyl, —$C_{1-5}$alkoxy, —$C_{1-3}$ alkyl-O—$C_{1-3}$alkyl, —$C_{1-3}$alkyl-NH—$C_{1-3}$alkyl, —$C_{1-3}$alkyl-NH—$C(O)R_3$, —$C_{1-3}$alkyl-$SO_2C_{1-3}$alkyl, —$C_{1-3}$alkyl-$C_{1-8}$heterocycloalkyl, —$C_{1-3}$alkyl-$C(O)NR_3R_4$, aryl, —$C_{1-5}$alkylheteroaryl, or heteroaryl, wherein each of —$C_{1-5}$alkyl, —$C_{3-7}$ cycloalkyl, —$C_{4-7}$heterocycloalkyl, —$C_{1-5}$alkoxy, —$C_{1-3}$alkyl-O—$C_{1-3}$alkyl, —$C_{1-3}$alkyl-NH—$C_{1-3}$alkyl, —C$_{1-3}$alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$alkylaryl, —C$_{1-3}$alkylheteroaryl, aryl, —C$_{1-3}$alkylC(O)R$_3$, —C$_{1-3}$alkylC(O)OH, —C$_{1-3}$alkylNC(O)OR$_4$, —C$_{1-3}$alkylOSi(R$_3$)$_3$, —C$_{1-3}$alkylOH, —C$_{1-3}$alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —N—C(O)—C$_{1-3}$alkyl, F, Cl, —CN, —CH—F$_2$, —CF$_3$, —(CH$_2$)$_n$—O—(CH$_2$), —CH$_3$, —O(CH$_2$)$_n$—O—(CH$_2$)$_m$—O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S;

or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—, —CH$_2$—N(-cyclopropyl)-CH$_2$—, —CH$_2$—N(CH$_3$)—CH$_2$— or —N—(CH$_3$)—CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

and wherein each of the tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CF$_3$, —CH$_2$—O—CH$_3$, and —OH;

and wherein the piperidinyl is further unsubstituted or substituted independently by pyrazolyl, —CH$_2$pyrazolyl, or oxadiazolyl, and wherein each of the pyrazolyl, —CH$_2$pyrazolyl, or oxadiazolyl is further unsubstituted or substituted independently by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;

and wherein the oxazepane is further unsubstituted or substituted independently by 1 or 2 of —C$_{1-3}$alkyl or —C$_{3-7}$cycloalkyl;

and wherein the morpholinyl is further unsubstituted or substituted by a phenyl which itself is optionally substituted independently by —C$_{1-3}$alkyl or —O—C$_{1-3}$alkyl;

and wherein the pyrrolidinyl is further unsubstituted or substituted by a triazolyl group which itself is optionally substituted by —C$_{1-3}$alkyl;

and wherein each of the imidazolyl, triazolyl, pyrazolyl, and tetrazolyl groups are further unsubstituted or substituted independently by —CH$_2$—C$_{4-7}$cycloalkyl, —CH$_2$—C$_{5-7}$heterocycloalkyl, —CH$_2$-azabicycloheptanyl, —CH$_2$-oxepane, or —CH$_2$-azabicyclohexanyl, all of which, including the —CH$_2$—, is optionally further substituted independently by 1 or 2 of —C$_{1-3}$alkyl or F;

or A is

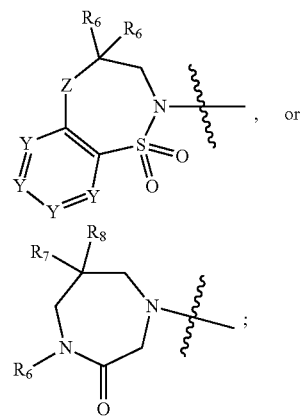

Y is independently selected from N or CH;
Z is O, CH$_2$, NR$_5$, S, S(O) or S(O)$_2$;
R$_6$ is independently hydrogen or —C$_{1-4}$alkyl;
R$_7$ is hydrogen, —C$_{1-5}$alkyl or —(CH$_2$), —C$_{3-5}$cycloalkyl;
R$_8$ is hydrogen or —C$_{1-4}$alkyl;
or R$_7$ and R$_8$, together with the carbon to which they are attached form a C$_3$-C$_5$-membered cycloalkyl ring;
and, wherein when A is

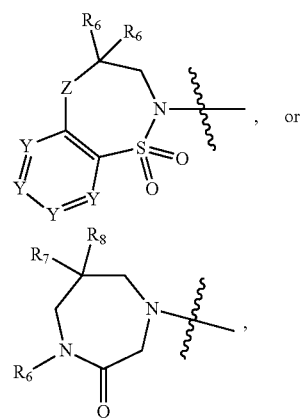

it is unsubstituted or substituted with one, two or three substituents independently selected from halo, —CF$_3$, —CN, —OMe, —C(O)NH$_2$, —OCF$_3$, —C$_1$-$_4$alkylNR$_8$R$_9$;

R$_9$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkylheteroaryl or —C$_{1-3}$alkylaryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$ cycloalkyl, —C$_{1-3}$alkylC$_{3-7}$heterocycloalkyl, —C$_1$-3alkylheteroaryl or —C$_{1-3}$ alkylaryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$ hetercycloalkyl, —O-aryl and —O-heteroaryl;

X is independently CH or N;

m is 1, 2 or 3; and n is 1, 2 or 3;

or a pharmaceutically acceptable salt thereof.

In another embodiment, the compound of Formula (I) is substituted as follows:

B is benzotriazolyl wherein benzotriazolyl is unsubstituted or substituted by 1, 2, or 3 substituents independently selected from —C$_{1-3}$alkyl and halo;

D is —C(O)—NR$_4$R$_5$;

R$_1$ is independently selected from hydrogen or methyl;

R$_2$ is methyl or halo;

R$_3$ is hydrogen, methyl or ethyl;

R$_4$ is hydrogen;

R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$ alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{1-8}$heterocloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$ cycloalkyl, —C$_{4-7}$ heterocycloalkyl, —C$_{1-5}$ alkoxy, —C$_{1-3}$alkyl-O—C$_{1-3}$alkyl, —C$_1$-3alkyl-NH—C$_{1-3}$ alkyl, —C$_{1-3}$ alkyl-C(O)NR$_3$R$_4$, aryl, —C$_{1-5}$alkyl-heteroaryl, or heteroaryl is unsubstituted or substituted by one or two substituents independently selected from —C$_{1-3}$alkyl, —C$_{1-3}$alkylaryl, —C$_{1-3}$alkylheteroaryl, aryl, —C$_{1-3}$alkylC(O)R$_3$, —C$_{1-3}$alkylC(O)OH, —C$_{1-3}$alkylNC(O)OR$_4$, —C$_{1-3}$ alkylOSi(R$_3$)$_3$, —C$_{1-3}$ alkylOH, —C$_{1-3}$ alkylNH$_2$, —SCH$_3$, —OCH$_3$, —C$_{4-8}$heterocloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —N—C(O)—C$_{1-3}$alkyl, F, Cl, —CN, —CH—F$_2$, —CF$_3$, —(CH$_2$)$_n$—O—(CH$_2$)$_m$—CH$_3$, —O(CH$_2$)$_n$—O—(CH$_2$)$_m$—O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S;

or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—;

A is tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl;

and wherein each of the tetrahydrobenzoxazepinyl, tetrahydro-pyrido-oxazepinyl, piperidinyl, tetrahydrobenzazepinyl, phenyl, pyrazolyl, imidazolyl, triazolyl, tetrazolyl, tetrahydropyrrolopyrazinyl, imidazopyridinyl, pyridyl, benzimidazolyl, tetrahydrobenzodiazepinyl, piperidopyrimidinyl, dioxidotetrahydrothiophenyl, tetrahydroimidazodiazepinyl, pyrrolidinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CF$_3$, —CH$_2$—O—CH$_3$, and —OH;

and wherein the piperidinyl is further unsubstituted or substituted independently by pyrazolyl, —CH$_2$pyrazolyl, or oxadiazolyl, and wherein each of the pyrazolyl, —CH$_2$pyrazolyl, or oxadiazolyl is further unsubstituted or substituted independently by —C$_{1-3}$alkyl, or, when A is piperidinyl, it is unsubstituted or substituted by —SO$_2$R, wherein R is —C$_{1-3}$alkyl, phenyl or —C$_{3-7}$cycloalkyl;

and wherein the oxazepane is further unsubstituted or substituted independently by 1 or 2 of —C$_{1-3}$alkyl or —C$_{3-7}$ cycloalkyl;

and wherein the morpholinyl is further unsubstituted or substituted by a phenyl which itself is optionally substituted independently by —C$_{1-3}$alkyl or —O—C$_{1-3}$alkyl;

and wherein the pyrrolidinyl is further unsubstituted or substituted by a triazolyl group which itself is optionally substituted by —C$_{1-3}$alkyl;

and wherein each of the imidazolyl, triazolyl, pyrazolyl, and tetrazolyl groups are further unsubstituted or substituted independently by —CH$_2$—C$_{4-7}$cycloalkyl, —CH$_2$—C$_{5-7}$ heterocycloalkyl, —CH$_2$-azabicycloheptanyl, —CH$_2$-oxepane, or —CH$_2$-azabicyclohexanyl, all of which, including the —CH$_2$—, is optionally further substituted independently by 1 or 2 of —C$_{1-3}$ alkyl or F;

or, A is

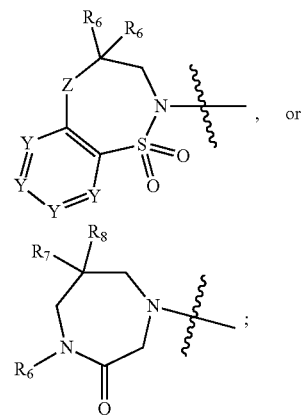

Y is independently selected from N or CH;

Z is O, CH$_2$, NR$_5$, S, S(O) or S(O)$_2$;

R$_6$ is hydrogen or —C$_{1-4}$alkyl;
R$_7$ is hydrogen, —C$_{1-5}$ alkyl or —(CH$_2$)$_m$—C$_{3-5}$ cycloalkyl;
R$_8$ is hydrogen or —C$_{1-4}$alkyl;
or R$_7$ and R$_8$, together with the carbon to which they are attached form a C$_3$-C$_5$-membered cycloalkyl ring;
and, wherein when A is

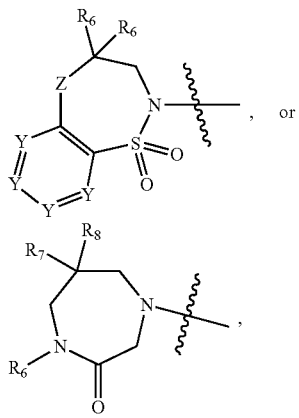, or it is unsubstituted or substituted with one, two or three substituents independently selected from halo, —CF$_3$, —C$_{1-4}$alkyl, —CN, —OMe, —C(O)NH$_2$, —OCF$_3$, —C$_{1-4}$alkylNR$_8$R$_9$;
R$_9$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, wherein each of —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$ alkylC$_{3-7}$cycloalkyl, —C$_{1-3}$alkylC$_{3-7}$heterocycloalkyl is unsubstituted or substituted by 1, 2 or 3 substituents independently selected from halo, —CF$_3$, —OCF$_3$ and —OCH$_3$;
X is independently CH or N;
m is 1, 2 or 3; and
n is 1, 2 or 3;
or a pharmaceutically acceptable salt thereof.

In another embodiment, the compound of Formula (I) is substituted as follows:
B is benzotriazolyl wherein benzotriazolyl is unsubstituted or substituted by 1, 2, or 3 substituents independently selected from —C$_{1-3}$alkyl and halo;
D is —C(O)—NR$_4$R$_5$, —NR$_4$—C(O)—R$_5$, —NR$_3$—C(O)—NR$_4$R$_5$; —NR$_4$—C(O)—O—R$_5$;
Each of R$_1$ is methyl;
R$_2$ is methyl or halo;
R$_3$ is hydrogen or —C$_{1-5}$alkyl;
R$_4$ is hydrogen;
R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$ alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{1-8}$heterocycloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$ cycloalkyl, —C$_{4-7}$heterocycloalkyl, —C$_{1-5}$alkoxy, —C$_{1-3}$alkyl-O—C$_{1-3}$alkyl, —C$_{1-3}$alkyl-NH—C$_{1-3}$ alkyl, —C$_{1-3}$ alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$alkylaryl, —C$_{1-3}$alkylheteroaryl, aryl, —C$_{1-3}$alkylC(O)R$_3$, —C$_{1-3}$alkylC(O)OH, —C$_{1-3}$alkylNC(O)OR$_4$, —C$_{1-3}$ alkylOSi(R$_3$)$_3$, —C$_{1-3}$ alkylOH, —C$_{1-3}$ alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$ alkoxy, oxo, —CO$_2$H, —C(O)NR$_3$R$_4$, —C(O)OR$_3$, —N—C(O)—C$_{1-3}$alkyl, F, Cl, —CN, —CH—F$_2$, —CF$_3$, —(CH$_2$)$_n$—O—(CH$_2$)$_m$—CH$_3$, —O(CH$_2$)$_n$—O—(CH$_2$)$_m$, —O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S:
or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;
Linker is —CH$_2$—;
A is

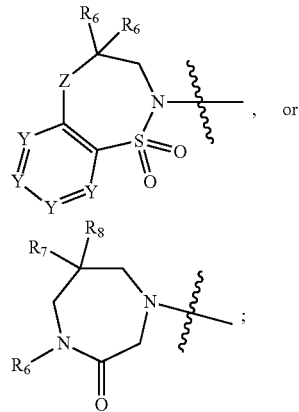;

Y is independently selected from N or CH;
Z is O, CH$_2$, NR$_5$, S, S(O) or S(O)$_2$;
R$_6$ is independently hydrogen or —C$_{1-4}$alkyl;
R$_7$ is hydrogen, —C$_{1-5}$alkyl or —(CH$_2$), —C$_{3-5}$cycloalkyl;
R$_8$ is hydrogen or —C$_{3-5}$alkyl;
or R$_7$ and R$_8$, together with the carbon to which they are attached form a C$_3$-C$_5$-membered cycloalkyl ring;

and, wherein when A is

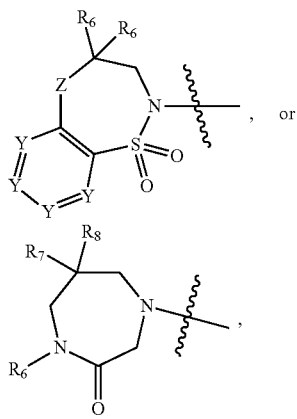

it is unsubstituted or substituted with one, two or three substituents independently selected from halo, —CF$_3$, —CN, —OMe, —C(O)NH$_2$, —OCF$_3$, —C$_{1-4}$alkylNR$_8$R$_9$;

R$_9$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$ alkylC$_{3-7}$cycloalkyl, —C$_{1-3}$ alkylC$_{3-7}$heterocycloalkyl, wherein each of —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$ alkylC$_{3-7}$cycloalkyl, —C$_{1-3}$alkylC$_{3-7}$heterocycloalkyl is unsubstituted or substituted by 1, 2 or 3 substituents independently selected from halo, —CF$_3$, —OCF$_3$ and —OCH$_3$;

X is independently CH or N;

m is 1, 2 or 3; and n is 1, 2 or 3;

or a pharmaceutically acceptable salt thereof.

In another embodiment, the compound of Formula (I) is substituted as follows:

B is benzotriazolyl wherein benzotriazolyl is unsubstituted or substituted by 1, 2, or 3 substituents independently selected from —C$_{1-3}$ alkyl and halo;

D is —C(O)—NR$_4$R$_5$;

Each of R$_1$ is methyl;

R$_2$ is methyl or halo;

R$_3$ is hydrogen or —C$_{1-5}$alkyl;

R$_4$ is hydrogen;

R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$ alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{1-8}$heterocycloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$ cycloalkyl, —C$_{4-7}$ heterocycloalkyl, —C$_{1-5}$ alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$ alkylaryl, —C$_{1-3}$ alkylheteroaryl, aryl, —C$_{1-3}$ alkylC(O)R$_3$, —C$_{1-3}$ alkylC(O)OH, —C$_{1-3}$ alkylNC(O)OR$_4$, —C$_{1-3}$ alkylOSi(R$_3$)$_3$, —C$_{1-3}$ alkylOH, —C$_{1-3}$ alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —N—C(O)—C$_{1-3}$ alkyl, F, Cl, —CN, —CH—F$_2$, —CF$_3$, —(CH$_2$)$_n$—O—(CH$_2$)$_m$—CH$_3$, —O(CH$_2$)$_n$—O—(CH$_2$)$_m$—O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$ cycloalkyl, and a 5-6-membered heteroaryl ring containing 1, 2 or 3 heteroatoms selected from O, N and S;

or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—;

A is

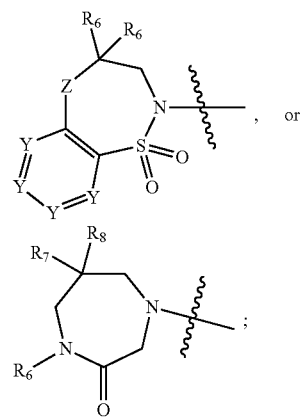

Y is independently selected from N or CH;

Z is O, CH$_2$, NR$_5$, S, S(O) or S(O)$_2$;

R$_6$ is independently hydrogen or —C$_{1-4}$alkyl;

R$_7$ is hydrogen, —C$_{1-5}$alkyl or —(CH$_2$), —C$_{3-5}$cycloalkyl;

R$_8$ is hydrogen or —C$_{1-4}$alkyl;

or R$_7$ and R$_8$, together with the carbon to which they are attached form a C$_3$-C$_5$-membered cycloalkyl ring;

and, wherein when A is

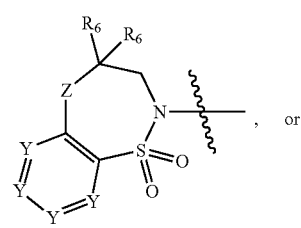

-continued

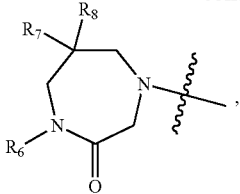

it is unsubstituted or substituted with one, two or three substituents independently selected from halo, —CF$_3$, —CN, —OMe, —C(O)NH$_2$, —OCF$_3$, —C$_{1-4}$alkylNR$_8$R$_9$;

R$_5$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, wherein each of —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$ alkylC$_{3-7}$cycloalkyl, —C$_{1-3}$alkylC$_{3-7}$heterocycloalkyl is unsubstituted or substituted by 1, 2 or 3 substituents independently selected from halo, —CF$_3$, —OCF$_3$ and —OCH$_3$;

X is independently CH or N;

m is 1, 2 or 3; and n is 1, 2 or 3;

or a pharmaceutically acceptable salt thereof.

In another embodiment, the compound of Formula (I) is substituted as follows:

B is benzotriazolyl wherein benzotriazolyl is unsubstituted or substituted by 1, 2, or 3 substituents independently selected from —C$_{1-3}$alkyl and halo;

D is —C(O)—NR$_4$R$_5$;

R$_1$ is independently selected from hydrogen or methyl;

R$_2$ is methyl or halo;

R$_3$ is hydrogen or —C$_{1-5}$alkyl;

R$_4$ is hydrogen;

R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$ alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{1-8}$heterocycloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$ cycloalkyl, —C$_{4-7}$ heterocycloalkyl, —C$_{1-5}$ alkoxy, —C$_{1-3}$alkyl-O—C$_{1-3}$alkyl, —C$_{1-3}$alkyl-NH—C$_{1-3}$ alkyl, —C$_{1-3}$ alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$alkylaryl, —C$_{1-3}$alkylheteroaryl, aryl, —C$_{1-3}$alkylC(O)R$_3$, —C$_{1-3}$alkylC(O)OH, —C$_{1-3}$alkylNC(O)OR$_4$, —C$_{1-3}$ alkylOSi(R$_3$)$_3$, —C$_{1-3}$ alkylOH, —C$_{1-3}$ alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —N—C(O)—C$_{1-3}$alkyl, F, Cl, —CN, —CH—F$_2$, —CF$_3$, —(CH$_2$)$_n$O—(CH$_2$)$_m$—CH$_3$, —O(CH$_2$)$_n$—O—(CH$_2$)$_m$—O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S.

Linker is —CH$_2$—;

A is

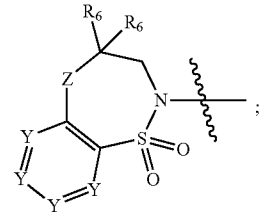

Y is independently selected from N or CH;

Z is O or CH$_2$;

R$_6$ is independently hydrogen or —C$_{1-4}$alkyl;

and, wherein A is unsubstituted or substituted with one, two or three substituents independently selected from halo, —CF$_3$, —CN, —OMe, —C(O)NH$_2$, —OCF$_3$, —C$_{1-3}$alkylNR$_8$R$_9$;

R$_9$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, wherein each of —C$_{1-3}$ alkyl, —C(O)C$_{1-3}$ alkyl, —SO$_2$C$_{1-3}$ alkyl, —C(O)aryl, —C(O)heteroaryl, —SO$_2$aryl, —SO$_2$heteroaryl, —C$_{3-7}$cycloalkyl, —C$_{1-3}$ alkylC$_{3-7}$cycloalkyl, —C$_{1-3}$alkylC$_{3-7}$heterocycloalkyl is unsubstituted or substituted by 1, 2 or 3 substituents independently selected from halo, —CF$_3$, —OCF$_3$ and —OCH$_3$;

X is CH;

m is 1, 2 or 3; and n is 1, 2 or 3;

or a pharmaceutically acceptable salt thereof.

In another embodiment, the compound of Formula (I) is substituted as follows:

B is benzotriazolyl wherein benzotriazolyl is unsubstituted or substituted by 1, 2, or 3 substituents independently selected from methyl and ethyl;

D is —C(O)—NR$_4$R$_5$;

R$_1$ is independently hydrogen or methyl;

R$_2$ is methyl;

R$_3$ is hydrogen or methyl;

R$_4$ is hydrogen;

R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$ alkyl-O—C$_{1-3}$alkyl, —C$_{1-3}$alkyl-NH—C$_{1-3}$alkyl, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_3$R$_4$, or heteroaryl, wherein each of —C$_{1-5}$ alkyl, —C$_{3-7}$ cycloalkyl, —C$_{4-7}$ heterocycloalkyl, —C$_{1-5}$ alkoxy, —C$_{1-3}$ alkyl-O—C$_{1-3}$ alkyl, —C$_{1-3}$ alkyl-NH—C$_{1-3}$ alkyl, —C$_{1-3}$alkyl-C(O)NR$_3$R$_4$, or heteroaryl is unsubstituted or substituted by one or two substituents selected from —OH, —C(O), —N—C(O)—C$_{1-3}$alkyl, F, CN, —CH—F$_2$, —CF$_3$, —(CH$_2$)$_n$—O—(CH$_2$)$_m$—CH$_3$, and —C$_{3-7}$cycloalkyl;

Linker is —CH$_2$—;

or A is

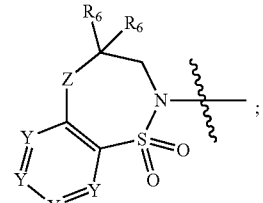

Y is independently selected from N or CH;
Z is O or CH₂;
R₆ is independently selected from hydrogen, methyl or ethyl;
and, wherein A is

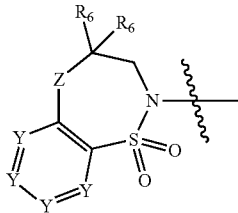

is unsubstituted or substituted with one, two or three substituents independently selected from halo, —CF₃, —CN, —OMe, —C(O)NH₂, or —OCF₃;
X is CH;
m is 1 or 2; and
n is 1 or 2;
or a pharmaceutically acceptable salt thereof.

In another embodiment, the compound of Formula (I) is substituted as follows:

B is benzotriazolyl wherein benzotriazolyl is unsubstituted or substituted by 1, 2, or 3 substituents independently selected from methyl and ethyl;
D is —C(O)—NR₄R₅, —NR₄—C(O)—R₅;
R₁ is independently hydrogen or methyl;
R₂ is methyl;
R₃ is hydrogen or methyl;
R₄ is hydrogen;
R₅ is hydrogen, —C₁₋₅ alkyl, —C₃₋₇ cycloalkyl, —C₄₋₈ heterocycloalkyl, —C₁₋₅ alkoxy, —C₁₋₃ alkyl-O—C₁₋₃alkyl, —C₁₋₃alkyl-NH—C₁₋₃alkyl, —C₁₋₃alkyl-SO₂C₁₋₃alkyl, —C₁₋₃alkyl-C₄₋₈heterocycloalkyl, —C₁₋₃alkyl-C(O)NR₃R₄, or heteroaryl, wherein each of —C₁₋₅ alkyl, —C₃₋₇ cycloalkyl, —C₄₋₇ heterocycloalkyl, —C₁₋₅ alkoxy, —C₁₋₃ alkyl-O—C₁₋₃ alkyl, —C₁₋₃ alkyl-NH—C₁₋₃ alkyl, —C₁₋₃alkyl-C(O)NR₃R₄, or heteroaryl is unsubstituted or substituted by one or two substituents selected from —OH, —C(O), —N—C(O)—C₁₋₃alkyl, F, CN, —CH—F₂, —CF₃, —(CH₂)ₙ—O—(CH₂)ₘ—CH₃, and —C₃₋₇cycloalkyl;
Linker is —CH₂—;
or A is

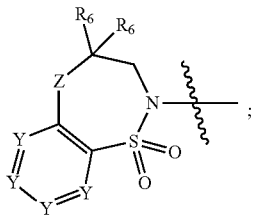

Y is independently selected from N or CH;
Z is O or CH₂;
R₆ is independently selected from hydrogen, methyl or ethyl;

and, wherein A is

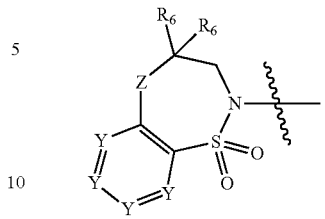

is unsubstituted or substituted with one, two or three substituents independently selected from halo, —CF₃, —CN, —OMe, —C(O)NH₂, or —OCF₃;
X is CH;
m is 1 or 2; and
n is 1 or 2;
or a pharmaceutically acceptable salt thereof.

In another embodiment, the compound of Formula (I) is substituted as follows:

B is benzotriazolyl, phenyl, triazolopyridinyl, —O—(CH₂)-triazolyl, or —(CH₂)₂-triazolyl wherein each of benzotriazolyl, phenyl, triazolopyridinyl, —O—(CH₂)₂triazolyl, or —(CH₂)₂ triazolyl is unsubstituted or substituted by 1, 2, or 3 substituents independently selected from —C₁₋₃ alkyl, —O—C₁₋₃alkyl, —CN, —(CH₂)₂—O—(CH₂)₂—OR₃ and halo;
D is —C(O)—NR₄R₅;
R₁ is independently selected from hydrogen or methyl;
R₂ is methyl or halo;
R₃ is hydrogen or —C₁₋₅alkyl;
R₄ is hydrogen;
R₅ is hydrogen, —C₁₋₅alkyl, —C₃₋₇cycloalkyl, —C₄₋₈heterocycloalkyl, —C₁₋₅alkoxy, —C₁₋₃ alkyl-O—C₁₋₃alkyl, —C₁₋₃alkyl-NH—C(O)R₃, —C₁₋₃alkyl-NH—C(O)R₃, —C₁₋₃alkyl-SO₂C₁₋₃alkyl, —C₁₋₃alkyl-C₄₋₈ heterocycloalkyl, —C₁₋₃alkyl-C(O)NR₃R₄, aryl, —C₁₋₅alkylheteroaryl, or heteroaryl, wherein each of —C₁₋₅alkyl, —C₃₋₇ cycloalkyl, —C₄₋₇heterocycloalkyl, —C₁₋₅alkoxy, —C₁₋₃alkyl-O—C₁₋₃alkyl, —C₁₋₃alkyl-NH—C₁₋₃ alkyl, —C₁₋₃ alkyl-C(O)NR₃R₄, aryl, —C₁₋₅alkylheteroaryl, or heteroaryl is unsubstituted or substituted by one or two substituents independently selected from —C₁₋₃alkyl, —C₁₋₃alkylaryl, —C₁₋₃alkylheteroaryl, aryl, —C₁₋₃alkylC(O)R₃, —C₁₋₃alkylC(O)OH, —C₁₋₃alkylNC(O)OR₄, —C₁₋₃alkylOSi(R₃)₃, —C₁₋₃alkylOH, —C₁₋₃alkylNH₂, —SCH₃, —OCH₃, —C₄₋₈heterocycloalkyl (optionally substituted with R₃), —NH—CH—(CH₂)ₙ(OH)₂, —O—CH₂—CH—(NH₂)—CH₂—OH, —SO₂R₃, —SO₂NR₃R₄, —OH, —C₁₋₃alkoxy, oxo, —CO₂H, —C(O)NR₃R₄, —C(O)OR₃, —N—C(O)—C₁₋₃alkyl, F, Cl, —CN, —CH—F₂, —CF₃, —(CH₂)ₙ—O—(CH₂), —CH₃, —O(CH₂)ₙ—O—(CH₂)ₘ—O(CH₂)ₙ—OH, —O(CH₂)ₙC(O)OR₃, —O(CH₂)ₙOR₃, —O(CH₂)ₙNC(O)OR₃, —O(CH₂)ₙNH₂, —C₃₋₇cycloalkyl, and a 5-6-membered heteroaryl ring containing 1, 2 or 3 heteroatoms selected from O, N and S;
Linker is —CH₂—;

or A is

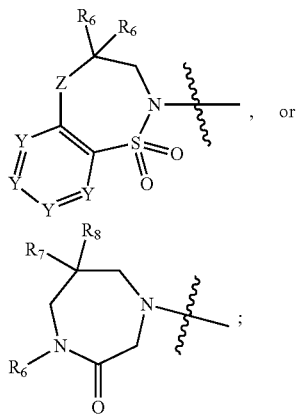

, or

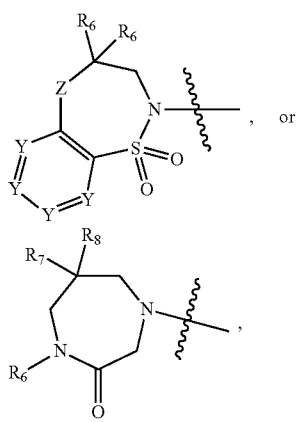

;

Y is independently selected from N or CH;
Z is O, CH$_2$, NR$_5$, S, S(O) or S(O)$_2$;
R$_6$ is independently hydrogen or —C$_{1-4}$alkyl;
R$_7$ is hydrogen, —C$_{1-5}$alkyl or —(CH$_2$), —C$_{3-5}$cycloalkyl;
R$_8$ is hydrogen or —C$_{1-4}$alkyl;
or R$_7$ and R$_8$, together with the carbon to which they are attached form a C$_3$-C$_5$-membered cycloalkyl ring;
and, wherein when A is

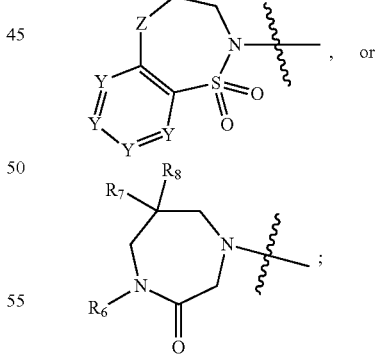

, or it is unsubstituted or substituted with one, two or three substituents independently selected from halo, —CF$_3$, —CN, —OMe, —C(O)NH$_2$, —OCF$_3$, —C$_{1-4}$alkylNR$_8$R$_9$;
R$_9$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, wherein each of —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, is unsubstituted or substituted by 1, 2 or 3 substituents independently selected from halo, —CF$_3$, —OCF$_3$ and —OCH$_3$;
X is independently CH or N;
m is 1, 2 or 3; and
n is 1, 2 or 3;
or a pharmaceutically acceptable salt thereof.
In another embodiment, the compound of Formula (I) is substituted as follows:

B is benzotriazolyl wherein benzotriazolyl is unsubstituted or substituted by 1, 2, or 3 substituents independently selected from methyl and ethyl;
D is —C(O)—NR$_4$R$_5$;
R$_1$ is hydrogen;
R$_2$ is methyl;
R$_4$ is hydrogen;
R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$ alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{1-8}$heterocycloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$ cycloalkyl, —C$_{4-7}$ heterocycloalkyl, —C$_{1-5}$ alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$ alkylaryl, —C$_{1-3}$ alkylheteroaryl, aryl, —C$_{1-3}$ alkylC(O)R$_3$, —C$_{1-3}$ alkylC(O)OH, —C$_{1-3}$ alkylNC(O)OR$_4$, —C$_{1-3}$ alkylOSi(R$_3$)$_3$, —C$_{1-3}$ alkylOH, —C$_{1-3}$ alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —N—C(O)—C$_{1-3}$ alkyl, F, Cl, —CN, —CH—F$_2$, —CF$_3$, —(CH$_2$)$_n$—O—(CH$_2$)$_m$—CH$_3$, —O(CH$_2$)$_m$—O—(CH$_2$)$_m$, —O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S;
Linker is —CH$_2$—;
or A is , or

;

Y is independently selected from N or CH;
Z is O, CH$_2$, NR$_5$, S, S(O) or S(O)$_2$;
R$_6$ is hydrogen or —C$_{1-4}$alkyl;
R$_7$ is hydrogen, —C$_{1-5}$alkyl or —(CH$_2$), —C$_{3-5}$cycloalkyl;
R$_8$ is hydrogen or —C$_{1-4}$alkyl;
or R$_7$ and R$_8$, together with the carbon to which they are attached form a C$_3$-C$_5$-membered cycloalkyl ring;

and, wherein when A is

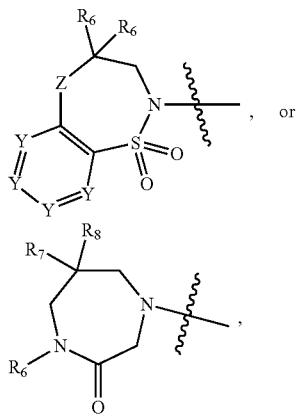, or

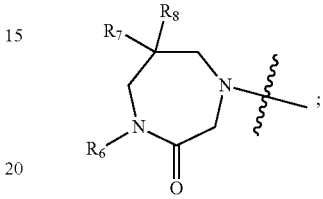

it is unsubstituted or substituted with one, two or three substituents independently selected from halo, —CF$_3$, —CN, —OMe, —C(O)NH$_2$, —OCF$_3$, —C$_{1-4}$alkylNR$_8$R$_9$;

R$_9$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkylheteroaryl or —C$_{1-3}$alkylaryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$ alkylC$_{3-7}$cycloalkyl, —C$_{1-3}$alkylC$_{3-7}$heterocycloalkyl, —C$_{1-3}$alkylheteroaryl or —C$_{1-3}$alkylaryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;

X is independently CH or N;
m is 1, 2 or 3; and
n is 1, 2 or 3;
or a pharmaceutically acceptable salt thereof.

In another embodiment, the compound of Formula (I) is substituted as follows:

B is benzotriazolyl wherein benzotriazolyl is unsubstituted or substituted by 1, 2, or 3 substituents independently selected from methyl and ethyl;
D is —C(O)—NR$_4$R$_5$;
R$_1$ is hydrogen;
R$_2$ is methyl;
R$_4$ is hydrogen;
R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$ alkyl-O—C$_{1-3}$alkyl, —C$_{1-3}$alkyl-NH—C$_{1-5}$alkyl, —C$_{1-3}$ alkyl-NH—C(O)R$_3$, —C$_{1-3}$ alkyl-SO$_2$C$_{1-3}$ alkyl, —C$_{1-3}$alkyl-C$_{4-8}$heterocycloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$cycloalkyl, C$_{4-7}$heterocycloalkyl, —C$_{1-5}$alkoxy, —C$_{1-3}$alkyl-O—C$_{1-3}$alkyl, —C$_{1-3}$alkyl-NH—C$_{1-5}$alkyl, —C$_{1-3}$ alkyl-C(O)NR$_3$R$_4$, aryl, —C$_{1-5}$alkylheteroaryl, or heteroaryl is unsubstituted or substituted by one or two substituents independently selected from —C$_{1-5}$alkyl, —C$_{1-5}$alkylaryl, —C$_{1-5}$alkylheteroaryl, aryl, —C$_{1-3}$alkylC(O)R$_3$, —C$_{1-3}$alkylC(O)OH, —C$_{1-3}$alkylNC(O)R$_4$, —C$_{1-3}$alkylOSi(R$_3$)$_3$, —C$_{1-3}$alkylOH, —C$_{1-3}$alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-5}$alkoxy, oxo, —CO$_2$H, —C(O)NR$_3$R$_4$, —C(O)OR$_3$, —N—C(O)—C$_{1-3}$alkyl, F, Cl, —CN, —CH—F$_2$, —CF$_3$, —(CH$_2$)$_n$—O—(CH$_2$)$_m$—CH$_3$, —O(CH$_2$)$_n$—O—(CH$_2$)$_m$—O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S;
Linker is —CH$_2$—;
or A is

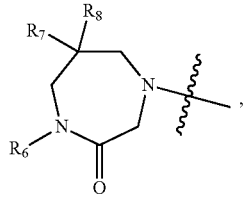;

Y is independently selected from N or CH;
Z is O, CH$_2$, NR$_5$, S, S(O) or S(O)$_2$;
R$_7$ is hydrogen, —C$_{1-5}$alkyl or —(CH$_2$), —C$_{3-5}$cycloalkyl;
R$_8$ is hydrogen or —C$_{1-4}$alkyl;
or R$_7$ and R$_8$, together with the carbon to which they are attached form a C$_3$-C$_5$-membered cycloalkyl ring;
and, wherein when A is

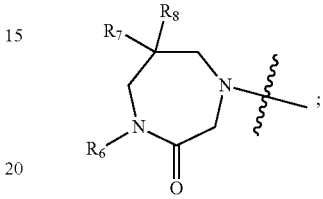, it is unsubstituted or substituted with one, two or three substituents independently selected from halo, —CF$_3$, —CN, —OMe, —C(O)NH$_2$, —OCF$_3$, —C$_{1-4}$alkylNR$_8$R$_9$;

R$_5$ is —C$_{1-3}$ alkyl, aryl, heteroaryl, —C(O)C$_{1-3}$ alkyl, —SO$_2$C$_{1-3}$ alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkylheteroaryl or —C$_{1-3}$alkylaryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$ alkylC$_{3-7}$cycloalkyl, —C$_{1-3}$alkylC$_{3-7}$heterocycloalkyl, —C$_{1-3}$alkylheteroaryl or —C$_{1-3}$alkylaryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;

X is independently CH or N;
m is 1, 2 or 3; and
n is 1, 2 or 3;
or a pharmaceutically acceptable salt thereof.

In another embodiment, the compound of Formula (I) is substituted as follows:

B is benzotriazolyl wherein benzotriazolyl is unsubstituted or substituted by 1, 2, or 3 substituents independently selected from methyl and ethyl;

D is —C(O)—NR$_4$R$_5$, —NR$_4$—C(O)—R$_5$, —NR$_3$—C(O)—NR$_4$R$_5$; —NR$_4$—C(O)—O—R$_5$;
R$_1$ is hydrogen;
R$_2$ is methyl;
R$_4$ is hydrogen;
R$_5$ is hydrogen, —C$_{1-5}$alkyl, —C$_{3-7}$ cycloalkyl, —C$_{4-8}$ heterocycloalkyl, —C$_{1-5}$alkoxy, —C$_{1-3}$ alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$ cycloalkyl, —C$_{4-7}$ heterocycloalkyl, —C$_{1-5}$ alkoxy, —C$_{1-3}$alkyl-O—C$_{1-3}$alkyl, —C$_{1-3}$alkyl-NH—C$_{1-3}$ alkyl, —C$_{1-3}$ alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$alkylaryl, —C$_{1-3}$alkylheteroaryl, aryl, —C$_{1-3}$alkylC(O)R$_3$, —C$_{1-3}$alkylC(O)OH, —C$_{1-3}$alkylNC(O)OR$_4$, —C$_{1-3}$ alkylOSi(R$_3$)$_3$, —C$_{1-3}$ alkylOH, —C$_{1-3}$ alkylNH$_2$, —SCH$_3$, —OCH$_3$, —C$_{4-8}$heterocycloalkyl (optionally substituted with R$_3$), —NH—CH—(CH$_2$)$_n$(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —N—C(O)—C$_{1-3}$alkyl, F, Cl, —CN, —CH—F$_2$, —CF$_3$, —(CH$_2$)$_n$O—(CH$_2$)$_m$—CH$_3$, —O(CH$_2$)$_n$—O—(CH$_2$)$_m$—O(CH$_2$)$_n$—OH, —O(CH$_2$)$_n$C(O)OR$_3$, —O(CH$_2$)$_n$OR$_3$, —O(CH$_2$)$_n$NC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S:
Linker is —CH$_2$—;
or A is

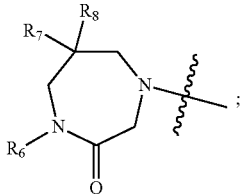

Y is independently selected from N or CH;
Z is O, CH$_2$, NR$_5$, S, S(O) or S(O)$_2$;
R$_7$ is hydrogen, —C$_{1-5}$alkyl or —(CH$_2$), —C$_{3-5}$cycloalkyl;
R$_8$ is hydrogen or —C$_{1-4}$alkyl;
or R$_7$ and R$_8$, together with the carbon to which they are attached form a C$_3$-C$_5$-membered cycloalkyl ring;
and, wherein when A is

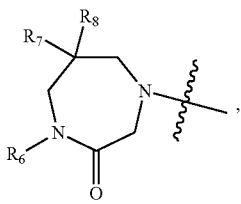

it is unsubstituted or substituted with one, two or three substituents independently selected from halo, —CF$_3$, —C$_{1-4}$alkyl, —CN, —OMe, —C(O)NH$_2$, —OCF$_3$, —C$_{1-4}$alkylNR$_8$R$_9$;
R$_5$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkylheteroaryl or —C$_{1-3}$alkylaryl, wherein each of —C$_{1-3}$alkyl, aryl, heteroaryl, —C(O)C$_{1-3}$ alkyl, —SO$_2$C$_{1-3}$ alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$ cycloalkyl, —C$_{1-3}$alkylC$_{3-7}$heterocycloalkyl, —C$_{1-3}$alkylheteroaryl or —C$_{1-3}$alkylaryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;
X is independently CH or N;
m is 1, 2 or 3; and
n is 1, 2 or 3;
or a pharmaceutically acceptable salt thereof.

It is to be understood that the present invention covers all combinations of particular groups described hereinabove.

Specific examples of compounds of the present invention include the following:

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-3-yl)propanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(isothiazol-4-yl)propanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(oxazol-2-ylmethyl)propanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(oxetan-3-yl)propanamide;

(3S)—N-(1,1-Dioxidotetrahydrothiophen-3-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide;

(S)-1-(3-Amino-1H-pyrazol-1-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propan-1-one;

(S)-1-(5-Amino-1H-pyrazol-1-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propan-1-one;

(S)—N-((1H-Imidazol-2-yl)methyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(1-methyl-1H-pyrazol-5-yl)propanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(4-methylpyridin-3-yl)propanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(4-methoxypyridin-3-yl)propanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(5-(trifluoromethyl)pyridin-3-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(5-methoxypyridin-3-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(6-(trifluoromethyl)pyridin-3-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(6-methylpyridin-3-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-((1-methyl-1H-imidazol-2-yl)methyl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(1-methyl-1H-imidazol-2-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(isoquinolin-4-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-4-yl)propanamide;
(R)-4-Benzyl-3-((2R,3S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2-methylpropanoyl)oxazolidin-2-one;
(S)—N-(3-(Dimethylamino)-3-oxopropyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide;
(3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(tetrahydrofuran-3-yl)propanamide;
(S)—N-(1-Amino-2-methyl-1-oxopropan-2-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(1-methylazetidin-3-yl)propanamide;
(3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(tetrahydro-2H-pyran-3-yl)propanamide;
(3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-((tetrahydrofuran-3-yl)methyl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-hydroxy-2-methylpropyl)propanamide;
(3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(1-(methylamino)-1-oxopropan-2-yl)propanamide;
(3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-oxopiperidin-3-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-sulfamoylethyl)propanamide;
(S)—N-Cyclopropyl-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-hydroxyethyl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(3-hydroxypropyl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(3-methoxypropyl)propanamide;
(S)—N-(2-Amino-2-oxoethyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylamino)ethyl)propanamide;
(3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-((tetrahydrofuran-2-yl)methyl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-fluoroethyl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylamino)-2-oxoethyl)propanamide;
(S)—N-(2-Ethoxyethyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-methoxyethyl)propanamide;
(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(isopropylamino)-2-oxoethyl)propanamide;
(3S)—N-(1-Amino-1-oxopropan-2-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide;
(S)—N-(3-Cyanopropyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide;

(S)—N-(2-Acetamidoethyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide; (R)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-N-(pyridin-3-yl)propanamide, Formic acid salt;

(S)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-N-(pyridin-3-yl)propanamide, Formic acid salt;

(R)-3-((1-Ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-N-(pyridin-3-yl)propanamide, Formic acid salt;

(R)-3-((1-Ethyl-1H-1,2,3-triazol-4-yl)methoxy)-2,2-dimethyl-3-(4-methyl-3-(((S)-4-methyl-1,1-dioxido-4,5-dihydrobenzo[f][1,2]thiazepin-2(3H)-yl)methyl)phenyl)-N-(pyridin-3-yl)propanamide, Formic acid salt;

(R)-2,2-Dimethyl-3-(4-methyl-3-(((S)-4-methyl-1,1-dioxido-4,5-dihydropyrido[2,3-f][1,2]thiazepin-2(3H)-yl)methyl)phenyl)-3-((1-propyl-1H-1,2,3-triazol-4-yl)methoxy)-N-(pyridin-3-yl)propanamide, Formic acid salt;

(R)-2,2-Dimethyl-3-(4-methyl-3-(((S)-4-methyl-1,1-dioxido-4,5-dihydrobenzo[f][1,2]thiazepin-2(3H)-yl)methyl)phenyl)-3-((1-propyl-1H-1,2,3-triazol-4-yl)methoxy)-N-(pyridin-3-yl)propanamide, Formic acid salt;

(R)-2,2-Dimethyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)-3-((1-propyl-1H-1,2,3-triazol-4-yl)methoxy)-N-(pyridin-3-yl)propanamide;

(R)-3-(3((4,4-Dimethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)-N-(pyridin-3-yl)propanamide;

(R)-2,2-Dimethyl-3-(4-methyl-3-(((S)-4-methyl-1,1-dioxido-4,5-dihydropyrido[4,3-f][1,2]thiazepin-2(3H)-yl)methyl)phenyl)-3-((1-propyl-1H-1,2,3-triazol-4-yl)methoxy)-N-(pyridin-3-yl)propanamide;

(R)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)-N-(pyridin-3-yl)propanamide;

(R)-3-(3-(((S)-8-Fluoro-4-methyl-1,1-dioxido-4,5-dihydrobenzo[f][1,2]thiazepin-2(3H)-yl)methyl)-4-methylphenyl)-2,2-dimethyl-3-((1-propyl-1H-1,2,3-triazol-4-yl)methoxy)-N-(pyridin-3-yl)propanamide;

(S)-3-(3-(((S)-4-Ethyl-1,1-dioxido-4,5-dihydrobenzo[f][1,2]thiazepin-2(3H)-yl)methyl)-4-methylphenyl)-3-((1-ethyl-1H-1,2,3-triazol-4-yl)methoxy)-2,2-dimethyl-N-(pyridin-3-yl)propanamide;

(S)-3-((1-Ethyl-1H-1,2,3-triazol-4-yl)methoxy)-2,2-dimethyl-3-(4-methyl-3-(((S)-4-methyl-1,1-dioxido-4,5-dihydropyrido[2,3-f][1,2]thiazepin-2(3H)-yl)methyl)phenyl)-N-(pyridin-3-yl)propanamide;

(S)-3-(1-Ethyl-7-methoxy-4-methyl-1H-benzo[d][1,2,3]triazol-5-yl)-2,2-dimethyl-3-(4-methyl-3-(((R)-4-methyl-1,1-dioxido-4,5-dihydrobenzo[f][1,2]thiazepin-2(3H)-yl)methyl)phenyl)-N-(pyridin-3-yl)propanamide;

(R)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-7-methoxy-4-methyl-1H-benzo[d][1,2,3]triazol-5-yl)-2,2-dimethyl-N-(pyridin-3-yl)propanamide;

3-(7-Methoxy-1-methyl-1H-benzo[d][1,2,3]triazol-5-yl)-3-(4-methyl-3-MS)-4-methyl-1,1-dioxido-8-(trifluoromethyl)-4,5-dihydrobenzo[f][1,2]thiazepin-2(3H)-yl)methyl)phenyl)-N-(pyridin-3-yl)propenamide;

(S)-3-(7-Methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)-N-(pyridin-3-yl)propenamide;

(S)-3-(1-Ethyl-7-methoxy-4-methyl-1H-benzo[d][1,2,3]triazol-5-yl)-2,2-dimethyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)-N-(pyridin-3-yl)propenamide;

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-7-methoxy-4-methyl-1H-benzo[d][1,2,3]triazol-5-yl)-2,2-dimethyl-N-(pyridin-3-yl)propenamide;

S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-7-methoxy-4-methyl-1H-benzo[d][1,2,3]triazol-5-yl)-N-(pyridin-3-yl)propenamide;

(S)-3-(1-Ethyl-7-methoxy-4-methyl-1H-benzo[d][1,2,3]triazol-5-yl)-2,2-dimethyl-3-(4-methyl-3-(((S)-4-methyl-1,1-dioxido-7-(trifluoromethyl)-4,5-dihydrobenzo[f][1,2]thiazepin-2(3H)-yl)methyl)phenyl)-N-(pyridin-3-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2H-tetrazol-5-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

3-(4-Cyano-2-methylphenyl)-3-(3-(((R)-4-ethyl-1,1-dioxido-3,4-dihydro-2H-pyrido[2,3-b][1,4,5]oxathiazepin-2-yl)methyl)-4-methylphenyl)-N-(pyridin-3-yl)propenamide;

3-(4-Cyano-2-methylphenyl)-3-(4-methyl-3-((4-methyl-1,1-dioxido-8-(trifluoromethyl)-4,5-dihydrobenzo[f][1,2]thiazepin-2(3H)-yl)methyl)phenyl)-N-(pyridin-3-yl)propenamide;

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1,2,4-thiadiazol-5-yl)propenamide;

(S)-3-(3-(((S)-4-Ethyl-1,1-dioxido-4,5-dihydrobenzo[f][1,2]thiazepin-2 (3H)-yl)methyl)-4-methylphenyl)-3-(1-ethyl-4-methyl-1H-benzo[d][1,2,3]triazol-5-yl)-2,2-dimethyl-N-(1-phenyl-1H-tetrazol-5-yl)propenamide;

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1-(2-oxopropyl)-1H-tetrazol-5-yl)propenamide;

(S)-3-(3-(((S)-4-Ethyl-1,1-dioxido-4,5-dihydrobenzo[f][1,2]thiazepin-2 (3H)-yl)methyl)-4-methylphenyl)-3-(1-ethyl-4-methyl-1H-benzo[d][1,2,3]triazol-5-yl)-2,2-dimethyl-N-(1-(pyridin-2-yl)-1H-tetrazol-5-yl)propenamide;

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1-(thiazol-2-ylmethyl)-1H-tetrazol-5-yl)propenamide;

2-(5-((S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanamido)-1H-tetrazol-1-yl)acetic acid;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1H-tetrazole-5-carboxamide, Trifluoroacetic acid salt;

N—((S)-1-(3-(((S)-4-Ethyl-1,1-dioxido-8-(trifluoromethyl)-4,5-dihydrobenzo[f][1,2]thiazepin-2(3H)-yl)methyl)-4-methylphenyl)-1-(1-ethyl-4-methyl-1H-benzo[d][1,2,3]triazol-5-yl)-2-methylpropan-2-yl)-2-(1H-tetrazol-5-yl)acetamide;

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(2-(methylamino)ethyl)propenamide;

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)-N-(pyridin-3-yl)propenamide;

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)-N-(2-(methylamino)ethyl)propenamide;

(S)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)-N-(pyridin-3-yl)pentanamide;

(R)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)-N-(pyridin-3-yl)pentanamide;

(S)-3-(4-Chloro-3-(((R)-4-ethyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)-2,2-dimethyl-N-(pyridin-3-yl)propenamide;

(S)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-3-(4-methyl-1-propyl-1H-benzo[d][1,2,3]triazol-5-yl)-N-(pyridin-3-yl)propenamide;

(S)—N-(2-Chloropyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanamide;

(S)-3-(4-chloro-3-(((R)-4-ethyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)-2,2-dimethylpropanamide;

(R)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-((1-ethyl-1H-1,2,3-triazol-4-yl)methoxy)-2,2-dimethylpropanamide;

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propenamide;

(S)-3-(3-(((S)-4-Ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(pyrimidin-5-yl)propenamide;

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(pyrimidin-5-yl)propenamide;

(S)-3-(1-Ethyl-4-methyl-1H-benzo[d][1,2,3]triazol-5-yl)-2,2-dimethyl-3-(4-methyl-3-(((S)-4-methyl-1,1-dioxido-7-(trifluoromethyl)-4,5-dihydrobenzo[f][1,2]thiazepin-2(3H)-yl)methyl)phenyl)-N-(pyrimidin-5-yl)propenamide;

(S)-3-(3-(((S)-4-Ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(pyrimidin-5-yl)propenamide;

(S)-3-(3-(((R)-4-Ethyl-1,1-dioxido-3,4-dihydro-2H-pyrido[4,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propenamide;

(S)-3-(3-(((R)-7-Bromo-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propenamide;

(S)-3-(3-(((R)-8-Bromo-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propenamide;

14(S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)urea;

(3S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(tetrahydrofuran-3-yl)propenamide;

(3S)-3-(1,4-Dimethyl-1H-benzo[d][1,2,3]triazol-5-yl)-N-(1,1-dioxidotetrahydrothiophen-3-yl)-3-(3-(((R)-2-ethyl-2,3-dihydropyrido[3,4-f][1,4]oxazepin-4(5H)-yl)methyl)-4-methylphenyl)-2,2-dimethylpropanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(2-(methylamino)ethyl)propenamide;

(S)-3-(3-(((S)-4-Ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)-N-(pyridin-3-yl)propenamide;

(S)—N-((1H-Imidazol-2-yl)methyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)-3-(3-(((S)-4-Ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)-N-(pyrimidin-5-yl)propenamide;

(3S)—N-(1,1-Dioxidotetrahydrothiophen-3-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridazin-4-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyrimidin-4-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyrimidin-5-yl)propenamide;

(S)-3-(4-Chloro-3-(((R)-4-ethyl-1,1-dioxido-3,4-dihydro-2H-pyrido[2,3-b][1,4,5]oxathiazepin-2-yl)methyl)phenyl)-3-(1-ethyl-4-methyl-1H-benzo[d][1,2,3]triazol-5-yl)-N-(pyridin-3-yl)propenamide;

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(pyridin-3-yl)propenamide;

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(pyridin-4-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N—((S)-tetrahydrofuran-3-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N—((R)-tetrahydrofuran-3-yl)propenamide;

S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(2-(methylthio)pyrimidin-5-yl)propenamide;

(R)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyridin-3-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyrazin-2-yl)propenamide;

(S)-3-(3-(((S)-4-Ethyl-1,1-dioxido-4,5-dhydropyrido[2,3-f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(pyridin-3-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyridin-3-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyrimidin-2-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridazin-3-yl)propenamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-methoxypyrimidin-5-yl)propenamide;

(S)—N-(2-(2-Ethoxyethoxy)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(piperidin-1-yl)pyrimidin-5-yl)propenamide;

S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylamino)pyrimidin-5-yl)propenamide;

(S)—N-(2-((1,3-Dihydroxypropan-2-yl)amino)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propenamide;

(S)—N-(2-((1,3-Dihydroxypropan-2-yl)amino)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(3S)—N-(2-(2-Amino-3-hydroxypropoxy)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)—N-(2-(Dimethylamino)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(2-(methylsulfonyl)pyrimidin-5-yl)propenamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)acetamide;

4-Acetamido-N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)butanamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)tetrahydrofuran-3-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)tetrahydro-2H-pyran-3-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)furan-2-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)furan-3-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)isothiazole-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1-methyl-6-oxo-1,6-dihydropyridine-3-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1-methyl-2-oxo-1,2-dihydropyridine-3-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1-methyl-2-oxo-1,2-dihydropyridine-4-carboxamide;

3-(((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)amino)-3-oxopropanoic acid;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(methylsulfonyl)acetamide;

2-Cyano-N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)acetamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-methoxypyrimidine-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(methylthio)pyrimidine-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1H-imidazole-4-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)thiazole-4-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1H-pyrazole-3-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)oxazole-4-carboxamide GSK3901456A N62324-100-A1;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)isoxazole-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)isoxazole-3-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-5-fluoronicotinamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-5-(trifluoromethyl)nicotinamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-6-oxo-1,6-dihydropyridine-3-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(methylsulfonyl)pyrimidine-5-carboxamide;

2-(Azetidin-1-yl)-N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(pyrrolidin-1-yl)pyrimidine-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(3-methoxypropoxy)pyrimidine-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(2-hydroxyethoxy)pyrimidine-5-carboxamide;

2-(Dimethylamino)-N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide;

2-(2-Ethoxyethoxy)-N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-morpholinopyrimidine-5-carboxamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(4-methylpiperazin-1-yl)pyrimidine-5-carboxamide;

N—((S)-1-(3-(((R)-4-Ethyl-1,1-dioxido-3,4-dihydro-2H-pyrido[2,3-b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)nicotinamide;

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-N-methylpyrimidine-5-carboxamide;

(S)-3-(3-(((R)-4-ethyl-1,1-dioxido-3,4-dihydro-2H-pyrido [2,3-b][1,4,5]oxathiazepin-2-yl)methyl)-4-methylphenyl)-3-(1-ethyl-4-methyl-1H-benzo[d][1,2,3]triazol-5-yl)-N-(pyridin-2-yl)propenamide;

(S)-3-(3-(((R)-4-ethyl-1,1-dioxido-3,4-dihydro-2H-pyrido [2,3-b][1,4,5]oxathiazepin-2-yl)methyl)-4-methylphenyl)-3-(1-ethyl-4-methyl-1H-benzo[d][1,2,3]triazol-5-yl)-N-methyl-N-(pyridin-3-yl)propenamide;

(S)-3-(3-(((R)-4-ethyl-1,1-dioxido-3,4-dihydro-2H-pyrido [2,3-b][1,4,5]oxathiazepin-2-yl)methyl)-4-methylphenyl)-3-(1-ethyl-4-methyl-1H-benzo[d][1,2,3]triazol-5-yl)-N-phenylpropanamide;

(S)—N-cyclopentyl-3-(3-(((R)-4-ethyl-1,1-dioxido-3,4-dihydro-2H-pyrido[2,3-b][1,4,5]oxathiazepin-2-yl) methyl)-4-methylphenyl)-3-(1-ethyl-4-methyl-1H-benzo [d][1,2,3]triazol-5-yl)propanamide;

(S)-3-(3-(((R)-4-ethyl-1,1-dioxido-3,4-dihydro-2H-pyrido [2,3-b][1,4,5]oxathiazepin-2-yl)methyl)-4-methylphenyl)-3-(1-ethyl-4-methyl-1H-benzo[d][1,2,3]triazol-5-yl)-N-(6-methoxypyridin-3-yl)propanamide;

(S)-3-(3-((2-(cycloheptylmethyl)-1H-imidazol-1-yl) methyl)-4-methylphenyl)-3-(1,4-dimethyl-1H-benzo[d] [1,2,3]triazol-5-yl)-2,2-dimethyl-N-(pyridin-3-yl)propanamide;

(S)-3-(1-ethyl-4-methyl-1H-benzo[d][1,2,3]triazol-5-yl)-3-(4-methyl-3-MS)-4-methyl-1,1-dioxido-8-(trifluoromethyl)-4,5-dihydrobenzo[f][1,2]thiazepin-2(3H)-yl) methyl)phenyl)-N-(pyridin-3-yl)propanamide;

(S)-3-(4-chloro-3-((2-((4-ethylpiperidin-1-yl)methyl)-1H-imidazol-1-yl)methyl)phenyl)-3-(1,4-dimethyl-1H-benzo [d][1,2,3]triazol-5-yl)-2,2-dimethyl-N-(pyridin-3-yl)propanamide;

((2R,3S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2-methyl-N-(pyridin-3-yl)propanamide;

(2R,3S)-3-(1-ethyl-4-methyl-1H-benzo[d][1,2,3]triazol-5-yl)-2-methyl-3-(4-methyl-3-(((S)-4-methyl-1,1-dioxido-7-(trifluoromethyl)-4,5-dihydrobenzo[f][1,2]thiazepin-2 (3H)-yl)methyl)phenyl)-N-(pyridin-3-yl)propanamide;

(S)-3-(1-ethyl-4-methyl-1H-benzo[d][1,2,3]triazol-5-yl)-3-(3-(((S)-8-fluoro-4-methyl-1,1-dioxido-4,5-dihydrobenzo [f][1,2]thiazepin-2(3H)-yl)methyl)-4-methylphenyl)-N-(pyridin-3-yl)propanamide;

(2R,3S)-3-(1-ethyl-4-methyl-1H-benzo[d][1,2,3]triazol-5-yl)-2-methyl-3-(4-methyl-3-(((S)-4-methyl-1,1-dioxido-8-(trifluoromethyl)-4,5-dihydrobenzo[f][1,2]thiazepin-2 (3H)-yl)methyl)phenyl)-N-(pyridin-3-yl)propanamide;

(2R,3S)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3] triazol-5-yl)-2-methyl-N-(pyridin-3-yl)propanamide;

(S)-3-(1-ethyl-7-methoxy-4-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2 (3H)-yl)methyl)phenyl)-N-(pyridin-3-yl)propanamide;

(2R,3S)-3-(3-(((R)-2-ethyl-2,3-dihydropyrido[2,3-f][1,4] oxazepin-4(5H)-yl)methyl)-4-methylphenyl)-3-(1-ethyl-4-methyl-1H-benzo[d][1,2,3]triazol-5-yl)-2-methylpropanamide;

(S)-3-(1-ethyl-4-methyl-1H-benzo[d][1,2,3]triazol-5-yl)-3-(3-(((S)-4-ethyl-9-(trifluoromethyl)-4,5-dihydro-1H-benzo[c]azepin-2(3H)-yl)methyl)-4-methylphenyl)-2,2-dimethylpropanamide;

(S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2,2-dimethylpropanamide;

(R)-3-(4-chloro-3-(((R)-4-ethyl-1,1-dioxido-3,4-dihydro-2H-benzo[b][1,4,5]oxathiazepin-2-yl)methyl)phenyl)-5-(1-cyclobutyl-1H-1,2,3-triazol-4-yl)-2,2-dimethylpentanamide;

(S)—N-(2-(((tert-Butyldimethylsilyl)oxy)methyl)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)—N-(2-(2-((tert-Butyldimethylsilyl)oxy)propan-2-yl)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3] triazol-5-yl)-2,2-dimethylpropanamide;

tert-Butyl ((5-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3] triazol-5-yl)-2,2-dimethylpropanamido)pyrimidin-2-yl)methyl)carbamate;

5-((S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-N,N-dimethylpyrimidine-2-carboxamide;

Methyl 2-((5-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3] triazol-5-yl)-2,2-dimethylpropanamido)pyrimidin-2-yl) oxy)acetate;

tert-Butyl (2-((5-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3] triazol-5-yl)-2,2-dimethylpropanamido)pyrimidin-2-yl) oxy)ethyl)carbamate;

(S)—N-(2-(2-(tert-Butoxy)ethoxy)pyrimidin-5-yl)-3-(3-(((R)-4-ethyl-1,1-dioxido-3,4-dihydro-2H-benzo[b][1,4, 5]oxathiazepin-2-yl)methyl)-4-methylphenyl)-3-(1-ethyl-4-methyl-1H-benzo[d][1,2,3]triazol-5-yl)-2,2-dimethylpropanamide;

(S)-3-(3-(((R)-4-Ethyl-1,1-dioxido-3,4-dihydro-2H-benzo [b][1,4,5]oxathiazepin-2-yl)methyl)-4-methylphenyl)-3-(1-ethyl-4-methyl-1H-benzo[d][1,2,3]triazol-5-yl)-N-(2-(2-methoxyethoxy)pyrimidin-5-yl)-2,2-dimethylpropanamide;

(S)-3-(3-(((R)-4-Ethyl-1,1-dioxido-3,4-dihydro-2H-benzo [b][1,4,5]oxathiazepin-2-yl)methyl)-4-methylphenyl)-3-(1-ethyl-4-methyl-1H-benzo[d][1,2,3]triazol-5-yl)-N-(2-(hydroxymethyl)pyrimidin-5-yl)-2,2-dimethylpropanamide;

5-((S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidine-2-carboxylic acid;

(S)—N-(2-(Aminomethyl)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

2-((5-((S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidin-2-yl)oxy)acetic acid;

(S)—N-(2-(2-Aminoethoxy)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-N-(2-(2-hydroxyethoxy)pyrimidin-5-yl)-2,2-dimethylpropanamide;

2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)acetate;

3-(((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)propanoic acid;

2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)succinic acid;

3-(((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pentanedioic acid;

3-(((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-3-(pyridin-4-yl)propanoic acid;

2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)propanoic acid;

(S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(3,3,3-trifluoropropyl)propenamide;

2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-2-methylpropanoic acid;

(S)—N-(2-amino-2-oxoethyl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide;

(S)-2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pentanedioic acid;

(R)-2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pentanedioic acid;

(S)-4-amino-2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-4-oxobutanoic acid;

(R)-4-amino-2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-4-oxobutanoic acid; and 3-((S)—N-(carboxymethyl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)propanoic acid;

or a pharmaceutically acceptable salt thereof.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general Formula (I) and pharmaceutically acceptable derivatives and salts thereof may be accomplished as outlined below in Schemes 1-17. In the following description, the groups are as defined above for compounds of Formula (I) unless otherwise indicated. Abbreviations are as defined in the Examples section. Starting materials are commercially available or are made from commercially available starting materials using methods known to those skilled in the art.

Scheme 1

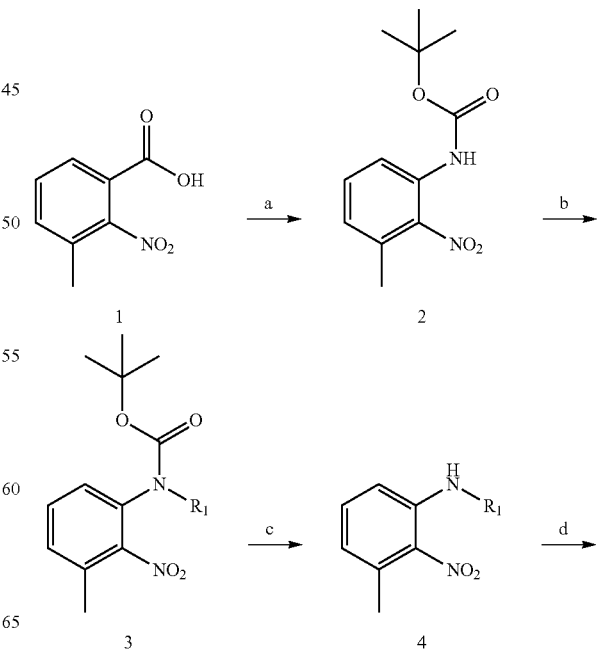

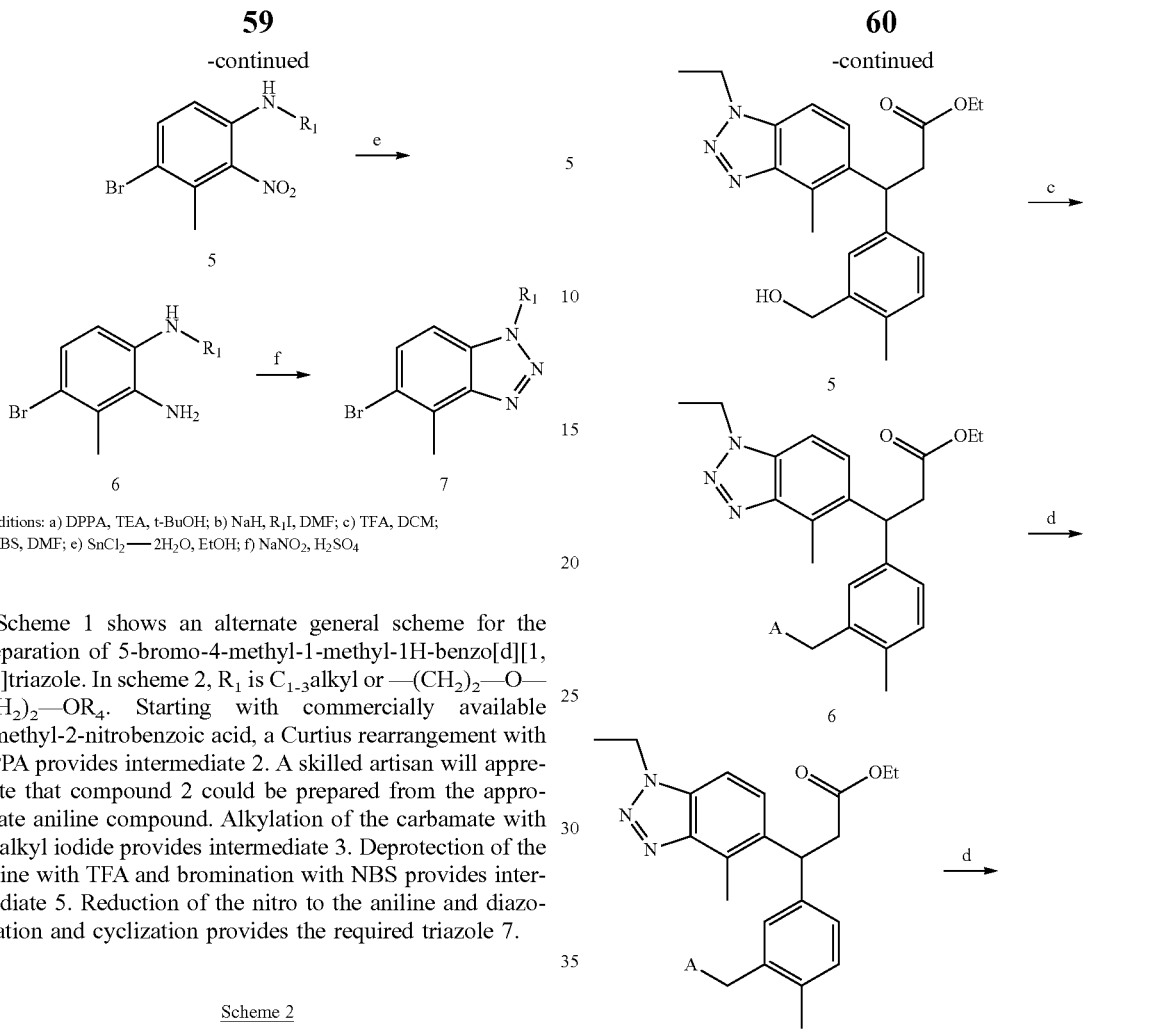

Conditions: a) DPPA, TEA, t-BuOH; b) NaH, $R_1I$, DMF; c) TFA, DCM; d) NBS, DMF; e) $SnCl_2$—$2H_2O$, EtOH; f) $NaNO_2$, $H_2SO_4$ Scheme 1 shows an alternate general scheme for the preparation of 5-bromo-4-methyl-1-methyl-1H-benzo[d][1,2,3]triazole. In scheme 2, $R_1$ is $C_{1-3}$alkyl or —$(CH_2)_2$—O—$(CH_2)_2$—$OR_4$. Starting with commercially available 3-methyl-2-nitrobenzoic acid, a Curtius rearrangement with DPPA provides intermediate 2. A skilled artisan will appreciate that compound 2 could be prepared from the appropriate aniline compound. Alkylation of the carbamate with an alkyl iodide provides intermediate 3. Deprotection of the amine with TFA and bromination with NBS provides intermediate 5. Reduction of the nitro to the aniline and diazotization and cyclization provides the required triazole 7.

Scheme 2

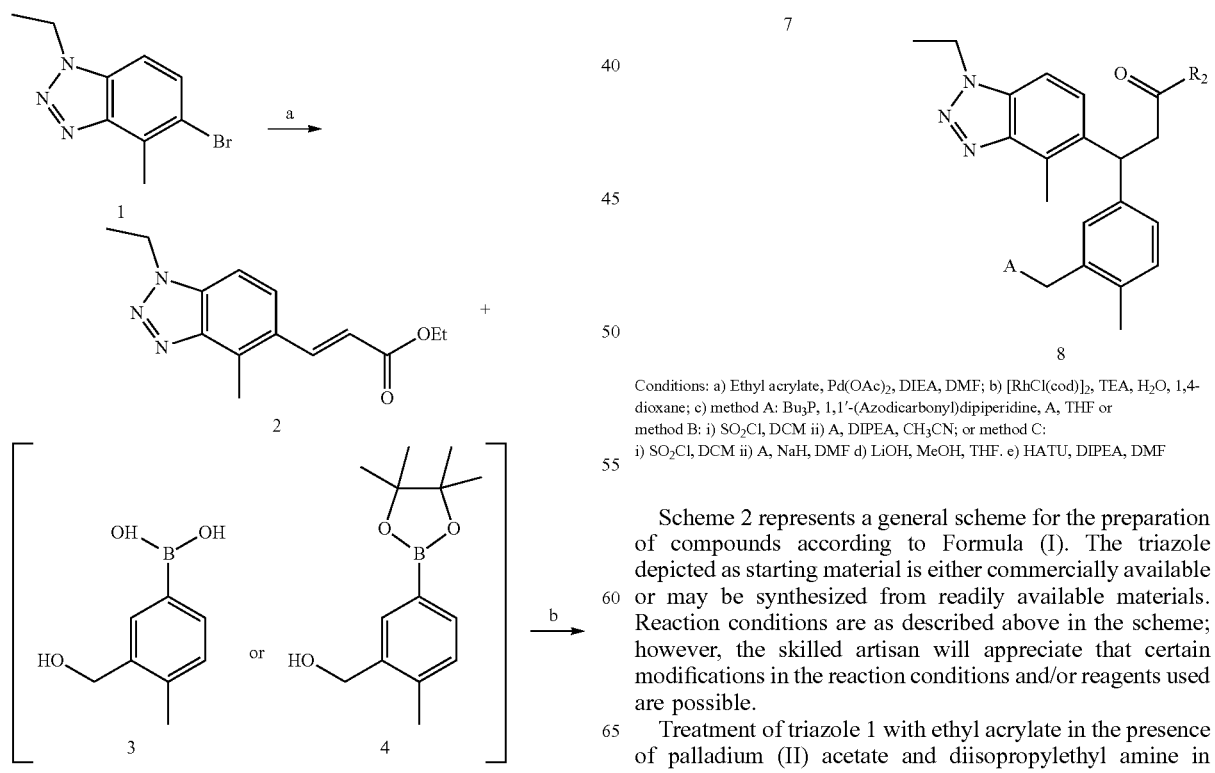

Conditions: a) Ethyl acrylate, $Pd(OAc)_2$, DIEA, DMF; b) [RhCl(cod)]$_2$, TEA, $H_2O$, 1,4-dioxane; c) method A: $Bu_3P$, 1,1'-(Azodicarbonyl)dipiperidine, A, THF or method B: i) $SO_2Cl$, DCM ii) A, DIPEA, $CH_3CN$; or method C: i) $SO_2Cl$, DCM ii) A, NaH, DMF d) LiOH, MeOH, THF. e) HATU, DIPEA, DMF Scheme 2 represents a general scheme for the preparation of compounds according to Formula (I). The triazole depicted as starting material is either commercially available or may be synthesized from readily available materials. Reaction conditions are as described above in the scheme; however, the skilled artisan will appreciate that certain modifications in the reaction conditions and/or reagents used are possible.

Treatment of triazole 1 with ethyl acrylate in the presence of palladium (II) acetate and diisopropylethyl amine in presence of a suitable solvent produces the desired Heck cross-coupling product 2. It will be appreciated by the skilled artisan that compound 2 may also be obtained via a Homer Wadsworth Emmons or Wittig olefination reaction starting from the appropriate aldehyde of compound 1. Further transformation of the olefin 2 can be achieved through rhodium mediated addition of the appropriate boronic acid or boronic ester 3 in the presence of triethylamine. Completion of the analog synthesis is accomplished via Mitsunobu reaction with the requisite sulfonamide followed by hydrolysis of the ester to produce 6. It will be appreciated by the skilled artisan that sulfonamides like 5, may be synthesized via conversion of the benzylic alcohol of 4 to a leaving group such as, but not limited to, mesylate, tosylate, chloride, bromide, or iodide followed by reaction with the requisite amine $NHR_6$ and subsequent reaction with a sulfonylating reagent such as a sulfonyl chloride.

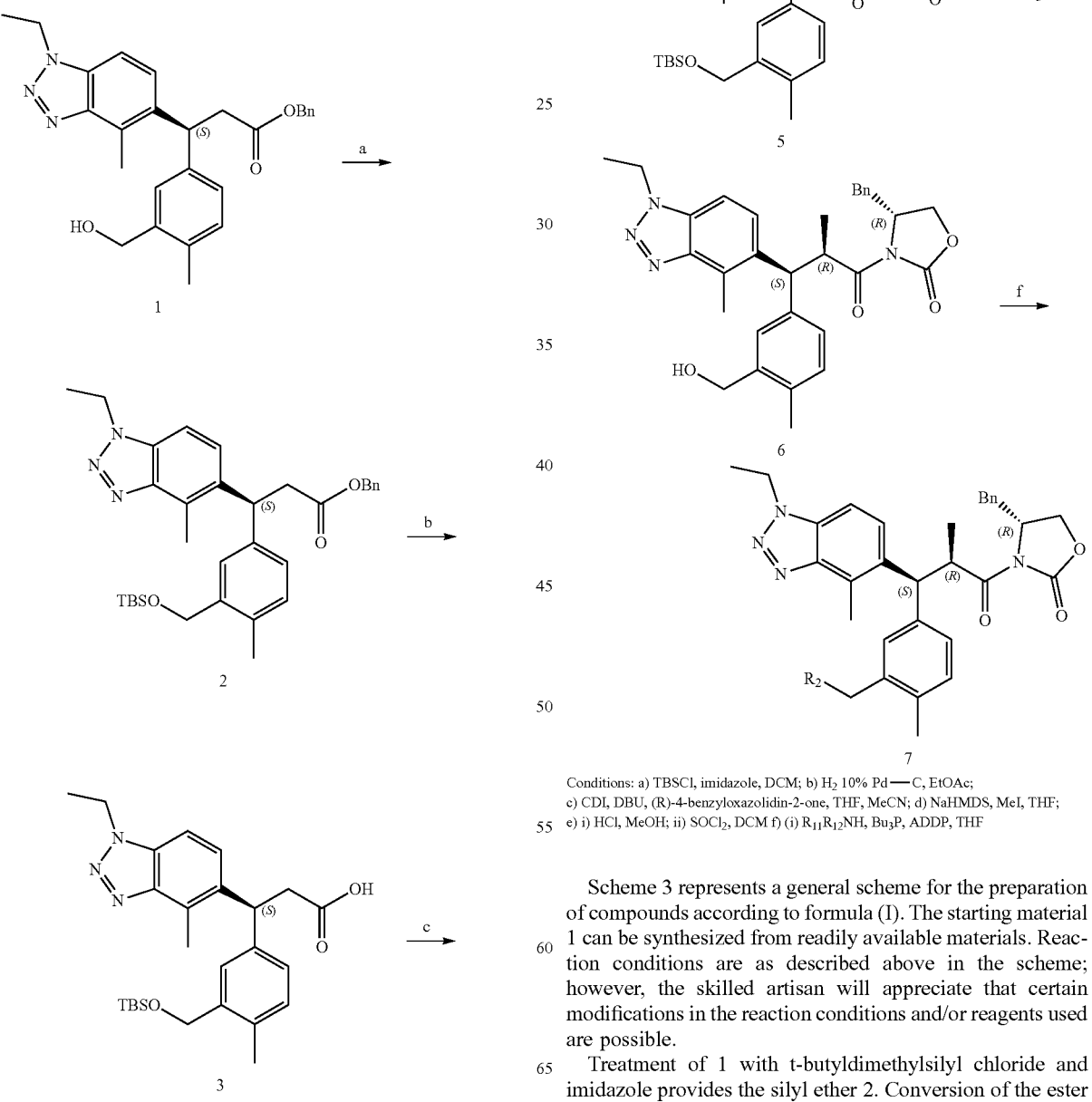

Conditions: a) TBSCl, imidazole, DCM; b) $H_2$ 10% Pd—C, EtOAc; c) CDI, DBU, (R)-4-benzyloxazolidin-2-one, THF, MeCN; d) NaHMDS, MeI, THF; e) i) HCl, MeOH; ii) $SOCl_2$, DCM f) (i) $R_{11}R_{12}NH$, $Bu_3P$, ADDP, THF Scheme 3 represents a general scheme for the preparation of compounds according to formula (I). The starting material 1 can be synthesized from readily available materials. Reaction conditions are as described above in the scheme; however, the skilled artisan will appreciate that certain modifications in the reaction conditions and/or reagents used are possible.

Treatment of 1 with t-butyldimethylsilyl chloride and imidazole provides the silyl ether 2. Conversion of the ester to the acid can be accomplished either via hydrogenation with 10% Pd—C to furnishes acid 3. Treatment with carbonyl diimidazole in tetrahydrofuran followed by reaction with 1,8-Diazabicyclo[5.4.0]undec-7-ene and (R)-4-benzyloxazolidin-2-one provides 4. Enolate formation with sodium bis(trimethylsilyl)amide and stereoselective trapping with methyl iodide gives 5. Removal of the t-butyldimethylsilyl ether with acid condition furnishes benzylic alcohol 6, which is converted to the requisite chloride with thionyl chloride. The synthesis can be completed to appropriate amine via misunobo reaction.

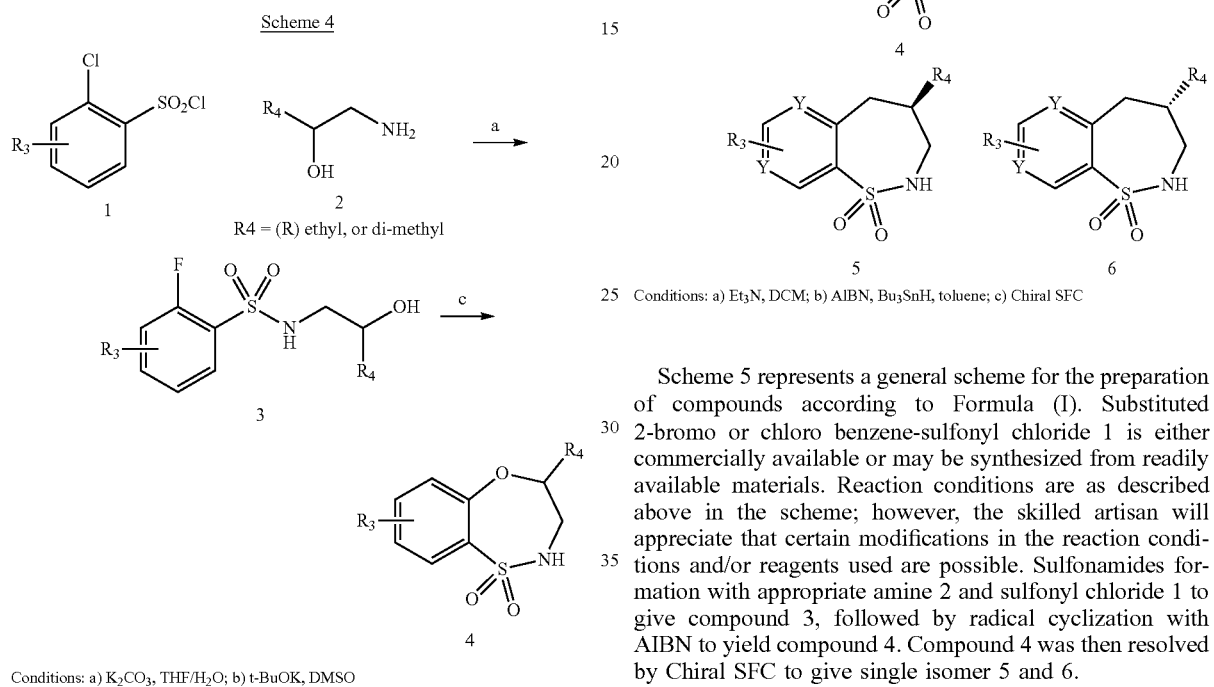

Conditions: a) K₂CO₃, THF/H₂O; b) t-BuOK, DMSO

Scheme 4 represents a general scheme for the preparation of sulfonamide 4. In this, amino alcohol 2 and substituted 2-cholorobenzene-1-sulfonyl chloride depicted as starting material are commercially available or may be synthesized from readily available materials. Reaction conditions are as described above in the scheme; however, the skilled artisan will appreciate that certain modifications in the reaction conditions and/or reagents used are possible.

Sulfonamide formation under basic condition with appropriate amino alcohol and commercially available 2-chloropyridine-3-sulfonyl chloride to give intermediate 3, followed by displacement of choloride with potassium tert-butoxide provides the required intermediate 4.

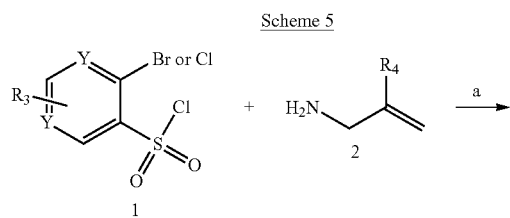

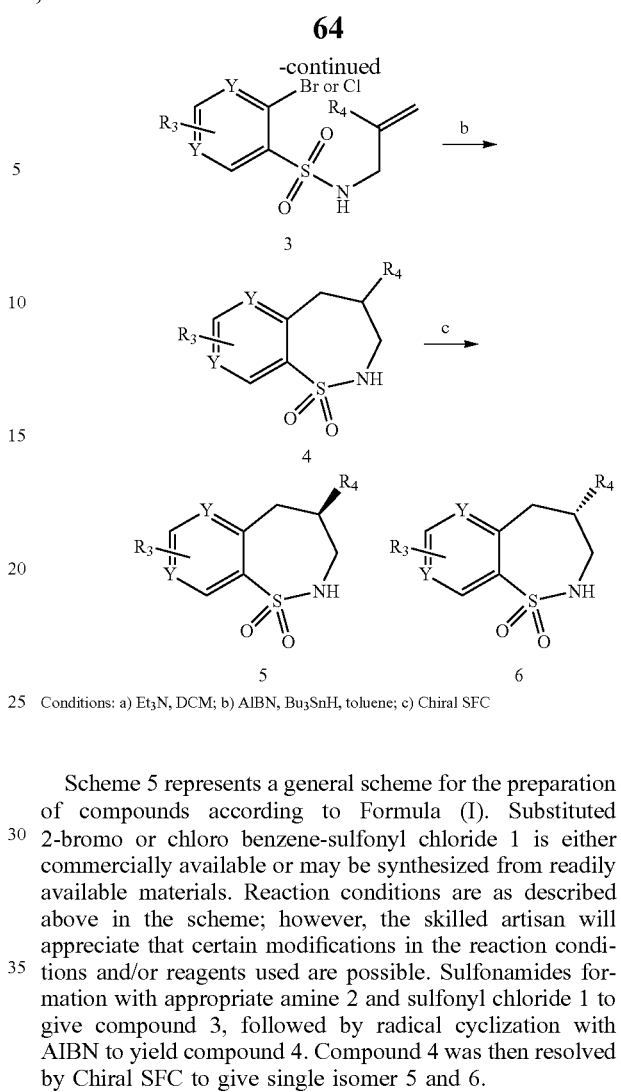

Conditions: a) Et₃N, DCM; b) AIBN, Bu₃SnH, toluene; c) Chiral SFC

Scheme 5 represents a general scheme for the preparation of compounds according to Formula (I). Substituted 2-bromo or chloro benzene-sulfonyl chloride 1 is either commercially available or may be synthesized from readily available materials. Reaction conditions are as described above in the scheme; however, the skilled artisan will appreciate that certain modifications in the reaction conditions and/or reagents used are possible. Sulfonamides formation with appropriate amine 2 and sulfonyl chloride 1 to give compound 3, followed by radical cyclization with AIBN to yield compound 4. Compound 4 was then resolved by Chiral SFC to give single isomer 5 and 6.

Scheme 6

Conditions: a) (R)—H₂NCH₂CH(Et)OH, K₂CO₃, THF/H₂O; b) t-BuOK, DMSO

Scheme 6 represents a general scheme for the preparation of (R)-4-ethyl-3,4-dihydro-2H-pyrido[2,3-b][1,4,5]oxathiazepine 1,1-dioxide, used in the invention. In this, the 2-chloropyridine-3-sulfonyl chloride depicted as starting material is commercially available. Reaction with the appropriate amino alcohol followed by displacement of the chloride with a base provides the required intermediate 3.

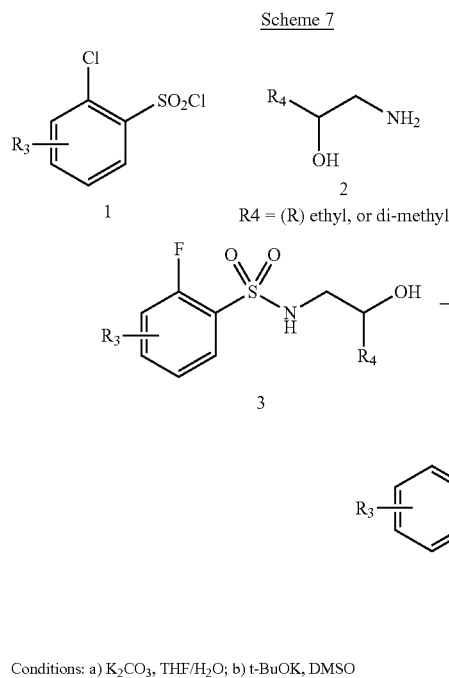

Scheme 7

R4 = (R) ethyl, or di-methyl

Conditions: a) K₂CO₃, THF/H₂O; b) t-BuOK, DMSO

Scheme 7 represents a general scheme for the preparation of sulfonamide 4. In this, amino alcohol 2 and substituted 2-cholorobenzene-1-sulfonyl chloride depicted as starting material are commercially available or may be synthesized from readily available materials. Reaction conditions are as described above in the scheme; however, the skilled artisan will appreciate that certain modifications in the reaction conditions and/or reagents used are possible. Sulfonamide formation under basic conditions with the appropriate amino alcohol and commercially available 2-chloro-pyridine-3-sulfonyl chloride to give intermediate 3, followed by displacement of the chloride with potassium tert-butoxide provides the required intermediate 4.

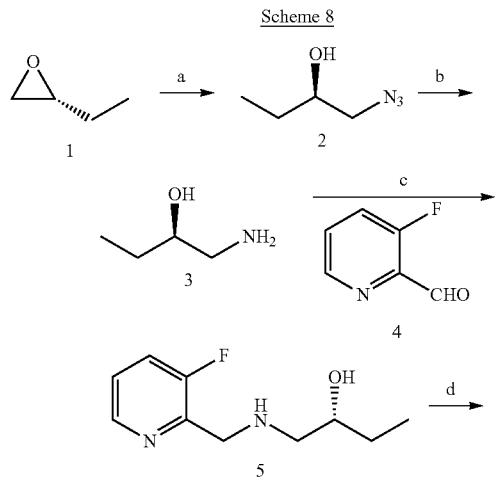

Scheme 8

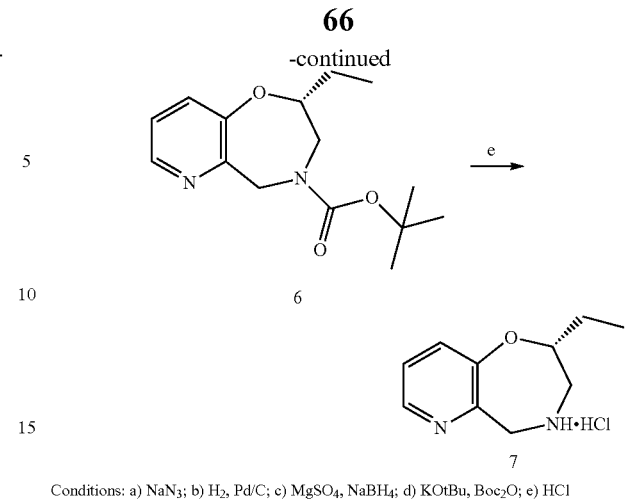

Conditions: a) NaN₃; b) H₂, Pd/C; c) MgSO₄, NaBH₄; d) KOtBu, Boc₂O; e) HCl

Scheme 8 represents a general scheme for the preparation of (R)-2-Ethyl-2,3,4,5-tetrahydropyrido[2,3-f][1,4]oxazepine, hydrochloride 7, used in the invention. Reaction conditions are as described above in the scheme; however, the skilled artisan will appreciate that certain modifications in the reaction conditions and/or reagents used are possible. The (R)-1-azidobutan-2-ol 2 is prepared from the commercially available (R)-2-ethyloxirane 1 and an azide source such as sodium azide. The azide can be reduced under hydrogenation conditions and a catalyst such as palladium on carbon to provide 3. A skilled artisan will appreciate that 3 can be prepared directly from the reaction of (R)-2-ethyloxirane and an ammonia source such as ammonium hydroxide. A reductive amination reaction is then performed using the commercially available 3-fluoropicolinaldehyde 4 and 3, using sodium borohydride. Displacement of the fluoride with the alcohol using potassium-t-butoxide as base followed by amidation of the amine with Boc anhydride provides 6. The protected amine is deprotected with a suitable acid such as HCl to provide the intermediate 7.

Scheme 9

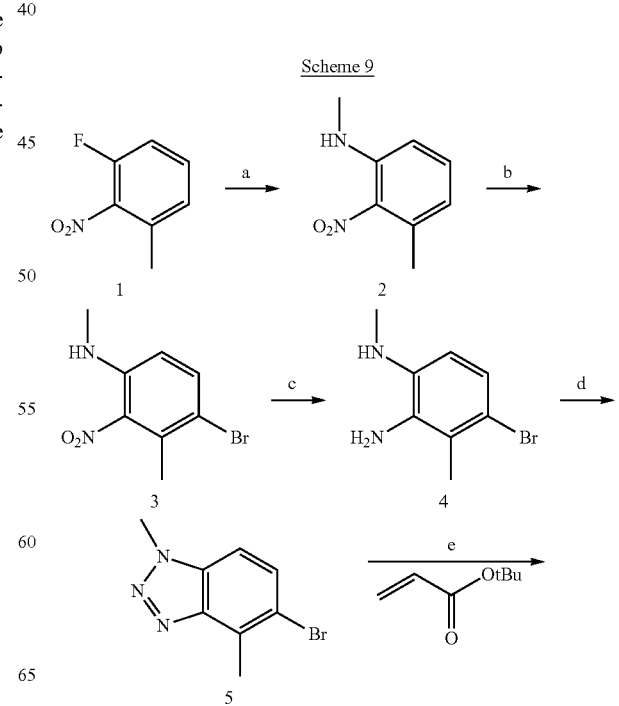

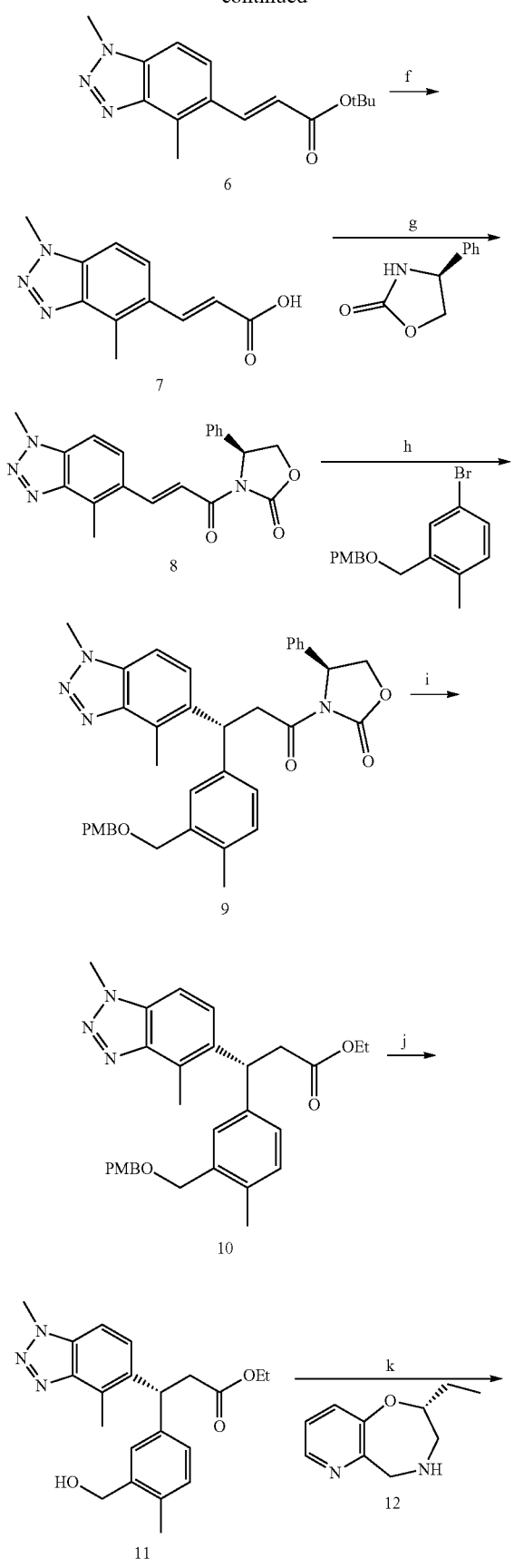

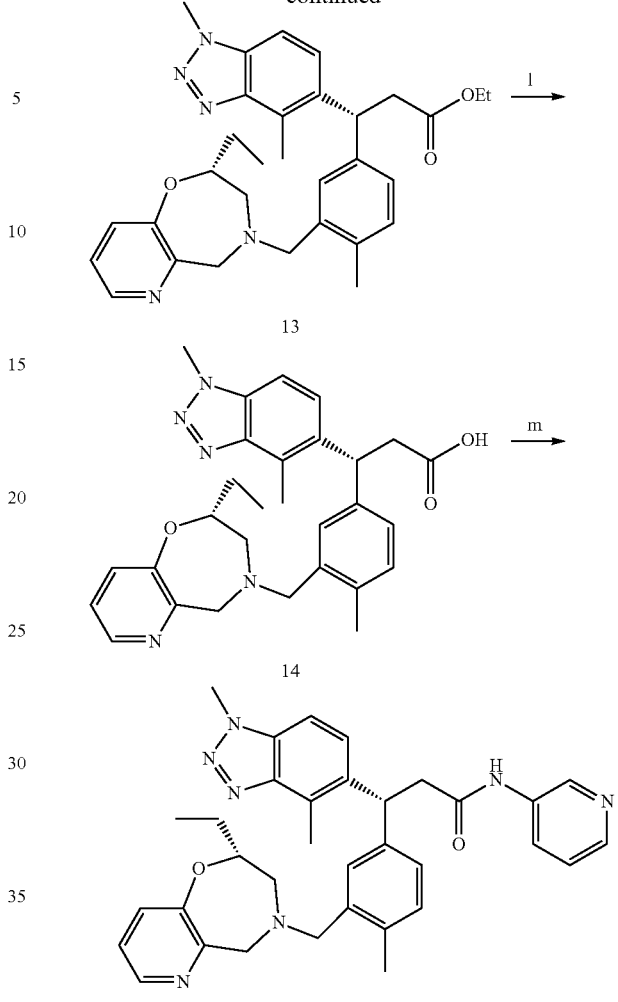

Conditions: a) MeNH$_2$, EtOH; b) NBS; c) Fe, HCl, HOAc, EtOH; d) t-BuONO, HF—BF$_3$; e) t-Bu-acrylate, Pd(OAc)$_2$, P(O-tol)$_3$; f) TFA; g) PivCl, LiCl; h) Mg, CuBr-DMS; i) MgBr, EtOH; j) DDQ; k) SOCl$_2$, 12, DIPEA; l) LiOH; m) HATU, DIEA, 3-aminopyridine.

Scheme 9 represents a general scheme for the preparation of (R)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-N-(pyridin-3-yl)propanamide, formic acid salt 7, used in the invention. Reaction conditions are as described above in the scheme; however, the skilled artisan will appreciate that certain modifications in the reaction conditions and/or reagents used are possible. N,3-Dimethyl-2-nitroaniline 2 was prepared by amination of the commercially available 1-fluoro-3-methyl-2-nitrobenzene 1. Bromination of 2 is achieved with NBS to provide 3. Iron powder in HOAc/EtOH was used for the nitro reduction of 3 to provide 4. Diazotization and cyclization provides the triazole 5. Treatment of triazole 5 with tert-butyl acrylate in the presence of palladium (II) acetate and tri-o-tolylphosphine in presence of a suitable solvent produces the desired Heck cross-coupling product 6. It will be appreciated by the skilled artisan that compound 6 may also be obtained via a Homer Wadsworth Emmons or Wittig olefination reaction starting from the appropriate aldehyde of compound 5. Hydrolysis of the t-butyl ester with TFA and amidation with the chiral auxiliary (S)-4-phenyloxazolidin- 2-one provides 8. Further transformation of the olefin 8 can be achieved through a copper mediated Grignard reaction to provide 9. The conversion of the amide chiral auxiliary to the ethyl ester 10 is achieved with magnesium bromide in ethanol. Removal of the para-methoxybenzyl group with DDQ furnishes the benzyl alcohol 6 which is converted to the chloride with thionyl chloride. The chloride is then displaced with sulfonamide 12 to provide 13. Alternatively, the benzylic alcohol may also be displaced by a suitably acidic nucleophile, such as a sulfonamide, under Mitsunobu conditions using tri-n-butyl phosphine and ADDP The ester is hydrolysed under basic conditions and an amidation reaction is performed on the carboxylic acid with a suitable amine such as 3-aminopyridine using an amide coupling reagent such as HATU to provide 15. Alternatively, the amide could be formed by activation of the carboxylic acid with a chlorinating reagent like thionyl chloride, and subsequent displacement of the chloride with a suitable amine.

Scheme 10

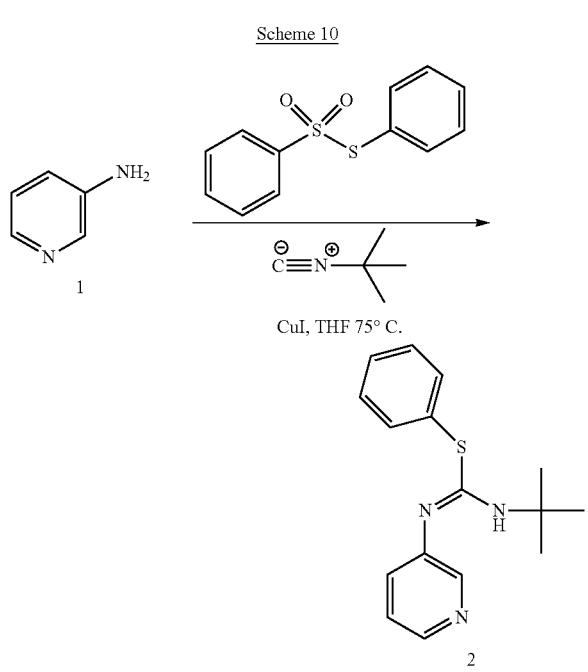

Scheme 10 represents a general scheme for the preparation of phenyl (E)-N-(tert-butyl)-N'-(pyridin-3-yl)carbamimidothioate, used in the invention. In this, pyridin-3-amine depicted as starting material is commercially available. The reaction with 2-isocyano-2-methylpropane and S-phenyl benzenesulfonothioate in 2-methyltetrahydrofuran is heated with copper(I) iodide and provides the required intermediate 2.

Scheme 11

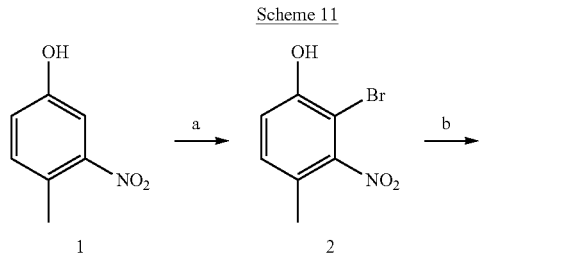

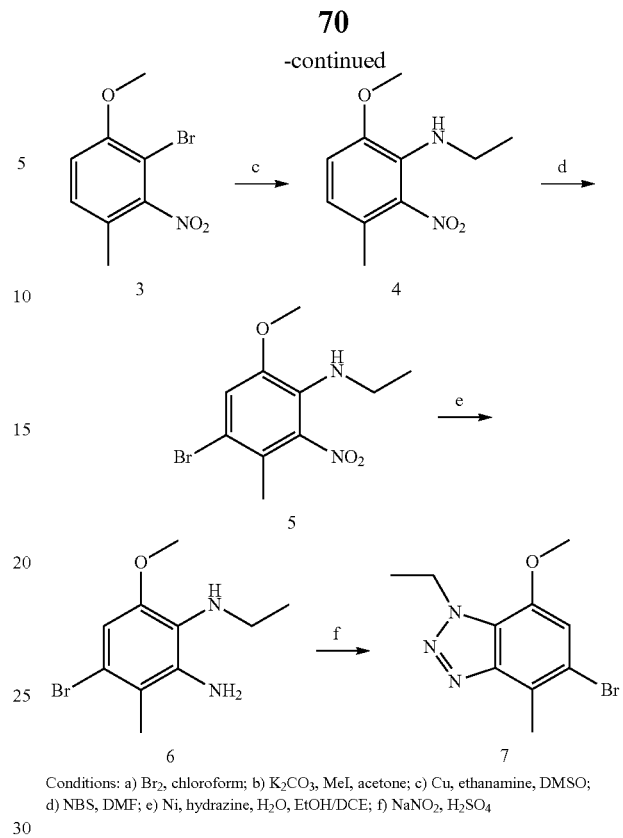

Conditions: a) Br$_2$, chloroform; b) K$_2$CO$_3$, MeI, acetone; c) Cu, ethanamine, DMSO; d) NBS, DMF; e) Ni, hydrazine, H$_2$O, EtOH/DCE; f) NaNO$_2$, H$_2$SO$_4$ Scheme 11 shows an general scheme for the preparation of 5-Bromo-1-ethyl-7-methoxy-4-methyl-1H-benzo[d][1,2,3]triazole. The triazole depicted as starting material is either commercially available or may be synthesized from readily available materials. Reaction conditions are as described above in the scheme; however, the skilled artisan will appreciate that certain modifications in the reaction conditions and/or reagents used are possible.

Bromination at C2 of the commercially available 4-methyl-3-nitrophenol 1 provides intermediate 2. Methylation of the corresponding phenol 2 with MeI under basic condition to give intermediate 3. It was then converted to ethyl amine under copper conditions to give intermediate 4. Bromination at C5 with NBS to give intermediate 5. Reductions with hydrazine hydrate catalyzed by Raney Nickel of 5 to yield aniline 6. Diazotization and cyclization provides the required triazole 7.

Scheme 12

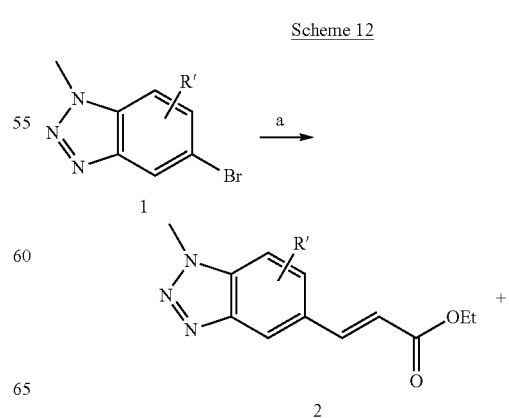

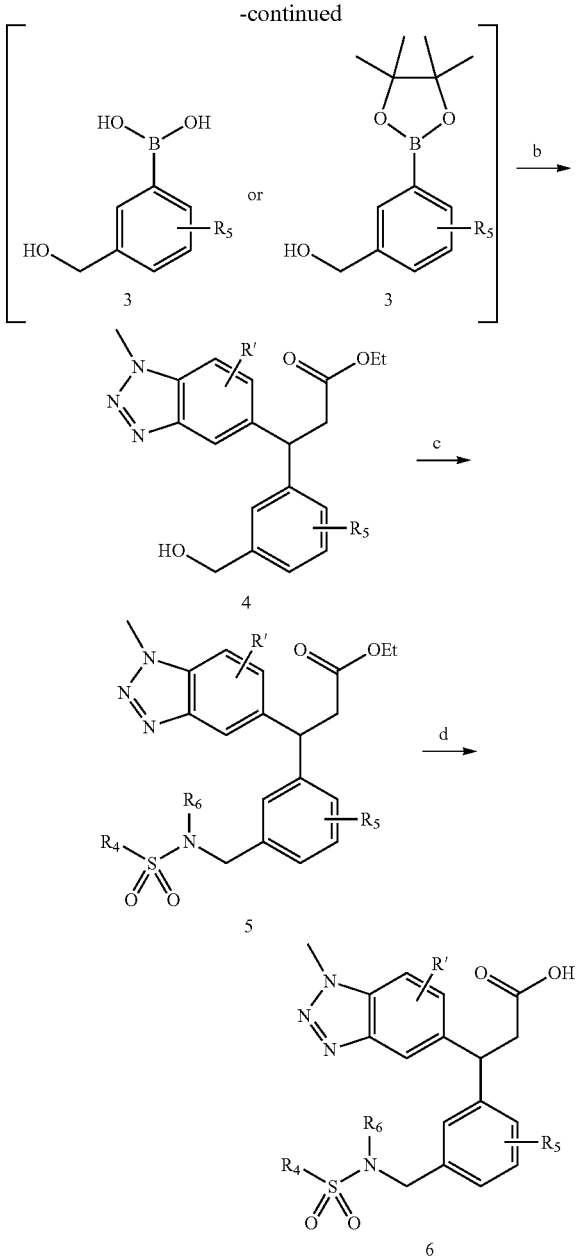

Conditions: a) Ethyl acrylate, Pd(OAc)₂, DIEA, DMF; b) [RhCl(cod)]₂, TEA, H₂O, 1,4-dioxane; c) R₇SO₂NHR₆, Bu₃P, 1,1'-(Azodicarbonyl)dipiperidine, THF; d) LiOH MeOH, THF Scheme 12 represents a general scheme for the preparation of compounds according to Formula (I). The triazole depicted as starting material is either commercially available or may be synthesized from readily available materials. Reaction conditions are as described above in the scheme; however, the skilled artisan will appreciate that certain modifications in the reaction conditions and/or reagents used are possible.

Treatment of triazole 1 with ethyl acrylate in the presence of palladium (II) acetate and diisopropylethyl amine in presence of a suitable solvent produces the desired Heck cross-coupling product 2. It will be appreciated by the skilled artisan that compound 2 may also be obtained via a Homer Wadsworth Emmons or Wittig olefination reaction starting from the appropriate aldehyde of compound 1.

Further transformation of the olefin 2 can be achieved through rhodium mediated addition of the appropriate boronic acid or boronic ester 3 in the presence of triethylamine. Completion of the analog synthesis is accomplished via Mitsunobu reaction with the requisite sulfonamide followed by hydrolysis of the ester to produce 6. It will be appreciated by the skilled artisan that sulfonamides like 5, may be synthesized via conversion of the benzylic alcohol of 4 to a leaving group such as, but not limited to, mesylate, tosylate, chloride, bromide, or iodide followed by reaction with the requisite amine NHR₆ and subsequent reaction with a sulfonylating reagent such as a sulfonyl chloride.

Scheme 13

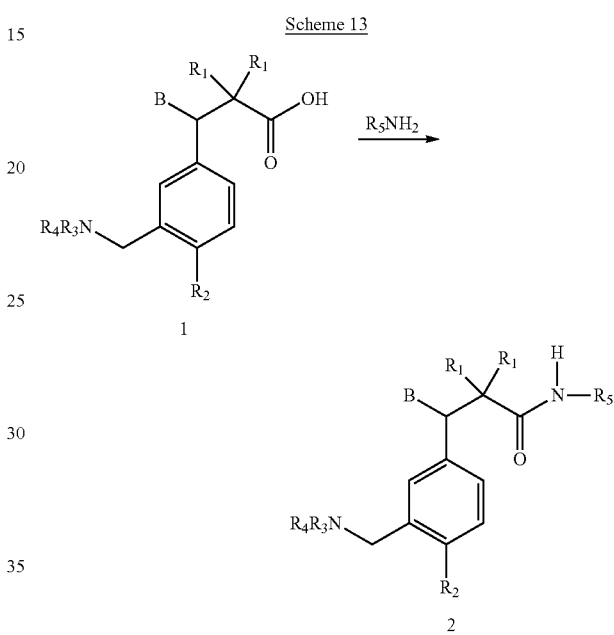

Scheme 13 represents a general scheme for the preparation of compounds according to Formula (I). Benzyl alcohols 1 are activated by typical amidation activation methods including, but not limited to, thionyl chloride, amide coupling reagents such as HATU, 1-(fluoro(pyrrolidin-1-yl) methylene)pyrrolidin-1-ium hexafluorophosphate(V) (BTFFH) or phenyl (E)-N-(tert-butyl)-N'-(pyridin-3-yl)carbamimidothioate. Amines R₅NH₂ are either combined during the activation process or after a period of time, to provide the desired amides.

Scheme 14

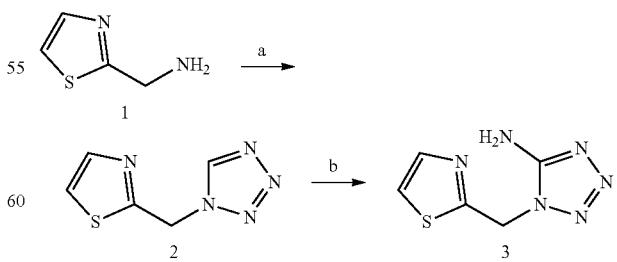

Conditions: a) NaN₃, triethylorthoformate, HOAc; b) NaN₃, NaOH, DMSO, TEA

Scheme 14 represents a general scheme for the preparation of 1-(thiazol-2-ylmethyl)-1H-tetrazol-5-amine. The tetrazole 2 is prepared from the commercially available thiazol-2-ylmethanamine using sodium azide and triethylorthoformate. The amino tetrazole is then prepared by addition of DMSO to a solution of 2, sodium azide and NaOH in IPA to provide 3.

Scheme 15

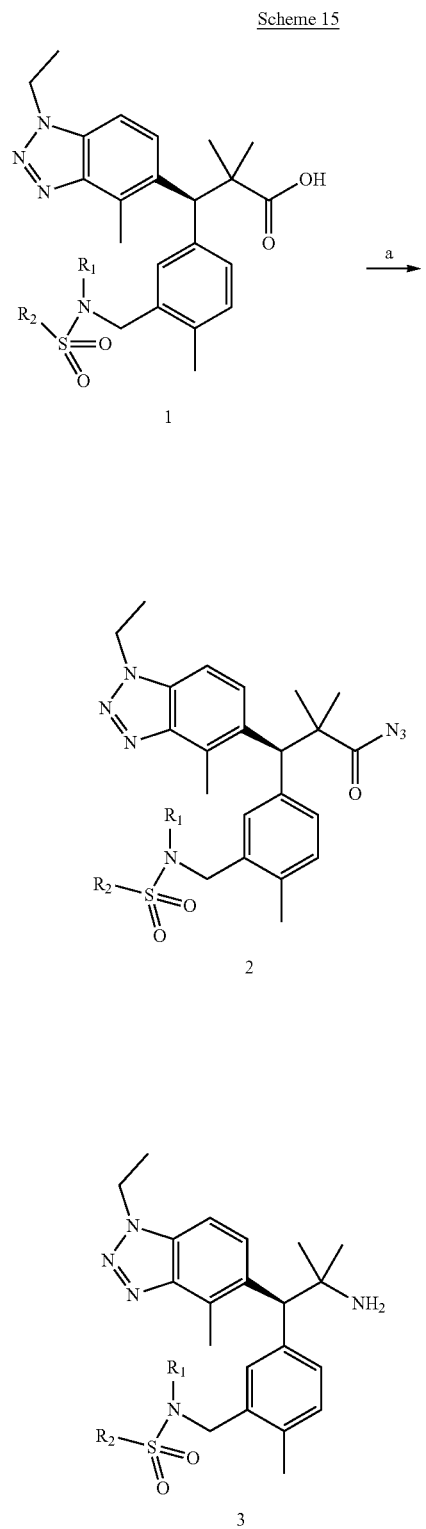

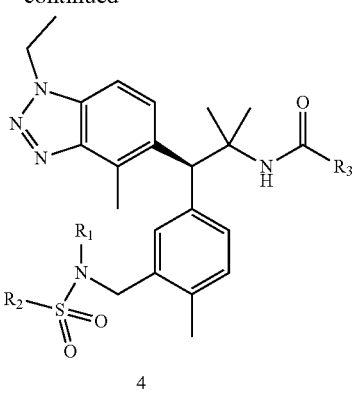

Conditions: a) DPPA, TEA, Toluene; b) Toluene 80° C.; c) coupling agent, R₃CO₂H

Scheme 15 represents a general scheme for the preparation of compounds according to Formula (I). Carboxylic acid 1 is prepared in a manner analogous to the method described in WO 2015/092713, Scheme 15 published Jun. 25, 2015. The carboxazide 2 is prepared from the reaction of the carboxylic acid 1 with DPPA and TEA in toluene. A rearrangement is performed on the carboxazide to afford the tertiary amine 3. The amide 4 is formed from the amine 3 by activation of a carboxylic acid, R₃CO₂H, with a suitable coupling agent like HATU. Alternatively, the amide could be formed by activation of the carboxylic acid with a chlorinating reagent like thionyl chloride, and subsequent displacement of the chloride with the amine 3 to afford amide 4.

Scheme 16

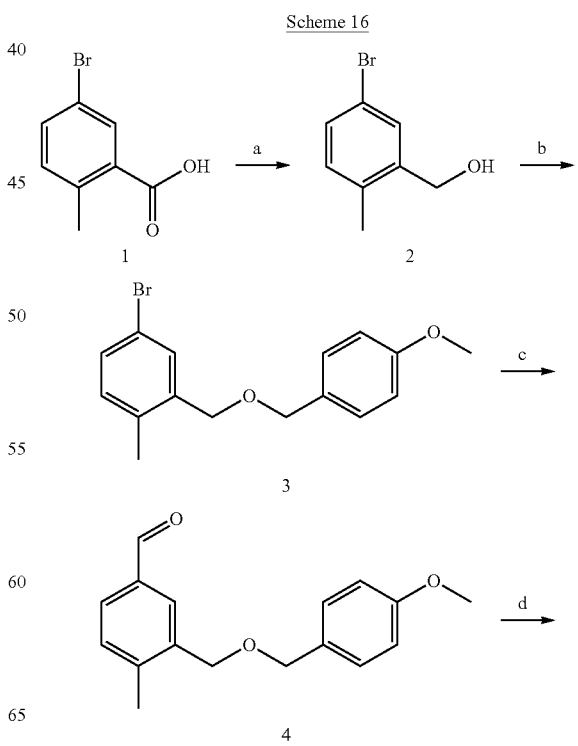

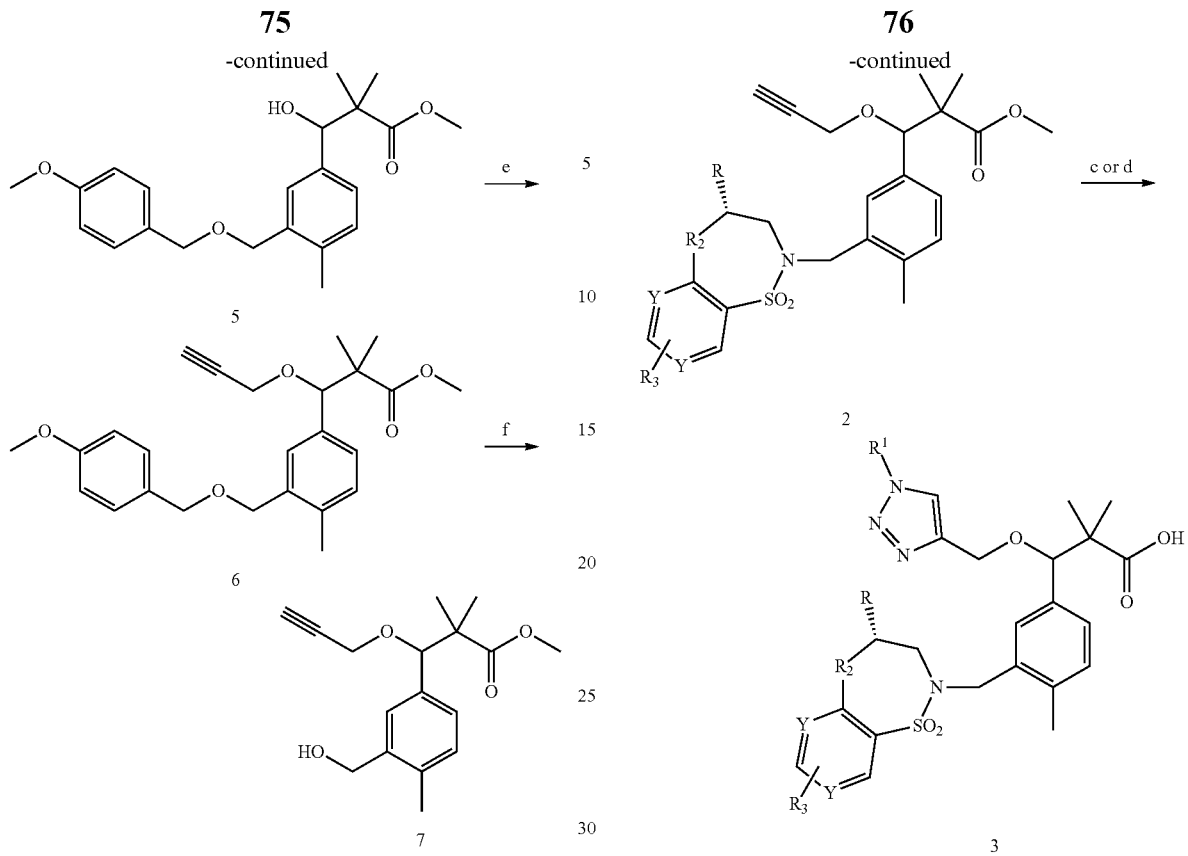

Conditions: a) BH₃—Me₂S, THF; b) NaH, DMF, PMB-Cl; c) nBuLi, THF, DMF; d) (i) 1-methylimidazole, ((1-methoxy-2-methylprop-1-en-1-yl)oxy)trimethylsilane, LiCl, DMF, (ii) NaOH, KHF₂, H₂O, HCl; e) 3-bromoprop-1-yne, NaH, DMF; f) DDQ, DCM/H₂O Conditions: a) cyclic sulfonamide, PS-PPh₃, DIAD, THF; b) (i) SOCl₂, DCM; (ii) cyclic sulfonamide, NaH, DMF; c) (i) R¹I or R¹Br, NaN₃, CuI, DIEA, i-PrOH/THF/)H₂O; (ii) NaOH, MeOH/H₂O; d) R¹N₃, CuI, DIEA, i-PrOH/(THF/)H₂O; (ii) NaOH, MeOH/H₂O Scheme 16 represents a general scheme for the preparation of compounds according to Formula I. Reaction conditions are as described above in the scheme; however, the skilled artisan will appreciate that certain modifications in the reaction conditions and/or reagents used are possible. Carboxylic acid 1 can be reduced to the benzyl alcohol in THF using a solution of borane-methyl sulfide complex to provide 2. Alkylation of the alcohol using a strong base and a suitable protecting group provides intermediate 3. Formylation of the bromide using n-butyl lithium and DMF affords 4. Intermediate 5, arises from treatment of aldehyde 4 with the appropriate silylketene acetal in the presence of lithium chloride. Intermediate 6 can be prepared by treatment of the alcohol with a strong base, like sodium hydride, followed by addition of 3-bromoprop-1-yne. Deprotection of the benzyl alcohol can be achieved using an oxidative reagent such as DDQ to provide 7.

Scheme 17 represents a general scheme for the preparation of compounds according to Formula (I). Reaction conditions are as described above in the scheme; however, the skilled artisan will appreciate that certain modifications in the reaction conditions and/or reagents used are possible.

Ether linked alkyne intermediate 1 was converted into cyclicsulfonamide substituted alkyne intermediate 2 by either treatment with cyclic sulfonamide, polymer supported PPh₃ and DIAD in THF or first treated with SOCl₂ in DCM then reaction with cyclicsulfonamide and NaH in DMF. Intermediate 2 was then converted to desired product 3 by either treatment with R¹I or R¹Br and NaN₃, CuI, DIEA in i-PrOH/THF/H₂O then followed by hydrolysis with NaOH in MeOH/H₂O or reaction with R¹N₃, CuI, DIEA in i-PrOH/THF/H₂O followed by hydrolysis with NaOH in MeOH/H₂O.

Biological Activity

As stated above, the compounds according to Formula I are NRF2 activators, and are useful in the treatment or prevention of human diseases that exhibit oxidative stress components such as respiratory and non-respiratory disorders, including COPD, asthma, ALI, ARDS, fibrosis, chronic asthma and acute asthma, lung disease secondary to environmental exposures, acute lung infection, chronic lung infection, a1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, Parkinson's disease (PD), Alzheimer's disease (AD), Friedreich's Ataxia (FA), amyo- Scheme 17

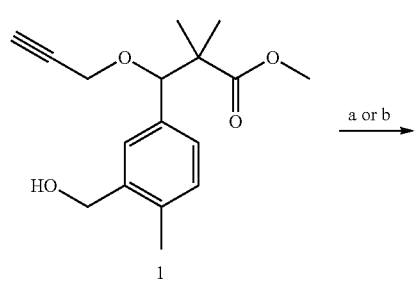

trophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness.

The biological activity of the compounds according to Formula I can be determined using any suitable assay for determining the activity of a candidate compound as a NRF2 antagonist, as well as tissue and in vivo models.

The biological activity of the compounds of Formula (I) are demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by NRF2, and thus NQO1 activity is a good marker for NRF2 activation. On day one, frozen BEAS-2B cells (ATCC) are thawed in a water bath, counted, and re-suspended at a concentration of 250,000 cells/mL. Fifty microliters of cells are plated in 384 well black clear-bottomed plates. Plates are incubated at 37° C., 5% $CO_2$ overnight. On day two, plates are centrifuged and 50 nL of compound or controls are added to the cells. Plates are then incubated at 37° C., 5% $CO_2$ for 48 hours. On day four, medium is aspirated from the plate and crude cell lysates are made by adding 13 uL of 1× Cell Signaling Technologies lysis buffer with 1 Complete, Mini, EDTA-free Protease Inhibitor Tablet (Roche) for each 10 mL of lysis buffer. After lysis plates are incubated for 20 minutes at room temperature. Two microliters of lysate are removed for use in Cell Titer Glo assay (Promega) and MTT cocktail is prepared (Prochaska et. al. 1998) for measurement of NQO1 activity. Fifty microliters of MTT cocktail is added to each well, plate is centrifuged, and analyzed on an Envision plate reader (Perkin Elmer) using Absorbance 570 nm label for 30 minutes. Product formation is measured kinetically and the $EC_{50}$ of NQO1 specific activity induction is calculated by plotting the change in absorbance (Delta OD/min) versus the log of compound concentration followed by 3-parameter fitting.

All examples described herein possessed activity in the Beas2b cell assay as listed (see table below) unless otherwise noted. $EC_{50}$s<1 nM (+++++), $EC_{50}$s 1 nM-10 nM (++++), $EC_{50}$s 10 nM-100 nM (+++), $EC_{50}$s 100 nM-1 uM (++), $EC_{50}$s 1-10 uM (+), $EC_{50}$s>10 uM (−), or were not determined (ND).

| Ex # | $EC_{50}$ |
|---|---|
| 1 | +++ |
| 2 | +++ |
| 3 | ++ |
| 4 | ++ |
| 5 | ++ |
| 6 | ++++ |
| 7 | ++++ |
| 8 | ++ |
| 9 | ++ |
| 10 | ++ |
| 11 | +++ |
| 12 | +++ |
| 13 | +++ |
| 14 | ++ |
| 15 | ++ |
| 16 | + |
| 17 | ++ |
| 18 | +++ |
| 19 | ++ |
| 20 | ++ |
| 21 | + |
| 22 | ++ |
| 23 | + |
| 24 | + |
| 25 | ++ |
| 26 | ++ |
| 27 | + |
| 28 | + |
| 29 | + |
| 30 | ++ |
| 31 | ++ |
| 32 | + |
| 33 | + |
| 34 | + |
| 35 | + |
| 36 | ++ |
| 37 | ++ |
| 38 | ++ |
| 39 | + |
| 40 | ++ |
| 41 | ++ |
| 42 | + |
| 43 | ++ |
| 44 | ++ |
| *45 | ++ |

*in some determinations $EC_{50}$ values were <170 pM

| Ex # | $EC_{50}$ |
|---|---|
| 46 | + |
| 47 | ++ |
| 48 | ++ |
| 49 | ++ |
| 50 | ++ |
| 51 | ++ |
| 52 | ++++ |
| 53 | ++ |
| 54 | +++ |
| 55 | ++ |
| 56 | ++ |
| 57 | +++ |
| 58 | ++ |
| 59 | ++ |
| 60 | ++ |
| 61 | +++ |
| 62 | +++ |
| 63 | ++++ |
| 64 | ++++ |
| 65 | +++ |
| 66 | +++ |
| 67 | ++ |
| 68 | ++++ |
| 69 | ++ |
| 70 | ++ |
| 71 | ++++ |
| 72 | +++ |
| 73 | +++ |
| 74 | ++++ |
| 75 | ++++ |
| 76 | +++ |
| 77 | ++ |
| 78 | +++ |
| 79 | ++ |
| 80 | +++ |

| Ex # | EC$_{50}$ |
|---|---|
| 81 | +++ |
| 82 | ++ |
| 83 | ++ |
| 84 | +++ |
| 85 | +++ |
| 86 | ++++ |
| 87 | ++++ |
| 88 | ++++ |
| 89 | +++ |
| 90 | ++ |
| 91 | ++++ |
| 92 | ++++ |
| 93 | ++++ |
| 94 | ++++ |
| 95 | ++++ |
| 96 | ++++ |
| 97 | ++++ |
| 98 | ++++ |
| 99 | ++ |
| 100 | ++ |
| 101 | +++ |
| 102 | +++ |
| 103 | +++ |
| 104 | ++ |
| 105 | +++ |
| 106 | ++ |
| 107 | ++ |
| 108 | ++ |
| 109 | +++ |
| 110 | +++ |
| 111 | ++ |
| 112 | ++ |
| 113 | +++ |
| 114 | +++ |
| 115 | ++++ |
| 116 | +++ |
| 117 | ++++ |
| 118 | +++ |
| 119 | ++++ |
| 120 | ++++ |
| 121 | ++ |
| 122 | ++ |
| 123 | +++ |
| 124 | ++++ |
| 125 | +++ |
| 126 | ++ |
| 127 | + |
| 128 | ++ |
| 129 | ++ |
| 130 | ++++ |
| 131 | +++ |
| 132 | +++ |
| 133 | + |
| 134 | +++ |
| 135 | +++ |
| 136 | ++ |
| 137 | +++ |
| 138 | +++ |
| 139 | +++ |
| 140 | +++ |
| 141 | +++ |
| 142 | +++ |
| 143 | +++ |
| 144 | +++ |
| 145 | ++++ |
| 146 | +++ |
| 147 | +++ |
| 148 | ++ |
| 149 | +++ |
| 150 | +++ |
| 151 | +++ |
| 152 | ++++ |
| 153 | +++ |
| 154 | +++ |
| 155 | +++ |
| 156 | ++ |
| 157 | ++ |
| 158 | +++ |
| 159 | +++ |
| 160 | ++++ |
| 161 | +++ |
| 162 | +++ |
| 163 | ++++ |
| 164 | +++ |
| 165 | +++ |
| 166 | ++++ |
| 167 | +++ |
| 168 | ++ |
| 169 | ++ |
| 170 | ++ |
| 171 | ++ |
| 172 | ++ |
| 173 | +++ |
| 174 | +++ |
| 175 | ++ |
| 176 | ++++ |
| 177 | ++++ |
| 178 | +++ |
| 179 | ++++ |
| 180 | ++++ |
| 181 | +++ |
| 182 | ++ |
| 183 | ++ |
| 184 | ++ |
| 185 | ++ |
| 186 | ++ |
| 187 | + |
| 188 | +++ |
| 189 | ++ |
| 190 | ++ |
| 191 | +++ |
| 192 | +++ |
| 193 | ++++ |
| 194 | +++ |
| 195 | +++ |
| 196 | ++ |
| 197 | +++ |
| 198 | +++ |
| 199 | +++ |
| 200 | +++ |
| 201 | ++ |
| 202 | ++++ |
| 203 | + |
| 204 | ++ |
| 205 | ++ |
| 206 | +++ |
| 207 | ++ |
| 208 | +++ |
| 209 | + |
| 210 | ++ |
| 211 | + |
| 212 | ++ |
| 213 | +++ |

Methods of Use

The compounds of Formula (I) are useful in treating respiratory and non-respiratory disorders, including COPD, asthma, ALI, ARDS, fibrosis, chronic asthma, acute asthma, lung disease secondary to environmental exposures, acute lung infection, chronic lung infection, a1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness, said disorders are treated by administering to a human in need thereof, a compound of Formula (I). Accordingly, in another aspect the invention is directed to methods of treating such conditions.

In one embodiment, the compounds of Formula (I) are useful in treating respiratory disorders including COPD, asthma, including chronic asthma and acute asthma.

In one embodiment, the compounds of Formula (I) are useful in treating hypertension, heart failure, acute coronary syndrome, myocardial infarction, myocardial repair, cardiac remodeling, cardiac arrhythmias, heart failure with preserved ejection fraction, heart failure with reduced ejection fraction and diabetic cardiomyopathy.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, optic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per day. Preferred dosages are 1-500 mg once daily, more preferred is 1-100 mg per person per day. IV dosages range form 0.1-000 mg/day, preferred is 0.1-500 mg/day, and more preferred is 0.1-100 mg/day. Inhaled daily dosages range from 10 ug-10 mg/day, with preferred 10 ug-2 mg/day, and more preferred 50 ug-500 ug/day.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus®, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g. as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g., in separate pharmaceutical compositions, for example as described in WO 03/061743 A1 WO 2007/012871 A1 and/or WO2007/068896, as well as U.S. Pat. Nos. 8,113,199, 8,161,968, 8,511,304, 8,534,281, 8,746,242 and 9,333,310.

In one embodiment, an inhalation device permitting separate containment of components is an inhaler device having two peelable blister strips, each strip containing pre-metered doses in blister pockets arranged along its length, e.g., multiple containers within each blister strip, e.g., as found in ELLIPTA®. Said device has an internal indexing mechanism which, each time the device is actuated, peels opens a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUGHALER™ of Innovata. In addition, various structures of inhalation devices provide for the sequential or separate delivery of the pharmaceutical composition(s) from the device, in addition to simultaneous delivery.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compounds of Formula (I) and pharmaceutically acceptable salts thereof may be used in combination with one or more other agents which may be useful in the prevention or treatment of allergic disease, inflammatory disease, autoimmune disease, for example; antigen immunotherapy, anti-histamines, corticosteroids, (eg fluticasone propionate, fluticasone furoate, beclomethasone dipropionate, budesonide, ciclesonide, mometasone furoate, triamcinolone, flunisolide), NSAIDs, leukotriene modulators (e.g. montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxpyridin-3-yl)benzyl)-5-((5-methylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compounds may also be used in combination with agents for aiding transplantation including Cyclosporines, Tacrolimus, Mycophenolate mofetil, Prednisone, Azathioprine, Sirolimus, Daclizumab, Basiliximab, or OKT3.

They may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics, and insulin.

The compounds may be used in combination with antihypertensives such as diuretics, ACE inhibitors, ARBS, calcium channel blockers, and beta blockers.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of the invention together with another therapeutically active agent.

EXAMPLES

The invention will now be described by reference to the following examples which are merely illustrative and are not to be construed as a limitation of the scope of the present invention. All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on silica gel 230-400, 100-200 & 60-120 Cilicant Brand. The CombiFlash® system used for purification in this application was purchased from Isco, Inc. CombiFlash® purification was carried out using prepacked silica gel columns, a detector with UV wavelength at 254 nm and a variety of solvents or solvent combinations.

Preparative HPLC was performed using a Gilson or Waters Preparative System with variable wavelength UV detection or an Agilent Mass Directed AutoPrep (MDAP) system or Shimadzu PREP LC 20AP with both mass and variable wavelength UV detection. A variety of reverse phase columns, e.g., Luna C18(2), SunFire C18, XBridge C18, Atlantics T3, Kromasil C18, Xbridge Phenyl-Hexyl columns were used in the purification with the choice of column support dependent upon the conditions used in the purification. The compounds are eluted using a gradient of $CH_3CN$ or methanol and water. Neutral conditions used an $CH_3CN$ and water gradient with no additional modifier, acidic conditions used an acid modifier, usually 0.1% TFA or 0.1% formic acid and basic conditions used a basic modifier, usually 0.1% $NH_4OH$ (added to the water) or 10 mM ammonium bicarbonate (added to the water), or 0.05% $NH_4HCO_3$ (added to water).

Analytical HPLC was run using an Agilent system or Waters Alliance HPLC with 2996 PDA detector, Waters Acquity UPLC-MS or Agilent Infinity 1290 with PDA or conducted on a Sunfire C18 column, alternative on XSELECT CSH C18 column using reverse phase chromatography with a $CH_3CN$ and water gradient with 0.1% formic acid modifier (added to each solvent) and basic conditions used a basic modifier, usually 5 mM ammonium bicarbonate or 10 mM ammonium bicarbonate in water adjusted pH to 10 with ammonia solution. The compound was analyzed by LCMS using a Shimadzu LC system with UV 214 nm wavelength detection and $H_2O$— $CH_3CN$ gradient elution (4-95% over 1.9 min.) acidified to 0.02% TFA. The reversed-phase column was a 2.1×20 mm Thermo Hypersil Gold C18 (1.9u particles) at 50° C. The single quadrupole MS detector was either a Sciex 150EX or a Waters ZQ operated in positive-ion. Alternatively, LC-MS was determined using either a PE Sciex Single Quadrupole 150EX LC-MS, or Waters ZQ Single Quadrupole, Waters 3100 Single Quadrupole, Agilent 6130 SQD or Agilent 6120 Single Quadrupole LC-MS instruments. The compound is analyzed using a reverse phase column, e.g., Thermo Hypersil Gold C18 and/or Luna C18 eluted using a gradient of $CH_3CN$ and water with a low percentage of an acid modifier such as 0.02% or 0.1% TFA.

Preparative Chiral SFC was performed using a Thar/Waters Preparative SFC System with single wavelength UV detection system. A variety of chiral SFC columns, e.g. Chiralpak IA, IC, AY, AD, IF, OJ were used in the purification. The compounds are eluted using supercritical fluid $CO_2$ and co-solvents, such as MeOH, EtOH, IPA, and combination of these solvent in different ratio based on the compound. Modifiers (0.1% to 0.4% of TFA, $NH_4OH$, DEA, TEA) can be used as needed. Normal phase chromatography is performed using the above mentioned chiral columns & pyridyl amide, ethyl pyridine achiral columns are used for chiral & achiral purifications respectively. Modifiers (0.1% of TFA, $NH_4OH$, DEA) would be used as needed. K PREP Lab 100 G-YMC instruments are used in normal phase preparative scale purifications.

Analytical Chiral SFC was run using a Thar/Waters SFC system with variable wavelength UV detection. A variety of chiral SFC columns, e.g. Chiralpak IA, IB, IC, ID, IF, AY, AD, OD, C2, AS, OJ, CCL4 were used in the purification.

The compounds are eluted using supercritical fluid $CO_2$ and co-solvents, such as MeOH, EtOH, IPA, and combination of these solvent in different ratio based on the compound selectivity. Modifiers (0.1% to 0.4% of TFA, $NH_4OH$, DEA, TEA) would be used as needed.

Celite® is a filter aid composed of acid-washed diatomaceous silica, and is a registered trademark of Manville Corp., Denver, Colo. Isolute® is a functionalized silica gel based sorbent, and is a registered trademark of Biotage AB Corp., Sweden.

Nuclear magnetic resonance spectra were recorded at 400 MHz using a Bruker AVANCE 400 or Brucker DPX400 spectrometer or Varian MR400 spectrometer. $CDCl_3$ is deuteriochloroform, DMSO-$D_6$ is hexadeuteriodimethylsulfoxide, and MeOD is tetradeuteriomethanol, $CD_2Cl_2$ is deuteriodichloromethane. Chemical shifts are reported in parts per million (δ) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiation was carried out on a Biotage Initiator® microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

Table of Abbreviations

[Rh(cod)Cl]2 or [RhCl(cod)]2: di-µ-chlorido-bis[η2,η2-(cycloocta-1,5-diene)rhodium
®T3P: 2,4,6-tripropyl-1,3,5,2,4,6-trioxatriphosphorinane 2,4,6-trioxide
° C.: degree Celsius
AcOH: acetic acid
ADDP: (E)-diazene-1,2-diylbis(piperidin-1-ylmethanone)
aq = aqueous
BINAP: 2,2'-bis(diphenylphosphino)-1,1'-binaphthalene
CDI: Carbonyl dimidazole
$CH_2Cl_2$: dichloromethane
$CH_3CN$: acetonitrile
$CH_3CN$: acetonitrile
$CHCl_3$: chloroform
$Cs_2CO_3$: cesium carbonate
DBU: 1,8-diazabicyclo[5.4.0]undec-7-ene
DCE: dichloroethane
DCM: dichloromethane
DIPEA or DIEA: diisopropylethyl amine
DME: dimethyl ether
DMF: N,N-dimethylformamide
DMF-DMA or DMF-dimethyl acetal: N,N-dimethylformaide-dimethyl acetal
DMSO: dimethyl sulfoxide
EDC: 1-ethyl-3-(3-dimethylaminopropyl)carbodiimide
$Et_2O$: diethyl ether
$Et_3N$: triethylamine
EtOAc: ethyl acetate
EtOH: ethanol
g: gram(s)
h: hour(s)
HATU: O-(7-azabenzotriazol-1-yl)-N,N,N',N'-tetramethyluronium hexafluorophosphate
HBTU: N,N,N',N'-tetramethyl-O-(1H-benzotriazol-1-yl)uronium hexafluorophosphate
HCl: hydrochloric acid

Table of Abbreviations (continued)

HOAt: 1-hydroxy-7-azabenzotriazole
HPLC: high performance liquid chromatography
IPA: isopropyl alcohol
$K_2CO_3$: potassium carbonate
KOAc: Potassium acetate
LAH: lithium aluminum hydride
LC: liquid chromatography
LC-MS: liquid chromatography-mass spectroscopy
$LiBH_4$: lithium borohydride
LiHMDS: lithium hexamethyldisilazane
LiOH: lithium hydroxide
M: molar
rt: retention time
MeCN: acetonitrile
MeI: methyl iodide
MeOH: methanol
mg: milligram(s)
$MgCl_2$: magnesium chloride
$MgSO_4$: magnesium sulfate
MHz: megahertz
min: minute(s)
mL: milliliter(s)
mmol: millimole(s)
MS: mass spectroscopy
$N_2$: nitrogen gas
$Na_2CO_3$: sodium carbonate
$Na_2SO_4$: sodium sulfate
$NaBH_3CN$ or $NaCNBH3$: sodium cyanoborohydride
NaCl: sodium chloride
NaH: sodium hydride
$NaHCO_3$: sodium bicarbonate
NaHMDS: sodium hexamethyldisilazane
$NaHSO_4$: sodium bisulfate
NaOAc: sodium acetate
NaOH: sodium hydroxide
NBS: N-Bromosuccinimide
nBuLi: n-butyl lithium
$NH_4Cl$: ammonium chloride
NMR: nuclear magnetic resonance
$P(tBu)_3$: tri-t-butyl phosphine
$Pd(PhP_3)4$: tetrakistriphenylphosphine palladium
Pd/C: palladium on carbon
$Pd_2(dba)_3$:tris(dibenzylideneacetone)-dipalladium(0)
$PdCl(dppf)$ or $Pd(dppf)Cl2$: [1,1'-bis(diphenylphosphino)-ferrocene] dichloropalladium(II)
Petrol: petroleum ether
PS-$PPh_3$: polymer supported triphenylphosphine
$PtO_2$: platinum(IV) oxide
RT: room temperature
T3P: 2,4,6-tripropyl-1,3,5,2,4,6-trioxatriphosphorinane-2,4,6-trioxide solution
TEA: triethylamine
TFA: trifluoroacetic acid
TFFH: Tetrafluoroformamidinium hexafluorophosphate
THF: tetrahydrofuran
triflic anhydride: trifluoromethanesulfonic anhydride
TsOH: p-toluenesulfonic acid
wt %: weight percent Mass Directed Auto Prep (MDAP) Conditions High pH and Low pH Column Details: Waters Xselect CSH C18 19×100 mm column The solvents employed were:

High pH

A=10 mM Ammonium Bicarbonate in water adjusted to pH 10 with aq. Ammonia solution B=Acetontrile+0.1% aq. Ammonia Low pH A=Water+0.1% Formic Acid B=Acetonitrile+0.1% Formic Acid Method A rt—(0.4 min to 0.65 min)

| Time (min) | Flow Rate (ml/min) | % A | % B |
|---|---|---|---|
| 0 | 20 | 95 | 5 |
| 1 | 20 | 95 | 5 |
| 10 | 20 | 70 | 30 |
| 10.5 | 20 | 1 | 99 |
| 12.0 | 20 | 1 | 99 |
| 12.2 | 20 | 95 | 5 |
| 15 | 20 | 95 | 5 |

Collection was triggered by uv, ms or a combination of the two.

The UV detection was at a selected wavelength generally 230 nm, 210 nm or 280 nm. Mass spectra were recorded on a mass spectrometer using an alternate-scan positive and negative mode electrospray ionization.

Method B (rt—0.65 min to 0.9 min)

| Time (min) | Flow Rate (ml/min) | % A | % B |
|---|---|---|---|
| 0 | 20 | 85 | 15 |
| 1 | 20 | 85 | 15 |
| 10 | 20 | 45 | 55 |
| 10.5 | 20 | 1 | 99 |
| 13 | 20 | 85 | 15 |
| 15 | 20 | 85 | 15 |

Collection was triggered by uv, ms or a combination of the two.

The UV detection was at a selected wavelength generally 230 nm, 210 nm or 280 nm. Mass spectra were recorded on a mass spectrometer using an alternate-scan positive and negative mode electrospray ionization Method C (rt—0.9 min to 1.16 min)

| Time (min) | Flow Rate (ml/min) | % A | % B |
|---|---|---|---|
| 0 | 20 | 70 | 30 |
| 1 | 20 | 70 | 30 |
| 10 | 20 | 15 | 85 |
| 10.5 | 20 | 1 | 99 |
| 13 | 20 | 70 | 30 |
| 15 | 20 | 70 | 30 |

Collection was triggered by uv, ms or a combination of the two.

The UV detection was at a selected wavelength generally 230 nm, 210 nm or 280 nm. Mass spectra were recorded on a mass spectrometer using an alternate-scan positive and negative mode electrospray ionization.

Method D (rt—1.16 min to 1.4 min)

| Time (min) | Flow Rate (ml/min) | % A | % B |
|---|---|---|---|
| 0 | 20 | 50 | 50 |
| 1 | 20 | 50 | 50 |
| 10 | 20 | 1 | 99 |
| 10.5 | 20 | 1 | 99 |
| 13 | 20 | 50 | 50 |
| 15 | 20 | 50 | 50 |

Collection was triggered by uv, ms or a combination of the two.

The UV detection was at a selected wavelength generally 230 nm, 210 nm or 280 nm. Mass spectra were recorded on a mass spectrometer using an alternate-scan positive and negative mode electrospray ionization.

Method E (rt—1.4 to 2.0 min)

| Time (min) | Flow Rate (ml/min) | % A | % B |
|---|---|---|---|
| 0 | 20 | 20 | 80 |
| 1 | 20 | 20 | 80 |
| 10 | 20 | 1 | 99 |
| 10.5 | 20 | 1 | 99 |
| 13 | 20 | 20 | 80 |
| 15 | 20 | 20 | 80 |

Collection was triggered by uv, ms or a combination of the two.

The UV detection was at a selected wavelength generally 230 nm, 210 nm or 280 nm. Mass spectra were recorded on a mass spectrometer using an alternate-scan positive and negative mode electrospray ionization.

INTERMEDIATES

Intermediate 1: (S)-4-Ethyl-2,3,4,5-tetrahydrobenzo[f][1,2]thiazepine 1,1-dioxide

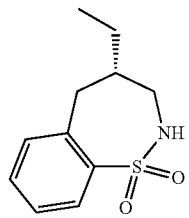

(S)-4-Ethyl-2,3,4,5-tetrahydrobenzo[f][1,2]thiazepine 1,1-dioxide of the invention was made using compounds described in WO 2017/060854 on page 135, published Apr. 13, 2017, and incorporated herein by reference.

Intermediate 2: (R)-4-Bromo-2-fluoro-N-(2-hydroxybutyl)benzenesulfonamide

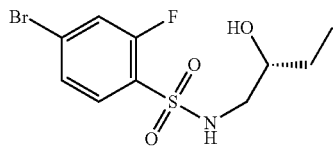 [SMILES: CC[C@@H](O)CNS(=O)(=O)c1ccc(Br)cc1F]

To a solution of 4-bromo-2-fluorobenzene-1-sulfonyl chloride (5 g, 18.28 mmol) in tetrahydrofuran (THF) (50 mL) and water (16.67 mL) were added (R)-4-bromo-2-fluoro-N-(2-hydroxybutyl)benzenesulfonamide (3.8 g, 10.51 mmol, 57.5% yield) and $K_2CO_3$ (3.28 g, 23.77 mmol) at 0° C. The reaction mixture was stirred at ambient temperature for 12 hr. To the reaction mixture was added water (30 mL) and extracted with ethyl acetate (2×30 ml). The combined organic layers were washed with a brine solution (20 L), dried over anhydrous $Na_2SO_4$, filtered and concentrated under reduced pressure to give crude compound. The product was purified by flash column chromatography using EtOAc:Hexane (4:6) as solvent. The eluted fractions were concentrated under vacuum to provide the title compound. (3.8 g, 10.51 mmol, 57.5% yield). LC-MS m/z=326/328 (M+H)$^+$, 2.34 min (ret. time).

Intermediate 3: (R)-7-bromo-4-ethyl-3,4-dihydro-2Hbenzo[b][1,4,5]oxathiazepine 1,1-dioxide

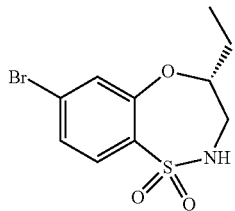 [SMILES: CC[C@@H]1CNS(=O)(=O)c2ccc(Br)cc2O1]

To a stirred solution of (R)-4-bromo-2-fluoro-N-(2-hydroxybutyl)benzenesulfonamide (21.8 g, 65.7 mmol) in dimethyl sulfoxide (DMSO) (200 mL) was added potassium tert-butoxide (18.42 g, 164 mmol) at 0° C. The reaction mixture was stirred at 80° C. for 16 h. To the reaction mixture was added water (100 ml) and organic layer was separated. The organic layer was washed with brine solution (100 ml), dried over anhydrous $Na_2SO_4$, filtered and concentrated under reduced pressure to get crude compound. The crude residue was purified by flash column chromotography using EtOAc:Hexane (2:6) as solvent. The eluted fractions were concentrated under vacuum to afford the title compound (8 g, 26.0 mmol, 39.6% yield). This product and the same product of another reaction performed in the same manner were combined and washed with diethyl ether and dried to afford the title compound. (8.38 g, 27.37 mmol). LCMS m/z=306 (M+H)$^+$, 2.17 min (ret. time).

Intermediate 4: (R)-5-bromo-2-fluoro-N-(2-hydroxybutyl)benzenesulfonamide

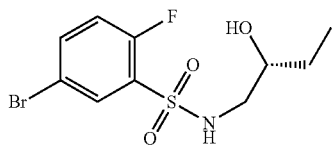 [SMILES: CC[C@@H](O)CNS(=O)(=O)c1cc(Br)ccc1F]

To a solution of 5-bromo-2-fluorobenzene-1-sulfonyl chloride (45 g, 165 mmol) in a mixture of tetrahydrofuran (THF) (300 mL) and water (150 mL) was added (R)-1-aminobutan-2-ol (14.67 g, 165 mmol) and $K_2CO_3$ (27.3 g, 197 mmol) at 0° C. The reaction mixture was stirred at ambient temperature for 16 h. The reaction mixture was evaporated under reduced pressure, quenched with water and extracted with DCM (2×). The organic layer was dried under anhydrous $Na_2SO_4$ and filtered. The filtrate was evaporated under reduced pressure to get the crude compound. The crude compound was washed with n-pentane (75 mL) and diethyl ether (35 mL) to afford the title compound (30 g, 77 mmol, 47.1% yield). LCMS m/z=324 (M–H)$^-$, 2.36 min (ret. time).

Intermediate 5: (R)-8-bromo-4-ethyl-3,4-dihydro-2Hbenzo[b][1,4,5]oxathiazepine 1,1-dioxide

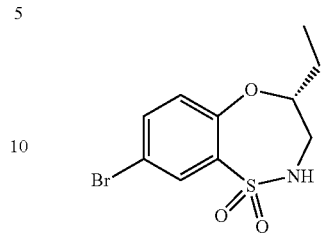

To a solution of (R)-5-bromo-2-fluoro-N-(2-hydroxybutyl)benzenesulfonamide (16 g, 41.2 mmol) in dimethyl sulfoxide (DMSO) (120 mL) was added KOtBu (9.25 g, 82 mmol) at 0° C. The reaction mixture was stirred at 70° C. for 6 h. The reaction mixture was cooled to ambient temperature, quenched with ice cold water (100 mL), neutralized with to pH=6 with 1N HCl and extracted with EtOAc (2×150 mL). The organic layer was washed with ice cold water (2×150 mL), brine solution (90 mL), dried under anhydrous $Na_2SO_4$ and filtered. The filtrate was evaporated under reduced pressure to get the crude compound. The crude product was washed with n-pentane (90 mL) & diethyl ether (50 mL) to afford the title compound. LCMS m/z=304/306 (M–H)$^-$, 2.14 min (ret. time).

Intermediate 6: 2-Bromo-N-(2-methylallyl)-4-(trifluoromethyl)benzenesulfonamide

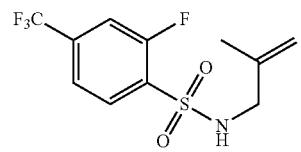 [SMILES: C=C(C)CNS(=O)(=O)c1ccc(C(F)(F)F)cc1F]

To a solution of 2-bromo-4-(trifluoromethyl)benzene-1-sulfonyl chloride (20 g, 61.8 mmol) in dichloromethane (DCM) (200 mL) at 0° C. was added 2-methylprop-2-en-1-amine (4.84 g, 68.0 mmol) and TEA (17.23 mL, 124 mmol). The reaction mixture was stirred at ambient temperature. The reaction mixture quenched with water (500 mL) and extracted with DCM (2×500 mL). The combined organic layer was washed with brine solution (100 ml), dried over anhydrous $Na_2SO_4$, filtered and concentrated to give the title compound (19 g). LCMS m/z=358 (M+H)$^+$, 2.46 mins (ret.time).

Intermediate 7: 4-Methyl-7-(trifluoromethyl)-2,3,4,5-tetrahydrobenzo[f][1,2]thiazepine 1,1-dioxide

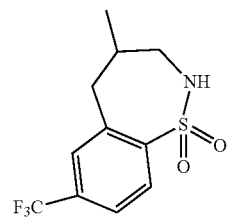 [SMILES: CC1CNS(=O)(=O)c2ccc(C(F)(F)F)cc2C1]

To a solution of 2-bromo-N-(2-methylallyl)-4-(trifluoromethyl)benzenesulfonamide (19 g, 53.0 mmol) in toluene (290 mL) was added AIBN (4.36 g, 26.5 mmol) and the reaction was heated to 70° C. Then Bu₃SnH (28.3 mL, 106 mmol) was added into the reaction mixture at this temperature. The reaction was stirred at 110° C. for 16 h. The reaction mixture was cooled to ambient temperature and concentrated under reduced pressure to get crude compound. The crude compound was purified by silica gel column chromatography (Mesh size 100-200) eluted with 30% EtOAc:Hexane to afford the title compound (6 g) as light brownish solid compound. LCMS m/z 278.14 (M−H)⁺, 2.094 mins (ret. time)

Intermediate 8: (R)-4-Methyl-7-(trifluoromethyl)-2,3,4,5-tetrahydrobenzo[f][1,2]thiazepine 1,1-dioxide and Intermediate 9: (S)-4-methyl-7-(trifluoromethyl)-2,3,4,5-tetrahydrobenzo[f][1,2]thiazepine 1,1-dioxide

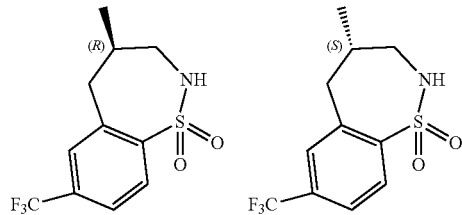

4-Methyl-7-(trifluoromethyl)-2,3,4,5-tetrahydrobenzo[f][1,2]thiazepine 1,1-dioxide (5.4 g, 19.34 mmol) was resolved by Chiral SFC (Column: Chiralpak AS-H (250×30) mm, 5 u; co-solvent: 50% IPA; flowrate:100 g/min; Back pressure: 100 Bar) to give (R)-4-methyl-7-(trifluoromethyl)-2,3,4,5-tetrahydrobenzo[f][1,2]thiazepine 1,1-dioxide (2.3 g, 8.17 mmol, 42.3 yield) as white solid 1H NMR (400 MHz, DMSO-d6) δ ppm 7.98 (d, J=7.89 Hz, 1H) 7.75-7.85 (m, 3H) 3.35 (br s, 1H) 3.21 (br s, 3H) 1.85 (br s, 1H) 0.85 (br d, J=5.92 Hz, 3H) LCMS m/z 278.07 (M−H)⁺, 2.715 mins (ret. time) (chiral SFC ret. time: 11.815 min) and (S)-4-methyl-7-(trifluoromethyl)-2,3,4,5-tetrahydrobenzo[f][1,2]thiazepine 1,1-dioxide (2.06 g, 7.32 mmol, 37.8% yield) as white solid 1H NMR (400 MHz, DMSO-d6) δ ppm 7.98 (d, J=7.89 Hz, 1H) 7.75-7.85 (m, 3H) 3.35 (br s, 1H) 3.21 (br s, 3H) 1.85 (br s, 1H) 0.85 (br d, J=5.92 Hz, 3H) LCMS m/z 278.07 (M−H)⁺, 2.715 mins (ret. time) (chiral SFC ret. time: 14.631 min)

Intermediate 10:
N-(2,4-Dimethoxybenzyl)-2-methylenebutan-1-amine

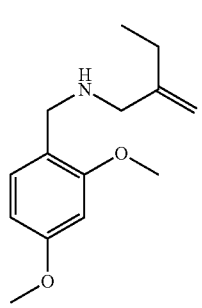 [SMILES: C=C(CC)CNCc1ccc(OC)cc1OC]

To a solution of 2-methylenebutanal (100 g, 1189 mmol) in toluene (135 mL) was added (2,4-dimethoxyphenyl)methanamine (199 g, 1189 mmol) and stirred at 110° C. for 48 hr. The reaction mixture was concentrated and dissolved in ethanol (82 mL). NaBH₄ (90 g, 2378 mmol) was added at 0° C. and the reaction stirred at ambient temperature for 6 h. The reaction mixture was evaporated under reduced pressure, quenched with water (200 mL) and extracted with DCM (2×200 mL). The organic layer was dried over anhydrous Na₂SO₄ and filtered. The filtrate was evaporated under reduced pressure and the residue was purified by flash chromatography eluting with 1:9 EtOAc:Hexane. To provide the title compound. (68 g, 16.53% yield). LC/MS m/z 236 (M+H)⁺, 3.62 min (ret. time).

Intermediate 11: 2-Bromo-N-(2,4-dimethoxybenzyl)-N-(2-methylenebutyl)-5-(trifluoromethyl)benzenesulfonamide

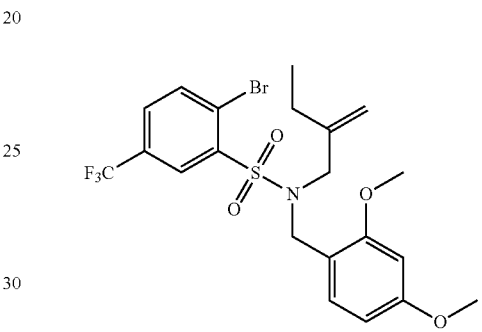

To a solution of N-(2,4-dimethoxybenzyl)-2-methylenebutan-1-amine (15 g, 43.3 mmol) in dichloromethane (DCM) (300 mL) was added Et₃N (12.08 mL, 87 mmol) at 0° C. followed by addition of 2-bromo-5-(trifluoromethyl)benzene-1-sulfonyl chloride (14.02 g, 43.3 mmol) and the reaction allowed to stir at ambient temperature for 16 h. The reaction mixture was evaporated under reduced pressure, quenched with water (300 mL) and extracted with DCM (2×300 mL). The organic layer was dried over anhydrous Na₂SO₄ and filtered. The filtrate was evaporated under reduced pressure and the residue was purified by flash chromatography eluting with 2%, 4% then 8% petroleum ether/ethyl acetate to provide the title compound. (20 g, 81% yield). GC/MS m/z 521/523 (M+H)⁺, 10.66 min (ret. time).

Intermediate 12: 2-Bromo-N-(2-methylenebutyl)-5-(trifluoromethyl)benzenesulfonamide

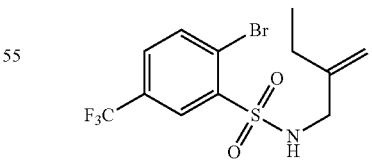

To a solution of 2-bromo-N-(2,4-dimethoxybenzyl)-N-(2-methylenebutyl)-5-(trifluoromethyl)benzenesulfonamide (39 g, 38.1 mmol) in dichloromethane (DCM) (300 mL) was added TFA (32 mL, 415 mmol) at 0° C. Anisole (10 mL, 92 mmol) was added and the reaction stirred at ambient temperature for 16 h. The reaction mixture was evaporated under reduced pressure, quenched with water (200 mL) and extracted with DCM (2×200 mL). The organic layer was dried over anhydrous Na$_2$SO$_4$ and filtered. The filtrate was evaporated under reduced pressure and the residue was purified by flash chromatography eluting with 2%, 4% then 8% petroleum ether/ethyl acetate to provide the title compound. (17 g, 96% yield). LC/MS m/z 369/371 (M−H)(M), 2.67 min (ret. time).

Intermediate 13: (S)-4-Ethyl-8-(trifluoromethyl)-2,3,4,5-tetrahydrobenzo[f][1,2]thiazepine 1,1-dioxide and Intermediate 14: (R)-4-ethyl-8-(trifluoromethyl)-2,3,4,5-tetrahydrobenzo[f][1,2]thiazepine 1,1-dioxide

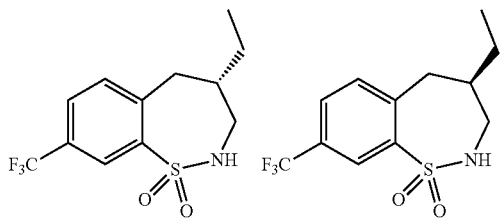 [SMILES: CC[C@@H]1CNS(=O)(=O)c2cc(C(F)(F)F)ccc2C1 ; CC[C@H]1CNS(=O)(=O)c2cc(C(F)(F)F)ccc2C1]

To a solution of 2-bromo-N-(2-methylenebutyl)-5-(trifluoromethyl)benzenesulfonamide (17.5 g, 45.1 mmol) in toluene (200 mL) was added AIBN (3.71 g, 22.57 mmol) and the reaction was heated to 70° C. Tri-n-butyltin hydride (36.4 mL, 135 mmol) was added and the reaction stirred at 110° C. for 16 h. The reaction mixture was cooled to ambient temperature and concentrated under reduced pressure. The residue was purified by flash chromatography eluting with EtOAc:Hexane (15:85) to provide the title compound as a racemate. (11.5 g, 79% yield). LC/MS m/z 292 (M−H), 2.54 min (ret. time). The compound was resolved by chiral SFC (Column: Lux Cellulose-2 30×250 mm, 5 u; Co-solvent: 20% (100% IPA); 80% CO2, Flowrate: 90 g/min; Back pressure: 90Bar) to provide (S)-4-ethyl-8-(trifluoromethyl)-2,3,4,5-tetrahydrobenzo[f][1,2]thiazepine 1,1-dioxide (4.2 g, 36% yield). m/z 294 (M+H)$^+$, 3.29 min (ret. time), (chiral SFC ret. time: 4.91 min) and (R)-4-ethyl-8-(trifluoromethyl)-2,3,4,5-tetrahydrobenzo[f][1,2]thiazepine 1,1-dioxide (3.8 g, 32% yield). LCMS m/z 294 (M+H)$^+$, 3.29 min (ret. time), (chiral SFC ret. time: 6.71 min).

Intermediate 15: 2-Bromo-N-(2-methylallyl)benzenesulfonamide

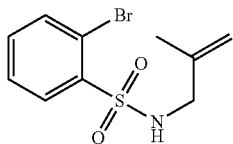

To a solution of 2-bromobenzene-1-sulfonyl chloride (25 g, 98 mmol) in dichloromethane (DCM) (250 mL) at 0° C. was added TEA (13.64 mL, 98 mmol) and 2-methylprop-2-en-1-amine (6.96 g, 98 mmol) and stirred for 10 min after which time the reaction was stirred at ambient temperature for 16 h. The reaction mixture was quenched with ice cold water and extracted with DCM (2×200 mL). The combined organic layer was washed with ice cold water (2×100 mL), washed with brine solution (100 mL), dried over anhydrous Na$_2$SO$_4$. It was filtered and concentrated to give the title compound (20 g, 68.3 mmol, 69.8% yield). LC-MS m/z=289.81 (M+H)$^+$, 2.20 min (ret. time).

Intermediate 16: 4-Methyl-2,3,4,5-tetrahydrobenzo[f][1,2]thiazepine 1,1-dioxide

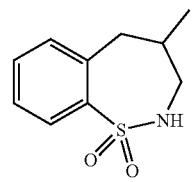

To a solution of 2-bromo-N-(2-methylallyl)benzenesulfonamide (16 g, 55.1 mmol) in toluene (160 mL) at ambient temperature was added AIBN (1.811 g, 11.03 mmol). The reaction mixture was heated to 75° C. and tri-n-butyltin hydride (29.4 mL, 110 mmol) was added and the reaction was heated at 110° C. for 18 h. The reaction mixture was cooled to ambient temperature and diluted with ice water (500 mL) and extracted with EtOAc (2×300 mL). The combined organic layer was washed with chilled brine solution (200 mL) and dried over anhydrous Na$_2$SO$_4$, filtered and concentrated. The crude residue was purified on flash column chromatography eluting with 15% ethyl acetate in hexane. Desired fractions were concentrated to give the title compound (8.51 g, 39.9 mmol, 72.3% yield) as a white solid. LC-MS m/z=211.11 (M+H)$^+$, 1.826 min (ret. time).

Intermediate 17: (S)-4-Methyl-2,3,4,5-tetrahydrobenzo[f][1,2]thiazepine 1,1-dioxide and (R)-4-methyl-2,3,4,5-tetrahydrobenzo[f][1,2]thiazepine 1,1-dioxide

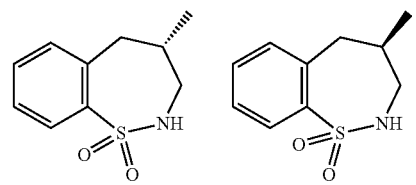

4-Methyl-2,3,4,5-tetrahydrobenzo[f][1,2]thiazepine 1,1-dioxide (4000 mg, 18.93 mmol) was resolved by Chiral SFC (Column: Chiralpak AY 20×250 mm, 5 u; co-solvent: 20% EtOH; Flow rate: 50 mg/min; Back pressure: 100Bar) to give (S)-4-methyl-2,3,4,5-tetrahydrobenzo[f][1,2]thiazepine 1,1-dioxide (2.2996 g, 10.88 mmol, 57.5% yield) (chiral SFC ret. time: 1.85 min) LC-MS m/z 211.9 (M+H)$^+$, 0.72 min (ret. time) and (R)-4-methyl-2,3,4,5-tetrahydrobenzo[f][1,2]thiazepine 1,1-dioxide (2.2195 g, 10.50 mmol, 55.5% yield) (chiral SFC ret. time: 2.5 min) LC-MS m/z=211.9 (M+H)$^+$, 0.72 min (ret. time).

Intermediate 18: 2-Chloropyridine-3-sulfonyl Chloride

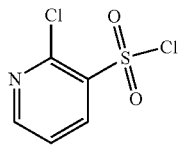 [SMILES: O=S(=O)(Cl)c1cccnc1Cl]

Step A: Thionyl chloride (159 mL, 2178 mmol) was added drop wise over 60 min to water (450 mL) at 0° C. The solution was allowed to stirred at ambient temperature for 17 h then copper(I) chloride (0.554 g, 5.60 mmol) was added to the mixture at –3° C. and the resulting yellow green solution was stirred for 1 hour at –3° C.

Step B: 37% HCl (503 mL, 6129 mmol) was added with vigorous stirring to 2-chloropyridin-3-amine (40 g, 311 mmol) at –5° C. and a solution of sodium nitrite (37.8 g, 548 mmol) in water (82 mL) was added drop wise over 45 min, the temperature of the reaction mixture was maintained at –5° C. and stirred for 10 min.

Step C: The mixture obtained from step B was added to the solution obtained from step A over 30 min at –3° C. The reaction mixture was maintained at 0° C. for 75 min with vigorous stirring. The solid was filtered and dried to give the title compound (20 g, 92 mmol, 29.5% yield) as brown color solid. LCMS m/z 212.02 (M+H)+, 2.058 min (ret. time)

Intermediate 19: 2-Chloro-N-(2-methylallyl)pyridine-3-sulfonamide

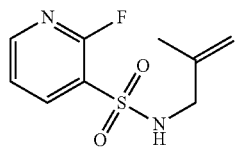

To a solution of 2-chloropyridine-3-sulfonyl chloride (20 g, 94 mmol) in dichloromethane (DCM) (200 mL) was added 2-methylprop-2-en-1-amine (7.38 g, 104 mmol) and TEA (26.3 mL, 189 mmol). It was stirred for 1 h at ambient temperature. The reaction mixture was quenched with water (100 mL) and extracted with DCM (3×80 mL). The combined organic layer was washed with brine solution (80 mL), dried over anhydrous $Na_2SO_4$, filtered and concentrated. The crude residue was purified by column chromatography eluting with 25% ethyl acetate in n-hexane. Desired fractions were concentrated to give the title compound (16 g, 63.5 mmol, 67.4% yield). LCMS m/z 246.97 (M+H)+, 1.800 min (ret. time)

Intermediate 20: 4-Methyl-2,3,4,5-tetrahydropyrido[2,3-f][1,2]thiazepine 1,1-dioxide

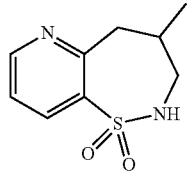

To a solution of 2-chloro-N-(2-methylallyl)pyridine-3-sulfonamide (15 g, 60.8 mmol) in toluene (150 mL) was added AIBN (1.997 g, 12.16 mmol) and heated to 75° C. then tri-n-butyltin hydride (48.7 mL, 182 mmol) was added and the reaction mixture was heated to 110° C. for 20 h. The reaction mixture was concentrated. The residue was diluted with ethyl acetate (200 mL), water was added and extracted. The organic layer was washed with brine solution (80 mL), dried over anhydrous $Na_2SO_4$, filtered and concentrated. The crude residue was purified by column chromatography eluting with 25% ethyl acetate in n-hexane. Desired fractions were concentrated to give the title compound (4.27 g, 19.80 mmol, 32.6% yield) LCMS m/z 213.07 (M+H)+, 1.372 min (ret. time)

Intermediate 21: (S)-4-Methyl-2,3,4,5-tetrahydropyrido[2,3-f][1,2]thiazepine 1,1-dioxide and (R)-4-methyl-2,3,4,5-tetrahydropyrido[2,3-f][1,2]thiazepine 1,1-dioxide

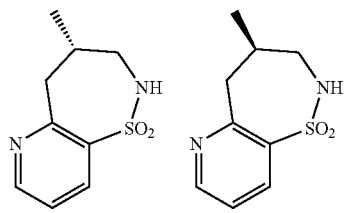

4-methyl-2,3,4,5-tetrahydropyrido[2,3-f][1,2]thiazepine 1,1-dioxide (4.27 g, 20.12 mmol) was resolved by Chiral SFC (Column: Chiralpak IC 20×150 mm, 5 u; co-solvent: 20% IPA; flowrate: 50 g/min; Back pressure: 100Bar) to give (S)-4-methyl-2,3,4,5-tetrahydropyrido[2,3-f][1,2]thiazepine 1,1-dioxide (1.96 g, 9.23 mmol, 45.9% yield) LC-MS m/z 213.0 (M+H)+, 0.43 min (ret. time) (chiral SFC ret. time: 2.95 min) and (R)-4-methyl-2,3,4,5-tetrahydropyrido[2,3-f][1,2]thiazepine 1,1-dioxide (1.96 g, 9.23 mmol, 45.9% yield) LC-MS m/z 213.0 (M+H)+, 0.44 min (ret. time) (chiral SFC ret. time: 4.09 min)

Intermediate 22: (R)-1-Azidobutan-2-ol

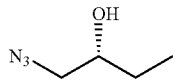

To a round bottom flask equipped with a reflux condenser was added (R)-2-ethyloxirane (26.0 g, 361 mmol), sodium azide (28.1 g, 433 mmol) and ammonium chloride (23.15 g, 433 mmol) followed by a solution of ethanol (200 mL) and water (200 mL). The reaction mixture was heated at 100° C. for 24 hr. The reaction mixture was cooled, the ethanol removed under reduced pressure and the residual aqueous layer extracted with diethyl ether (3×250 mL). The organic extracts were combined, washed with brine, dried over sodium sulfate, filtered and the solvent evaporated under reduced pressure to afford an oil. The oil was purified by silica gel chromatography (0-10% MeOH/DCM) to afford (R)-1-azidobutan-2-ol (19.8 g, 172 mmol, 47.7% yield). $^1$H NMR ($CHCl_3$-d) δ: 3.64-3.76 (m, 1H), 3.35-3.46 (m, 1H), 3.20-3.34 (m, 1H), 2.19 (s, 1H), 1.47-1.60 (m, 2H), 0.90-1.06 (m, 3H)

Intermediate 23: (R)-1-Aminobutan-2-ol

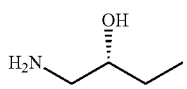

To a solution of (R)-1-azidobutan-2-ol (19.80 g, 172 mmol) in ethanol (250 mL) was added 10% palladium on carbon (1.830 g, 17.20 mmol) and the suspension was placed under a hydrogen atmosphere for 72 hr. Additional 10% palladium on carbon (1.830 g, 17.20 mmol) was added at 24 and 48 hr time points. The reaction mixture was filtered through celite and then evaporated under reduced pressure to afford a light yellow oil (R)-1-aminobutan-2-ol (13.5 g, 151 mmol, 88% yield). $^1$H NMR (CHCl$_3$-d) δ: 3.43 (m, 1H), 2.77 (m, 1H), 2.64 (br. s., 3H), 2.52 (m, 1H), 1.36-1.48 (m, 2H), 0.87-0.96 (m, 3H).

Intermediate 24: (R)-2-Chloro-N-(2-hydroxybutyl)pyridine-3-sulfonamide

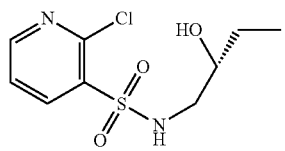 [SMILES: CC[C@@H](O)CNS(=O)(=O)c1cccnc1Cl]

To a solution of 2-chloropyridine-3-sulfonyl chloride (15 g, 70.7 mmol) in tetrahydrofuran (THF) (100 mL) was added (R)-1-aminobutan-2-ol (6.31 g, 70.7 mmol), potassium carbonate (9.78 g, 70.7 mmol) and water (30 mL). The reaction mixture was stirred for 2 h at ambient temperature. The reaction mixture was quenched with water (20 mL) and extracted with EtOAc (3×20 mL). The combined organic layer was dried over anhydrous Na$_2$SO$_4$, filtered and concentrated to give the title compound (14 g, 43.6 mmol, 61.7% yield). LC-MS m/z 262.95 (M–H)$^+$, 2.627 min (ret. time).

Intermediate 25: (R)-4-Ethyl-3,4-dihydro-2H-pyrido[2,3-b][1,4,5]oxathiazepine 1,1-dioxide

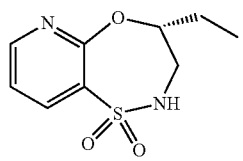

To a solution of (R)-2-chloro-N-(2-hydroxybutyl)pyridine-3-sulfonamide (13 g, 49.1 mmol) in tetrahydrofuran (THF) (130 mL) at 5° C. was added potassium tert-butoxide (16.53 g, 147 mmol), and the reaction was heated to 75° C. for 3 h. The reaction mixture was cooled to ambient temperature and then quenched with ice water (200 mL) and neutralized with 1N HCl (10 mL) solution. It was extracted with ethyl acetate (4×100 mL). The combined organic layer was washed with ice cold water (30 mL), washed with brine solution (30 mL), dried over anhydrous Na$_2$SO$_4$, filtered and concentrated. The crude residue was purified via flash chromatography eluting with EtOAc:hexane (4:6). Desired fractions were concentrated to give the title compound (4.9 g, 20.77 mmol, 42.3% yield) as an off-white solid. LCMS m/z=229.08 (M+H)$^+$, 2.555 min (ret. time).

Intermediate 26: (R)-2-Fluoro-N-(2-hydroxybutyl)benzenesulfonamide

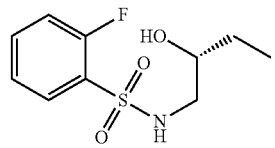 [SMILES: CC[C@@H](O)CNS(=O)(=O)c1ccccc1F]

To a solution of (R)-1-aminobutan-2-ol (14.66 g, 164 mmol) in tetrahydrofuran (THF) (200 mL) and water (60 mL) at ambient temperature was added K$_2$CO$_3$ (14.20 g, 103 mmol) and 2-fluorobenzene-1-sulfonyl chloride (20 g, 103 mmol). It was stirred for 16 h. The reaction mixture was diluted with water (100 mL) and extracted with EtOAc (2×100 mL). The combined organic layer was washed with brine solution (200 mL) and dried over anhydrous Na$_2$SO$_4$, filtered and concentrated to give the title compound (14 g, 53.8 mmol, 52.3% yield) as a gummy liquid. LC-MS m/z 494.83 (2M–H)$^+$, 1.660 min (ret. time).

Intermediate 27: (R)-4-Ethyl-3,4-dihydro-2H-benzo[b][1,4,5]oxathiazepine 1,1-dioxide

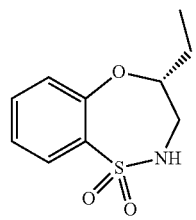

To a solution of (R)-2-fluoro-N-(2-hydroxybutyl)benzenesulfonamide (14 g, 56.6 mmol) in dimethyl sulfoxide (DMSO) (140 mL) at 0° C. was added potassium tert-butoxide (6.35 g, 56.6 mmol). It was then heated at 80° C. for 4 h. The reaction mixture was cooled and neutralized with 1N HCl, diluted with ice water (500 mL) and extracted with EtOAc (2×400 mL). The combined organic layer was washed with chilled brine solution (200 mL) and dried over anhydrous Na$_2$SO$_4$, filtered and concentrated. The crude residue was purified on flash column chromatography eluting with 50% EtOAc in hexane. Desired fractions were concentrated to give the title compound (11.12 g, 48.9 mmol, 86% yield) as a white solid. LC-MS m/z 228.05 (M+H)$^+$, 1.84 min (ret. time).

Intermediate 28: (S)-4-Methyl-8-(trifluoromethyl)-2,3,4,5-tetrahydrobenzo[f][1,2]thiazepine 1,1-dioxide

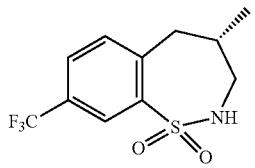 [SMILES: C[C@@H]1CNS(=O)(=O)c2cc(C(F)(F)F)ccc2C1]

(S)-4-Methyl-8-(trifluoromethyl)-2,3,4,5-tetrahydrobenzo[f][1,2]thiazepine 1,1-dioxide of the invention was made using compounds described in WO 2017/060854 on page 137, published Apr. 13, 2017, and incorporated herein by reference.

Intermediate 29: (R)-4-Methyl-3,4-dihydro-2H-benzo[b][1,4,5]oxathiazepine 1,1-dioxide

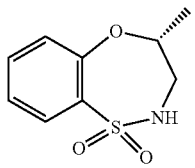

(R)-4-Methyl-3,4-dihydro-2H-benzo[b][1,4,5]oxathiazepine 1,1-dioxide of the invention was made using compounds described in WO 2015/092713, published Jun. 15, 2015, and incorporated herein by reference.

Intermediate 30: 4-Methyl-8-(trifluoromethyl)-2,3,4,5-tetrahydrobenzo[f][1,2]thiazepine 1,1-dioxide

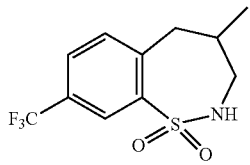 [SMILES: CC1CNS(=O)(=O)c2cc(C(F)(F)F)ccc2C1]

4-Methyl-8-(trifluoromethyl)-2,3,4,5-tetrahydrobenzo[f][1,2]thiazepine 1,1-dioxide of the invention was made using compounds described in WO 2015/092713 for Example 209, published Jun. 15, 2015, and incorporated herein by reference.

Intermediate 31: 2-Fluoro-N-(2-hydroxy-2-methylpropyl)benzenesulfonamide

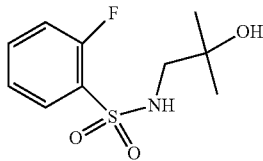 [SMILES: CC(C)(O)CNS(=O)(=O)c1ccccc1F]

To a solution of 2-fluorobenzene-1-sulfonyl chloride (15 g, 77 mmol) in tetrahydrofuran (THF) (300 mL) at 0° C. was added potassium carbonate (13.85 g, 100 mmol), water (110 mL) and 1-amino-2-methylpropan-2-ol (6.87 g, 77 mmol) and was stirred for 4 h at 25° C. The reaction mixture was quenched with ice cold water (200 mL) and extracted with ethyl acetate (2×200 mL), washed with brine (100 mL) then concentrated to provide the title compound as a white solid. (17 g, 67.9 mmol, 88% yield). LCMS m/z 248.2 (M+H)+, 1.678 min (ret.time).

Intermediate 32: 4,4-Dimethyl-3,4-dihydro-2Hbenzo[b][1,4,5]oxathiazepine 1,1-dioxide

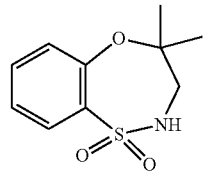

To a solution of 2-fluoro-N-(2-hydroxy-2-methylpropyl)benzenesulfonamide (10 g, 40.4 mmol) in dimethyl sulfoxide (DMSO) (100 mL) was added potassium tert-butoxide (13.61 g, 121 mmol) at 10° C. then heated to 90° C. for 4 hr in a sealed tube. The reaction mixture was cooled to ambient temperature and poured into ice water (100 mL), then extracted with ethyl acetate (2×200 mL) and concentrated to give the crude compound. The crude residue was purified by flash column chromotography using EtOAc:Hexane (4:6) as solvent, to provide the title compound. (5 g, 21.92 mmol, 54.2% yield). LCMS m/z 228 (M+H)+, 1.73 min (ret.time).

Intermediate 33: 4-Chloropyridine-3-sulfonyl Chloride

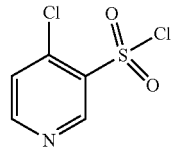

To a suspension of 4-hydroxypyridine-3-sulfonic acid (25 g, 143 mmol) was added PCl$_5$ (104 g, 500 mmol) and POCl$_3$ (26.6 ml, 285 mmol) at 0° C. and stirred at 120° C. for 1 h. The reaction mixture was cool to ambient temperature, the reaction mass was concentrated. The residue was diluted with EtOAc and poured in to ice. Solid NaHCO$_3$ was added and the aqueous phase was extracted with EtOAc. The organic layer was dried over anhydrous Na$_2$SO$_4$ and filtered to afford the title compound (25 g, 98 mmol, 68.6% yield). LCMS m/z 212 (M+H)+, 1.93 min (ret. time).

Intermediate 34:
4-Chloro-N-(2-methylallyl)pyridine-3-sulfonamide

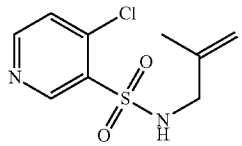

To a solution of 4-chloropyridine-3-sulfonyl chloride (25 g, 98 mmol) in dichloromethane (DCM) (200 mL) at 0° C. was added 2-methylprop-2-en-1-amine (7.66 g, 108 mmol) and TEA (27.3 mL, 196 mmol). The reaction mixture was stirred at ambient temperature for 16 h. The reaction mixture was quenched with cold water, extracted with DCM (2×). The combined organic layers were washed with brine, dried over anhydrous $Na_2SO_4$ and filtered. The filtrate was evaporated under reduced pressure to afford the title compound which was used without further purification for the next step. (21 g, 85 mmol, 87% yield). LCMS m/z 246 (M+H)$^+$, 2.11 min (ret. time).

Intermediate 35: 4-Methyl-2,3,4,5-tetrahydropyrido[4,3-f][1,2]thiazepine 1,1-dioxide

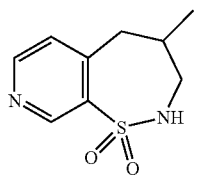

To a solution of 4-chloro-N-(2-methylallyl)pyridine-3-sulfonamide (10 g, 35.7 mmol) in benzene (90 mL) was added AIBN (1.757 g, 10.70 mmol) and heated at 70° C. Tributylstannane (11.42 g, 39.2 mmol) was added at this temperature. The reaction was stirred at 85° C. for 16 h. The reaction mixture was concentrated to get the crude compound of 4-methyl-2,3,4,5-tetrahydropyrido[4,3-f][1,2]thiazepine 1,1-dioxide (10 g, 3.77 mmol, 10.57% yield). LCMS m/z 213 (M+H)$^+$, 1.77 min (ret. time). This batch of compound was combined with other batches prepared by the same method and purified by column chromatography by using EtOAc:Petroleum ether (1:1) to afford the title compound (2.7 g), LCMS m/z 213 (M+H)$^+$, 1.79 min (ret. time).

Intermediate 36: (R)-4-Methyl-2,3,4,5-tetrahydropyrido[4,3-f][1,2]thiazepine 1,1-dioxide and (S)-4-methyl-2,3,4,5-tetrahydropyrido[4,3-f][1,2]thiazepine 1,1-dioxide

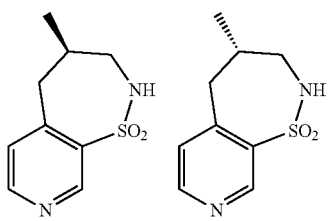

4-methyl-2,3,4,5-tetrahydropyrido[4,3-f][1,2]thiazepine 1,1-dioxide (2.39 g, 11.28 mmol) was purified with chiral SFC (Column: Chiralpak IC, 20×250 mm, 5 u; Co-Solvent: 30% EtOH; Total flow rate: 50 g/min; Pressure: 100 Bar) to give (R)-4-methyl-2,3,4,5-tetrahydropyrido[4,3-f][1,2]thiazepine 1,1-dioxide (1.10 g, 45% yield). LC-MS m/z 213 (M+H)$^+$, 0.49 min (ret. time), and (S)-4-methyl-2,3,4,5-tetrahydropyrido[4,3-f][1,2]thiazepine 1,1-dioxide (1.07 g, 45% yield). LCMS m/z 213 (M+H)$^+$, 0.49 min (ret. time).

Intermediate 37: 2-Bromo-5-fluoro-N-(2-methylallyl)benzenesulfonamide

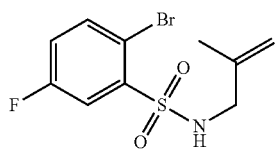 [SMILES: C=C(C)CNS(=O)(=O)c1cc(F)ccc1Br]

To a solution of 2,5-dibromobenzene-1-sulfonyl chloride (25 g, 74.8 mmol) in dichloromethane (250 mL) 2-methylprop-2-en-1-amine (5.32 g, 74.8 mmol) and TEA (10.42 mL, 74.8 mmol) was added at 0° C. and stirred for 10 min. The reaction was then stirred at ambient temperature for 16 h. The reaction mixture was quenched with ice cold water (50 mL) and extracted with DCM (2×100 mL). The combined organic layers were washed with ice cold water (2×50 mL), washed with brine (50 mL), dried over anhydrous $Na_2SO_4$ and concentrated under reduced pressure to afford the title compound (20 g, 44.3 mmol, 59.3% yield), LCMS m/z 308 (M+H)$^+$, 2.23 min (ret. time).

Intermediate 38: 8-Fluoro-4-methyl-2,3,4,5-tetrahydrobenzo[f][1,2]thiazepine 1,1-dioxide

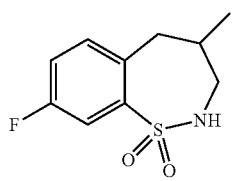

To a solution of 2-bromo-5-fluoro-N-(2-methylallyl)benzenesulfonamide (6.5 g, 20.04 mmol) in toluene (50 mL) was added AIBN (0.617 g, 3.75 mmol) at ambient temperature. The reaction mixture was heated to 75° C. and tri-n-butyltin hydride (7.52 mL, 28.2 mmol) was added and stirred at 110° C. for 18 h. The reaction mixture was quenched with ice cold water (40 mL) and extracted with ethyl acetate (2×50 mL). The combined organic layers were washed with ice cold water (2×50 mL), brine (50 mL) and dried over anhydrous $Na_2SO_4$. The solvent was concentrated and the residue was purified by flash chromatography eluting with 12% EtOAc/petroleum ether to provide the title compound. (1.5 g, 33% yield) LC/MS m/z=228 (M+H)$^+$, 1.97 min (ret time).

Intermediate 39: (S)-8-Fluoro-4-methyl-2,3,4,5-tetrahydrobenzo[f][1,2]thiazepine 1,1-dioxide and Intermediate 40: (R)-8-fluoro-4-methyl-2,3,4,5-tetrahydrobenzo[f][1,2]thiazepine 1,1-dioxide

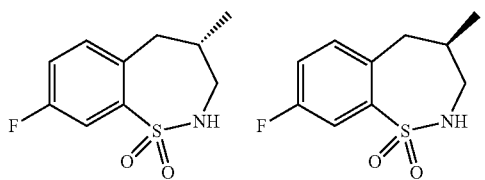

8-fluoro-4-methyl-2,3,4,5-tetrahydrobenzo[f][1,2]thiazepine 1,1-dioxide (14 g, 59.8 mmol) was purified with chiral SFC (Column: Lux Amylose-2 (250×30)mm, 5μ; Co-Solvent: 10% EtOH; Total flow rate: 100 g/min; Pressure: 100 Bar, 90% CO2) to give (S)-8-fluoro-4-methyl-2,3,4,5-tetrahydrobenzo[f][1,2]thiazepine 1,1-dioxide (5.7 g, 40% yield). LC-MS m/z 228 (M+H)$^+$, 2.42 min (ret. time), and (R)-8-fluoro-4-methyl-2,3,4,5-tetrahydrobenzo[f][1,2]thiazepine 1,1-dioxide (5.2 g, 36% yield). LCMS m/z 228 (M+H)$^+$, 2.42 min (ret. time).

Example 1

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-3-yl)propanamide

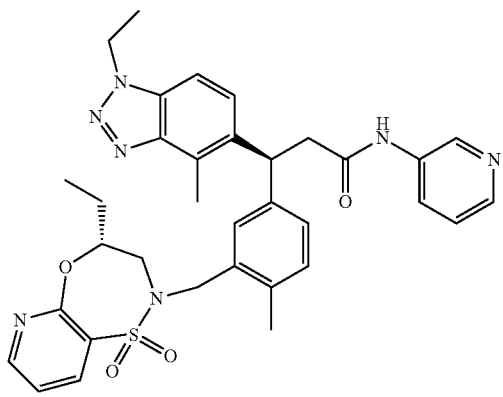 [SMILES: CC[C@@H]1CN(Cc2cc([C@H](CC(=O)Nc3cccnc3)c3ccc4c(nnn4CC)c3C)ccc2C)S(=O)(=O)c2cccnc2O1]

tert-Butyl (3-methyl-2-nitrophenyl)carbamate

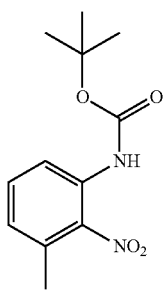 [SMILES: Cc1cccc(NC(=O)OC(C)(C)C)c1[N+](=O)[O-]]

To the mixture of 3-methyl-2-nitrobenzoic acid (30 g, 166 mmol) in tert-butanol (250 mL) was added diphenyl phosphorazidate (50.1 g, 182 mmol) and TEA (25.4 mL, 182 mmol). The reaction mixture was stirred at 82° C. for 10 hrs after which time 2000 mL of water was added. The resulting precipitate was filtered to afford the title compound tert-butyl (3-methyl-2-nitrophenyl)carbamate (41 g, 135 mmol, 82% yield). LC-MS m/z 153.1 (M-Boc)+, 1.78 (ret. time).

Tert-Butyl ethyl(3-methyl-2-nitrophenyl)carbamate

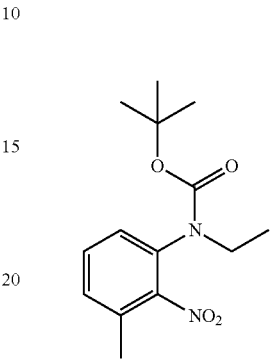

To a solution of tert-butyl (3-methyl-2-nitrophenyl)carbamate (36 g, 143 mmol) in N,N-dimethylformamide (300 mL) was added sodium hydride (6.28 g, 157 mmol) at 0° C. After the reaction mixture was stirred at 0° C. for 1 hr, iodoethane (12.69 mL, 157 mmol) was added. The reaction mixture was stirred at ambient temperature for 1 hr after which time it was quenched with NH$_4$Cl, extracted with EtOAc (3×30 mL), washed with saturated NaCl, dried with Na$_2$SO$_4$ and concentrated to give the title compound tert-butyl ethyl(3-methyl-2-nitrophenyl)carbamate (39 g, 90%). LC-MS m/z 303.1 (M+Na)$^+$, 1.39 (ret. time).

N-Ethyl-3-methyl-2-nitroaniline

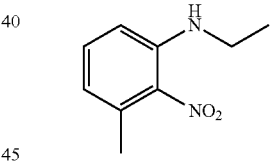

To a solution of tert-butyl methyl (3-methyl-2-nitrophenyl)carbamate (39 g, 146 mmol) in dichloromethane (300 mL), TFA (110 mL, 1428 mmol) was added. The reaction mixture was stirred at 80° C. for 2 hrs after which time the solvent was removed and the pH adjusted to pH=9, extracted with EtOAc (3×30 mL) and concentrated to give title compound N-ethyl-3-methyl-2-nitroaniline (22 g, 113 mmol, 84% yield). LC-MS m/z 181 (M+H)$^+$, 1.34 (ret. time).

4-Bromo-N-ethyl-3-methyl-2-nitroaniline

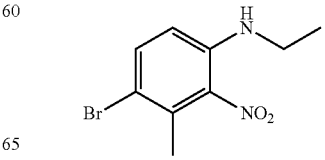

To a solution of N-ethyl-3-methyl-2-nitroaniline (22 g, 113 mmol) in N,N-dimethylformamide (150 mL), the mixture of NBS (18.11 g, 102 mmol) in N,N-dimethylformamide (150 mL) was added slowly at 0° C. The resulting reaction mixture was stirred at ambient temperature for 16 hrs after which time it was extracted with EtOAc (3×30 mL), washed with brine, dried with Mg$_2$SO$_4$ and concentrated to afford the title compound 4-bromo-N-ethyl-3-methyl-2-nitroaniline (28 g, 106 mmol, 94% yield). LC-MS m/z 261.0, 262.0 (M+H)$^+$, 1.89 (ret. time).

4-Bromo-N1-ethyl-3-methylbenzene-1,2-diamine

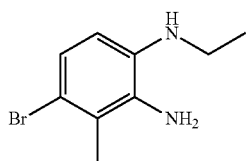

To a solution of 4-bromo-N-ethyl-3-methyl-2-nitroaniline (28 g, 108 mmol) in ethanol (100 mL) was added tin(II) chloride dihydrate (98 g, 432 mmol) in ethanol (100 mL). The reaction mixture was stirred at 95° C. for 2 hrs. Sodium hydroxide solution was added until the pH was greater than 14. The solid was filtered to afford the title compound 4-bromo-N1-ethyl-3-methylbenzene-1,2-diamine (17 g, 68.7% yield). LC-MS m/z 230.9 [(M+H)$^+$, 1.58 (ret. time).

5-Bromo-1-ethyl-4-methyl-1H-benzo[d][1,2,3]triazole

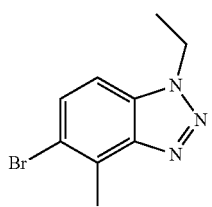

A stirred suspension of 4-bromo-N1-ethyl-3-methylbenzene-1,2-diamine (8 g, 34.9 mmol) in sulfuric acid (7.44 ml, 140 mmol) was treated with a solution of sodium nitrite (3.61 g, 52.4 mmol) in water (150 ml). The mixture was stirred at 0° C. for 2 hr after which time it was filtered to afford the title compound 5-bromo-1-ethyl-4-methyl-1H-benzo[d][1,2,3]triazole (6.7 g, 26.5 mmol, 76% yield). LC-MS m/z 240.1, 243.1 [(M+H)$^+$, 1.92 (ret. time).

(E)-Ethyl 3-(1-ethyl-4-methyl-1H-benzo[d][1,2,3]triazol-5-yl)acrylate

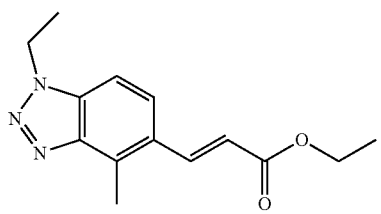 [SMILES: CCOC(=O)/C=C/c1ccc2c(nnn2CC)c1C]

A mixture of tri-o-tolylphosphine (0.849 g, 2.79 mmol), ethyl acrylate (5.59 g, 55.8 mmol), 5-bromo-1-ethyl-4-methyl-1H-benzo[d][1,2,3]triazole (6.7 g, 27.9 mmol), PdOAc$_2$ (0.313 g, 1.395 mmol), and K$_2$CO$_3$ (7.71 g, 55.8 mmol) in N,N-dimethylformamide (50 mL) was stirred at 120° C. for 12 hrs. The reaction mixture was poured into water and extracted with ethyl acetate (3×30 mL). The organic layer was dried and concentrated. The product was purified over a silica gel column and eluted with hexane:ethyl acetate (4:1) to give the title compound (E)-ethyl 3-(1-ethyl-4-methyl-1H-benzo[d][1,2,3]triazol-5-yl)acrylate (5 g, 18.50 mmol, 66.3% yield). LC-MS m/z 260.2 [(M+H)$^+$, 1.63 (ret. time).

(R)-1-Aminobutan-2-ol

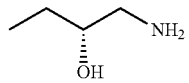

To a solution of ammonium hydroxide (~28% solution in H$_2$O) (21.60 mL, 555 mmol) was added (R)-2-ethyloxirane (4 g, 55.5 mmol). The resulting reaction mixture was stirred at ambient temperature for 20 hrs. The reaction mixture was concentrated under reduced pressure to afford the desired product (R)-1-aminobutan-2-ol (4.5 g, 50.5 mmol, 91% yield). 1H NMR (400 MHz, CHLOROFORM-d) δ ppm 0.97 (t, J=7.53 Hz, 3H) 1.42-1.53 (m, 2H) 1.71 (br. s., 3H) 2.47-2.59 (m, 1H) 2.85 (dd, J=12.80, 3.26 Hz, 1H) 3.39-3.49 (m, 1H).

(R)-2-Chloro-N-(2-hydroxypropyl)pyridine-3-sulfonamide

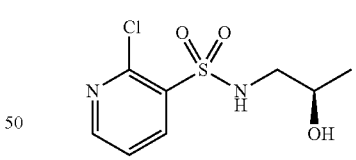

To a solution of (R)-1-amino-2-butanol (2.5 g, 28.0 mmol) in tetrahydrofuran (80 mL) and water (16 mL) was added K$_2$CO$_3$ (2.477 g, 17.92 mmol) followed by 2-chloropyridine-3-sulfonyl chloride (3.8 g, 17.92 mmol). The resulting reaction mixture was stirred at ambient temperature for 5 hrs. The reaction mixture was diluted with H$_2$O (100 mL) and extracted with EtOAc (2×100 mL). The combined organic layer was washed with brine (15 mL), dried over MgSO$_4$ and concentrated under reduced pressure to afford the title compound 2-chloro-N-(2-hydroxybutyl)pyridine-3-sulfonamide (5.1 g, 17.56 mmol, 98% yield). LC-MS m/z 265.1 (M+H)$^+$, 1.29 (ret. time).

(R)-4-Ethyl-3,4-dihydro-2H-pyrido[2,3-b][1,4,5] oxathiazepine 1,1-dioxide

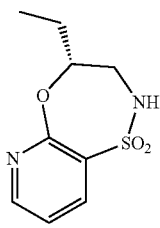

To a solution of (R)-2-chloro-N-(2-hydroxybutyl)pyridine-3-sulfonamide (3 g, 11.33 mmol) in dimethyl sulfoxide (10 mL) was added KOtBu (3.81 g, 34.0 mmol). The resulting reaction was stirred at 80° C. for 2 hrs. The reaction mixture was diluted with ice H$_2$O (30 mL) and extracted with EtOAc (2×30 mL). The combined organic layer was washed with brine (20 mL), dried over MgSO$_4$ and concentrated under reduced pressure, purified by silica gel chromatography (Hexane:Ethyl acetate) to afford the title compound (R)-4-ethyl-3,4-dihydro-2H-pyrido[2,3-b][1,4,5] oxathiazepine 1,1-dioxide (2.0 g, 8.76 mmol, 77% yield). LC-MS m/z 228.9 (M+H)$^+$, 1.18 (ret. time).

Methyl 5-bromo-2-methylbenzoate

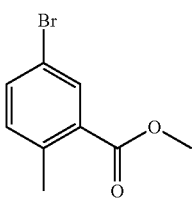

To a solution of 5-bromo-2-methylbenzoic acid (15 g, 69.8 mmol) in methanol (100 ml) was added H$_2$SO$_4$ (1 ml, 18.76 mmol) slowly under nitrogen at ambient temperature. The resulting reaction mixture was stirred at 65° C. for 16 hrs. Water (50 mL) was added to the reaction mixture and extracted with ethyl acetate (3×60 ml). The combined organic layer was concentrated to afford the title compound methyl 5-bromo-2-methylbenzoate (15 g, 65.5 mmol, 94% yield). LC-MS MS m/z 231.1 (M+H)$^+$, 1.98 (ret. time)

5-Bromo-2-methylphenyl)methanol

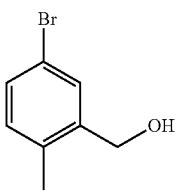

To a solution of methyl 5-bromo-2-methylbenzoate (108 g, 471 mmol) in tetrahydrofuran (1600 mL) was added LiAlH$_4$ (21.47 g, 566 mmol) slowly under nitrogen at 0° C. The resulting mixture was stirred at 0° C. for 1 hr. Then 3.73 mL of water was added to the reaction mixture, followed by 3.75 ml of 10% NaOH, and 11.19 ml of water, filtered and concentrated to afford the title compound (5-bromo-2-methylphenyl)methanol (88 g, 416 mmol, 88% yield). LC-MS MS m/z 185.1 (M−OH)$^+$, 1.59 (ret. time)

(2-Methyl-5-(4,4,5,5-tetramethyl-1,3,2-dioxaborolan-2-yl)phenyl)methanol

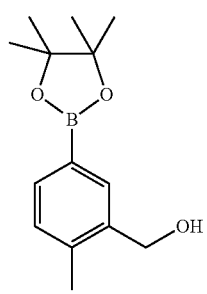 [SMILES: Cc1ccc(B2OC(C)(C)C(C)(C)O2)cc1CO]

To a solution of (5-bromo-2-methylphenyl)methanol (55 g, 274 mmol) in 1,4-dioxane (1000 mL) was added potassium acetate (81 g, 821 mmol) and bis(pinacolato)diboron (104 g, 410 mmol). The reaction mixture was degassed with argon for 30 min, and then PdCl2(dppf)-CH$_2$Cl$_2$ adduct (13.40 g, 16.41 mmol) was added and the reaction mixture stirred at 100° C. for 16 hrs after which time it was filtered through a pad of celite. The filtrate was concentrated under reduced pressure. The crude residue was purified via silica gel chromatography using EtOAc:Hexane (3:7) to afford the title compound (2-methyl-5-(4,4,5,5-tetramethyl-1,3,2-dioxaborolan-2-yl)phenyl)methanol (60 g, 230 mmol, 84% yield). LC-MS m/z 271.3 (M+H)$^+$, 1.17 (ret. time).

(S)-Ethyl 3-(1-ethyl-4-methyl-1H-benzo[d][1,2,3] triazol-5-yl)-3-(3-(hydroxymethyl)-4-methylphenyl) propanoate

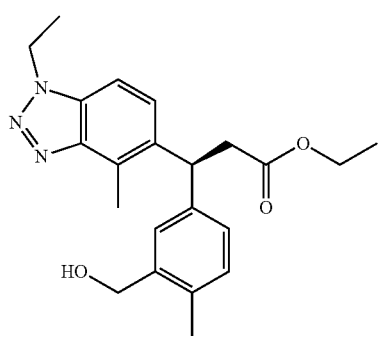 [SMILES: CCOC(=O)C[C@@H](c1ccc(C)c(CO)c1)c1ccc2c(nnn2CC)c1C]

To a solution of (2-methyl-5-(4,4,5,5-tetramethyl-1,3,2-dioxaborolan-2-yl)phenyl)methanol (11.48 g, 46.3 mmol), (E)-ethyl 3-(1-ethyl-4-methyl-1H-benzo[d][1,2,3]triazol-5-yl)acrylate (4 g, 15.43 mmol), Bis(norbornadiene)rhodium (I)tetrafluoroborate (0.577 g, 1.543 mmol), (R)-(+)-2,2'-Bis (di-p-tolylphosphine)-1,1'-binaphthyl (1.131 g, 1.666 mmol) in 1,4-dioxane (100 mL), was added a solution of potassium hydroxide (0.865 g, 15.43 mmol) in water (15.43 mL). The reaction mixture was stirred at 25° C. for 20 hrs under nitrogen after which time 800 mL of water was added and the reaction extracted with EtOAc (3×80 mL). The organic phase was dried over Mg₂SO₄ and concentrated. The crude product was purified by silica gel chromatography (hexane/EtOAc) to afford ethyl 3-(1-ethyl-4-methyl-1H-benzo[d][1,2,3]triazol-5-yl)-3-(3-(hydroxymethyl)-4-methylphenyl)propanoate (4.0 g, 9.25 mmol, 97.7% yield). LC-MS m/z 382.2 (M+H)⁺, 1.58 (ret. time). Ethyl 3-(1-ethyl-4-methyl-1H-benzo[d][1,2,3]triazol-5-yl)-3-(3-(hydromethyl)-4-methylphenyl)propanoate (5.2 g) was separated by Chiral SFC (Column: Chiralpak AD-H 50*250 mm 5 um (Daicel); column temperature: 35° C.; Mobile phase: CO₂/Methanol (0.5% DEA)=60/40; Flow: 160 g/min; Back pressure: 100 Bar) to give a single enantiomerically pure (S)-ethyl 3-(1-ethyl-4-methyl-1H-benzo[d][1,2,3]triazol-5-yl)-3-(3-(hydroxymethyl)-4-methylphenyl)propanoate (3.8 g, 9.25 mmol, 59.9% yield) (chiral SFC ret. time: 1.75 min). LC/MS: m/z 382.2 (M+H)⁺, 1.58 min (ret. time).

(S)-Ethyl 3-(3-(chloromethyl)-4-methylphenyl)-3-(1-ethyl-4-methyl-1H-benzo[d][1,2,3]triazol-5-yl)propanoate

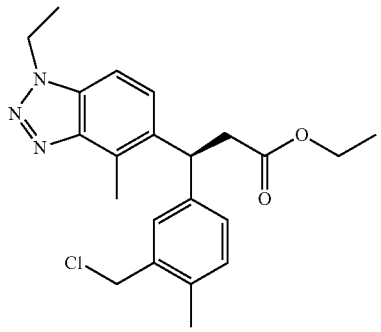 [SMILES: CCOC(=O)C[C@@H](c1ccc(C)c(CCl)c1)c1ccc2c(nnn2CC)c1C]

To a solution of (S)-ethyl 3-(1-ethyl-4-methyl-1H-benzo[d][1,2,3]triazol-5-yl)-3-(3-(hydroxymethyl)-4-methylphenyl)propanoate (3 g, 7.86 mmol) in dichloromethane (30 mL) was added thionyl chloride (0.689 mL, 9.44 mmol) and one drop of N,N-dimethylformamide. The reaction mixture was stirred at ambient temperature for 1 hr. The solvent was removed by reduced pressure to afford the title compound (S)-ethyl 3-(3-(chloromethyl)-4-methylphenyl)-3-(1-ethyl-4-methyl-1H-benzo[d][1,2,3]triazol-5-yl)propanoate (3.1 g, 7.54 mmol, 96% yield). LC-MS m/z 400.2 (M+H)⁺, 1.77 (ret. time).

(S)-Ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate

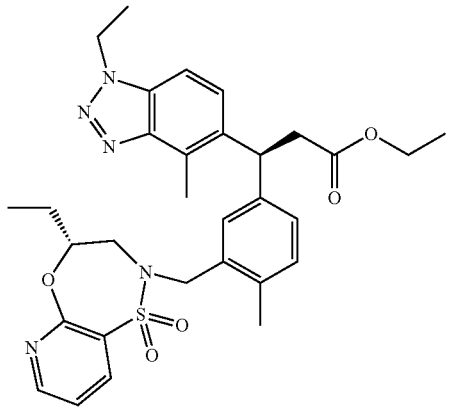 [SMILES: CCOC(=O)C[C@@H](c1ccc(C)c(CN2C[C@@H](CC)Oc3ncccc3S2(=O)=O)c1)c1ccc2c(nnn2CC)c1C]

To a solution of (R)-4-ethyl-3,4-dihydro-2H-pyrido[2,3-b][1,4,5]oxathiazepine 1,1-dioxide (1.946 g, 8.53 mmol) in N,N-dimethylformamide (50 mL) was added sodium hydride (0.465 g, 11.63 mmol) under nitrogen at 0° C. The reaction mixture was stirred for 10 minutes, then (S)-ethyl 3-(3-(chloromethyl)-4-methylphenyl)-3-(1-ethyl-4-methyl-1H-benzo[d][1,2,3]triazol-5-yl)propanoate (3.1 g, 7.75 mmol) was added to the reaction mixture. The reaction mixture was stirred at 10° C. for 2 hrs. Water (50 mL) was added to the reaction mixture and extracted with EtOAc (3×50 mL). The combined organic layer was washed with brine, dried over magnesium sulfate and concentrated to afford the title compound (S)-ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate (4.5 g, 6.90 mmol, 89% yield). LC-MS m/z 592.3 (M+H)⁺, 2.07 (ret. time).

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic Acid

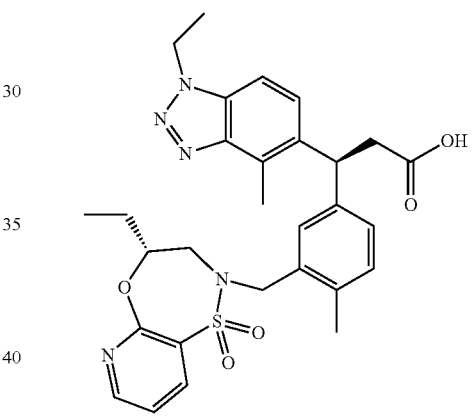

To a solution of (S)-ethyl 3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoate (4.5 g, 6.90 mmol) in methanol (36 mL) and tetrahydrofuran (THF) (30.0 mL) was added a solution of sodium hydroxide (1.657 g, 41.4 mmol) in water (30.0 mL). The reaction mixture was stirred at 10° C. for 24 hrs. 2 N HCl was added until pH=1 and the mixture filtered. The solid was washed with ether to afford the title compound (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (3.6 g, 6.39 mmol, 93% yield). LC-MS m/z 564.2 (M+H)⁺, 1.88 (ret. time).

¹H NMR (400 MHz, DMSO-d₆) δ ppm 0.95 (t, J=7.15 Hz, 3H) 1.27-1.57 (m, 4H) 1.77 (br. s., 1H) 2.25 (s, 3H) 2.76 (s, 3H) 2.84 (d, J=15.31 Hz, 1H) 3.04 (d, J=8.03 Hz, 2H) 3.57-3.74 (m, 2H) 3.94 (d, J=14.05 Hz, 1H) 4.35 (br. s., 1H) 4.44 (d, J=14.05 Hz, 1H) 4.68 (q, J=7.45 Hz, 2H) 4.81 (t, J=7.91 Hz, 1H) 7.13 (d, J=7.53 Hz, 1H) 7.19-7.28 (m, 2H) 7.47 (d, J=7.78 Hz, 2H) 7.60 (d, J=8.53 Hz, 1H) 8.24 (d, J=7.53 Hz, 1H) 8.56 (d, J=4.77 Hz, 1H) 12.13 (s, 1H).

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-3-yl)propanamide

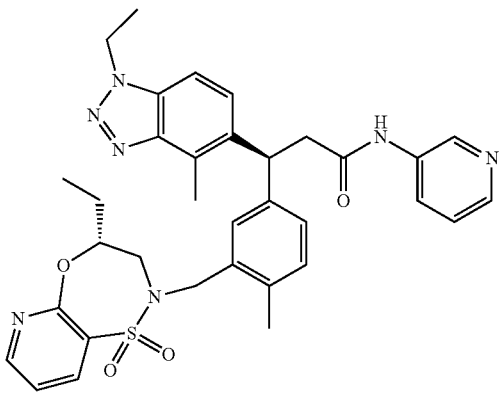 [SMILES: CC[C@@H]1CN(Cc2cc([C@H](CC(=O)Nc3cccnc3)c3ccc4c(nnn4CC)c3C)ccc2C)S(=O)(=O)c2cccnc2O1]

To a solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (80 mg, 0.142 mmol) in N,N-dimethylformamide (DMF) (0.71 mL were added DIPEA (0.074 mL, 0.426 mmol) and HATU (54.0 mg, 0.142 mmol) It was stirred at 25° C. for 3 min followed by addition of pyridin-3-amine (16.03 mg, 0.170 mmol) stirred at 25° C. for 22 h. The reaction was then diluted with water and extracted with ethyl acetate (3×10 mL). The combined organic layer was then concentrated to dryness and dissolved in 3 mL of DMSO. It was filtered and purified by reverse-phase HPLC under neutral conditions to give the title compound (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-3-yl)propanamide (80 mg, 0.125 mmol, 88% yield) as a white solid. LC-MS m/z 640.2 (M+H)$^+$, 0.88 min (ret. time). $^1$H NMR (400 MHz, DMSO-d6) δ ppm 0.91 (t, J=7.28 Hz, 3H) 1.23-1.34 (m, 1H) 1.47 (t, J=7.15 Hz, 4H) 2.22 (s, 3H) 2.75 (s, 3H) 2.86 (d, J=15.31 Hz, 1H) 3.12-3.27 (m, 2H) 3.67 (dd, J=15.31, 10.29 Hz, 1H) 3.98 (d, J=14.56 Hz, 1H) 4.29 (br. s., 1H) 4.40 (d, J=14.31 Hz, 1H) 4.66 (q, J=7.19 Hz, 2H) 4.97 (t, J=7.78 Hz, 1H) 7.10-7.26 (m, 3H) 7.40-7.50 (m, 4H) 7.64 (d, J=8.53 Hz, 1H) 8.23 (d, J=7.53 Hz, 1H) 8.36 (d, J=5.27 Hz, 2H) 8.55 (d, J=4.77 Hz, 1H) 10.42 (s, 1H).

The compounds in Table 1 were prepared by a method similar to the one described for the preparation of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-3-yl)propanamide. As is appreciated by those skilled in the art, these analogous examples may involve variations in general reaction conditions.

TABLE 1

| Ex # | Structure | Name | LCMS [M + H]$^+$ | Retention Time (min) |
|---|---|---|---|---|
| Example 2 | (structure) | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(isothiazol-4-yl)propanamide | 646.2 | 1.06 |
| Example 3 | (structure) | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(oxazol-2-ylmethyl)propanamide | 644.3 | 0.96 |

TABLE 1-continued

| Ex # | Structure | Name | LCMS [M + H]+ | Retention Time (min) |
|---|---|---|---|---|
| Example 4 | 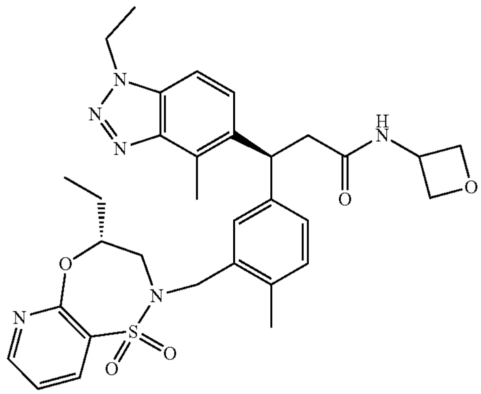 [SMILES: CC[C@@H]1CN(Cc2cc([C@H](CC(=O)NC3COC3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(oxetan-3-yl)propanamide | 619.3 | 0.95 |
| Example 5 | 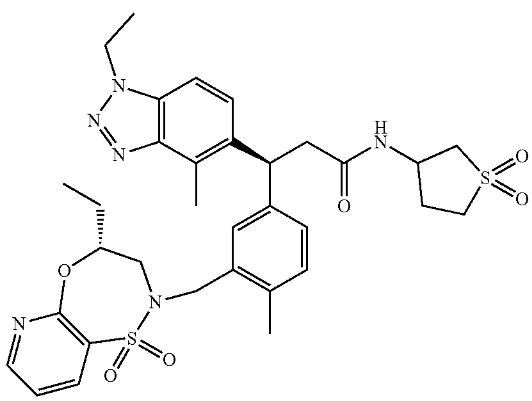 [SMILES: CC[C@@H]1CN(Cc2cc([C@H](CC(=O)NC3CCS(=O)(=O)C3)c3ccc4c(nnn4CC)c3C)ccc2C)S(=O)(=O)c2cccnc2O1] | (3S)-N-(1,1-Dioxidotetrahydrothiophen-3-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide | 681.3 | 0.97 |
| Example 6 | 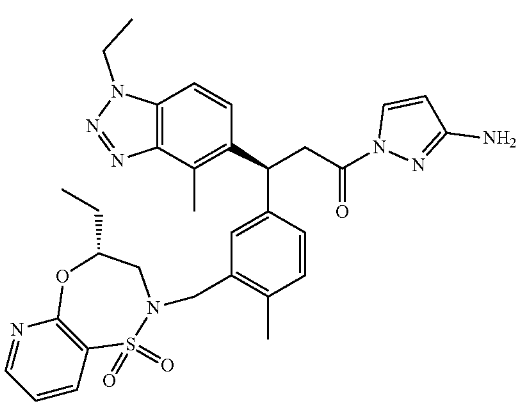 [SMILES: CC[C@@H]1CN(Cc2cc([C@H](CC(=O)n3ccc(N)n3)c3ccc4c(nnn4CC)c3C)ccc2C)S(=O)(=O)c2cccnc2O1] | (S)-1-(3-Amino-1H-pyrazol-1-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propan-1-one | 629.4 | 1.04 |

TABLE 1-continued

| Ex # | Structure | Name | LCMS [M + H]+ | Retention Time (min) |
|---|---|---|---|---|
| Example 7 | 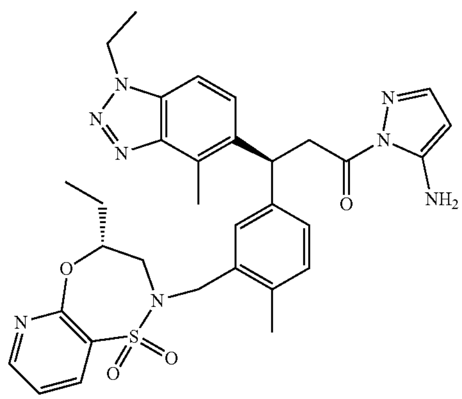 [SMILES: CC[C@@H]1CN(Cc2cc([C@H](CC(=O)n3nccc3N)c3ccc4c(nnn4CC)c3C)ccc2C)S(=O)(=O)c2cccnc2O1] | (S)-1-(5-Amino-1H-pyrazol-1-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propan-1-one | 629.4 | 1.12 |
| Example 8 | 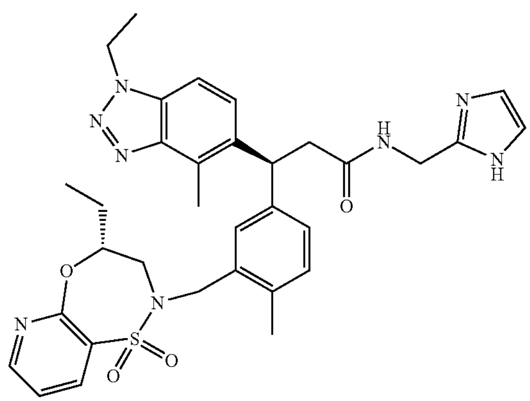 [SMILES: CC[C@@H]1CN(Cc2cc([C@H](CC(=O)NCc3ncc[nH]3)c3ccc4c(nnn4CC)c3C)ccc2C)S(=O)(=O)c2cccnc2O1] | (S)-N-((1H-Imidazol-2-yl)methyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide | 643.4 | 0.84 |
| Example 9 | 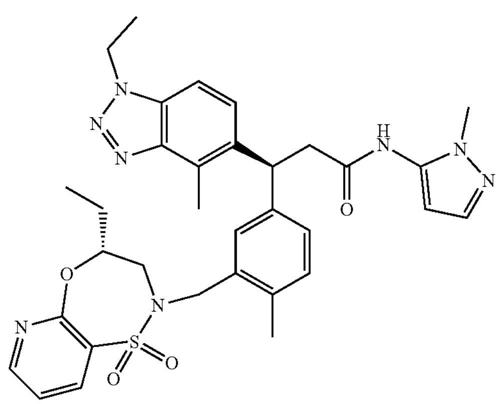 [SMILES: CC[C@@H]1CN(Cc2cc([C@H](CC(=O)Nc3ccnn3C)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(1-methyl-1H-pyrazol-5-yl)propanamide | 643.4 | 0.99 |

TABLE 1-continued

| Ex # | Structure | Name | LCMS [M + H]+ | Retention Time (min) |
|---|---|---|---|---|
| Example 10 | 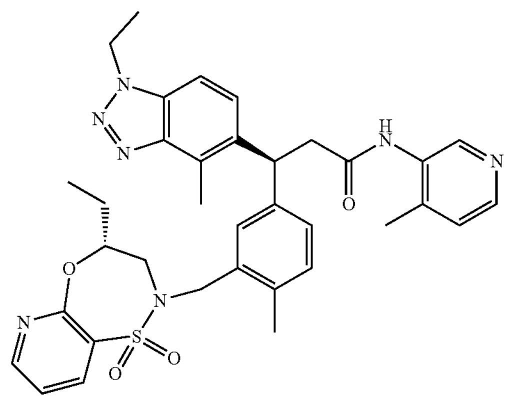 [SMILES: CC[C@@H]1CN(Cc2cc([C@H](CC(=O)Nc3cnccc3C)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(4-methylpyridin-3-yl)propanamide | 654.5 | 0.76 |
| Example 11 | 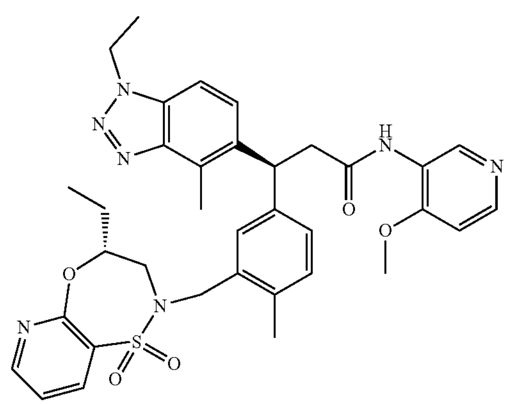 [SMILES: CC[C@@H]1CN(Cc2cc([C@H](CC(=O)Nc3cnccc3OC)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(4-methoxypyridin-3-yl)propanamide | 670.4 | 0.75 |
| Example 12 | 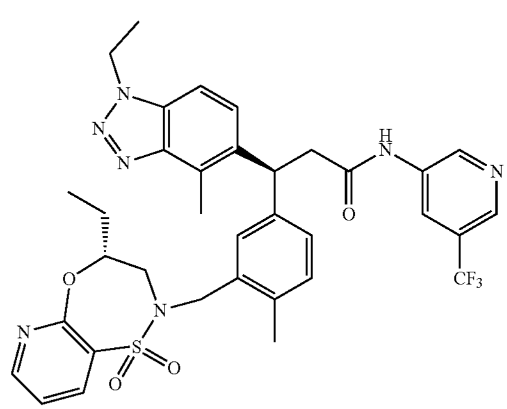 [SMILES: CC[C@@H]1CN(Cc2cc([C@H](CC(=O)Nc3cncc(C(F)(F)F)c3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(5-(trifluoromethyl)pyridin-3-yl)propanamide | 708.4 | 1.18 |

TABLE 1-continued

| Ex # | Structure | Name | LCMS [M + H]+ | Retention Time (min) |
|---|---|---|---|---|
| Example 13 | 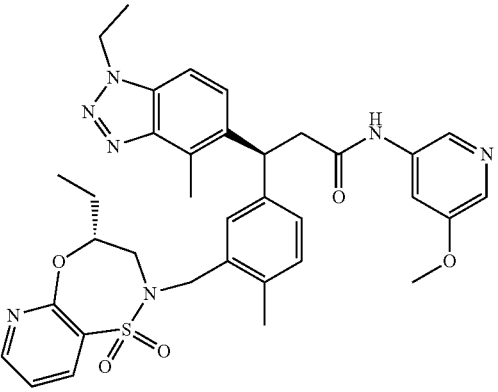 [SMILES: CC[C@@H]1CN(Cc2cc([C@H](CC(=O)Nc3cncc(OC)c3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(5-methoxypyridin-3-yl)propanamide | 670.5 | 0.87 |
| Example 14 | 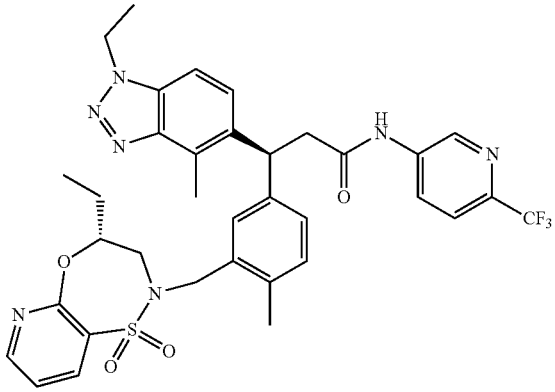 [SMILES: CC[C@@H]1CN(Cc2cc([C@H](CC(=O)Nc3ccc(C(F)(F)F)nc3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(6-(trifluoromethyl)pyridin-3-yl)propanamide | 708.3 | 1.18 |
| Example 15 | 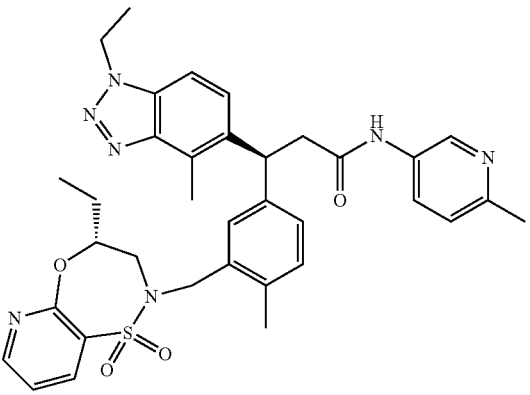 [SMILES: CC[C@@H]1CN(Cc2cc([C@H](CC(=O)Nc3ccc(C)nc3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(6-methylpyridin-3-yl)propanamide | 654.5 | 0.76 |

TABLE 1-continued

| Ex # | Structure | Name | LCMS [M + H]+ | Retention Time (min) |
|---|---|---|---|---|
| Example 16 | 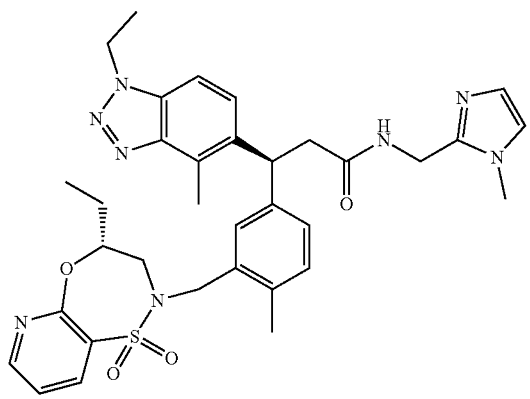 [SMILES: CC[C@@H]1CN(Cc2cc([C@H](CC(=O)NCc3nccn3C)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-((1-methyl-1H-imidazol-2-yl)methyl)propanamide | 657.4 | 0.70 |
| Example 17 | 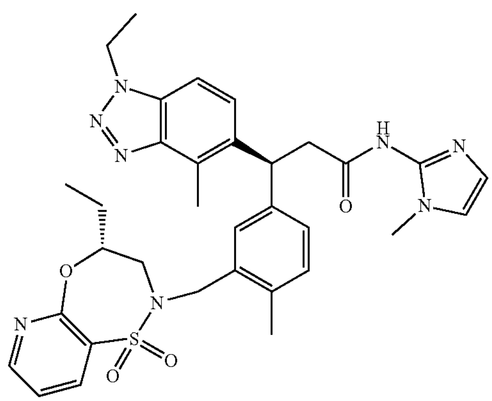 [SMILES: CC[C@@H]1CN(Cc2cc([C@H](CC(=O)Nc3nccn3C)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(1-methyl-1H-imidazol-2-yl)propanamide | 643.4 | 0.74 |
| Example 18 | 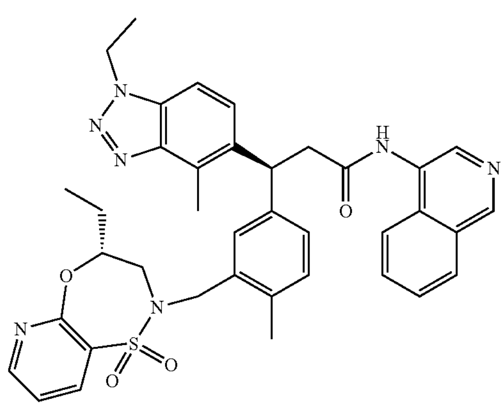 [SMILES: CC[C@@H]1CN(Cc2cc([C@H](CC(=O)Nc3cncc4ccccc34)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-d][1,4,5]oxathiazepin-2-yl)methyl)-4-methylphenyl)-3-(1-ethyl-4-methyl-1H-benzo[d][1,2,3]triazol-5-yl)-N-(isoquinolin-4-yl)propanamide | 690.6 | 0.83 |

TABLE 1-continued

| Ex # | Structure | Name | LCMS [M + H]+ | Retention Time (min) |
|---|---|---|---|---|
| Example 19 | 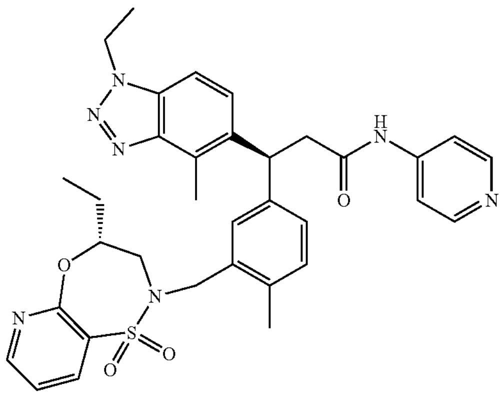 [SMILES: CC[C@@H]1CN(Cc2cc([C@H](CC(=O)Nc3ccncc3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-4-yl)propanamide | 640.4 | 0.76 |

Example 20

(R)-4-Benzyl-3-((2R,3S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2-methylpropanoyl)oxazolidin-2-one

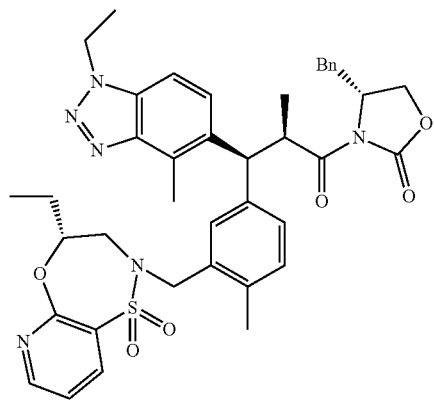 [SMILES: CC[C@@H]1CN(Cc2cc([C@@H](c3ccc4c(nnn4CC)c3C)[C@@H](C)C(=O)N3C(=O)OC[C@H]3Cc3ccccc3)ccc2C)S(=O)(=O)c2cccnc2O1]

(E)-Ethyl 3-(1-ethyl-4-methyl-1H-benzo[d][1,2,3]triazol-5-yl)acrylate

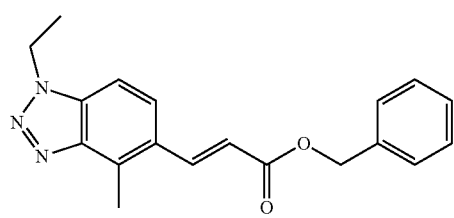 [SMILES: CCn1nnc2c(C)c(/C=C/C(=O)OCc3ccccc3)ccc21]

A mixture of tri-o-tolylphosphine (1.724 g, 5.66 mmol), ethyl acrylate (7.09 g, 70.8 mmol), 5-bromo-1-ethyl-4-methyl-1H-benzo[d][1,2,3]triazole (8.5 g, 35.4 mmol), PdOAc$_2$ (0.636 g, 2.83 mmol), K$_2$CO$_3$ (9.79 g, 70.8 mmol) and N,N-dimethylformamide (200 mL) was stirred at 120° C. for 12 h. The mixture was poured into water and extracted with ethyl acetate (3×30 mL). The organic layer was dried and concentrated. The isolute-adsorbed crude product was purified by silica gel chromatography (hexane:ethyl acetate=4:1). Desired fractions were concentrated to give the title compound (7.24 g, 27.9 mmol, 79% yield) as a solid. LC-MS: 262.0 (M+H)+, 1.71 min (ret. time).

Benzyl 3-(1-ethyl-4-methyl-1H-benzo[d][1,2,3]triazol-5-yl)-3-(3-(hydroxymethyl)-4-methylphenyl)propanoate

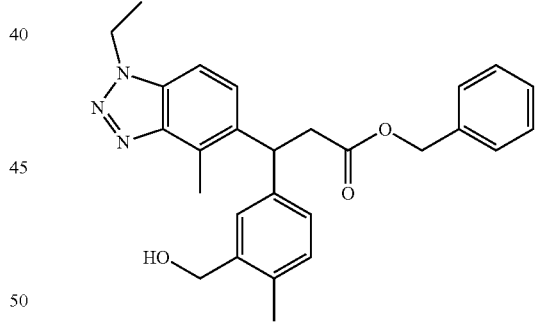

(3-(Hydroxymethyl)-4-methylphenyl)boronic acid (3.49 g, 21.05 mmol) was added to a solution of (E)-benzyl 3-(1-ethyl-4-methyl-1H-benzo[d][1,2,3]triazol-5-yl)acrylate (6.15 g, 19.14 mmol) and triethylamine (8.00 mL, 57.4 mmol) in dioxane (144 mL) and water (47.8 mL). The solution was degassed with argon for 30 minutes. Chloro(1,5-cyclooctadiene)rhodium(I) dimer (0.472 g, 0.957 mmol) was then added and the solution stirred at 90° C. under nitrogen for 5 hrs. The solution was then extracted with ethyl acetate (3×50 mL). The combined organic fraction was washed with brine, dried over sodium sulfate, filtered and concentrated. The crude product was purified by silica gel chromatography to give the title compound (6.15 g, 13.87 mmol, 72.5% yield). LC/MS: m/z 444.0 (M+H)+, 1.12 min (ret. time) 1H NMR (400 MHz, CHLOROFORM-d) L=7.36 (s, 1H), 7.30-7.18 (m, 5H), 7.14-7.03 (m, 4H), 5.01 (s, 3H), 4.68-4.59 (m, 4H), 3.27-3.06 (m, 2H), 2.82 (s, 3H), 2.29 (s, 3H), 1.74 (br. s., 1H), 1.61 (t, J=7.3 Hz, 3H).

Benzyl 3-(3-(((tert-butyldimethylsilyl)oxy)methyl)-4-methylphenyl)-3-(1-ethyl-4-methyl-1H-benzo[d][1,2,3]triazol-5-yl)propanoate

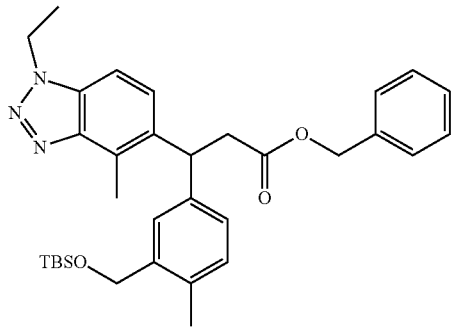 [SMILES: CCn1nnc2c(C)c(C(CC(=O)OCc3ccccc3)c3ccc(C)c(CO[Si](C)(C)C(C)(C)C)c3)ccc21]

1H-Imidazole (1.477 g, 21.69 mmol) and tert-butylchlorodimethylsilane (3.02 g, 20.02 mmol) were added to a solution of benzyl 3-(1-ethyl-4-methyl-1H-benzo[d][1,2,3]triazol-5-yl)-3-(3-(hydroxymethyl)-4-methylphenyl)propanoate (7.4 g, 16.68 mmol) in dichloromethane (33.4 mL) at ambient temperature. The solution was stirred for 2 hrs and then quenched with water, extracted with DCM (3×), washed (brine) and dried (sodium sulfate). The product was purified by silica gel chromatography to give the title compound (8.38 g, 15.02 mmol, 90% yield). LC/MS: m/z 558.2 (M+H)+, 1.71 min (ret. time)

(S)-Benzyl 3-(3-(((tert-butyldimethylsilyl)oxy)methyl)-4-methylphenyl)-3-(1-ethyl-4-methyl-1H-benzo[d][1,2,3]triazol-5-yl)propanoate and (R)-benzyl 3-(3-(((tert-butyldimethylsilyl)oxy)methyl)-4-methylphenyl)-3-(1-ethyl-4-methyl-1H-benzo[d][1,2,3]triazol-5-yl)propanoate

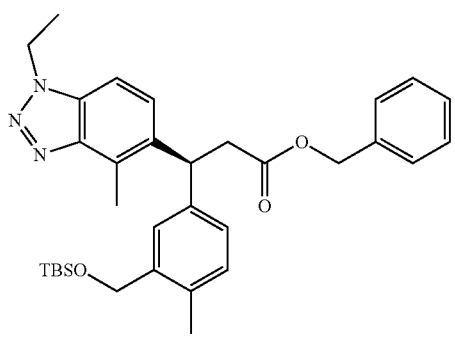

-continued

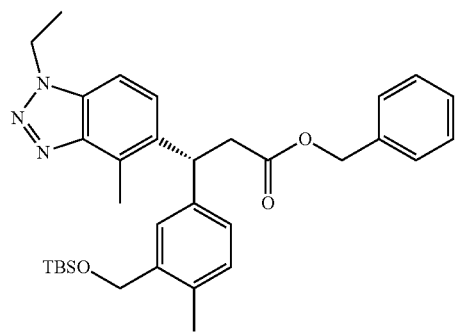

Benzyl 3-(3-(((tert-butyldimethylsilyl)oxy)methyl)-4-methylphenyl)-3-(1-ethyl-4-methyl-1H-benzo[d][1,2,3]triazol-5-yl)propanoate (10 g, 17.93 mmol) was separated by Chiral SFC (Column: Chiralpak IA 20×250 mm, 5 u; Co-solvent: 20% EtOH; Flowrate: 50 g/min; Back pressure: 100Bar) to give a single enantiomerically pure (S)-benzyl 3-(3-(((tert-butyldimethylsilyl)oxy)methyl)-4-methylphenyl)-3-(1-ethyl-4-methyl-1H-benzo[d][1,2,3]triazol-5-yl)propanoate (3.7 g, 6.63 mmol, 46.3%) (chiral SFC ret. time: 3.42 min). LC/MS: m/z 558.3 (M+H)+, 1.70 min (ret. time) and (R)-benzyl 3-(3-(((tert-butyldimethylsilyl)oxy)methyl)-4-methylphenyl)-3-(1-ethyl-4-methyl-1H-benzo[d][1,2,3]triazol-5-yl)propanoate (3.77 g, 6.76 mmol, 47.1%) (chiral SFC ret. time: 6.18 min). LC/MS: m/z 558.4 (M+H)+, 1.71 min (ret. time)

(S)-3-(3-(((tert-Butyldimethylsilyl)oxy)methyl)-4-methylphenyl)-3-(1-ethyl-4-methyl-1H-benzo[d][1,2,3]triazol-5-yl)propanoic Acid

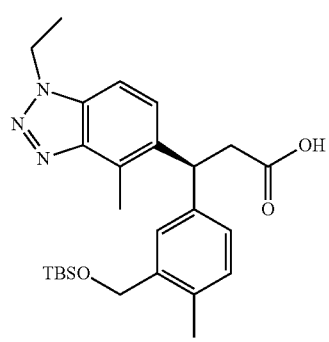 [SMILES: CCn1nnc2c(C)c([C@@H](CC(=O)O)c3ccc(C)c(CO[Si](C)(C)C(C)(C)C)c3)ccc21]

(S)-Benzyl 3-(3-(((tert-butyldimethylsilyl)oxy)methyl)-4-methylphenyl)-3-(1-ethyl-4-methyl-1H-benzo[d][1,2,3]triazol-5-yl)propanoate (3.7 g, 6.63 mmol) in methanol (221 mL) was passed through an H-cube flow reactor with a 10% Pd—C cartridge for 7 h at 1 mL/min on full H2 mode. The methanol was removed in vacuo and the product purified by silica gel chromatography to give the title compound (2.1 g, 4.49 mmol, 67.7% yield). LC/MS: m/z 468.3 (M+H)+, 1.38 min (ret. time)

(R)-4-Benzyl-3-(((S)-3-(3-(((tert-butyldimethylsilyl)oxy)methyl)-4-methylphenyl)-3-(1-ethyl-4-methyl-1H-benzo[d][1,2,3]triazol-5-yl)propanoyl)oxazolidin-2-one

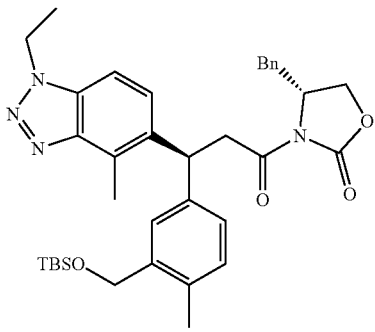 [SMILES: CCn1nnc2c(C)c([C@@H](CC(=O)N3C(=O)OC[C@H]3Cc3ccccc3)c3ccc(C)c(CO[Si](C)(C)C(C)(C)C)c3)ccc21]

Di(1H-Imidazol-1-yl)methanone (1.092 g, 6.74 mmol) was added to a solution of (S)-3-(3-(((tert-butyldimethylsilyl)oxy)methyl)-4-methylphenyl)-3-(1-ethyl-4-methyl-1H-benzo[d][1,2,3]triazol-5-yl)propanoic acid (2.1 g, 4.49 mmol) in tetrahydrofuran (112 mL) and the reaction stirred at ambient temperature for 16 hrs. Water was added and the solution was extracted with ethyl acetate (3×). The combined organic fractions were washed (brine), dried (sodium sulfate), filtered and concentrated. The crude intermediate was re-dissolved in acetonitrile (112 mL), (R)-4-benzyloxazolidin-2-one (0.875 g, 4.94 mmol) and 2,3,4,6,7,8,9,10-octahydropyrimido[1,2-a]azepine (0.135 ml, 0.898 mmol) were added and the solution stirred at ambient temperature for 16 hrs. The reaction was quenched with water and extracted with ethyl acetate (3×). The combined organic fractions were washed (brine), dried (sodium sulfate), filtered and concentrated. The product was purified by silica gel chromatography to give the title compound (1.43 g, 2.281 mmol, 50.8% yield). LC/MS: m/z 627.2 (M+H)$^+$, 1.62 min (ret. time)

(R)-4-Benzyl-3-((2R,3S)-3-(3-(((tert-butyldimethylsilyl)oxy)methyl)-4-methylphenyl)-3-(1-ethyl-4-methyl-1H-benzo[d][1,2,3]triazol-5-yl)-2-methylpropanoyl)oxazolidin-2-one

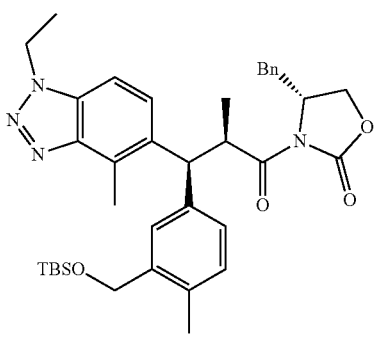 [SMILES: CCn1nnc2c(C)c([C@H](c3ccc(C)c(CO[Si](C)(C)C(C)(C)C)c3)[C@@H](C)C(=O)N3C(=O)OC[C@H]3Cc3ccccc3)ccc21]

Sodium bis(trimethylsilyl)amide (2.457 ml, 2.457 mmol) was added dropwise to a solution of (R)-4-benzyl-3-(((S)-3-(3-(((tert-butyldimethylsilyl)oxy)methyl)-4-methylphenyl)-3-(1-ethyl-4-methyl-1H-benzo[d][1,2,3]triazol-5-yl)propanoyl)oxazolidin-2-one (1.4 g, 2.233 mmol) in tetrahydrofuran (22.33 mL) at −78° C. and the reaction stirred for 30 minutes. Methyl iodide (5.58 mL, 11.17 mmol) was then added and the solution stirred for 3 h at −78° C. and then warmed to ambient temperature. The reaction was quenched with saturated aqueous ammonium chloride and extracted with ethyl acetate (3×). The combined organic fractions were washed (brine), dried (sodium sulfate), filtered and concentrated. The crude product was purified by silica gel chromatography to give the title compound (1.22 g, 1.904 mmol, 85 yield). LC/MS: m/z 641.1 (M+H)$^+$, 1.70 min (ret. time)

(R)-4-Benzyl-3-((2R,3S)-3-(1-ethyl-4-methyl-1H-benzo[d][1,2,3]triazol-5-yl)-3-(3-(hydroxymethyl)-4-methylphenyl)-2-methylpropanoyl)oxazolidin-2-one

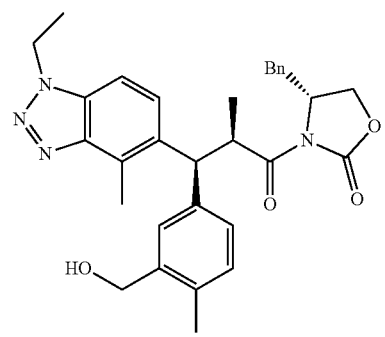 [SMILES: CCn1nnc2c(C)c([C@H](c3ccc(C)c(CO)c3)[C@@H](C)C(=O)N3C(=O)OC[C@H]3Cc3ccccc3)ccc21]

HCl (234 µL, 1.404 mmol) was added to a solution of (R)-4-benzyl-3-((2R,3S)-3-(3-(((tert-butyldimethylsilyl)oxy)methyl)-4-methylphenyl)-3-(1-ethyl-4-methyl-1H-benzo[d][1,2,3]triazol-5-yl)-2-methylpropanoyl)oxazolidin-2-one (300 mg, 0.468 mmol) in methanol (4.68 mL) and the reaction stirred for 5 minutes at which time the reaction was complete. The solution was filtered over sodium sulfate, filtered and concentrated to give the title compound (247 mg, 0.468 mmol, 100% yield). LC/MS: m/z 527.4 (M+H)$^+$, 1.19 min (ret. time)

(R)-4-Benzyl-3-((2R,3S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2-methylpropanoyl)oxazolidin-2-one

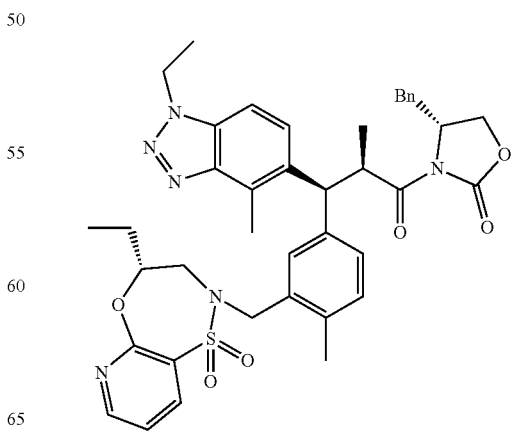

To a solution of (R)-4-benzyl-3-((2R,3S)-3-(1-ethyl-4-methyl-1H-benzo[d][1,2,3]triazol-5-yl)-3-(3-(hydroxymethyl)-4-methylphenyl)-2-methylpropanoyl)oxazolidin-2-one (1240 mg, 2.355 mmol), (R)-4-ethyl-3,4-dihydro-2H-pyrido[2,3-b][1,4,5]oxathiazepine 1,1-dioxide (645 mg, 2.83 mmol), and 1,1'-(Azodicarbonyl)dipiperidine (1188 mg, 4.71 mmol) in tetrahydrofuran (THF) (50 mL) at ambient temperature was added tri-n-butylphosphine (1.162 mL, 4.71 mmol). The reaction mixture was stirring at ambient temperature for 72 h. It was quenched with water and extracted with ethyl acetate twice. The combined organic layer was washed with brine and concentrated. It was purified by silica gel chromatography (Combiflash) (product came out at 50% ethyl acetate in hexane) three times. Desired fractions were concentrated to give the title compound (1320 mg, 1.791 mmol, 76% yield). LC-MS m/z 737.4 (M+H)$^+$, 1.35 min (ret. time)

Example 21

(S)—N-(3-(Dimethylamino)-3-oxopropyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide

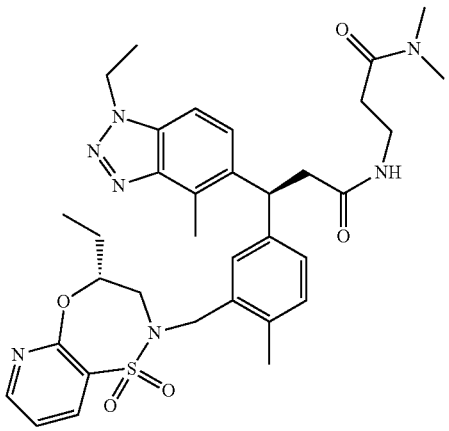 [SMILES: CC[C@@H]1CN(Cc2cc([C@H](CC(=O)NCCC(=O)N(C)C)c3ccc4c(nnn4CC)c3C)ccc2C)S(=O)(=O)c2cccnc2O1]

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (0.056 g, 0.1 mmol), N,N,N',N'-tetramethyl-O-(7-azabenzotriazol-1-yl) uronium hexafluorophosphate (0.038 g, 0.1 mmol) and N,N-Diisopropylethylamine (0.052 ml, 0.3 mmol) were combined in N,N-dimethylformamide (DMF) (0.5 mL) and the solution left for 3 min. The solution was dispensed to 3-amino-N,N-dimethylpropanamide (13.94 mg, 0.12 mmol). The reaction vessel was sealed and left for 3 h at 22° C. The sample in DMF (0.5 ml) was purified by MDAP using a high pH ammonium carbonate buffer (pH 10) to give the title compound (4.6 mg, 6.26% yield). LC-MS m/z 662 (M+H)$^+$, 0.97 min (ret. time)

Example 22

(3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(tetrahydrofuran-3-yl)propanamide

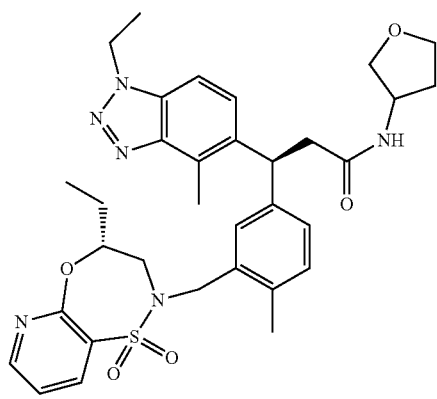 [SMILES: CC[C@@H]1CN(Cc2cc([C@H](CC(=O)NC3CCOC3)c3ccc4c(nnn4CC)c3C)ccc2C)S(=O)(=O)c2cccnc2O1]

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (0.056 g, 0.1 mmol), N,N,N',N'-tetramethyl-O-(7-azabenzotriazol-1-yl) uronium hexafluorophosphate (0.038 g, 0.1 mmol) and N,N-diisopropylethylamine (0.052 ml, 0.3 mmol) were combined in N,N-dimethylformamide (DMF) (0.5 mL) and the solution was left for 3 min. The solution was dispensed to tetrahydrofuran-3-amine (10.45 mg, 0.12 mmol). The reaction vessel was sealed and left for 18 h at ambient temperature. The sample in DMF (0.5 ml) purified by MDAP (method C) using a high pH ammonium carbonate buffer (pH 10) to give the title compound (3S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(tetrahydrofuran-3-yl)propanamide (35.4 mg, 50.3% yield). LC-MS m/z 633 (M+H)$^+$, 1.01 min (ret. time)

The compounds in Table 2 were prepared by a method similar to the one described for the preparation of (3S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(tetrahydrofuran-3-yl)propanamide. As is appreciated by those skilled in the art, these analogous examples may involve variations in general reaction conditions.

TABLE 2

| Ex # | Structure | Name | LCMS [M + H]+ | Retention Time (min) | MDAP method |
|---|---|---|---|---|---|
| Example 23 | 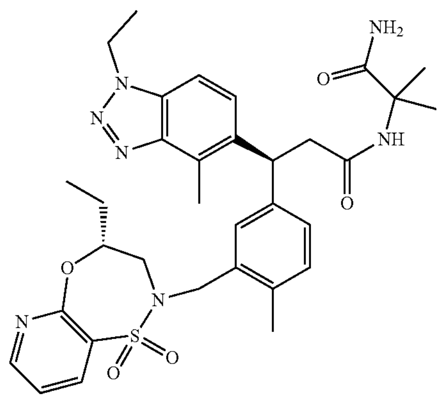 [SMILES: CC[C@@H]1CN(Cc2cc([C@H](CC(=O)NC(C)(C)C(N)=O)c3ccc4c(nnn4CC)c3C)ccc2C)S(=O)(=O)c2cccnc2O1] | (S)-N-(1-Amino-2-methyl-1-oxopropan-2-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide | 648 | 0.94 | B |
| Example 24 | 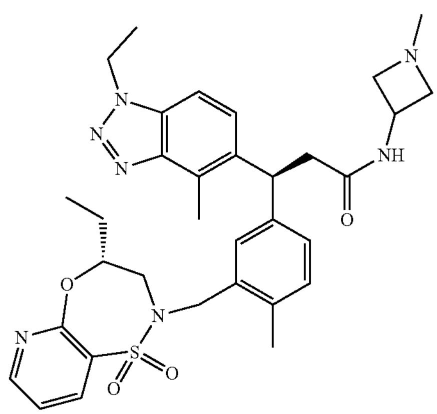 [SMILES: CC[C@@H]1CN(Cc2cc([C@H](CC(=O)NC3CN(C)C3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(1-methylazetidin-3-yl)propanamide | 632 | 0.71 | C |
| Example 25 | 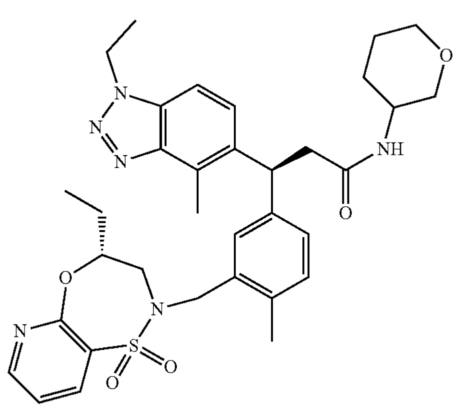 [SMILES: CC[C@@H]1CN(Cc2cc([C@H](CC(=O)NC3CCCOC3)c3ccc4c(nnn4CC)c3C)ccc2C)S(=O)(=O)c2cccnc2O1] | (3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(tetrahydro-2H-pyran-3-yl)propanamide | 647 | 1.05 | C |

TABLE 2-continued

| Ex # | Structure | Name | LCMS [M + H]+ | Retention Time (min) | MDAP method |
|---|---|---|---|---|---|
| Example 26 | 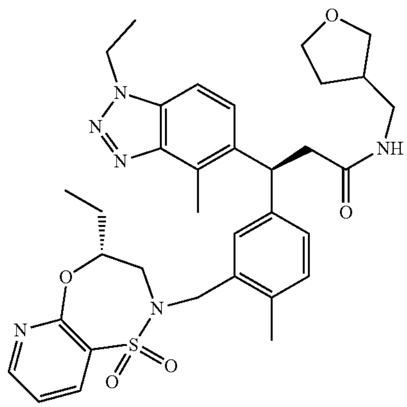 [SMILES: CC[C@@H]1CN(Cc2cc([C@H](CC(=O)NCC3CCOC3)c3ccc4c(nnn4CC)c3C)ccc2C)S(=O)(=O)c2cccnc2O1] | (3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-((tetrahydrofuran-3-yl)methyl)propanamide | 647 | 1 | C |
| Example 27 | 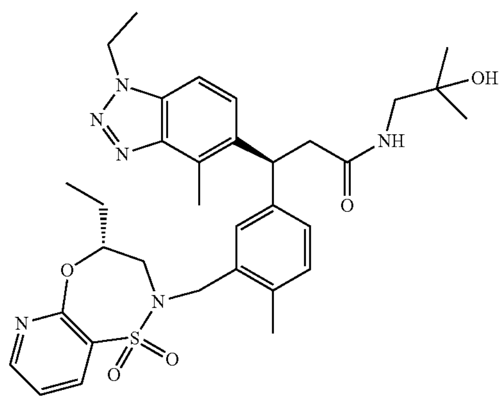 [SMILES: CC[C@@H]1CN(Cc2cc([C@H](CC(=O)NCC(C)(C)O)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-hydroxy-2-methylpropyl)propanamide | 635 | 0.97 | C |
| Example 28 | 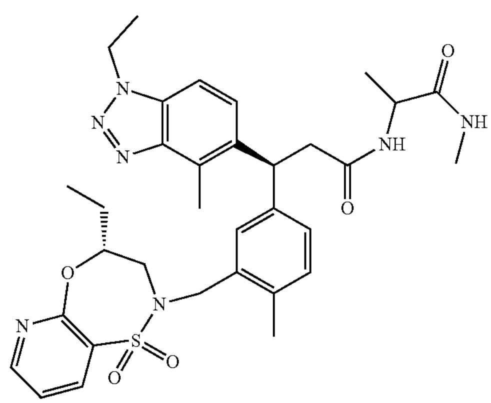 [SMILES: CC[C@@H]1CN(Cc2cc([C@H](CC(=O)NC(C)C(=O)NC)c3ccc4c(nnn4CC)c3C)ccc2C)S(=O)(=O)c2cccnc2O1] | (3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(1-(methylamino)-1-oxopropan-2-yl)propanamide | 648 | 0.96 | C |

TABLE 2-continued

| Ex # | Structure | Name | LCMS [M + H]+ | Retention Time (min) | MDAP method |
|---|---|---|---|---|---|
| Example 29 | 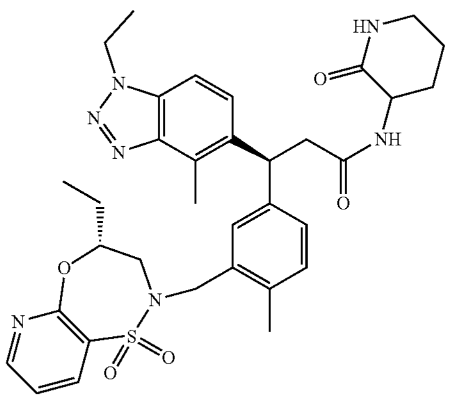 [SMILES: CC[C@@H]1CN(Cc2cc([C@H](CC(=O)NC3CCCNC3=O)c3ccc4c(nnn4CC)c3C)ccc2C)S(=O)(=O)c2cccnc2O1] | (3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-oxopiperidin-3-yl)propanamide | 660 | 0.98 | B |

Example 30

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-sulfamoylethyl)propanamide

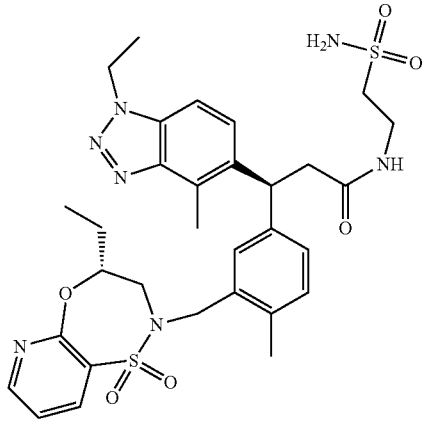 [SMILES: CC[C@@H]1CN(Cc2cc([C@H](CC(=O)NCCS(N)(=O)=O)c3ccc4c(nnn4CC)c3C)ccc2C)S(=O)(=O)c2cccnc2O1]

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (0.056 g, 0.1 mmol), N,N,N',N'-tetramethyl-O-(7-azabenzotriazol-1-yl) uronium hexafluorophosphate (0.038 g, 0.1 mmol) and N,N-diisopropylethylamine (0.052 ml, 0.3 mmol) were combined in N,N-dimethylformamide (DMF) (0.5 mL) and the solution left for 3 min. The solution then dispensed to 2-aminoethanesulfonamide (14.9 mg, 0.12 mmol). Reaction vessel was sealed and left for 18 h at ambient temperature. The sample in DMF (0.5 ml) was purified by MDAP (method C) using a high pH ammonium carbonate buffer (pH 10). Further purification required by MDAP (method B) using a formic acid buffer to give the title compound (4.7 mg, 6.32% yield). LC-MS m/z 670 (M+H)+, 0.94 min (ret. time)

Example 31

(S)—N-Cyclopropyl-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide

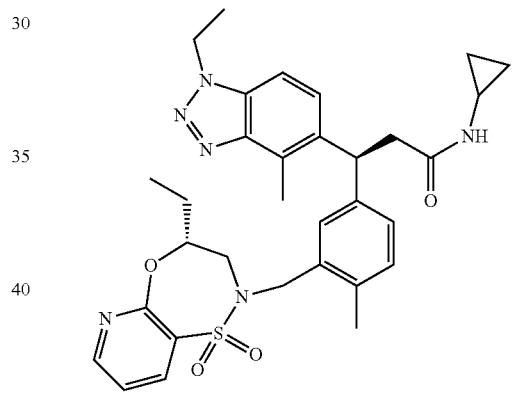

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (0.056 g, 0.1 mmol), N,N,N',N'-tetramethyl-O-(7-azabenzotriazol-1-yl) uronium hexafluorophosphate (0.038 g, 0.1 mmol) and N,N-diisopropylethylamine (0.055 ml, 0.315 mmol) were combined in N,N-dimethylformamide (DMF) (0.5 mL). The solution was dispensed to cyclopropanamine (0.007 g, 0.12 mmol). Reaction vessel was sealed and left for 18 h at ambient temperature. The sample in DMF (0.6 ml) purified by MDAP (method C) using a high pH ammonium carbonate buffer (pH 10) to give the title compound (40.9 mg, 61.1% yield). LC-MS m/z 603 (M+H)+, 1.05 min (ret. time)

The compounds in Table 3 were prepared by a method similar to the one described for the preparation of (S)—N-cyclopropyl-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide. As is appreciated by those skilled in the art, these analogous examples may involve variations in general reaction conditions.

TABLE 3

| Ex # | Structure | Name | LCMS [M + H]⁺ | Retention Time (min) | MDAP Method |
|---|---|---|---|---|---|
| Example 32 | 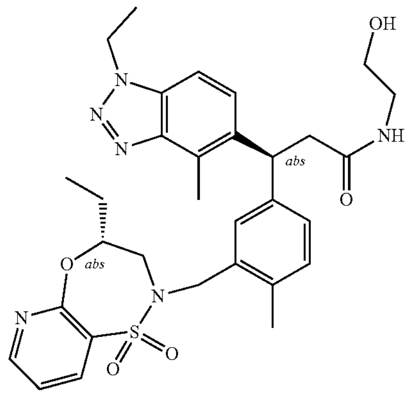 [SMILES: CC[C@@H]1CN(Cc2cc([C@H](CC(=O)NCCO)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-hydroxyethyl)propanamide | 607 | 0.94 | C |
| Example 33 | 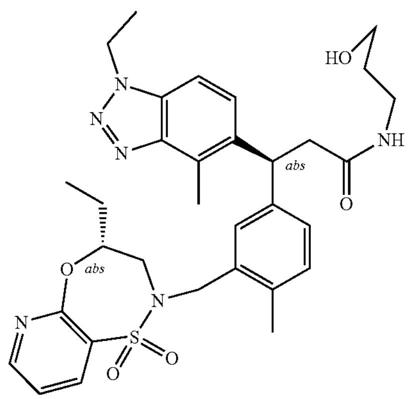 [SMILES: CC[C@@H]1CN(Cc2cc([C@H](CC(=O)NCCCO)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(3-hydroxypropyl)-propanamide | 621 | 0.95 | C |
| Example 34 | 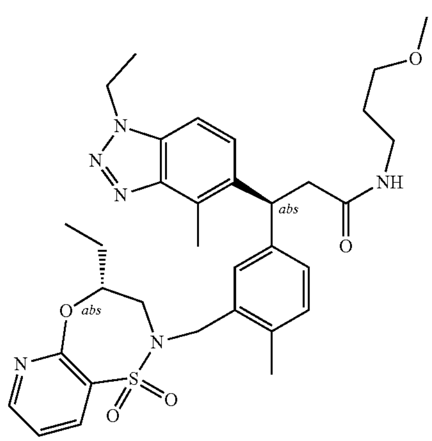 [SMILES: CC[C@@H]1CN(Cc2cc([C@H](CC(=O)NCCCOC)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(3-methoxypropyl)-propanamide | 635 | 1.03 | C |

Example 35

(S)—N-(2-Amino-2-oxoethyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide

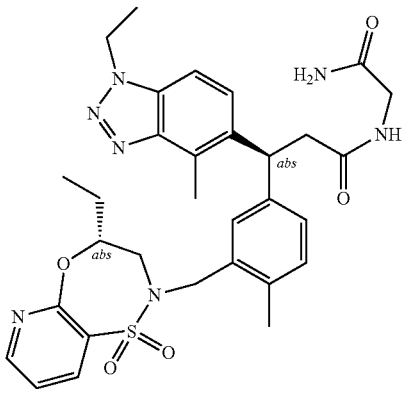 [SMILES: CC[C@@H]1CN(Cc2cc([C@H](CC(=O)NCC(N)=O)c3ccc4c(nnn4CC)c3C)ccc2C)S(=O)(=O)c2cccnc2O1]

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (0.056 g, 0.1 mmol), N,N,N',N'-tetramethyl-O-(7-azabenzotriazol-1-yl) uronium hexafluorophosphate (0.038 g, 0.1 mmol) and N,N-diisopropylethylamine (0.055 ml, 0.315 mmol) were combined in N,N-dimethylformamide (DMF) (0.5 mL). The solution then dispensed to 2-aminoacetamide (0.013 g, 0.12 mmol). Reaction vessel was sealed and left for 2 h at ambient temperature. The sample in DMF (0.6 ml) purified by MDAP (method C) using a high pH ammonium carbonate buffer (pH 10) to give the title compound (S)—N-(2-amino-2-oxoethyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide (39 mg, 56.6% yield). LC-MS m/z 620 $(M+H)^+$, 0.94 min (ret. time)

The compounds in Table 4 were prepared by a method similar to the one described for the preparation of (S)—N-(2-amino-2-oxoethyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide. As is appreciated by those skilled in the art, these analogous examples may involve variations in general reaction conditions.

TABLE 4

| Ex # | Structure | Name | LCMS [M + H]+ | Retention Time (min) | MDAP Method |
|---|---|---|---|---|---|
| Example 36 | 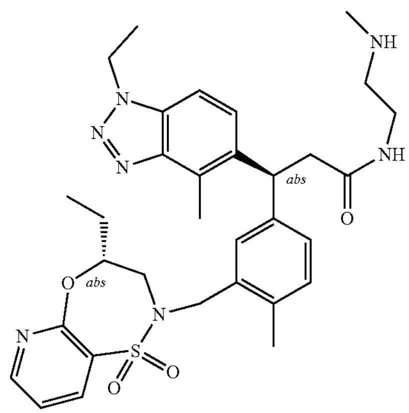 [SMILES: CC[C@@H]1CN(Cc2cc([C@H](CC(=O)NCCNC)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d]-[1,2,3]triazol-5-yl)-N-(2-(methylamino)ethyl)propanamide | 620 | 0.73 | C |
| Example 37 | 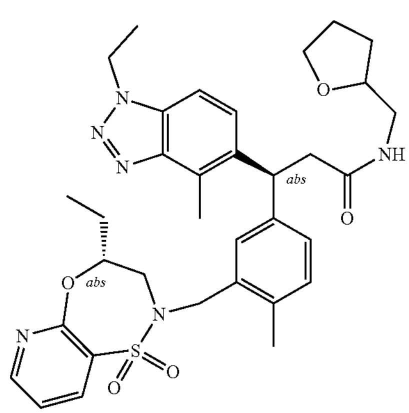 [SMILES: CC[C@@H]1CN(Cc2cc([C@H](CC(=O)NCC3CCCO3)c3ccc4c(nnn4CC)c3C)ccc2C)S(=O)(=O)c2cccnc2O1] | (3S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-((tetrahydrofuran-2-yl)methyl)propanamide | 647 | 1.06 | C |

TABLE 4-continued

| Ex # | Structure | Name | LCMS [M + H]+ | Retention Time (min) | MDAP Method |
|---|---|---|---|---|---|
| Example 38 | 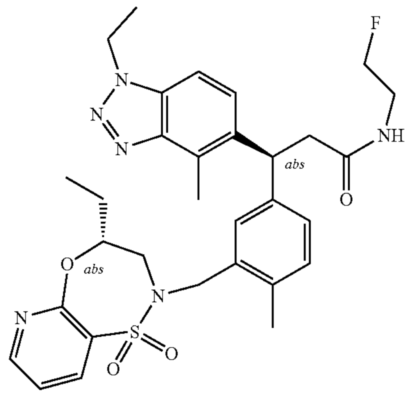 [SMILES: CC[C@@H]1CN(Cc2cc([C@H](CC(=O)NCCF)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-fluoroethyl)propanamide | 609 | 1.06 | C |
| Example 39 | 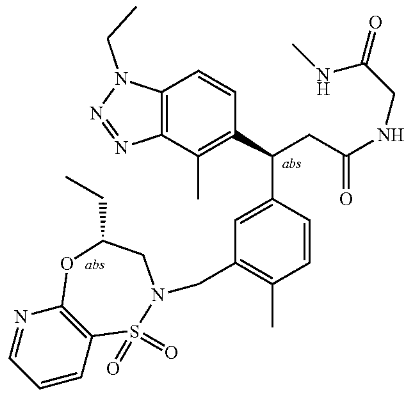 [SMILES: CC[C@@H]1CN(Cc2cc([C@H](CC(=O)NCC(=O)NC)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylamino)-2-oxoethyl)propanamide | 634 | 0.96 | C |
| Example 40 | 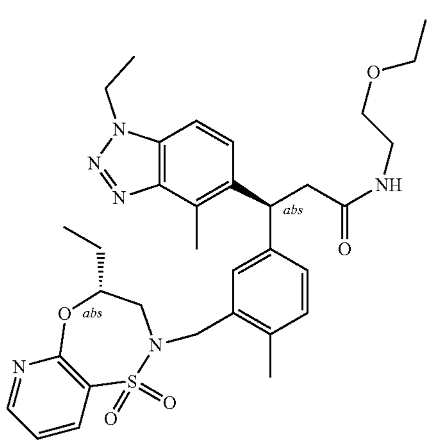 [SMILES: CCOCCNC(=O)C[C@@H](c1ccc(C)c(CN2C[C@@H](CC)Oc3ncccc3S2(=O)=O)c1)c1ccc2c(nnn2CC)c1C] | (S)-N-(2-Ethoxyethyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide | 635 | 1.08 | C |

TABLE 4-continued

| Ex # | Structure | Name | LCMS [M + H]+ | Retention Time (min) | MDAP Method |
|---|---|---|---|---|---|
| Example 41 | 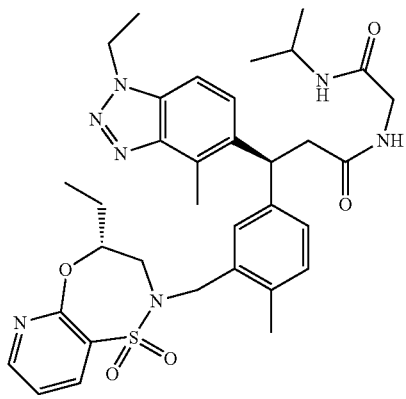 [SMILES: CC[C@@H]1CN(Cc2cc([C@H](CC(=O)NCC(=O)NC(C)C)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-methoxyethyl)propanamide | 621 | 1.03 | C |

Example 42

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(isopropylamino)-2-oxoethyl)propanamide (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (0.056 g, 0.1 mmol), N,N,N',N'-tetramethyl-O-(7-azabenzotriazol-1-yl) uronium hexafluorophosphate (0.038 g, 0.1 mmol) and N,N-Diisopropylethylamine (0.055 ml, 0.315 mmol) were combined in N,N-dimethylformamide (DMF) (0.5 mL). The solution then dispensed to 2-amino-N-isopropylacetamide (0.014 g, 0.12 mmol). Reaction vessel was sealed and left for 2 h at ambient temperature. The sample in DMF (0.6 ml) purified by MDAP (method C) using a high pH ammonium carbonate buffer (pH 10) to give the title compound (S)-3-(3-(((R)-4-ethyl-1,1-dioxido-3,4-dihydro-2H-pyrido[2,3-b][1,4,5]oxathiazepin-2-yl)methyl)-4-methyl-1H-benzo[d][1,2,3]triazol-5-yl)-N-(2-(isopropylamino)-2-oxoethyl)propanamide (18 mg, 24.48% yield). LC-MS m/z 662 (M+H)+, 1.01 min (ret. time)

Example 43

(3S)—N-(1-Amino-1-oxopropan-2-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (0.056 g, 0.1 mmol), N,N,N',N'-tetramethyl-O-(7-azabenzotriazol-1-yl) uronium hexafluorophosphate (0.038 g, 0.1 mmol) and N,N-Diisopropylethylamine (0.055 ml, 0.315 mmol) were combined in N,N-dimethylformamide (DMF) (0.5 mL). The solution then dispensed to 2-aminopropanamide (0.011 g, 0.12 mmol). Reaction vessel was sealed and left for 2 h at ambient temperature. A solution of propylphosphonic anhydride solution (50% EtOAc, 120 ul) was added followed by N,N-diisopropylethylamine (0.055 ml, 0.315 mmol). Reaction vessel was sealed and left at ambient temperature for 1 h. The sample in reaction solvent was purified by MDAP (method C) using a high pH ammonium carbonate buffer (pH 10) to give the title compound (3S)—N-(1-amino-1-oxopropan-2-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide (4.6 mg, 6.53% yield). LC-MS m/z 634 (M+H)⁺, 0.93 min (ret. time)

The compound in Table 5 were prepared by a method similar to the one described for the preparation of (3S)—N-(1-amino-1-oxopropan-2-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide. As is appreciated by those skilled in the art, these analogous examples may involve variations in general reaction conditions.

To a solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (150 mg, 0.266 mmol) in dichloromethane (DCM) (10 mL), N-(2-aminoethyl)acetamide (32.6 mg, 0.319 mmol), HATU (111 mg, 0.293 mmol) and DIEA (0.116 mL, 0.665 mmol) were added. Then the reaction mixture was stirred at room temperature for 18 h. The solvent was evaporated and the residue was purified by reverse-phase HPLC under acidic condition to obtain the title compound (115 mg, 0.169 mmol, 63.7% yield). LC-MS m/z 648.7 (M+H)⁺, 0.91 min (ret. time)

TABLE 5

| Ex # | Structure | Name | LCMS [M + H]⁺ | Retention Time (min) | MDAP Method |
|---|---|---|---|---|---|
| Example 44 | 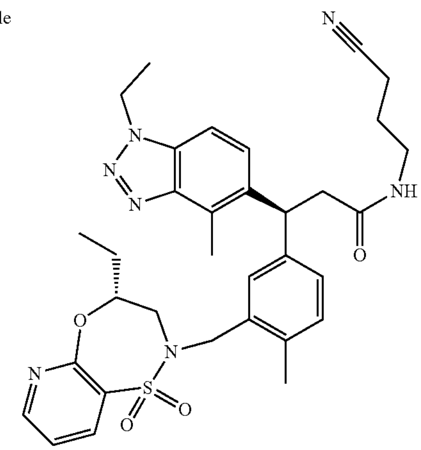 | (S)-N-(3-Cyanopropyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide | 630 | 1.01 | C |

Example 45

(S)—N-(2-Acetamidoethyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide

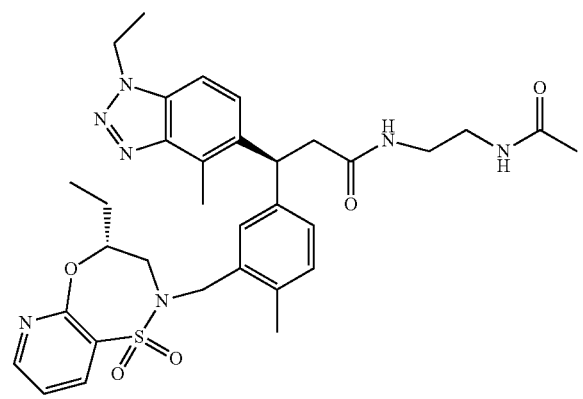 [SMILES: CC[C@@H]1CN(Cc2cc([C@H](CC(=O)NCCNC(C)=O)c3ccc4c(nnn4CC)c3C)ccc2C)S(=O)(=O)c2cccnc2O1]

Example 46

(R)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-N-(pyridin-3-yl)propanamide, Formic Acid Salt

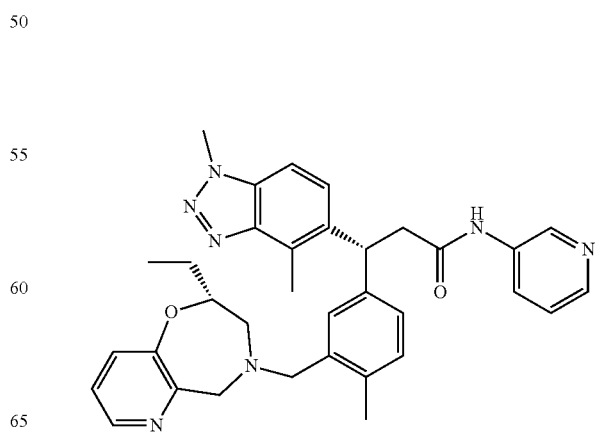

(R)-1-(((3-Fluoropyridin-2-yl)methyl)amino)butan-2-ol

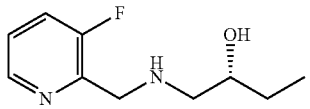

To a solution of (R)-1-aminobutan-2-ol (3.70 g, 41.5 mmol) in methanol (150 mL) was added 3-fluoropicolinaldehyde (4.67 g, 37.4 mmol) followed by magnesium sulfate (4.50 g, 37.4 mmol) and the reaction mixture was stirred at 0° C. for 1 hr. The reaction mixture was filtered through celite and washed with methanol (300 ml). Sodium borohydride (1.413 g, 37.4 mmol) was added in two portions to the filtrate and the reaction mixture was stirred at ambient temperature for 30 min. The reaction mixture was quenched with 10% sodium bicarbonate solution and the methanol evaporated under reduced pressure. The remaining aqueous phase was extracted with ethyl acetate (3×125 mL) and the combined organic extracts were washed with brine, dried over sodium sulfate, filtered and the solvent evaporated under reduced pressure. The crude residue was purified by silica gel chromatography (0-100%/3:1 ethyl acetate:ethanol/hexanes) to afford a yellow oil (R)-1-(((3-fluoropyridin-2-yl)methyl)amino)butan-2-ol (5.3 g, 24.06 mmol, 58.0% yield). $^1$H NMR (CHCl$_3$-d) δ: 8.36-8.45 (m, 1H), 7.37-7.45 (m, 1H), 7.22-7.32 (m, 1H), 4.10-4.16 (m, 2H), 3.68-3.77 (m, 1H), 2.89 (m, 1H), 2.64 (m, 1H), 1.43-1.55 (m, 2H), 0.90-1.02 (m, 3H). LC-MS: m/z 199.2 (M+H)$^+$

(R)-Tert-butyl 2-ethyl-2,3-dihydropyrido[2,3-f][1,4]oxazepine-4(5H)-carboxylate

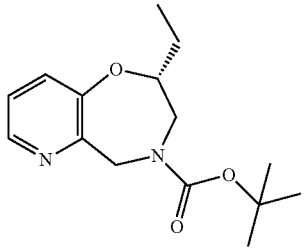 [SMILES: CC[C@@H]1CN(C(=O)OC(C)(C)C)Cc2ncccc2O1]

To a solution of (R)-1-(((3-fluoropyridin-2-yl)methyl)amino)butan-2-ol (5.20 g, 26.2 mmol) in dimethyl sulfoxide (100 mL) was added potassium tert-butoxide (3.68 g, 32.8 mmol) and the reaction mixture was stirred at 90° C. for 45 min. The reaction mixture was cooled to ambient temperature to afford a deep red-colored solution. Boc-anhydride (6.09 mL, 26.2 mmol) was added and the reaction mixture was allowed to stir for 18 hr. The reaction mixture was diluted with ethyl acetate (500 mL) and the organic phase washed with water (4×200 mL), brine, dried over sodium sulfate, filtered and the solvent evaporated under reduced pressure. The crude residue was purified by silica gel chromatography (0-50% ethyl acetate/hexanes) to afford an orange oil (R)-tert-butyl 2-ethyl-2,3-dihydropyrido[2,3-f][1,4]oxazepine-4(5H)-carboxylate (4.84 g, 17.39 mmol, 66.3% yield). $^1$H NMR (DMSO-d$_6$) δ: 8.17 (m, 1H), 7.36 (m, 1H), 7.24 (m, 1H), 4.49-4.76 (m, 2H), 3.93 (br. s., 1H), 3.47-3.74 (m, 2H), 1.52-1.66 (m, 2H), 1.36 (br. s., 4H), 1.25 (s, 5H), 0.96-1.07 (m, 3H). LC-MS: m/z 279.2 (M+H)$^+$.

(R)-2-Ethyl-2,3,4,5-tetrahydropyrido[2,3-f][1,4]oxazepine, hydrochloride

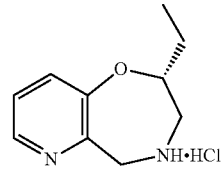

To a solution of (R)-tert-butyl 2-ethyl-2,3-dihydropyrido[2,3-f][1,4]oxazepine-4(5H)-carboxylate (4.84 g, 17.39 mmol) in 1,4-dioxane (20 mL), at ambient temperature, was added 4N HCl in dioxane (100 mL, 400 mmol) and the reaction mixture was stirred at ambient temperature for 2 h. The solvent was evaporated under reduced pressure and azeotroped with diethyl ether (3×) to afford a cream solid (R)-2-ethyl-2,3,4,5-tetrahydropyrido[2,3-f][1,4]oxazepine, hydrochloride (3.55 g, 16.54 mmol, 95% yield). $^1$H NMR (DMSO-d$_6$) δ: 9.95-10.36 (m, 2H), 8.38 (m, 1H), 7.66 (m, 1H), 7.51 (m, 1H), 4.39-4.57 (m, 2H), 4.04-4.18 (m, 1H), 3.47-3.60 (m, 1H), 3.24-3.40 (m, 1H), 1.69 (m, 2H), 1.05 (m, 3H). LC-MS: m/z 179.2 (M+H)$^+$

N,3-Dimethyl-2-nitroaniline

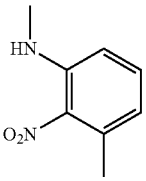

1-fluoro-3-methyl-2-nitrobenzene (50 g, 322 mmol) was dissolved in ethanol (250 mL) and 40% methanamine in water (98 mL, 1128 mmol) was added. The reaction mixture was heated to reflux for 8 hr and then cooled back to ambient temperature. The reaction mixture was filtered to afford an orange solid N,3-dimethyl-2-nitroaniline (47.9 g, 288 mmol, 89 yield). $^1$H NMR (DMSO-d$_6$) δ: 7.29 (t, J=8.0 Hz, 1H), 6.70 (d, J=8.5 Hz, 1H), 6.55 (d, J=7.3 Hz, 1H), 6.51 (d, J=4.3 Hz, 1H), 2.78 (d, J=4.8 Hz, 3H), 2.30 (s, 3H). LC-MS: m/z 167.2 (M+H)$^+$.

4-Bromo-N,3-dimethyl-2-nitroaniline

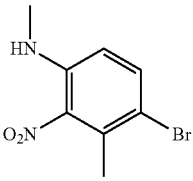

N,3-dimethyl-2-nitroaniline (47.9 g, 288 mmol) was dissolved in N,N-dimethylformamide (250 mL). The mixture was cooled to 5° C. N-Bromosuccinimide (51.3 g, 288 mmol) dissolved in 150 mL N,N-dimethylformamide was added dropwise via an addition funnel and was stirred at ambient temperature for 24 hr. The reaction mixture was poured into water (1.5 L) and filtered to afford an orange solid 4-bromo-N,3-dimethyl-2-nitroaniline (73.5 g, 300 mmol, 104% yield). $^1$H NMR (DMSO-d$_6$) δ: 7.56 (d, J=9.3 Hz, 1H), 6.66 (d, J=9.3 Hz, 1H), 6.26 (d, J=4.5 Hz, 1H), 2.73 (d, J=4.8 Hz, 3H), 2.25 (s, 3H). LC-MS: m/z 245.0 (M+H)$^+$.

Bromo-N1,3-dimethylbenzene-1,2-diamine

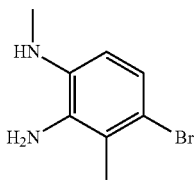

To a solution of 4-bromo-N,3-dimethyl-2-nitroaniline (78.4 g, 320 mmol) in acetic acid (500 mL) and ethanol (500 mL) at 0° C. was added iron powder (89 g, 1600 mmol) followed by 2N HCl (320 mL, 640 mmol). The mixture was stirred for 1 hr and then filtered through celite and the filtrate concentrated to remove the majority of ethanol. The residue was diluted with ethyl acetate (800 ml) and water (800 ml) and the layers separated. The organic extract was washed with water (500 mL), 10% sodium bicarbonate solution (500 mL), brine and concentrated under reduced pressure to afford a red oil 4-bromo-N1,3-dimethylbenzene-1,2-diamine (67 g, 311 mmol, 97% yield). $^1$H NMR (DMSO-d$_6$) δ: 6.75 (d, J=8.5 Hz, 1H), 6.22 (d, J=8.5 Hz, 1H), 4.48-4.90 (m, 2H), 2.69 (s, 3H), 2.17 (s, 3H). LC-MS: m/z=215.2 (M+H)$^+$.

5-Bromo-1,4-dimethyl-1H-benzo[d][1,2,3]triazole

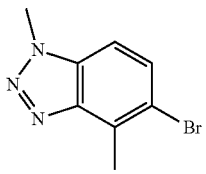

Tert-butyl nitrite (61.5 mL, 467 mmol, 90% tech grade) and tetrafluoroboric acid (97 mL, 623 mmol, 48% aqueous solution) were dissolved in 50 mL of acetonitrile and cooled to 0° C. Then, a solution of 4-bromo-N1,3-dimethylbenzene-1,2-diamine (67 g, 311 mmol) dissolved in a solution of acetonitrile (200 ml) and tetrafluoroboric acid, (97 mL, 623 mmol, 48% aqueous solution) was added slowly, so that the internal temperature never rose above 5° C. The reaction mixture was stirred at 5° C. for 2 hr and then ambient temperature for 1 hr. The reaction mixture was poured into a stirred solution of sodium hydroxide (100 g, 2500 mmol) in water (4 L). Sodium chloride was added until the solution reached saturation. The resulting solid was collected by filtration and washed with water (2×3 L), air dried and purified by silica gel column chromatography (25-100% ethyl acetate/hexanes) to afford a light yellow solid 5-bromo-1,4-dimethyl-1H-benzo[d][1,2,3]triazole (61 g, 267 mmol, 86% yield). $^1$H NMR (DMSO-d$_6$) δ: 7.66 (m, 2H), 4.30 (s, 3H), 2.70 (s, 3H). LC-MS: m/z=226 (M+H)$^+$.

tert-Butyl (E)-3-(1,4-dimethyl-1H-benzo[d][1,2,3]triazol-5-yl)acrylate

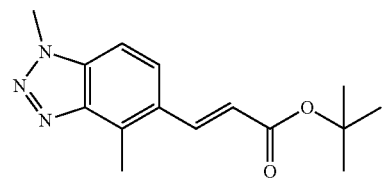 [SMILES: Cc1c(/C=C/C(=O)OC(C)(C)C)ccc2c1nnn2C]

A solution of 5-bromo-1,4-dimethyl-1H-benzo[d][1,2,3]triazole (100 g, 443 mmol) and N,N-dimethylformamide (1000 mL) was purged with nitrogen for 30 min after which time tri-o-tolylphosphine (27.0 g, 89 mmol), Pd(OAc)$_2$ (9.95 g, 44.3 mmol), and potassium carbonate (184 g, 1330 mmol) and tert-butyl acrylate (130 mL, 886 mmol) were added and the reaction mixture was heated at 100° C. for 24 hr under a nitrogen atmosphere. The reaction mixture was cooled to ambient temperature, diluted with water (1 L) and ethyl acetate (1 L) and the layers separated. The aqueous layer was extracted with ethyl acetate (2×1 L) and then the combined organic extracts were washed with water (2×), brine, dried over sodium sulfate, filtered and the solvent evaporated under reduced pressure. The crude dark solid was triturated with diethyl ether, filtered and dried under vacuum to afford a light brown solid tert-butyl (E)-3-(1,4-dimethyl-1H-benzo[d][1,2,3]triazol-5-yl)acrylate (109.3 g, 89% yield). $^1$H NMR (DMSO-d$_6$) δ: 7.89-8.00 (m, 2H), 7.67 (m, 1H), 6.54 (d, J=15.8 Hz, 1H), 4.29 (s, 3H), 2.79 (s, 3H), 1.51 (s, 9H). LCMS: m/z 274.2 [M+H]$^+$.

(E)-3-(1,4-Dimethyl-1H-benzo[d][1,2,3]triazol-5-yl)acrylic Acid

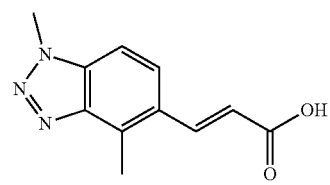 [SMILES: Cc1c(/C=C/C(=O)O)ccc2c1nnn2C]

To a solution of tert-butyl (E)-3-(1,4-dimethyl-1H-benzo[d][1,2,3]triazol-5-yl)acrylate (107 g, 391 mmol) in dichloromethane (300 mL) was added cold trifluoroacetic acid (250 mL) and the reaction mixture was stirred at ambient temperature for 2 hr. The solvent was evaporated under reduced pressure and then azeotroped with chloroform. The resulting solid was triturated in diethyl ether to afford a beige solid (E)-3-(1,4-dimethyl-1H-benzo[d][1,2,3]triazol-5-yl) acrylic acid (80 g, 368 mmol, 94% yield). $^1$H NMR (DMSO-d$_6$) δ: 7.90-8.02 (m, 2H), 7.69 (m, 1H), 6.55 (d, J=16.1 Hz, 1H), 4.30 (s, 3H), 2.80 (s, 3H) LC-MS: m/z 218.2 [M+H]$^+$.

(S,E)-3-(3-(1,4-Dimethyl-1H-benzo[d][1,2,3]triazol-5-yl)acryloyl)-4-phenyloxazolidin-2-one

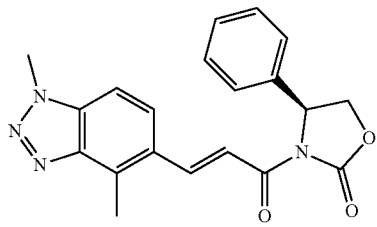 [SMILES: Cc1c(/C=C/C(=O)N2C(=O)OC[C@@H]2c2ccccc2)ccc2c1nnn2C]

To a suspension of (E)-3-(1,4-dimethyl-1H-benzo[d][1,2,3]triazol-5-yl)acrylic acid (82 g, 376 mmol) in tetrahydrofuran (1.5 L) was added triethylamine (131 mL, 939 mmol). The reaction mixture was cooled to −25° C. and pivaloyl chloride (46 ml, 376 mmol) was added dropwise and stirred for 30 min at −25° C. Lithium chloride (17.52 g, 413 mmol) was added in one-portion, followed by (S)-4-phenyloxazolidin-2-one (58.8 g, 361 mmol) and the reaction mixture was allowed to warm to ambient temperature and was stirred for 1 hr. The mixture was cooled to −25° C. and pivaloyl chloride (12 ml, 98 mmol) was added dropwise and allowed to stir for an additional 1 hr. THF (300 mL) was added followed by (S)-4-phenyloxazolidin-2-one (10 g, 61 mmol) and pivaloyl chloride (18 ml, 147 mmol) and the mixture was stirred at 10° C. for 1 hr and then ambient temperature for 18 hr. The reaction mixture was diluted with ethyl acetate (1 L) and washed with 5% NaHSO$_3$ (1 L). The resulting solid was collected by filtration and washed with water and diethyl ether to afford a light yellow solid (S,E)-3-(3-(1,4-dimethyl-1H-benzo[d][1,2,3]triazol-5-yl)acryloyl)-4-phenyloxazolidin-2-one (104.39 g, 288 mmol, 77% yield). $^1$H NMR (DMSO-d6) δ: 8.05 (d, J=15.8 Hz, 1H), 7.71-7.88 (m, 3H), 7.30-7.45 (m, 5H), 5.61 (m, 1H), 4.83 (m, 1H), 4.30 (s, 3H), 4.24 (m, 1H), 2.78 (s, 3H). LC-MS: m/z=363.2 [M+H]$^+$.

(S)-3-(((R)-3-(1,4-Dimethyl-1H-benzo[d][1,2,3]triazol-5-yl)-3-(3-(((4-methoxybenzyl)oxy)methyl)-4-methylphenyl)propanoyl)-4-phenyloxazolidin-2-one

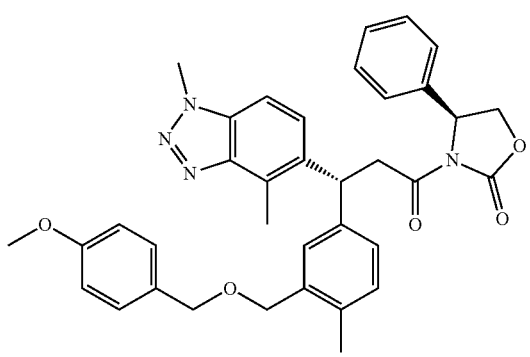 [SMILES: COc1ccc(COCc2cc([C@@H](CC(=O)N3C(=O)OC[C@@H]3c3ccccc3)c3ccc4c(nnn4C)c3C)ccc2C)cc1]

A mixture of magnesium (4.87 g, 200 mmol) and iodine (0.141 g, 0.556 mmol) was heated to 75° C. for 5 min. A solution of 4-bromo-2-(((4-methoxybenzyl)oxy)methyl)-1-methylbenzene (50.0 g, 156 mmol) in THF (200 mL) was added portion wise over 15 min and the mixture was stirred at reflux for 1 hr and then cooled to ambient temperature to give solution A. Separately, a mixture of copper(I) bromide-dimethyl sulfide complex (16.00 g, 78 mmol) in tetrahydrofuran (150 mL) was cooled to −40° C. and treated with dimethyl sulfide (41.1 mL, 556 mmol). The reaction mixture was stirred at −40° C. for 25 min. The cooled solution A was added dropwise over 1 hr maintaining a temperature between −35 and −45° C. The reaction mixture was allowed to warm to −20° C. and then (S,E)-3-(3-(1,4-dimethyl-1H-benzo[d][1,2,3]triazol-5-yl)acryloyl)-4-phenyloxazolidin-2-one (20.15 g, 55.6 mmol) was added in one portion. The resultant mixture was stirred at −20° C. for 30 min, then allowed to warm to −10° C. and was stirred for 30 minutes. Saturated aqueous ammonium chloride solution was added followed by ethyl acetate (1.5 L) and the layers were separated. The organic extract was washed with water (4×500 mL), brine, dried over sodium sulfate, filtered and the solvent evaporated to afford an oil which was purified by silica gel chromatography (0-100% ethyl acetate/hexane) to afford a white foam (S)-3-((R)-3-(1,4-dimethyl-1H-benzo[d][1,2,3]triazol-5-yl)-3-(3-(((4-methoxybenzyl)oxy)methyl)-4-methylphenyl)propanoyl)-4-phenyloxazolidin-2-one (24.5 g, 40.5 mmol, 73% yield). $^1$H NMR (DMSO-d$_6$) δ: 7.56 (m, 1H), 7.41 (d, m 1H), 7.21-7.25 (m, 3H), 7.16-7.20 (m, 3H), 7.04-7.16 (m, 4H), 6.82-6.89 (m, 2H), 5.36 (m, 1H), 4.91 (m, 1H), 4.69 (m, 1H), 4.34-4.41 (m, 4H), 4.24 (s, 3H), 4.10 (m, 1H), 3.88 (m, 1H), 3.74 (s, 3H), 3.60 (m, 1H), 2.70 (s, 3H), 2.18 (s, 3H). LC-MS: m/z 605.2 [M+H]+.

Ethyl (R)-3-(1,4-dimethyl-1H-benzo[d][1,2,3]triazol-5-yl)-3-(3-(((4-methoxybenzyl)oxy)methyl)-4-methylphenyl)propanoate

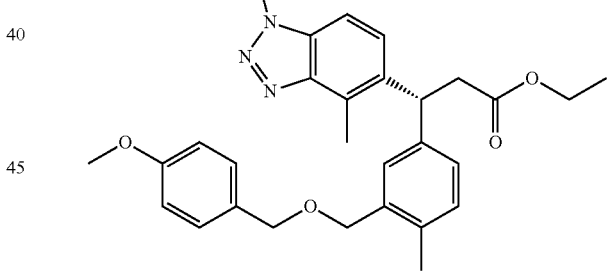

To a solution of (S)-3-((R)-3-(1,4-dimethyl-1H-benzo[d][1,2,3]triazol-5-yl)-3-(3-(((4-methoxybenzyl)oxy)methyl)-4-methylphenyl)propanoyl)-4-phenyloxazolidin-2-one (2.140 g, 3.54 mmol) in ethanol (30 mL) was added magnesium bromide (1.629 g, 8.85 mmol) and the reaction mixture was stirred for 4 hr. Additional magnesium bromide (0.81 g, 4.5 mmol) was added and the mixture was stirred for 18 hr. Saturated aqueous ammonium chloride solution was added and the resultant white precipitate was collected and washed with ethanol to afford ethyl (R)-3-(1,4-dimethyl-1H-benzo[d][1,2,3]triazol-5-yl)-3-(3-(((4-methoxybenzyl)oxy)methyl)-4-methylphenyl)propanoate (1.46 g, 2.99 mmol, 85% yield). $^1$H NMR (DMSO-d$_6$) δ: 7.56-7.62 (m, 1H), 7.48 (m, 1H), 7.12-7.22 (m, 4H), 7.05-7.11 (m, 1H), 6.83-6.90 (m, 2H), 4.84 (m, 1H), 4.39 (m, 4H), 4.24 (s, 3H), 3.87-3.97 (m, 2H), 3.75 (s, 3H), 3.08-3.23 (m, 2H), 2.75 (s, 3H), 2.18 (s, 3H), 1.01 (m, 3H) LC-MS: m/z=488.2 [M+H]$^+$.

Ethyl (R)-3-(1,4-dimethyl-1H-benzo[d][1,2,3]tri-azol-5-yl)-3-(3-(hydroxymethyl)-4-methylphenyl)propanoate

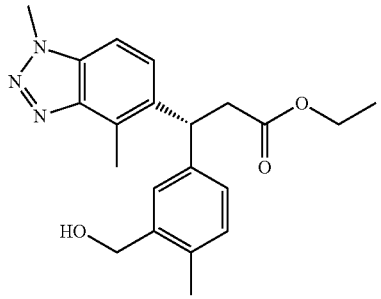 [SMILES: CCOC(=O)C[C@H](c1ccc(C)c(CO)c1)c1ccc2c(nnn2C)c1C]

To a solution of ethyl (R)-3-(1,4-dimethyl-1H-benzo[d][1,2,3]triazol-5-yl)-3-(3-(((4-methoxybenzyl)oxy)methyl)-4-methylphenyl)propanoate (53.6 g, 110 mmol), in dichloromethane (DCM) (700 mL) was added water (35.0 mL). The reaction mixture was cooled to 0° C. in an ice-bath, to which was added DDQ (37.4 g, 165 mmol) (in 2 equal portions) and the reaction mixture was stirred at 0° C. for 2 h while slowly allowing to warm up in ice bath. The reaction mixture was carefully poured into a solution of 10% NaHCO$_3$. The black solid was filtered, the flask rinsed with H$_2$O, added to the black solid and the solid further washed with DCM (750 mL). The combined phases were separated, the aqueous phase extracted with DCM (3×750 mL), the organic phases combined, washed with H$_2$O, dried over Na$_2$SO$_4$, and filtered and the solvent evaporated under reduced pressure. The crude residue was purified by flash column chromatography eluting with a 100% hexanes to 100% EtOAc gradient over 40 min, to afford the title compound (38.1 g, 104 mmol, 94% yield). LC-MS m/z=368 (M+H)$^+$, 1.2 min (ret. time).

Ethyl (R)-3-(1,4-dimethyl-1H-benzo[d][1,2,3]tri-azol-5-yl)-3-(3-(((R)-2-ethyl-2,3-dihydropyrido[2,3-f][1,4]oxazepin-4(5H)-yl)methyl)-4-methylphenyl)propanoate

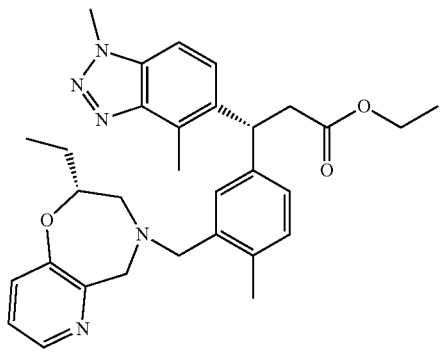 [SMILES: CCOC(=O)C[C@H](c1ccc(C)c(CN2Cc3ncccc3O[C@H](CC)C2)c1)c1ccc2c(nnn2C)c1C]

To a solution of ethyl (R)-3-(1,4-dimethyl-1H-benzo[d][1,2,3]triazol-5-yl)-3-(3-(hydroxymethyl)-4-methylphenyl)propanoate (10.10 g, 27.5 mmol) in chloroform (100 mL) was added thionyl chloride (4.01 mL, 55.0 mmol) and the reaction mixture was stirred for 1.5 hr at ambient temperature. The solvent was evaporated under reduced pressure and then azeotroped (3×chloroform). The residue was dissolved in acetonitrile (100 mL) and (R)-2-ethyl-2,3,4,5-tetrahydropyrido[2,3-f][1,4]oxazepine, hydrochloride (7.67 g, 35.7 mmol) and DIPEA (14.36 mL, 82 mmol) were added. The reaction mixture was heated to 60° C. for 18 hr. The reaction mixture was cooled, diluted with ethyl acetate, washed with water (2×), brine, dried over sodium sulfate, filtered and the solvent evaporated under reduced pressure. The crude residue was purified by silica gel chromatography (0-100% ethyl acetate/hexanes) to afford a white foam (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoate (13.76 g, 26.1 mmol, 95% yield). $^1$H NMR (DMSO-d$_6$) δ: 8.17 (m, 1H), 7.50-7.57 (m, 1H), 7.44-7.49 (m, 1H), 7.39 (m, 1H), 7.26 (m, 1H), 7.13 (s, 1H), 7.01-7.10 (m, 2H), 4.82 (m, 1H), 4.24 (s, 3H), 3.77-3.97 (m, 5H), 3.52 (s, 2H), 3.12 (m, 2H), 2.76-2.91 (m, 2H), 2.74 (s, 3H), 2.20 (s, 3H), 1.43-1.57 (m, 1H), 1.32 (m, 1H), 1.01 (m, 3H), 0.91 (m, 3H). LC-MS: m/z=528.4 [M+H]$^+$.

(R)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic Acid

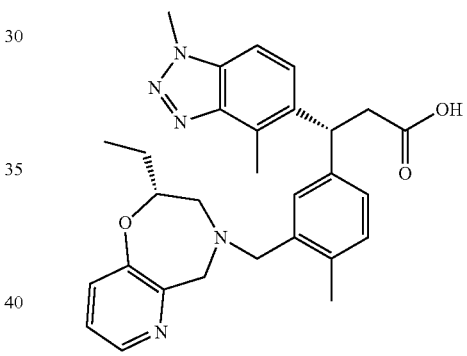

To a solution of ethyl (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoate (23.00 g, 43.6 mmol) in methanol (350 mL) was added lithium hydroxide (10.44 g, 436 mmol) followed by water (350 mL) and the reaction mixture was stirred at 75° C. for 4 hr then cooled to ambient temperature and the solvents removed under reduced pressure. The residue was dissolved in water (500 mL) and the pH adjusted with 6N HCl and then 1N HCl to pH 5. The resultant precipitate was collected by filtration, washed with water and dried under vacuum to afford an off white solid. The solid was purified by silica gel chromatography (50-100% 3:1EtOAc:EtOH/hexane) to afford a white foam, which was dried under vacuum to afford a cream solid (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5l-1)-yl)methyl)-4-methylphenyl)propanoic acid (16.29 g, 32.5 mmol, 74.6% yield). $^1$H NMR (DMSO-d$_6$) δ: 12.14 (s, 1H), 8.17 (m, 1H), 7.50-7.56 (m, 1H), 7.44-7.49 (m, 1H), 7.40 (m, 1H), 7.27 (m, 1H), 7.00-7.15 (m, 3H), 4.80 (m, 1H), 4.23 (s, 3H), 3.77-3.98 (m, 3H), 3.52 (s, 2H), 2.93-3.11 (m, 2H), 2.69-2.92 (m, 5H), 2.20 (s, 3H), 1.48 (m, 1H), 1.29 (m, 1H), 0.90 (t, J=7.3 Hz, 3H). LC-MS: m/z 500.3 [M+H]$^+$

159

(R)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-N-(pyridin-3-yl)propanamide, Formic Acid Salt

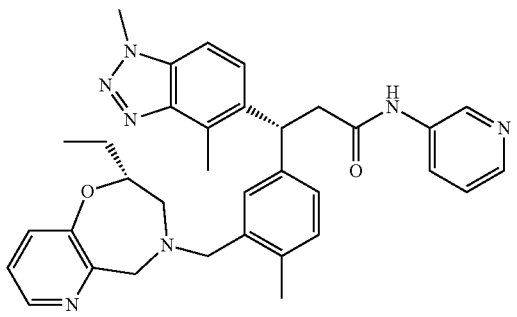 [SMILES: CC[C@@H]1CN(Cc2cc([C@@H](CC(=O)Nc3cccnc3)c3ccc4c(nnn4C)c3C)ccc2C)Cc2ncccc2O1]

To a solution of (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, Formic acid salt (50 mg, 0.092 mmol) in N,N-dimethylformamide (DMF) (3 mL) was added 3-aminopyridine (10.35 mg, 0.110 mmol), HATU (34.8 mg, 0.092 mmol) and then DIEA (0.048 mL, 0.275 mmol) and stirred at ambient temperature for 18 h. The solvent was concentrated and the residue was purified twice by reverse phase preparative HPLC under formic acid conditions to provide the title compound (0.017 g, 29% yield, 98% pure). LC/MS m/z=576 (M+H)$^+$, 0.55 min (ret. time).

Example 47

(S)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-N-(pyridin-3-yl)propanamide, Formic Acid Salt

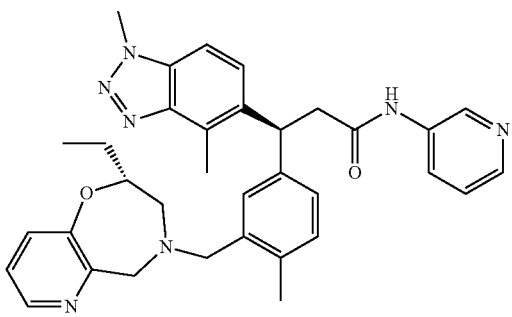 [SMILES: CC[C@@H]1CN(Cc2cc([C@H](CC(=O)Nc3cccnc3)c3ccc4c(nnn4C)c3C)ccc2C)Cc2ncccc2O1]

(S)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic Acid

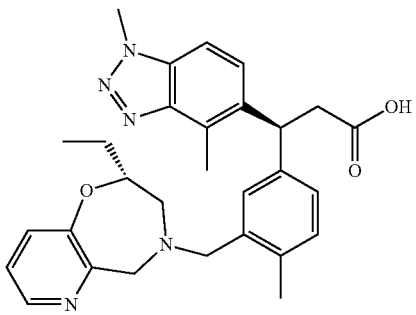 [SMILES: CC[C@@H]1CN(Cc2cc([C@H](CC(=O)O)c3ccc4c(nnn4C)c3C)ccc2C)Cc2ncccc2O1]

160

(S)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid of the invention was made using compounds described in WO 2016/202253, Example 258, published Dec. 22, 2016, and incorporated herein by reference.

(S)-3-(1,4-Dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)-N-(pyridin-3-yl)propanamide, Formic Acid Salt

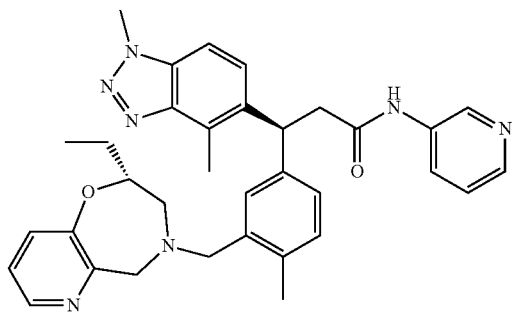 [SMILES: CC[C@@H]1CN(Cc2cc([C@H](CC(=O)Nc3cccnc3)c3ccc4c(nnn4C)c3C)ccc2C)Cc2ncccc2O1]

To a solution of (S)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, formic acid salt (30 mg, 0.055 mmol) in N,N-dimethylformamide (DMF) (3 mL) was added, HATU (20.91 mg, 0.055 mmol) and then DIEA (0.029 mL, 0.165 mmol) and stirred at ambient temperature for 3 min. 3-aminopyridine (6.21 mg, 0.066 mmol) was then added and stirred at ambient temperature for 18 h. The solvent was concentrated and the residue was purified by reverse phase preparative HPLC under formic acid conditions to provide the title compound (0.023 g, 69% yield, 100% pure). LC/MS m/z=576 (M+H)$^+$, 0.55 min (ret. time).

Example 48

(R)-3-((1-Ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-N-(pyridin-3-yl)propanamide, Formic Acid Salt

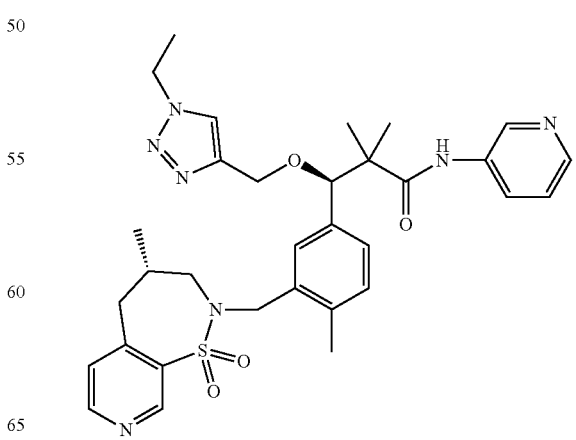

161

Methyl 3-hydroxy-3-(3-(((4-methoxybenzyl)oxy)methyl)-4-methylphenyl)-2,2-dimethylpropanoate

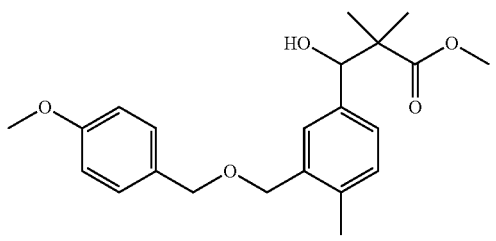

A mixture of 3-(((4-methoxybenzyl)oxy)methyl)-4-methylbenzaldehyde (4 g, 14.80 mmol), 1-methylimidazole (0.118 mL, 1.480 mmol), ((1-methoxy-2-methylprop-1-en-1-yl)oxy)trimethylsilane (5.16 g, 29.6 mmol) and lithium chloride (0.125 g, 2.96 mmol) in N,N-dimethylformamide (DMF) (15 mL) was stirred at ambient temperature for 17 h. NaOH (14.80 mL, 14.80 mmol) was added and the reaction mixture was stirred for 2 h. Water (20 mL) and potassium hydrogen fluoride (1.734 g, 22.20 mmol) were added and stirred for 2 h, followed by addition of 1N HCl (14.80 mL, 14.80 mmol). It was stirred for 16 h. The reaction mixture was diluted with ice water (10 mL) and extracted with EtOAc (2×20 mL). The combined organic layer was washed with brine solution (20 mL), dried over $Na_2SO_4$, filtered and concentrated. The crude residue was purified with flash chromatography over silica gel column to give the title compound (2 g, 5.37 mmol, 36.3% yield) as yellow liquid. LCMS m/z=390.23 (M+18)$^+$, 4.07 min (ret. time).

Methyl (R)-3-hydroxy-3-(3-(((4-methoxybenzyl)oxy)methyl)-4-methylphenyl)-2,2-dimethylpropanoate

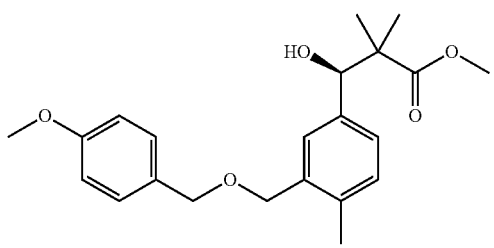

Methyl 3-hydroxy-3-(3-(((4-methoxybenzyl)oxy)methyl)-4-methylphenyl)-2,2-dimethylpropanoate (5.9 g, 15.84 mmol) was purified with chiral SFC (Column: AY, 20×250 mm, 5 u; Co-Solvent: 30% EtOH; Total flow rate: 50 g/min; Pressure: 100 Bar) to give the title compound (3.7614 g, 10.10 mmol, 63.8% yield). LC-MS m/z 395.2 (M+Na)$_+$, 1.17 min (ret. time).

162

Methyl 3-(3-(((4-methoxybenzyl)oxy)methyl)-4-methylphenyl)-2,2-dimethyl-3-(prop-2-yn-1-yloxy)propanoate

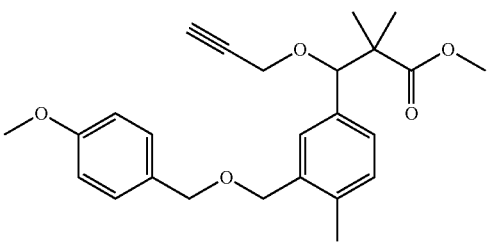

To a solution of methyl 3-hydroxy-3-(3-(((4-methoxybenzyl)oxy)methyl)-4-methylphenyl)-2,2-dimethylpropanoate (24 g, 64.4 mmol) and 3-bromoprop-1-yne in toluene (14.37 g, 97 mmol) in N,N-dimethylformamide (DMF) (250 mL) at 0° C. was added NaH (2.320 g, 97 mmol) under nitrogen. It was stirred for 30 min. The reaction mixture was quenched with saturated $NaHCO_3$ solution and extracted with EtOAc. The organic layer was concentrated under vacuum to give the title compound (26 g, 55.2 mmol, 86% yield) as liquid. LCMS m/z=428.17 (M+18)$^+$, 2.92 min (ret. time).

Methyl 3-(3-(hydroxymethyl)-4-methylphenyl)-2,2-dimethyl-3-(prop-2-yn-1-yloxy)propanoate

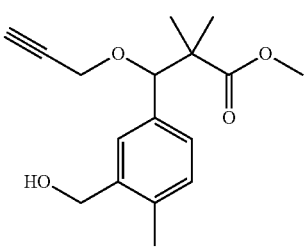 [SMILES: C#CCOC(c1ccc(C)c(CO)c1)C(C)(C)C(=O)OC]

To a solution of methyl 3-(3-(((4-methoxybenzyl)oxy)methyl)-4-methylphenyl)-2,2-dimethyl-3-(prop-2-yn-1-yloxy)propanoate (13 g, 31.7 mmol) in dichloromethane (DCM) (40 mL) and water (10 mL) at 0° C. was added DDQ (10.78 g, 47.5 mmol). It was stirred at ambient temperature for 30 min. It was quenched with ice water, extracted with DCM twice. The organic layer was dried under anhydrous $Na_2SO_4$, filtered and concentrated. The crude residue was purified with flash chromatography over silica gel column to give the title compound (8 g, 13.63 mmol, 43.0% yield). LC MS m/z=291.20 (M+H)$^+$, 2.20 min (ret. time).

Methyl (R)-3-(3-(((4-methoxybenzyl)oxy)methyl)-4-methylphenyl)-2,2-dimethyl-3-(prop-2-yn-1-yloxy)propanoate

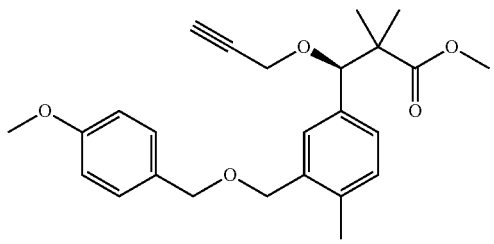

To a mixture of methyl (R)-3-hydroxy-3-(3-(((4-methoxybenzyl)oxy)methyl)-4-methylphenyl)-2,2-dimethylpropanoate (2.6 g, 6.98 mmol) in N,N-dimethylformamide (30 mL) was added 3-bromoprop-1-yne (80% in toluene) (1.128 mL, 10.47 mmol) followed by NaH (0.251 g, 10.47 mmol). The resulting reaction mixture was stirred at ambient temperature for 30 min after which was added a solution of sodium bicarbonate (0.586 g, 6.98 mmol) in water (40 mL) and extracted with EtOAc (2×40 mL). The combined organic layer was washed with LiCl (30 mL, 5%) then brine (30 mL), dried over MgSO₄, filtered, evaporated down under vacuum, purified via flash chromatography over silica gel using ethyl acetate/hexanes to get the title compound (2.2200 g, 5.41 mmol, 77% yield). LC-MS m/z 433.3 (M+Na)$^+$, 1.38 min (ret. time).

Methyl (R)-3-(3-(hydroxymethyl)-4-methylphenyl)-2,2-dimethyl-3-(prop-2-yn-1-yloxy)propanoate

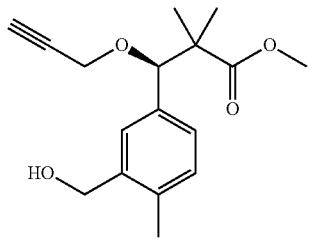 [SMILES: C#CCO[C@H](c1ccc(C)c(CO)c1)C(C)(C)C(=O)OC]

To a mixture of methyl (R)-3-(3-(((4-methoxybenzyl)oxy)methyl)-4-methylphenyl)-2,2-dimethyl-3-(prop-2-yn-1-yloxy)propanoate (2.22 g, 5.41 mmol) in acetonitrile (25 mL) and water (5 mL) was added ceric ammonium nitrate (5.93 g, 10.82 mmol). The resulting reaction mixture was stirred at ambient temperature for 20 min then was evaporated down under vacuum, extracted with DCM (2×30 mL), purified via flash chromatography over silica gel to give the title compound (1.1404 g, 3.93 mmol, 72.6% yield). LC-MS m/z 313.1 (M+Na)$^+$, 0.94 min (ret. time).

Methyl (R)-3-(3-(hydroxymethyl)-4-methylphenyl)-2,2-dimethyl-3-((1-propyl-1H-1,2,3-triazol-4-yl)methoxy)propanoate

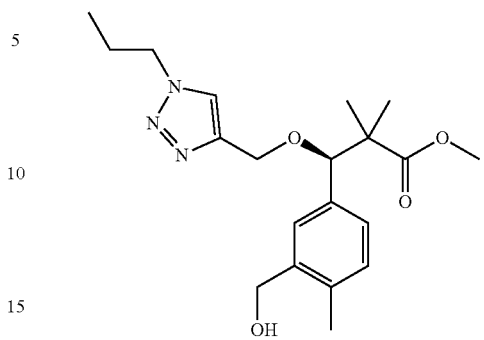

To a mixture of methyl (R)-3-(3-(hydroxymethyl)-4-methylphenyl)-2,2-dimethyl-3-(prop-2-yn-1-yloxy)propanoate (1.12 g, 3.86 mmol) in isopropanol (6 mL), tetrahydrofuran (8 mL) and water (4 mL) was added sodium azide (0.627 g, 9.64 mmol), DIEA (0.135 mL, 0.771 mmol), iodopropane (0.863 mL, 8.87 mmol) and copper(I) iodide (0.110 g, 0.579 mmol). The resulting reaction mixture was heated with microwave at 80° C. for 60 min then was evaporated down under vacuum, purified via flash chromatography over silica gel to the title compound (825.6 mg, 2.199 mmol, 57.0% yield). LC-MS m/z 376.2 (M+H)$^+$, 0.89 min (ret. time).

Methyl (R)-3-((1-ethyl-1H-1,2,3-triazol-4-yl)methoxy)-3-(3-(hydroxymethyl)-4-methylphenyl)-2,2-dimethylpropanoate

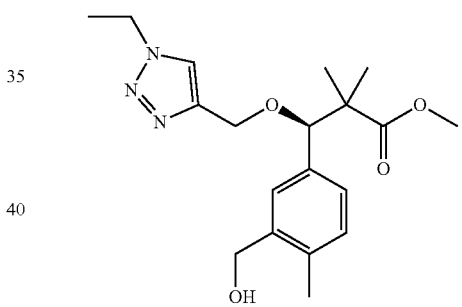

To a mixture of methyl 3-(3-(hydroxymethyl)-4-methylphenyl)-2,2-dimethyl-3-(prop-2-yn-1-yloxy)propanoate (1.12 g, 3.86 mmol) in isopropanol (10 mL), tetrahydrofuran (4 mL) and water (4 mL) was added NaN₃ (0.627 g, 9.64 mmol), DIEA (0.135 mL, 0.771 mmol), iodoethane (0.717 mL, 8.87 mmol) and copper(I) iodide (0.110 g, 0.579 mmol). The resulting reaction mixture was heated with microwave at 70° C. for 60 min then was evaporated down under vacuum, purified by purified with flash chromatography over silica gel column then further purified with chiral SFC (Instrument: Thar 80; Column: Chiralpak AY 20×250 mm, 5 u; Co-solvent: 20% EtOH; Flow rate: 50 g/min; Back pressure: 100Bar; UV wavelength: 220 nm; Temperature: 30° C.; Injection vol: 2.5 ml) to give the title chiral compound (0.4838 g, 1.339 mmol, 34.7% yield). LC-MS m/z=362.1 (M+H)$^+$, 0.82 min (ret. time) (chiral SFC ret. time: 1.47 min).

The compound in Table 6 were prepared by a method similar to the one described for the preparation of methyl (R)-3-((1-ethyl-1H-1,2,3-triazol-4-yl)methoxy)-3-(3-(hydroxymethyl)-4-methylphenyl)-2,2-dimethylpropanoate. As is appreciated by those skilled in the art, these analogous examples may involve variations in general reaction conditions.

TABLE 6

| Structure | Name | LCMS [M + H]+ | Retention Time (min) |
|---|---|---|---|
| 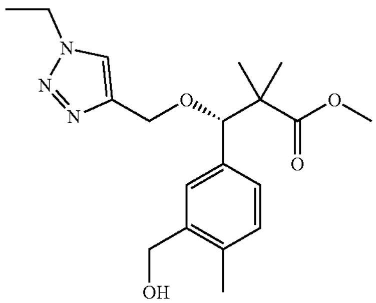 [SMILES: CCn1cc(CO[C@@H](c2ccc(C)c(CO)c2)C(C)(C)C(=O)OC)nn1] | Methyl (S)-3-((1-ethyl-1H-1,2,3-triazol-4-yl)methoxy)-3-(3-(hydroxymethyl)-4-methylphenyl)-2,2-dimethylpropanoate | 361.1 | 0.82 |

(3R)-((1-ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)propanoic Acid

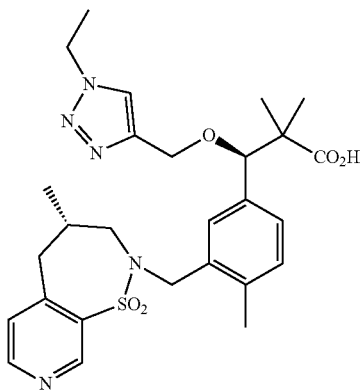 [SMILES: CCn1cc(CO[C@H](c2ccc(C)c(CN3C[C@@H](C)Cc4ccncc4S3(=O)=O)c2)C(C)(C)C(=O)O)nn1]

To the mixture of methyl (R)-3-((1-ethyl-1H-1,2,3-triazol-4-yl)methoxy)-3-(3-(hydroxymethyl)-4-methylphenyl)-2,2-dimethylpropanoate (54.2 mg, 0.15 mmol) in tetrahydrofuran (2 mL) was added (S)-4-methyl-2,3,4,5-tetrahydropyrido[4,3-f][1,2]thiazepine 1,1-dioxide (47.8 mg, 0.225 mmol), PS—PPh$_3$ (188 mg, 0.300 mmol) and DIAD (0.058 mL, 0.300 mmol). The resulting reaction mixture was stirred at ambient temperature for 2 h. The reaction mixture was then filtered, evaporated down under vacuum. The residue was dissolved in methanol (2.000 mL) after which was added NaOH (6.0 N) (0.200 mL, 1.200 mmol). The resulting reaction mixture was heated with microwave at 120° C. for 30 min. To the reaction mixture was added HCl (6.0 N) (0.200 mL, 1.200 mmol), evaporated down under vacuum, purified with reverse phase HPLC (formic acid modifier) to give the title product (34.2 mg, 0.063 mmol, 42.1% yield). LC/MS: m/z 542.4 (M+H)+, 0.96 min (ret. time).

The compounds in Table 7 were prepared by a method similar to the one described for the preparation of (R)-3-((1-ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)propanoic acid. As is appreciated by those skilled in the art, these analogous examples may involve variations in general reaction conditions.

TABLE 7

| Structure | Name | LCMS [M + H]+ | Retention Time (min) |
|---|---|---|---|
| 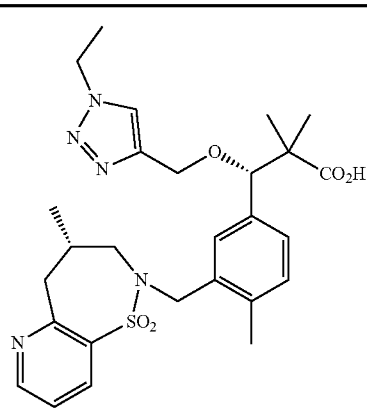 | (3S)-((1-Ethyl-1H-1,2,3-triazol-4-yl)methoxy)-2,2-dimethyl-3-(4-methyl-3-(((S)-4-methyl-1,1-dioxido-4,5-dihydropyrido[2,3-f][1,2]thiazepin-2(3H)-yl)methyl)phenyl)propanoic acid | 542.4 | 0.99 |

TABLE 7-continued

| Structure | Name | LCMS [M + H]+ | Retention Time (min) |
|---|---|---|---|
| 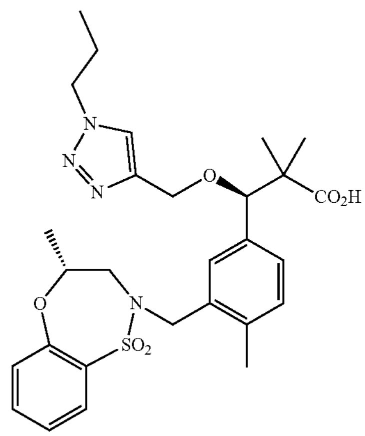 [SMILES: CCCn1cc(CO[C@H](c2ccc(C)c(CN3C[C@@H](C)Oc4ccccc4S3(=O)=O)c2)C(C)(C)C(=O)O)nn1] | (R)-3-(3-((4,4-Dimethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)propanoic acid | 571.4 | 1.15 |
| 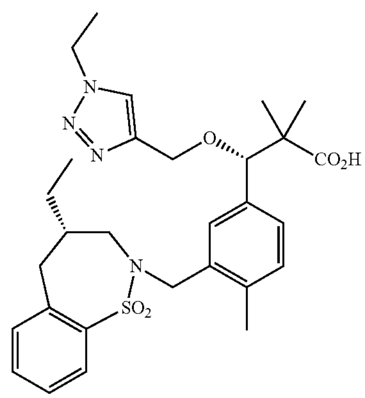 [SMILES: CC[C@H]1Cc2ccccc2S(=O)(=O)N(Cc2cc([C@H](OCc3cn(CC)nn3)C(C)(C)C(=O)O)ccc2C)C1] | (3S)-((1-Ethyl-1H-1,2,3-triazol-4-yl)methoxy)-2,2-dimethyl-3-(4-methyl-3-(((S)-4-ethyl-1,1-dioxido-4,5-dihydrobenzo[b][1,2]thiazepin-2(3H)-yl)methyl)phenyl)propanoic acid | 555.4 | 1.20 |
| 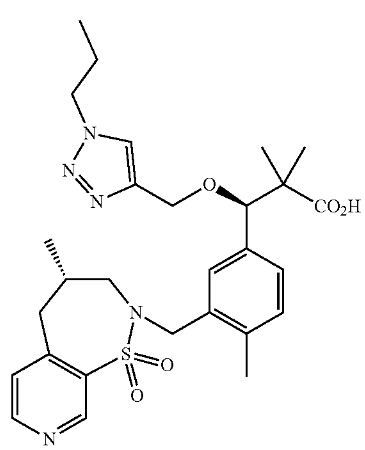 [SMILES: CCCn1cc(CO[C@H](c2ccc(C)c(CN3C[C@@H](C)Cc4ccncc4S3(=O)=O)c2)C(C)(C)C(=O)O)nn1] | (R)-2,2-Dimethyl-3-(4-methyl-3-(((S)-4-methyl-1,1-dioxido-4,5-dihydropyrido[4,3-f][1,2]thiazepin-2(3H)-yl)methyl)phenyl)-3-((1-propyl-1H-1,2,3-triazol-4-yl)methoxy)propanoic acid | 556.4 | 1.01 |

TABLE 7-continued

| Structure | Name | LCMS [M + H]+ | Retention Time (min) |
|---|---|---|---|
| 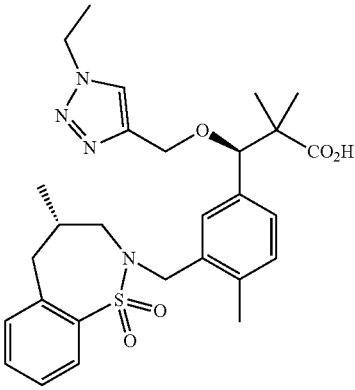 [SMILES: CCn1cc(CO[C@H](c2ccc(C)c(CN3C[C@@H](C)Cc4ccccc4S3(=O)=O)c2)C(C)(C)C(=O)O)nn1] | (3R)-((1-Ethyl-1H-1,2,3-triazol-4-yl)methoxy)-2,2-dimethyl-3-(4-methyl-3-(((S)-4-methyl-1,1-dioxido-4,5-dihydrobenzo[f][1,2]thiazepin-2(3H)-yl)methyl)phenyl)propanoic acid | 541.4 | 1.15 |
| 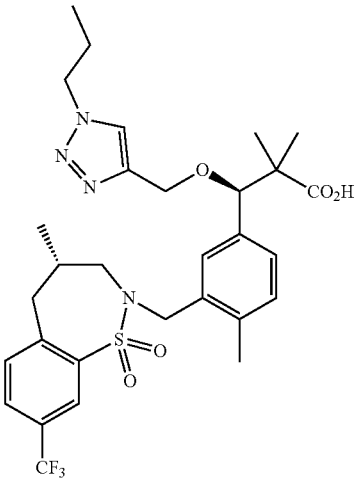 [SMILES: CCCn1cc(CO[C@H](c2ccc(C)c(CN3C[C@@H](C)Cc4ccc(C(F)(F)F)cc4S3(=O)=O)c2)C(C)(C)C(=O)O)nn1] | (R)-2,2-Dimethyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)-3-((1-propyl-1H-1,2,3-triazol-4-yl)methoxy)propanoic acid | 623.5 | 1.32 |
| 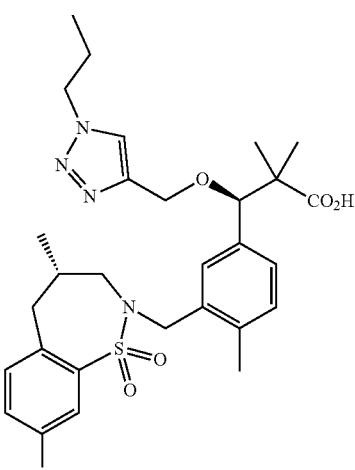 | (R)-3-(3-(((S)-8-Fluoro-4-methyl-1,1-dioxido-4,5-dihydrobenzo[f][1,2]thiazepin-2(3H)-yl)methyl)-4-methylphenyl)-2,2-dimethyl-3-((1-propyl-1H-1,2,3-triazol-4-yl)methoxy)propanoic acid | 573.4 | 1.23 |

TABLE 7-continued

| Structure | Name | LCMS [M + H]+ | Retention Time (min) |
|---|---|---|---|
| 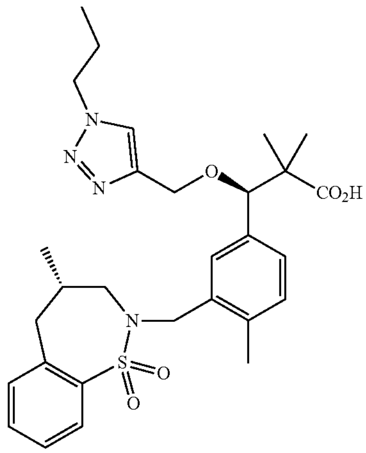 [SMILES: CCCn1cc(CO[C@H](c2ccc(C)c(CN3C[C@@H](C)Cc4ccccc4S3(=O)=O)c2)C(C)(C)C(=O)O)nn1] | (R)-2,2-Dimethyl-3-(4-methyl-3-(((S)-4-methyl-1,1-dioxido-4,5-dihydrobenzo[f][1,2]thiazepin-2(3H)-yl)methyl)phenyl)-3-((1-propyl-1H-1,2,3-triazol-4-yl)methoxy)propanoic acid | 555.2 | 1.18 |
| 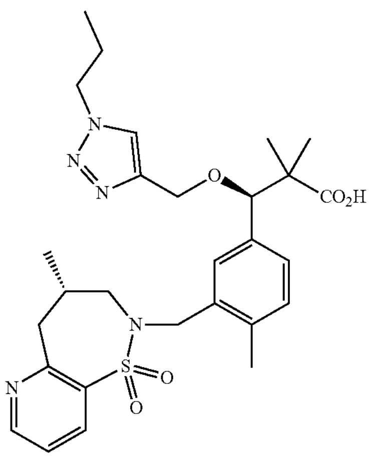 [SMILES: CCCn1cc(CO[C@H](c2ccc(C)c(CN3C[C@@H](C)Cc4ncccc4S3(=O)=O)c2)C(C)(C)C(=O)O)nn1] | (R)-2,2-Dimethyl-3-(4-methyl-3-(((S)-4-methyl-1,1-dioxido-4,5-dihydropyrido[2,3-f][1,2]thiazepin-2(3H)-yl)methyl)phenyl)-3-((1-propyl-1H-1,2,3-triazol-4-yl)methoxy)propanoic acid | 556.2 | 1.02 |
| 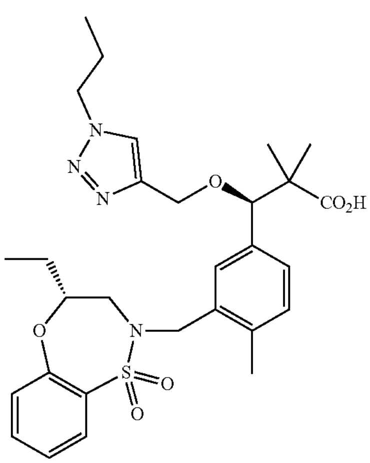 [SMILES: CCCn1cc(CO[C@H](c2ccc(C)c(CN3C[C@@H](CC)Oc4ccccc4S3(=O)=O)c2)C(C)(C)C(=O)O)nn1] | (R)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)propanoic acid | 571.2 | 1.16 |

Phenyl (E)-N-(tert-butyl)-N-(pyridin-3-yl)carbamimidothioate

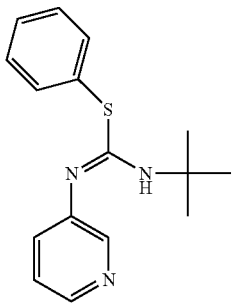 [SMILES: CC(C)(C)N/C(=N\c1cccnc1)Sc1ccccc1]

To a solution of 2-isocyano-2-methylpropane (0.282 ml, 2.497 mmol), S-phenyl benzenesulfonothioate (250 mg, 0.999 mmol), and pyridin-3-amine (160 mg, 1.698 mmol) in 2-methyltetrahydrofuran (2-MeTHF) (2.5 mL) was added copper(I) iodide (1.902 mg, 9.99 µmol). The reaction mixture was stirred for 20 hours at 75° C. After 20 hours, the reaction mixture was filtered through a celite cake and the celite was washed with EtOAc. The solution was then concentrated and purified via flash chromatography to give the desired product (274.4 mg, 0.961 mmol, 96% yield). LCMS m/z=286.1 (M+H)$^+$, 0.64 min (ret. time). $^1$H NMR (400 MHz, METHANOL-d$_4$) δ ppm 1.39 (s, 9H) 7.18 (br. s., 2H) 7.32 (s, 5H) 7.93 (s, 1H) 8.03 (br. s., 1H).

(R)-3-((1-Ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-N-(pyridin-3-yl)propanamide, Formic Acid Salt

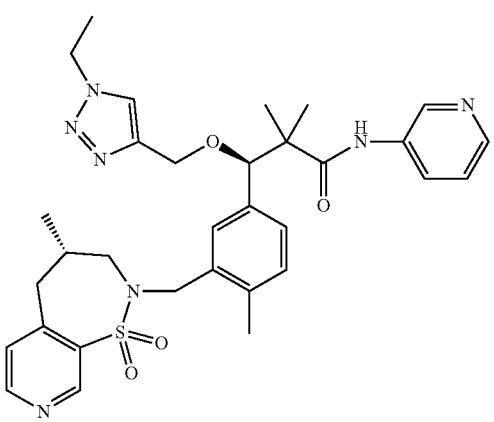 [SMILES: CCn1cc(CO[C@H](c2ccc(C)c(CN3C[C@@H](C)Cc4ccncc4S3(=O)=O)c2)C(C)(C)C(=O)Nc2cccnc2)nn1]

To a solution of (R)-3-((1-ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)propanoic acid (29.00 mg, 0.054 mmol) in Isopropanol (1.5 mL) in a microwave reaction vessel as added phenyl (E)-N-(tert-butyl)-N'-(pyridin-3-yl)carbamimidothioate (21.6 mg, 0.076 mmol) and ferric acetylacetonate (0.922 mg, 2.61 µmol) and heated via microwave at 120° C. for 2 h. The solvent was concentrated and the residue was purified by reverse phase preparative HPLC under formic acid conditions to provide the title compound (0.018 g, 50% yield, 99% pure). LC/MS m/z=618 (M+H)$^+$, 0.76 min (ret. time).

Acids and Esters Supporting Compounds of Table 8

(E)-ethyl 3-(7-methoxy-3-methyl-1H-benzo[d][1,2,3]triazol-5-yl)acrylate

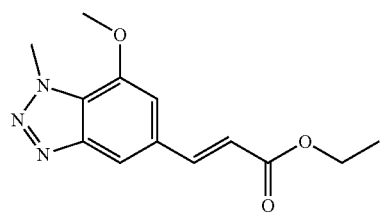 [SMILES: CCOC(=O)/C=C/c1cc(OC)c2c(c1)nnn2C]

(E)-ethyl 3-(7-methoxy-1-methyl-1H-benzo[d][1,2,3]triazol-5l)acrylate of the invention was made using compounds described in WO 2015/092713, published Jun. 15, 2015, and incorporated herein by reference.

(S)-Ethyl 3-(3-(hydroxymethyl)-4-methylphenyl)-3-(7-methoxy-1-methyl-1H-benzo[d][1,2,3]triazol-5-yl)propanoate

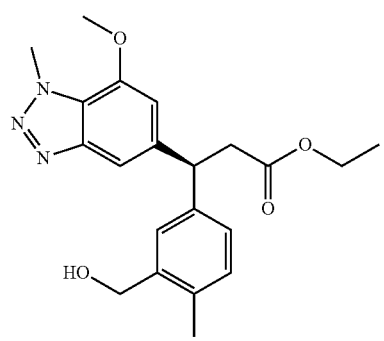 [SMILES: CCOC(=O)C[C@@H](c1ccc(C)c(CO)c1)c1cc(OC)c2c(c1)nnn2C]

A solution of (E)-ethyl 3(7-methoxy-1-methyl-1H-benzo[d][1,2,3]triazol-5-yl)acrylate (5 g, 19.14 mmol) in 1,4-dioxane (100 mL) stirred under nitrogen at 27° C. was degassed with argon for 30 min, (2R,3R)-Butane-2,3-diylbis(diphenylphosphine) (0.816 g, 1.914 mmol), (3-(hydroxymethyl)-4-methylphenyl)boronic acid (9.53 g, 57.4 mmol), (bicyclo[2.2.1]hepta-2,5-diene)-rhodium(I)chloride dialer (0.881 g, 1.914 mmol) and KOH (19.14 mL, 19.14 mmol) were added together and stirred at 27° C. for 4 h. The reaction mixture was diluted with ethyl acetate (1000 mL) and washed with water (500 mL). The organic layer was dried over sodium sulphate and evaporated in vacuo. The residue was purified by column chromatography silica gel (Elution 40% Ethyl acetate-Hexane), to afford the title compound. (5 g, 11.54 mmol, 60% yield), LC-MS m/z 384 (M+H)$^+$, 3.45 min (ret. time).

175

(S)-Ethyl 3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate

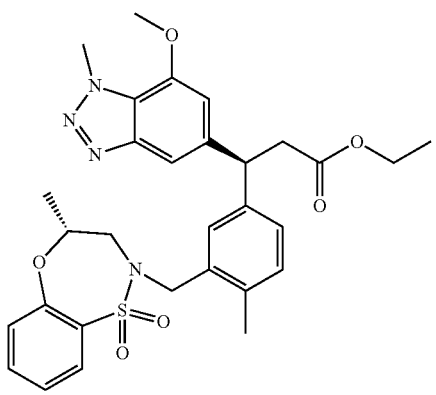 [SMILES: CCOC(=O)C[C@@H](c1ccc(C)c(CN2C[C@@H](C)Oc3ccccc3S2(=O)=O)c1)c1cc(OC)c2c(c1)nnn2C]

To stirred solution of (S)-ethyl 3-(3-(hydroxymethyl)-4-methylphenyl)-3-(7-methoxy-1-methyl-1H-benzo[d][1,2,3]triazol-5-yl)propanoate (3.6 g, 9.39 mmol) in dichloromethane (DCM) (50 mL), SOCl$_2$ (0.685 mL, 9.39 mmol) was added and stirred for 3 hr at 0° C. The reaction mixture was then concentrated under reduced pressure. The residue was combined with potassium carbonate (1.298 g, 9.39 mmol) and (R)-4-methyl-3,4-dihydro-2H-benzo[b][1,4,5]oxathiazepine 1,1-dioxide (2.002 g, 9.39 mmol) in acetonitrile (100 mL) was stirred under nitrogen at 27° C. The reaction mixture was stirred at 95° C. for 3 hr. The reaction mixture was diluted with Ethyl acetate (500 mL), organic phase was washed with water (1000 mL) and NaCl solution (500 mL) then dried over sodium sulphate and evaporated in vacuo. The crude product was purified by column chromatography (Elution 40% Ethyl acetate-Hexane), to afford the title compound. (4 g, 6.63 mmol, 70.6% yield), LC-MS m/z 579 (M+H)$^+$, 3.82 min (ret. time).

176

(S)-3-(7-Methoxy-1-methyl-1Hbenzo[d][1,2,3]triazol-5-yl)-3-(4-methyl-3-(((R)-4-methyl-1,1-dioxido-3,4-dihydro-2Hbenzo[b][1,4,5]oxathiazepin-2-yl)methyl)phenyl)propanoic Acid

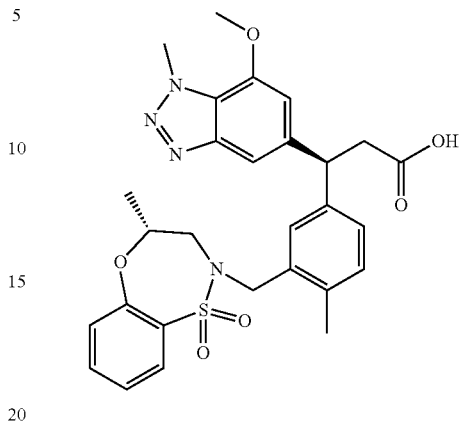

To a solution of (S)-ethyl 3-(7-methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoate (4 g, 6.91 mmol) in tetrahydrofuran (THF) (25 mL), methanol (5.00 mL) and water (25.00 mL) was added LiOH (0.166 g, 6.91 mmol) at 23° C. The reaction mixture was stirred at 40° C. for 2 hr. The reaction mixture was concentrated, diluted with water (100 mL) and then it was washed with diethyl ether (150 mL). The aqueous layer was acidified to pH<3 with 1N HCl (20 mL) and extracted with ethyl acetate (2×50 mL), and the combined organic layers were concentrated under reduced pressure. The residue was purified by flash chromatography eluting with 0-55% EtOAc/Hexane to afford the title compound. (2.5 g, 4.54 mmol, 65.7% yield), LC-MS m/z 551 (M+H)$^+$, 2.37 min (ret. time).

The compounds in Table A were prepared by a method similar to the one described for the preparation of (S)-3-(7-methoxy-1-methyl-1Hbenzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)propanoic acid. As is appreciated by those skilled in the art, these analogous examples may involve variations in general reaction conditions.

TABLE A

| Structure | Name | LCMS [M + 1] | Retention Time (min) |
|---|---|---|---|
| 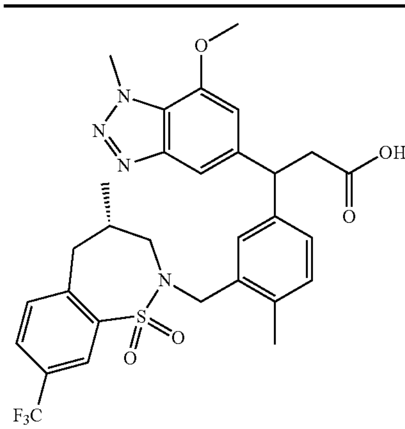 | 3-(7-methoxy-1-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]-thiazepin-2(3H)-yl)methyl)phenyl)-propanoic acid | 617 | 1.23 |

2-Bromo-4-methyl-3-nitrophenol

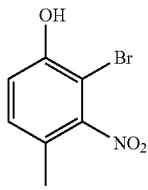

To a solution of 4-methyl-3-nitrophenol (10 g, 65.3 mmol) in chloroform (30 mL) was added bromine (3.37 mL, 65.3 mmol) solution in chloroform (200 mL) slowly under nitrogen at 35° C. The reaction was stirred at 35° C. for 40 hours. 100 mL water was added to the solution. It was extracted with DCM (3×200 mL). The organic layer was concentrated to give the title compound (8 g, 13% yield) which was used for the next step without further purification. $^{1}$H NMR (500 MHz, CDCl3) δ 7.16 (d, J=8.5 Hz, 1H), 7.05 (d, J=8.5 Hz, 1H), 2.27 (s, 3H).

N-Ethyl-6-methoxy-3-methyl-2-nitroaniline

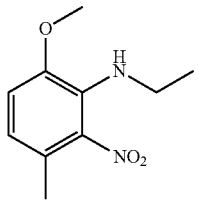

To a solution of 2-bromo-4-methyl-3-nitrophenol (40 g, 172 mmol) in acetone (200 mL) at ambient temperature was added $K_2CO_3$ (47.7 g, 345 mmol), MeI (21.56 mL, 345 mmol) slowly under nitrogen. The reaction mixture was stirred at 65° C. for 40 hours. 200 mL of water was added and was extracted with ethyl acetate (3×200 mL). The combined organic layers were concentrated under a stream of nitrogen at 50° C. to give 2-bromo-1-methoxy-4-methyl-3-nitrobenzene (35 g, 142 mmol) which was used for the next step without further purification. To a solution of 2-bromo-1-methoxy-4-methyl-3-nitrobenzene (35 g, 142 mmol) in dimethyl sulfoxide (DMSO) (500 mL) was added copper (0.904 g, 14.22 mmol) and ethanamine (641 mL, 4267 mmol) slowly under nitrogen at ambient temperature. The reaction mixture was stirred at 100° C. for 16 hours. 500 mL of water was added and extracted with ethyl acetate (3×300 mL). The organic layer was concentrated. The crude product was purified with silica gel column eluting with (hexane:ethyl acetate=20:1) to give the title compound (16.5 g, 39.2 mmol, 27.6% yield) as red oil. LC-MS m/z 211.1 (M+H)$^+$, 2.04 (ret. time).

4-Bromo-N-ethyl-6-methoxy-3-methyl-2-nitroaniline

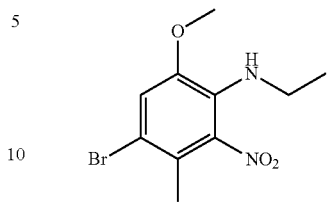

To a solution of N-ethyl-6-methoxy-3-methyl-2-nitroaniline (28.6 g, 68.0 mmol) in N,N dimethylformamide (DMF) (300 mL) was added a solution of NBS (12.11 g, 68.0 mmol) in N,N dimethylformamide (DMF) (300 mL) slowly under nitrogen at ambient temperature. The reaction mixture was stirred at ambient temperature for 14 hours. 100 mL of water was added and filtered. The solid was dried with high vacuum to give the title compound (30 g, 51.9 mmol, 76% yield). LC-MS m/z=289.0 (M+H)$^+$, 2.24 (ret. time).

4-Bromo-N$^1$-ethyl-6-methoxy-3-methylbenzene-1,2-diamine

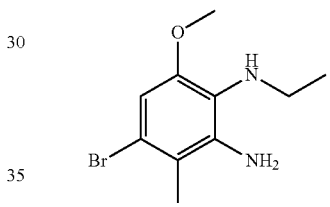

To a solution of 4-bromo-N-ethyl-6-methoxy-3-methyl-2-nitroaniline (30 g, 104 mmol) in ethanol (200 mL) and 1,2-dichloroethane (DCE) (200 mL) was added nickel (6.09 g, 104 mmol) slowly under nitrogen at 0° C. Hydrazine, $H_2O$ (6.10 mL, 125 mmol) was added dropwise. The reaction mixture was stirred at 0° C. for 0.5 hour. It was filtered and 200 mL of water was added. It was extracted with ethyl acetate (3×200 mL). The organic layer was concentrated. The crude product was added to a silica gel column and was eluted with (hexane:ethyl acetate=20:1) to give the title compound (16 g, 49.4 mmol, 47.6% yield). It was carried to next step without further purification. LC-MS m/z=261.0 (M+H)$^+$ 1.28 (ret. time).

5-Bromo-1-ethyl-7-methoxy-4-methyl-1H-benzo[d][1,2,3]triazole

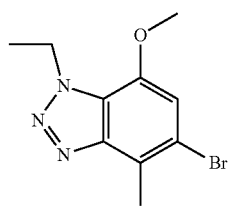

To a solution of $H_2SO_4$ (11.52 mL, 216 mmol) in water (100 mL) was added 4-bromo-N$^1$-ethyl-6-methoxy-3-methylbenzene-1,2-diamine (16 g, 61.7 mmol). A solution of sodium nitrite (8.52 g, 123 mmol) in water (20 mL) was added dropwise at 0° C. The reaction mixture was stirred at 0° C. for 16 hours. 200 mL of water was added. It was filtered and the solid was dissolved in 500 ml of DCM, washed with aqueous NaCl (2×50 mL), dried with MgSO$_4$, filtered and concentrated. The Isolute-adsorbed crude product was added to a silica gel column and was eluted with (hexane:ethyl acetate=4:1) to give the title compound (10.6 g, 37.7 mmol, 61.0% yield) as a solid. LC-MS m/z=256.0 (M+H)$^+$, 1.56 (ret. time).

Methyl 5-bromo-2-methylbenzoate

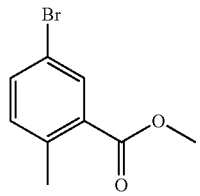

To a solution of 5-bromo-2-methylbenzoic acid (15 g, 69.8 mmol) in methanol (100 ml) was added H$_2$SO$_4$ (1 ml, 18.76 mmol) slowly under nitrogen at ambient temperature. The resulting reaction mixture was stirred at 65° C. for 16 hrs. Water (50 mL) was added to the reaction mixture and extracted with ethyl acetate (3×60 ml). The combined organic layer was concentrated to afford the title compound methyl 5-bromo-2-methylbenzoate (15 g, 65.5 mmol, 94% yield). LC-MS MS m/z=231.1 (M+H)$^+$, 1.98 (ret. time).

(5-Bromo-2-methylphenyl)methanol

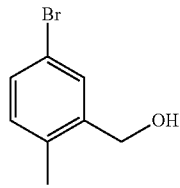

To a solution of 5-bromo-2-methylbenzoic acid (70 g, 326 mmol) in tetrahydrofuran (THF) (700 mL) stirred under nitrogen at 0° C. was added a toluene solution of borane-methyl sulfide complex (244 mL, 488 mmol) drop wise during 15 min. The reaction mixture was stirred for 16 h. The reaction was cooled to 0° C. and quenched with methanol (500 mL) drop wise. The reaction mixture was stirred at ambient temperature for 3 h and then concentrated. The crude residue was diluted with ethyl acetate (1 L) and washed with 1N HCl (500 mL), brine solution (500 mL) and dried over Na$_2$SO$_4$, filtered and concentrated to give the title compound (49 g, 244 mmol, 74.9% yield). $^1$H NMR (400 MHz, DMSO) δ=7.52 (d, J=2.6 Hz, 1H), 7.31 (dd, J=8.0, 2.2 Hz, 1H), 7.12-7.03 (m, 1H), 5.22 (td, J=5.5, 1.8 Hz, 1H), 4.48 (dd, J=5.1, 1.8 Hz, 2H), 2.17 (s, 3H).

4-Bromo-2-(((4-methoxybenzyl)oxy)methyl)-1-methylbenzene

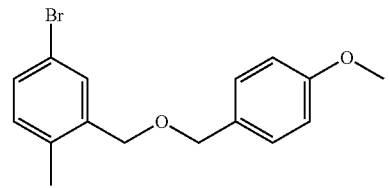 [SMILES: COc1ccc(COCc2cc(Br)ccc2C)cc1]

To a stirred solution of (5-bromo-2-methylphenyl)methanol (100 g, 497 mmol) in dry DMF (800 mL) was added 60% NaH (21.88 g, 547 mmol). After the reaction mixture was stirred for 30 minutes, 1-(chloromethyl)-4-methoxybenzene (82 g, 522 mmol) was added at 0° C. and the reaction mixture was stirred for another 2 h at ambient temperature. The reaction was then diluted with Et$_2$O (200 mL) and water (200 mL). The organic phase was washed with brine (300 mL) and dried with Na$_2$SO$_4$ and concentrated under reduced pressure. The residue was purified via silica gel column to yield 4-bromo-2-(((4-methoxybenzyl)oxy)methyl)-1-methylbenzene (140 g, 436 mmol, 88% yield) as a clear oil. $^1$H NMR (400 MHz, CHLOROFORM-d) δ ppm 2.27 (s, 3H) 3.84 (s, 3H) 4.49 (s, 2H), 4.54 (s, 2H), 6.92 (d, J=8.8, 2H), 6.94 (d, J=8.4, 1H), 7.31-7.35 (m, 3H), 7.54 (d, J=2, 1H).

3-(4-Methoxybenzyl)oxy)methyl)-4-methylbenzaldehyde

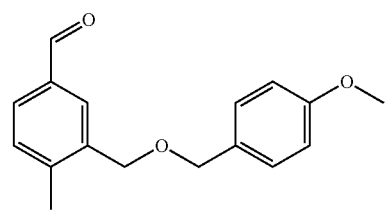 [SMILES: COc1ccc(COCc2cc(C=O)ccc2C)cc1]

To a stirred solution of 4-bromo-2-(((4-methoxybenzyl)oxy)methyl)-1-methylbenzene (80 g, 249 mmol) in THF (800 mL) at −78° C. under N$_2$, 2.5 M n-BuLi in hexane (120 mL, 299 mmol) was carefully added. The reaction mixture was stirred at −78° C. for 65 min, and then DMF (38.6 mL, 498 mmol) was added. The reaction mixture was stirred at −78° C. to 25° C. for another 30 min. The mixture was quenched with saturated NH$_4$Cl (300 mL), and extracted with EtOAc (2×500 mL). The organic layer was washed with water (300 mL) and brine (2×100 mL), dried (Na$_2$SO$_4$) and concentrated. The residue was washed with petroleum ether:EtOAc=10/1 (2000 mL) to give the title compound (50 g, 185 mmol, 74.3% yield) as a solid. LC-MS m/z=288.1 (M+H$_2$O)$^+$, 2.04 min (ret. time).

(1-Ethyl-7-methoxy-4-methyl-1H-benzo[d][1,2,3]triazol-5-yl)(3-(((4-methoxybenzyl)oxy)methyl)-4-methylphenyl)methanol

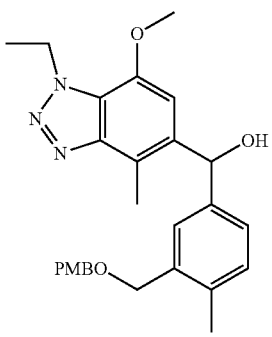

1.6M n-Butyllithium (9.02 ml, 14.44 mmol) was added dropwise to a solution of 5-bromo-1-ethyl-7-methoxy-4-methyl-1H-benzo[d][1,2,3]triazole (3 g, 11.11 mmol) in tetrahydrofuran (THF) (40.0 ml) at −78° C. under a nitrogen atmosphere and stirred for 30 minutes. A solution of 3-(((4-methoxybenzyl)oxy)methyl)-4-methylbenzaldehyde (3.60 g, 13.33 mmol) in THF (5 mL) was then added dropwise and stirred at −78° C. for 1.5 hours followed by warming to ambient temperature and stirring for an additional hour. Saturated aqueous ammonium chloride (30 mL) was added to the solution and the mixture was extracted with ethyl acetate (3×60 mL). The combined organic fractions were washed (brine), dried (sodium sulfate), and the solvent was removed. It was purified by silica gel chromatography. Desired fractions were concentrated to give the title compound (4.2 g, 9.10 mmol, 82% yield) as solid. LC/MS: m/z=462.3 (M+H)$^+$, 1.19 min (ret. time).

Methyl 3-(1-ethyl-7-methoxy-4-methyl-1H-benzo[d][1,2,3]triazol-5-yl)-3-(3-(hydroxymethyl)-4-methylphenyl)-2,2-dimethylpropanoate

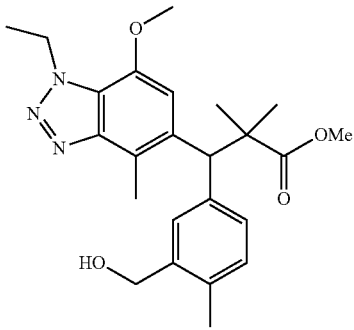 [SMILES: CCn1nnc2c(C)c(C(c3ccc(C)c(CO)c3)C(C)(C)C(=O)OC)cc(OC)c21]

2,2,2-Trichloroacetonitrile (1.825 mL, 18.20 mmol) and 2,3,4,6,7,8,9,10-octahydropyrimido[1,2-a]azepine (DBU) (0.063 mL, 0.455 mmol) were added sequentially to a solution of (1-ethyl-7-methoxy-4-methyl-1H-benzo[d][1,2,3]triazol-5-yl)(3-(((4-methoxybenzyl)oxy)methyl)-4-methylphenyl)methanol (4.2 g, 9.10 mmol) in acetonitrile (60 mL) at ambient temperature. 10 mL DCM was added and stirred for 2 h. Solid was filtered. TLC showed mother liquor was activated to desired intermediate. To the mother liquor was added ((1-methoxy-2-methylprop-1-en-1-yl)oxy)trimethylsilane (5.55 mL, 27.3 mmol) followed by 1,1,1-trifluoro-N-((trifluoromethyl)sulfonyl)methanesulfonamide (0.256 g, 0.910 mmol). It was stirred at ambient temperature for 2 hours. The reaction was quenched with saturated sodium bicarbonate (10 mL). The solvent was concentrated, and extracted with ethyl acetate twice (3×20 mL). The organic layer was dried over sodium sulfate, filtered and concentrated. It was redissolved in dichloromethane (DCM) (60.0 mL) and water (6.00 mL). It was cooled to 0° C. and DDQ (2.066 g, 9.10 mmol) was added. The solution was stirred at 0° C. for 1 hour at which time LC-MS showed the reaction was complete. The reaction was quenched with saturated sodium bicarbonate (10 mL) and extracted with DCM (3×15 mL) and dried over sodium sulfate. The crude product was combined with below batch. Solid from filtration was dissolved in dichloromethane (DCM) (60.0 mL) (starting material was more soluble in DCM than acetonitrile). 2,2,2-trichloroacetonitrile (1.825 mL, 18.20 mmol) and 2,3,4,6,7,8,9,10-octahydropyrimido[1,2-a]azepine (DBU) (0.063 mL, 0.455 mmol) were added sequentially to it at ambient temperature. It was monitor by TLC. Reaction was completed after 40 min. ((1-methoxy-2-methylprop-1-en-1-yl)oxy)trimethylsilane (5.55 mL, 27.3 mmol) followed by 1,1,1-trifluoro-N-((trifluoromethyl)sulfonyl)methanesulfonamide (0.256 g, 0.910 mmol). It was stirred at ambient temperature for 1 h. The reaction was quenched with saturated sodium bicarbonate (10 mL). Solvent was concentrated, and extracted with ethyl acetate twice (3×20 mL). The organic layer was dried over sodium sulfate, filtered and concentrated. It was redissolved in dichloromethane (DCM) (60.0 mL) and water (6.00 mL). It was cooled to 0° C. and DDQ (2.066 g, 9.10 mmol) was added. The solution was stirred at 0° C. for 1 hour at which time LC-MS showed the reaction was complete. The reaction was quenched with saturated sodium bicarbonate (10 mL) and extracted with DCM (3×15 mL) and dried over sodium sulfate. Both batches were combined and was purified by silica gel chromatography. Pure fractions were concentrated to give the title compound (665 mg, 1.563 mmol, 17.17% yield) as lot 1 and an impure batch. The impure batch was purified via silica gel chromatography to give the title compound (1.292 g, 3.04 mmol, 33.4% yield) as lot 2 and 1.024 g of impure batch. LC-MS m/z=426.3 (M+H)$^+$, 1.09 min (ret. time).

Methyl (S)-3-(1-ethyl-7-methoxy-4-methyl-1H-benzo[d][1,2,3]triazol-5-yl)-3-(3-(hydroxymethyl)-4-methylphenyl)-2,2-dimethylpropanoate and

Methyl (R)-3-(1-ethyl-7-methoxy-4-methyl-1H-benzo[d][1,2,3]triazol-5-yl)-3-(3-(hydroxymethyl)-4-methylphenyl)-2,2-dimethylpropanoate

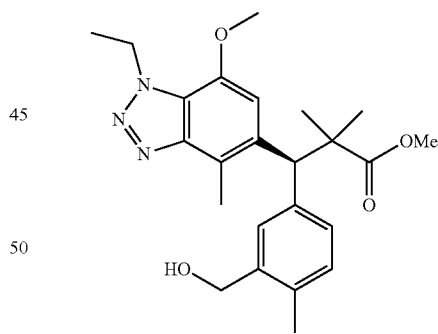

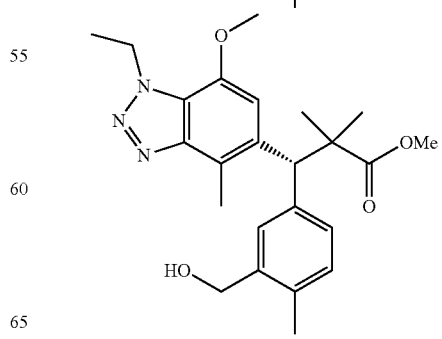

Methyl 3-(1-ethyl-7-methoxy-4-methyl-1H-benzo[d][1,2,3]triazol-5-yl)-3-(3-(hydroxymethyl)-4-methylphenyl)-2,2-dimethylpropanoate (665 mg, 1.563 mmol) (N38007-62-A1) was resolved by Chiral SFC (Column: Chiralpak CC4 20×250 mm, 5 u; Column: Co-solvent: 20% IPA; Flow: 50 g/min; Back pressure: 100 Bar) to give methyl (S)-3-(1-ethyl-7-methoxy-4-methyl-1H-benzo[d][1,2,3]triazol-5-yl)-3-(3-(hydroxymethyl)-4-methylphenyl)-2,2-dimethylpropanoate (218 mg, 0.512 mmol, 32.8% yield) (chiral SFC ret. time: 6.93 min) and methyl (R)-3-(1-ethyl-7-methoxy-4-methyl-1H-benzo[d][1,2,3]triazol-5-yl)-3-(3-(hydroxymethyl)-4-methylphenyl)-2,2-dimethylpropanoate (238 mg, 0.559 mmol, 35.8% yield) (chiral SFC ret. time: 10.07 min).

(S)-3-(1-Ethyl-7-methoxy-4-methyl-1H-benzo[d][1,2,3]triazol-5-yl)-2,2-dimethyl-3-(4-methyl-3-(((R)-4-methyl-1,1-dioxido-4,5-dihydrobenzo[f][1,2]thiazepin-2(3H)-yl)methyl)phenyl)propanoic Acid

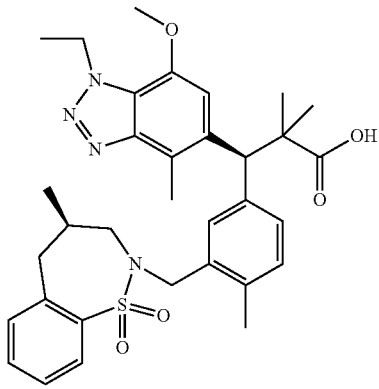 [SMILES: CCn1nnc2c(C)c([C@H](c3ccc(C)c(CN4C[C@H](C)Cc5ccccc5S4(=O)=O)c3)C(C)(C)C(=O)O)cc(OC)c21]

To a solution of methyl (S)-3-(1-ethyl-7-methoxy-4-methyl-1H-benzo[d][1,2,3]triazol-5-yl)-3-(3-(hydroxymethyl)-4-methylphenyl)-2,2-dimethylpropanoate (80 mg, 0.188 mmol), (R)-4-methyl-2,3,4,5-tetrahydrobenzo[f][1,2]thiazepine 1,1-dioxide (39.7 mg, 0.188 mmol), and 1,1'-(Azodicarbonyl)dipiperidine (95 mg, 0.376 mmol) in tetrahydrofuran (THF) (3 mL) at ambient temperature was added tri-n-butylphosphine (0.093 mL, 0.376 mmol). The reaction mixture was stirred at ambient temperature for 20 h. It was quenched with water and extracted with ethyl acetate twice. The combined organic layer was washed with brine and concentrated. It was purified on a silica cartridge (12 g) eluting at 30 mL/min with a gradient running from 0% EtOAc/hexanes to 90% EtOAc/hexanes over 35 min The desired fractions were concentrated under reduced pressure to give methyl (S)-3-(1-ethyl-7-methoxy-4-methyl-1H-benzo[d][1,2,3]triazol-5-yl)-2,2-dimethyl-3-(4-methyl-3-(((R)-4-methyl-1,1-dioxido-4,5-dihydrobenzo[f][1,2]thiazepin-2(3H)-yl)methyl)phenyl)propanoate. It was redissolved in methanol (2 mL), 2 M LiOH (0.564 mL, 1.128 mmol) was added and heated in Biotage microwave at high absorption for 2 h at 120° C. The solvent was evaporated. It was quenched with 1N HCl (1 mL), 2 mL DMSO was added. Solvent was concentrated, then filtered. The residue was purified via preparative HPLC to give the title compound (69 mg, 0.114 mmol, 60.7% yield) as solid. LC-MS m/z=605.3 (M+H)$^+$, 1.30 min (ret. time).

The compounds in Table B were prepared by a method similar to the one described for the preparation of (S)-3-(1-Ethyl-7-methoxy-4-methyl-1H-benzo[d][1,2,3]triazol-5-yl)-2,2-dimethyl-3-(4-methyl-3-(((R)-4-methyl-1,1-dioxido-4,5-dihydrobenzo[f][1,2]thiazepin-2(3H)-yl)methyl)phenyl)propanoic acid. As is appreciated by those skilled in the art, these analogous examples may involve variations in general reaction conditions.

TABLE B

| Structure | Name | LCMS [M + H]$^+$ | Retention Time (min) |
|---|---|---|---|
| 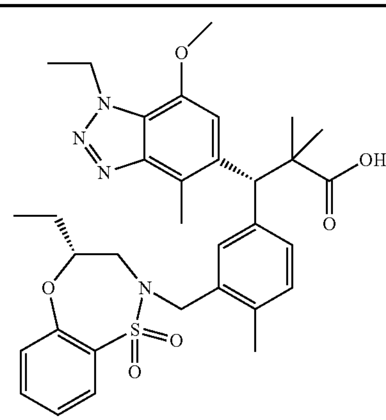 | (R)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-7-methoxy-4-methyl-1H-benzo[d][1,2,3]triazol-5-yl)-2,2-dimethylpropanoic acid | 621.5 | 1.27 |

TABLE B-continued

| Structure | Name | LCMS [M + H]+ | Retention Time (min) |
|---|---|---|---|
| 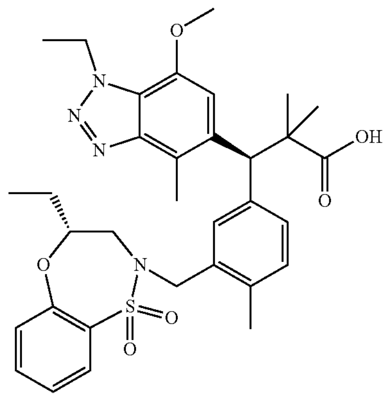 [SMILES: CC[C@@H]1CN(Cc2cc([C@@H](c3cc(OC)c4c(nnn4CC)c3C)C(C)(C)C(=O)O)ccc2C)S(=O)(=O)c2ccccc2O1] | (S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-7-methoxy-4-methyl-1H-benzo[d][1,2,3]triazol-5-yl)-2,2-dimethylpropanoic acid | 621.3 | 1.27 |
| 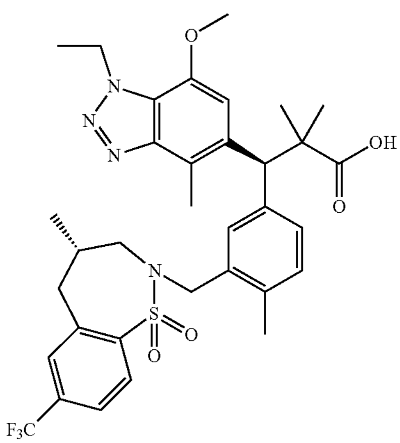 [SMILES: CCn1nnc2c(C)c([C@H](c3ccc(C)c(CN4C[C@@H](C)Cc5cc(C(F)(F)F)ccc5S4(=O)=O)c3)C(C)(C)C(=O)O)cc(OC)c21] | (S)-3-(1-Ethyl-7-methoxy-4-methyl-1H-benzo[d][1,2,3]triazol-5-yl)-2,2-dimethyl-3-(4-methyl-3-(((S)-4-methyl-1,1-dioxido-7-(trifluoromethyl)-4,5-dihydrobenzo[f][1,2]thiazepin-2(3H)-yl)methyl)phenyl)propanoic acid | 673.5 | 1.43 |
| 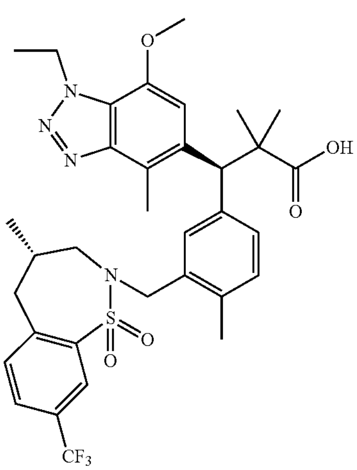 [SMILES: CCn1nnc2c(C)c([C@H](c3ccc(C)c(CN4C[C@@H](C)Cc5ccc(C(F)(F)F)cc5S4(=O)=O)c3)C(C)(C)C(=O)O)cc(OC)c21] | (S)-3-(1-Ethyl-7-methoxy-4-methyl-1H-benzo[d][1,2,3]triazol-5-yl)-2,2-dimethyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoic acid | 673 | 1.41 |

187

(2-Methyl-5-(4,4,5,5-tetramethyl-1,3,2-dioxaboro-lan-2-yl)phenyl)methanol

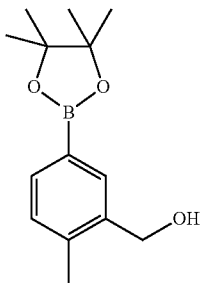

188

Benzyl (S)-3-(1-ethyl-7-methoxy-4-methyl-1H-benzo[d][1,2,3]triazol-5-yl)-3-(3-(hydroxymethyl)-4-methylphenyl)propanoate

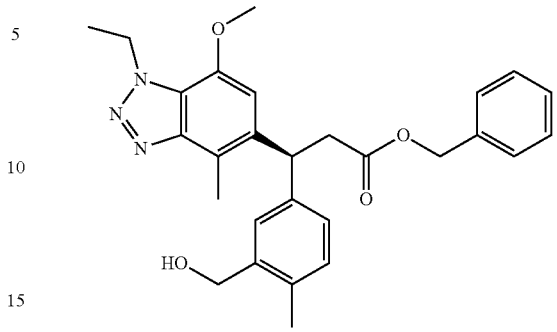

To a solution of (5-bromo-2-methylphenyl)methanol (55 g, 274 mmol) in 1,4-dioxane (1000 mL) was added potassium acetate (81 g, 821 mmol) and bis(pinacolato)diboron (104 g, 410 mmol). The reaction mixture was degassed with argon for 30 min, and then $PdCl_2(dppf)\text{-}CH_2Cl_2$ adduct (13.40 g, 16.41 mmol) was added and the reaction mixture stirred at 100° C. for 16 hrs after which time it was filtered through a pad of celite. The filtrate was concentrated under reduced pressure. The crude residue was purified via silica gel chromatography using EtOAc:Hexane (3:7) to afford the title compound (2-methyl-5-(4,4,5,5-tetramethyl-1,3,2-dioxaborolan-2-yl)phenyl)methanol (60 g, 230 mmol, 84% yield). LC-MS m/z=271.3 $(M+H)^+$, 1.17 (ret. time).

Benzyl (E)-3-(1-ethyl-7-methoxy-4-methyl-1H-benzo[d][1,2,3]triazol-5-yl)acrylate

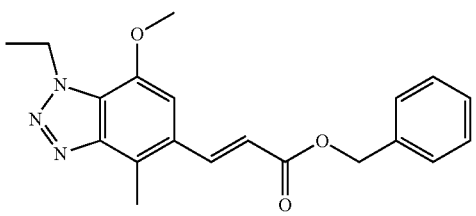 [SMILES: CCn1nnc2c(C)c(/C=C/C(=O)OCc3ccccc3)cc(OC)c21]

To a solution of 5-bromo-1-ethyl-7-methoxy-4-methyl-1H-benzo[d][1,2,3]triazole (1.5 g, 5.55 mmol) in N,N-dimethylformamide (DMF) (8 mL) at ambient temperature was added benzyl acrylate (3.40 mL, 22.21 mmol) and N-ethyl-N-isopropylpropan-2-amine (3.88 mL, 22.21 mmol), tri-o-tolylphosphane (0.507 g, 1.666 mmol), followed by palladium(II) acetate (0.187 g, 0.833 mmol). The reaction mixture was heated via microwave under high absorption at 150° C. for 2 h. It was passed through celite and washed with EtOAc. The filtrate was washed with water and brine. The organic layer was collected and concentrated to give the crude product. The crude product was purified by flash chromatography, with a gradient running from 0-60% EtOAc/hexanes give the title compound (1812 mg, 5.16 mmol, 93% yield). LC/MS: m/z=352.2 $(M+H)^+$, 1.25 min. (ret. time). $^1H$ NMR (400 MHz, DMSO-$d_6$) L=8.05 (d, J=15.8 Hz, 1H), 7.54-7.27 (m, 6H), 6.83 (d, J=15.8 Hz, 1H), 5.26 (s, 2H), 4.78 (q, J=7.0 Hz, 2H), 4.03 (s, 3H), 2.70 (s, 3H), 1.57-1.40 (m, 3H).

To a suspension of benzyl (E)-3-(1-ethyl-7-methoxy-4-methyl-1H-benzo[d][1,2,3]triazol-5-yl)acrylate (1800 mg, 5.12 mmol), (2-methyl-5-(4,4,5,5-tetramethyl-1,3,2-dioxaborolan-2-yl)phenyl)methanol (1906 mg, 7.68 mmol), and $[RhCl(cod)]_2$ (253 mg, 0.512 mmol) in 1,4-dioxane (8 mL) and water (2.000 mL) at ambient temperature was added triethylamine (2.142 mL, 15.37 mmol). It was degassed for 10 min and heated in a Biotage microwave at high absorption for 1 h at 120° C. The reaction mixture was passed through celite and washed with EtOAc. The organic layer was collected and concentrated to give the crude product. The reaction mixture was purified by silica gel. Desired fractions were concentrated to give the title compound benzyl 3-(1-ethyl-7-methoxy-4-methyl-1H-benzo[d][1,2,3]triazol-5-yl)-3-(3-(hydroxymethyl)-4-methylphenyl)propanoate (1866 mg, 3.94 mmol, 77% yield). It was resolved by Chiral SFC (Column: Chiralpak IA 20×250 mm, 5 u; Co-solvent: 25% EtOH; Flowrate: 50 g/min; Back pressure: 100 Bar) to give benzyl (S)-3-(1-ethyl-7-methoxy-4-methyl-1H-benzo[d][1,2,3]triazol-5-yl)-3-(3-(hydroxymethyl)-4-methylphenyl)propanoate (804.6 mg, 1.699 mmol, 33.2% yield) (chiral SFC ret. time: 2.31 min) LC-MS m/z=474.3840 $(M+H)^+$, 1.15 min (ret. time) and benzyl (R)-3-(1-ethyl-7-methoxy-4-methyl-1H-benzo[d][1,2,3]triazol-5-yl)-3-(3-(hydroxymethyl)-4-methylphenyl)propanoate (778.9 mg, 1.645 mmol, 32.1% yield) (chiral SFC ret. time: 2.96 min) LC-MS m/z=474.4581 $(M+H)^+$, 1.15 min (ret. time).

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-7-methoxy-4-methyl-1H-benzo[d][1,2,3]triazol-5-yl)propanoic Acid

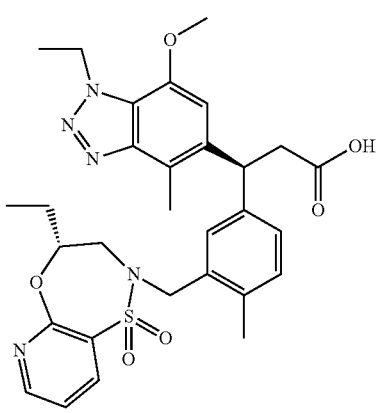 [SMILES: CC[C@@H]1CN(Cc2cc([C@H](CC(=O)O)c3cc(OC)c4c(nnn4CC)c3C)ccc2C)S(=O)(=O)c2cccnc2O1]

To a solution of benzyl (S)-3-(1-ethyl-7-methoxy-4-methyl-1H-benzo[d][1,2,3]triazol-5-yl)-3-(3-(hydroxymethyl)-4-methylphenyl)propanoate (80 mg, 0.169 mmol), (R)-4-ethyl-3,4-dihydro-2H-pyrido[2,3-b][1,4,5]oxathiazepine 1,1-dioxide (38.6 mg, 0.169 mmol), and 1,1'-(Azodicarbonyl)dipiperidine (85 mg, 0.338 mmol) in tetrahydrofuran (THF) (3 mL) at ambient temperature was added tri-n-butylphosphine (0.083 mL, 0.338 mmol). The reaction mixture was stirred at ambient temperature for 18 h. It was concentrated and purified by flash chromatography (ethyl acetate in hexane), to provide benzyl (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-7-methoxy-4-methyl-1H-benzo[d][1,2,3]triazol-5-yl)propanoate (119 mg, 0.174 mmol, 103% yield). The benzyl ester intermediate was dissolved in methanol (3.00 mL), and treated with 2M LiOH (0.507 mL, 1.014 mmol) and stirred at ambient temperature for 5 h. The solvent was concentrated and the residue was treated with 1 mL 1N HCl and 3 mL DMSO and purified with preparative HPLC under neutral conditions to give the title compound (95 mg, 0.160 mmol, 95% yield). LC-MS m/z=594.4448 (M+H)$^+$, 1.06 min (ret. time)$^1$H NMR (400 MHz, DMSO-d$_6$) L=8.54 (d, J=4.8 Hz, 1H), 8.22 (d, J=7.5 Hz, 1H), 7.45 (dd, J=5.0, 7.5 Hz, 1H), 7.23-7.03 (m, 3H), 6.94 (s, 1H), 4.83-4.68 (m, 3H), 4.39 (d, J=14.1 Hz, 1H), 4.25 (br. s., 1H), 3.99-3.90 (m, 4H), 3.64 (dd, J=10.2, 15.4 Hz, 1H), 2.85 (d, J=15.1 Hz, 1H), 2.55 (s, 4H), 2.23 (s, 3H), 2.08 (s, 1H), 1.51-1.36 (m, 4H), 1.29-1.17 (m, 1H), 0.86 (t, J=7.3 Hz, 3H).

The compounds in Table 8 were prepared by a method similar to the one described for the preparation of (R)-3-((1-Ethyl-1H-1,2,3-triazol-4-yl)methoxy)-2,2-dimethyl-3-(4-methyl-3-(((S)-4-methyl-1,1-dioxido-4,5-dihydropyrido[4,3-f][1,2]thiazepin-2(3H)-yl)methyl)phenyl)-N-(pyridin-3-yl)propanamide, formic acid salt. As is appreciated by those skilled in the art, these analogous examples may involve variations in general reaction conditions.

TABLE 8

| Ex # | Structure | Name | LCMS [M + 1] | Retention Time (min) |
|---|---|---|---|---|
| Example 49 | 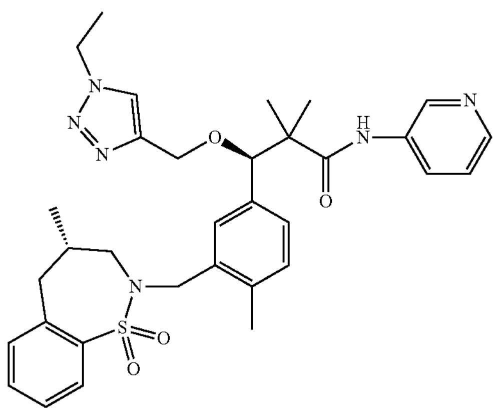 [SMILES: CCn1cc(CO[C@H](c2ccc(C)c(CN3C[C@@H](C)Cc4ccccc4S3(=O)=O)c2)C(C)(C)C(=O)Nc2cccnc2)nn1] | (R)-3-((1-Ethyl-1H-1,2,3-triazol-4-yl)methoxy)-2,2-dimethyl-3-(4-methyl-3-(((S)-4-methyl-1,1-dioxido-4,5-dihydrobenzo[f][1,2]thiazepin-2(3H)-yl)methyl)phenyl)-N-(pyridin-3-yl)propanamide, Formic acid salt | 617 | 0.99 |
| Example 50 | 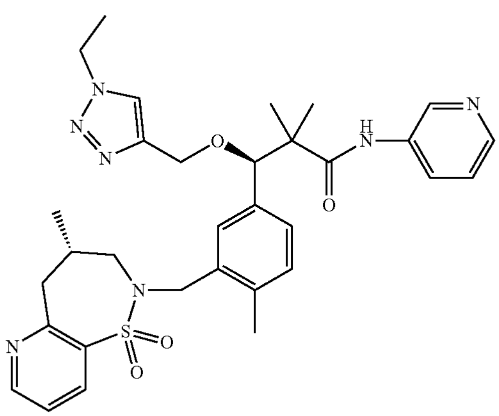 [SMILES: CCn1cc(CO[C@H](c2ccc(C)c(CN3C[C@@H](C)Cc4ncccc4S3(=O)=O)c2)C(C)(C)C(=O)Nc2cccnc2)nn1] | (R)-2,2-Dimethyl-3-(4-methyl-3-(((S)-4-methyl-1,1-dioxido-4,5-dihydropyrido[2,3-f][1,2]thiazepin-2(3H)-yl)methyl)phenyl)-3-((1-propyl-1H-1,2,3-triazol-4-yl)methoxy)-N-(pyridin-3-yl)propanamide, Formic acid salt | 632 | 0.82 |

TABLE 8-continued

| Ex # | Structure | Name | LCMS [M + 1] | Retention Time (min) |
|---|---|---|---|---|
| Example 51 | 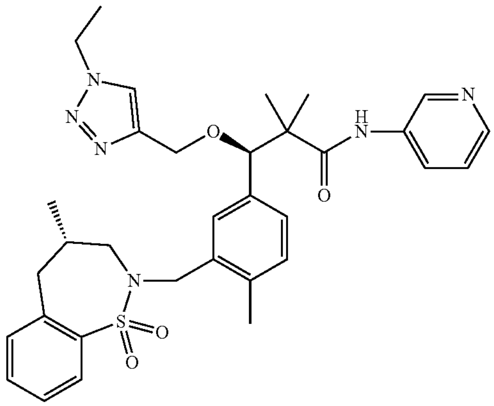 [SMILES: CCn1cc(CO[C@H](c2ccc(C)c(CN3C[C@@H](C)Cc4ccccc4S3(=O)=O)c2)C(C)(C)C(=O)Nc2cccnc2)nn1] | (R)-2,2-Dimethyl-3-(4-methyl-3-(((S)-4-methyl-1,1-dioxido-4,5-dihydrobenzo[f][1,2]thiazepin-2(3H)-yl(methyl)phenyl)-3-((1-propyl-1H-1,2,3-triazol-4-yl)methoxy)-N-(pyridin-3-yl)propanamide, Formic acid salt | 631 | 0.94 |
| Example 52 | 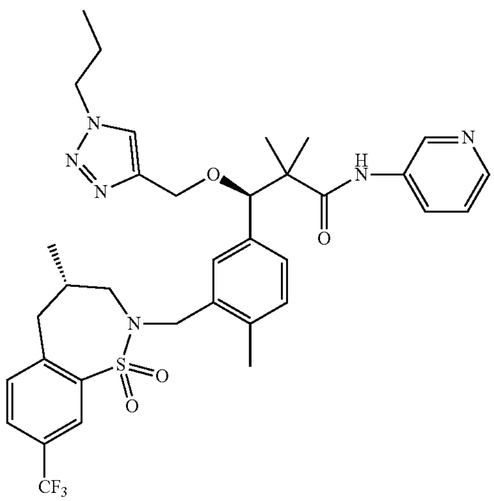 [SMILES: CCCn1cc(CO[C@H](c2ccc(C)c(CN3C[C@@H](C)Cc4ccc(C(F)(F)F)cc4S3(=O)=O)c2)C(C)(C)C(=O)Nc2cccnc2)nn1] | (R)-2,2-Dimethyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)-3-((1-propyl-1H-1,2,3-triazol-4-yl)methoxy)-N-(pyridin-3-yl)propanamide | 698 | 1.08 |
| Example 53 | 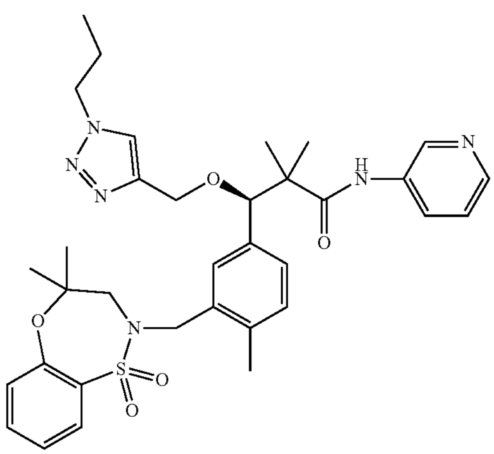 [SMILES: CCCn1cc(CO[C@H](c2ccc(C)c(CN3CC(C)(C)Oc4ccccc4S3(=O)=O)c2)C(C)(C)C(=O)Nc2cccnc2)nn1] | (R)-3-(3-((4,4-Dimethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)-N-(pyridin-3-yl)propanamide | 647 | 1.04 |

TABLE 8-continued

| Ex # | Structure | Name | LCMS [M + 1] | Retention Time (min) |
|---|---|---|---|---|
| Example 54 | 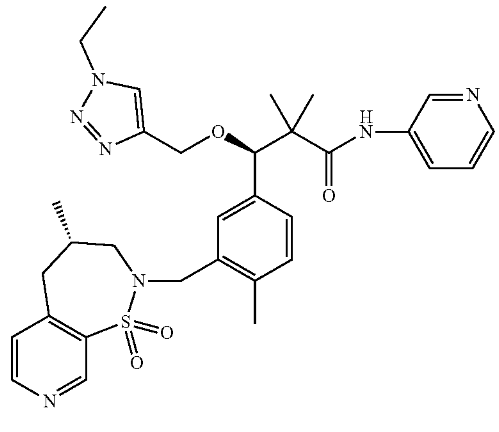 [SMILES: CCn1cc(CO[C@H](c2ccc(C)c(CN3C[C@@H](C)Cc4ccncc4S3(=O)=O)c2)C(C)(C)C(=O)Nc2cccnc2)nn1] | (R)-2,2-Dimethyl-3-(4-methyl-3-(((S)-4-methyl-1,1-dioxido-4,5-dihydropyrido[4,3-f][1,2]thiazepin-2(3H)-yl(methyl)phenyl)-3-((1-propyl-1H-1,2,3-triazol-4-yl)methoxy)-N-(pyridin-3-yl)propanamide | 632 | 0.83 |
| Example 55 | 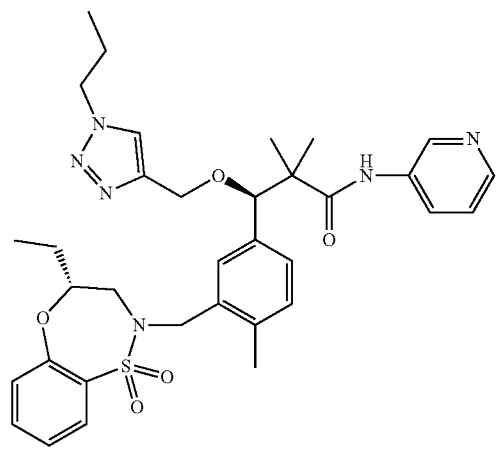 [SMILES: CCCn1cc(CO[C@H](c2ccc(C)c(CN3C[C@@H](CC)Oc4ccccc4S3(=O)=O)c2)C(C)(C)C(=O)Nc2cccnc2)nn1] | (R)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-3-((1-propyl-1H-1,2,3-triazol-4-yl)methoxy)-N-(pyridin-3-yl)propanamide | 647 | 0.95 |
| Example 56 | 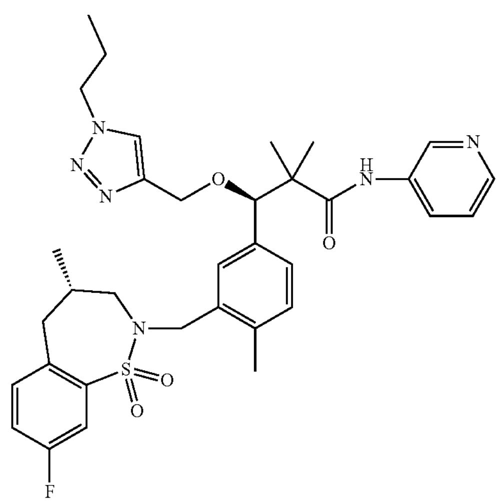 [SMILES: CCCn1cc(CO[C@H](c2ccc(C)c(CN3C[C@@H](C)Cc4ccc(F)cc4S3(=O)=O)c2)C(C)(C)C(=O)Nc2cccnc2)nn1] | (R)-3-(3-(((S)-8-Fluoro-4-methyl-1,1-dioxido-4,5-dihydrobenzo[f][1,2]thiazepin-2(3H)-yl)methyl)-4-methylphenyl)-2,2-dimethyl-3-((1-propyl-1H-1,2,3-triazol-4-yl)methoxy)-N-(pyridin-3-yl)propanamide | 649 | 1.00 |

TABLE 8-continued

| Ex # | Structure | Name | LCMS [M + 1] | Retention Time (min) |
|---|---|---|---|---|
| Example 57 | 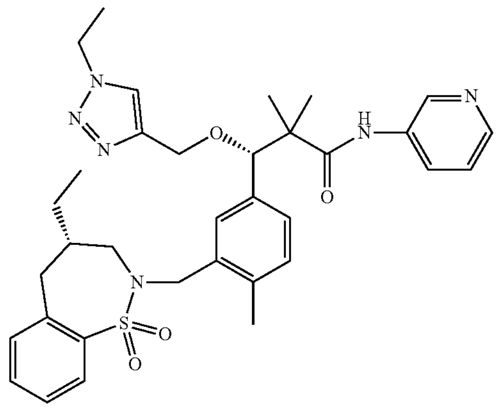 [SMILES: CC[C@H]1Cc2ccccc2S(=O)(=O)N(Cc2cc([C@H](OCc3cn(CC)nn3)C(C)(C)C(=O)Nc3cccnc3)ccc2C)C1] | (S)-3-(3-(((S)-4-Ethyl-1,1-dioxido-4,5-dihydrobenzo[f][1,2]thiazepin-2(3H)-yl)methyl)-4-methylphenyl)-3-((1-ethyl-1H-1,2,3-triazol-4-yl)methoxy)-2,2-dimethyl-N-(pyridin-3-yl)propanamide | 631 | 0.95 |
| Example 58 | 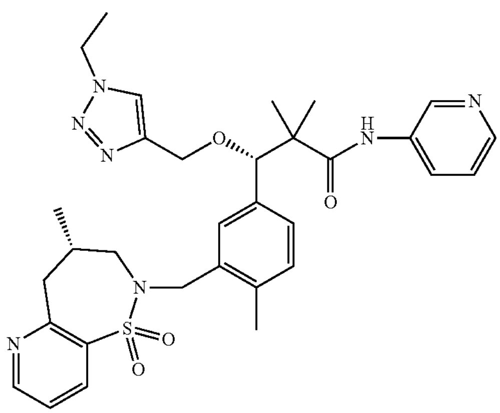 [SMILES: CCn1cc(CO[C@@H](c2ccc(C)c(CN3C[C@@H](C)Cc4ncccc4S3(=O)=O)c2)C(C)(C)C(=O)Nc2cccnc2)nn1] | (S)-3-((1-Ethyl-1H-1,2,3-triazol-4-yl)methoxy)-2,2-dimethyl-3-(4-methyl-3-(((S)-4-methyl-1,1-dioxido-4,5-dihydropyrido[2,3-f][1,2]thiazepin-2(3H)-yl)methyl)phenyl)-N-(pyridin-3-yl)propanamide | 618 | 0.80 |
| Example 59 | 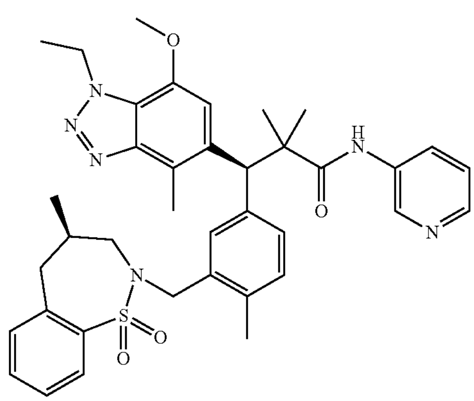 [SMILES: CCn1nnc2c(C)c([C@H](c3ccc(C)c(CN4C[C@H](C)Cc5ccccc5S4(=O)=O)c3)C(C)(C)C(=O)Nc3cccnc3)cc(OC)c21] | (S)-3-(1-Ethyl-7-methoxy-4-methyl-1H-benzo[d][1,2,3]triazol-5-yl)-2,2-dimethyl-3-(4-methyl-3-(((R)-4-methyl-1,1-dioxido-4,5-dihydrobenzo[f][1,2]thiazepin-2(3H)-yl)methyl)phenyl)-N-(pyridin-3-yl)propanamide | 681 | 1.05 |

TABLE 8-continued

| Ex # | Structure | Name | LCMS [M + 1] | Retention Time (min) |
|---|---|---|---|---|
| Example 60 | 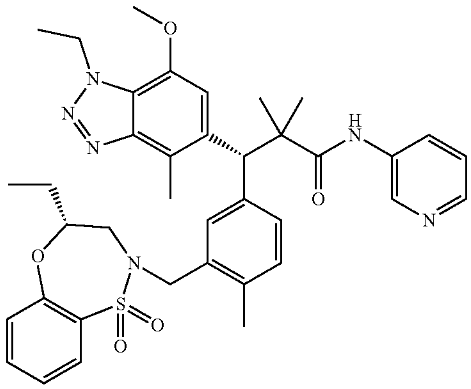 [SMILES: CC[C@@H]1CN(Cc2cc([C@H](c3cc(OC)c4c(nnn4CC)c3C)C(C)(C)C(=O)Nc3cccnc3)ccc2C)S(=O)(=O)c2ccccc2O1] | (R)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-7-methoxy-4-methyl-1H-benzo[d][1,2,3]triazol-5-yl)-2,2-dimethyl-N-(pyridin-3-yl)propanamide | 697 | 1.105 |
| Example 61 | 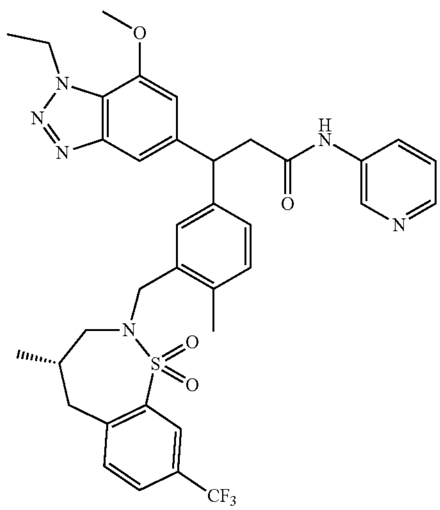 [SMILES: CCn1nnc2cc(C(CC(=O)Nc3cccnc3)c3ccc(C)c(CN4C[C@@H](C)Cc5ccc(C(F)(F)F)cc5S4(=O)=O)c3)cc(OC)c21] | 3-(7-Methoxy-1-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl(methyl)phenyl)-N-(pyridin-3-yl)propanamide | 693 | 1.02 |
| Example 62 | 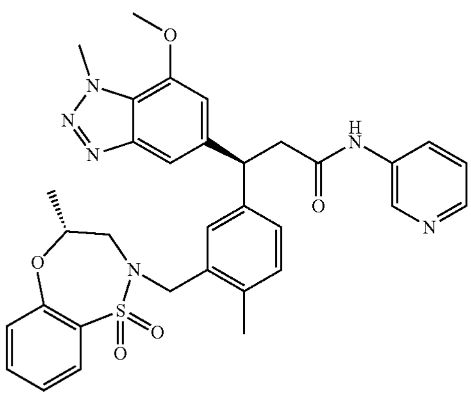 [SMILES: COc1cc([C@@H](CC(=O)Nc2cccnc2)c2ccc(C)c(CN3C[C@@H](C)Oc4ccccc4S3(=O)=O)c2)cc2nnn(C)c12] | (S)-3-(7-Methoxy-1-methyl-1H-benzo[d][1,2,3]triazol-5-yl)-3-(4-methyl-3-(((R)-4-methyl-1,1-dioxido-3,4-dihydro-2H-benzo[b][1,4,5]oxathiazepin-2-yl)methyl)phenyl)-N-(pyridin-3-yl)propanamide | 627 | 0.84 |

TABLE 8-continued

| Ex # | Structure | Name | LCMS [M + 1] | Retention Time (min) |
|---|---|---|---|---|
| Example 63 | 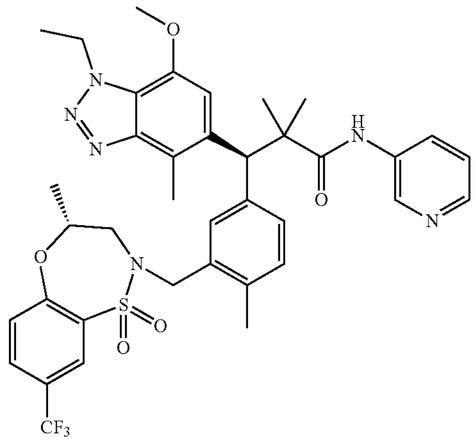 [SMILES: CCn1nnc2c(C)c([C@H](c3ccc(C)c(CN4C[C@@H](C)Oc5ccc(C(F)(F)F)cc5S4(=O)=O)c3)C(C)(C)C(=O)Nc3cccnc3)cc(OC)c21] | (S)-3-(1-Ethyl-7-methoxy-4-methyl-1H-benzo[d][1,2,3]triazol-5-yl)-2,2-dimethyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)-N-(pyridin-3-yl)propanamide | 749 | 1.12 |
| Example 64 | 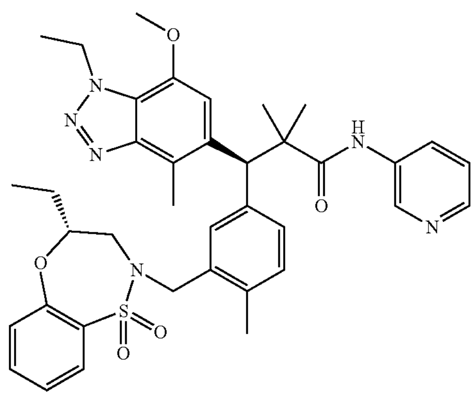 [SMILES: CC[C@@H]1CN(Cc2cc([C@@H](c3cc(OC)c4c(nnn4CC)c3C)C(C)(C)C(=O)Nc3cccnc3)ccc2C)S(=O)(=O)c2ccccc2O1] | (S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-7-methoxy-4-methyl-1H-benzo[d][1,2,3]triazol-5-yl)-2,2-dimethyl-N-(pyridin-3-yl)propanamide | 697 | 1.03 |
| Example 65 | 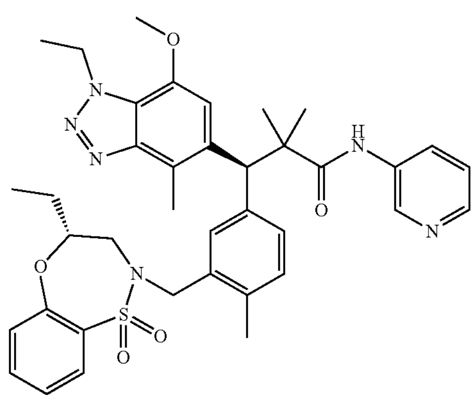 [SMILES: CC[C@@H]1CN(Cc2cc([C@@H](c3cc(OC)c4c(nnn4CC)c3C)C(C)(C)C(=O)Nc3cccnc3)ccc2C)S(=O)(=O)c2ccccc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-7-methoxy-4-methyl-1H-benzo[d][1,2,3]triazol-5-yl)-N-(pyridin-3-yl)propanamide | 670 | 0.86 |

TABLE 8-continued

| Ex # | Structure | Name | LCMS [M + 1] | Retention Time (min) |
|---|---|---|---|---|
| Example 66 | 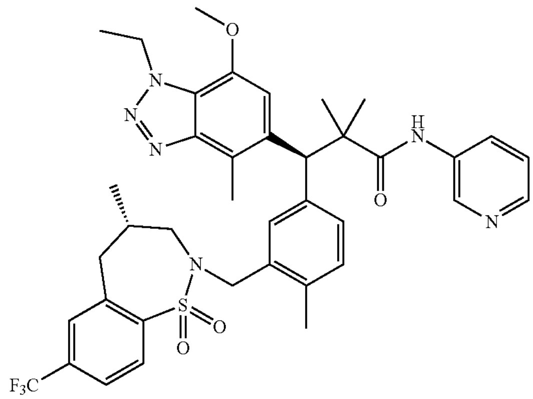 [SMILES: CCn1nnc2c(C)c([C@H](c3ccc(C)c(CN4C[C@@H](C)Cc5cc(C(F)(F)F)ccc5S4(=O)=O)c3)C(C)(C)C(=O)Nc3cccnc3)cc(OC)c21] | (S)-3-(1-Ethyl-7-methoxy-4-methyl-1H-benzo[d][1,2,3]triazol-5-yl)-2,2-dimethyl-3-(4-methyl-3-(((S)-4-methyl-1,1-dioxido-7-(trifluoromethyl)-4,5-dihydrobenzo[f][1,2]thiazepin-2(3H)-yl)methyl)phenyl)-N-(pyridin-3-yl)propanamide | 749 | 1.13 |

Example 67

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2H-tetrazol-5-yl)propanamide

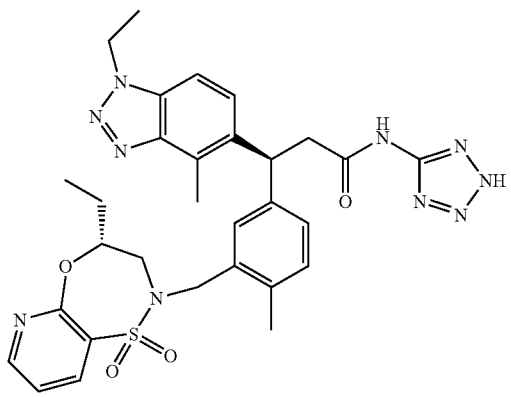

To a solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (0.100 g, 0.177 mmol) and 2H-tetrazol-5-amine hydrate (0.022 g, 0.213 mmol) in N,N-dimethylformamide (DMF) (5 mL) was added HATU (0.081 g, 0.213 mmol) and DIEA (0.124 mL, 0.710 mmol) and stirred at ambient temperature for 3 h. The solvent was concentrated and the residue was purified by reverse phase preparative HPLC under formic acid conditions to provide the title compound (0.032 g, 28% yield, 99% pure). LC/MS m/z=631 (M+H)⁺, 0.97 min (ret. time).

Example 68

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

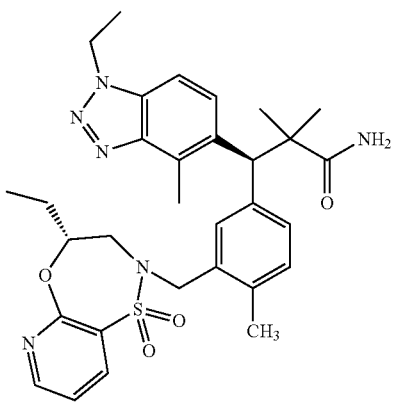 [SMILES: CC[C@@H]1CN(Cc2cc([C@@H](c3ccc4c(nnn4CC)c3C)C(C)(C)C(N)=O)ccc2C)S(=O)(=O)c2cccnc2O1]

(1-Ethyl-4-methyl-1H-benzo[d][1,2,3]triazol-5-yl)(3-(((4-methoxybenzyl)oxy)methyl)-4-methylphenyl)methanol

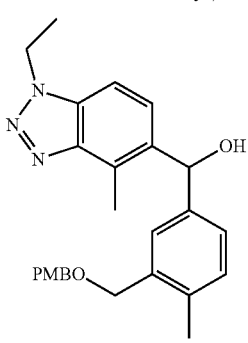

To a solution of 5-bromo-1-ethyl-4-methyl-1H-benzo[d][1,2,3]triazole (15.0 g, 62.5 mmol) in tetrahydrofuran (THF) (750 mL) 2.5M butyllithium (24.99 mL, 62.5 mmol) was added at −78° C. under N2 protection. The mixture was stirred at −78° C. for half an hour under N2 protection, then 3-(((4-methoxybenzyl)oxy)methyl)-4-methylbenzaldehyde (17.73 g, 65.6 mmol) dissolved in tetrahydrofuran (THF) (50 mL) was added dropwise and continually stirred for 2 hrs at −78° C. The mixture was slowly warmed to 20° C. and stirred for another 2 hrs. The reaction was quenched with saturated aqueous NH4Cl solution (80 mL). The mixture was extracted with ethyl acetate (3×200 mL). The combined organic layer was washed with brine (150 mL) and dried over anhydrous Na2SO4. After filtration and concentration, the residue was purified by flash chromatography (petroleum ether:ethyl acetate=2:1) to obtain the title compound (14.0 g, 30.8 mmol, 49.3% yield). LC-MS m/z=432.3 (M+Na)+, 1.92 min (ret. time).

Methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate

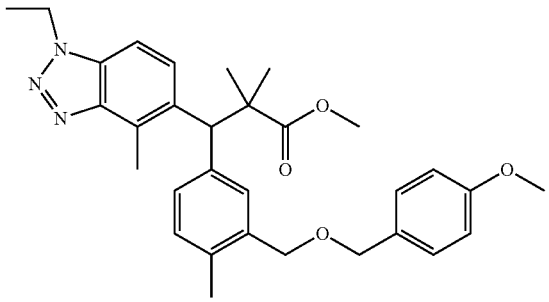 [SMILES: CCn1nnc2c(C)c(C(c3ccc(C)c(COCc4ccc(OC)cc4)c3)C(C)(C)C(=O)OC)ccc21]

To a solution of (1-ethyl-4-methyl-1H-benzo[d][1,2,3]triazol-5-yl)(3-(((4-methoxybenzyl)oxy)methyl)-4-methylphenyl)methanol (22.0 g, 51.0 mmol), was slowly added 2,2,2-trichloroacetonitrile (6.65 mL, 66.3 mmol) and DBU (0.231 mL, 1.529 mmol) dropwise under N2 protection at 15° C. The mixture was stirred at 15° C. for 2 hrs after which ((1-methoxy-2-methylprop-1-en-1-yl)oxy)trimethylsilane (25.9 mL, 127 mmol) was added dropwise, after 10 mins, BF3OEt2 (6.46 mL, 51.0 mmol) was added dropwise and the mixture was stirred for 1.6 hrs. Then 180 mL of H2O was added to quench the reaction. The mixture was extracted with ethyl acetate (3×150 ml) and the combined organic layers were washed with brine (100 mL) and dried over Na2SO4. After filtration and concentration, the residue was purified by flash chromatography (petroleum ether:ethyl acetate=3:1)) to obtain the title compound (20.0 g, 36.8 mmol, 72.3% yield). LC-MS m/z=516.2 (M+H)+, 2.21 min (ret. time). 1H NMR (500 MHz, CDCl3) δ 7.57 (d, J=8.8 Hz, 1H), 7.27-7.25 (m, 1H), 7.19 (dd, J=8.8, 5.2 Hz, 3H), 7.09 (dd, J=7.9, 1.9 Hz, 1H), 7.04 (d, J=7.9 Hz, 1H), 6.86-6.81 (m, 2H), 4.89 (s, 1H), 4.62 (q, J=7.3 Hz, 2H), 4.44 (dd, J=16.2, 11.0 Hz, 4H), 3.80 (s, 3H), 3.48 (s, 3H), 2.83 (s, 3H), 2.24 (s, 3H), 1.59 (t, J=7.3 Hz, 3H), 1.41 (s, 3H), 1.31 (s, 3H).

Methyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate

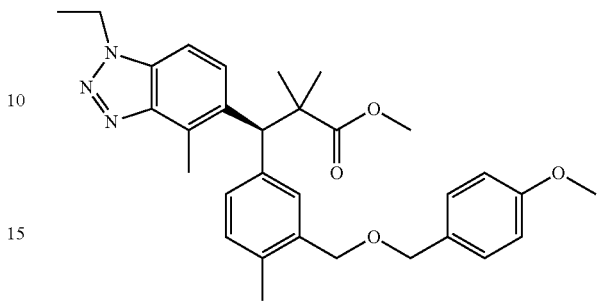

Methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate was resolved by Chiral SFC (Column: Chiralpak IG, 5 u; Co-solvent: 30% EtOH; Flow-rate: 80 g/min; Back pressure: 100 Bar) to give Methyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (chiral SFC ret. time: 2.83 min) and Methyl (R)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (chiral SFC ret. time: 3.88 min).

Benzyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate

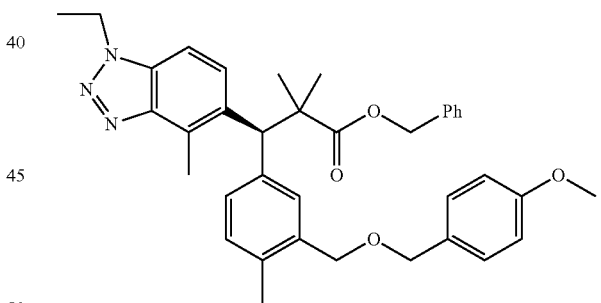

To a solution of methyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (3.1 g, 6.01 mmol) in methanol (32 mL), LiOH (30.1 mL, 60.1 mmol) was added. The reaction mixture was heated with microwave at 120° C. for 2 hr. The solvent was evaporated and dissolved in N,N-dimethylformamide (DMF) (30.0 mL), benzyl bromide (1.430 mL, 12.02 mmol) was added. The reaction mixture was stirred at ambient temperature for 2 hrs. The reaction mixture was partitioned between ethyl acetate and water. The water layer was extracted with ethyl acetate (2×). The combined organic phase was dried over MgSO4 and concentrated. The crude product was purified via silica gel flash chromatography (hexane/ethyl acetate) to obtain the title compound benzyl (S)-3-(1-ethyl-4-methyl-1H-benzo[d][1,2,3]triazol-5-yl)-3-(3-(((4-methoxybenzyl)

oxy)methyl)-4-methylphenyl)-2,2-dimethylpropanoate (3.2 g, 5.41 mmol, 90% yield). LC-MS m/z=592.35 (M−1)⁺, 1.53 min (ret. time).

Benzyl (S)-3-(1-ethyl-4-methyl-1H-benzo[d][1,2,3] triazol-5-yl)-3-(3-(hydroxymethyl)-4-methylphenyl)-2,2-dimethylpropanoate

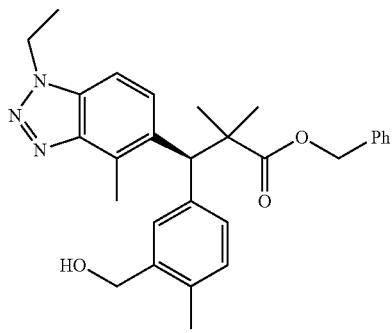 [SMILES: CCn1nnc2c(C)c([C@H](c3ccc(C)c(CO)c3)C(C)(C)C(=O)OCc3ccccc3)ccc21]

To a solution of benzyl (S)-3-(1-ethyl-4-methyl-1H-benzo [d][1,2,3]triazol-5-yl)-3-(3-(((4-methoxybenzyl)oxy) methyl)-4-methylphenyl)-2,2-dimethylpropanoate (3.2 g, 5.41 mmol) in a mixture of acetonitrile (20.00 mL) and water (2 mL), CAN (5.93 g, 10.82 mmol) was added at 0° C. Then the reaction mixture was stirred at ambient temperature for 2 hrs. The reaction mixture was partitioned between ethyl acetate and saturated NH₄Cl. The water layer was extracted with ethyl acetate (2×). The combined organic phase was dried over MgSO₄ and concentrated. The crude product was purified by flash chromatography with ethyl acetate/hexane to obtain the title compound benzyl (S)-3-(1-ethyl-4-methyl-1H-benzo[d][1,2,3]triazol-5-yl)-3-(3-(hydroxymethyl)-4-methylphenyl)-2,2-dimethylpropanoate (2.1 g, 4.45 mmol, 82% yield). LC-MS m/z=472.34 (M+1)⁺, 1.2 min (ret. time).

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic Acid

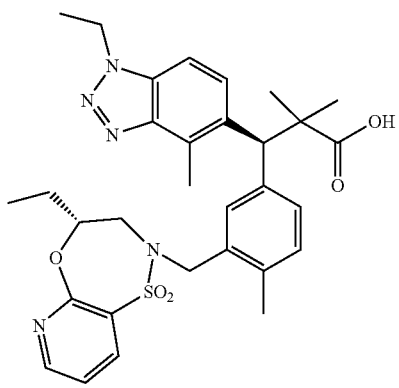 [SMILES: CC[C@@H]1CN(Cc2cc([C@@H](c3ccc4c(nnn4CC)c3C)C(C)(C)C(=O)O)ccc2C)S(=O)(=O)c2cccnc2O1]

To a solution of benzyl (S)-3-(1-ethyl-4-methyl-1H-benzo [d][1,2,3]triazol-5-yl)-3-(3-(hydroxymethyl)-4-methylphenyl)-2,2-dimethylpropanoate (2100 mg, 4.45 mmol) in tetrahydrofuran (THF) (15 mL), (R)-4-ethyl-3,4-dihydro-2H-pyrido[2,3-b][1,4,5]oxathiazepine 1,1-dioxide (1220 mg, 5.34 mmol) and (E)-diazene-1,2-diylbis(piperidin-1-yl-methanone) (2247 mg, 8.91 mmol) were added, then tributylphosphane (2.224 mL, 8.91 mmol) was added. The reaction mixture was stirred at ambient temperature for 18 hrs. The solvent was evaporated and the product purified by flash chromatography with ethyl acetate/hexane to obtain benzyl (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoate (2500 mg, 3.67 mmol, 82% yield). This compound was dissolved in 250 mL ethyl acetate and ethanol (3:1) and hydrogenated with on an H-Cube to get crude title compound. This product was purified by reversed phase HPLC under acidic conditions to obtain the title compound (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (1200 mg, 2.028 mmol, 45.5% yield). LC-MS m/z=592.29 (M+H)⁺, 1.1 min (ret. time).

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

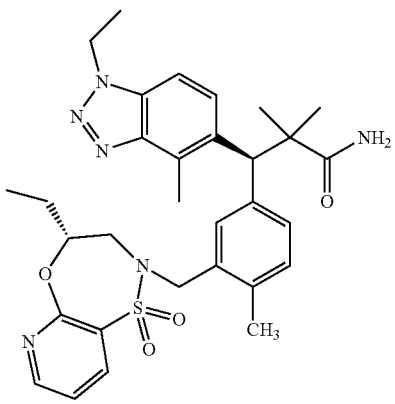 [SMILES: CC[C@@H]1CN(Cc2cc([C@@H](c3ccc4c(nnn4CC)c3C)C(C)(C)C(N)=O)ccc2C)S(=O)(=O)c2cccnc2O1]

A mixture of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (0.464 g, 0.784 mmol) and thionyl chloride (4.01 mL, 54.9 mmol) was stirred in a 1 dram vial at ambient temperature for 3 h. The thionyl chloride was evaporated under vacuum and the residue was dissolved in tetrahydrofuran (THF) (10 mL) and cooled in an ice bath. Ammonia gas was bubbled into the solution for 2 min. A white precipitate formed and the solution turned pink and was stirred for 18 h. The resultant product was purified by reverse phase preparative HPLC under trifluoroacetic acid conditions to provide the title compound as a TFA salt. The compound was dissolved in EtOAc and washed with sat NaHCO₃. The organic layer was dried with MgSO₄, concentrated and pumped on high vacuum to provide the title compound. (0.266 g, 57% yield, 100% pure). LC/MS m/z=591 (M+H)⁺, 1.00 min (ret time).

Example 69

3-(4-Cyano-2-methylphenyl)-3-(3-(((R)-4-ethyl-1,1-dioxido-3,4-dihydro-2H-pyrido[2,3-b][1,4,5]oxathiazepin-2-yl)methyl)-4-methylphenyl)-N-(pyridin-3-yl)propanamide

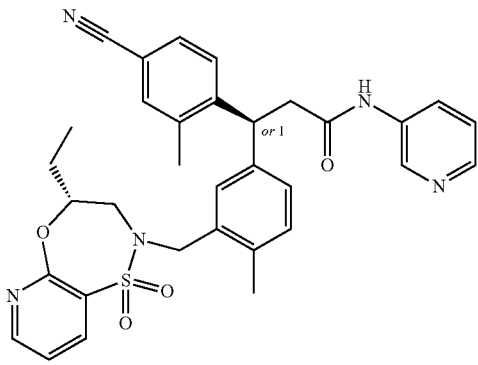 [SMILES: CC[C@@H]1CN(Cc2cc([C@H](CC(=O)Nc3cccnc3)c3ccc(C#N)cc3C)ccc2C)S(=O)(=O)c2cccnc2O1]

(E)-Methyl 3-(4-cyano-2-methylphenyl)acrylate

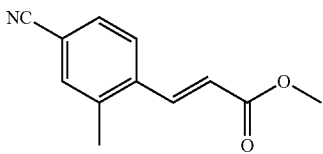

To a solution of 4-bromo-3-methylbenzonitrile (1 g, 5.10 mmol) in DMF (8 mL) was added methyl acrylate (2.311 mL, 25.5 mmol), DIEA (2.227 mL, 12.75 mmol), palladium (II) acetate (0.115 g, 0.510 mmol), and tri-o-tolylphosphine (0.311 g, 1.020 mmol). The reaction vessel was heated in a Biotage Initiator microwave at high absorption for 1 h at 150° C. The reaction was repeated twice. LCMS showed the reactions were complete. The combined reaction mixture (containing all three batches) was evaporated then diluted with H$_2$O (25 mL), and extracted with EtOAc (3×25 mL). The combined organic layer was concentrated under reduced pressure. The residue was purified by flash chromatography eluting with 0-40% EtOAc/hexanes to provide the title compound. (3.04 g, 15.10 mmol, 99% yield). LC/MS m/z=202 (M+H)$^+$, 0.91 min (ret time).

Methyl 3-(4-cyano-2-methylphenyl)-3-(3-(hydroxymethyl)-4-methylphenyl)propanoate

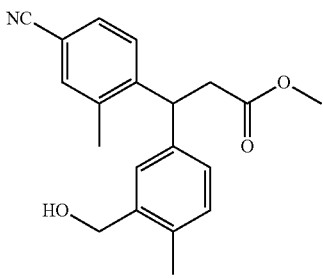 [SMILES: COC(=O)CC(c1ccc(C)c(CO)c1)c1ccc(C#N)cc1C]

To a solution of (E)-methyl 3-(4-cyano-2-methylphenyl)acrylate (1.500 g, 7.45 mmol) in 1,4-dioxane (25.04 ml) and water (8 ml) was added (2-methyl-5-(4,4,5,5-tetramethyl-1,3,2-dioxaborolan-2-yl)phenyl)methanol (3.70 g, 14.91 mmol), [RhCl(cod)]$_2$ (0.184 g, 0.373 mmol) and triethylamine (4.13 ml, 29.8 mmol). The reaction mixture was stirred at 90° C. for 2 h. The reaction mixture was filtered and extracted with EtOAc (3×25 mL). The combined organic layers were concentrated under reduced pressure. The residue was purified by flash chromatography eluting with 0-70% EtOAc/hexanes to provide the title compound. (2.60 g, 8.06 mmol). LC/MS m/z=647 (M+H)$^+$, 0.97 min (ret time).

Methyl 3-(4-cyano-2-methylphenyl)-3-(3-(((R)-4-ethyl-1,1-dioxido-3,4-dihydro-2H-pyrido[2,3-b][1,4,5]oxathiazepin-2-yl)methyl)-4-methylphenyl)propanoate

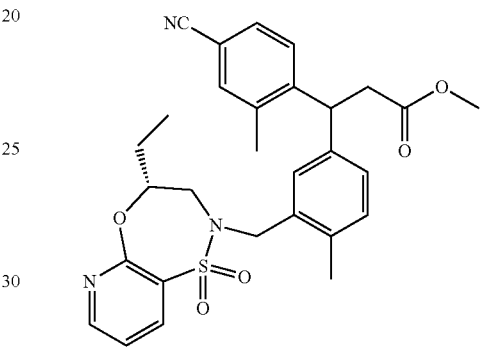

To a solution of methyl 3-(4-cyano-2-methylphenyl)-3-(3-(hydroxymethyl)-4-methylphenyl)propanoate (1.5 g, 4.64 mmol), (R)-4-ethyl-3,4-dihydro-2H-pyrido[2,3-b][1,4,5]oxathiazepine 1,1-dioxide (1.059 g, 4.64 mmol), and 1,1'-(Azodicarbonyl)dipiperidine (2.341 g, 9.28 mmol) in tetrahydrofuran (THF) (35 mL) was added tri-n-butylphosphine (2.289 mL, 9.28 mmol). The reaction mixture was stirred under argon at ambient temperature for 19 h. The reaction mixture was diluted with H$_2$O (25 mL) and extracted with EtOAc (3×25 mL). The combined organic fractions were dried over MgSO$_4$, filtered, and concentrated to afford the crude product. The residue was purified by flash chromatography eluting with 0-100% EtOAc/hexanes to provide the title compound. (1.89 g, 3.56 mmol, 77% yield) LC/MS m/z=534 (M+H)$^+$, 1.16 min (ret time).

Isomers of 3-(4-Cyano-2-methylphenyl)-3-(3-(((R)-4-ethyl-1,1-dioxido-3,4-dihydro-2H-pyrido[2,3-b][1,4,5]oxathiazepin-2-yl)methyl)-4-methylphenyl)propanoic Acid

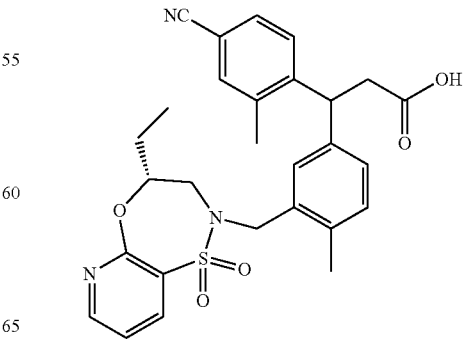

To a solution of methyl 3-(4-cyano-2-methylphenyl)-3-(3-(((R)-4-ethyl-1,1-dioxido-3,4-dihydro-2H-pyrido[2,3-b][1,4,5]oxathiazepin-2-yl)methyl)-4-methylphenyl)propanoate (1.8972 g, 3.56 mmol) in methanol (50 mL) was added 2M LiOH (10.67 mL, 21.33 mmol). The reaction mixture was stirred at ambient temperature for 19 h. The reaction mixture was concentrated under reduced pressure, and diluted with H₂O (20 mL). To the reaction mixture was added 1N HCl (about 12 mL) until acidic pH obtained. The reaction mixture was extracted with EtOAc (3×30 mL). The combined organic layer was dried over MgSO₄, filtered and concentrated under reduced pressure. The residue was purified by reverse phase preparative HPLC under trifluoroacetic acid conditions to provide the title compound as a racemate. The compound was resolved by chiral SFC (Column: Chiralpak AD 20×250 mm, 5 u; Co-solvent: 20% EtOH; Flowrate: 50 g/min; Back pressure: 100Bar) to provide Isomer 1 of 3-(4-cyano-2-methylphenyl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid (0.384 g, 20% yield). LCMS m/z=520 (M+H)⁺, 1.01 min (ret. time), (chiral SFC ret. time: 5.51 min) and Isomer 2 of 3-(4-cyano-2-methylphenyl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid (0.397 g, 21% yield). LCMS m/z=520 (M+H)⁺, 1.02 min (ret. time), (chiral SFC ret. time: 8.85 min).

Isomer of 3-(4-Cyano-2-methylphenyl)-3-(3-(((R)-4-ethyl-1,1-dioxido-3,4-dihydro-2H-pyrido[2,3-b][1,4,5]oxathiazepin-2-yl)methyl)-4-methylphenyl)-N-(pyridin-3-yl)propanamide

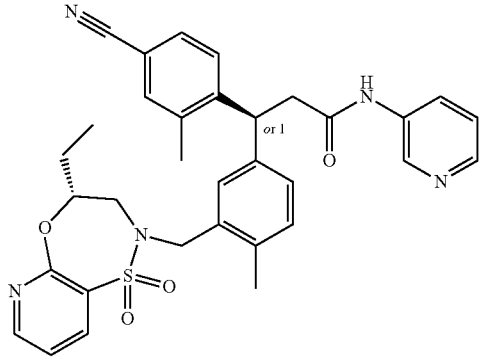 [SMILES: CC[C@@H]1CN(Cc2cc([C@H](CC(=O)Nc3cccnc3)c3ccc(C#N)cc3C)ccc2C)S(=O)(=O)c2cccnc2O1]

To a solution of Isomer 1 of 3-(4-cyano-2-methylphenyl)-3-(3-(((R)-4-ethyl-1,1-dioxido-3,4-dihydro-2H-pyrido[2,3-b][1,4,5]oxathiazepin-2-yl)methyl)-4-methylphenyl)propanoic acid (40.31 mg, 0.078 mmol) in N,N-dimethylformamide (DMF) (3 mL) in a 20 ml vial was added HATU (29.5 mg, 0.078 mmol) and DIEA (0.041 mL, 0.233 mmol). The reaction was stirred for 10 min after which 3-aminopyridine (8.76 mg, 0.093 mmol) was added and stirred at ambient temperature for 3 h. The solvent was concentrated and the residue was purified by reverse phase preparative HPLC under formic acid conditions to provide the title compound (0.039 g, 86% yield, 100% pure). LC/MS m/z=596 (M+H)⁺, 0.85 min (ret. time).

Example 70

3-(4-Cyano-2-methylphenyl)-3-(4-methyl-3-((4-methyl-1,1-dioxido-8-(trifluoromethyl)-4,5-dihydrobenzo[f][1,2]thiazepin-2(3H)-yl)methyl)phenyl)-N-(pyridin-3-yl)propanamide

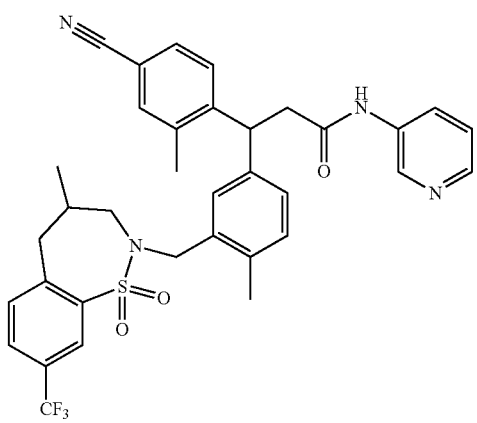 [SMILES: Cc1ccc(C(CC(=O)Nc2cccnc2)c2ccc(C#N)cc2C)cc1CN1CC(C)Cc2ccc(C(F)(F)F)cc2S1(=O)=O]

Methyl 3-(4-cyano-2-methylphenyl)-3-(4-methyl-3-((4-methyl-1,1-dioxido-8-(trifluoromethyl)-4,5-dihydrobenzo[f][1,2]thiazepin-2(3H)-yl)methyl)phenyl)propanoate

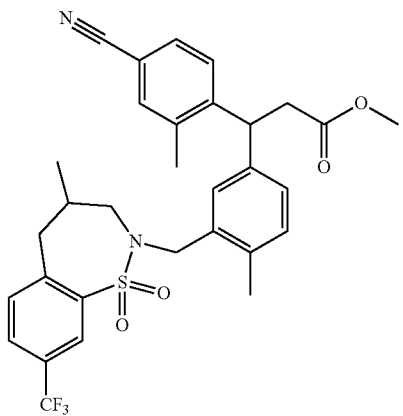 [SMILES: COC(=O)CC(c1ccc(C)c(CN2CC(C)Cc3ccc(C(F)(F)F)cc3S2(=O)=O)c1)c1ccc(C#N)cc1C]

To a solution of methyl 3-(4-cyano-2-methylphenyl)-3-(3-(hydroxymethyl)-4-methylphenyl)propanoate (80 mg, 0.247 mmol), 4-methyl-8-(trifluoromethyl)-2,3,4,5-tetrahydrobenzo[f][1,2]thiazepine 1,1-dioxide (69.1 mg, 0.247 mmol), and 1,1'-(Azodicarbonyl)dipiperidine (125 mg, 0.495 mmol) in tetrahydrofuran (THF) (3 mL) was added tri-n-butylphosphine (0.122 mL, 0.495 mmol). The reaction mixture was stirred under argon at ambient temperature for 17 h. Solvent was concentrated and the crude product was purified by reverse phase preparative HPLC under neutral conditions to provide the title compound (91.0 mg, 0.156 mmol, 62.9% yield). LC/MS m/z=585 (M+H)⁺, 1.38 min (ret. time).

3-(4-Cyano-2-methylphenyl)-3-(4-methyl-3-((4-methyl-1,1-dioxido-8-(trifluoromethyl)-4,5-dihydrobenzo[f][1,2]thiazepin-2(3H)-yl)methyl)phenyl)propanoic Acid

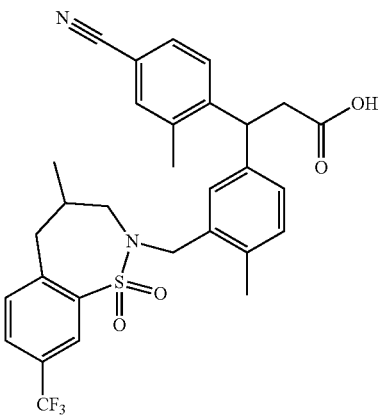 [SMILES: Cc1ccc(C(CC(=O)O)c2ccc(C#N)cc2C)cc1CN1CC(C)Cc2ccc(C(F)(F)F)cc2S1(=O)=O]

To a solution of methyl 3-(4-cyano-2-methylphenyl)-3-(4-methyl-3-((4-methyl-1,1-dioxido-8-(trifluoromethyl)-4,5-dihydrobenzo[f][1,2]thiazepin-2(3H)-yl)methyl)phenyl)propanoate (82.3 mg, 0.141 mmol) in methanol (3 mL) was added 2M LiOH (0.422 mL, 0.845 mmol). The reaction vessel was heated in a Biotage microwave at high absorption for 1 hr at 80° C. To the reaction was added 1N HCl (1 mL) and DMSO (2 mL). The reaction mixture was concentrated and the crude product was purified by reverse phase preparative HPLC under trifluoroacetic acid conditions to provide the title compound (52.1 mg, 0.091 mmol, 64.9% yield). LC/MS m/z=571 (M+H)$^+$, 1.27 min (ret. time).

3-(4-Cyano-2-methylphenyl)-3-(4-methyl-3-((4-methyl-1,1-dioxido-8-(trifluoromethyl)-4,5-dihydrobenzo[f][1,2]thiazepin-2(3H)-yl)methyl)phenyl)-N-(pyridin-3-yl)propanamide

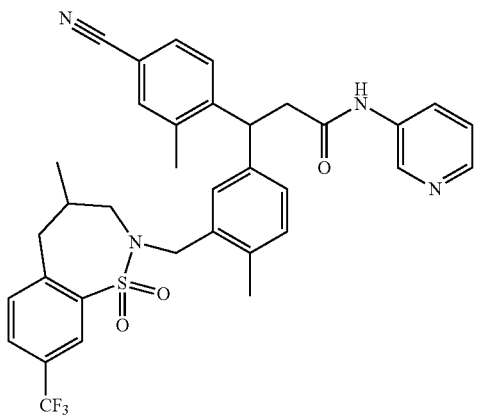 [SMILES: Cc1ccc(C(CC(=O)Nc2cccnc2)c2ccc(C#N)cc2C)cc1CN1CC(C)Cc2ccc(C(F)(F)F)cc2S1(=O)=O]

To a solution of 3-(4-cyano-2-methylphenyl)-3-(4-methyl-3-((4-methyl-1,1-dioxido-8-(trifluoromethyl)-4,5-dihydrobenzo[f][1,2]thiazepin-2(3H)-yl)methyl)phenyl)propanoic acid (29.86 mg, 0.052 mmol) in N,N-dimethylformamide (DMF) (3 mL) in a 20 ml vial was added HATU (19.90 mg, 0.052 mmol) and DIEA (0.027 mL, 0.157 mmol). The reaction was stirred for 10 min after which 3-aminopyridine (5.91 mg, 0.063 mmol) was added and stirred at ambient temperature for 3 h. The solvent was concentrated and the residue was purified by reverse phase preparative HPLC under formic acid conditions to provide the title compound (0.027 g, 82% yield, 100% pure). LC/MS m/z=646 (M+H)$^+$, 1.08 min (ret. time).

Example 71

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1,2,4-thiadiazol-5-yl)propanamide

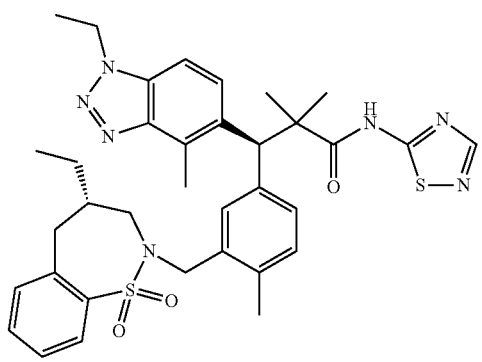 [SMILES: CC[C@H]1Cc2ccccc2S(=O)(=O)N(Cc2cc([C@@H](c3ccc4c(nnn4CC)c3C)C(C)(C)C(=O)Nc3ncns3)ccc2C)C1]

Benzyl (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoate

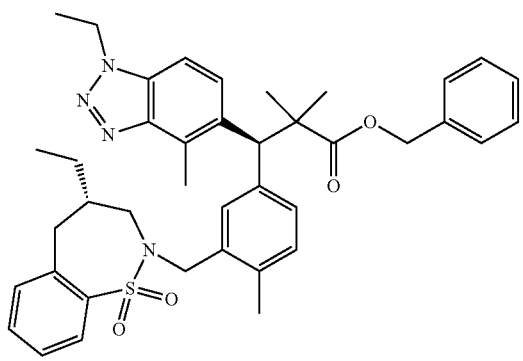 [SMILES: CC[C@H]1Cc2ccccc2S(=O)(=O)N(Cc2cc([C@@H](c3ccc4c(nnn4CC)c3C)C(C)(C)C(=O)OCc3ccccc3)ccc2C)C1]

To a solution benzyl (S)-3-(1-ethyl-4-methyl-1H-benzo[d][1,2,3]triazol-5-yl)-3-(3-(hydroxymethyl)-4-methylphenyl)-2,2-dimethylpropanoate (0.700 g, 1.484 mmol), (S)-4-ethyl-2,3,4,5-tetrahydrobenzo[f][1,2]thiazepine 1,1-dioxide (0.334 g, 1.484 mmol) in tetrahydrofuran (THF) (29.7 ml) in a nitrogen purged 100 ml flask was added (E)-diazene-1,2-diylbis(piperidin-1-ylmethanone) (ADDP) (0.375 g, 1.484 mmol). After all dissolved, the reaction was flushed with nitrogen and tri-n-butylphosphine (0.366 ml, 1.484 mmol) was added and stirred at ambient temperature for 18 h. Additional (S)-4-ethyl-2,3,4,5-tetrahydrobenzo[f][1,2]thiazepine 1,1-dioxide (0.167 g, 0.742 mmol) and (E)-diazene-1,2-diylbis(piperidin-1-ylmethanone) (ADDP) (0.375 g, 1.484 mmol) was added followed by the addition of tri-n-butylphosphine (0.366 ml, 1.484 mmol) and stirred at ambient temperature for 3 days. The solvent was concentrated and the residue was dissolved in EtOAc, washed with water and brine and dried with MgSO$_4$. The solvent was concentrated and the residue was purified by flash chromatography eluting with 0-50% EtOAc/hexanes to provide the title compound. (0.758 g, 75% yield). LC/MS m/z=679 (M+H)$^+$, 1.66 min (ret time).

(S)-3-(3-(((S)-4-Ethyl-1,1-dioxido-4,5-dihydrobenzo [f][1,2]thiazepin-2(3H)-yl)methyl)-4-methylphenyl)-3-(1-ethyl-4-methyl-1H-benzo[d][1,2,3]triazol-5-yl)-2,2-dimethylpropanoic Acid

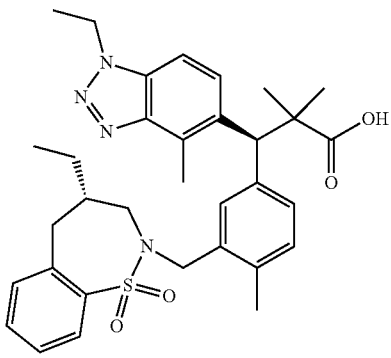 [SMILES: CC[C@H]1Cc2ccccc2S(=O)(=O)N(Cc2cc([C@@H](c3ccc4c(nnn4CC)c3C)C(C)(C)C(=O)O)ccc2C)C1]

A solution of benzyl (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoate (0.758 g, 1.117 mmol) in methanol (48.5 ml) was flushed with nitrogen after which 5% Pd/C (0.238 g, 0.112 mmol) was added to the solution. The flask was evacuated and purged with hydrogen gas and stirred under a hydrogen balloon 18 h. The reaction was filtered through Celite and the solvent was concentrated. The residue was purified by reverse phase preparative HPLC under neutral conditions to provide the title compound (0.038 g, 75% yield, 98% pure). LC/MS m/z=589 (M+H)$^+$, 1.39 min (ret. time).

S)-3-(3-(((S)-4-Ethyl-1,1-dioxido-4,5-dihydrobenzo [f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1,2,4-thiadiazol-5-yl)propanamide

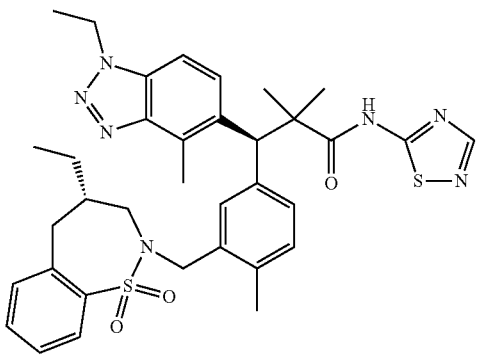 [SMILES: CC[C@H]1Cc2ccccc2S(=O)(=O)N(Cc2cc([C@@H](c3ccc4c(nnn4CC)c3C)C(C)(C)C(=O)Nc3ncns3)ccc2C)C1]

(S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoic acid (0.050 g, 0.085 mmol) was stirred in thionyl chloride (1 ml, 13.70 mmol) in a 20 ml vial for 1 h at ambient temperature. The reaction was concentrated under vacuum and dissolved in dichloroethane and concentrated under vacuum. Repeated process again. The residue was dissolved in 1,2-Dichloroethane (DCE) (4 ml), and 1,2,4-thiadiazol-5-amine (0.013 g, 0.127 mmol) was added followed by DIEA (0.052 ml, 0.297 mmol) and stirred at ambient temperature for 18 h. The solvent was concentrated and the residue was purified by reverse phase preparative HPLC under neutral conditions to provide the title compound (0.011 g, 18% yield, 96% pure). LC/MS m/z=672 (M+H)$^+$, 1.32 min (ret. time).

Example 72

(S)-3-(3-(((S)-4-Ethyl-1,1-dioxido-4,5-dihydrobenzo [f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1-phenyl-1H-tetrazol-5-yl) propanamide

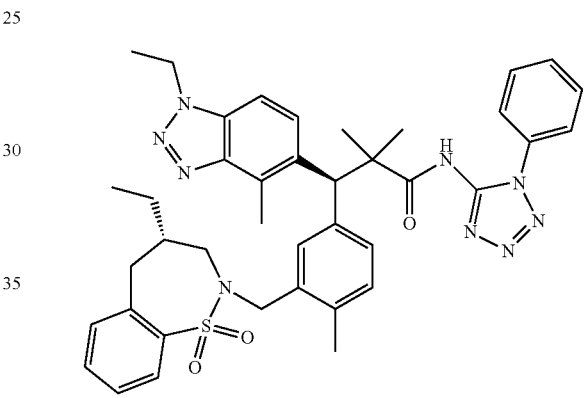

To a dry Biotage 10 ml reaction vial was added (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoic acid (32.9 mg, 0.056 mmol) and 1-(fluoro(pyrrolidin-1-yl)methylene)pyrrolidin-1-ium hexafluorophosphate(V) (BTFFH) (26.5 mg, 0.084 mmol) and dichloromethane (DCM) (1 mL) under argon. DIEA (0.044 mL, 0.251 mmol) was then added and stirred for 30 min. 1-phenyl-1H-tetrazol-5-amine (9 mg, 0.056 mmol) was then added and the vial was sealed and heated to 80° C. in an oil bath for 18 h. Additional 1-phenyl-1H-tetrazol-5-amine (9.00 mg, 0.056 mmol) was added and the reaction heated in oil bath at 100° C. for 18 h. An additional portion of 1-phenyl-1H-tetrazol-5-amine (9.00 mg, 0.056 mmol) was added and heated via microwave at 100° C. for 4 h. The solvent was concentrated and the residue was purified by reverse phase preparative HPLC under neutral conditions to provide the title compound (0.025 g, 61% yield, 100% pure). LC/MS m/z=732 (M+H)$^+$, 1.36 min (ret. time).

The compounds in Table 9 were prepared by a method similar to the one described for the preparation of (S)-3-(3-MS)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1-phenyl-1H-tetrazol-5-yl)propanamide. As is appreciated by those skilled in the art, these analogous examples may involve variations in general reaction conditions.

TABLE 9

| Ex # | Structure | Name | LCMS [M + H] | Retention Time (min) |
|---|---|---|---|---|
| Example 73 | 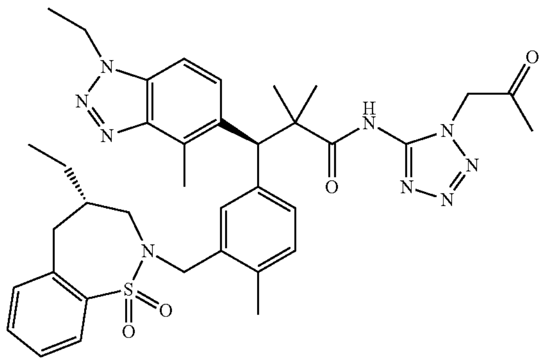 [SMILES: CC[C@H]1Cc2ccccc2S(=O)(=O)N(Cc2cc([C@@H](c3ccc4c(nnn4CC)c3C)C(C)(C)C(=O)Nc3nnnn3CC(C)=O)ccc2C)C1] | (S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1-(2-oxopropyl)-1H-tetrazol-5-yl)propanamide | 712 | 1.32 |
| Example 74 | 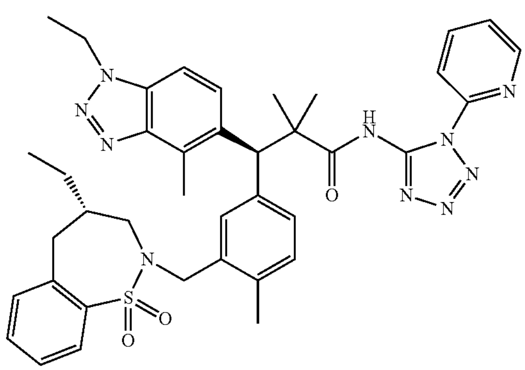 [SMILES: CC[C@H]1Cc2ccccc2S(=O)(=O)N(Cc2cc([C@@H](c3ccc4c(nnn4CC)c3C)C(C)(C)C(=O)Nc3nnnn3-c3ccccn3)ccc2C)C1] | (S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1-(pyridin-2-yl)-1H-tetrazol-5-yl)propanamide | 733 | 1.33 |

Example 75

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1-(thiazol-2-ylmethyl)-1H-tetrazol-5-yl)propanamide

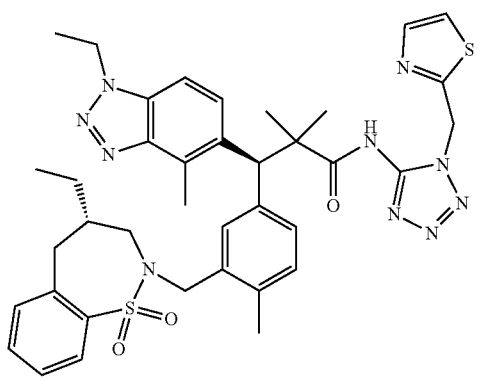 [SMILES: CC[C@H]1Cc2ccccc2S(=O)(=O)N(Cc2cc([C@@H](c3ccc4c(nnn4CC)c3C)C(C)(C)C(=O)Nc3nnnn3Cc3nccs3)ccc2C)C1]

2-((1H-Tetrazol-1-yl)methyl)thiazole

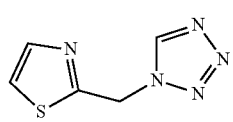 [SMILES: c1csc(Cn2cnnn2)n1]

To a suspension of thiazol-2-ylmethanamine (0.300 g, 2.63 mmol), sodium azide (0.188 g, 2.89 mmol) and triethyl orthoformate (1.313 ml, 7.88 mmol) was added acetic acid (1.051 ml) and the reaction mixture heated to 90° C. for 3 h. Reaction was cooled and diluted with water and extracted with EtOAc (3×). Combined organics were washed with water, brine and dried with $MgSO_4$ and concentrated. The residue was purified by flash chromatography eluting with 0-5% MeOH/MeOH to provide the title compound. (0.220 g, 48% yield, 97% pure). LC/MS m/z=168 (M+H)$^+$, 0.31 min (ret time).

1-(Thiazol-2-ylmethyl)-1H-tetrazol-5-amine

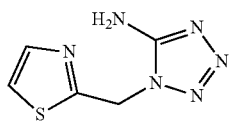 [SMILES: Nc1nnnn1Cc1nccs1]

To a suspension of 2-((1H-tetrazol-1-yl)methyl)thiazole (100 mg, 0.598 mmol), sodium azide (58.3 mg, 0.897 mmol), sodium hydroxide (35.9 mg, 0.897 mmol) and triethylamine (0.167 mL, 1.196 mmol) in Isopropanol (0.20 mL) was added dimethyl sulfoxide (DMSO) (0.50 mL) dropwise and stirred for 10 min until the reaction stopped bubbling. The reaction was then treated with acetic acid (0.103 mL, 1.794 mmol) and then heated to 70° C. for 3 h. The reaction was cooled and diluted with brine. The precipitate was filtered solid and washed with water. The filtrate was diluted with EtOAc and the layers were separated. The organic layer was washed with water. The combined aqueous layers were extracted with EtOAc. The combined organic layers were washed with brine and dried with MgSO$_4$ and the solvent was concentrated to provide the title product (0.079 g, 65% yield, 90% pure). LC/MS m/z=183 (M+H)$^+$, 0.30 min (ret time). which was used without further purification.

Methyl (S)-3-(1-ethyl-4-methyl-1H-benzo[d][1,2,3]triazol-5-yl)-3-(3-(hydroxymethyl)-4-methylphenyl)-2,2-dimethylpropanoate

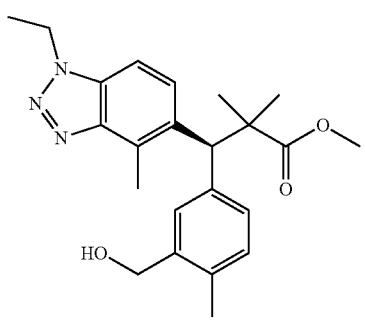 [SMILES: CCn1nnc2c(C)c([C@H](c3ccc(C)c(CO)c3)C(C)(C)C(=O)OC)ccc21]

To a solution of (S)-methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (1.60 g, 2.73 mmol) in acetonitrile (15 mL) and water (1.5 mL) at 0° C. was added ceric ammonium nitrate (2.99 g, 5.46 mmol) and stirred at ambient temperature for 1.5 h. The reaction was diluted with water and extracted with EtOAc (3×). The combined organics were washed with brine and dried with MgSO$_4$. The solvent was concentrated and the residue was purified by flash chromatography eluting with 0-60% EtOAc/hexanes to provide the title compound. (0.662 g, 59% yield, 97% pure) LC/MS m/z=396 (M+H)$^+$, 1.07 min (ret time).

Methyl (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoate

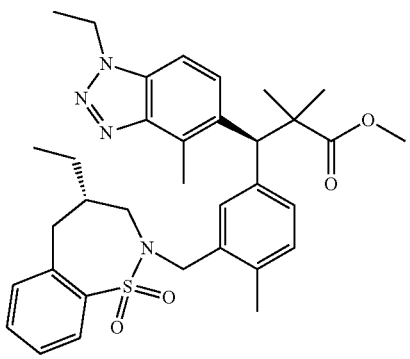 [SMILES: CC[C@H]1Cc2ccccc2S(=O)(=O)N(Cc2cc([C@@H](c3ccc4c(nnn4CC)c3C)C(C)(C)C(=O)OC)ccc2C)C1]

To a solution methyl (S)-3-(1-ethyl-4-methyl-1H-benzo[d][1,2,3]triazol-5-yl)-3-(3-(hydroxymethyl)-4-methylphenyl)-2,2-dimethylpropanoate (0.642 g, 1.623 mmol), (S)-4-ethyl-2,3,4,5-tetrahydrobenzo[f][1,2]thiazepine 1,1-dioxide (0.378 g, 1.678 mmol) in tetrahydrofuran (THF) (32.5 ml) in a nitrogen purged 100 ml flask was added (E)-diazene-1,2-diylbis(piperidin-1-ylmethanone) (ADDP) (0.687 g, 2.72 mmol). After all dissolved, the reaction was flushed with nitrogen and tri-n-butylphosphine (0.672 ml, 2.72 mmol) was added and stirred at ambient temperature for 18 h. The solvent was concentrated and the residue was dissolved in EtOAc/water. The aqueous layer was extracted with EtOAc (3×). The combined organics were washed with water, brine and dried with MgSO$_4$, and concentrated. The residue was purified by flash chromatography eluting with 0-50% EtOAc/hexanes to provide the title compound. (0.764 g, 78% yield, 100% pure) LC/MS m/z=603 (M+H)$^+$, 1.44 min (ret time).

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoic Acid

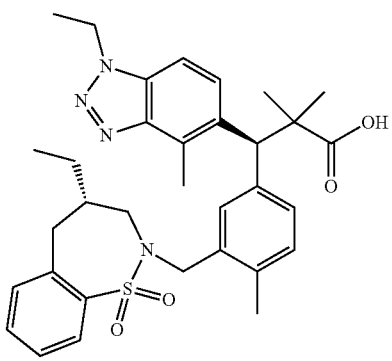 [SMILES: CC[C@H]1Cc2ccccc2S(=O)(=O)N(Cc2cc([C@@H](c3ccc4c(nnn4CC)c3C)C(C)(C)C(=O)O)ccc2C)C1]

This reaction was split equally between two 20 ml microwave reaction vessels. Reaction conditions were identical. To a solution methyl (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoate (0.764 g, 1.267 mmol), in tetrahydrofuran (THF) (10 mL), methanol (10.00 mL) and water (5.00 mL) in a 20 ml microwave reaction vessel, was added LiOH (0.152 g, 6.34 mmol). The reaction was heated via microwave at 120° C. for 4 h. Both reactions were combined and the solvents were concentrated to dryness. The residue was dissolved in acetonitrile and acidified with formic acid. The crude compound was purified by reverse phase preparative HPLC under neutral conditions to provide the title compound (0.670 g, 90% yield, 100% pure). LC/MS m/z=589 (M+H)$^+$, 1.28 min (ret. time).

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(1-(thiazol-2-ylmethyl)-1H-tetrazol-5-yl)propanamide

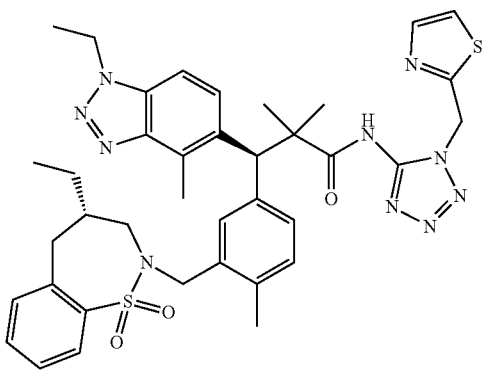 [SMILES: CC[C@H]1Cc2ccccc2S(=O)(=O)N(Cc2cc([C@@H](c3ccc4c(nnn4CC)c3C)C(C)(C)C(=O)Nc3nnnn3Cc3nccs3)ccc2C)C1]

To a dry Biotage 10 ml reaction vial was added (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoic acid (0.050 g, 0.085 mmol) and 1-(fluoro(pyrrolidin-1-yl)methylene)pyrrolidin-1-ium hexafluorophosphate(V) (BTFFH) (0.040 g, 0.127 mmol) and dichloromethane (DCM) (1 mL) under argon. DIEA (0.044 mL, 0.255 mmol) was then added and stirred for 30 min. Additional 1-(thiazol-2-ylmethyl)-1H-tetrazol-5-amine (0.019 g, 0.093 mmol) was added followed by and DBU (6.40 µl, 0.042 mmol) and heated via microwave at 100° C. for 2 h. Additional 1-(thiazol-2-ylmethyl)-1H-tetrazol-5-amine (0.050 g, 0.274 mmol) was added and heated via microwave at 100° C. for 16 h. The solvent was concentrated and the residue was purified by reverse phase preparative HPLC under neutral conditions. The still impure product was purified by chiral HPLC using a Chromega Chiral CC4, 20×250 mm, 5 u column eluting with 40% EtOH/Heptane, to provide the title compound. (0.010 g, 15% yield, 100% pure). LC/MS m/z=752 (M+H)$^+$, 1.29 min (ret. time).

Example 76

2-(5-((S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanamido)-1H-tetrazol-1-yl)acetic Acid

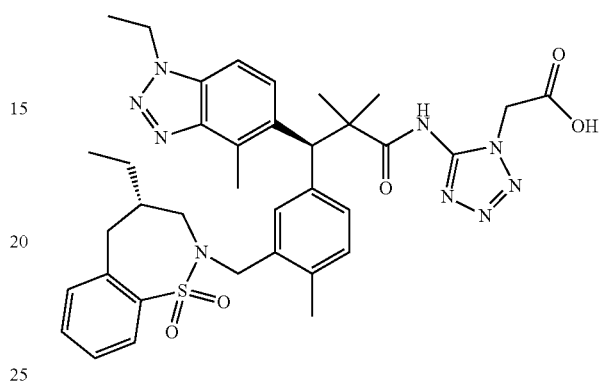

To a dry Biotage 10 ml reaction vial was added (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoic acid (0.161 g, 0.273 mmol) and 1-(fluoro(pyrrolidin-1-yl)methylene)pyrrolidin-1-ium hexafluorophosphate(V) (BTFFH) (0.130 g, 0.410 mmol) and dichloromethane (DCM) (6 mL) under nitrogen. DIEA (0.215 mL, 1.231 mmol) was then added and stirred for 2 h. Ethyl 2-(5-amino-1H-tetrazol-1-yl)acetate (0.094 g, 0.547 mmol) was then added and the vial was sealed and heated via microwave at 100° C. for 2 h. Additional ethyl 2-(5-amino-1H-tetrazol-1-yl)acetate (0.047 g, 0.273 mmol) was added and heated for 1 h at 100° C. The solvent was concentrated, the residue was dissolved in EtOAc and washed with water. Emulsions were broken up with a small amount of 1N HCl. The layers were separated and the organic layer was washed with water and emulsions were again broken up with 1N HCl. The organic layer was washed with brine and dried with MgSO$_4$ and concentrated. The residue was purified by flash chromatography eluting with 0-70% EtOAc/Hexane to provide the title compound mixed with carboxylic acid starting material. Compound mixture was dissolved in 5 ml DCM and to it was added PS-CDI (0.107 g, 0.137 mmol) and stirred for 2 h. The solvent was concentrated and the residue was dissolved in tetrahydrofuran (THF) (2 mL) and water (0.2 mL). LiOH (0.013 g, 0.547 mmol) was added and the reaction heated to 60° C. for 2 h. The reaction was cooled and acidified with formic acid. The solvent was concentrated and the residue was purified by reverse phase preparative HPLC under neutral conditions to provide the title compound (0.010 g, 4.8% yield, 95% pure). LC/MS m/z=742 (M+H)$^+$, 1.23 min (ret. time).

Example 77

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1H-tetrazole-5-carboxamide, Trifluoroacetic Acid Salt

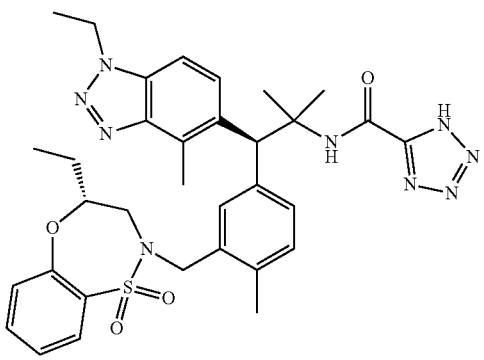 [SMILES: CC[C@@H]1CN(Cc2cc([C@@H](c3ccc4c(nnn4CC)c3C)C(C)(C)NC(=O)c3nnn[nH]3)ccc2C)S(=O)(=O)c2ccccc2O1]

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic Acid

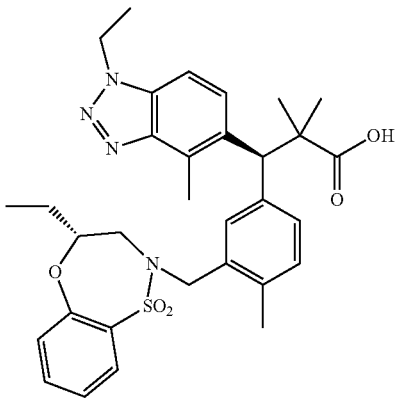 [SMILES: CC[C@@H]1CN(Cc2cc([C@@H](c3ccc4c(nnn4CC)c3C)C(C)(C)C(=O)O)ccc2C)S(=O)(=O)c2ccccc2O1]

To a solution of methyl (S)-3-(1-ethyl-4-methyl-1H-benzo[d][1,2,3]triazol-5-yl)-3-(3-(hydroxymethyl)-4-methylphenyl)-2,2-dimethylpropanoate (1.75 g, 4.42 mmol) in tetrahydrofuran (THF) (40 mL), were added (R)-4-ethyl-3,4-dihydro-2H-benzo[b][1,4,5]oxathiazepine 1,1-dioxide (1.106 g, 4.87 mmol) and (E)-diazene-1,2-diylbis (piperidin-1-ylmethanone) (2.233 g, 8.85 mmol), followed by tributylphosphane (2.210 mL, 8.85 mmol) was added. The reaction mixture was stirred at ambient temperature for 16 h. The solvent was evaporated. The crude product was purified by flash chromatography eluting with ethyl acetate/hexane to get methyl (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoate (2.5 g, 4.13 mmol, 93% yield). The intermediate methyl ester was dissolved in methanol (15.00 mL), and treated with LiOH (22.12 mL, 44.2 mmol). The reaction mixture was heated via microwave at 120° C. for 3 h. The solvent was evaporated. The residue was partitioned between ethyl acetate and 1N HCl. The aqueous layer was extracted with ethyl acetate (3×). The combined organic phases were dried over MgSO$_4$ and concentrated. The residue was purified by flash chromatography eluting with ethyl acetate/hexane to obtain the title compound (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (2.2 g, 3.72 mmol, 84% yield). LC-MS m/z=591.4 (M+H)$^+$, 1.23 min (ret. time).

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoyl Azide

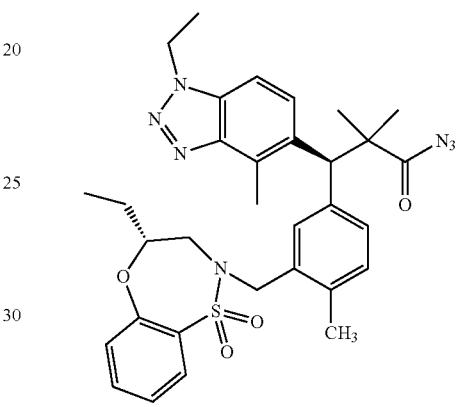

To a stirred solution of (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (1.6239 g, 2.75 mmol) and triethylamine (1.149 mL, 8.25 mmol) in toluene (10 mL) was added diphenyl phosphorazidate (0.889 mL, 4.12 mmol). The reaction was stirred at ambient temperature for 90 minutes. The reaction mixture was then concentrated to dryness and purified via flash chromatography to give the desired product (1.3560 g, 2.202 mmol, 80% yield). LCMS m/z=616.5 (M+H)$^+$, 1.42 min (ret. time).

(R)-2-(5-((S)-2-Amino-1-(1-ethyl-4-methyl-1H-benzo[d][1,2,3]triazol-5-yl)-2-methylpropyl)-2-methylbenzyl)-4-ethyl-3,4-dihydro-2H-benzo[b][1,4,5]oxathiazepine 1,1-dioxide

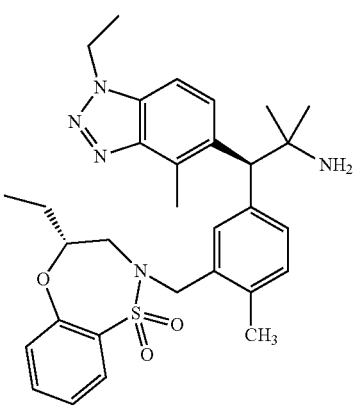 [SMILES: CC[C@@H]1CN(Cc2cc([C@@H](c3ccc4c(nnn4CC)c3C)C(C)(C)N)ccc2C)S(=O)(=O)c2ccccc2O1]

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoyl azide (1.3558 g, 2.202 mmol) was stirred in toluene (8 mL) and heated to 80° C. for 1 h. The reaction mixture was concentrated to dryness, dissolved in acetonitrile (8.00 mL) and 4M HCl in 1,4 dioxane (4.40 mL, 17.61 mmol) was added. The reaction was allowed to stir at ambient temperature for 26 h. The reaction mixture was then diluted with EtOAc and washed with a saturated solution of sodium bicarbonate. The aqueous phase was then extracted with EtOAc (2×). The combined organic layers were dried over sodium sulfate, filtered, and concentrated. The residue was purified via preparative HPLC under formic acid conditions to give the title compound. (691.1 mg, 1.230 mmol, 55.9% yield). LCMS m/z=562.6 (M+H)+, 0.84 min (ret. time).

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1H-tetrazole-5-carboxamide, Trifluoroacetic Acid Salt

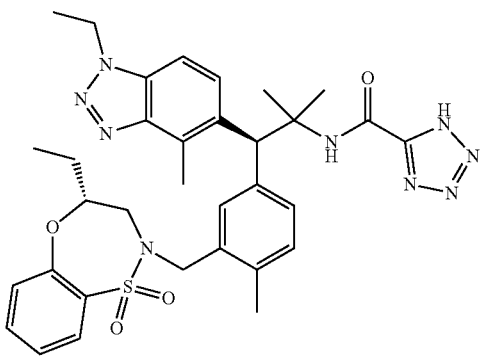 [SMILES: CC[C@@H]1CN(Cc2cc([C@@H](c3ccc4c(nnn4CC)c3C)C(C)(C)NC(=O)c3nnn[nH]3)ccc2C)S(=O)(=O)c2ccccc2O1]

To a solution of (R)-2-(5-((S)-2-amino-1-(1-ethyl-4-methyl-1H-benzo[d][1,2,3]triazol-5-yl)-2-methylpropyl)-2-methylbenzyl)-4-ethyl-3,4-dihydro-2H-benzo[b][1,4,5]oxathiazepine 1,1-dioxide (0.032 g, 0.057 mmol), 1H-tetrazole-5-carboxylic acid (8.45 mg, 0.074 mmol) and HATU (0.026 g, 0.068 mmol) in N,N-dimethylformamide (DMF) (2 mL) was added DIEA (0.030 mL, 0.171 mmol) and stirred at ambient temperature for 5 h. Additional 1H-tetrazole-5-carboxylic acid (8.45 mg, 0.074 mmol) and HATU (0.026 g, 0.068 mmol) was added and stirred for 18 h. The solvent was concentrated and the residue was purified by reverse phase preparative HPLC under trifluoroacetic acid conditions to provide the title compound (0.005 g, 11% yield, 98% pure). LC/MS m/z=658 (M+H)+, 1.27 min (ret. time).

Example 78

N—((S)-1-(3-(((S)-4-Ethyl-1,1-dioxido-8-(trifluoromethyl)-4,5-dihydrobenzo[f][1,2]thiazepin-2(3H)-yl)methyl)-4-methylphenyl)-1-(1-ethyl-4-methyl-1H-benzo[d][1,2,3]triazol-5-yl)-2-methylpropan-2-yl)-2-(1H-tetrazol-5-yl)acetamide

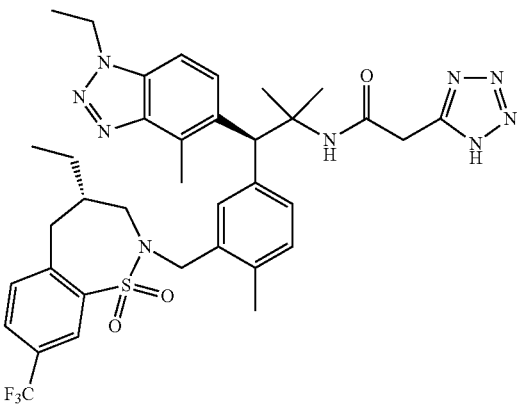 [SMILES: CC[C@H]1Cc2ccc(C(F)(F)F)cc2S(=O)(=O)N(Cc2cc([C@@H](c3ccc4c(nnn4CC)c3C)C(C)(C)NC(=O)Cc3nnn[nH]3)ccc2C)C1]

Ethyl 3-(3-(hydroxymethyl)-4-methylphenyl)-3-(7-methoxy-1-methyl-1H-benzo[d][1,2,3]triazol-5-yl)propanoate

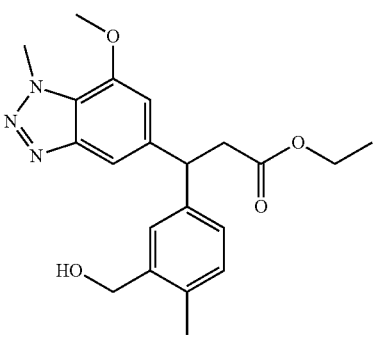 [SMILES: CCOC(=O)CC(c1ccc(C)c(CO)c1)c1cc(OC)c2c(c1)nnn2C]

Ethyl 3-(3-(hydroxymethyl)-4-methylphenyl)-3-(7-methoxy-1-methyl-1H-benzo[d][1,2,3]triazol-5-yl)propanoate of the invention was made using compounds described in WO 2015/092713, Example 145, published Jun. 25, 2015, and incorporated herein by reference.

Ethyl 3-(7-methoxy-1-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoate

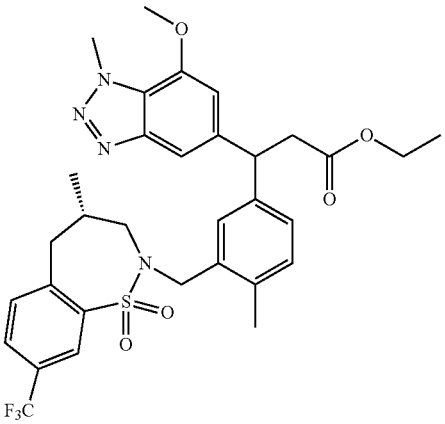 [SMILES: CCOC(=O)CC(c1ccc(C)c(CN2C[C@@H](C)Cc3ccc(C(F)(F)F)cc3S2(=O)=O)c1)c1cc(OC)c2c(c1)nnn2C]

To a solution of ethyl 3-(3-(hydroxymethyl)-4-methylphenyl)-3-(7-methoxy-1-methyl-1H-benzo[d][1,2,3]triazol-5-yl)propanoate (0.080 g, 0.209 mmol), (S)-4-methyl-8-(trifluoromethyl)-2,3,4,5-tetrahydrobenzo[f][1,2]thiazepine 1,1-dioxide (0.067 g, 0.240 mmol), and (E)-diazene-1,2-diylbis (piperidin-1-ylmethanone) (0.069 g, 0.273 mmol) in tetrahydrofuran (THF) (2 mL) at ambient temperature was added tributylphosphane (0.062 ml, 0.251 mmol). After 17 hrs the reaction mixture purified by flash chromatography eluting with 0-85% EtOAc/Hexane to give the title compound. (0.101 g 75% yield), $^1$H NMR (400 MHz, CHLOROFORM-d) δ ppm 0.68-0.94 (m, 3H) 1.09-1.21 (m, 3H) 1.68-1.80 (m, 2H) 2.30 (s, 3H) 2.65-2.93 (m, 2H) 2.96-3.19 (m, 2H) 3.42-3.55 (m, 2H) 3.68 (br s, 1H) 3.90 (d, J=2.51 Hz, 3H) 4.05 (q, J=7.28 Hz, 2H) 4.41 (s, 3H) 4.54-4.72 (m, 1H) 6.56 (d, J=6.27 Hz, 1H) 6.97-7.22 (m, 3H) 7.41-7.53 (m, 2H) 7.67-7.81 (m, 1H) 8.18-8.30 (m, 1H)

3-(7-Methoxy-1-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoic Acid

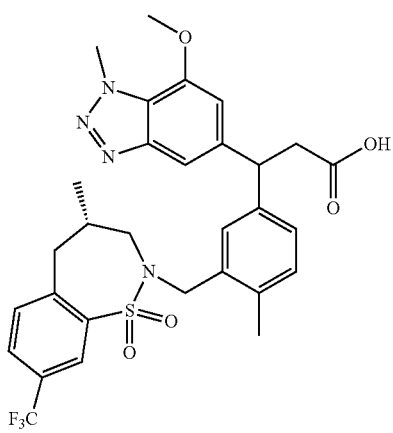 [SMILES: COc1cc(C(CC(=O)O)c2ccc(C)c(CN3C[C@@H](C)Cc4ccc(C(F)(F)F)cc4S3(=O)=O)c2)cc2nnn(C)c12]

To a solution of ethyl 3-(7-methoxy-1-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoate (0.093 g, 0.144 mmol) in tetrahydrofuran (THF) (1 mL) and at ambient temperature was added 1M lithium hydroxide (1.1 mL, 1.100 mmol) followed by methanol (1 ml). After 3 hr 10 min the reaction was quenched via addition of 1N HCl to pH 1-3 and extracted with ethyl acetate (2×). The combined organics were washed with saturated sodium bicarbonate solution (2×) and an emulsion formed. The organic phase was acidified with 1N HCl to pH~1, dried over magnesium sulfate and concentrated to give 0.093 g of a clear, colorless oil. This was taken into acetonitrile and water and lyophilized to give the title compound (0.086 g, 97% yield, 90% pure), LC/MS m/z=617 (M+H)$^+$, 1.23 min (ret. time).

(S)-3-(1,4-dimethyl-1H-benzo[d][1,2,3]triazol-5-yl)-3-(3-(((R)-2-ethyl-2,3-dihydropyrido[3,44][1,4]oxazepin-4(5H)-yl)methyl)-4-methylphenyl)-2,2-dimethylpropanoic Acid

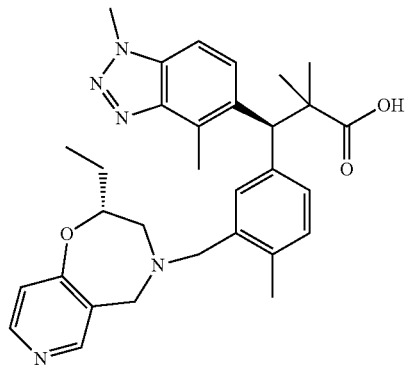 [SMILES: CC[C@@H]1CN(Cc2cc([C@@H](c3ccc4c(nnn4C)c3C)C(C)(C)C(=O)O)ccc2C)Cc2cnccc2O1]

(S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid of the invention was made using compounds described in WO 2016/202253 page 202, published December, 2016, and incorporated herein by reference.

Example 79

(S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(2-(methylamino)ethyl)propanamide

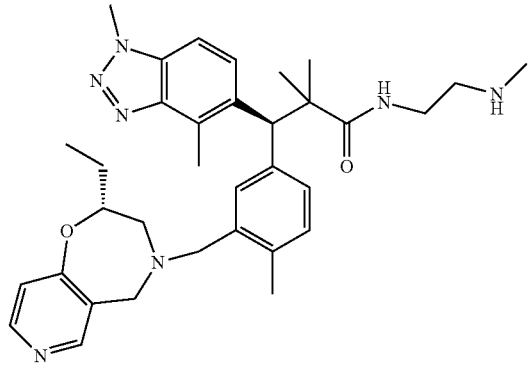 [SMILES: CC[C@@H]1CN(Cc2cc([C@@H](c3ccc4c(nnn4C)c3C)C(C)(C)C(=O)NCCNC)ccc2C)Cc2cnccc2O1]

To a solution of (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (160 mg, 0.303 mmol) in dichloromethane (DCM) (5 mL), HATU (173 mg, 0.455 mmol) and DIEA (0.159 mL, 0.910 mmol) were added. The reaction mixture was stirred at ambient temperature for 16 hrs. The solvent was evaporated. The residue was purified by silica gel chromatography with ethyl acetate and hexane and then was purified by preparative reverse phase HPLC under basic conditions to provide the title compound (S)-3-(1,4-dimethyl-1H-benzo[d][1,2,3]triazol-5-yl)-3-(3-(((R)-2-ethyl-2,3dihydropyrido[3,44][1,4]oxazepin-4(5H)-yl)methyl)-4- methylphenyl)-2,2-dimethyl-N-(2-(methylamino)ethyl) propanamide (10.57 mg, 0.017 mmol, 5.67% yield). LC-MS m/z 584.5 (M+H)$^+$, 0.66 min (ret. time). $^1$H NMR (400 MHz, CHLOROFORM-d) L L ppm 0.95-1.10 (m, 3H) 1.35 (d, J=13.55 Hz, 6H) 1.60-1.75 (m, 1H) 2.26 (s, 3H) 2.47 (br. s., 3H) 2.64 (s, 5H) 2.88 (br. s., 2H) 2.97 (br. s., 2H) 3.40 (br. s., 2H) 3.56 (br. s., 2H) 3.70-3.86 (m, 2H) 3.99 (br. s., 1H) 4.24 (s, 3H) 4.81 (s, 1H) 6.97 (d, J=5.27 Hz, 1H) 7.03-7.10 (m, 1H) 7.18 (br. s., 1H) 7.26-7.38 (m, 3H) 7.67 (d, J=8.78 Hz, 1H) 8.10-8.55 (m, 2H)

Example 80

(S)-3-(3-(((S)-4-Ethyl-1,1-dioxido-4,5-dihydrobenzo [f][1,2]thiazepin-2(3H)-yl)methyl)-4-methylphenyl)-3-(1-ethyl-4-fluoro-1H-benzo[d][1,2,3]triazol-5-yl)-N-(pyridin-3-yl)propanamide

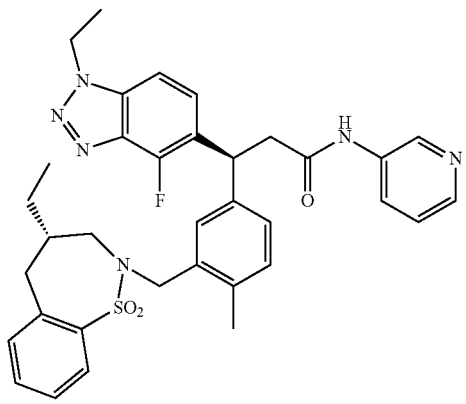 [SMILES: CC[C@H]1Cc2ccccc2S(=O)(=O)N(Cc2cc([C@H](CC(=O)Nc3cccnc3)c3ccc4c(nnn4CC)c3F)ccc2C)C1]

N-Ethyl-3-fluoro-2-nitroaniline

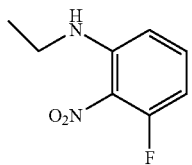

To a solution of 1,3-difluoro-2-nitrobenzene (10 g, 62.9 mmol) in ethanol (300 mL) was added ethanamine (47.2 g, 314 mmol) slowly at 0° C. The reaction mixture was stirred at 0° C. for 0.5 h and then warmed to 25° C. for another 4 h. After removing the solvent, the residue was purified via silica gel chromatography (80 g, PE/EA=5%) to give the title compound (8.0 g, 43.4 mmol, 69.1% yield) as a solid. LC/MS: m/z 185 (M+H)$^+$, 1.70 min (ret. time)

4-Bromo-N-ethyl-3-fluoro-2-nitroaniline

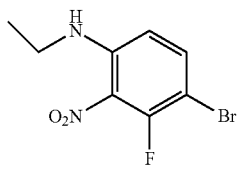

To a solution of N-ethyl-3-fluoro-2-nitroaniline (8.0 g, 43.4 mmol) in DMF (100 mL) at 0° C. was added a solution of N-bromosuccinimide (6.19 g, 34.8 mmol) dropwise. The mixture was stirred at 0° C. for 6 h. The mixture was quenched with water (500 mL) and extracted with ethyl acetate (3×400 mL). The combined organic layer was washed with water (2×100 mL), brine (2×100 mL), dried (Na$_2$SO$_4$) and concentrated. The residue was purified by silica gel chromatography (PE/EA=12%) to give the title compound (8.2 g, 31.2 mmol, 71.8% yield) as yellow oil. LCMS: m/z 263 (M+H)$^+$1.80 min (ret. time)

4-Bromo-N1-ethyl-3-fluorobenzene-1,2-diamine

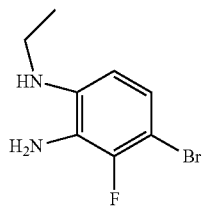

To a solution of 4-bromo-N-ethyl-3-fluoro-2-nitroaniline (8000 mg, 30.4 mmol) in ethanol (100 mL) and 1,2-dichloroethane (DCE) (100 mL) under nitrogen at 0° C. was added Raney nickel (1983 mg, 30.4 mmol, 90% in water) slowly. Hydrazine hydrate (2.237 mL, 45.6 mmol) was added dropwise. The reaction mixture was stirred at 0° C. for 1 h, filtered, and concentrated. The residue was purified by silica gel chromatography (hexane:ethyl acetate=4:1) to give the title compound (6500 mg, 27.9 mmol, 92% yield). LC-MS m/z 233.0 (M+H)$^+$1.90 (ret. time)

5-Bromo-1-ethyl-4-fluoro-1H-benzo[d][1,2,3]triazole

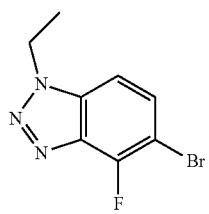

A stirred suspension of 4-bromo-N1-ethyl-3-fluorobenzene-1,2-diamine (6.5 g, 27.9 mmol) and sulfuric acid (5.95 mL, 112 mmol) in water (300 mL) at 0° C. was treated with a solution of sodium nitrite (2.89 g, 41.8 mmol) in water (50 mL). The mixture was stirred at 0° C. for 2 h. The mixture at 0° C. was basified to pH 8 using 2 N NaOH and extracted with DCM (3×200 mL). The combined organics were washed with water (2×80 mL), brine (2×80 mL), dried (Na$_2$SO$_4$) and concentrated. The residue was purified by silica gel chromatography (120 g, PE/EA=60%) to give the title compound (5.2 g, 21.31 mmol, 76% yield) as a colorless oil. LCMS: m/z 243.9 (M+H)$^+$1.63 min (ret. time)

229

(E)-Benzyl 3-(1-ethyl-4-fluoro-1H-benzo[d][1,2,3]triazol-5-yl)acrylate

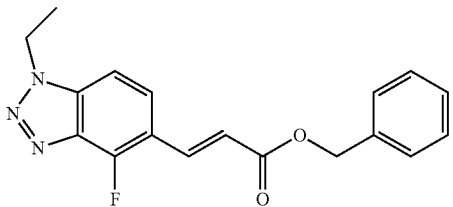

A mixture of 5-bromo-1-ethyl-4-fluoro-1H-benzo[d][1,2,3]triazole (5.2 g, 21.31 mmol), benzyl acrylate (6.91 g, 42.6 mmol), diacetoxypalladium (0.239 g, 1.065 mmol), tri-otolylphosphine (0.648 g, 2.131 mmol) and triethylamine (14.85 ml, 107 mmol) was heated to 120° C. for 6 h under N2. The reaction mixture was quenched with 200 mL ethyl acetate, and then washed with water (3×100 mL). The organics were dried over $Na_2SO_4$ and the solvent was removed. The residue was purified by silica gel chromatography (120 g, eluted with PE:EA=2:1-1:1) to give the title compound (2.7 g, 8.30 mmol, 39.0% yield) as a solid. LCMS m/z 326.3 $(M+H)^+$, 2.02 min (ret. time)

Benzyl 3-(1-ethyl-4-fluoro-1H-benzo[d][1,2,3]triazol-5-yl)-3-(3-(hydroxymethyl)-4-methyl phenyl)propanoate

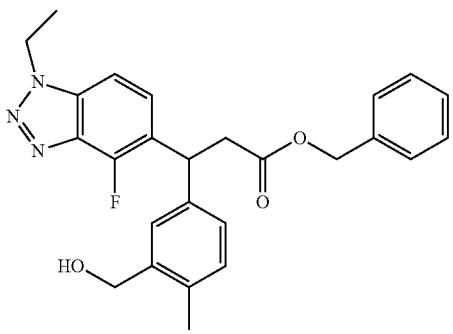 [SMILES: CCn1nnc2c(F)c(C(CC(=O)OCc3ccccc3)c3ccc(C)c(CO)c3)ccc21]

To a solution of (E)-benzyl 3-(1-ethyl-4-fluoro-1H-benzo[d][1,2,3]triazol-5-yl)acrylate (2.7 g, 8.30 mmol) in dioxane (40 mL) and water (20 mL) was added (2-methyl-5-(4,4,5,5-tetramethyl-1,3,2-dioxaborolan-2-yl)phenyl)methanol (6.18 g, 24.90 mmol) and TEA (3.47 mL, 24.90 mmol). The reaction was stirred for 5 min, then chloro(1,5-cyclooctadiene)rhodium(I) dimer (0.205 g, 0.415 mmol) was added under nitrogen. The reaction mixture was stirred at 90° C. for 16 h. The solvent was removed and the residue was purified by silica gel chromatography (PE:EtOAc=6:1) to give title compound (2.0 g, 4.47 mmol, 53.9% yield) as a yellow oil. LC-MS m/z 448.1 (M+18)+, 2.10 (ret. time)

230

(S)-Benzyl 3-(1-ethyl-4-fluoro-1H-benzo[d][1,2,3]triazol-5-yl)-3-(3-(hydroxymethyl)-4-methylphenyl)propanoate and (R)-benzyl 3-(1-ethyl-4-fluoro-1H-benzo[d][1,2,3]triazol-5-yl)-3-(3-(hydroxymethyl)-4-methylphenyl)propanoate

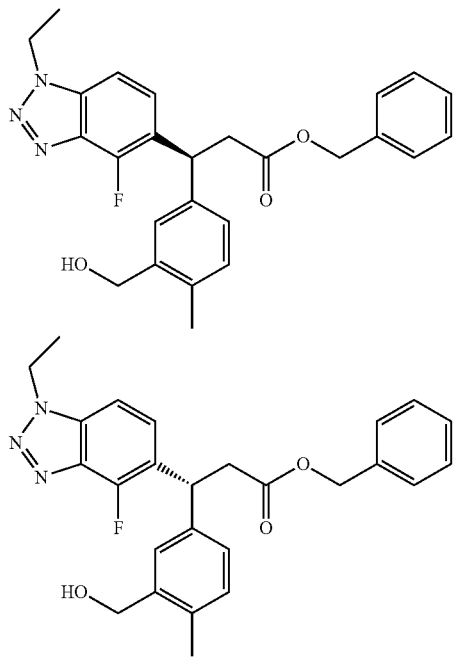

Benzyl 3-(1-ethyl-4-fluoro-1H-benzo[d][1,2,3]triazol-5-yl)-3-(3-(hydroxymethyl)-4-methylphenyl)propanoate (2 g, 4.47 mmol) was separated by Chiral SFC (Column: AS-H 20*250 mm, 5 um; Co-solvent: $CO_2$/MeOH (0.1DEA)=85/15; Flowrate: 80 g/min; Back pressure: 100Bar) to give (S)-benzyl 3-(1-ethyl-4-fluoro-1H-benzo[d][1,2,3]triazol-5-yl)-3-(3-(hydroxymethyl)-4-methylphenyl)propanoate (0.9 g, 2.011 mmol, 45%) (chiral SFC ret. time: 2.4 min). LCMS m/z 448.1 $(M+H)^+$, 1.69 (ret. time) and (R)-benzyl 3-(1-ethyl-4-fluoro-1H-benzo[d][1,2,3]triazol-5-yl)-3-(3-(hydroxymethyl)-4-methylphenyl)propanoate (0.8 g, 1.788 mmol, 40%) (chiral SFC ret. time: 5.43 min) LCMS m/z 448.1 $(M+H)^+$, 1.69 (ret. time)

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)propanoic Acid

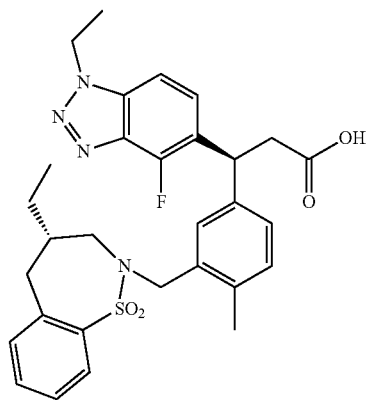 [SMILES: CC[C@H]1Cc2ccccc2S(=O)(=O)N(Cc2cc([C@H](CC(=O)O)c3ccc4c(nnn4CC)c3F)ccc2C)C1]

To a solution of benzyl (S)-3-(1-ethyl-4-fluoro-1H-benzo[d][1,2,3]triazol-5-yl)-3-(3-(hydroxymethyl)-4-methylphenyl)propanoate (535 mg, 1.196 mmol) in tetrahydrofuran (THF) (20 mL), (S)-4-Ethyl-2,3,4,5-tetrahydrobenzo[f][1,2]thiazepine 1,1-dioxide (323 mg, 1.435 mmol), (E)-diazene-1,2-diylbis(piperidin-1-ylmethanone) (603 mg, 2.391 mmol) and tributylphosphane (0.597 mL, 2.391 mmol) were added. The reaction mixture was stirred at ambient temperature for 1 hr. The solvent was evaporated. The crude product was purified by silica gel chromatography with ethyl acetate and hexane to obtain benzyl (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)propanoate (598 mg, 0.914 mmol, 76% yield). To this product in a mixture of methanol (5.00 mL) and tetrahydrofuran (THF) (10.00 mL), LiOH (5.98 mL, 11.96 mmol, 2 M) was added. The reaction mixture was stirred at ambient temperature for 16 hrs. The solvent was evaporated, the residue was partitioned between 1N HCl and ethyl acetate. The water layer was extracted with ethyl acetate (2×). The combined organic phase was dried over MgSO4 and concentrated. The crude product was purified by preparative reverse phase HPLC under acidic (formic acid) to provide the title compound (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4fluoro1Hbenzo[d][1,2,3]triazol-5-yl)propanoic acid (481 mg, 0.852 mmol, 71.3% yield). LC-MS m/z 563.3 (M+H)+, 1.21 min (ret. Time). $^1$H NMR (400 MHz, DMSO-d6) δ ppm 0.60-0.84 (m, 3H) 0.95-1.29 (m, 2H) 1.49 (t, J=7.15 Hz, 3H) 1.82 (br. s., 1H) 2.23 (s, 3H) 2.69-2.99 (m, 2H) 3.06-3.16 (m, 2H) 3.15-3.23 (m, 1H) 3.42-3.64 (m, 2H) 4.27 (d, J=13.80 Hz, 1H) 4.65-4.91 (m, 3H) 7.02-7.32 (m, 3H) 7.38-7.72 (m, 5H) 7.84 (d, J=7.78 Hz, 1H) 12.18 (br. s., 1H)

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)-N-(pyridin-3-yl)propanamide

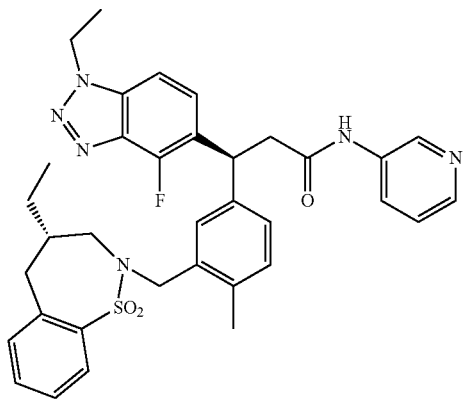 [SMILES: CC[C@H]1Cc2ccccc2S(=O)(=O)N(Cc2cc([C@H](CC(=O)Nc3cccnc3)c3ccc4c(nnn4CC)c3F)ccc2C)C1]

To a solution of (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)propanoic acid (126 mg, 0.223 mmol) in N,N-dimethylformamide (DMF) (2 mL), HATU (85 mg, 0.223 mmol) and DIEA (0.117 mL, 0.669 mmol) were added. After 10 min, pyridin-3-amine (25.2 mg, 0.268 mmol) was added. The reaction mixture was stirred at ambient temperature for 2 hrs then the reaction mixture was partitioned between ethyl acetate and water. The water layer was extracted with ethyl acetate (2×). The combined organic phase was dried over MgSO4 and concentrated. The crude product was purified by preparative reverse phase HPLC under neutral conditions to provide the title compound (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)-N-(pyridin-3-yl)propanamide (88.3 mg, 0.138 mmol, 61.8% yield). LC-MS m/z 641.4 (M+H)+, 0.96 min (ret. Time). $^1$H NMR (400 MHz, METHANOL-d4) δ ppm 0.58-0.77 (m, 3H) 0.97-1.23 (m, 2H) 1.60 (t, J=7.15 Hz, 4H) 2.05 (s, 1H) 2.27 (s, 3H) 2.86 (br.s., 2H) 3.23 (s, 1H) 3.40 (br. s., 2H) 3.46-3.69 (m, 2H) 4.38 (d, J=14.05 Hz, 1H) 4.74 (q, J=7.28 Hz, 2H) 5.13 (t, J=8.03 Hz, 1H) 7.11-7.49 (m, 6H) 7.51-7.65 (m, 3H) 7.84-8.08 (m, 2H) 8.22 (d, J=4.02 Hz, 1H) 8.52-8.72 (m, 1H)

Example 81

(S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)-N-(2-(methylamino)ethyl)propanamide

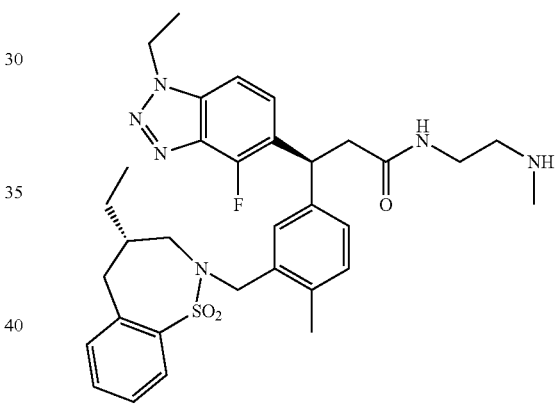

To a solution of(S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)propanoic acid (126 mg, 0.223 mmol) in N,N-dimethylformamide (DMF) (2 mL), HATU (85 mg, 0.223 mmol) and DIEA (0.117 mL, 0.669 mmol) were added. After 10 mins, N1-methylethane-1,2-diamine (0.023 mL, 0.268 mmol) was added. The reaction mixture was stirred at ambient temperature for 1 hr. The reaction mixture was partitioned between ethyl acetate and water. The water layer was extracted with ethyl acetate 2×. The combined organic phase was dried over MgSO4 and concentrated. The crude product was purified by preparative reverse phase HPLC under basic conditions to afford the title compound (S)-3-(3-(((S)-4-ethyl-1,1-dioxido-4,5-dihydrobenzo[f][1,2]thiazepin-2(3H)-yl)methyl)-4-methylphenyl)-3-(1-ethyl-4-fluoro-1H-benzo[d][1,2,3]triazol-5-yl)-N-(2-(methylamino)ethyl)propanamide (38.7 mg, 0.062 mmol, 27.9% yield). LC-MS m/z 621.4 (M+H)+, 0.86 min (ret. Time). $^1$H NMR (400 MHz, METHANOL-d4) δ ppm 0.67-0.83 (m, 3H) 1.03-1.26 (m, 2H) 1.54-1.81 (m, 4H) 2.16-2.37 (m, 6H) 2.40-2.51 (m, 2H) 2.86 (br. s., 2H) 2.96-3.12 (m, 2H) 3.19 (t, J=6.02 Hz, 2H) 3.37-3.51 (m, 2H) 3.58 (br. s., 2H) 4.38

(d, J=14.05 Hz, 1H) 4.75 (q, J=7.11 Hz, 2H) 5.01 (t, J=8.16 Hz, 1H) 7.08-7.31 (m, 3H) 7.38-7.48 (m, 2H) 7.49-7.64 (m, 3H) 7.91 (d, J=7.78 Hz, 1H)

Example 82

(S)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)-N-(pyridin-3-yl)pentanamide

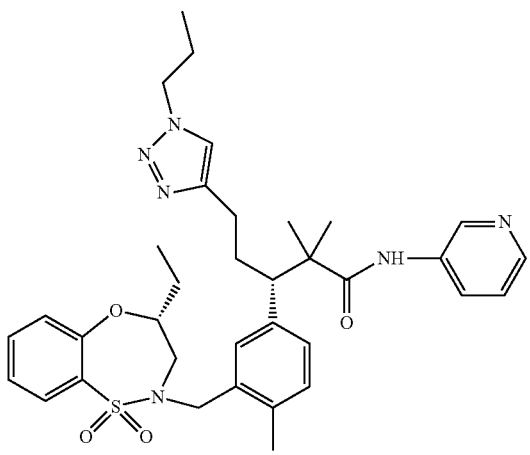 [SMILES: CCCn1cc(CC[C@@H](c2ccc(C)c(CN3C[C@@H](CC)Oc4ccccc4S3(=O)=O)c2)C(C)(C)C(=O)Nc2cccnc2)nn1]

(R)-benzyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoate and (S)-benzyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoate

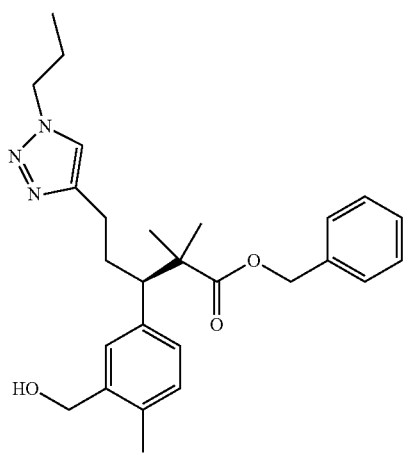

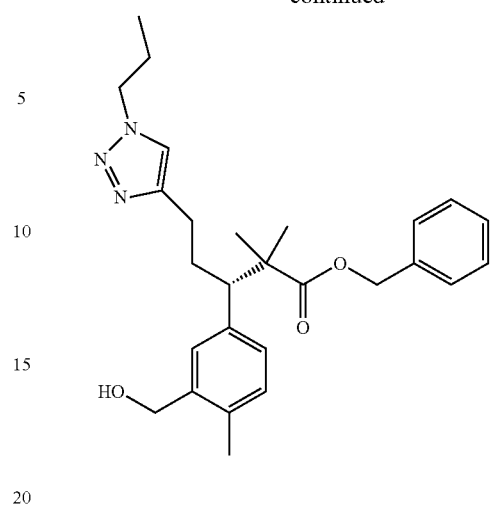

Benzyl 3-(3-(hydroxymethyl)-4-methylphenyl)-2,2-dimethyl-5-(1-propyl-1H-1,2,3-triazol-4-yl)pentanoate (prepared as described in WO2016/202253, published Dec. 22, 2016) was resolved by chiral SFC (Column: Chiralpak IA 20×250 mm, 5 u; Co-solvent: 35% EtOH; Flowrate: 50 g/min; Back pressure: 100Bar, 30° C.) to elute first (R)-benzyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoate LCMS (ES+) [M+H]=450.1 (1.17 min) and then (S)-benzyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoate LCMS (ES+) [M+H]=450.1 (1.17 min)

(R)-benzyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoate

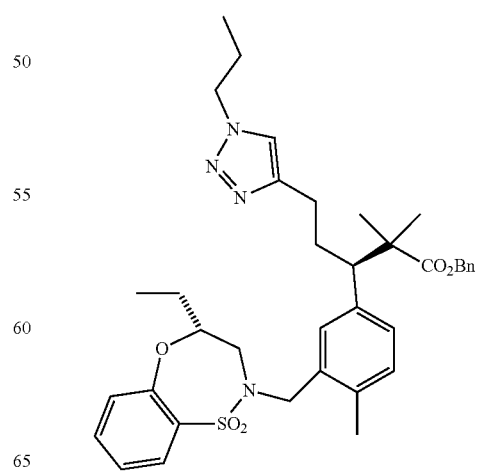

A solution of (R)-benzyl 3-(3-(hydroxymethyl)-4-methylphenyl)-2,2-dimethyl-5-(1-propyl-1H-1,2,3-triazol-4-yl)pentanoate (171 mg, 0.380 mmol) in tetrahydrofuran (THF) (7 mL) was treated with (R)-4-ethyl-3,4-dihydro-2H-benzo[b][1,4,5]oxathiazepine 1,1-dioxide (173 mg, 0.761 mmol), (E)-diazene-1,2-diylbis(piperidin-1-ylmethanone) (192 mg, 0.761 mmol) and then tributylphosphine (0.190 mL, 0.761 mmol). The reaction was stirred 1 h and concentrated and purified by reverse phase HPLC (Sunfire Prep C18 OBD 5 mm 30×250 mm preparatory column), eluting at 30 mL/min with a linear gradient running from 30% CH$_3$CN/H$_2$O 0.1% TFA to 100% acetonitrile 0.1% TFA over 15 min. The desired pools were combined and concentrated and redissolved in EtOAc (75 mL) and washed with 1 M aq NaOH (25 mL) then water (25 mL) and then satd aq NaCl and then dried (Na$_2$SO$_4$) filtered and concentrated to afford (R)-benzyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoate (188 mg, 0.285 mmol, 75% yield) LCMS (ES+) [M+H]=659.3 (1.43 min)

(R)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoic Acid

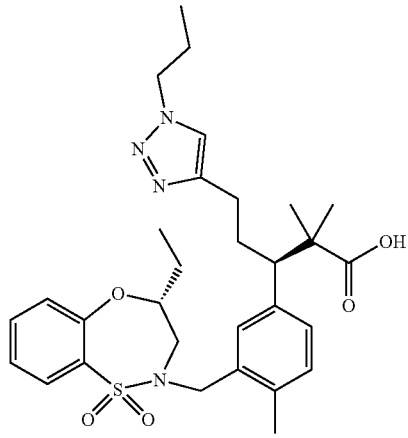 [SMILES: CCCn1cc(CC[C@H](c2ccc(C)c(CN3C[C@@H](CC)Oc4ccccc4S3(=O)=O)c2)C(C)(C)C(=O)O)nn1]

(R)-benzyl 3-(3-(((R)-4-ethyl-1,1-dioxido-3,4-dihydro-2H-pyrido[2,3-b][1,4,5]oxathiazepin-2-yl)methyl)-4-methylphenyl)-2,2-dimethyl-5-(1-propyl-1H-1,2,3-triazol-4-yl)pentanoate (188 mg, 0.285 mmol) was dissolved in methanol (10 mL) and hydrogenated on an H-cube (flow hydrogenator) at 1 atm for 50 min with a 20% Pd(OH)2 catalyst cartridge. The resulting solution was concentrated and purified by reverse phase HPLC (Altantics T3, 19×100 mm, 5 u, 18 ml/min 40% acetonitrile water to 80% acetonitrile water in 10 min). The purified fractions were pooled and concentrated to afford (R)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoic acid (127 mg, 0.223 mmol, 78% yield). LCMS (ES+) [M+H]=569.5 (1.20 min)

(S)-benzyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoate

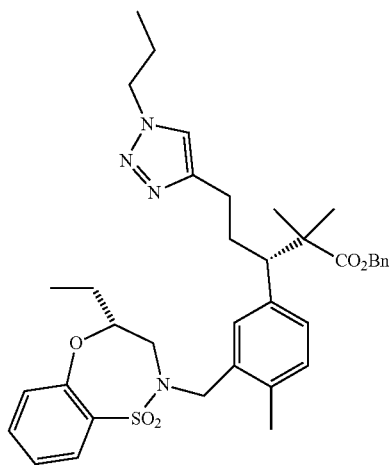 [SMILES: CCCn1cc(CC[C@@H](c2ccc(C)c(CN3C[C@@H](CC)Oc4ccccc4S3(=O)=O)c2)C(C)(C)C(=O)OCc2ccccc2)nn1]

(S)-benzyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoate was prepared by a method similar to the one described for the preparation of (R)-benzyl 3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoate. As is appreciated by those skilled in the art, these analogous examples may involve variations in general reaction conditions. LCMS (ES+) [M+H]=659.5 (1.44 min).

(S)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoic Acid (S)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoic acid was prepared by a method similar to the one described for the preparation of (R)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoic acid (Acid 5R). As is appreciated by those skilled in the art, these analogous examples may involve variations in general reaction conditions. LCMS (ES+) [M+H]=569.5 (1.20 min).

(S)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)-N-(pyridin-3-yl)pentanamide

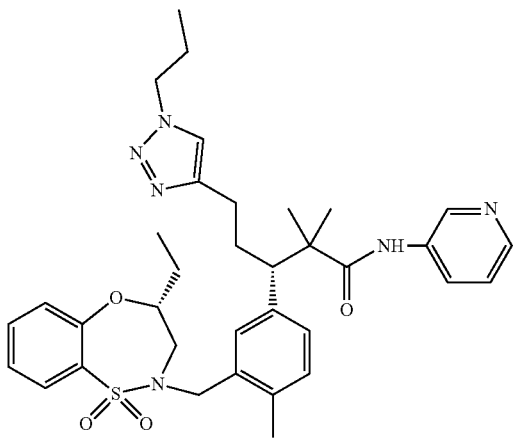 [SMILES: CCCn1cc(CC[C@@H](c2ccc(C)c(CN3C[C@@H](CC)Oc4ccccc4S3(=O)=O)c2)C(C)(C)C(=O)Nc2cccnc2)nn1]

To a solution of (S)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoic acid (76 mg, 0.134 mmol) in isopropanol (4 mL), phenyl (E)-N-(tert-butyl)-N'-(pyridin-3-yl)carbamimidothioate (49.6 mg, 0.174 mmol) and tris(((Z)-4-oxopent-2-en-2-yl)oxy) iron (2.360 mg, 6.68 µmol) were added. The reaction mixture was heated with microwave at 120° C. for 2 hrs. The solvent was evaporated. The crude product was purified by preparative reverse phase HPLC under acidic conditions (formic acid) to afford the title compound (S)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)-N-(pyridin-3-yl)pentanamide (18.8 mg, 0.029 mmol, 21.82% yield). LC-MS m/z 645.5 (M+H)$^+$, 0.95 min (ret. Time). $^1$H NMR (400 MHz, METHANOL-d4) δ ppm 0.90 (t, J=7.40 Hz, 3H) 1.07-1.20 (m, 6H) 1.30 (s, 3H) 1.43-1.70 (m, 2H) 1.87 (sxt, J=7.28 Hz, 2H) 1.98-2.11 (m, 1H) 2.15-2.59 (m, 6H) 2.95 (d, J=15.31 Hz, 1H) 3.03-3.14 (m, 1H) 3.74 (dd, J=15.18, 10.42 Hz, 1H) 3.88 (d, J=14.81 Hz, 1H) 4.01-4.09 (m, 1H) 4.19-4.35 (m, 2H) 4.51 (d, J=14.81 Hz, 1H) 7.18-7.22 (m, 2H) 7.27-7.42 (m, 3H) 7.53-7.71 (m, 2H) 7.85 (d, J=7.78 Hz, 1H) 7.98 (d, J=8.53 Hz, 1H) 8.17-8.32 (m, 2H) 8.61 (s, 1H)

Example 83

(R)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)-N-(pyridin-3-yl)pentanamide

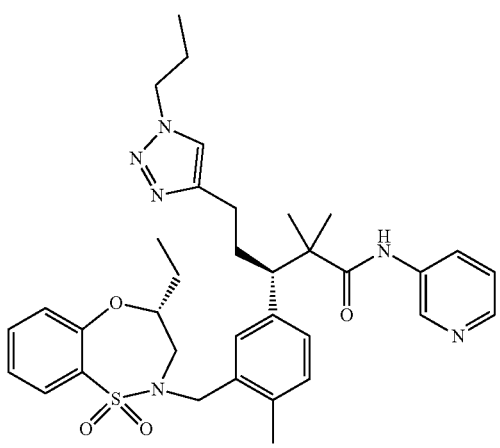

To a solution of (R)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)pentanoic acid (58 mg, 0.102 mmol) in isopropanol (4 mL), phenyl (E)-N-(tert-butyl)-N'-(pyridin-3-yl)carbamimidothioate (37.8 mg, 0.133 mmol) and tris(((Z)-4-oxopent-2-en-2-yl)oxy) iron (1.801 mg, 5.10 µmol) were added. The reaction mixture was heated with microwave at 120° C. for 2 hrs. The solvent was evaporated and then purified by preparative reverse phase HPLC under acidic conditions (formic acid) to afford the title compound (R)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-5-(1-propyl-1H-1,2,3-triazol-4-yl)-N-(pyridin-3-yl)pentanamide (14.6 mg, 0.023 mmol, 22.20% yield). LC-MS m/z 645.5 (M+H)$^+$, 0.94 min (ret. Time). $^1$H NMR (400 MHz, METHANOL-d4) δ ppm 0.91 (t, J=7.40 Hz, 3H) 1.07-1.23 (m, 6H) 1.22-1.33 (m, 3H) 1.35-1.53 (m, 2H) 1.60 (dd, J=14.93, 7.40 Hz, 1H) 1.79-1.92 (m, 2H) 1.98-2.13 (m, 1H) 2.18-2.26 (m, 1H) 2.31-2.56 (m, 5H) 2.96-3.13 (m, 2H) 3.71 (dd, J=15.18, 10.67 Hz, 1H) 3.89 (d, J=14.31 Hz, 1H) 4.01-4.17 (m, 1H) 4.27 (t, J=7.03 Hz, 2H) 4.52 (d, J=14.56 Hz, 1H) 7.19 (s, 3H) 7.24-7.40 (m, 2H) 7.44-7.56 (m, 1H) 7.57-7.70 (m, 2H) 7.85 (d, J=7.78 Hz, 1H) 8.04 (d, J=8.28 Hz, 1H) 8.09-8.91 (m, 2H)

Example 84

(S)-3-(4-Chloro-3-(((R)-4-ethyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)-2,2-dimethyl-N-(pyridin-3-yl)propanamide

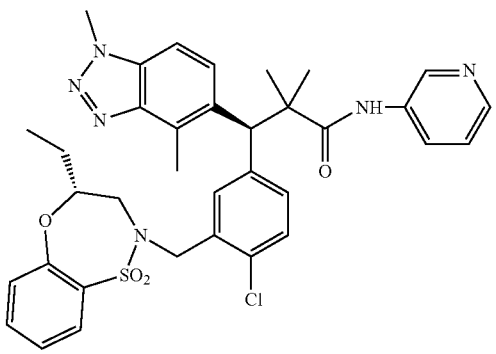 [SMILES: CC[C@@H]1CN(Cc2cc([C@@H](c3ccc4c(nnn4C)c3C)C(C)(C)C(=O)Nc3cccnc3)ccc2Cl)S(=O)(=O)c2ccccc2O1]

((5-Bromo-2-chlorobenzyl)oxy)(tert-butyl)dimethylsilane

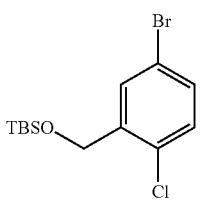 [SMILES: CC(C)(C)[Si](C)(C)OCc1cc(Br)ccc1Cl]

To a solution of (5-bromo-2-chlorophenyl)methanol (12 g, 54.2 mmol) in dichloromethane (DCM) (150 mL), tert-butylchlorodimethylsilane (12.25 g, 81 mmol) and 1H-imidazole (7.38 g, 108 mmol) were added. The reaction mixture was stirred at 0° C. to 25° C. for 2 h. The reaction mixture was quenched with water and extracted with DCM (3×). The combined organic layer was washed with water (2×), brine (2×), dried over $Na_2SO_4$ and concentrated. The residue was purified by silica gel chromatography (petroleum ether:ethyl acetate=1:10) to obtain the title compound ((5-bromo-2-chlorobenzyl)oxy)(tert-butyl)dimethylsilane (16 g, 39.1 mmol, 72.1% yield) as a colorless oil. $^1$H NMR ($CDCl_3$, 500 MHz): δ ppm 7.72-7.71 (m, 1H), 7.35-7.33 (m, 1H), 7.20-7.18 (m, 1H), 4.77 (s, 2H), 1.00 (s, 9H), 0.17 (s, 6H).

3-(((Tert-butyldimethylsilyl)oxy)methyl)-4-chlorobenzaldehyde

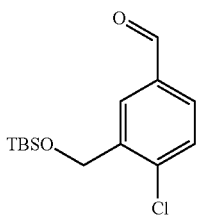 [SMILES: CC(C)(C)[Si](C)(C)OCc1cc(C=O)ccc1Cl]

To a solution of ((5-bromo-2-chlorobenzyl)oxy)(tert-butyl)dimethylsilane (16.0 g, 47.7 mmol) in tetrahydrofuran (THF) (150 mL) was added n-butyllithium (22.87 mL, 57.2 mmol, 2.5 M solution in THF) at −78° C. under nitrogen. After the reaction mixture was stirred at −78° C. for 30 mins, DMF (18.45 mL, 238 mmol) was slowly added. The reaction mixture was continuously stirred for 2 h at −78° C. and quenched with saturated $NH_4CL$ solution and extracted with ethyl acetate (3×). The combined organic layer was washed with water, brine, dried over anhydrous $Na_2SO_4$ and concentrated. The residue was purified by silica gel chromatography (petroleum ether:ethyl acetate=4:1) to obtain the title compound 3-(((tert-butyldimethylsilyl)oxy)methyl)-4-chlorobenzaldehyde (9.0 g, 30.0 mmol, 63.0% yield) as a light yellow oil. $^1$H NMR ($CDCl_3$, 500 MHz): δ ppm 10.03 (s, 1H), 8.11 (s, 1H), 7.77-7.75 (m, 1H), 7.51-7.49 (m, 1H), 4.85 (s, 2H), 1.01 (s, 9H), 0.19 (s, 6H).

(3-(((Tert-butyldimethylsilyl)oxy)methyl)-4-chlorophenyl)(1,4-dimethyl-1H-benzo[d][1,2,3]triazol-5-yl)methanol

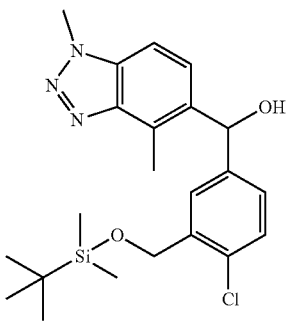 [SMILES: Cc1c(C(O)c2ccc(Cl)c(CO[Si](C)(C)C(C)(C)C)c2)ccc2c1nnn2C]

To a solution of 5-bromo-1,4-dimethyl-1H-benzo[d][1,2,3]triazole (6 g, 26.5 mmol) in tetrahydrofuran (THF) (100 mL) was added tert-butyllithium (20.42 mL, 26.5 mmol, 1.3 M solution in hexane) at −78° C. under nitrogen. After the reaction mixture was stirred at −78° C. for 30 min, 3-(((tert-butyldimethylsilyl)oxy)methyl)-4-chlorobenzaldehyde (7.94 g, 27.9 mmol) in tetrahydrofuran (THF) (100 mL) was added dropwise and continually stirred for 2 hrs at −78° C. The reaction mixture was slowly warmed to ambient temperature and stirred for an additional 2 h. The reaction mixture was quenched with saturated $NH_4Cl$ solution and extracted with ethyl acetate (3×). The combined organic layer was washed with brine and dried over anhydrous $Na_2SO_4$ and concentrated. The residue was purified by silica gel chromatography (petroleum ether:ethyl acetate=3:1) to give the title compound (3-(((tert-butyldimethylsilyl)oxy)methyl)-4-chlorophenyl)(1,4-dimethyl-1H-benzo[d][1,2,3]triazol-5-yl)methanol (3.8 g, 6.42 mmol, 24.19% yield) as a light yellow oil. LC/MS m/z 432.1 $(M+H)^+$, 1.97 (ret. time).

Methyl 3-(3-(((tert-butyldimethylsilyl)oxy)methyl)-4-chlorophenyl)-3-(1,4-dimethyl-1H-benzo[d][1,2,3]triazol-5-yl)-2,2-dimethylpropanoate

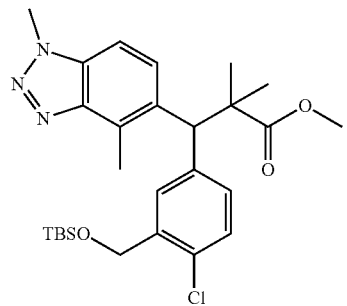 [SMILES: COC(=O)C(C)(C)C(c1ccc(Cl)c(CO[Si](C)(C)C(C)(C)C)c1)c1ccc2c(nnn2C)c1C]

To a solution of (3-(((tert-butyldimethylsilyl)oxy)methyl)-4-chlorophenyl)(1,4-dimethyl-1H-benzo[d][1,2,3]triazol-5-yl)methanol (1.4 g, 3.24 mmol) in dry acetonitrile (30 mL) was slowly added DBU (9.77 μL, 0.065 mmol) and 2,2,2-trichloroacetonitrile (0.561 g, 3.89 mmol) under nitrogen at 25° C. After the reaction mixture was stirred at 25° C. for 30 mins, ((1-methoxy-2-methylprop-1-en-1-yl)oxy)trimethylsilane (1.412 g, 8.10 mmol) was added, followed by 1,1,1-trifluoro-N-((trifluoromethyl)sulfonyl)methanesulfonamide (0.046 g, 0.162 mmol). The reaction mixture was stirred at ambient temperature for 2 h after which 30 mL of water was added to quench the reaction. The mixture was extracted with ethyl acetate (3×). The combined organic layer was washed with brine and concentrated. The crude product was purified by silica gel chromatography (petroleum ether:ethyl acetate=4:1) to give the title compound methyl 3-(3-(((tert-butyldimethylsilyl)oxy)methyl)-4-chlorophenyl)-3-(1,4-dimethyl-1H-benzo[d][1,2,3]triazol-5-yl)-2,2-dimethylpropanoate (1.2 g, 2.209 mmol, 68.2% yield) as a yellow solid. LC/MS m/z 516.1 $(M+H)^+$, 2.19 (ret. time).

241

Methyl 3-(4-chloro-3-(hydroxymethyl)phenyl)-3-(1,4-dimethyl-1H-benzo[d][1,2,3]triazol-5-yl)-2,2-dimethylpropanoate

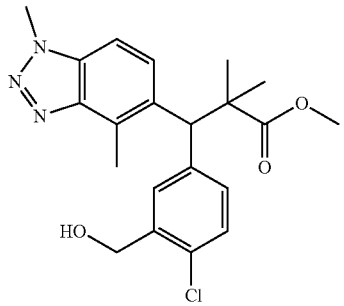 [SMILES: COC(=O)C(C)(C)C(c1ccc(Cl)c(CO)c1)c1ccc2c(nnn2C)c1C]

To a solution of methyl 3-(3-(((tert-butyldimethylsilyl)oxy)methyl)-4-chlorophenyl)-3-(1,4-dimethyl-1H-benzo[d][1,2,3]triazol-5-yl)-2,2-dimethylpropanoate (2.8 g, 4.88 mmol) in tetrahydrofuran (THF) (20 mL) was added TBAF (5.86 mL, 5.86 mmol) slowly under nitrogen at 25° C. The reaction mixture was stirred at 25° C. for 16 h. Water (30 mL) was added and the reaction mixture was extracted with ethyl acetate (3×). The combined organic layer was concentrated. The crude product was purified by silica gel chromatography (hexane:ethyl acetate=1:1) to provide the title compound methyl 3-(4-chloro-3-(hydroxymethyl)phenyl)-3-(1,4-dimethyl-1H-benzo[d][1,2,3]triazol-5-yl)-2,2-dimethylpropanoate (1.67 g, 3.95 mmol, 81 yield) as a white solid. LC/MS m/z 402.1 (M+H)$^+$, 1.99 (ret. time).

(S)-Methyl 3-(4-chloro-3-(hydroxymethyl)phenyl)-3-(1,4-dimethyl-1H-benzo[d][1,2,3]triazol-5-yl)-2,2-dimethylpropanoate

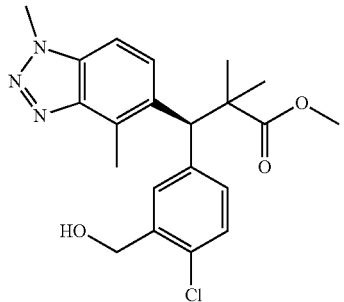 [SMILES: COC(=O)C(C)(C)[C@@H](c1ccc(Cl)c(CO)c1)c1ccc2c(nnn2C)c1C]

This was resolved by Chiral SFC (Column: ASH 20×250 mm, 5 u; Co-solvent: 100% MeOH; Flowrate: 80 g/min; Back pressure: 100 Bar) to give (S)-Methyl 3-(4-chloro-3-(hydroxymethyl)phenyl)-3-(1,4-dimethyl-1H-benzo[d][1,2,3]triazol-5-yl)-2,2-dimethylpropanoate (chiral SFC ret. time: 3.55 min) and (R)-Methyl 3-(4-chloro-3-(hydroxymethyl)phenyl)-3-(1,4-dimethyl-1H-benzo[d][1,2,3]triazol-5-yl)-2,2-dimethylpropanoate (chiral SFC ret. time: 4.33 min)

242

(S)-methyl 3-(4-chloro-3-(chloromethyl)phenyl)-3-(1,4-dimethyl-1H-benzo[d][1,2,3]triazol-5-yl)-2,2-dimethylpropanoate

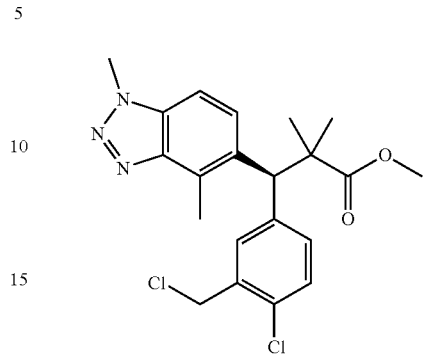

To a solution of (S)-Methyl 3-(4-chloro-3-(hydroxymethyl)phenyl)-3-(1,4-dimethyl-1H-benzo[d][1,2,3]triazol-5-yl)-2,2-dimethylpropanoate (65 mg, 0.170 mmol) in dichloromethane (DCM) (5 mL), SOCl$_2$ (0.025 mL, 0.341 mmol) was added. Then the reaction mixture was stirred at ambient temperature for 30 mins. The solvent was evaporated to obtain the title compound (S)-methyl 3-(4-chloro-3-(chloromethyl)phenyl)-3-(1,4-dimethyl-1H-benzo[d][1,2,3]triazol-5-yl)-2,2-dimethylpropanoate (65 mg, 0.163 mmol, 95% yield) which was carried over to next step without further purification. LC/MS m/z 400.1 (M+H)$^+$, 1.9 (ret. time).

(S)-3-(4-Chloro-3-(((R)-4-ethyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)-2,2-dimethylpropanoic Acid

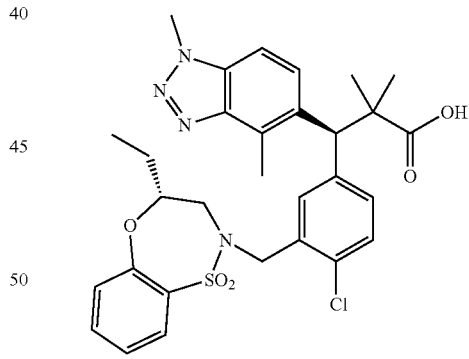

To a solution of methyl (S)-3-(4-chloro-3-(hydroxymethyl)phenyl)-3-(1,4-dimethyl-1H-benzo[d][1,2,3]triazol-5-yl)-2,2-dimethylpropanoate (700 mg, 1.742 mmol) in tetrahydrofuran (THF) (4 mL), (R)-4-ethyl-3,4-dihydro-2H-benzo[b][1,4,5]oxathiazepine 1,1-dioxide (475 mg, 2.090 mmol), (E)-diazene-1,2-diylbis(piperidin-1-ylmethanone) (879 mg, 3.48 mmol) and tributylphosphane (0.870 mL, 3.48 mmol) were added. The reaction mixture was stirred at ambient temperature for 30 min. The solvent was evaporated and the product purified via silica gel chromatography with hexane and ethyl acetate to obtain the methyl (S)-3-(4-chloro-3-(((R)-4-ethyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)-2,2-dimethylpropanoate (1.0034 g, 1.642 mmol, 94% yield). To this product in methanol (3 mL), LiOH (8.71 mL, 17.42 mmol) was added. The reaction mixture was heated with microwave at 120° C. for 3 hrs. The solvent was evaporated. The residue was partitioned between ethyl acetate and 1N HCl. The aqueous layer was extracted with EtOAc (2×). The combined organic phase was dried over MgSO₄ and concentrated and purified by preparative reverse phase HPLC to obtain the title compound (750 mg, 1.256 mmol, 72.1 yield). LC/MS m/z 597.4 (M+H)⁺, 1.22 (ret. time).

(S)-3-(4-Chloro-3-(((R)-4-ethyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)-2,2-dimethyl-N-(pyridin-3-yl)propanamide

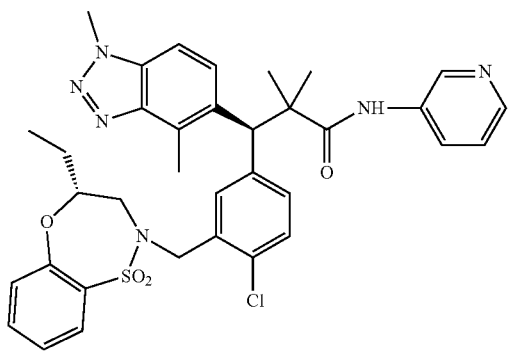 [SMILES: CC[C@@H]1CN(Cc2cc([C@@H](c3ccc4c(nnn4C)c3C)C(C)(C)C(=O)Nc3cccnc3)ccc2Cl)S(=O)(=O)c2ccccc2O1]

To a solution of (S)-3-(4-chloro-3-(((R)-4-ethyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)-2,2-dimethylpropanoic acid (53 mg, 0.089 mmol) in isopropanol (4 mL), phenyl (E)-N-(tert-butyl)-N'-(pyridin-3-yl)carbamimidothioate (32.9 mg, 0.115 mmol) and tris (((Z)-4-oxopent-2-en-2-yl)oxy) iron (3.13 mg, 8.88 µmol) were added. The reaction mixture was heated with microwave at 120° C. for 2 hrs. The solvent was evaporated. The crude product was purified by preparative reverse phase HPLC under acidic (formic acid) condition to afford the title compound (S)-3-(4-chloro-3-(((R)-4-ethyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)-2,2-dimethyl-N-(pyridin-3-yl)propanamide (48.7 mg, 0.072 mmol, 81% yield). LC-MS m/z 673.4 (M+H)⁺, 0.97 min (ret. Time). ¹H NMR (400 MHz, METHANOL-d4) δ ppm 1.05 (t, J=7.40 Hz, 3H) 1.29-1.65 (m, 8H) 2.83 (s, 3H) 2.99 (d, J=15.06 Hz, 1H) 3.76 (dd, J=14.93, 10.42 Hz, 1H) 3.92 (td, J=9.22, 2.89 Hz, 1H) 4.10 (d, J=15.81 Hz, 1H) 4.28 (s, 3H) 4.41 (d, J=15.81 Hz, 1H) 5.13 (s, 1H) 7.21-7.39 (m, 5H) 7.51-7.70 (m, 3H) 7.72-7.83 (m, 2H) 7.88 (d, J=8.28 Hz, 1H) 8.23 (d, J=3.76 Hz, 1H) 8.49 (br. s., 1H)

Example 85

(S)-3-(3-(((R)-4-Ethyl-1,1-dioxido-3,4-dihydro-2H-benzo[b][1,4,5]oxathiazepin-2-yl)methyl)-4-methylphenyl)-2,2-dimethyl-3-(4-methyl-1-propyl-1H-benzo[d][1,2,3]triazol-5-yl)-N-(pyridin-3-yl)propanamide

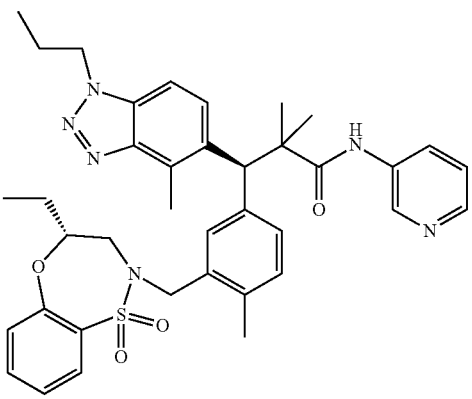 [SMILES: CCCn1nnc2c(C)c([C@H](c3ccc(C)c(CN4C[C@@H](CC)Oc5ccccc5S4(=O)=O)c3)C(C)(C)C(=O)Nc3cccnc3)ccc21]

To a solution of (S)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-(4-methyl-1-propyl-1H-benzo[d][1,2,3]triazol-5-yl)propanoic acid (24 mg, 0.040 mmol) in isopropanol (4 mL), phenyl (E)-N-(tert-butyl)-N'-(pyridin-3-yl)carbamimidothioate (14.72 mg, 0.052 mmol)) and) were added. The reaction mixture was heated with microwave at 120° C. for 2 hrs. The solvent was evaporated. The crude product was purified by preparative reverse phase HPLC under acidic (formic acid) to afford the title compound (S)-3-(3-(((R)-4-ethyl-1,1-dioxido-3,4-dihydro-2H-benzo[b][1,4,5]oxathiazepin-2-yl)methyl)-4-methylphenyl)-2,2-dimethyl-3-(4-methyl-1-propyl-1H-benzo[d][1,2,3]triazol-5-yl)-N-(pyridin-3-yl)propanamide (5.6 mg, 8.22 µmol, 20.73% yield). LC-MS m/z 681.0 (M+H)⁺, 1.47 min (ret. Time). ¹H NMR (400 MHz, METHANOL-d4) δ ppm 0.78-1.00 (m, 6H) 1.03-1.17 (m, 1H) 1.33-1.57 (m, 7H) 1.91-2.10 (m, 3H) 2.30 (s, 3H) 2.78 (s, 3H) 3.61 (dd, J=15.18, 10.42 Hz, 1H) 3.73-3.97 (m, 2H) 4.50 (d, J=14.31 Hz, 1H) 4.63 (t, J=6.90 Hz, 2H) 5.02 (s, 1H) 7.10-7.35 (m, 6H) 7.47-7.66 (m, 2H) 7.70-7.87 (m, 3H) 8.21 (d, J=3.76 Hz, 1H) 8.38 (br. s., 1H)

Example 86

(S)—N-(2-Chloropyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

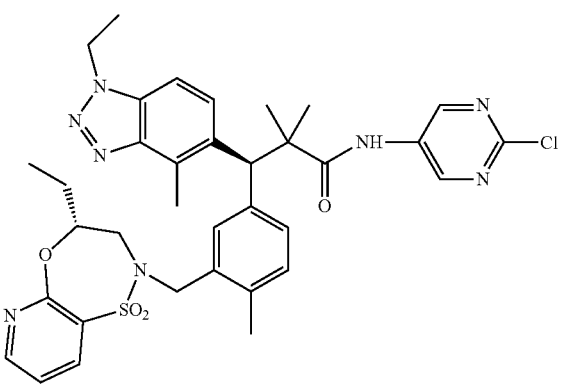 [SMILES: CC[C@@H]1CN(Cc2cc([C@@H](c3ccc4c(nnn4CC)c3C)C(C)(C)C(=O)Nc3cnc(Cl)nc3)ccc2C)S(=O)(=O)c2cccnc2O1]

4-Bromo-2-(((4-methoxybenzyl)oxy)methyl)-1-methylbenzene

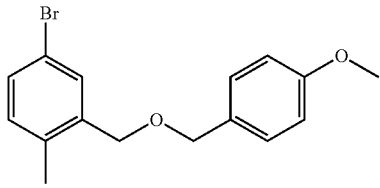 [SMILES: COc1ccc(COCc2cc(Br)ccc2C)cc1]

To a solution of (5-bromo-2-methylphenyl)methanol (100 g, 497 mmol) in N,N-dimethylformamide (DMF) (800 mL) at 0° C. under $N_2$, NaH (23.87 g, 597 mmol) was added in portion wise and stirred for 30 mins. Then 1-(chloromethyl)-4-methoxybenzene (86 g, 547 mmol) was added to the mixture and stirred at 20° C. for 1 hr. 300 mL of water was added slowly and the mixture was extracted by ethyl acetate (3×300 mL). The combined organic layers were washed with the brine (2×150 mL), dried with $Na_2SO_4$, and the solvent was removed in vacuo. The residue was purified by silica gel chromatography, 120 g column and eluted with petroleum ether:ethyl acetate=10:1 to obtain the title compound 4-bromo-2-(((4-methoxybenzyl)oxy)methyl)-1-methylbenzene (110 g, 325 mmol, 65.4% yield). LC-MS m/z 343.0/345.0 $(M+Na)^+$, 2.02 min (ret. Time)

3-(((4-Methoxybenzyl)oxy)methyl)-4-methylbenzaldehyde

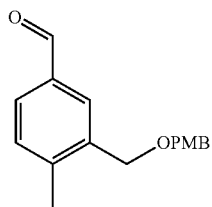

To a solution of 4-bromo-2-(((4-methoxybenzyl)oxy)methyl)-1-methylbenzene (30 g, 93 mmol) in tetrahydrofuran (THF) (250 mL) at −78° C. under $N_2$, butyllithium (44.8 mL, 112 mmol) was carefully added. The reaction mixture was stirred at −78° C. for 65 mins, then DMF (21.70 mL, 280 mmol) was added. The reaction mixture was stirred at −78° C. to 25° C. for another 30 mins. The mixture was quenched with saturated $NH_4Cl$ (150 mL×1) and extracted with ethyl acetate (200 mL×3), the combined organic layer was washed with water (160 mL×2) and brine (120 mL×2), dried ($Na_2SO_4$) and concentrated. The residue was purified by silica gel chromatography (silica gel column 120 g, petroleum ether:ethyl acetate=10:1) to obtain the title compound 3-(((4-methoxybenzyl)oxy)methyl)-4-methylbenzaldehyde (20.0 g, 70.3 mmol, 75% yield). LC-MS m/z 293.1 $(M+Na)^+$, 1.81 min (ret. Time)

(1-Ethyl-4-methyl-1H-benzo[d][1,2,3]triazol-5-yl)(3-(((4-methoxybenzyl)oxy)methyl)-4-methylphenyl)methanol

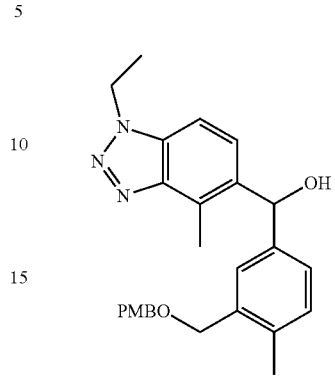

To a solution of 5-bromo-1-ethyl-4-methyl-1H-benzo[d][1,2,3]triazole (15.0 g, 62.5 mmol) in tetrahydrofuran (THF) (750 mL) butyllithium (24.99 mL, 62.5 mmol) was added at −78° C. under N2 protection. The mixture was stirred at −78° C. for half an hour under N2 protection, then 3-(((4-methoxybenzyl)oxy)methyl)-4-methylbenzaldehyde (17.73 g, 65.6 mmol) dissolved in tetrahydrofuran (THF) (50 mL) was added dropwise continually stirred for 2 hrs at −78° C. The mixture was slowly warmed into 20° C. and stirred for another 2 hrs. Then the reaction was quenched with saturated aqueous $NH_4Cl$ solution (80 mL). The mixture was extracted with ethyl acetate (200 mL×3). The combined organic layer was washed with brine (150 mL) and dried over anhydrous $Na_2SO_4$. After filtration and concentration, the residue was purified by silica gel chromatography (petroleum ether:ethyl acetate=2:1) to obtain the title compound (1-ethyl-4-methyl-1H-benzo[d][1,2,3]triazol-5-yl)(3-(((4-methoxybenzyl)oxy)methyl)-4-methylphenyl)methanol (14.0 g, 30.8 mmol, 49.3% yield). LC-MS m/z 432.3 $(M+Na)^+$, 1.92 min (ret. Time)

Methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate

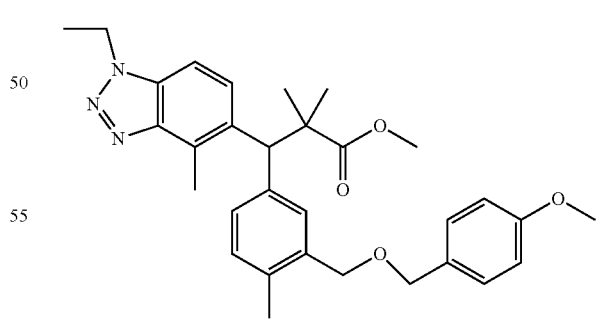

To a solution of (1-ethyl-4-methyl-1H-benzo[d][1,2,3]triazol-5-yl)(3-(((4-methoxybenzyl)oxy)methyl)-4-methylphenyl)methanol (22.0 g, 51.0 mmol), was slowly added 2,2,2-trichloroacetonitrile (6.65 mL, 66.3 mmol) and DBU (0.231 mL, 1.529 mmol) dropwise under N2 protection at 15° C. The mixture was stirred at 15° C. for 2 hrs then ((1-methoxy-2-methylprop-1-en-1-yl)oxy)trimethylsilane (25.9 mL, 127 mmol) was added dropwise, after 10 mins, BF$_3$OEt$_2$ (6.46 mL, 51.0 mmol) was added dropwise and the mixture was stirred for 1.6 hrs. Then 180 mL of H$_2$O was added to quench the reaction. The mixture was extracted with ethyl acetate (150 ml) for three times and the combined organic layer was washed with brine (100 mL) and dried over Na$_2$SO$_4$. After filtration and concentration, the residue was purified by silica gel chromatography (petroleum ether: ethyl acetate=3:1)) to obtain the title compound methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (20.0 g, 36.8 mmol, 72.3% yield). LC-MS m/z 516.2 (M+1)$^+$, 2.21 min (ret. Time). $^1$H NMR (500 MHz, CDCl3) δ 7.57 (d, J=8.8 Hz, 1H), 7.27-7.25 (m, 1H), 7.19 (dd, J=8.8, 5.2 Hz, 3H), 7.09 (dd, J=7.9, 1.9 Hz, 1H), 7.04 (d, J=7.9 Hz, 1H), 6.86-6.81 (m, 2H), 4.89 (s, 1H), 4.62 (q, J=7.3 Hz, 2H), 4.44 (dd, J=16.2, 11.0 Hz, 4H), 3.80 (s, 3H), 3.48 (s, 3H), 2.83 (s, 3H), 2.24 (s, 3H), 1.59 (t, J=7.3 Hz, 3H), 1.41 (s, 3H), 1.31 (s, 3H).

(S)-Methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate

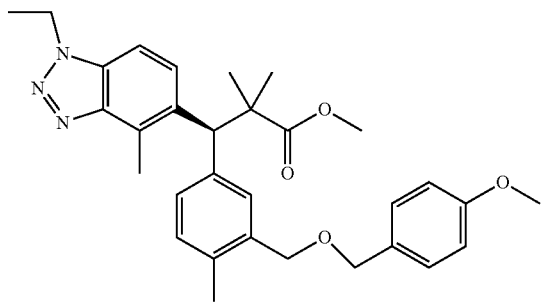 [SMILES: CCn1nnc2c(C)c([C@H](c3ccc(C)c(COCc4ccc(OC)cc4)c3)C(C)(C)C(=O)OC)ccc21]

This was resolved by Chiral SFC (Column: Chiralpak IG, 5 u; Co-solvent: 30%% EtOH; Flowrate: 80 g/min; Back pressure: 100 Bar) to give (S)-Methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (chiral SFC ret. time: 2.83 min) and (R)-Methyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (chiral SFC ret. time: 3.88 min)

(S)-Benzyl 3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate

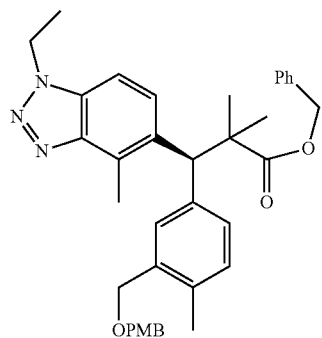

To a solution of methyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (3.1 g, 6.01 mmol) in methanol (32 mL), LiOH (30.1 mL, 60.1 mmol) was added. The reaction mixture was heated with microwave at 120° C. for 2 hr. The solvent was evaporated and the crude product dissolved in N,N-dimethylformamide (DMF) (30.0 mL), benzyl bromide (1.430 mL, 12.02 mmol) was added. The reaction mixture was stirred at ambient temperature for 2 hrs. The reaction mixture was partitioned between ethyl acetate and water. The water layer was extracted with ethyl acetate (2×). The combined organic phase was dried over MgSO$_4$ and concentrated. The crude product was purified by silica gel chromatography (hexane/ethyl acetate) to obtain the title compound benzyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (3.2 g, 5.41 mmol, 90% yield). LC-MS m/z 592.35 (M+1)$^+$, 1.53 min (ret. Time).

(S)-Benzyl 3-(1-ethyl-4-methyl-1H-benzo[d][1,2,3]triazol-5-yl)-3-(3-(hydroxymethyl)-4-methylphenyl)-2,2-dimethylpropanoate

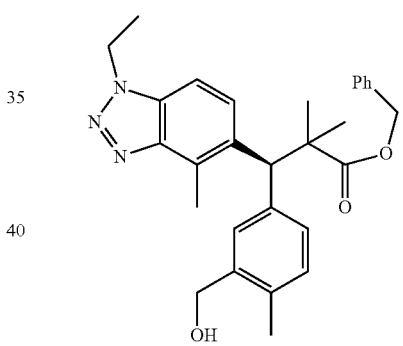

To a solution of benzyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (3.2 g, 5.41 mmol) in a mixture of acetonitrile (20.00 mL) and water (2 mL), CAN (5.93 g, 10.82 mmol) was added at 0° C. Then the reaction mixture was stirred at ambient temperature for 2 hrs. The reaction mixture was partitioned between ethyl acetate and saturated NH$_4$Cl. The water layer was extracted with ethyl acetate (2×). The combined organic phase was dried over MgSO$_4$ and concentrated. The crude product was purified by silica gel chromatography with ethyl acetate/hexane to obtain the title compound benzyl (S)-3-(1-ethyl-4-methyl-1H-benzo[d][1,2,3]triazol-5-yl)-3-(3-(hydroxymethyl)-4-methylphenyl)-2,2-dimethylpropanoate (2.1 g, 4.45 mmol, 82% yield). LC-MS m/z 472.34 (M+1)$^+$, 1.2 min (ret. Time).

(S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic Acid

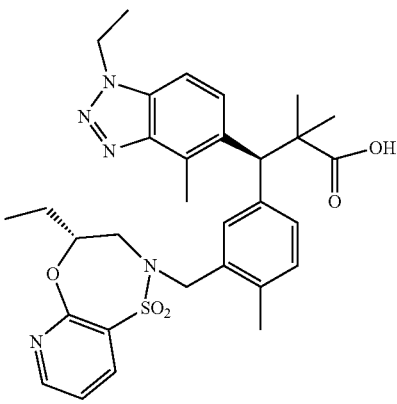 [SMILES: CC[C@@H]1CN(Cc2cc([C@@H](c3ccc4c(nnn4CC)c3C)C(C)(C)C(=O)O)ccc2C)S(=O)(=O)c2cccnc2O1]

To a solution of benzyl (S)-3-(1-ethyl-4-methyl-1H-benzo[d][1,2,3]triazol-5-yl)-3-(3-(hydroxymethyl)-4-methylphenyl)-2,2-dimethylpropanoate (2100 mg, 4.45 mmol) in tetrahydrofuran (THF) (15 mL), (R)-4-ethyl-3,4-dihydro-2H-pyrido[2,3-b][1,4,5]oxathiazepine 1,1-dioxide (1220 mg, 5.34 mmol) and (E)-diazene-1,2-diylbis (piperidin-1-yl-methanone) (2247 mg, 8.91 mmol) were added, then tributylphosphane (2.224 mL, 8.91 mmol) was added. The reaction mixture was stirred at ambient temperature for 18 hrs. The solvent was evaporated and the product purified by silica gel chromatography with ethyl acetate and hexane to obtain benzyl (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoate (2500 mg, 3.67 mmol, 82% yield). This was taken into 250 mL of ethyl acetate and ethanol (3:1) and hydrogenated with H-cube to get crude product which was purified by preparative reverse phase HPLC under acidic conditions to obtain the title compound (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (1200 mg, 2.028 mmol, 45.5% yield). LC-MS m/z 592.29 (M+1)$^+$, 1.1 min (ret. Time).

(S)—N-(2-Chloropyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

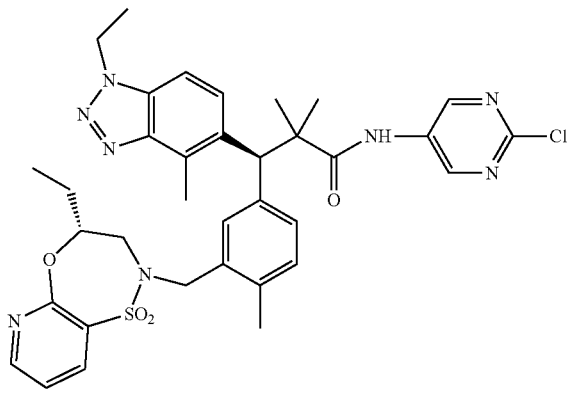 [SMILES: CC[C@@H]1CN(Cc2cc([C@@H](c3ccc4c(nnn4CC)c3C)C(C)(C)C(=O)Nc3cnc(Cl)nc3)ccc2C)S(=O)(=O)c2cccnc2O1]

To a solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (226 mg, 0.382 mmol) in isopropanol (4 mL), phenyl (E)-N-(tert-butyl)-N'-(2-chloropyrimidin-5-yl)carbamimidothioate (159 mg, 0.497 mmol) and tris(((Z)-4-oxopent-2-en-2-yl)oxy) iron (13.49 mg, 0.038 mmol) were added. The reaction mixture was heated with microwave at 120° C. for 2 hrs. The solvent was evaporated. The crude product was purified by preparative reverse phase HPLC under acidic (formic acid) condition to afford the title compound (S)—N-(2-chloropyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide (148.7 mg, 0.211 mmol, 55.4% yield). LC-MS m/z 673.38 (M+H)$^+$, 0.97 min (ret. Time). $^1$H NMR (400 MHz, DMSO-d6) δ ppm 0.87 (t, J=7.28 Hz, 3H) 1.06-1.24 (m, 1H) 1.33 (s, 2H) 1.41-1.51 (m, 5H) 2.01-2.24 (m, 6H) 2.69-2.83 (m, 4H) 3.63 (dd, J=15.31, 10.29 Hz, 1H) 4.01 (d, J=14.81 Hz, 1H) 4.21-4.46 (m, 2H) 4.66 (q, J=7.28 Hz, 2H) 4.95 (s, 1H) 7.01-7.22 (m, 2H) 7.30 (s, 1H) 7.39-7.73 (m, 3H) 8.22 (dd, J=7.65, 1.88 Hz, 1H) 8.56 (dd, J=4.77, 2.01 Hz, 1H) 8.73 (s, 2H) 9.81 (s, 1H)

Example 87

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

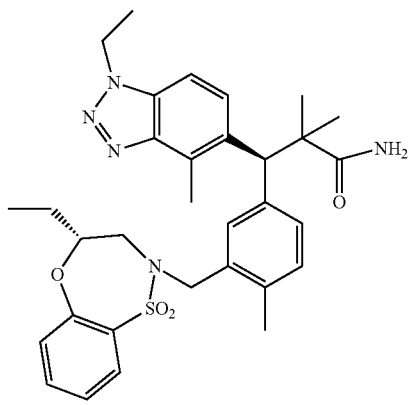 [SMILES: CC[C@@H]1CN(Cc2cc([C@@H](c3ccc4c(nnn4CC)c3C)C(C)(C)C(N)=O)ccc2C)S(=O)(=O)c2ccccc2O1]

(S)-Methyl 3-(1-ethyl-4-methyl-1H-benzo[d][1,2,3]triazol-5-yl)-3-(3-(hydroxymethyl)-4-methylphenyl)-2,2-dimethylpropanoate

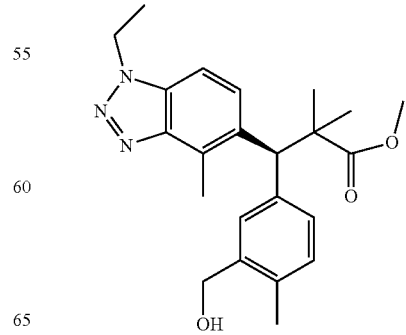

To a solution of methyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (2.46 g, 4.77 mmol) in a mixture of acetonitrile (20.00 mL) and water (2 mL), CAN (5.23 g, 9.54 mmol) was added at 0° C. Then the reaction mixture was stirred at ambient temperature for 3 hrs. The reaction mixture was partitioned between ethyl acetate and H₂O. The water layer was extracted with ethyl acetate (2×). The combined organic phase was dried over MgSO₄ and concentrated. The crude product was purified by silica gel chromatography with ethyl acetate/hexane to obtain the title compound methyl (S)-3-(1-ethyl-4-methyl-1H-benzo[d][1,2,3]triazol-5-yl)-3-(3-(hydroxymethyl)-4-methylphenyl)-2,2-dimethylpropanoate (1.7150 g, 4.34 mmol, 91% yield). LC-MS m/z 396.3 (M+H)⁺, 1.08 min (ret. Time).

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic Acid

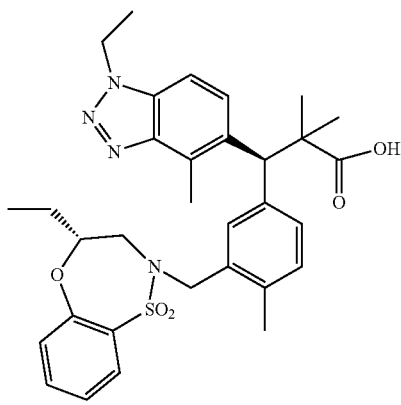 [SMILES: CC[C@@H]1CN(Cc2cc([C@@H](c3ccc4c(nnn4CC)c3C)C(C)(C)C(=O)O)ccc2C)S(=O)(=O)c2ccccc2O1]

To a solution of methyl (S)-3-(1-ethyl-4-methyl-1H-benzo[d][1,2,3]triazol-5-yl)-3-(3-(hydroxymethyl)-4-methylphenyl)-2,2-dimethylpropanoate (1.75 g, 4.42 mmol) in tetrahydrofuran (THF) (40 mL), (R)-4-ethyl-3,4-dihydro-2H-benzo[b][1,4,5]oxathiazepine 1,1-dioxide (1.106 g, 4.87 mmol) and (E)-diazene-1,2-diylbis(piperidin-1-ylmethanone) (2.233 g, 8.85 mmol) were added, then tributylphosphane (2.210 mL, 8.85 mmol) was added. The reaction mixture was stirred at ambient temperature for 16 hrs. The solvent was evaporated. The crude product was purified by silica gel chromatography with ethyl acetate/hexane to get methyl (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoate (2.5 g, 4.13 mmol, 93% yield). To this product in methanol (15.00 mL), LiOH (22.12 mL, 44.2 mmol) was added. Then the reaction mixture was heated with microwave at 120° C. for 3 hrs. The solvent was evaporated. The residue was partitioned between ethyl acetate and 1N HCl. The water layer was extracted with ethyl acetate (3×). The combined organic phase was dried over MgSO₄ and concentrated and purified by silica gel chromatography with ethyl acetate/hexane to obtain the title compound (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (2.2 g, 3.72 mmol, 84% yield). LC-MS m/z 591.4 (M+H)⁺, 1.23 min (ret. Time).

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

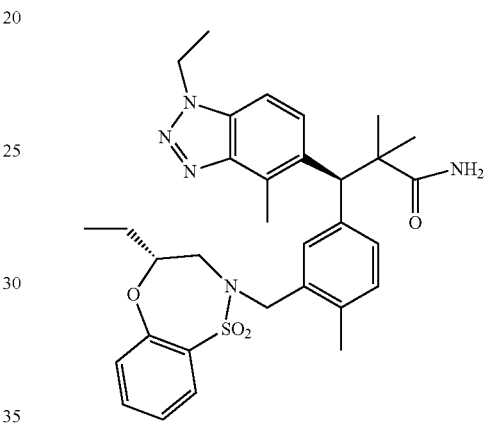

The (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (1.225 g, 2.074 mmol) in thionyl chloride (10.59 mL, 145 mmol) was stirred for 2 hrs. Then extra thionyl chloride was evaporated. The residue was dissolved in tetrahydrofuran (THF) (40 mL), ammonia was bubbled through the solution for 10 mins, and was stirred at ambient temperature for 18 hrs. The solid was filtered. The liquid was evaporated and the product purified by silica gel chromatography with hexane and ethyl acetate to obtain the title compound (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide (1.12 g, 1.899 mmol, 92% yield). LC-MS m/z 590.3 (M+H)⁺, 1.13 min (ret. Time). 1H NMR (400 MHz, DMSO-d6) δ ppm 0.90 (t, J=7.28 Hz, 3H) 1.04-1.27 (m, 7H) 1.29-1.53 (m, 4H) 2.24 (s, 3H) 2.64-2.75 (m, 4H) 3.58 (dd, J=15.06, 10.79 Hz, 1H) 3.83 (d, J=14.05 Hz, 1H) 3.94-4.12 (m, 1H) 4.38 (d, J=14.05 Hz, 1H) 4.67 (q, J=7.19 Hz, 2H) 4.81 (s, 1H) 6.70 (br. s., 1H) 7.05-7.21 (m, 4H) 7.23-7.40 (m, 2H) 7.56 (d, J=8.78 Hz, 1H) 7.61-7.74 (m, 2H) 7.77 (dd, J=7.78, 1.76 Hz, 1H)

Acids Supporting Compounds of Table 10

(S)-3-(3-(((S)-4-Ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoic Acid

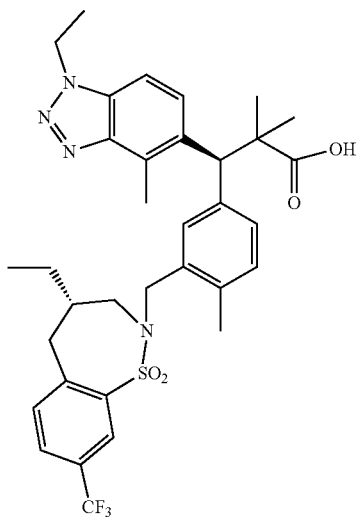 [SMILES: CC[C@H]1Cc2ccc(C(F)(F)F)cc2S(=O)(=O)N(Cc2cc([C@@H](c3ccc4c(nnn4CC)c3C)C(C)(C)C(=O)O)ccc2C)C1]

To a solution of methyl (S)-3-(1-ethyl-4-methyl-1H-benzo[d][1,2,3]triazol-5-yl)-3-(3-(hydroxymethyl)-4-methylphenyl)-2,2-dimethylpropanoate (884 mg, 2.235 mmol) in tetrahydrofuran (THF) (40 mL), (S)-4-ethyl-8-(trifluoromethyl)-2,3,4,5-tetrahydrobenzo[f][1,2]thiazepine 1,1-dioxide (721 mg, 2.459 mmol) and (E)-diazene-1,2-diylbis(piperidin-1-ylmethanone) (1128 mg, 4.47 mmol) were added, then tributylphosphane (904 mg, 4.47 mmol) was added. The reaction mixture was stirred at ambient temperature for 3 days. The solvent was evaporated. The crude product was purified by silica gel chromatography with ethyl acetate and hexane to obtain methyl (S)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoate (1.2 g, 1.789 mmol, 80% yield). To this in methanol (10 mL), LiOH (11.18 mL, 22.35 mmol) was added and the reaction heated with microwave at 120° C. for 3 hrs. The solvent was evaporated and the residue was partitioned between ethyl acetate and 1 N HCl. The water layer was extracted with ethyl acetate 2×. The combined organic phase was dried with MgSO$_4$ and concentrated and purified by silica gel chromatography with ethyl acetate and hexane to obtain the title compound (S)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanoic acid (1.04 g, 1.584 mmol, 70.8% yield). LC-MS m/z 657.8 (M+H)$^+$, 1.41 min (ret. Time). $^1$H NMR (400 MHz, METHANOL-d4) σppm 0.62 (t, J=7.40 Hz, 3H) 0.91-1.14 (m, 2H) 1.29 (s, 3H) 1.37 (s, 3H) 1.55-1.74 (m, 4H) 2.31 (s, 3H) 2.71 (s, 3H) 2.96 (br. s., 2H) 3.38-3.66 (m, 3H) 4.44 (d, J=13.80 Hz, 1H) 4.72 (q, J=7.36 Hz, 2H) 4.91 (s, 1H) 7.08-7.31 (m, 3H) 7.46-7.68 (m, 2H) 7.73-7.93 (m, 2H) 8.13 (d, J=1.51 Hz, 1H)

(R)-3-(3-(((S)-4-Ethyl-1,1-dioxido-8-(trifluoromethyl)-4,5-dihydrobenzo[f][1,2]thiazepin-2(3H)-yl)methyl)-4-methylphenyl)-3-((1-ethyl-1H-1,2,3-triazol-4-yl)methoxy)-2,2-dimethylpropanoic Acid

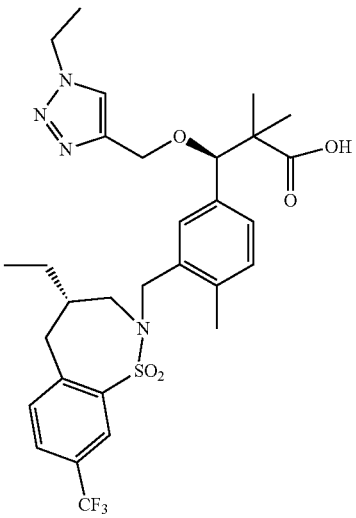 [SMILES: CC[C@H]1Cc2ccc(C(F)(F)F)cc2S(=O)(=O)N(Cc2cc([C@@H](OCc3cn(CC)nn3)C(C)(C)C(=O)O)ccc2C)C1]

To a solution of methyl (R)-3-((1-ethyl-1H-1,2,3-triazol-4-yl)methoxy)-3-(3-(hydroxymethyl)-4-methylphenyl)-2,2-dimethylpropanoate (158 mg, 0.437 mmol) in tetrahydrofuran (THF) (10 mL), ((S)-4-ethyl-8-(trifluoromethyl)-2,3,4,5-tetrahydrobenzo[f][1,2]thiazepine 1,1-dioxide (141 mg, 0.481 mmol) and (E)-diazene-1,2-diylbis (piperidin-1-ylmethanone) (221 mg, 0.874 mmol) were added, then tributylphosphane (0.218 mL, 0.874 mmol) was added. The reaction mixture was stirred at ambient temperature for 4 hrs. The solvent was evaporated. The crude product was purified by silica gel chromatography (solid loading) with ethyl acetate/hexane to obtain methyl (R)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-((1-ethyl-1H-1,2,3-triazol-4-yl)methoxy)-2,2-dimethylpropanoate (220 mg, 0.346 mmol, 79% yield). To this product in methanol (5 mL), LiOH (2.186 mL, 4.37 mmol, 2M) was added and the reaction was heated with microwave at 120° C. for 2 hrs. The solvent was evaporated. The crude product was partitioned between ethyl acetate and 1N HCl. The water layer was extracted with ethyl acetate (3×). The combined organic phase was dried over MgSO$_4$ and concentrated and purified by silica gel chromatography with ethyl acetate and hexane to obtain the title compound (R)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-((1-ethyl-1H-1,2,3-triazol-4-yl)methoxy)-2,2-dimethylpropanoic acid (182 mg, 0.292 mmol, 66.9% yield). LC-MS m/z 623.5 (M+H)$^+$, 1.33 min (ret. Time).

The compounds in Table 10 were prepared by a method similar to the one described for the preparation of (S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide. As is appreciated by those skilled in the art, these analogous examples may involve variations in general reaction conditions.

TABLE 10

| Ex # | Structure | Name | LCMS [M + 1] | Retention Time (min) |
|---|---|---|---|---|
| Example 88 | 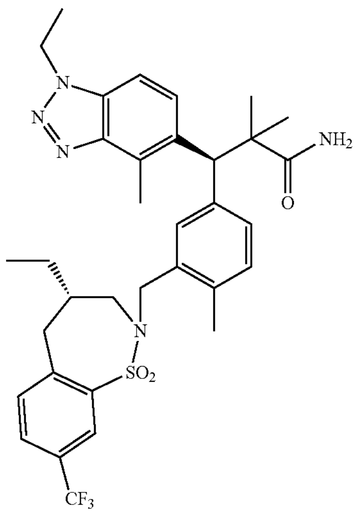 [SMILES: CC[C@H]1Cc2ccc(C(F)(F)F)cc2S(=O)(=O)N(Cc2cc([C@@H](c3ccc4c(nnn4CC)c3C)C(C)(C)C(N)=O)ccc2C)C1] | (S)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethylpropanamide | 656.6 | 1.31 |
| Example 89 | 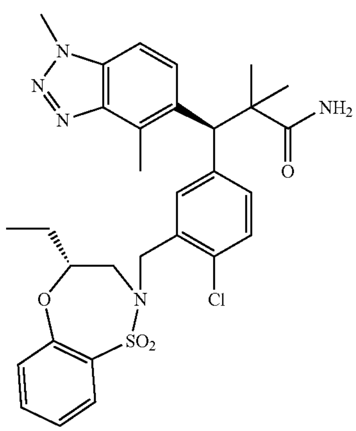 [SMILES: CC[C@@H]1CN(Cc2cc([C@@H](c3ccc4c(nnn4C)c3C)C(C)(C)C(N)=O)ccc2Cl)S(=O)(=O)c2ccccc2O1] | (S)-3-(4-chloro-3-(((R)-4-ethyl-1,1-dioxido-3,4-dihydro-2H-benzo[b][1,4,5]oxathiazepin-2-yl)methyl)phenyl)-3-(1,4-dimethyl-1H-benzo[d][1,2,3]triazol-5-yl)-2,2-dimethylpropanamide | 596.5 | 1.13 |
| Example 90 | 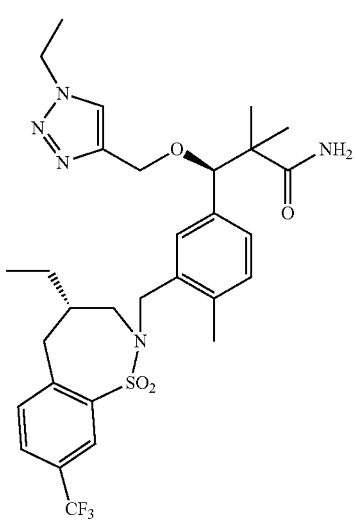 [SMILES: CC[C@H]1Cc2ccc(C(F)(F)F)cc2S(=O)(=O)N(Cc2cc([C@@H](OCc3cn(CC)nn3)C(C)(C)C(N)=O)ccc2C)C1] | (R)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-((1-ethyl-1H-1,2,3-triazol-4-yl)methoxy)-2,2-dimethylpropanamide | 622.6 | 1.24 |

Example 91

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propanamide

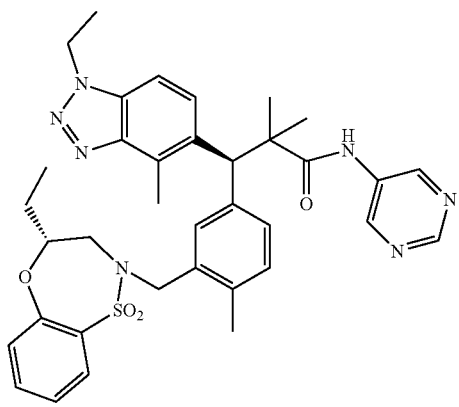 [SMILES: CC[C@@H]1CN(Cc2cc([C@@H](c3ccc4c(nnn4CC)c3C)C(C)(C)C(=O)Nc3cncnc3)ccc2C)S(=O)(=O)c2ccccc2O1]

(S)-3-(1-Ethyl-4-methyl-1H-benzo[d][1,2,3]triazol-5-yl)-3-(3-(((4-methoxybenzyl)oxy)methyl)-4-methylphenyl)-2,2-dimethylpropanoic acid

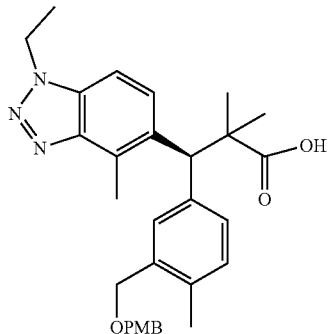

To a solution of methyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (2400 mg, 4.65 mmol) in methanol (15.00 mL), LiOH (23.27 mL, 46.5 mmol) was added. The mixture was heated via microwave at high absorption for 3 hrs at 120° C. The solvent was evaporated. The residue was partitioned between ethyl acetate and 1 N HCl. The water layer was extracted with ethyl acetate (3×). The combined organic phase was dried over MgSO$_4$ and concentrated. The product was purified by silica gel chromatography with hexane and ethyl acetate to obtain the title compound (S)-3-(1-ethyl-4-methyl-1H-benzo[d][1,2,3]triazol-5-yl)-3-(3-(((4-methoxybenzyl)oxy) methyl)-4-methylphenyl)-2,2-dimethylpropanoic acid (2.2 g, 4.39 mmol, 94% yield). LC-MS m/z 502.4 (M+H)$^+$, 1.23 min (ret. Time).

Phenyl N-tert-butyl-N'-(pyrimidin-5-yl)carbamimidothioate

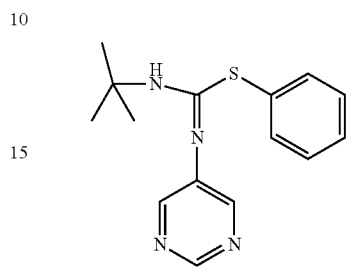

To a solution of 2-isocyano-2-methylpropane (2.033 mL, 17.98 mmol), S-phenyl benzenesulfonothioate (1800 mg, 7.19 mmol) and pyrimidin-5-amine (1026 mg, 10.79 mmol) in 2-methyltetrahydrofuran (2-MeTHF) (10 mL), copper(I) iodide (137 mg, 0.719 mmol) was added. The reaction mixture was stirred at 75° C. for 16 hrs. The reaction mixture was filtered through silica and the solvent was evaporated and the product purified by silica gel chromatography with hexane and ethyl acetate to obtain the title compound phenyl N-(tert-butyl)-N'-(pyrimidin-5-yl)carbamimidothioate (1.98 g, 6.91 mmol, 96% yield). LC-MS m/z 287.2 (M+H)$^+$, 1.06 min (ret. Time).

(S)-3-(1-ethyl-4-methyl-1H-benzo[d][1,2,3]triazol-5-yl)-3-(3-(((4-methoxybenzyl)oxy)methyl)-4-methylphenyl)-2,2-dimethyl-N-(pyrimidin-5-yl)propanamide

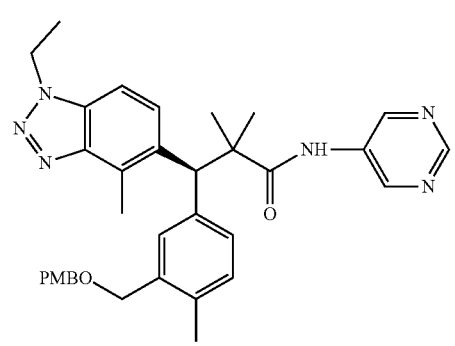

To a solution of (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoic acid (1400 mg, 2.79 mmol) in isopropanol (4 mL), phenyl (E)-N-(tert-butyl)-N'-(pyrimidin-5-yl)carbamimidothioate (1039 mg, 3.63 mmol) and tris(((Z)-4-oxopent-2-en-2-yl)oxy) iron (99 mg, 0.279 mmol) were added. The reaction mixture was heated in a Biotage microwave at high absorption for 2 hrs at 120° C. The solvent was evaporated and the product purified by silica gel chromatography with DCM and MeOH to get the desired product which was then purified by preparative reverse phase HPLC under acid (TFA) to obtain the title compound (S)-3-(1-ethyl-4-methyl-1H-benzo[d][1,2,3]triazol-5-yl)-3-(3-(((4-methoxybenzyl)oxy)methyl)-4-methylphenyl)-2,2-dimethyl-N-(pyrimidin-5-yl)propanamide (300 mg, 0.518 mmol, 18.57% yield). LC-MS m/z 579.5 (M+H)+, 1.17 min (ret. Time).

(S)-3-(1-Ethyl-4-methyl-1H-benzo[d][1,2,3]triazol-5-yl)-3-(3-(hydroxymethyl)-4-methylphenyl)-2,2-dimethyl-N-(pyrimidin-5-yl)propanamide

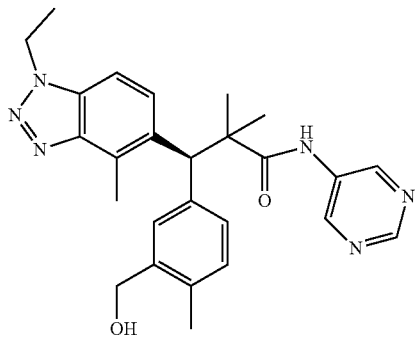 [SMILES: CCn1nnc2c(C)c([C@H](c3ccc(C)c(CO)c3)C(C)(C)C(=O)Nc3cncnc3)ccc21]

To a solution of (S)-3-(1-ethyl-4-methyl-1H-benzo[d][1,2,3]triazol-5-yl)-3-(3-(((4-methoxybenzyl)oxy)methyl)-4-methylphenyl)-2,2-dimethyl-N-(pyrimidin-5-yl)propanamide (1.46 g, 2.52 mmol) in a mixture of acetonitrile (20.00 mL) and water (2 mL), CAN (2.77 g, 5.05 mmol) was added at 0° C. Then the reaction mixture was stirred at ambient temperature for 4 hrs. The reaction mixture was partitioned between ethyl acetate and water. The water layer was extracted with ethyl acetate (2×). The combined organic phase was dried over MgSO4 and concentrated. The crude product was purified by silica gel chromatography with DCM and MeOH to get the desired product which was then purified by preparative reverse phase HPLC under acidic (TFA) condition to provide the title compound (S)-3-(1-ethyl-4-methyl-1H-benzo[d][1,2,3]triazol-5-yl)-3-(3-(hydroxymethyl)-4-methylphenyl)-2,2-dimethyl-N-(pyrimidin-5-yl)propanamide (750 mg, 1.636 mmol, 64.8% yield). LC-MS m/z 459.4 (M+H)+, 0.81 min (ret. Time).

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propanamide

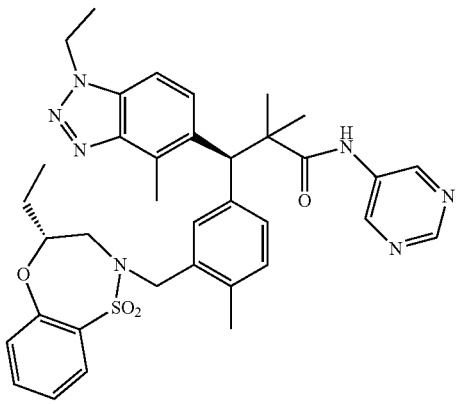 [SMILES: CC[C@@H]1CN(Cc2cc([C@@H](c3ccc4c(nnn4CC)c3C)C(C)(C)C(=O)Nc3cncnc3)ccc2C)S(=O)(=O)c2ccccc2O1]

To a solution of (S)-3-(1-ethyl-4-methyl-1H-benzo[d][1,2,3]triazol-5-yl)-3-(3-(hydroxymethyl)-4-methylphenyl)-2,2-dimethyl-N-(pyrimidin-5-yl)propanamide (48 mg, 0.105 mmol) in dichloromethane (DCM) (2 mL), thionyl chloride (0.015 mL, 0.209 mmol) was added. The reaction was stirred at ambient temperature for 1 hr. The solvent was evaporated and the crude product carried to the next step without further purification.

To a solution of (R)-4-ethyl-3,4-dihydro-2H-benzo[b][1,4,5]oxathiazepine 1,1-dioxide (26.2 mg, 0.115 mmol) in N,N-dimethylformamide (DMF) (2.000 mL) at ambient temperature, NaH (60% by weight) (8.37 mg, 0.209 mmol) was added. The reaction mixture was stirred at ambient temperature for 1 hr, then crude chloride compound in N,N-dimethylformamide (DMF) (1.000 mL) was added. The reaction mixture was stirred at ambient temperature for 16 hrs. The reaction mixture was partitioned between ethyl acetate and water. The water layer was extracted with ethyl acetate (2×). The combined organic phase was dried over MgSO4 and concentrated and purified by preparative reverse phase HPLC under acidic (formic acid) condition to obtain the title compound (S)-3-(3-(((R)-4-ethyl-1,1-dioxido-3,4-dihydro-2H-benzo[b][1,4,5]oxathiazepin-2-yl)methyl)-4-methylphenyl)-3-(1ethyl4methyl-1H-benzo[d][1,2,3]triazol-5-yl)-2,2-dimethyl-N-(pyrimidin-5-yl)propanamide (45 mg, 0.064 mmol, 61.2% yield). LC-MS m/z 668.6 (M+H)+, 1.18 min (ret. Time). 1H NMR (400 MHz, DMSO-d6) δ ppm 0.89 (t, J=7.28 Hz, 3H) 1.12 (d, J=4.02 Hz, 1H) 1.36-1.52 (m, 7H) 1.97-2.16 (m, 3H) 2.21 (s, 3H) 2.69-2.82 (m, 4H) 3.57 (dd, J=15.06, 10.29 Hz, 1H) 3.78-3.91 (m, 1H) 3.90-4.08 (m, 1H) 4.35 (d, J=14.56 Hz, 1H) 4.65 (q, J=7.28 Hz, 2H) 4.97 (s, 1H) 7.05-7.22 (m, 2H) 7.26-7.40 (m, 3H) 7.54-7.80 (m, 4H) 8.67-8.85 (m, 3H) 9.64 (s, 1H)

The compounds in Table 11 were prepared by a method similar to the one described for the preparation of (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propanamide As is appreciated by those skilled in the art, these analogous examples may involve variations in general reaction conditions.

TABLE 11

| Ex # | Structure | Name | LCMS [M + 1] | Retention Time (min) |
|---|---|---|---|---|
| Example 92 | 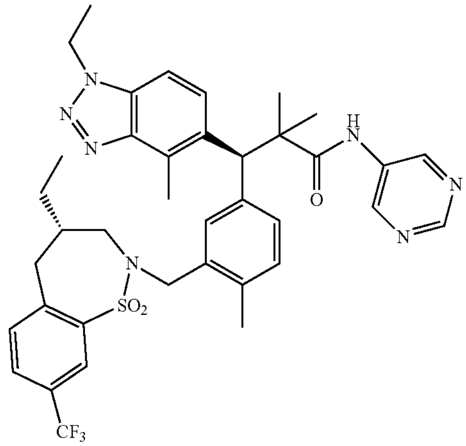 [SMILES: CC[C@H]1Cc2ccc(C(F)(F)F)cc2S(=O)(=O)N(Cc2cc([C@@H](c3ccc4c(nnn4CC)c3C)C(C)(C)C(=O)Nc3cncnc3)ccc2C)C1] | (S)-3-(3-(((S)-4-Ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(pyrimidin-5-yl)propanamide | 734.7 | 1.36 |
| Example 93 | 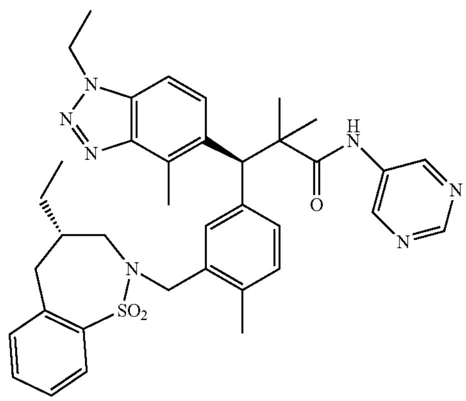 [SMILES: CC[C@H]1Cc2ccccc2S(=O)(=O)N(Cc2cc([C@@H](c3ccc4c(nnn4CC)c3C)C(C)(C)C(=O)Nc3cncnc3)ccc2C)C1] | (S)-3-(3-(((S)-4-Ethyl-1,1-dioxido-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(pyrimidin-5-yl)propanamide | 666.6 | 1.25 |
| Example 94 | 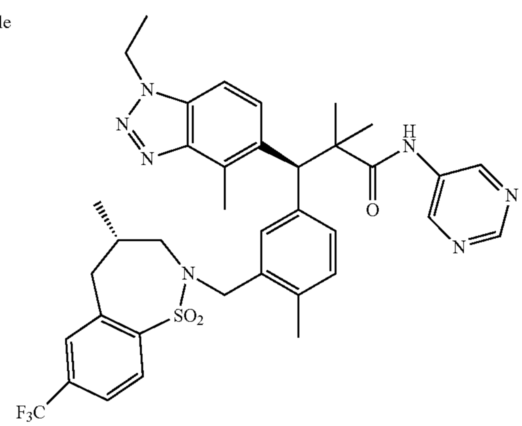 | (S)-3-(1-Ethyl-4-methyl-1H-benzo[d][1,2,3]triazol-5-yl)-2,2-dimethyl-3-(4-methyl-3-(((S)-4-methyl-1,1-dioxido-7-(trifluoromethyl)-4,5-dihydrobenzo[f][1,2]thiazepin-2(3H)-yl)methyl)phenyl)-N-(pyrimidin-5-yl)propanamide | 720.6 | 1.30 |

TABLE 11-continued

| Ex # | Structure | Name | LCMS [M + 1] | Retention Time (min) |
|---|---|---|---|---|
| Example 95 | 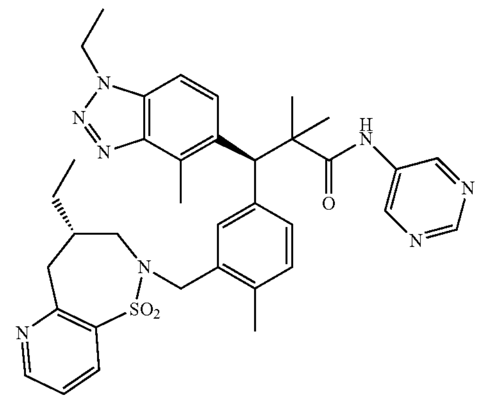 [SMILES: CC[C@H]1Cc2ncccc2S(=O)(=O)N(Cc2cc([C@@H](c3ccc4c(nnn4CC)c3C)C(C)(C)C(=O)Nc3cncnc3)ccc2C)C1] | (S)-3-(3-(((S)-4-Ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(pyrimidin-5-yl)propanamide | 667.6 | 1.11 |
| Example 96 | 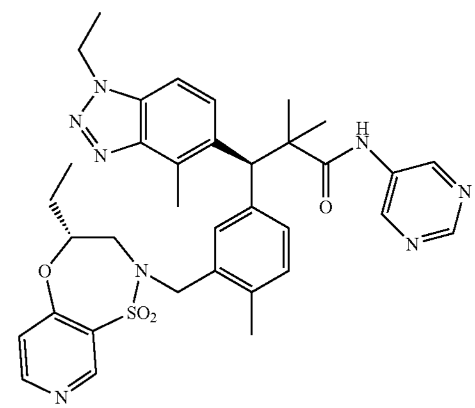 [SMILES: CC[C@@H]1CN(Cc2cc([C@@H](c3ccc4c(nnn4CC)c3C)C(C)(C)C(=O)Nc3cncnc3)ccc2C)S(=O)(=O)c2cnccc2O1] | (S)-3-(3-(((R)-4-Ethyl-1,1-dioxido-3,4-dihydro-2H-pyrido[4,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propanamide | 669.5 | 1.04 |
| Example 97 | 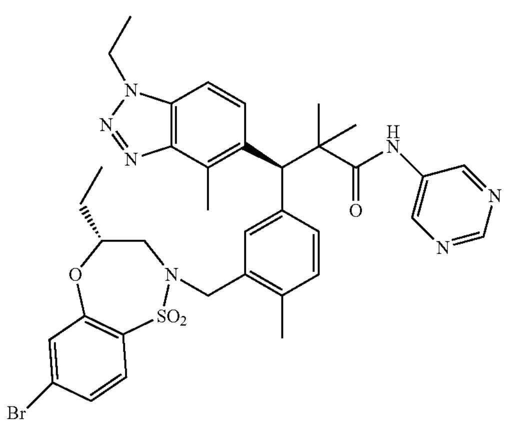 [SMILES: CC[C@@H]1CN(Cc2cc([C@@H](c3ccc4c(nnn4CC)c3C)C(C)(C)C(=O)Nc3cncnc3)ccc2C)S(=O)(=O)c2ccc(Br)cc2O1] | (S)-3-(3-(((R)-7-Bromo-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propanamide | 746.4, 748.5 | 1.30 |

TABLE 11-continued

| Ex # | Structure | Name | LCMS [M + 1] | Retention Time (min) |
|---|---|---|---|---|
| Example 98 | 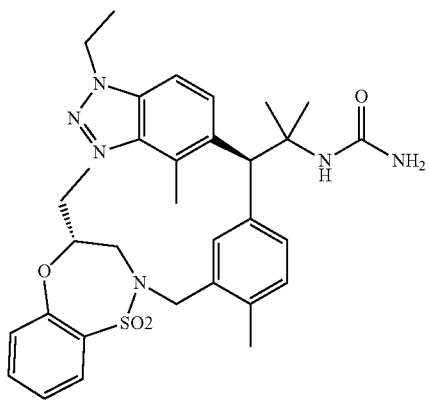 [SMILES: CC[C@@H]1CN(Cc2cc([C@@H](c3ccc4c(nnn4CC)c3C)C(C)(C)NC(N)=O)ccc2C)S(=O)(=O)c2ccccc2O1] | (S)-3-(3-(((R)-8-Bromo-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propanamide | 746.5 | 1.30 |

Example 99

1-((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)urea

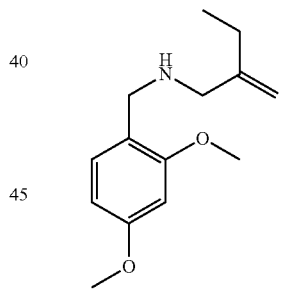

Isocyanatotrimethylsilane (8.68 µl, 0.064 mmol) was added to (R)-2-(5-((S)-2-amino-1-(1-ethyl-4-methyl-1H-benzo[d][1,2,3]triazol-5-yl)-2-methylpropyl)-2-methylbenzyl)-4-ethyl-3,4-dihydro-2H-benzo[b][1,4,5]oxathiazepine 1,1-dioxide (30 mg, 0.053 mmol). The reaction was stirred at 90° C. for 2 hrs. Then the reaction mixture was treated with MeOH. The solvent was evaporated and the product purified by preparative reverse phase HPLC under acidic (TFA) conditions to obtain the title compound 1-((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)urea (5.6 mg, 9.26 µmol, 17.34% yield). LC-MS m/z 605.5 (M+H)$^+$, 1.11 min (ret. Time). 1H NMR (400 MHz, CHLOROFORM-d) σppm 1.08 (t, J=7.28 Hz, 3H) 1.38-1.53 (m, 4H) 1.58-1.81 (m, 4H) 2.15-2.27 (m, 6H) 2.79 (s, 3H) 3.21 (dd, J=14.81, 1.76 Hz, 1H) 3.68 (dd, J=14.93, 10.67 Hz, 1H) 3.91-4.17 (m, 2H) 4.27 (d, J=15.81 Hz, 1H) 4.58-4.73 (m, 2H) 4.81 (s, 1H) 5.22 (br. s., 1H) 7.08-7.34 (m, 6H) 7.35-7.46 (m, 2H) 7.57 (td, J=7.78, 1.76 Hz, 1H) 7.85 (dd, J=7.91, 1.63 Hz, 1H) 8.01 (d, J=8.78 Hz, 1H)

N-(2,4-Dimethoxybenzyl)-2-methylenebutan-1-amine

To a solution of 2-methylenebutanal (50 g, 594 mmol) in toluene (500 mL) was added (2,4-dimethoxyphenyl)methanamine (99 g, 594 mmol) and stirred at 110° C. for 48 hr. The reaction mixture was concentrated and dissolved in ethanol (300 mL). NaBH$_4$ (45.0 g, 1189 mmol) was added at 0° C. and the reaction stirred at ambient temperature for 6 hr. The reaction mixture was evaporated under reduced pressure, quenched with water (400 mL) and extracted with DCM (2×800 mL). The organic layer was dried over anhydrous Na$_2$SO$_4$ and filtered. The filtrate was evaporated under reduced pressure and the crude product was purified by column chromatography eluting with EtOAc:Hexane (15:85), to afford the title compound (75 g, 185 mmol, 31.1% yield), LCMS m/z 236 (M+H)$^+$, 1.51 min (ret. time).

2-Chloropyridine-3-sulfonyl Chloride

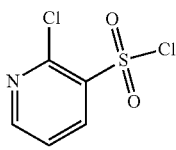 [SMILES: O=S(=O)(Cl)c1cccnc1Cl]

Step A: Thionyl chloride (159 mL, 2178 mmol) was added drop wise over 60 min to water (450 mL) at 0° C. The solution was allowed to stirred at ambient temperature for 17 h then copper(I) chloride (0.554 g, 5.60 mmol) was added to the mixture at −3° C. and the resulting yellow green solution was stirred for 1 hour at −3° C.

Step B: 37% HCl (503 mL, 6129 mmol) was added with vigorous stirring to 2-chloropyridin-3-amine (40 g, 311 mmol) at −5° C. and a solution of sodium nitrite (37.8 g, 548 mmol) in water (82 mL) was added drop wise over 45 min, the temperature of the reaction mixture was maintained at −5° C. and stirred for 10 min.

Step C: The mixture obtained from step B was added to the solution obtained from step A over 30 min at −3° C. The reaction mixture was maintained at 0° C. for 75 min with vigorous stirring. The solid was filtered and dried to give the title compound (20 g, 92 mmol, 29.5% yield) as brown color solid. LCMS m/z 212.02 (M+H)$^+$, 2.058 min (ret. time)

2-Chloro-N-(2,4-dimethoxybenzyl)-N-(2-methylenebutyl)pyridine-3-sulfonamide

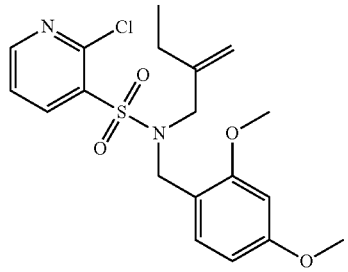 [SMILES: C=C(CC)CN(Cc1ccc(OC)cc1OC)S(=O)(=O)c1cccnc1Cl]

To a solution of N-(2,4-dimethoxybenzyl)-2-methylenebutan-1-amine (30 g, 83 mmol) in dichloromethane (DCM) (300 mL) was added 2-chloropyridine-3-sulfonyl chloride (17.57 g, 83 mmol) and TEA (23.10 mL, 166 mmol) at 0° C. The reaction mixture was stirred at ambient temperature for 16 h. The reaction mixture was quenched with ice water, and extracted with DCM (2×300 mL). The organic layer was washed with cold water (2×300 mL), and brine (200 mL). The organic layer was dried over anhydrous Na$_2$SO$_4$ and filtered. The filtrate was evaporated under reduced pressure and the crude compound was purified by column chromatography eluting with EtOAc:Hexane (11:89) as solvent to afford the title compound. (28 g, 53.5 mmol, 64.5% yield). LCMS m/z 411 (M+H)$^+$, 2.73 min (ret. time).

2-Chloro-N-(2-methylenebutyl)pyridine-3-sulfonamide N60160-98-A2

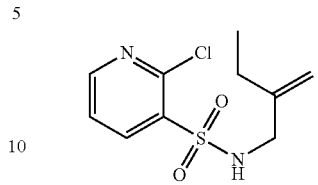

To a solution of 2-chloro-N-(2,4-dimethoxybenzyl)-N-(2-methylenebutyl)pyridine-3-sulfonamide (28 g, 53.1 mmol) in dichloromethane (DCM) (280 mL) was added anisole (9 mL, 82 mmol) and TFA (30 mL, 389 mmol) at 0° C. The reaction mixture was stirred at ambient temperature for 16 h. The reaction mixture was concentrated under vacuum, quenched with saturated NaHCO$_3$, and extracted with DCM (2×250 mL). The organic layer was dried over anhydrous Na$_2$SO$_4$ and filtered. The filtrate was evaporated under reduced pressure and purified by column chromatography eluting with EtOAc:Hexane (12:88) as solvent to afford the title compound. (13 g, 38.0 mmol, 71.6% yield), LCMS m/z 260 (M+H)$^+$, 1.97 min (ret. time).

4-Ethyl-2,3,4,5-tetrahydropyrido[2,3-f][1,2]thiazepine 1,1-dioxide

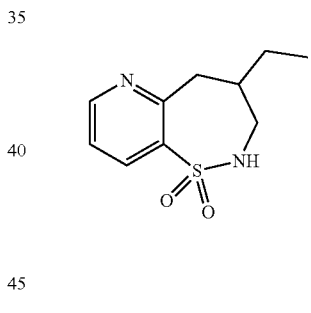

To a solution of 2-chloro-N-(2-methylenebutyl)pyridine-3-sulfonamide (14 g, 46.2 mmol) in benzene (90 mL) was added AIBN (3.79 g, 23.09 mmol) and tributylstannane (40.3 g, 139 mmol) at 65° C. The reaction was stirred at 85° C. for 16 h. The reaction mixture was evaporated under reduced pressure and purified by column chromatography eluting with EtOAc:Hexane (14:86) as solvent to afford the title compound (14 g, 28.2 mmol, 61.1% yield) LCMS m/z 227 (M+H)$^+$, 1.74 min (ret. time). This batch compound was combined with other batches of this compound prepared by the same method, and purified by column chromatography eluting with using EtOAc:Hexane (12:88) as solvent. The solvents were concentrated and the compound was cooled to 0° C. and washed with pentane (40 mL) and diethyl ether (15 mL) to afford the title compound. (5.1 g, 97% pure) LCMS m/z 227 (M+H)$^+$, 1.55 min (ret. time).

(S)-4-Ethyl-2,3,4,5-tetrahydropyrido[2,3-f][1,2]thi-
azepine 1,1-dioxide and (R)-4-ethyl-2,3,4,5-tetrahy-
dropyrido[2,3-f][1,2]thiazepine 1,1-dioxide

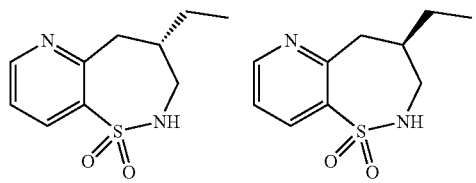

The compound was resolved by chiral SFC (Column: Chiralpak AS-H (30×250 mm), 5p; Co-solvent: 20% EtOH; Flowrate: 100 g/min; Back pressure: 100Bar, 80% $CO_2$) to provide (S)-4-ethyl-2,3,4,5-tetrahydropyrido[2,3-f][1,2]thiazepine 1,1-dioxide (2.29 g, 45% yield). LCMS m/z 227 $(M+H)^+$, 1.94 min (ret. time), (chiral SFC ret. time: 4.07 min) and (R)-4-ethyl-2,3,4,5-tetrahydropyrido[2,3-f][1,2] thiazepine 1,1-dioxide (2.3 g, 46% yield). LCMS m/z 227 $(M+H)^+$, 1.98 min (ret. time), (chiral SFC ret. time: 4.53 min).

Example 100

(3S)-3-(1,4-Dimethyl-1H-benzo[d][1,2,3]triazol-5-yl)-3-(3-(((R)-2-ethyl-2,3-dihydropyrido[3,44][1,4] oxazepin-4(5H)-yl)methyl)-4-methylphenyl)-2,2-dimethyl-N-(tetrahydrofuran-3-yl)propanamide

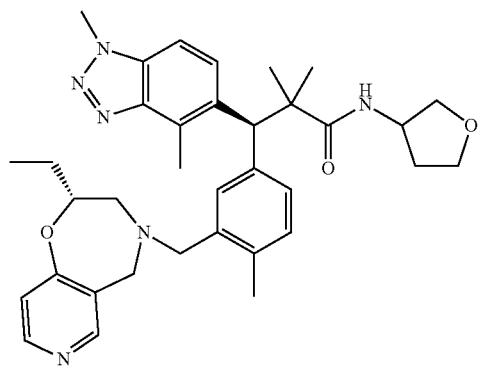 [SMILES: CC[C@@H]1CN(Cc2cc([C@@H](c3ccc4c(nnn4C)c3C)C(C)(C)C(=O)NC3CCOC3)ccc2C)Cc2cnccc2O1]

To a solution of (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (100 mg, 0.190 mmol) and tetrahydrofuran-3-amine (19.81 mg, 0.227 mmol) in N,N-dimethylformamide (DMF) (1 mL) was added DIEA (0.099 mL, 0.569 mmol) and HATU (72.1 mg, 0.190 mmol). The mixture was allowed to stir at 25° C. for 20 hrs. The reaction was then diluted with water and extracted with ethyl acetate (3×30 mL). The combined organic layer was dried over magnesium sulfate, filtered, and concentrated to dryness. The residue was dissolved in 3 mL of DMSO, filtered, and purified by reverse phase preparative HPLC under neutral conditions to obtain the title compound (42.9 mg, 0.072 mmol, 37.9% yield) as a colorless solid. LC-MS m/z 598.5 $(M+H)^+$, 0.88 min (ret. time). $^1$H NMR (400 MHz, METHANOL-$d_4$) δ ppm 0.82-1.00 (m, 3H) 1.30-1.39 (m, 7H) 1.39-1.68 (m, 3H) 1.89-2.04 (m, 1H) 2.26 (s, 3H) 2.68-2.90 (m, 5H) 3.17-3.29 (m, 1H) 3.55-3.78 (m, 6H) 3.81-3.99 (m, 2H) 4.15-4.33 (m, 4H) 4.89 (d, J=7.53 Hz, 1H) 6.98 (d, J=5.52 Hz, 1H) 7.04-7.19 (m, 3H) 7.48 (d, J=8.78 Hz, 1H) 7.69-7.80 (m, 1H) 8.09 (s, 1H) 8.30 (d, J=5.27 Hz, 1H)

Intermediate for Making Example 104

(E)-tert-butyl 3-(1-Ethyl-4-methyl-1H-benzo[d][1,2,3]triazol-5-yl)acrylate

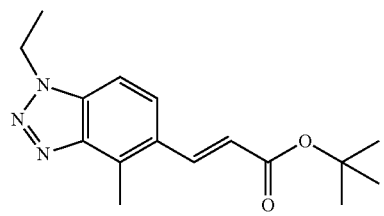 [SMILES: CCn1nnc2c(C)c(/C=C/C(=O)OC(C)(C)C)ccc21]

A mixture of tri-o-tolylphosphine (3.80 g, 12.49 mmol) tert-butyl acrylate (32.0 g, 250 mmol) triethylamine (17.42 mL, 125 mmol) 5-bromo-1-ethyl-4-methyl-1H-benzo[d][1,2,3]triazole (30.0 g, 125 mmol) and PdOAc$_2$ (2.244 g, 10.00 mmol) in N,N-dimethylformamide (DMF) (250.0 mL) was stirred at 120° C. under nitrogen for 12 hrs. The mixture was poured into water and extracted with ethyl acetate (300 ml×3). The organic layer was dried over Na$_2$SO$_4$ and concentrated. The residue was purified by combiflash chromatography eluting with (hexane:ethyl acetate=4:1) (silica gel, 120 g), to obtain the title compound (E)-tert-butyl 3-((1-ethyl-4-methyl-1H-benzo[d][1,2,3]triazol-5-yl)acrylate (26.3 g, 87 mmol, 69.6% yield) LCMS m/z 288.0 $(M+H)^+$, 1.87 min (ret. time). $^1$H NMR (500 MHz, CDCl3) δ 8.05 (d, J=15.9 Hz, 1H), 7.70 (d, J=8.7 Hz, 1H), 7.34 (d, J=8.7 Hz, 1H), 6.35 (d, J=15.9 Hz, 1H), 4.67 (q, J=7.4 Hz, 2H), 2.90 (s, 3H), 1.65-1.61 (t, 3H), 1.56 (s, 9H).

Tert-butyl 3-(1-Ethyl-4-methyl-1H-benzo[d][1,2,3]triazol-5-yl)-3-(3-(hydroxymethyl)-4-methylphenyl)propanoate

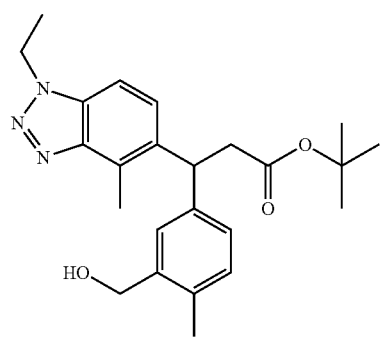 [SMILES: CCn1nnc2c(C)c(C(CC(=O)OC(C)(C)C)c3ccc(C)c(CO)c3)ccc21]

To [Rh(nbd)$_2$]BF4 (0.976 g, 2.61 mmol) was added (R,R)-Chiraphos (1.224 g, 2.87 mmol) and (2-methyl-5-(4,4,5,5-tetramethyl-1,3,2-dioxaborolan-2-yl)phenyl)methanol (6.48 g, 26.1 mmol), followed by 1,4-dioxane (60 mL), purged with N2 and the reaction was stirred at ambient temperature for 45 mins. Then tert-butyl (E)-3-(1-ethyl-4-methyl-1H-benzo[d][1,2,3]triazol-5-yl)acrylate (3 g, 10.44 mmol), and KOH (10.44 mL, 10.44 mmol) were added and purged with N2. The reaction mixture was stirred at 95° C. under nitrogen atmosphere for 3 hrs. After it was cooled to ambient temperature, the solvent was evaporated. The residue was partitioned between EtOAc and H$_2$O. The water layer was extracted with EtOAc (2×). The combined organic phase was dried over MgSO$_4$ and concentrated. The crude product was purified via silica gel chromatography with hexane and ethyl acetate to obtain the title compound get the title compound tert-butyl 3-(1-ethyl-4-methyl-1H-benzo[d][1,2,3]triazol-5-yl)-3-(3-(hydroxymethyl)-4-methylphenyl)propanoate (3.9 g, 9.52 mmol, 91% yield). LCMS m/z 430.2 (M+H)$^+$, 1.12 min (ret. time).

(S)-tert-butyl 3-(1-Ethyl-4-methyl-1H-benzo[d][1,2,3]triazol-5-yl)-3-(3-(hydroxymethyl)-4-methylphenyl)propanoate

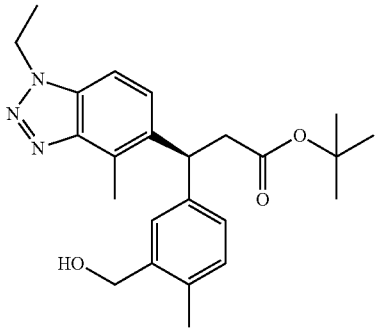 [SMILES: CCn1nnc2c(C)c([C@@H](CC(=O)OC(C)(C)C)c3ccc(C)c(CO)c3)ccc21]

This was resolved by Chiral SFC (Column: IA 20×250 mm, 5 u; Co-solvent: 20% EtOH; Flowrate: 80 g/min; Back pressure: 100 Bar) to give (S)-tert-butyl 3-(1-ethyl-4-methyl-1H-benzo[d][1,2,3]triazol-5-yl)-3-(3-(hydroxymethyl)-4-methylphenyl)propanoate (chiral SFC ret. time: 2.37 min) and (R)-tert-butyl 3-(1-ethyl-4-methyl-1H-benzo[d][1,2,3]triazol-5-yl)-3-(3-(hydroxymethyl)-4-methylphenyl)propanoate (chiral SFC ret. time: 3.87 min)

Tert-Butyl (S)-3-(3-(((S)-4-ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)propanoate

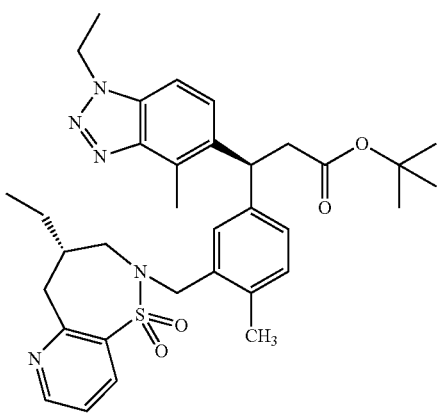 [SMILES: CC[C@H]1Cc2ncccc2S(=O)(=O)N(Cc2cc([C@H](CC(=O)OC(C)(C)C)c3ccc4c(nnn4CC)c3C)ccc2C)C1]

To a solution of tert-butyl (S)-3-(1-ethyl-4-methyl-1H-benzo[d][1,2,3]triazol-5-yl)-3-(3-(hydroxymethyl)-4-methylphenyl)propanoate (440 mg, 1.074 mmol) in dichloromethane (DCM) (6 mL) was added thionyl chloride (0.157 mL, 2.149 mmol). The reaction was stirred at ambient temperature for 25 minutes at which point LCMS showed the reaction to be complete. The reaction mixture was then concentrated to dryness to give tert-butyl (S)-3-(3-(chloromethyl)-4-methylphenyl)-3-(1-ethyl-4-methyl-1H-benzo[d][1,2,3]triazol-5-yl)propanoate to be used in the following step without purification.

A solution of (S)-4-ethyl-2,3,4,5-tetrahydropyrido[2,3-f][1,2]thiazepine 1,1-dioxide (292 mg, 1.289 mmol) in N,N-dimethylformamide (DMF) (6.00 mL) was cooled to 0° C. and NaH (129 mg, 3.22 mmol) was added. The reaction was stirred for 30 minutes and then a solution of tert-butyl (S)-3-(3-(chloromethyl)-4-methylphenyl)-3-(1-ethyl-4-methyl-1H-benzo[d][1,2,3]triazol-5-yl)propanoate in N,N-dimethylformamide (DMF) (6.00 mL) was added in. The reaction was allowed to warm to ambient temperature as it stirred for 17 hours. After 17 hrs, LCMS showed the reaction to be complete. The reaction mixture was then diluted with water and extracted with EtOAc (×3). The combined organic layers were washed with brine, dried over sodium sulfate, filtered, and concentrated to dryness. The crude product was then purified via flash chromatography to give the desired product (666.1 mg, 1.078 mmol, 100% yield). LCMS m/z 618.4 (M+H)$^+$, 1.38 min (ret. time).

(S)-3-(3-(((S)-4-Ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)propanoic Acid

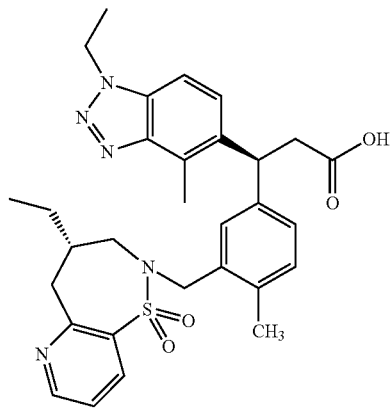 [SMILES: CC[C@H]1Cc2ncccc2S(=O)(=O)N(Cc2cc([C@H](CC(=O)O)c3ccc4c(nnn4CC)c3C)ccc2C)C1]

To a solution of tert-butyl (S)-3-(3-MS)-4-ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)propanoate (664 mg, 1.075 mmol) in dichloromethane (DCM) (8 mL) was added TFA (0.662 ml, 8.60 mmol). The reaction was allowed to stir for 21 hours at ambient temperature. LCMS showed the reaction to be complete. The reaction mixture was then evaporated, dissolved in DMSO, and purified via preparative HPLC under acidic (formic acid) conditions to give the title compound (563 mg, 1.002 mmol, 93% yield). LCMS m/z 562.3 (M+H)$^+$, 1.07 min (ret. time).

The compounds in Table 12 were prepared by a method similar to the one described for the preparation of (3S)-3-

(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(tetrahydrofuran-3-yl)propanamide. As is appreciated by those skilled in the art, these analogous examples may involve variations in general reaction conditions.

TABLE 12

| Ex # | Structure | Name | LCMS [M + 1] | Retention Time (min) |
|---|---|---|---|---|
| Example 101 | 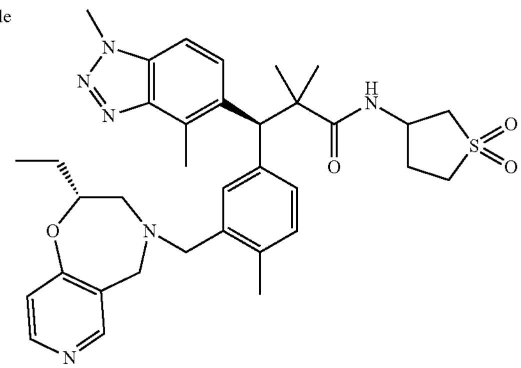 | (3S)-3-(1,4-Dimethyl-1H-benzo[d][1,2,3]triazol-5-yl)-N-(1,1-dioxidotetrahydrothiophen-3-yl)-3-(3-(((R)-2-ethyl-2,3-dihydropyrido[3,4-f][1,4]oxazepin-4(5H)-yl)methyl)-4-methylphenyl)-2,2-dimethylpropanamide | 646.6 | 0.64 |
| Example 102 | 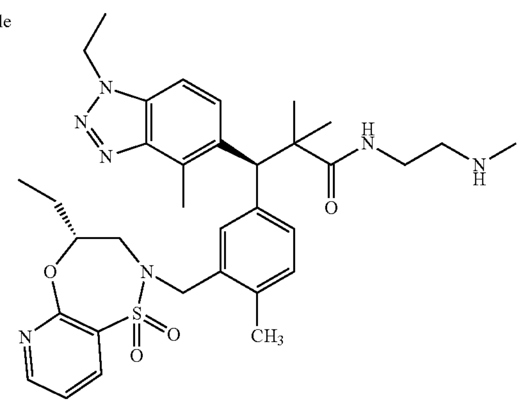 | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(2-(methylamino)ethyl)propanamide | 648.5 | 0.76 |
| Example 103 | 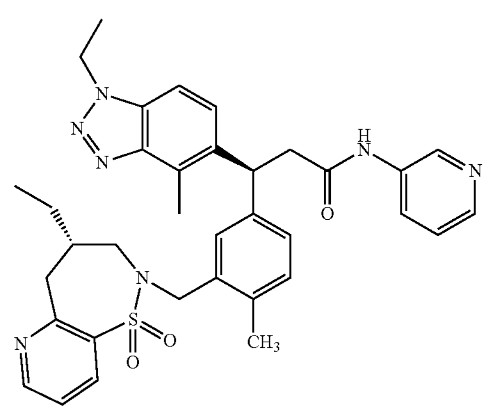 [SMILES: CC[C@H]1Cc2ncccc2S(=O)(=O)N(Cc2cc([C@H](CC(=O)Nc3cccnc3)c3ccc4c(nnn4CC)c3C)ccc2C)C1] | (S)-3-(3-(((S)-4-Ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)-N-(pyridin-3-yl)propanamide | 638.4 | 0.85 |

TABLE 12-continued

| Ex # | Structure | Name | LCMS [M + 1] | Retention Time (min) |
|---|---|---|---|---|
| Example 104 | 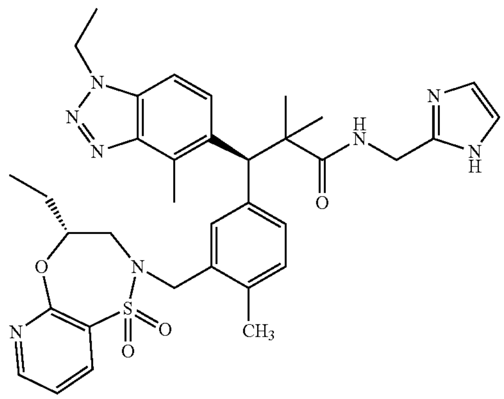 [SMILES: CC[C@@H]1CN(Cc2cc([C@@H](c3ccc4c(nnn4CC)c3C)C(C)(C)C(=O)NCc3ncc[nH]3)ccc2C)S(=O)(=O)c2cccnc2O1] | (S)-N-((1H-Imidazol-2-yl)methyl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide | 671.6 | 0.76 |
| Example 105 | 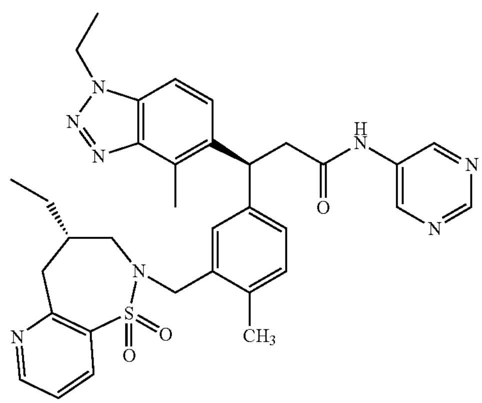 [SMILES: CC[C@H]1Cc2ncccc2S(=O)(=O)N(Cc2cc([C@H](CC(=O)Nc3cncnc3)c3ccc4c(nnn4CC)c3C)ccc2C)C1] | (S)-3-(3-(((S)-4-Ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)-N-(pyrimidin-5-yl)propanamide | 639.5 | 1.02 |
| Example 106 | 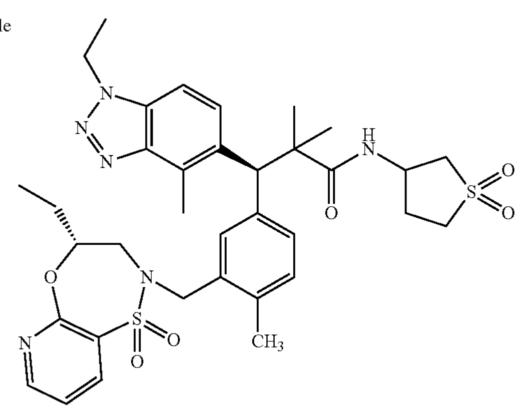 | (3S)-N-(1,1-Dioxidotetrahydrothiophen-3-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide | 709.6 | 1.03 |

TABLE 12-continued

| Ex # | Structure | Name | LCMS [M + 1] | Retention Time (min) |
|---|---|---|---|---|
| Example 107 | 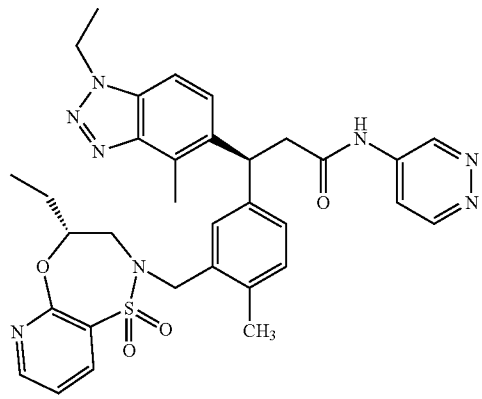 [SMILES: CC[C@@H]1CN(Cc2cc([C@H](CC(=O)Nc3ccnnc3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridazin-4-yl)propanamide | 641.4 | 0.87 |
| Example 108 | 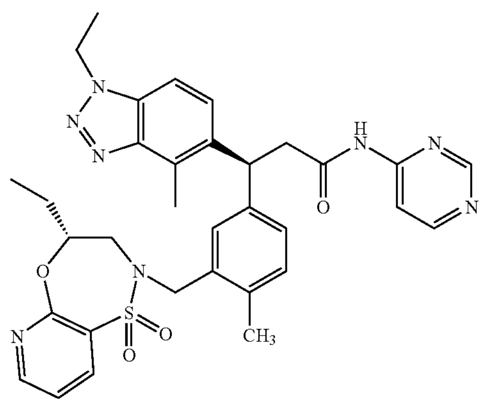 [SMILES: CC[C@@H]1CN(Cc2cc([C@H](CC(=O)Nc3ccncn3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyrimidin-4-yl)propanamide | 641.4 | 0.98 |
| Example 109 | 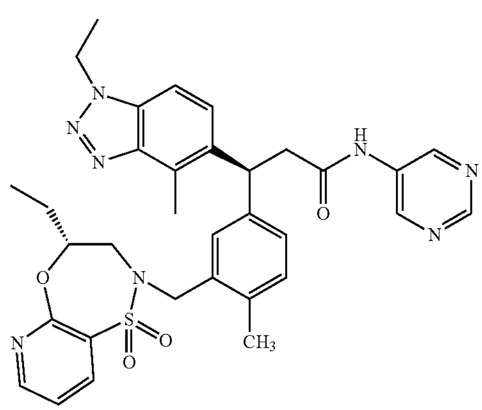 [SMILES: CC[C@@H]1CN(Cc2cc([C@H](CC(=O)Nc3cncnc3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyrimidin-5-yl)propanamide | 641.3 | 0.98 |

TABLE 12-continued

| Ex # | Structure | Name | LCMS [M + 1] | Retention Time (min) |
|---|---|---|---|---|
| Example 110 | 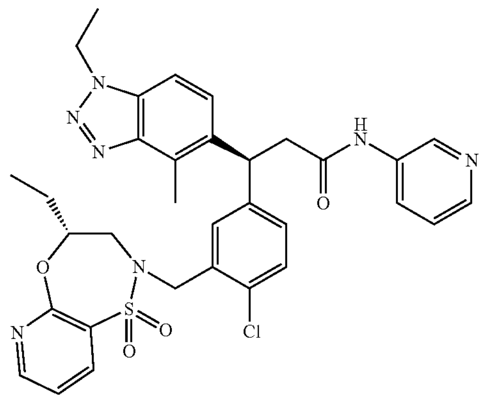 [SMILES: CC[C@@H]1CN(Cc2cc([C@H](CC(=O)Nc3cccnc3)c3ccc4c(nnn4CC)c3C)ccc2Cl)S(=O)(=O)c2cccnc2O1] | (S)-3-(4-Chloro-3-(((R)-4-ethyl-1,1-dioxido-3,4-dihydro-2H-pyrido[2,3-b][1,4,5]oxathiazepin-2-yl)methyl)phenyl)-3-(1-ethyl-4-methyl-1H-benzo[d][1,2,3]triazol-5-yl)-N-(pyridin-3-yl)propanamide | 660.3 | 0.83 |

(5-Bromo-2-chlorophenyl)methanol

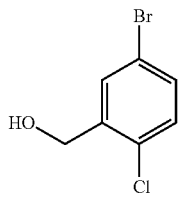

5-bromo-2-chlorobenzoic acid (2.5 g, 10.62 mmol) was dissolved in THF (53.1 mL) and the mixture was stirred at ambient temperature under nitrogen. Then, $BH_3$·THF (1.0 M in THF) (26.5 mL, 26.5 mmol) was added slowly and the light-yellow reaction mixture was stirred at ambient temperature for 22 h. Ethanol (2 mL) was added slowly to the reaction mixture followed by water (4 mL). The mixture was diluted with water (20 mL) and ethyl acetate (35 mL). More water (10 mL; 30 mL overall) was added. The aqueous layer was extracted with ethyl acetate (2×20 mL). Combined organic extracts were washed with a saturated aqueous solution of $NaHCO_3$ (2×10 mL), saturated aqueous NaCl (10 mL), dried ($Na_2SO_4$), filtered, and concentrated under reduced pressure to yield the crude product. This crude material was recrystallized from dichloromethane, and the filtrate resulting from the recrystallization was concentrated and purified on a silica cartridge (40 g) eluting at 40 mL/min with a gradient running from 100% hexanes to 40% ethyl acetate over 20 min. The pure products resulting from recrystallization and silica gel purification were combined to give the title compound as a white solid (1.6319 g, 69.4%). LC-MS m/z 203.0 (M−OH)+, 0.79 (ret. time).

(2-Chloro-5-(4,4,5,5-tetramethyl-1,3,2-dioxaborolan-2-yl)phenyl)methanol

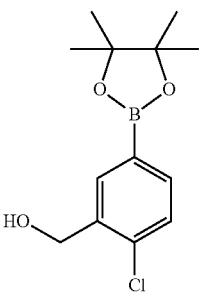 [SMILES: CC1(C)OB(c2ccc(Cl)c(CO)c2)OC1(C)C]

(5-bromo-2-chlorophenyl) methanol (0.5 g, 2.258 mmol) was dissolved in DMF (9 mL). Then, bis(pinacolato)diboron (0.688 g, 2.71 mmol) was added and the mixture was stirred. Potassium acetate (0.665 g, 6.77 mmol) was added quickly followed by $PdCl_2$ (dppf) (0.050 g, 0.068 mmol). The reaction mixture was heated via microwave at 100° C. (high absorption) for 1 h. This procedure was performed two more times to give two additional batches prepared in a similar manner to that reported here. Material from all three batches was combined and the combined reaction mixture was concentrated. The residue was taken up in ethyl acetate (100 mL) and filtered through a short pad of celite (1.5 g). The resulting black solids were discarded. The filtrate was transferred into a separatory funnel and washed with water (4×10 mL gently). The organic layer was then washed with saturated NaCl solution (10 mL), dried ($MgSO_4$) and filtered. An initial attempt to purify the combined crude material via silica gel chromatography (40 g column, 40 mL/min flow rate, 100% hexanes to 50 ethyl acetate gradient over 23 min) did not produce clean product. Fractions were recombined and the crude material was adsorbed onto isolute and repurified on a silica cartridge (40 g) eluting at 40 mL/min with a gradient running from 100% hexanes to 60 acetone over 45 min to yield the title compound as a white solid (0.6382 g, 40.2%). LC-MS m/z 251.0 (M−OH)+, 0.97 (ret. time).

(E)-tert-butyl 3-(1-Ethyl-4-methyl-1H-benzo[d][1,2,3]triazol-5-yl)acrylate

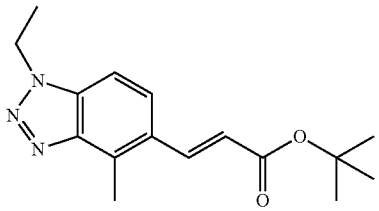

A mixture of tri-o-tolylphosphine (3.80 g, 12.49 mmol) tert-butyl acrylate (32.0 g, 250 mmol) triethylamine (17.42 mL, 125 mmol) 5-bromo-1-ethyl-4-methyl-1H-benzo[d][1,2,3]triazole (30.0 g, 125 mmol) and PdOAc2 (2.244 g, 10.00 mmol) in N,N-dimethylformamide (DMF) (250.0 mL) was stirred at 120° C. under nitrogen for 12 hrs. The mixture was poured into water and extracted with ethyl acetate (300 mL×3). The combined organic layer was dried over Na$_2$SO$_4$ and concentrated. The residue was purified via silica gel chromatography eluting with (hexane:ethyl acetate=4:1) (silica gel, 120 g). The appropriate fractions were combined and solvent remove in vacuo to afford the title compound (E)-tert-butyl 3-(1-ethyl-4-methyl-1H-benzo[d][1,2,3]triazol-5-yl)acrylate (26.3 g, 87 mmol, 69.6% yield). LC-MS m/z 288.0 (M+1)$^+$, 1.87 (ret. time).

(S)-tert-butyl 3-(4-Chloro-3-(hydroxymethyl)phenyl)-3-(1-ethyl-4-methyl-1H-benzo[d][1,2,3]triazol-5-yl)propanoate

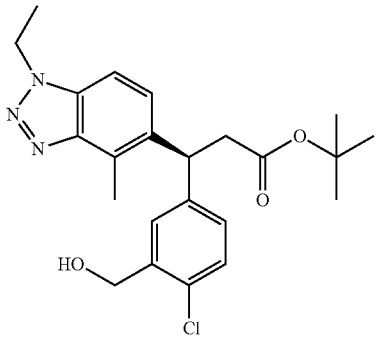 [SMILES: CCn1nnc2c(C)c([C@@H](CC(=O)OC(C)(C)C)c3ccc(Cl)c(CO)c3)ccc21]

To [Rh(nbd)$_2$]BF4 (0.716 g, 1.914 mmol) was added (R,R)-Chiraphos (0.898 g, 2.105 mmol) and (2-chloro-5-(4,4,5,5-tetramethyl-1,3,2-dioxaborolan-2-yl)phenyl)methanol (5.14 g, 19.14 mmol), followed by 1,4-dioxane (60 mL), purged with N2, and the reaction was stirred at ambient temperature for 45 min. Tert-butyl (E)-3-(1-ethyl-4-methyl-1H-benzo[d][1,2,3]triazol-5-yl)acrylate (2.2 g, 7.66 mmol), and KOH (7.66 mL, 7.66 mmol) were added and purged with N$_2$, the reaction was stirred at 95° C. under nitrogen atmosphere for 3 hrs. After it was cooled to ambient temperature, the solvent was evaporated. The residue was partitioned between EtOAc and H$_2$O. The water layer was extracted with EtOAc (2×). The combined organic phase was dried over MgSO$_4$ and concentrated. The crude product was purified via silica gel chromatography with hexane and ethyl acetate to provide racemic of title compound (3.1 g, 7.21 mmol, 94% yield). Then the title compound was resolved by Chiral SFC (Column: Chiralpak IA 20×250 mm, 5 u; Co-solvent: 25% EtOH; Flowrate: 50 g/min; Back pressure: 100 Bar) to give (S)-tert-butyl 3-(4-Chloro-3-(hydroxymethyl)phenyl)-3-(1-ethyl-4-methyl-1H-benzo[d][1,2,3]triazol-5-yl)propanoate (2.21 g, 5.14 mmol, 67.1% yield). LC-MS m/z 430.2 (M+1)$^+$, 1.12 (ret. time).

(S)-3-(4-chloro-3-(((R)-4-ethyl-1,1-dioxido-3,4-dihydro-2H-pyrido[2,3-b][1,4,5]oxathiazepin-2-yl)methyl)phenyl)-3-(1-ethyl-4-methyl-1H-benzo[d][1,2,3]triazol-5-yl)propanoic Acid

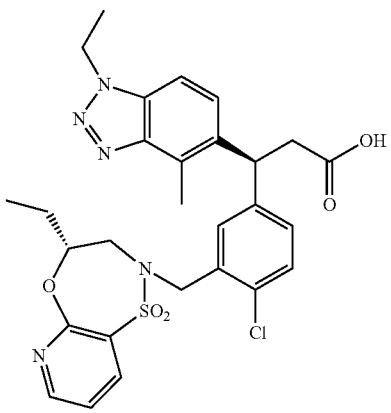 [SMILES: CC[C@@H]1CN(Cc2cc([C@H](CC(=O)O)c3ccc4c(nnn4CC)c3C)ccc2Cl)S(=O)(=O)c2cccnc2O1]

To a solution of tert-butyl (S)-3-(4-chloro-3-(hydroxymethyl)phenyl)-3-(1-ethyl-4-methyl-1H-benzo[d][1,2,3]triazol-5-yl)propanoate (2.21 g, 5.14 mmol) in tetrahydrofuran (THF) (40 mL), (R)-4-ethyl-3,4-dihydro-2H-pyrido[2,3-b][1,4,5]oxathiazepine 1,1-dioxide (1.408 g, 6.17 mmol), (E)-diazene-1,2-diylbis (piperidin-1-ylmethanone) (2.59 g, 10.28 mmol) and tributylphosphane (2.57 mL, 10.28 mmol) were added. The reaction mixture was stirred at ambient temperature for 16 hrs. The solvent was evaporated and purified by silica gel chromatography with hexane and ethyl acetate to obtain the product tert-butyl (S)-3-(4-chloro-3-(((R)-4-ethyl-1,1-dioxido-3,4-dihydro-2H-pyrido[2,3-b][1,4,5]oxathiazepin-2-yl)methyl)phenyl)-3-(1-ethyl-4-methyl-1H-benzo[d][1,2,3]triazol-5-yl)propanoate (3.1 g, 4.84 mmol, 94% yield). To it in dichloromethane (DCM) (40.0 mL), TFA (60 mL, 779 mmol) was added. The reaction mixture was stirred at ambient temperature for 1 hr. The solvent was evaporated. The residue was partitioned between ethyl acetate and water. The water layer was extracted with ethyl acetate (3×). The combined organic phase was dried with MgSO$_4$ and concentrated. The crude product was purified by reverse phase preparative HPLC under acidic (formic acid) condition to obtain the title compound (S)-3-(4-chloro-3-(((R)-4-ethyl-1,1-dioxido-3,4-dihydro-2H-pyrido[2,3-b][1,4,5]oxathiazepin-2-yl)methyl)phenyl)-3-(1-ethyl-4-methyl-1H-benzo[d][1,2,3]triazol-5-yl)propanoic acid (2.1555 g, 3.69 mmol, 71.8% yield). LC-MS m/z 584.4 (M+1)$^+$, 1.02 (ret. time). $^1$H NMR (400 MHz, DMSO-d6) δ ppm 0.99 (t, J=7.28 Hz, 3H) 1.35-1.65 (m, 5H) 2.77 (s, 3H) 3.02-3.19 (m, 3H) 3.80 (dd, J=15.06, 10.29 Hz, 1H) 4.09-4.33 (m, 2H) 4.43 (d, J=15.06 Hz, 1H) 4.68 (q, J=7.03 Hz, 2H) 4.86 (t, J=7.78 Hz, 1H) 7.24-7.53 (m, 5H) 7.64 (d, J=8.53 Hz, 1H) 8.23 (d, J=7.78 Hz, 1H) 8.45-8.70 (m, 1H)

Example 111

(S)-3-(1,4-Dimethyl-1H-benzo[d][1,2,3]triazol-5-yl)-3-(3-(((R)-2-ethyl-2,3-dihydropyrido[3,44][1,4]oxazepin-4(5H)-yl)methyl)-4-methylphenyl)-2,2-dimethyl-N-(pyridin-3-yl)propanamide

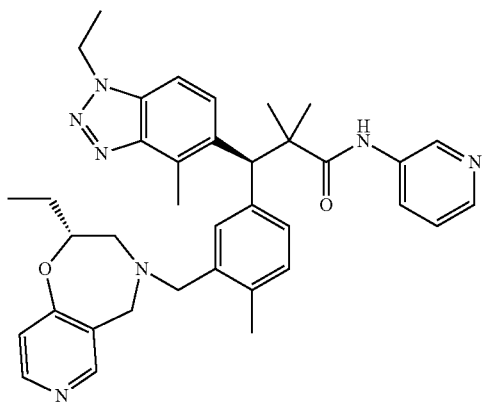 [SMILES: CC[C@@H]1CN(Cc2cc([C@@H](c3ccc4c(nnn4CC)c3C)C(C)(C)C(=O)Nc3cccnc3)ccc2C)Cc2cnccc2O1]

To a solution of (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethylpropanoic acid (100 mg, 0.190 mmol) in N,N-dimethylformamide (DMF) (1 mL) were added HATU (72.1 mg, 0.190 mmol) and DMAP (46.3 mg, 0.379 mmol) and stirred at ambient temperature for 15 minutes. Pyridin-3-amine (26.8 mg, 0.284 mmol) was then added and allowed to stir for 48 hours at 85° C. LCMS showed that some product had formed but some starting material still remained. The mixture was then diluted with EtOAc and washed with water (15 mL). The aqueous layer was then extracted with EtOAc (2×10 mL) and the combined organic layers were dried over magnesium sulfate, filtered and evaporated to dryness. The residue was dissolved in DMSO and purified via preparative HPLC under acidic (formic acid) conditions to give the title compound (15 mg, 0.025 mmol, 13.11% yield). LC-MS m/z 604.5 (M+H)$^+$, 0.58 min (ret. time). $^1$H NMR (400 MHz, METHANOL-$d_4$) δ ppm 0.91 (t, J=7.28 Hz, 3H) 1.27-1.37 (m, 1H) 1.40-1.54 (m, 7H) 2.27 (s, 3H) 2.74-2.87 (m, 5H) 3.04 (s, 1H) 3.60 (s, 2H) 3.66-3.74 (m, 1H) 3.78-3.87 (m, 1H) 3.92 (br. s., 1H) 4.27 (s, 3H) 5.01 (s, 1H) 6.98 (d, J=5.27 Hz, 1H) 7.10 (d, J=7.53 Hz, 1H) 7.17-7.24 (m, 2H) 7.29 (dd, J=8.03, 5.02 Hz, 1H) 7.48 (d, J=8.78 Hz, 1H) 7.79 (t, J=8.78 Hz, 2H) 8.05 (s, 1H) 8.20 (d, J=3.76 Hz, 1H) 8.30 (d, J=5.52 Hz, 1H) 8.40 (s, 1H)

The compounds in Table 13 were prepared by a method similar to the one described for the preparation of (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(pyridin-3-yl)propanamide. As is appreciated by those skilled in the art, these analogous examples may involve variations in general reaction conditions.

TABLE 13

| Ex # | Structure | Name | LCMS [M + 1] | Retention Time (min) |
| --- | --- | --- | --- | --- |
| Example 112 | 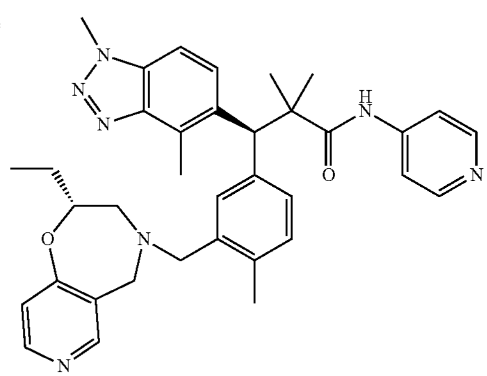 [SMILES: CC[C@@H]1CN(Cc2cc([C@@H](c3ccc4c(nnn4C)c3C)C(C)(C)C(=O)Nc3ccncc3)ccc2C)Cc2cnccc2O1] | (S)-3-(1,4-Dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(pyridin-4-yl)propanamide | 604.5 | 0.56 |
| Example 113 | 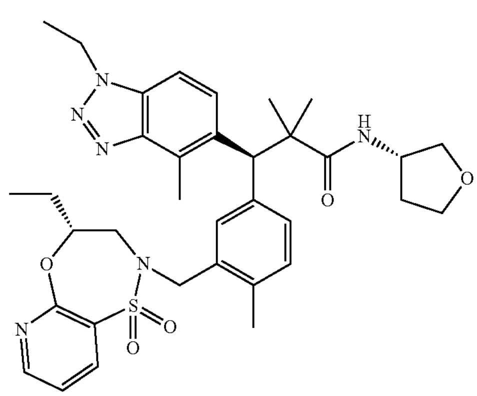 [SMILES: CC[C@@H]1CN(Cc2cc([C@@H](c3ccc4c(nnn4CC)c3C)C(C)(C)C(=O)N[C@H]3CCOC3)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-((S)-tetrahydrofuran-3-yl)propanamide | 661.5 | 1.03 |

| Ex # | Structure | Name | LCMS [M + 1] | Retention Time (min) |
|---|---|---|---|---|
| Example 114 | 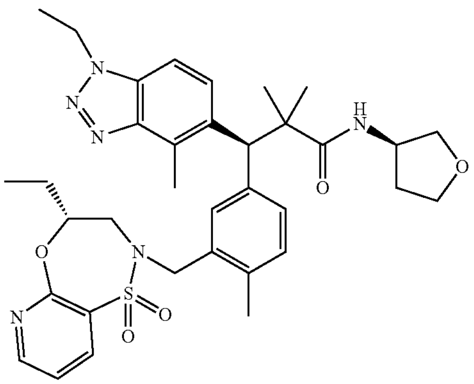 [SMILES: CC[C@@H]1CN(Cc2cc([C@@H](c3ccc4c(nnn4CC)c3C)C(C)(C)C(=O)N[C@@H]3CCOC3)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-((R)-tetrahydrofuran-3-yl)propanamide | 661.5 | 1.03 |

Example 115

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(2-(methylthio)pyrimidin-5-yl)propanamide

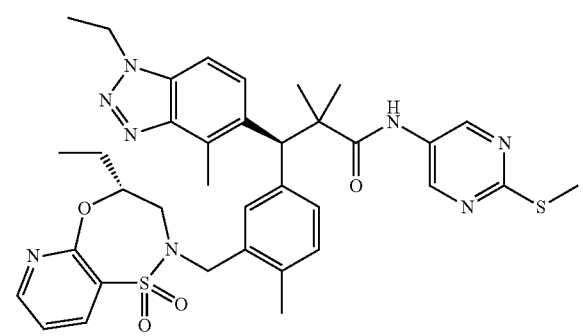 [SMILES: CC[C@@H]1CN(Cc2cc([C@@H](c3ccc4c(nnn4CC)c3C)C(C)(C)C(=O)Nc3cnc(SC)nc3)ccc2C)S(=O)(=O)c2cccnc2O1]

Phenyl N-(tert-butyl)-N'-(2-(methylthio)pyrimidin-5-yl)carbamimidothioate

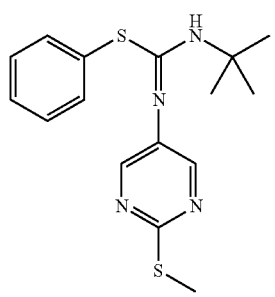 [SMILES: CSc1ncc(N=C(NC(C)(C)C)Sc2ccccc2)cn1]

To a solution of 2-isocyano-2-methylpropane (1.130 mL, 9.99 mmol), S-phenyl benzenesulfonothioate (1000 mg, 3.99 mmol) and 2-(methylthio)pyrimidin-5-amine (959 mg, 6.79 mmol) in 2-methyltetrahydrofuran (2-MeTHF) (10 mL), 200 mg of 4 Å molecular sieves and copper(I) iodide (76 mg, 0.399 mmol) were added. The reaction mixture was stirred at 75° C. for 16 hours after which time LCMS showed the reaction to be complete. The reaction mixture was filtered through a pad of silica and concentrated. The crude product was purified by flash chromatography over silica gel using ethyl acetate/hexanes to get 1.20 g (90% yield) of desired product. LC-MS m/z 333.10 (M+H)$^+$, 1.35 min (ret. time).

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(2-(methylthio)pyrimidin-5-yl)propanamide

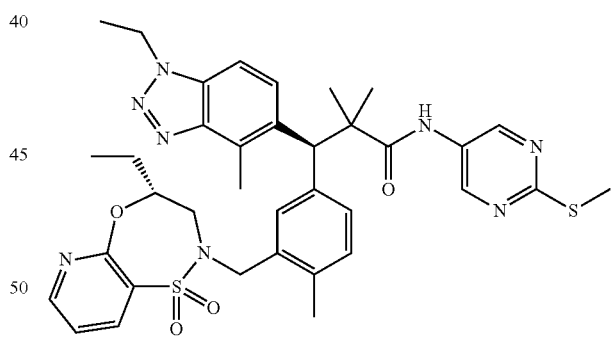

To a solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (402 mg, 0.679 mmol) and phenyl (E)-N-(tert-butyl)-N'-(2-(methylthio)pyrimidin-5-yl)carbamimidothioate (316 mg, 0.951 mmol) in isopropanol (6 mL) was added ferric acetylacetonate (12.00 mg, 0.034 mmol). The reaction was heated at 120° C. for 135 minutes. After 135 minutes, LCMS showed that the reaction was complete. The reaction mixture was concentrated, dissolved in DMSO, filtered, and purified via reverse phase preparative HPLC under acidic (formic acid) conditions to give the title compound (498.2 mg, 0.697 mmol, 103% yield). LCMS m/z 715.6 (M+H)$^+$, 1.20 min (ret. time).

¹H NMR (400 MHz, METHANOL-d₄) δ ppm 0.87 (t, J=7.40 Hz, 3H) 1.13-1.64 (m, 12H) 2.26-2.36 (m, 3H) 2.52 (s, 3H) 2.74-2.91 (m, 4H) 3.64 (dd, J=15.06, 10.54 Hz, 1H) 3.98 (d, J=14.56 Hz, 1H) 4.15-4.24 (m, 1H) 4.50 (d, J=14.31 Hz, 1H) 4.65-4.76 (m, 2H) 5.00 (s, 1H) 7.17 (d, J=7.78 Hz, 1H) 7.24-7.32 (m, 2H) 7.41 (dd, J=7.65, 4.89 Hz, 1H) 7.55 (d, J=8.78 Hz, 1H) 7.81 (d, J=8.78 Hz, 1H) 8.29 (dd, J=7.78, 2.01 Hz, 1H) 8.40-8.51 (m, 3H)

The compounds in Table 14 were prepared by a method similar to the one described for the preparation of (S)-3-(1,4-dimethyl-1H-benzo[d][1,2,3]triazol-5-yl)-3-(3-(((R)-2-ethyl-2,3-dihydropyrido[3,4-f][1,4]oxazepin-4(5H)-yl)methyl)-4-methylphenyl)-2,2-dimethyl-N-(pyridin-3-yl)propanamide. As is appreciated by those skilled in the art, these analogous examples may involve variations in general reaction conditions.

TABLE 14

| Ex # | Structure | Name | LCMS [M + 1] | Retention Time (min) |
|---|---|---|---|---|
| Example 116 | 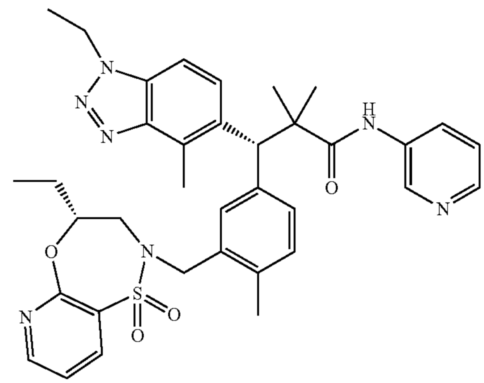 [SMILES: CC[C@@H]1CN(Cc2cc([C@H](c3ccc4c(nnn4CC)c3C)C(C)(C)C(=O)Nc3cccnc3)ccc2C)S(=O)(=O)c2cccnc2O1] | (R)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyridin-3-yl)propanamide | 668.4 | 0.84 |
| Example 117 | 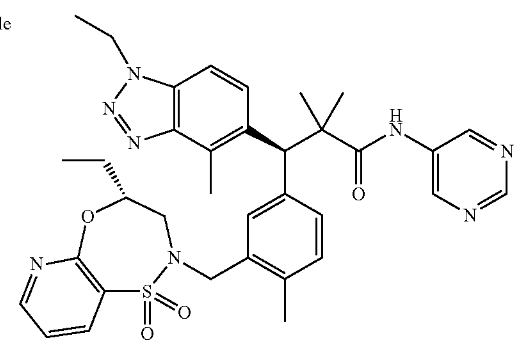 | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyrimidin-5-yl)propanamide | 669.5 | 1.04 |
| Example 118 | 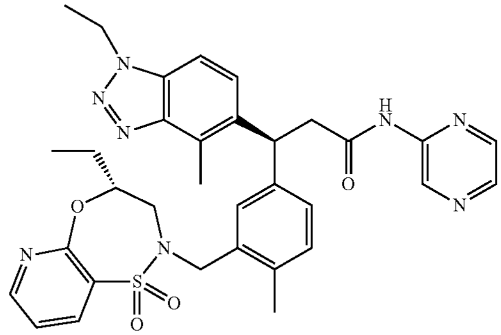 [SMILES: CC[C@@H]1CN(Cc2cc([C@H](CC(=O)Nc3cnccn3)c3ccc4c(nnn4CC)c3C)ccc2C)S(=O)(=O)c2cccnc2O1] | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyrazin-2-yl)propanamide | 641.4 | 1.03 |

Example 119

(S)-3-(3-(((S)-4-Ethyl-1,1-dioxido-4,5-dihydro-pyrido[2,3-f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(pyridin-3-yl)propanamide

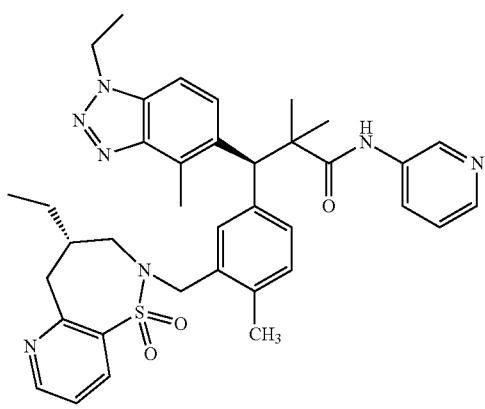 [SMILES: CC[C@H]1Cc2ncccc2S(=O)(=O)N(Cc2cc([C@@H](c3ccc4c(nnn4CC)c3C)C(C)(C)C(=O)Nc3cccnc3)ccc2C)C1]

(S)-3-(1-Ethyl-4-methyl-1H-benzo[d][1,2,3]triazol-5-yl)-3-(3-(((4-methoxybenzyl)oxy)methyl)-4-methylphenyl)-2,2-dimethylpropanoic Acid

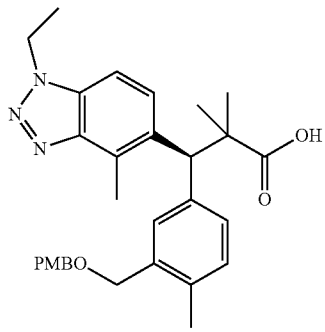

A solution of methyl (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoate (3.3208 g, 6.44 mmol) and 2M LiOH (25.8 mL, 51.5 mmol) in methanol (10 mL) was heated via microwave at 120° C. for 2 hours. After 2 hours LCMS showed the reaction to be complete. The methanol was then evaporated and 1M HCl was added to the mixture until a pH of ~2 was reached and white product began to precipitate. The mixture was then extracted with EtOAc (3×). The combined organic layers were washed with brine and dried over sodium sulfate, filtered, and concentrated to dryness to give the desired product (3.31 g, 6.60 mmol, 102% yield). The crude product was then carried forward to the next reaction with no further purification. LCMS m/z 502.4 (M+H)$^+$, 1.22 min (ret. time).

Phenyl (E)-N-(tert-butyl)-N'-(pyridin-3-yl)carbamimidothioate

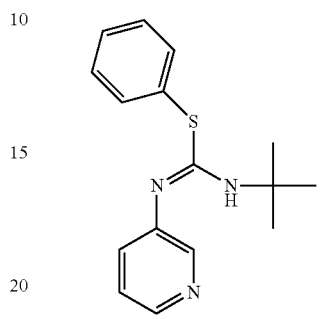

To a solution of 2-isocyano-2-methylpropane (0.282 ml, 2.497 mmol), S-phenyl benzenesulfonothioate (250 mg, 0.999 mmol), and pyridin-3-amine (160 mg, 1.698 mmol) in 2-methyltetrahydrofuran (2-MeTHF) (2.5 mL) was added copper(I) iodide (1.902 mg, 9.99 µmol). The reaction mixture was allowed to stir for 20 hours at 75° C. After 20 hours, LCMS showed the reaction to be complete. The reaction mixture was filtered through a celite cake and the celite was washed with EtOAc. The solution was then concentrated and purified via flash chromatography to give the desired product (274.4 mg, 0.961 mmol, 96% yield). LCMS m/z 286.1 (M+H)$^+$, 0.64 min (ret. time). $^1$H NMR (400 MHz, METHANOL-d$_4$) L ppm 1.39 (s, 9H) 7.18 (br. s., 2H) 7.32 (s, 5H) 7.93 (s, 1H) 8.03 (br. s., 1H)

(S)-3-(1-Ethyl-4-methyl-1H-benzo[d][1,2,3]triazol-5-yl)-3-(3-(((4-methoxybenzyl)oxy)methyl)-4-methylphenyl)-2,2-dimethyl-N-(pyridin-3-yl)propanamide

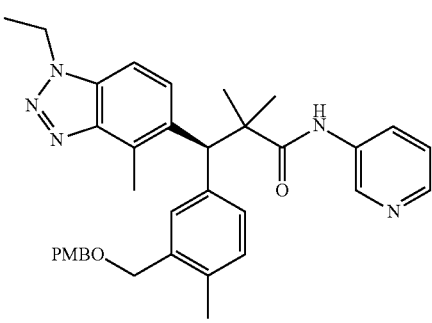

To a solution of (S)-3-(1-ethyl-4-methyl-1H-benzo[d][1,2,3]triazol-5-yl)-3-(3-(((4-methoxybenzyl)oxy)methyl)-4-methylphenyl)-2,2-dimethylpropanoic acid (1.47 g, 2.93 mmol) and phenyl (E)-N-(tert-butyl)-N'-(pyridin-3-yl)carbamimidothioate (1.213 g, 4.25 mmol) in isopropanol (10 mL) was added ferric acetylacetonate (0.052 g, 0.147 mmol). The reaction was heated via microwave for 2 hours at 120° C. After 2 hours LCMS showed that the reaction was complete. The reaction mixture was concentrated, filtered, and purified via flash chromatography to give the desired product (1.3618 g, 2.357 mmol, 80% yield). LCMS m/z 578.4 (M+H)⁺, 0.95 min (ret. time).

(S)-3-(1-Ethyl-4-methyl-1H-benzo[d][1,2,3]triazol-5-yl)-3-(3-(hydroxymethyl)-4-methylphenyl)-2,2-dimethyl-N-(pyridin-3-yl)propanamide

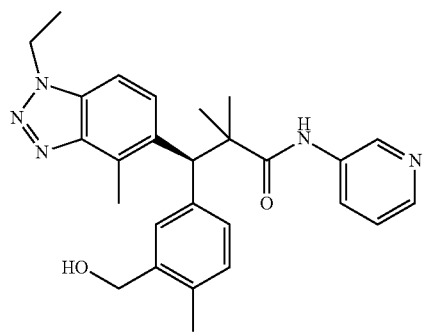 [SMILES: CCn1nnc2c(C)c([C@H](c3ccc(C)c(CO)c3)C(C)(C)C(=O)Nc3cccnc3)ccc21]

A solution of (S)-3-(1-ethyl-4-methyl-1H-benzo[d][1,2,3]triazol-5-yl)-3-(3-(((4-methoxybenzyl)oxy)methyl)-4-methylphenyl)-2,2-dimethyl-N-(pyridin-3-yl)propanamide (1.3618 g, 2.357 mmol) in acetonitrile (5 mL) and water (0.556 mL) was cooled to 0° C. and CAN (2.58 g, 4.71 mmol) was slowly added. The reaction was stirred for 100 minutes as it slowly warmed to ambient temperature. After 100 minutes, LCMS showed the reaction to be complete. The reaction was quenched with a saturated solution of ammonium chloride and extracted with EtOAc (3×). The combined organic layers were dried over sodium sulfate, filtered, and concentrated to dryness. The crude product was purified via flash chromatography to give the desired product (592.8 mg, 1.296 mmol, 55.0% yield). LCMS m/z 458.3 (M+H)⁺, 0.63 min (ret. time).

(S)-3-(3-(((S)-4-Ethyl-1,1-dioxido-4,5-dihydropyrido[2,3-f][1,2]thiazepin-2(3H)-yl)methyl)-4-methylphenyl)-3-(1-ethyl-4-methyl-1H-benzo[d][1,2,3]triazol-5-yl)-2,2-dimethyl-N-(pyridin-3-yl)propanamide

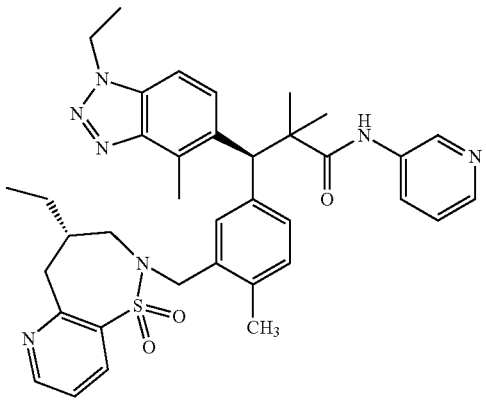 [SMILES: CC[C@H]1Cc2ncccc2S(=O)(=O)N(Cc2cc([C@@H](c3ccc4c(nnn4CC)c3C)C(C)(C)C(=O)Nc3cccnc3)ccc2C)C1]

To a solution of (S)-3-(1-ethyl-4-methyl-1H-benzo[d][1,2,3]triazol-5-yl)-3-(3-(hydroxymethyl)-4-methylphenyl)-2,2-dimethyl-N-(pyridin-3-yl)propanamide (54.3 mg, 0.119 mmol) in dichloromethane (DCM) (2 mL) was added thionyl chloride (0.017 mL, 0.237 mmol). The reaction was stirred at ambient temperature for 15 minutes. After 15 minutes, LCMS showed the reaction to be complete. The reaction mixture was concentrated to dryness to give (S)-3-(3-(chloromethyl)-4-methylphenyl)-3-(1-ethyl-4-methyl-1H-benzo[d][1,2,3]triazol-5-yl)-2,2-dimethyl-N-(pyridin-3-yl)propanamide.

A solution of (S)-4-ethyl-2,3,4,5-tetrahydropyrido[2,3-f][1,2]thiazepine 1,1-dioxide (32.2 mg, 0.142 mmol) in N,N-dimethylformamide (DMF) (2 mL) was cooled to 0° C. and NaH (60%) (14.24 mg, 0.356 mmol) was added. The mixture was stirred for 30 minutes and then a solution of (S)-3-(3-(chloromethyl)-4-methylphenyl)-3-(1-ethyl-4-methyl-1H-benzo[d][1,2,3]triazol-5-yl)-2,2-dimethyl-N-(pyridin-3-yl)propanamide in N,N-dimethylformamide (DMF) (2 mL) was added. The reaction was stirred for 17 hours as it was allowed to warm to ambient temperature. After 17 hours, LCMS showed the reaction to be complete. The reaction mixture was diluted with water and extracted with EtOAc (×3). The combined organic layers were washed with brine, dried over sodium sulfate, filtered, and concentrated to dryness. The crude product was then dissolved in DMSO and purified via preparative HPLC under acidic conditions (formic acid) to give the title compound (52.9 mg, 0.079 mmol, 66.9% yield). LCMS m/z 666.4 (M+H)⁺, 0.91 min (ret. time). ¹H NMR (400 MHz, METHANOL-d₄) δ ppm 0.60 (t, J=7.28 Hz, 3H) 0.87-1.05 (m, 2H) 1.41 (s, 3H) 1.48-1.61 (m, 6H) 1.70 (br. s., 1H) 2.17 (s, 4H) 2.27 (s, 3H) 2.76 (s, 3H) 3.11 (d, J=11.80 Hz, 1H) 3.46-3.70 (m, 3H) 4.38 (d, J=14.31 Hz, 1H) 4.69 (q, J=7.11 Hz, 2H) 5.01 (s, 1H) 7.13 (d, J=7.53 Hz, 1H) 7.20-7.34 (m, 3H) 7.42-7.55 (m, 2H) 7.80 (t, J=10.04 Hz, 2H) 8.23 (d, J=7.78 Hz, 2H) 8.40 (br. s., 1H) 8.63 (d, J=4.77 Hz, 1H).

The compounds in Table 15 were prepared by a method similar to the one described for the preparation of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyridin-3-yl)propanamide. As is appreciated by those skilled in the art, these analogous examples may involve variations in general reaction conditions.

TABLE 15

| Ex # | Structure | Name | LCMS [M + 1] | Retention Time (min) |
|---|---|---|---|---|
| Example 120 | 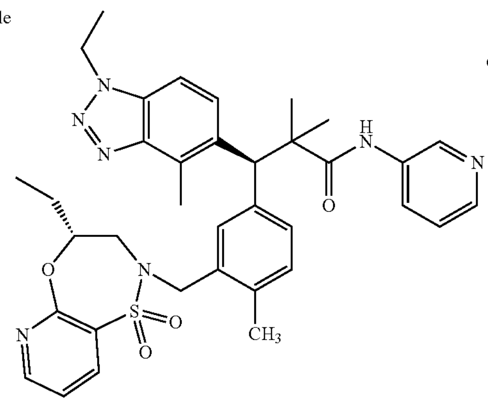 | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(pyridin-3-yl)propanamide | 668.4 | 0.86 |

Example 121

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyrimidin-2-yl)propanamide

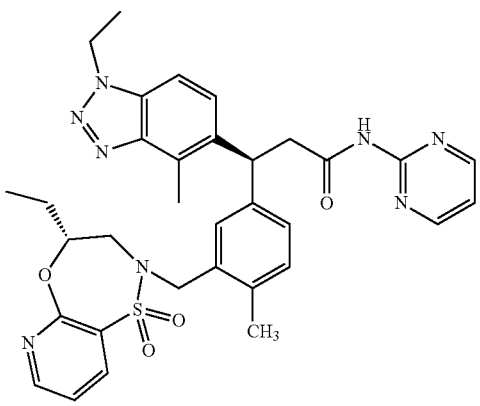 [SMILES: CC[C@@H]1CN(Cc2cc([C@H](CC(=O)Nc3ncccn3)c3ccc4c(nnn4CC)c3C)ccc2C)S(=O)(=O)c2cccnc2O1]

To a stirred solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (51 mg, 0.090 mmol), DCC (28.0 mg, 0.136 mmol), and pyrimidin-2-amine (10.33 mg, 0.109 mmol) in dichloromethane (DCM) (2 mL) was added DMAP (33.2 mg, 0.271 mmol). The reaction mixture was stirred for 64 hours at which point LCMS showed the reaction to be complete. The reaction mixture was diluted with water and extracted with EtOAc (×3). The combined organic layers were washed with brine, dried over sodium sulfate, filtered, and concentrated to dryness. To help remove DCU, the crude product was dissolved in cold acetonitrile and filtered through a pad of celite. The crude product was then dissolved in DMSO and purified via preparative HPLC under acidic conditions (formic acid) to give the title compound (17.8 mg, 0.028 mmol, 30.7% yield). LCMS m/z 641.4 (M+H)$^+$, 0.96 min (ret. time). $^1$H NMR (400 MHz, METHANOL-$d_4$) δ ppm 0.88 (t, J=7.40 Hz, 3H) 1.29 (ddd, J=14.49, 7.47, 4.14 Hz, 1H) 1.41-1.65 (m, 4H) 2.17 (s, 1H) 2.30 (s, 3H) 2.78 (s, 3H) 2.94 (dd, J=15.18, 1.13 Hz, 1H) 3.35-3.48 (m, 2H) 3.65 (dd, J=15.18, 10.42 Hz, 1H) 3.96 (d, J=14.05 Hz, 1H) 4.16-4.26 (m, 1H) 4.53 (d, J=14.05 Hz, 1H) 4.69 (q, J=7.28 Hz, 2H) 5.14 (t, J=7.91 Hz, 1H) 7.05-7.20 (m, 3H) 7.25 (dd, J=7.91, 1.63 Hz, 1H) 7.40 (dd, J=7.65, 4.89 Hz, 1H) 7.56 (s, 2H) 8.28 (dd, J=7.65, 1.88 Hz, 1H) 8.47 (dd, J=4.89, 1.88 Hz, 1H) 8.56 (d, J=4.77 Hz, 2H).

The compounds in Table 16 were prepared by a method similar to the one described for the preparation of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyrimidin-2-yl)propanamide. As is appreciated by those skilled in the art, these analogous examples may involve variations in general reaction conditions.

TABLE 16

| Ex # | Structure | Name | LCMS [M + 1] | Retention Time (min) |
|---|---|---|---|---|
| Example 122 | 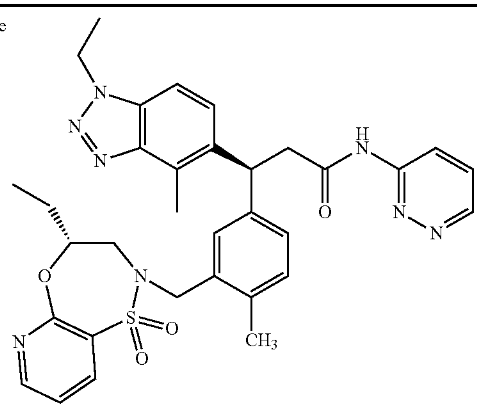 | (S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridazin-3-yl)propanamide | 641.4 | 0.99 |

Example 123

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-methoxypyrimidin-5-yl)propanamide

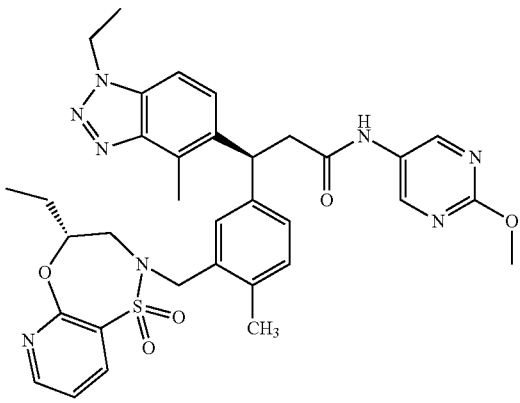 [SMILES: CC[C@@H]1CN(Cc2cc([C@H](CC(=O)Nc3cnc(OC)nc3)c3ccc4c(nnn4CC)c3C)ccc2C)S(=O)(=O)c2cccnc2O1]

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylthio)pyrimidin-5-yl)propanamide

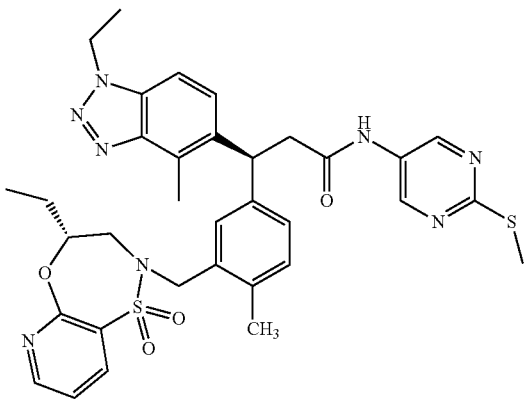 [SMILES: CC[C@@H]1CN(Cc2cc([C@H](CC(=O)Nc3cnc(SC)nc3)c3ccc4c(nnn4CC)c3C)ccc2C)S(=O)(=O)c2cccnc2O1]

To a stirred solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (1.5 g, 2.66 mmol), HATU (1.113 g, 2.93 mmol), and DIEA (1.394 mL, 7.98 mmol) in N,N-dimethylformamide (DMF) (10 mL) was added 2-(methylthio)pyrimidin-5-amine (0.451 g, 3.19 mmol). The reaction mixture was stirred for 4 hours at which point LCMS showed the reaction to be complete. The reaction mixture was diluted with water and extracted with EtOAc (×3). The combined organic layers were washed with brine, dried over sodium sulfate, filtered and concentrated to dryness. The crude product was then dissolved in DMSO and purified via preparative HPLC under acidic conditions (formic acid) to give the desired product (1.7186 g, 2.502 mmol, 94% yield). LCMS m/z 687.4 (M+H)$^+$, 1.12 min (ret. time).

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylsulfonyl)pyrimidin-5-yl)propanamide

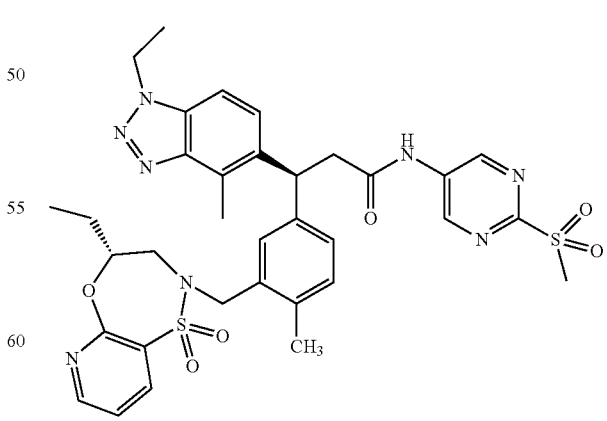

To a stirred solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo

[d][1,2,3]triazol-5-yl)-N-(2-(methylthio)pyrimidin-5-yl) propanamide (104 mg, 0.151 mmol) in dichloromethane (DCM) (2 mL) was added m-CPBA (52.3 mg, 0.303 mmol) at ambient temperature. The solution was stirred for 100 minutes at which point LCMS showed the reaction to be complete. The mixture was then directly loaded onto a column and purified via flash chromatography to give the desired product (85.3 mg, 0.119 mmol, 78% yield) LCMS m/z 719.4 (M+H)$^+$, 1.02 min (ret. time).

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-methoxypyrimidin-5-yl) propanamide

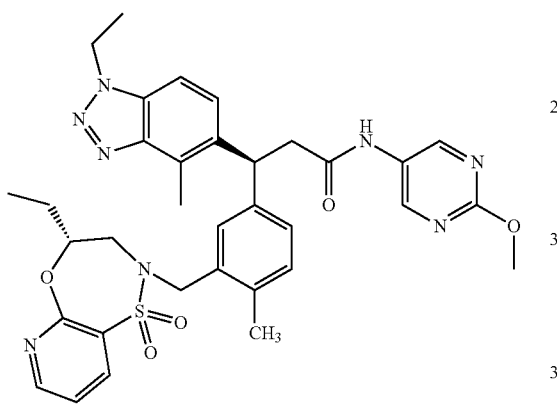

To a solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylsulfonyl)pyrimidin-5-yl) propanamide (42 mg, 0.058 mmol) in methanol (1 mL) and tetrahydrofuran (THF) (1 mL) was added NaH (60%) (7.01 mg, 0.175 mmol). The reaction was stirred at ambient temperature for 1 hour at which point LCMS showed the reaction to be complete. The reaction mixture was diluted with water and extracted with EtOAc (×3). The combined organic layers were dried over sodium sulfate, filtered, and concentrated to dryness. The crude product was dissolved in DMSO and purified via reverse phase preparative HPLC under acidic (formic acid) conditions to give the title compound (15.8 mg, 0.024 mmol, 40.3% yield). LCMS m/z 671.3 (M+H)$^+$, 1.02 min (ret. time). $^1$H NMR (400 MHz, METHANOL-d$_4$) δ ppm 0.89 (t, J=7.40 Hz, 3H) 1.30 (ddd, J=14.12, 7.34, 4.39 Hz, 1H) 1.45-1.62 (m, 4H) 2.30 (s, 3H) 2.77 (s, 3H) 2.89-2.96 (m, 1H) 3.10-3.30 (m, 2H) 3.63 (dd, J=15.31, 10.54 Hz, 1H) 3.91-4.01 (m, 4H) 4.17-4.27 (m, 1H) 4.53 (d, J=14.05 Hz, 1H) 4.71 (q, J=7.28 Hz, 2H) 5.09 (t, J=7.91 Hz, 1H) 5.51 (s, 1H) 7.11-7.28 (m, 3H) 7.41 (dd, J=7.65, 4.89 Hz, 1H) 7.51-7.63 (m, 2H) 8.29 (dd, J=7.65, 1.88 Hz, 1H) 8.47 (dd, J=4.89, 1.88 Hz, 1H) 8.61 (s, 2H).

Example 124

(S)—N-(2-(2-Ethoxyethoxy)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

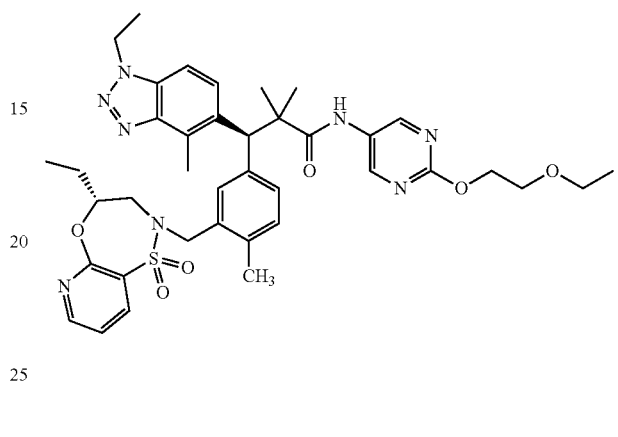

To a solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3] triazol-5-yl)-2,2-dimethyl-N-(2-(methylsulfonyl)pyrimidin-5-yl)propanamide (30.5 mg, 0.041 mmol) and 2-ethoxyethane-1-ol (147 mg, 1.633 mmol) was added NaH (2.94 mg, 0.123 mmol). The reaction was stirred for 5 hours at ambient temperature. After 5 hours, LCMS showed the reaction to be complete. The reaction mixture was diluted with water and extracted with EtOAc (×3). The combined organic layers were dried over sodium sulfate, filtered, and concentrated to dryness. The crude product was purified via preparative HPLC under acidic (formic acid) conditions to give the title compound (22.4 mg, 0.030 mmol, 72.5% yield). LCMS m/z 757.7 (M+H)$^+$, 1.15 min (ret. time). $^1$H NMR (400 MHz, METHANOL-d$_4$) δ ppm m 0.87 (t, J=7.28 Hz, 3H) 1.15-1.22 (m, 3H) 1.19-1.28 (m, 2H) 1.39-1.54 (m, 7H) 1.59 (t, J=7.28 Hz, 3H) 2.31 (s, 3H) 2.78 (s, 3H) 2.87 (dd, J=15.31, 1.25 Hz, 1H) 3.57 (q, J=7.03 Hz, 2H) 3.65 (dd, J=15.18, 10.42 Hz, 1H) 3.74-3.80 (m, 2H) 3.98 (d, J=14.31 Hz, 1H) 4.15-4.26 (m, 1H) 4.41-4.48 (m, 2H) 4.51 (d, J=14.56 Hz, 1H) 4.71 (q, J=7.28 Hz, 2H) 4.99 (s, 1H) 7.17 (d, J=8.03 Hz, 1H) 7.24-7.33 (m, 2H) 7.41 (dd, J=7.53, 5.02 Hz, 1H) 7.55 (d, J=8.78 Hz, 1H) 7.82 (d, J=8.78 Hz, 1H) 8.29 (dd, J=7.65, 1.88 Hz, 1H) 8.34 (s, 2H) 8.47 (dd, J=4.89, 1.88 Hz, 1H)

Example 125

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(piperidin-1-yl)pyrimidin-5-yl)propanamide

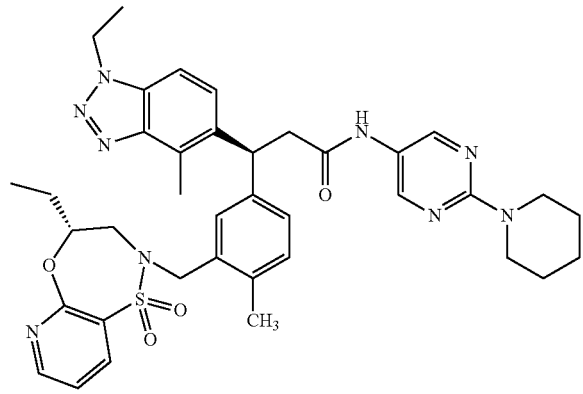 [SMILES: CC[C@@H]1CN(Cc2cc([C@H](CC(=O)Nc3cnc(N4CCCCC4)nc3)c3ccc4c(nnn4CC)c3C)ccc2C)S(=O)(=O)c2cccnc2O1]

(S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylsulfonyl)pyrimidin-5-yl)propanamide (12.6 mg, 0.018 mmol) was stirred in piperidine (0.25 mL, 2.53 mmol). The reaction mixture was sealed in a microwave vial and heated at 120° C. for 30 minutes. LCMS showed the reaction to be mostly complete. The mixture was diluted with water and extracted with DCM (×3). The combined organic layers were dried over sodium sulfate, filtered, and concentrated to dryness. The crude product was then taken up in DMSO and purified via preparative HPLC under acidic (formic acid) conditions to give the title compound (3.3 mg, 4.56 μmol, 26.0% yield). LCMS m/z 724.4 (M+H)$^+$, 1.17 min (ret. time). $^1$H NMR (400 MHz, METHANOL-$d_4$) δ ppm 0.90 (t, J=7.40 Hz, 3H) 1.23-1.37 (m, 1H) 1.42-1.76 (m, 10H) 2.18 (s, 1H) 2.33 (s, 3H) 2.76 (s, 3H) 2.87-2.97 (m, 1H) 3.06-3.25 (m, 2H) 3.58-3.77 (m, 5H) 3.96 (d, J=14.05 Hz, 1H) 4.17-4.28 (m, 1H) 4.55 (d, J=14.31 Hz, 1H) 4.73 (q, J=7.28 Hz, 2H) 5.06 (t, J=8.03 Hz, 1H) 7.10-7.28 (m, 3H) 7.42 (dd, J=7.65, 4.89 Hz, 1H) 7.52-7.65 (m, 2H) 8.25 (s, 2H) 8.30 (dd, J=7.65, 1.88 Hz, 1H) 8.48 (dd, J=4.89, 1.88 Hz, 1H)

Example 126

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylamino)pyrimidin-5-yl)propanamide

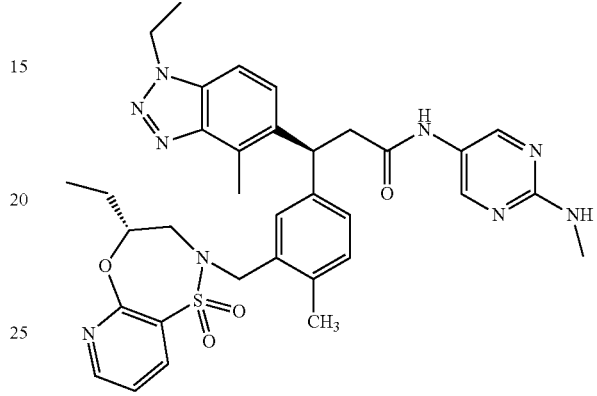

A solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylsulfonyl)pyrimidin-5-yl)propanamide (15.2 mg, 0.021 mmol) in methanamine (0.5 mL, 1.000 mmol) (2M in THF) was stirred at ambient temperature for 80 hours. After 80 hours, LCMS showed the reaction to be finished. The reaction mixture was diluted with water and extracted with EtOAc (×3). The combined organic layers were dried over sodium sulfate, filtered, and concentrated to dryness. The crude product was dissolved in DMSO and purified via preparative HPLC under acidic (formic acid) conditions to give the title compound (7.1 mg, 10.60 μmol, 50.1% yield). LCMS m/z 670.5 (M+H)$^+$, 0.98 min (ret. time). $^1$H NMR (400 MHz, METHANOL-$d_4$) δ ppm 0.89 (t, J=7.40 Hz, 3H) 1.30 (ddd, J=14.24, 7.34, 4.27 Hz, 1H) 1.42-1.62 (m, 4H) 2.32 (s, 3H) 2.67 (s, 1H) 2.71-2.79 (m, 3H) 2.84-2.99 (m, 4H) 3.04-3.26 (m, 2H) 3.63 (dd, J=15.31, 10.54 Hz, 1H) 3.97 (d, J=14.05 Hz, 1H) 4.16-4.27 (m, 1H) 4.54 (d, J=14.31 Hz, 1H) 4.72 (q, J=7.28 Hz, 2H) 5.06 (t, J=7.91 Hz, 1H) 7.10-7.27 (m, 3H) 7.41 (dd, J=7.65, 4.89 Hz, 1H) 7.58 (q, J=8.78 Hz, 2H) 8.17-8.34 (m, 3H) 8.47 (dd, J=4.89, 1.88 Hz, 1H)

Example 127

(S)—N-(2-((1,3-Dihydroxypropan-2-yl)amino)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide

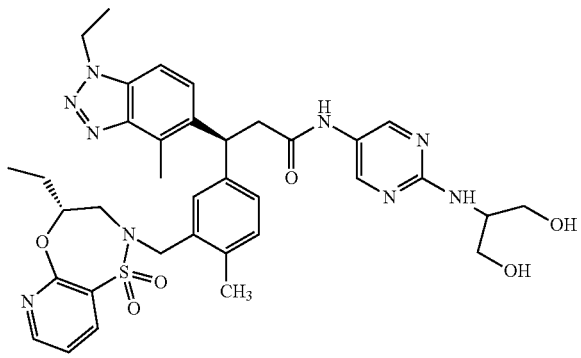 [SMILES: CC[C@@H]1CN(Cc2cc([C@H](CC(=O)Nc3cnc(NC(CO)CO)nc3)c3ccc4c(nnn4CC)c3C)ccc2C)S(=O)(=O)c2cccnc2O1]

A mixture of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(2-(methylsulfonyl)pyrimidin-5-yl)propanamide (16.2 mg, 0.023 mmol) and 2-aminopropane-1,3-diol (100 mg, 1.098 mmol) was heated to 80° C. and stirred for 33 hours. After 33 hours LCMS showed the reaction to be mostly complete. The reaction mixture was cooled to ambient temperature and then diluted with water. The solution was extracted with EtOAc (×3) and the combined organic layers were dried over sodium sulfate, filtered, and concentrated to dryness. The crude product was purified via preparative HPLC under acidic (formic acid) conditions to give the title compound (9.9 mg, 0.014 mmol, 60.2% yield). LCMS m/z 730.6 (M+H)$^+$, 0.86 min (ret. time). $^1$H NMR (400 MHz, METHANOL-$d_4$) δ ppm 0.83-0.95 (m, 3H) 1.31 (ddd, J=14.24, 7.34, 4.52 Hz, 1H) 1.39-1.66 (m, 4H) 2.32 (s, 3H) 2.70-2.81 (m, 3H) 2.93 (dd, J=15.31, 1.25 Hz, 1H) 3.04-3.25 (m, 2H) 3.57-3.75 (m, 5H) 3.91-4.06 (m, 2H) 4.17-4.26 (m, 1H) 4.54 (d, J=14.31 Hz, 1H) 4.72 (q, J=7.36 Hz, 2H) 5.06 (t, J=8.03 Hz, 1H) 7.09-7.27 (m, 3H) 7.41 (dd, J=7.65, 4.89 Hz, 1H) 7.51-7.63 (m, 2H) 8.19-8.38 (m, 4H) 8.47 (dd, J=4.89, 1.88 Hz, 1H)

The compounds in Table 17 were prepared by a method similar to the one described for the preparation of (S)—N-(2-((1,3-dihydroxypropane-2-yl)amino)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide. As is appreciated by those skilled in the art, these analogous examples may involve variations in general reaction conditions.

TABLE 17

| Ex # | Structure | Name | LCMS [M + 1] | Retention Time (min) |
|---|---|---|---|---|
| Example 128 | 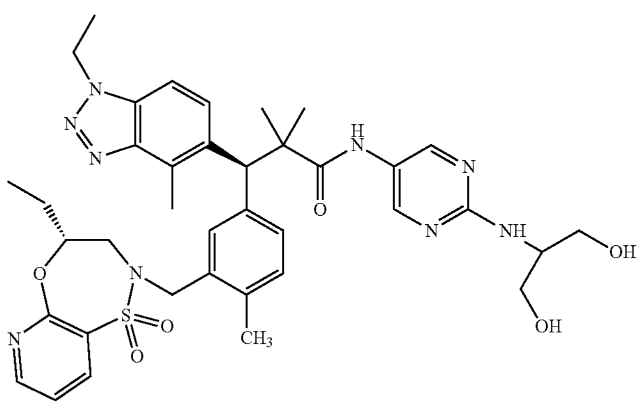 [SMILES: CC[C@@H]1CN(Cc2cc([C@@H](c3ccc4c(nnn4CC)c3C)C(C)(C)C(=O)Nc3cnc(NC(CO)CO)nc3)ccc2C)S(=O)(=O)c2cccnc2O1] | (S)-N-(2-((1,3-Dihydroxypropan-2-yl)amino)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide | 758.9 | 0.93 |
| Example 129 | 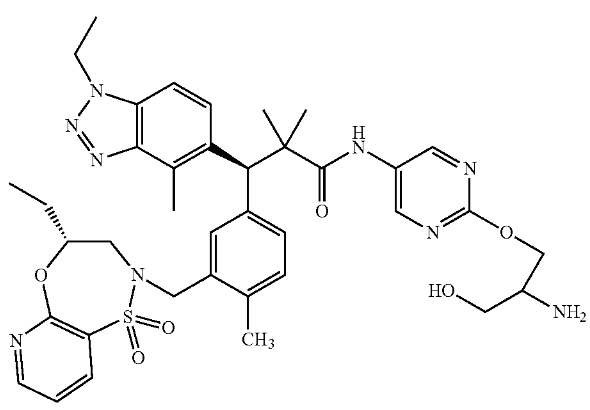 [SMILES: CC[C@@H]1CN(Cc2cc([C@@H](c3ccc4c(nnn4CC)c3C)C(C)(C)C(=O)Nc3cnc(OCC(N)CO)nc3)ccc2C)S(=O)(=O)c2cccnc2O1] | (3S)-N-(2-(2-Amino-3-hydroxypropoxy)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide | 758.5 | 0.79 |

TABLE 17-continued

| Ex # | Structure | Name | LCMS [M + 1] | Retention Time (min) |
|---|---|---|---|---|
| Example 130 | 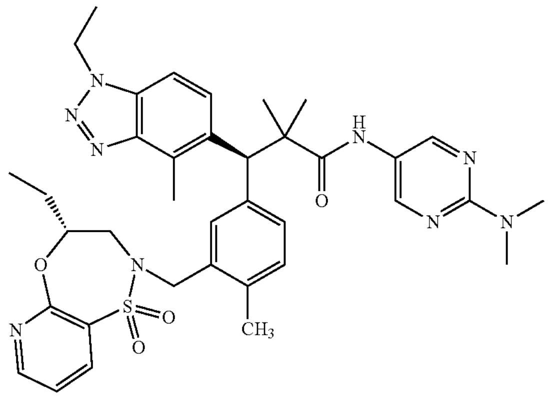 [SMILES: CC[C@@H]1CN(Cc2cc([C@@H](c3ccc4c(nnn4CC)c3C)C(C)(C)C(=O)Nc3cnc(N(C)C)nc3)ccc2C)S(=O)(=O)c2cccnc2O1] | (S)-N-(2-(Dimethylamino)pyrimidin-5-yl)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide | 712.9 | 1.07 |

Example 131

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(2-(methylsulfonyl)pyrimidin-5-yl)propanamide

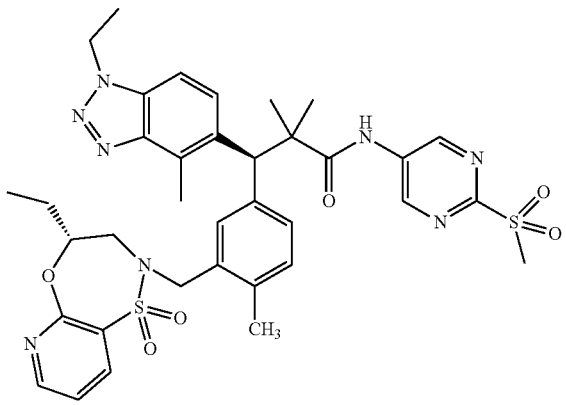 [SMILES: CC[C@@H]1CN(Cc2cc([C@@H](c3ccc4c(nnn4CC)c3C)C(C)(C)C(=O)Nc3cnc(S(C)(=O)=O)nc3)ccc2C)S(=O)(=O)c2cccnc2O1]

To a stirred solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(2-(methylthio)pyrimidin-5-yl)propanamide (483.2 mg, 0.676 mmol) in dichloromethane (DCM) (6 mL) was added m-CPBA (233 mg, 1.352 mmol) at ambient temperature. The solution was stirred for 40 minutes at which point LCMS showed the reaction to be complete. The mixture was then directly loaded onto a column and purified via flash chromatography to give the title compound (404.8 mg, 0.542 mmol, 80% yield). LCMS m/z 747.8 (M+H)$^+$, 1.09 min (ret. time). $^1$H NMR (400 MHz, METHANOL-d4) δ ppm 0.83-0.95 (m, 3H) 1.22-1.32 (m, 1H) 1.42-1.63 (m, 11H) 2.25-2.31 (m, 3H) 2.79 (s, 3H) 2.89 (dd, J=15.06, 1.51 Hz, 1H) 3.31 (s, 2H) 3.37 (s, 1H) 3.65 (dd, J=15.18, 10.42 Hz, 1H) 3.99 (d, J=14.56 Hz, 1H) 4.13-4.27 (m, 1H) 4.46 (d, J=14.56 Hz, 1H) 4.64-4.74 (m, 2H) 5.04 (s, 1H) 7.15 (d, J=7.53 Hz, 1H) 7.23-7.32 (m, 2H) 7.40 (dd, J=7.78, 5.02 Hz, 1H) 7.54 (d, J=8.78 Hz, 1H) 7.80 (d, J=9.03 Hz, 1H) 8.28 (dd, J=7.65, 1.88 Hz, 1H) 8.47 (dd, J=5.02, 2.01 Hz, 1H) 9.01 (s, 2H)

Example 132

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)acetamide

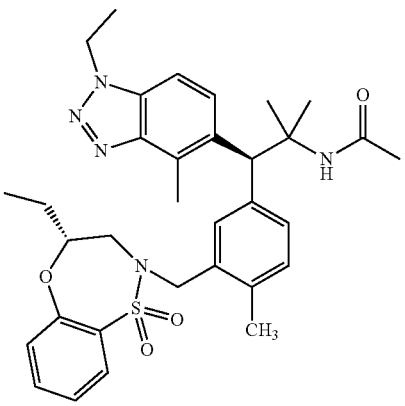 [SMILES: CC[C@@H]1CN(Cc2cc([C@@H](c3ccc4c(nnn4CC)c3C)C(C)(C)NC(C)=O)ccc2C)S(=O)(=O)c2ccccc2O1]

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoyl Azide

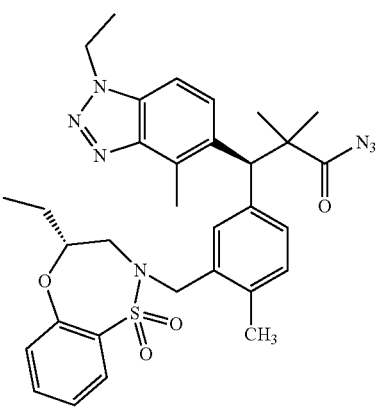 [SMILES: CC[C@@H]1CN(Cc2cc([C@@H](c3ccc4c(nnn4CC)c3C)C(C)(C)C(=O)N=[N+]=[N-])ccc2C)S(=O)(=O)c2ccccc2O1]

To a stirred solution of (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (1.6239 g, 2.75 mmol) and triethylamine (1.149 mL, 8.25 mmol) in toluene (10 mL) was added diphenyl phosphorazidate (0.889 mL, 4.12 mmol). The reaction was stirred at ambient temperature for 90 minutes at which point LCMS showed the reaction to be complete. The reaction mixture was then concentrated to dryness and purified via flash chromatography to give the desired product (1.3560 g, 2.202 mmol, 80% yield). LCMS m/z 616.5 (M+H)⁺, 1.42 min (ret. time).

(R)-2-(5-((S)-2-Amino-1-(1-ethyl-4-methyl-1H-benzo[d][1,2,3]triazol-5-yl)-2-methylpropyl)-2-methylbenzyl)-4-ethyl-3,4-dihydro-2H-benzo[b][1,4,5]oxathiazepine 1,1-dioxide

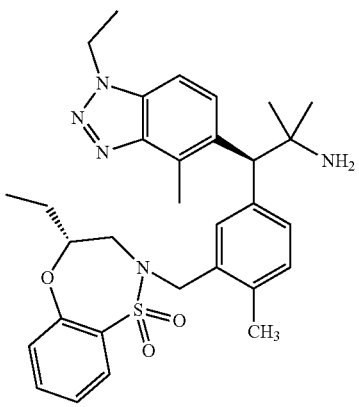 [SMILES: CC[C@@H]1CN(Cc2cc([C@@H](c3ccc4c(nnn4CC)c3C)C(C)(C)N)ccc2C)S(=O)(=O)c2ccccc2O1]

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoyl azide (1.3558 g, 2.202 mmol) was stirred in toluene (8 mL) and heated to 80° C. for 1 hour. After 1 hour LCMS showed that (R)-4-ethyl-2-(5-((S)-1-(1-ethyl-4-methyl-1H-benzo[d][1,2,3]triazol-5-yl)-2-isocyanato-2-methylpropyl)-2-methylbenzyl)-3,4-dihydro-2H-benzo[b][1,4,5]oxathiazepine 1,1-dioxide had formed. The reaction mixture was then concentrated to dryness, dissolved in acetonitrile (8.00 mL) and HCl (4.40 mL, 17.61 mmol) (4M in dioxane) was added. The reaction was allowed to stir at ambient temperature for 26 hours at which point LCMS showed the reaction to be complete. The reaction mixture was then diluted with EtOAc and washed with a saturated solution of sodium bicarbonate. The aqueous phase was then washed with EtOAc (×2). The combined organic layers were dried over sodium sulfate, filtered, and concentrated. The residue was dissolved in DMSO and purified via preparative HPLC under acidic (formic acid) conditions to give the desired product (691.1 mg, 1.230 mmol, 55.9% yield). LCMS m/z 562.6 (M+H)⁺, 0.84 min (ret. time).

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)acetamide

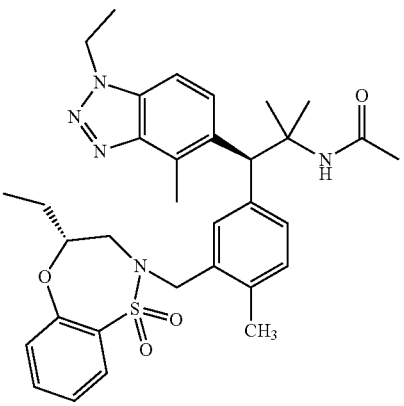 [SMILES: CC[C@@H]1CN(Cc2cc([C@@H](c3ccc4c(nnn4CC)c3C)C(C)(C)NC(C)=O)ccc2C)S(=O)(=O)c2ccccc2O1]

To a solution of (R)-2-(5-((S)-2-amino-1-(1-ethyl-4-methyl-1H-benzo[d][1,2,3]triazol-5-yl)-2-methylpropyl)-2-methylbenzyl)-4-ethyl-3,4-dihydro-2H-benzo[b][1,4,5]oxathiazepine 1,1-dioxide (30 mg, 0.053 mmol), acetic acid (3.97 µl, 0.069 mmol), and HATU (24.37 mg, 0.064 mmol) in N,N-dimethylformamide (DMF) (0.75 mL) was added DIEA (0.028 mL, 0.160 mmol). The reaction was stirred at ambient temperature for 2 hours. After 2 hours, LCMS showed the reaction to be complete. The reaction mixture was diluted with water and extracted with EtOAc (×3). The combined organic layers were washed with brine, dried over sodium sulfate, filtered, concentrated and then dissolved in DMSO and purified via preparative HPLC under acidic (formic acid) conditions to give the title compound (14.7 mg, 0.024 mmol, 45.6% yield). LCMS m/z 604.5 (M+H)⁺, 1.18 min (ret. time). ¹H NMR (400 MHz, METHANOL-d₄) δ ppm 0.82-0.93 (m, 3H) 1.12 (dd, J=6.90, 3.89 Hz, 1H) 1.37-1.46 (m, 4H) 1.52 (s, 3H) 1.62 (t, J=7.40 Hz, 3H) 1.75 (s, 3H) 2.31 (s, 3H) 2.71-2.85 (m, 4H) 3.65 (dd, J=15.06, 10.54 Hz, 1H) 3.82 (d, J=14.05 Hz, 1H) 3.92 (d, J=3.76 Hz, 1H) 4.54 (d, J=14.05 Hz, 1H) 4.73 (q, J=7.28 Hz, 2H) 5.58 (s, 1H) 7.15 (d, J=7.78 Hz, 1H) 7.21-7.38 (m, 4H) 7.56-7.66 (m, 3H) 7.83 (dd, J=7.78, 1.76 Hz, 1H) 7.95 (d, J=8.78 Hz, 1H)

The compounds in Table 18 were prepared by a method similar to the one described for the preparation of N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)acetamide. As is appreciated by those skilled in the art, these analogous examples may involve variations in general reaction conditions.

TABLE 18

| Ex # | Structure | Name | LCMS [M + 1] | Retention Time (min) |
|---|---|---|---|---|
| Example 133 | 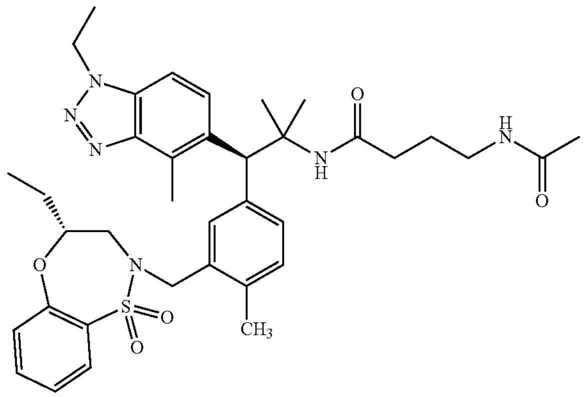 [SMILES: CC[C@@H]1CN(Cc2cc([C@@H](c3ccc4c(nnn4CC)c3C)C(C)(C)NC(=O)CCCNC(C)=O)ccc2C)S(=O)(=O)c2ccccc2O1] | 4-Acetamido-N-((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)butanamide | 689.5 | 1.09 |
| Example 134 | 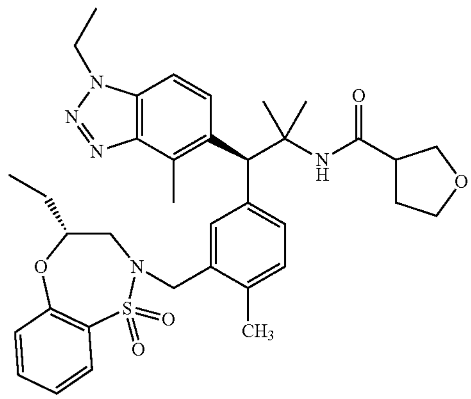 [SMILES: CC[C@@H]1CN(Cc2cc([C@@H](c3ccc4c(nnn4CC)c3C)C(C)(C)NC(=O)C3CCOC3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)tetrahydrofuran-3-carboxamide | 660.7 | 1.19 |
| Example 135 | 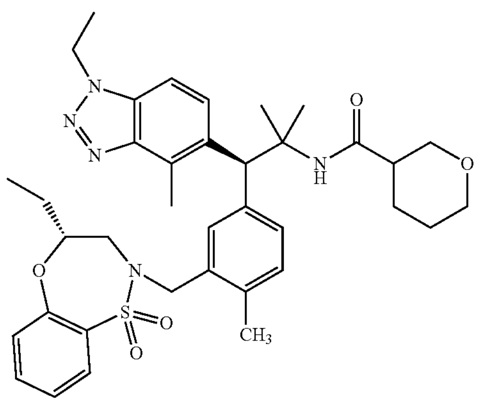 [SMILES: CC[C@@H]1CN(Cc2cc([C@@H](c3ccc4c(nnn4CC)c3C)C(C)(C)NC(=O)C3CCCOC3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)tetrahydro-2H-pyran-3-carboxamide | 674.7 | 1.23 |
| Example 136 | 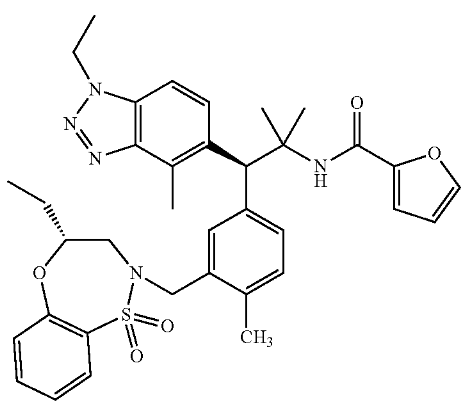 [SMILES: CC[C@@H]1CN(Cc2cc([C@@H](c3ccc4c(nnn4CC)c3C)C(C)(C)NC(=O)c3ccco3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)furan-2-carboxamide | 656.7 | 1.28 |

TABLE 18-continued

| Ex # | Structure | Name | LCMS [M + 1] | Retention Time (min) |
|---|---|---|---|---|
| Example 137 | 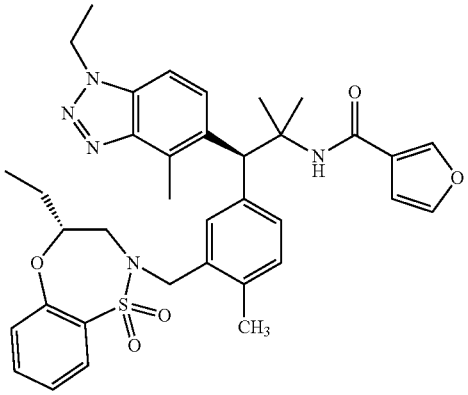 [SMILES: CC[C@@H]1CN(Cc2cc([C@@H](c3ccc4c(nnn4CC)c3C)C(C)(C)NC(=O)c3ccoc3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)furan-3-carboxamide | 656.7 | 1.26 |
| Example 138 | 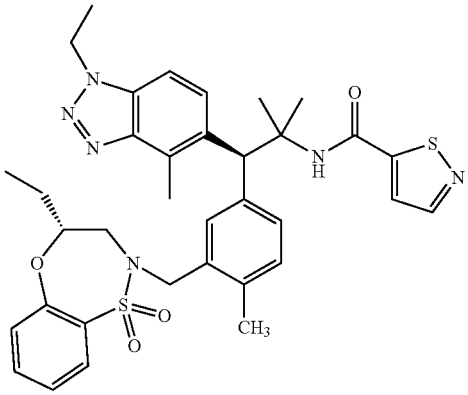 [SMILES: CC[C@@H]1CN(Cc2cc([C@@H](c3ccc4c(nnn4CC)c3C)C(C)(C)NC(=O)c3ccns3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)isothiazole-5-carboxamide | 673.6 | 1.28 |
| Example 139 | 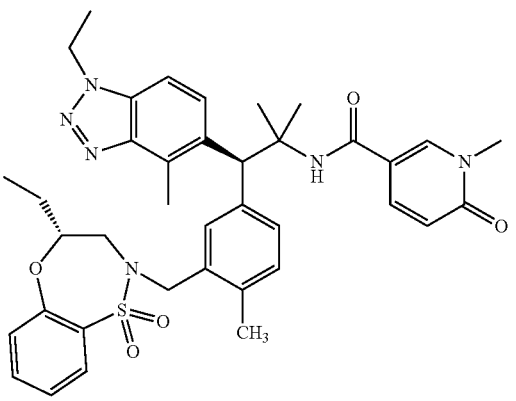 [SMILES: CC[C@@H]1CN(Cc2cc([C@@H](c3ccc4c(nnn4CC)c3C)C(C)(C)NC(=O)c3ccc(=O)n(C)c3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1-methyl-6-oxo-1,6-dihydropyridine-3-carboxamide | 697.7 | 1.13 |

TABLE 18-continued

| Ex # | Structure | Name | LCMS [M + 1] | Retention Time (min) |
|---|---|---|---|---|
| Example 140 | 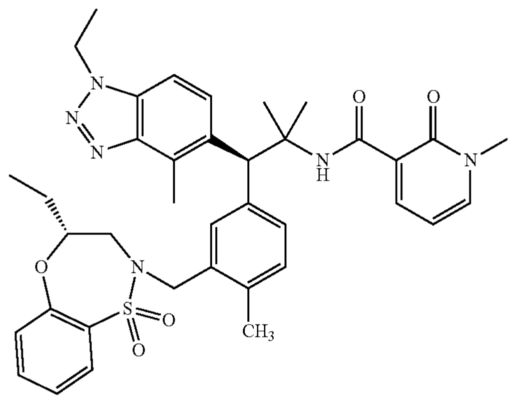 [SMILES: CC[C@@H]1CN(Cc2cc([C@@H](c3ccc4c(nnn4CC)c3C)C(C)(C)NC(=O)c3cccn(C)c3=O)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1-methyl-2-oxo-1,2-dihydropyridine-3-carboxamide | 697.7 | 1.24 |
| Example 141 | 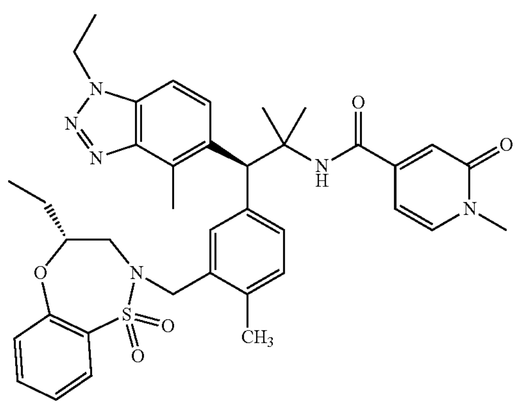 [SMILES: CC[C@@H]1CN(Cc2cc([C@@H](c3ccc4c(nnn4CC)c3C)C(C)(C)NC(=O)c3ccn(C)c(=O)c3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1-methyl-2-oxo-1,2-dihydropyridine-4-carboxamide | 697.7 | 1.12 |
| Example 142 | 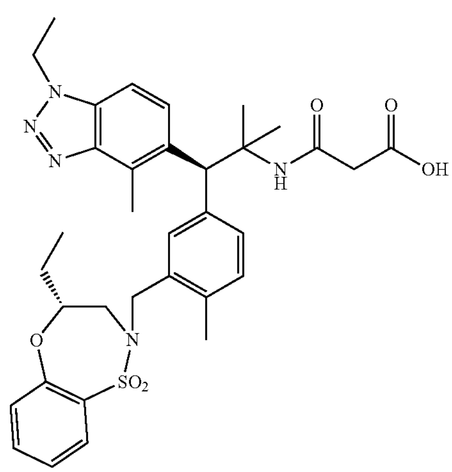 [SMILES: CC[C@@H]1CN(Cc2cc([C@@H](c3ccc4c(nnn4CC)c3C)C(C)(C)NC(=O)CC(=O)O)ccc2C)S(=O)(=O)c2ccccc2O1] | 3-(((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)amino)-3-oxopropanoic acid | 648.5 | 1.14 |

TABLE 18-continued

| Ex # | Structure | Name | LCMS [M + 1] | Retention Time (min) |
|---|---|---|---|---|
| Example 143 | 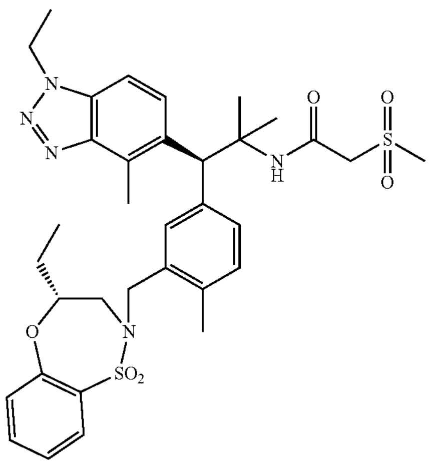 [SMILES: CC[C@@H]1CN(Cc2cc([C@@H](c3ccc4c(nnn4CC)c3C)C(C)(C)NC(=O)CS(C)(=O)=O)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(methylsulfonyl)acetamide | 682.6 | 1.16 |
| Example 144 | 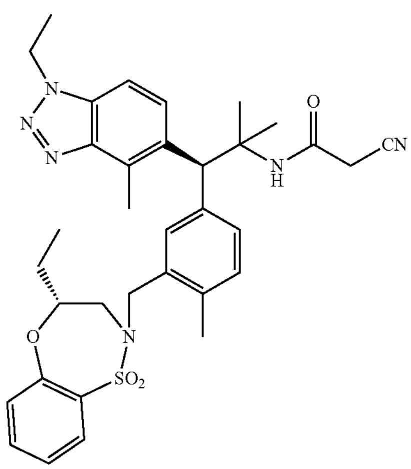 [SMILES: CC[C@@H]1CN(Cc2cc([C@@H](c3ccc4c(nnn4CC)c3C)C(C)(C)NC(=O)CC#N)ccc2C)S(=O)(=O)c2ccccc2O1] | 2-Cyano-N-((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)acetamide | 629.5 | 1.19 |
| Example 145 | 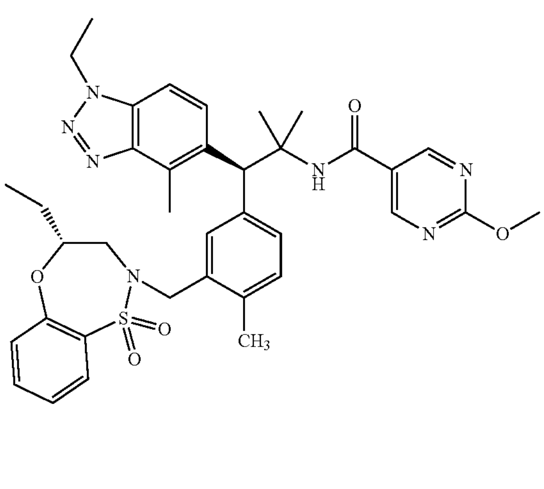 [SMILES: CC[C@@H]1CN(Cc2cc([C@@H](c3ccc4c(nnn4CC)c3C)C(C)(C)NC(=O)c3cnc(OC)nc3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-methoxypyrimidine-5-carboxamide | 698.5 | 1.23 |

TABLE 18-continued

| Ex # | Structure | Name | LCMS [M + 1] | Retention Time (min) |
|---|---|---|---|---|
| Example 146 | 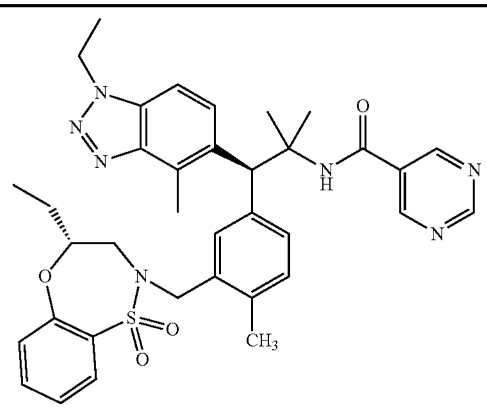 | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide | 668.6 | 1.17 |
| Example 147 | 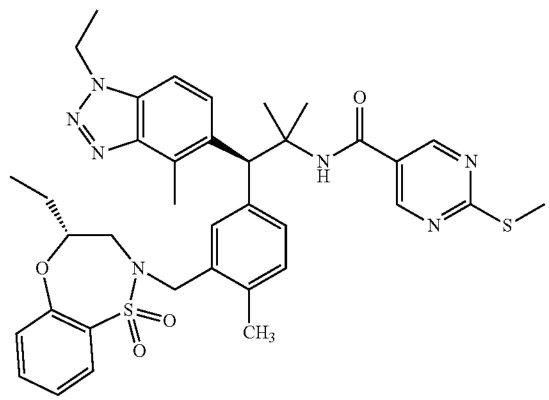 | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(methylthio)pyrimidine-5-carboxamide | 714.7 | 1.32 |
| Example 148 | 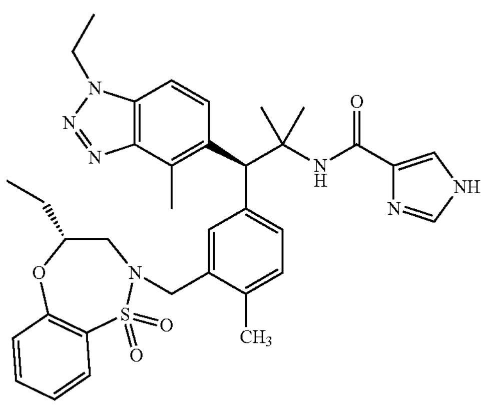 [SMILES: CC[C@@H]1CN(Cc2cc([C@@H](c3ccc4c(nnn4CC)c3C)C(C)(C)NC(=O)c3c[nH]cn3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1H-imidazole-4-carboxamide | 656.6 | 0.96 |
| Example 149 | 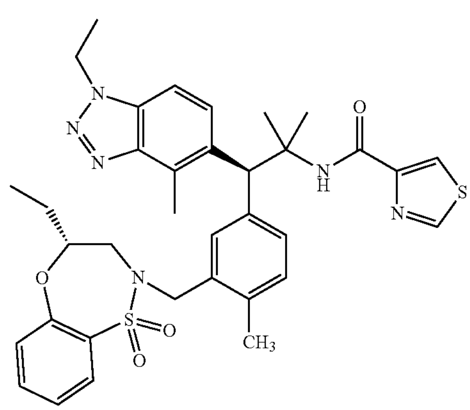 [SMILES: CC[C@@H]1CN(Cc2cc([C@@H](c3ccc4c(nnn4CC)c3C)C(C)(C)NC(=O)c3cscn3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)thiazole-4-carboxamide | 673.5 | 1.29 |

TABLE 18-continued

| Ex # | Structure | Name | LCMS [M + 1] | Retention Time (min) |
|---|---|---|---|---|
| Example 150 | 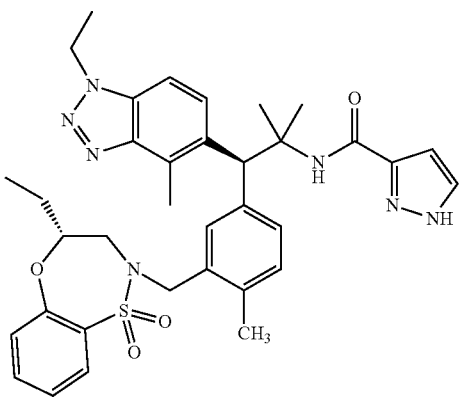 [SMILES: CC[C@@H]1CN(Cc2cc([C@@H](c3ccc4c(nnn4CC)c3C)C(C)(C)NC(=O)c3cc[nH]n3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-1H-pyrazole-3-carboxamide | 656.6 | 1.18 |
| Example 151 | 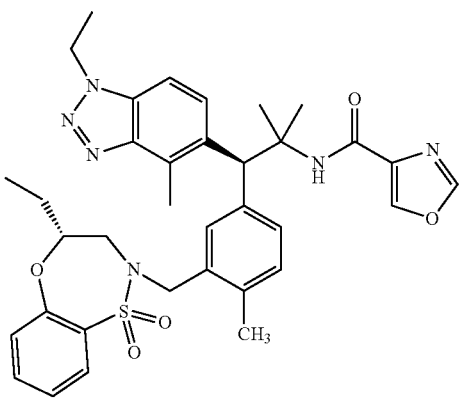 [SMILES: CC[C@@H]1CN(Cc2cc([C@@H](c3ccc4c(nnn4CC)c3C)C(C)(C)NC(=O)c3cocn3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)oxazole-4-carboxamide | 757.5 | 1.25 |
| Example 152 | 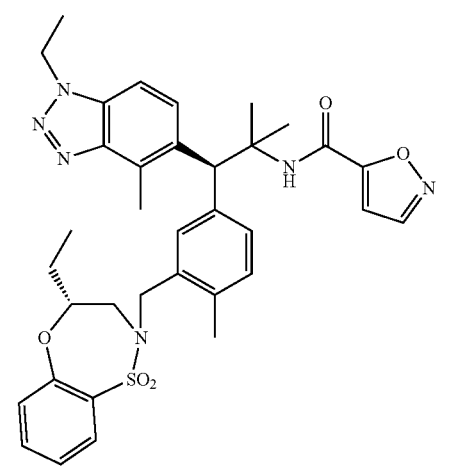 [SMILES: CC[C@@H]1CN(Cc2cc([C@@H](c3ccc4c(nnn4CC)c3C)C(C)(C)NC(=O)c3ccno3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)isoxazole-5-carboxamide | 648.5 | 1.14 |

TABLE 18-continued

| Ex # | Structure | Name | LCMS [M + 1] | Retention Time (min) |
|---|---|---|---|---|
| Example 153 | 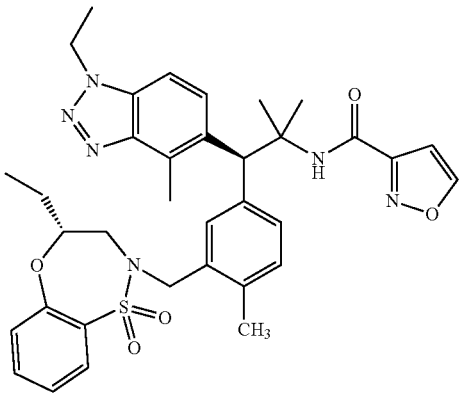 [SMILES: CC[C@@H]1CN(Cc2cc([C@@H](c3ccc4c(nnn4CC)c3C)C(C)(C)NC(=O)c3ccon3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)isoxazole-3-carboxamide | 657.6 | 1.29 |
| Example 154 | 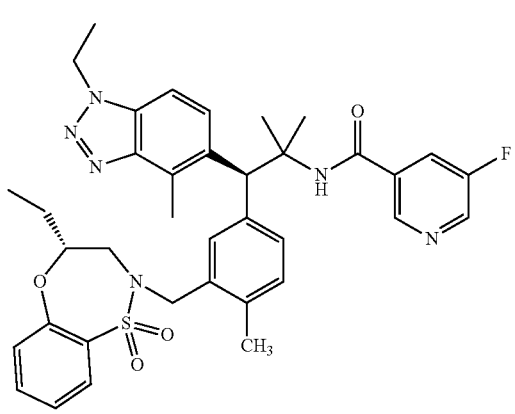 [SMILES: CC[C@@H]1CN(Cc2cc([C@@H](c3ccc4c(nnn4CC)c3C)C(C)(C)NC(=O)c3cncc(F)c3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-5-fluoronicotinamide | 685.7 | 1.26 |
| Example 155 | 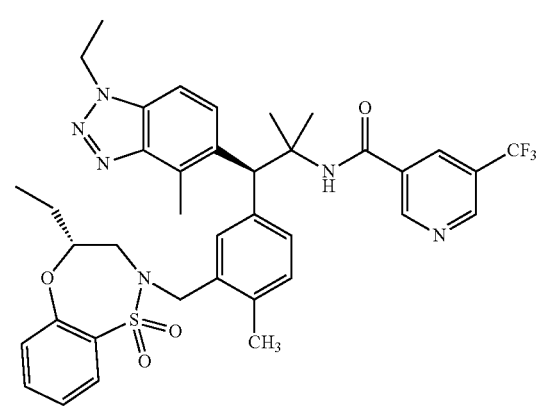 [SMILES: CC[C@@H]1CN(Cc2cc([C@@H](c3ccc4c(nnn4CC)c3C)C(C)(C)NC(=O)c3cncc(C(F)(F)F)c3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-5-(trifluoromethyl)nicotinamide | 736.1 | 1.35 |

TABLE 18-continued

| Ex # | Structure | Name | LCMS [M + 1] | Retention Time (min) |
|---|---|---|---|---|
| Example 156 | 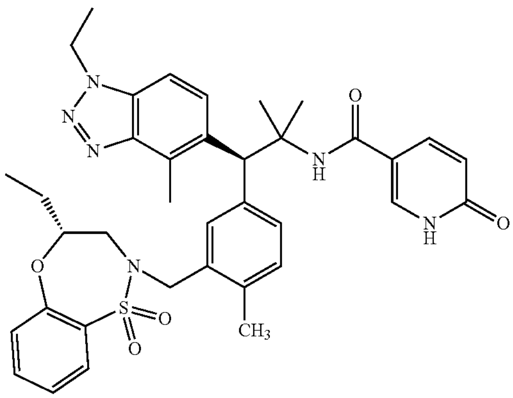 [SMILES: CC[C@@H]1CN(Cc2cc([C@@H](c3ccc4c(nnn4CC)c3C)C(C)(C)NC(=O)c3ccc(=O)[nH]c3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-6-oxo-1,6-dihydropyridine-3-carboxamide | 683.7 | 1.09 |

Example 157

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(methylsulfonyl)pyrimidine-5-carboxamide

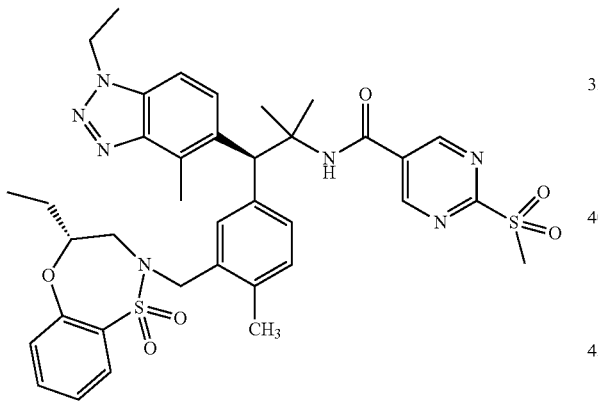

To a stirred solution of N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(methylthio)pyrimidine-5-carboxamide (156 mg, 0.219 mmol) in dichloromethane (DCM) (3 mL) was added m-CPBA (226 mg, 1.311 mmol) at ambient temperature. The solution was stirred for 3 hrs at which point LCMS showed the reaction to be complete. The mixture was then directly loaded onto a column and purified via silica gel chromatography to obtain the title compound N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(methylsulfonyl)pyrimidine-5-carboxamide (122.2 mg, 0.164 mmol, 75.0% yield). LC-MS m/z 747.0 (M+H)$^+$, 1.20 min (ret. Time). $^1$H NMR (400 MHz, CHLOROFORM-d) δ ppm 1.04 (t, J=7.28 Hz, 3H) 1.37 (ddd, J=14.31, 7.28, 4.02 Hz, 1H) 1.60-1.69 (m, 12H) 1.75 (s, 3H) 2.25 (s, 3H) 2.82 (s, 2H) 2.91 (s, 3H) 3.00 (dd, J=14.93, 1.63 Hz, 1H) 3.34 (s, 3H) 3.65 (dd, J=14.81, 10.54 Hz, 1H) 3.88-4.07 (m, 2H) 4.41 (d, J=15.06 Hz, 1H) 4.67 (q, J=7.36 Hz, 2H) 5.35 (s, 1H) 6.53 (s, 1H) 7.10 (d, J=7.78 Hz, 1H) 7.21 (dd, J=8.16, 0.88 Hz, 2H) 7.40 (d, J=8.78 Hz, 1H) 7.49-7.58 (m, 2H) 7.79-7.87 (m, 2H) 9.03 (s, 2H).

Example 158

2-(Azetidin-1-yl)-N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide

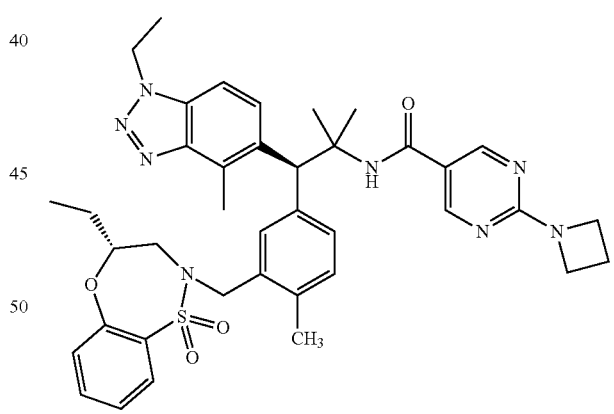

To a solution of N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(methylsulfonyl)pyrimidine-5-carboxamide (24.75 mg, 0.033 mmol) and dichloromethane (DCM) (0.75 mL) was added azetidine (5.68 mg, 0.100 mmol). The reaction was allowed to stir at ambient temperature for 1 hr at which point LCMS showed it to be complete. The reaction mixture was concentrated to dryness, dissolved in DMSO and purified via reverse phase preparative HPLC under acidic (formic acid) conditions to give the title compound 2-(azetidin-1-yl)-N—((S)-1-(3-

(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide (12.5 mg, 0.017 mmol, 52.1% yield). LC-MS m/z 723.8 (M+H)+, 1.20 min (ret. Time). $^1$H NMR (400 MHz, METHANOL-d4) δ ppm 0.84-0.94 (m, 3H) 1.13 (ddd, J=14.18, 7.28, 3.89 Hz, 1H) 1.41 (ddd, J=14.24, 8.72, 7.40 Hz, 1H) 1.50-1.69 (m, 9H) 2.30 (s, 3H) 2.35-2.45 (m, 2H) 2.72-2.82 (m, 4H) 3.60 (dd, J=15.18, 10.42 Hz, 1H) 3.82 (d, J=14.05 Hz, 1H) 3.92 (td, J=9.10, 3.64 Hz, 1H) 4.11-4.20 (m, 4H) 4.51 (d, J=14.05 Hz, 1H) 4.70 (q, J=7.28 Hz, 2H) 5.70 (s, 1H) 7.14 (d, J=7.78 Hz, 1H) 7.21-7.38 (m, 4H) 7.55-7.64 (m, 2H) 7.81 (dd, J=7.78, 1.76 Hz, 1H) 8.00 (d, J=8.78 Hz, 1H) 8.40 (s, 2H)

The compounds in Table 19 were prepared by a method similar to the one described for the preparation of 2-(Azetidin-1-yl)-N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide. As is appreciated by those skilled in the art, these analogous examples may involve variations in general reaction conditions.

TABLE 19

| Ex # | Structure | Name | LCMS [M + 1] | Retention Time (min) |
|---|---|---|---|---|
| Example 159 | 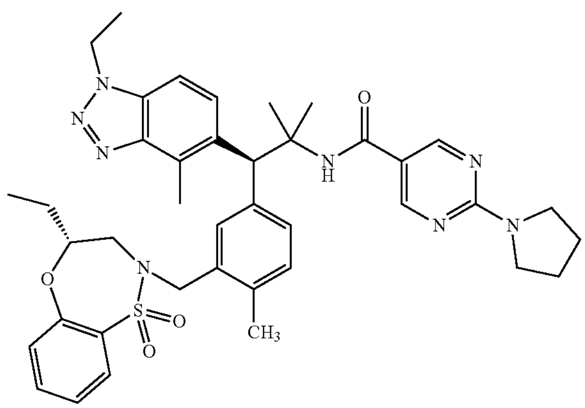 [SMILES: CC[C@@H]1CN(Cc2cc([C@@H](c3ccc4c(nnn4CC)c3C)C(C)(C)NC(=O)c3cnc(N4CCCC4)nc3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(pyrrolidin-1-yl)pyrimidine-5-carboxamide | 737.7 | 1.27 |
| Example 160 | 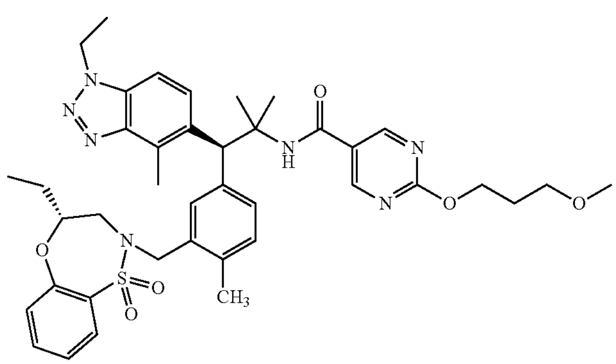 [SMILES: CC[C@@H]1CN(Cc2cc([C@@H](c3ccc4c(nnn4CC)c3C)C(C)(C)NC(=O)c3cnc(OCCCOC)nc3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(3-methoxypropoxy)pyrimidine-5-carboxamide | 756.7 | 1.27 |
| Example 161 | 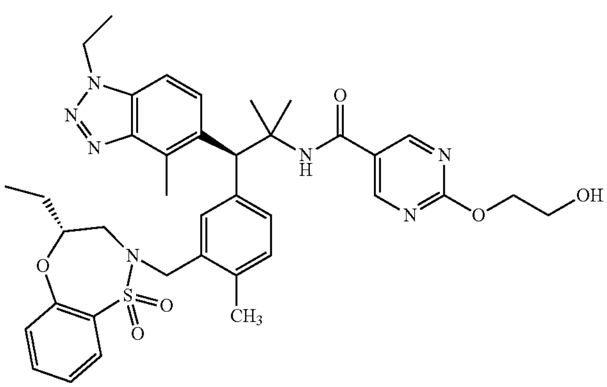 [SMILES: CC[C@@H]1CN(Cc2cc([C@@H](c3ccc4c(nnn4CC)c3C)C(C)(C)NC(=O)c3cnc(OCCO)nc3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(2-hydroxyethoxy)pyrimidine-5-carboxamide | 728.8 | 1.13 |

TABLE 19-continued

| Ex # | Structure | Name | LCMS [M + 1] | Retention Time (min) |
|---|---|---|---|---|
| Example 162 | 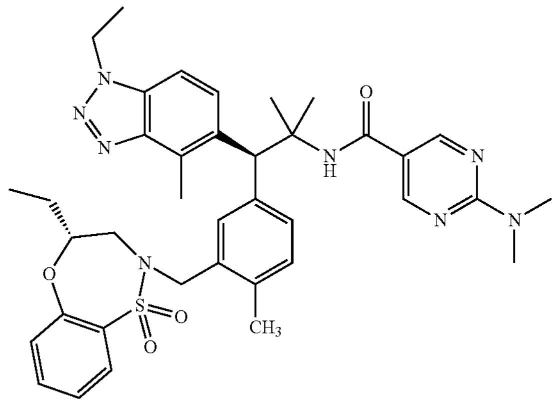 [SMILES: CC[C@@H]1CN(Cc2cc([C@@H](c3ccc4c(nnn4CC)c3C)C(C)(C)NC(=O)c3cnc(N(C)C)nc3)ccc2C)S(=O)(=O)c2ccccc2O1] | 2-(Dimethylamino)-N-((S)-1-(3-(((R)-4-ethyl-1,1-dioxido-3,4-dihydro-2H-benzo[b][1,4,5]oxathiazepin-2-yl)methyl)-4-(methylphenyl)-1-(1-ethyl-4-methyl-1H-benzo[d][1,2,3]triazol-5-yl)-2-methylpropan-2-yl)pyrimidine-5-carboxamide | 711.7 | 1.26 |
| Example 163 | 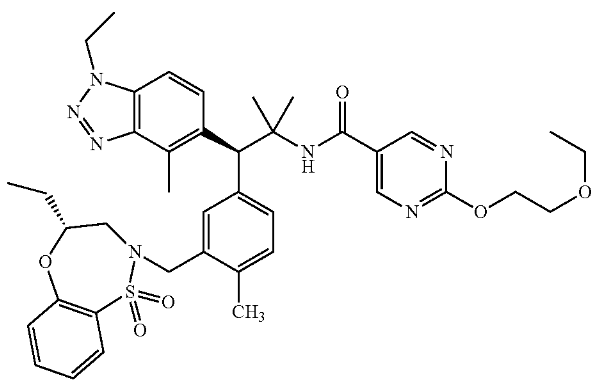 [SMILES: CCOCCOc1ncc(C(=O)NC(C)(C)[C@@H](c2ccc(C)c(CN3C[C@@H](CC)Oc4ccccc4S3(=O)=O)c2)c2ccc3c(nnn3CC)c2C)cn1] | 2-(2-Ethoxyethoxy)-N-((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide | 756.7 | 1.28 |
| Example 164 | 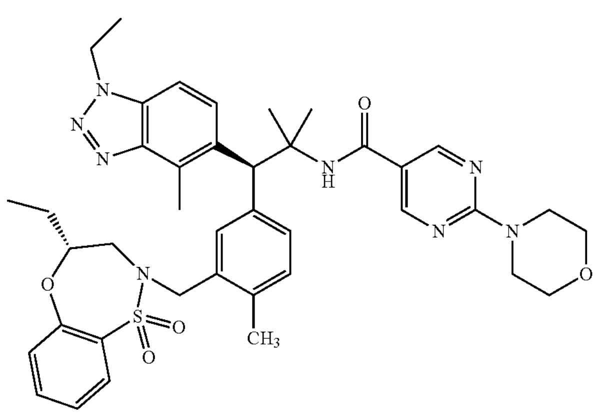 [SMILES: CC[C@@H]1CN(Cc2cc([C@@H](c3ccc4c(nnn4CC)c3C)C(C)(C)NC(=O)c3cnc(N4CCOCC4)nc3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-morpholinopyrimidine-5-carboxamide | 754.7 | 1.26 |

TABLE 19-continued

| Ex # | Structure | Name | LCMS [M + 1] | Retention Time (min) |
|---|---|---|---|---|
| Example 165 | 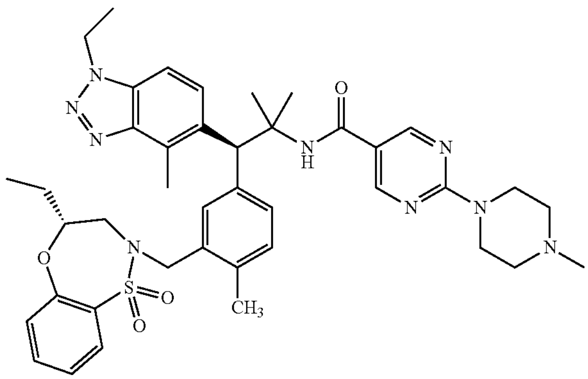 [SMILES: CC[C@@H]1CN(Cc2cc([C@@H](c3ccc4c(nnn4CC)c3C)C(C)(C)NC(=O)c3cnc(N4CCN(C)CC4)nc3)ccc2C)S(=O)(=O)c2ccccc2O1] | N-((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-2-(4-methylpiperazin-1-yl)pyrimidine-5-carboxamide | 766.8 | 0.92 |

Example 166

N—((S)-1-(3-(((R)-4-Ethyl-1,1-dioxido-3,4-dihydro-2H-pyrido[2,3-b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)nicotinamide

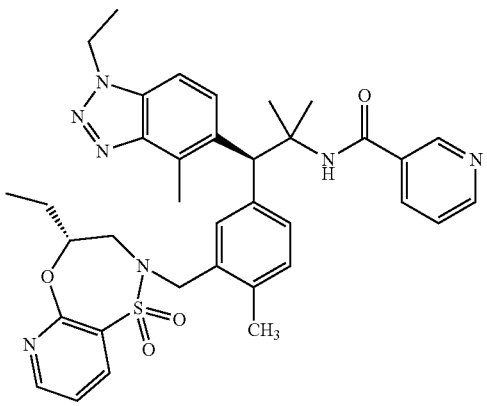 [SMILES: CC[C@@H]1CN(Cc2cc([C@@H](c3ccc4c(nnn4CC)c3C)C(C)(C)NC(=O)c3cccnc3)ccc2C)S(=O)(=O)c2cccnc2O1]

(S)-3-(3-(((R)-4-Ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoyl Azide

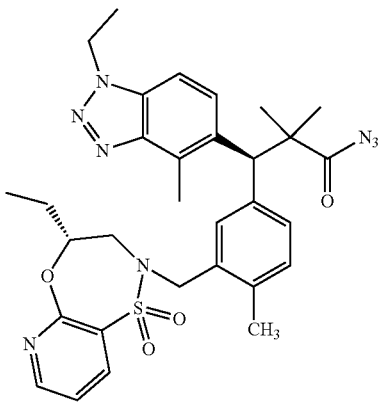 [SMILES: CC[C@@H]1CN(Cc2cc([C@@H](c3ccc4c(nnn4CC)c3C)C(C)(C)C(=O)N=[N+]=[N-])ccc2C)S(=O)(=O)c2cccnc2O1]

To a stirred solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (257.0 mg, 0.434 mmol) and triethylamine (0.182 ml, 1.303 mmol) in toluene (5 mL) was slowly added diphenyl phosphorazidate (0.140 ml, 0.651 mmol). The reaction was allowed to stir at ambient temperature for 18 hrs at which point LCMS showed the reaction to be complete. The reaction mixture was then concentrated and purified via reverse phase preparative HPLC under acidic conditions (formic acid) to obtain the title compound (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoyl azide (234.6 mg, 0.380 mmol, 88% yield). LC-MS m/z 617.5 (M+H)$^+$, 1.30 min (ret. Time).

(R)-2-(5-((S)-2-Amino-1-(1-ethyl-4-methyl-1H-benzo[d][1,2,3]triazol-5-yl)-2-methylpropyl)-2-methylbenzyl)-4-ethyl-3,4-dihydro-2H-pyrido[2,3-b][1,4,5]oxathiazepine 1,1-dioxide

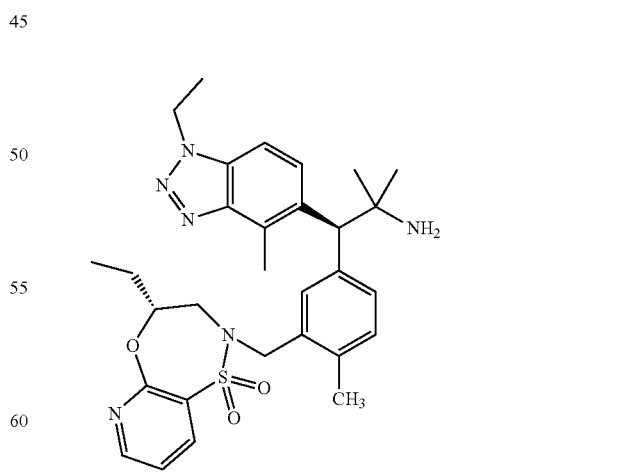

A solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2,2-dimethylpropanoyl azide (229.2 mg, 0.372 mmol) in toluene (5 mL) was heated to 80° C. and stirred for 1 hr. The solution was cooled to ambient temperature and then concentrated to give (R)-4-ethyl-2-(5-((S)-1-(1-ethyl-4-methyl-1H-benzo[d][1,2,3]triazol-5-yl)-2-isocyanato-2-methylpropyl)-2-methylbenzyl)-3,4-dihydro-2H-pyrido[2,3-b][1,4,5]oxathiazepine 1,1-dioxide which was used without further purification.

The crude (R)-4-ethyl-2-(5-((S)-1-(1-ethyl-4-methyl-1H-benzo[d][1,2,3]triazol-5-yl)-2-isocyanato-2-methylpropyl)-2-methylbenzyl)-3,4-dihydro-2H-pyrido[2,3-b][1,4,5]oxathiazepine 1,1-dioxide was then dissolved in acetonitrile (5.00 mL) and HCl (0.279 mL, 1.115 mmol) (4M in dioxane) was added. The reaction was allowed to stir for 2 hrs at which point LCMS showed the reaction to be complete. The reaction mixture was diluted with water and extracted with EtOAc (×3). The combined organic layers were washed with brine, dried over sodium sulfate, filtered and concentrated to dryness to obtain the title compound crude (R)-2-(5-((S)-2-amino-1-(1-ethyl-4-methyl-1H-benzo[d][1,2,3]triazol-5-yl)-2-methylpropyl)-2-methylbenzyl)-4-ethyl-3,4-dihydro-2H-pyrido[2,3-b][1,4,5]oxathiazepine 1,1-dioxide. LC-MS m/z 563.4 (M+H)$^+$, 0.72 min (ret. Time).

N—((S)-1-(3-(((R)-4-Ethyl-1,1-dioxido-3,4-dihydro-2H-pyrido[2,3-b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)nicotinamide

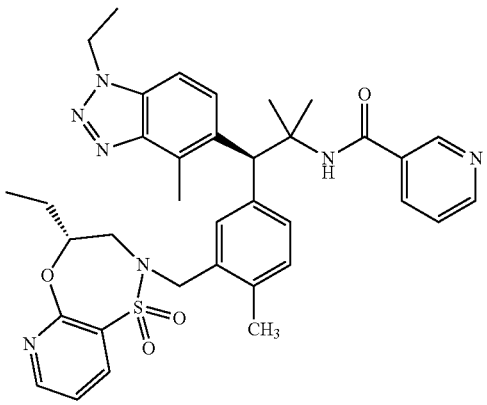 [SMILES: CC[C@@H]1CN(Cc2cc([C@@H](c3ccc4c(nnn4CC)c3C)C(C)(C)NC(=O)c3cccnc3)ccc2C)S(=O)(=O)c2cccnc2O1]

To a solution of (R)-2-(5-((S)-2-amino-1-(1-ethyl-4-methyl-1H-benzo[d][1,2,3]triazol-5-yl)-2-methylpropyl)-2-methylbenzyl)-4-ethyl-3,4-dihydro-2H-pyrido[2,3-b][1,4,5]oxathiazepine 1,1-dioxide (52 mg, 0.092 mmol), nicotinic acid (14.79 mg, 0.120 mmol), and HATU (42.2 mg, 0.111 mmol) in N,N-dimethylformamide (DMF) (1 mL) was added DIEA (0.048 mL, 0.277 mmol). The reaction mixture was stirred for 30 minutes at ambient temperature at which point LCMS showed the reaction to be complete. The reaction mixture was then diluted with water and extracted with EtOAc (×3). The combined organic layers were washed with brine, dried over sodium sulfate, filtered and concentrated to dryness. The crude product was then purified via silica gel chromatography using ethyl acetate/hexanes to obtain the title compound N—((S)-1-(3-(((R)-4-ethyl-1,1-dioxido-3,4-dihydro-2H-pyrido[2,3-b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)nicotinamide (34.3 mg, 0.051 mmol, 55.6% yield). LC-MS m/z 668.5 (M+H)$^+$, 1.01 min (ret. Time). $^1$H NMR (400 MHz, METHANOL-d4) δ ppm 0.85 (t, J=7.28 Hz, 3H) 1.34-1.43 (m, 5H) 1.53-1.64 (m, 6H) 1.70 (s, 3H) 2.31 (s, 3H) 2.75-2.89 (m, 4H) 3.99 (d, J=14.31 Hz, 1H) 4.16-4.28 (m, 1H) 4.54 (d, J=14.31 Hz, 1H) 4.71 (q, J=7.28 Hz, 2H) 5.75 (s, 1H) 7.17 (d, J=7.78 Hz, 1H) 7.33 (d, J=1.51 Hz, 1H) 7.38-7.46 (m, 3H) 7.60 (d, J=8.78 Hz, 1H) 7.89 (dt, J=7.97, 1.91 Hz, 1H) 8.03 (d, J=8.78 Hz, 1H) 8.29 (dd, J=7.78, 2.01 Hz, 1H) 8.48 (dd, J=4.89, 1.88 Hz, 1H) 8.52-8.62 (m, 2H)

Example 167

N—((S)-1-(3-(((R)-4-Ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-N-methylpyrimidine-5-carboxamide

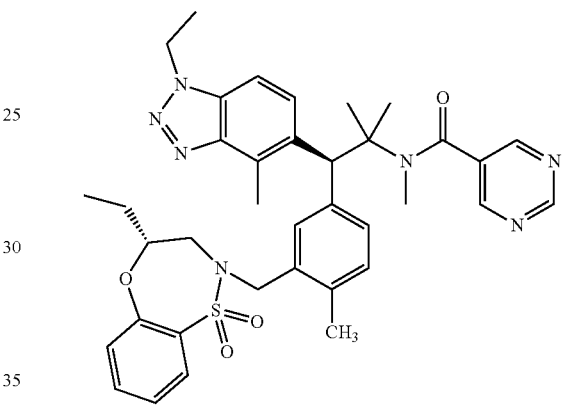

To solution of (R)-2-(5-((S)-2-amino-1-(1-ethyl-4-methyl-1H-benzo[d][1,2,3]triazol-5-yl)-2-methylpropyl)-2-methylbenzyl)-4-ethyl-3,4-dihydro-2H-benzo[b][1,4,5]oxathiazepine 1,1-dioxide (61.5 mg, 0.109 mmol) in dichloromethane (DCM) (2 mL) was added MeI (7.53 μl, 0.120 mmol) and DIEA (0.057 mL, 0.328 mmol). The reaction was stirred at ambient temperature for 18 hrs. The reaction mixture was concentrated to dryness and carried forward to the next step without purification.

N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)pyrimidine-5-carboxamide was dissolved in N,N-dimethylformamide (DMF) (1 mL) and HATU (50.0 mg, 0.131 mmol), pyrimidine-5-carboxylic acid (17.66 mg, 0.142 mmol), and DIEA (0.057 mL, 0.328 mmol) were added. The reaction was stirred at ambient temperature for 41 hrs at which point LCMS showed the reaction to be complete.

The reaction mixture was diluted with water and extracted with EtOAc (×3). The combined organic layers were washed with brine, dried over sodium sulfate, filtered and concentrated to dryness. The crude product was purified via reverse phase preparative HPLC under acidic (formic acid) conditions to obtain the title compound N—((S)-1-(3-(((R)-4-ethyl-1,1-dioxido-3,4-dihydro-2H-benzo[b][1,4,5]oxathiazepin-2-yl)methyl)-4-methylphenyl)-1-(1-ethyl-4-methyl-1H-benzo[d][1,2,3]triazol-5-yl)-2-methylpropan-2-yl)-N-methylpyrimidine-5-carboxamide (51.0 mg, 0.075 mmol, 68.3% yield). LC-MS m/z 682.6 (M+H)$^+$, 1.20 min (ret.

Time). ¹H NMR (400 MHz, METHANOL-d4) δ ppm 0.86-0.97 (m, 3H) 1.15 (ddd, J=10.73, 7.22, 3.64 Hz, 1H) 1.41 (ddd, J=14.24, 8.60, 7.28 Hz, 1H) 1.58-1.67 (m, 6H) 1.79 (s, 3H) 2.28-2.38 (m, 3H) 2.74-2.84 (m, 4H) 2.93 (s, 3H) 3.62 (dd, J=15.06, 10.54 Hz, 1H) 3.78-4.02 (m, 2H) 4.55 (d, J=14.31 Hz, 1H) 4.75 (q, J=7.28 Hz, 2H) 6.09 (s, 1H) 7.14-7.35 (m, 3H) 7.35-7.43 (m, 2H) 7.57-7.73 (m, 2H) 7.83 (dd, J=7.78, 1.76 Hz, 1H) 8.01 (d, J=8.78 Hz, 1H) 8.19 (s, 2H) 9.07 (s, 1H)

(S)-3-(1-ethyl-7-methoxy-4-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoic Acid

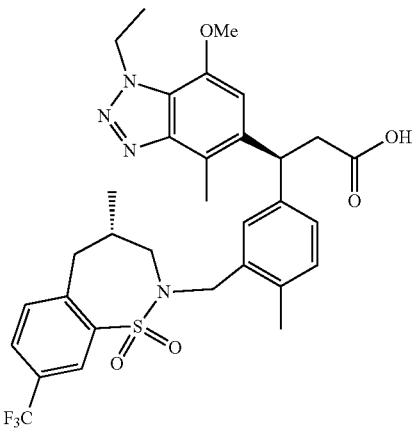 [SMILES: CCn1nnc2c(C)c([C@@H](CC(=O)O)c3ccc(C)c(CN4C[C@@H](C)Cc5ccc(C(F)(F)F)cc5S4(=O)=O)c3)cc(OC)c21]

2-Bromo-4-methyl-3-nitrophenol

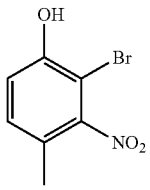

To a solution of 4-methyl-3-nitrophenol (10 g, 65.3 mmol) in chloroform (30 mL) was added bromine (3.37 mL, 65.3 mmol) solution in chloroform (200 mL) slowly under nitrogen at 35° C. The reaction was stirred at 35° C. for 40 hours. 100 mL water was added to the solution. It was extracted with DCM (3×200 mL). The organic layer was concentrated to give the title compound (8 g, 13% yield) which was used for the next step without further purification. ¹H NMR (500 MHz, CDCl3) δ 7.16 (d, J=8.5 Hz, 1H), 7.05 (d, J=8.5 Hz, 1H), 2.27 (s, 3H).

N-Ethyl-6-methoxy-3-methyl-2-nitroaniline

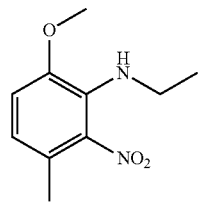

To a solution of 2-bromo-4-methyl-3-nitrophenol (40 g, 172 mmol) in acetone (200 mL) at ambient temperature was added K₂CO₃ (47.7 g, 345 mmol), MeI (21.56 mL, 345 mmol) slowly under nitrogen. The reaction mixture was stirred at 65° C. for 40 hours. 200 mL of water was added and was extracted with ethyl acetate (3×200 mL). The combined organic layers were concentrated under a stream of nitrogen at 50° C. to give 2-bromo-1-methoxy-4-methyl-3-nitrobenzene (35 g, 142 mmol) which was used for the next step without further purification. To a solution of 2-bromo-1-methoxy-4-methyl-3-nitrobenzene (35 g, 142 mmol) in dimethyl sulfoxide (DMSO) (500 mL) was added copper (0.904 g, 14.22 mmol) and ethanamine (641 mL, 4267 mmol) slowly under nitrogen at ambient temperature. The reaction mixture was stirred at 100° C. for 16 hours. 500 mL of water was added and extracted with ethyl acetate (3×300 mL). The organic layer was concentrated. The crude product was purified with silica gel column eluting with (hexane:ethyl acetate=20:1) to give the title compound (16.5 g, 39.2 mmol, 27.6% yield) as red oil. LC-MS m/z 211.1 (M+H)⁺, 2.04 (ret. time).

4-Bromo-N-ethyl-6-methoxy-3-methyl-2-nitroaniline

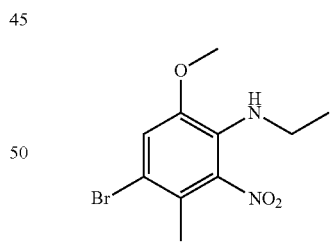

To a solution of N-ethyl-6-methoxy-3-methyl-2-nitroaniline (28.6 g, 68.0 mmol) in N,N dimethylformamide (DMF) (300 mL) was added a solution of NBS (12.11 g, 68.0 mmol) in N,N dimethylformamide (DMF) (300 mL) slowly under nitrogen at ambient temperature. The reaction mixture was stirred at ambient temperature for 14 hours. 100 mL of water was added and filtered. The solid was dried with high vacuum to give the title compound (30 g, 51.9 mmol, 76% yield). LC-MS m/z=289.0 (M+H)⁺, 2.24 (ret. time).

333

4-Bromo-N¹-ethyl-6-methoxy-3-methylbenzene-1,2-diamine

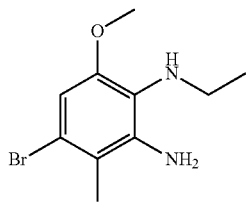

To a solution of 4-bromo-N-ethyl-6-methoxy-3-methyl-2-nitroaniline (30 g, 104 mmol) in ethanol (200 mL) and 1,2-dichloroethane (DCE) (200 mL) was added nickel (6.09 g, 104 mmol) slowly under nitrogen at 0° C. Hydrazine, H₂O (6.10 mL, 125 mmol) was added dropwise. The reaction mixture was stirred at 0° C. for 0.5 hour. It was filtered and 200 mL of water was added. It was extracted with ethyl acetate (3×200 mL). The organic layer was concentrated. The crude product was added to a silica gel column and was eluted with (hexane:ethyl acetate=20:1) to give the title compound (16 g, 49.4 mmol, 47.6% yield). It was carried to next step without further purification. LC-MS m/z=261.0 (M+H)⁺ 1.28 (ret. time).

5-Bromo-1-ethyl-7-methoxy-4-methyl-1H-benzo[d][1,2,3]triazole

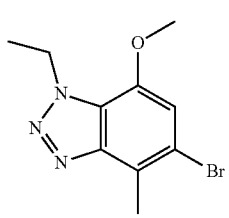

To a solution of H₂SO₄ (11.52 mL, 216 mmol) in water (100 mL) was added 4-bromo-N¹-ethyl-6-methoxy-3-methylbenzene-1,2-diamine (16 g, 61.7 mmol). A solution of sodium nitrite (8.52 g, 123 mmol) in water (20 mL) was added dropwise at 0° C. The reaction mixture was stirred at 0° C. for 16 hours. 200 mL of water was added. It was filtered and the solid was dissolved in 500 ml of DCM, washed with aqueous NaCl (2×50 mL), dried with MgSO₄, filtered and concentrated. The Isolute-adsorbed crude product was added to a silica gel column and was eluted with (hexane:ethyl acetate=4:1) to give the title compound (10.6 g, 37.7 mmol, 61.0% yield) as a solid. LC-MS m/z=256.0 (M+H)⁺, 1.56 (ret. time).

334

Benzyl (E)-3-(1-ethyl-7-methoxy-4-methyl-1H-benzo[d][1,2,3]triazol-5-yl)acrylate

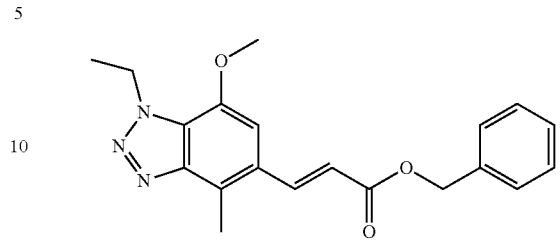

To the mixture of 5-bromo-1-ethyl-7-methoxy-4-methyl-1H-benzo[d][1,2,3]triazole (1.5 g, 5.55 mmol) in N,N-dimethylformamide (8 mL) at ambient temperature was added benzyl acrylate (3.40 mL, 22.21 mmol) and N-ethyl-N-isopropylpropan-2-amine (3.88 mL, 22.21 mmol), tri-o-tolylphosphane (0.507 g, 1.666 mmol), followed by palladium(II)acetate (0.187 g, 0.833 mmol). The reaction mixture was heated via microwave at 150° C. for 2 then filtered and extracted with EtOAc. The combined organic layer was washed with water and brine, concentrated and purified with silica gel flash chromatograph to give the title compound (1812 mg, 5.16 mmol, 93% yield). LC-MS m/z 352.2 (M+H)⁺, 1.25 min (ret. time).

Benzyl (S)-3-(1-ethyl-7-methoxy-4-methyl-1H-benzo[d][1,2,3]triazol-5-yl)-3-(3-(hydroxymethyl)-4-methylphenyl)propanoate

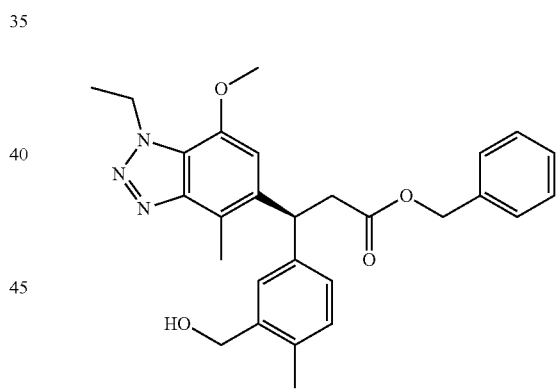

To the mixture of benzyl (E)-3-(1-ethyl-7-methoxy-4-methyl-1H-benzo[d][1,2,3]triazol-5-yl)acrylate (1800 mg, 5.12 mmol), (2-methyl-5-(4,4,5,5-tetramethyl-1,3,2-dioxaborolan-2-yl)phenyl)methanol (1906 mg, 7.68 mmol), and [RhCl(cod)]₂ (253 mg, 0.512 mmol) in 1,4-dioxane (8 mL) and water (2.000 mL) at ambient temperature was added triethylamine (2.142 mL, 15.37 mmol). The mixture was degassed for 10 min and then heated with microwave at 120° C. for 1 h. The reaction mixture was filtered and extracted with EtOAc. The organic layer was collected, concentrated, purified by silica gel chromatography and further purified with chiral SFC (Column: Chiralpak IA 20×250 mm, 5 u; Co-solvent: 25% EtOH; Flowrate: 50 g/min; Back pressure: 100 Bar) to give the title compound (804.6 mg, 1.699 mmol, 33.2% yield). LC-MS m/z 474.4 (M+H)⁺, 1.15 min (ret. time).

335

(S)-3-(1-ethyl-7-methoxy-4-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoic Acid

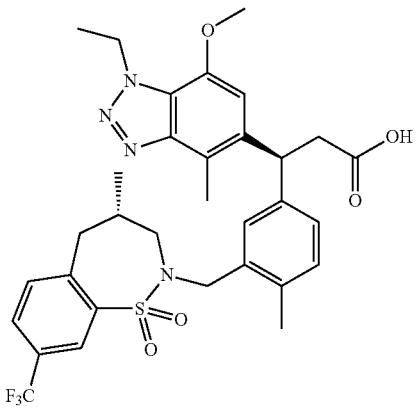 [SMILES: CCn1nnc2c(C)c([C@@H](CC(=O)O)c3ccc(C)c(CN4C[C@@H](C)Cc5ccc(C(F)(F)F)cc5S4(=O)=O)c3)cc(OC)c21]

To a solution of benzyl (S)-3-(1-ethyl-7-methoxy-4-methyl-1H-benzo[d][1,2,3]triazol-5-yl)-3-(3-(hydroxymethyl)-4-methylphenyl)propanoate (80 mg, 0.169 mmol), (S)-4-methyl-8-(trifluoromethyl)-2,3,4,5-tetrahydrobenzo[f][1,2]thiazepine 1,1-dioxide (47.2 mg, 0.169 mmol), and 1,1'-(Azodicarbonyl)dipiperidine (85 mg, 0.338 mmol) in tetrahydrofuran (3 mL) at ambient temperature was added tri-n-butylphosphine (0.083 mL, 0.338 mmol). The reaction mixture was stirring at ambient temperature for 20 h. It was concentrated and purified by silica gel chromatography to give the intermediate benzyl ester which was dissolved in methanol (3.00 mL). LiOH (2M, 0.507 mL, 1.014 mmol) was added. The resulting reaction mixture was stirred at ambient temperature for 18 h then was concentrated, purified with reverse phase HPLC under neutral conditions to give the title compound (48 mg, 0.074 mmol, 44.1% yield). LC-MS m/z 645.4 (M+H)$^+$, 1.33 min (ret. time).

(S)-3-(1-ethyl-4-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoic Acid

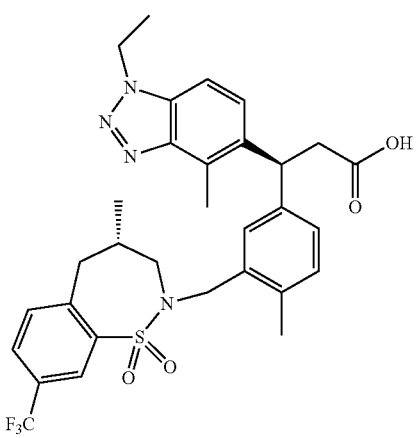 [SMILES: CCn1nnc2c(C)c([C@@H](CC(=O)O)c3ccc(C)c(CN4C[C@@H](C)Cc5ccc(C(F)(F)F)cc5S4(=O)=O)c3)ccc21]

336

Ethyl (S)-3-(1-ethyl-4-methyl-1H-benzo[d][1,2,3]triazol-5-yl)-3-(3-(hydroxymethyl)-4-methylphenyl)propanoate

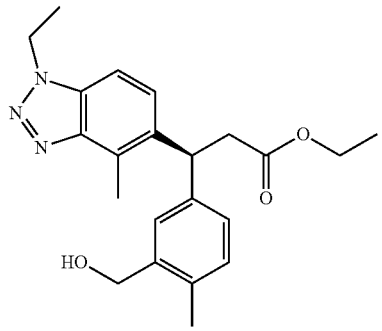 [SMILES: CCOC(=O)C[C@@H](c1ccc(C)c(CO)c1)c1ccc2c(nnn2CC)c1C]

Ethyl (S)-3-(1-ethyl-4-methyl-1H-benzo[d][1,2,3]triazol-5-yl)-3-(3-(hydroxymethyl)-4-methylphenyl)propanoate of the invention was made using compounds described in WO 2015/092713 on page 352, published Jun. 25, 2015, and incorporated herein by reference.

Ethyl (S)-3-(1-ethyl-4-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoate

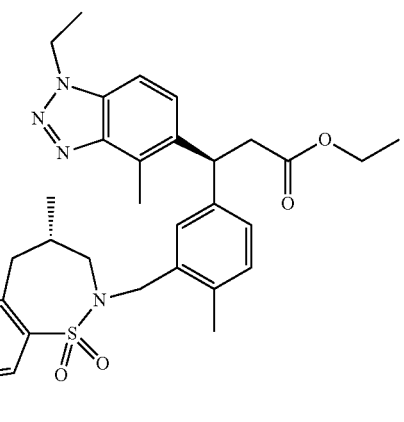

To a solution of (S)-ethyl-3-(1-ethyl-4-methyl-1H-benzo[d][1,2,3]triazol-5-yl)-3-(3-(hydroxymethyl)-4-methylphenyl)propanoate (120 mg, 0.315 mmol), (S)-4-methyl-8-(trifluoromethyl)-2,3,4,5-tetrahydrobenzo[f][1,2]thiazepine 1,1-dioxide (105 mg, 0.377 mmol) and 1,1'-(azodicarbonyl)dipiperidine (159 mg, 0.629 mmol) in THF (4 mL) at ambient temperature was added tributylphosphine (0.157 ml, 0.629 mmol). The reaction mixture was stirred at ambient temperature for 3 h. The reaction mixture was quenched with water and extracted with ethyl acetate three times. The combined organic layer was washed with brine and concentrated. It was purified by flash chromatography (ethyl acetate/hexane) to give the title compound (109.7 mg, 0.171 mmol, 54.3% yield). LC-MS m/z 643.4 (M+H)$^+$, 1.44 min (ret. time).

337

(S)-3-(1-ethyl-4-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoic Acid

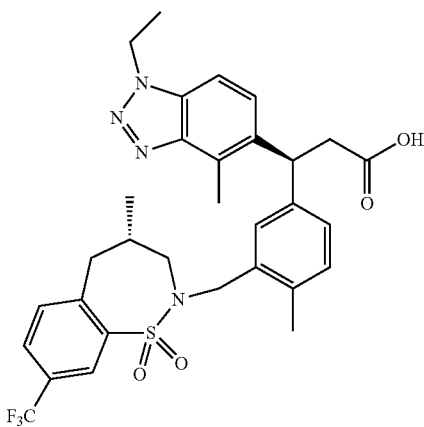 [SMILES: CCn1nnc2c(C)c([C@@H](CC(=O)O)c3ccc(C)c(CN4C[C@@H](C)Cc5ccc(C(F)(F)F)cc5S4(=O)=O)c3)ccc21]

To a solution of ethyl (S)-3-(1-ethyl-4-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoate (109.7 mg, 0.171 mmol) in methanol (3.793 ml) was added 2 M LiOH (0.512 ml, 1.024 mmol) and then stirred at ambient temperature for 23.5 h. The reaction was acidified with 1 M HCl until pH=2, concentrated, purified with preparative HPLC (with 0.1% Formic acid as modifier) to give the title compound (61.5 mg, 0.100 mmol, 58.6% yield). LC-MS m/z 615.3 (M+H)+, 1.28 min (ret. time).

(2R,3S)-3-(1-ethyl-4-methyl-1H-benzo[d][1,2,3]triazol-5-yl)-2-methyl-3-(4-methyl-3-(((S)-4-methyl-1,1-dioxido-7-(trifluoromethyl)-4,5-dihydrobenzo[f][1,2]thiazepin-2(3H)-yl)methyl)phenyl)propanoic Acid

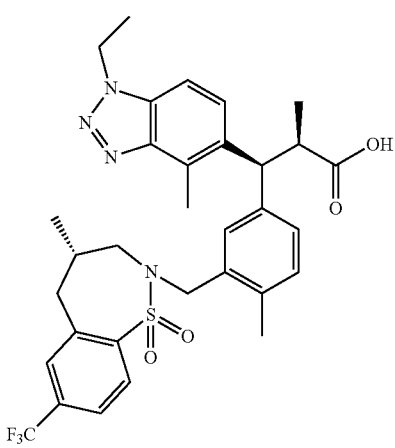 [SMILES: CCn1nnc2c(C)c([C@H](c3ccc(C)c(CN4C[C@@H](C)Cc5cc(C(F)(F)F)ccc5S4(=O)=O)c3)[C@@H](C)C(=O)O)ccc21]

338

(E)-3-(1-e\Ethyl-4-methyl-1H-benzo[d][1,2,3]triazol-5-yl)acrylic Acid

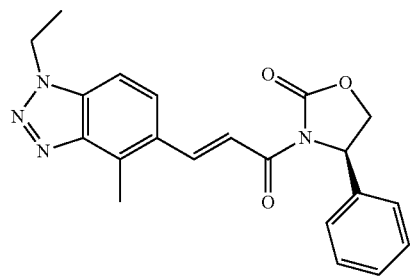 [SMILES: CCn1nnc2c(C)c(/C=C/C(=O)N3C(=O)OC[C@H]3c3ccccc3)ccc21]

To a solution of (E)-ethyl 3-(1-ethyl-4-methyl-1H-benzo[d][1,2,3]triazol-5-yl)acrylate (75 g, 289 mmol) in ethanol (150 mL) was added lithium hydroxide (13.85 g, 578 mmol) in water (150 mL). The reaction mixture was stirred at 20° C. for 16 hrs. The organic solvent was removed. The pH was adjusted with HCl (2M) until a white solid appeared. Then the solid was filtered and collected to give the title compound (E)-3-(1-ethyl-4-methyl-1H-benzo[d][1,2,3]triazol-5-yl)acrylic acid (60 g, 241 mmol, 83% yield) as a white solid. LC-MS m/z 232.1 (M+H)+, 1.24 min (ret. time). $^1$H NMR (500 MHz, DMSO) δ 7.95 (dd, J=19.8, 12.3 Hz, 2H), 7.73 (d, J=8.8 Hz, 1H), 6.55 (d, J=15.9 Hz, 1H), 4.73 (q, J=7.3 Hz, 2H), 2.80 (s, 3H), 1.50 (t, J=7.3 Hz, 3H).

(R,E)-3-(3-(1-Ethyl-4-methyl-1H-benzo[d][1,2,3]triazol-5-yl)acryloyl)-4-phenyloxazolidin-2-one Mixture A: To a solution of (E)-3-(1-ethyl-4-methyl-1H-benzo[d][1,2,3]triazol-5-yl)acrylic acid (20 g, 86 mmol) TEA (24.11 mL, 173 mmol) and pivaloyl chloride (11.47 g, 95 mmol) was added at −78° C. and stirred for 15 mins. Then the mixture A was stirred at 0 C for 45 mins.

Mixture B: To a solution of (R)-4-phenyloxazolidin-2-one (14.11 g, 86 mmol) in tetrahydrofuran (THF) (800 mL) at −78° C., n-butyllithium in THF (34.6 mL, 86 mmol) was added and stirred for 20 mins. Mixture A was added to Mixture B dropwise over 5 mins and the resulting mixture was warmed to 10° C. over 1 hr. The reaction mixture was quenched with saturated aqueous NH$_4$Cl (300 mL) and extracted with ethyl acetate (2×400 mL). The organic layer was combined and washed with brine (400 mL), dried over Na$_2$SO$_4$ and concentrated. The residue was purified by Combiflash chromatography (silica gel column 330 g, hexane:ethyl acetate=2:1) to give the title compound (R,E)-3-(3-(1-ethyl-4-methyl-1H-benzo[d][1,2,3]triazol-5-yl)acryloyl)-4-phenyloxazolidin-2-one (18 g, 41.6 mmol, 48.1% yield) as a yellow solid. LC-MS m/z 377.2 (M+H)+, 1.38 min (ret. time). $^1$H NMR (500 MHz, DMSO) δ 8.39-7.95 (m, 1H), 7.92-7.45 (m, 1H), 7.58-6.57 (m, 2H), 5.61 (dd, J=8.6, 3.9 Hz, 1H), 5.13-4.44 (m, 1H), 4.44-3.97 (m, 1H), 2.79 (s, 1H), 1.94-0.93 (m, 1H).

(5-Bromo-2-methylphenyl)methanol

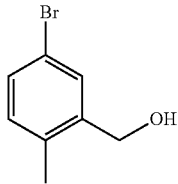

To a solution of methyl 5-bromo-2-methylbenzoate (151 g, 659 mmol) in tetrahydrofuran (THF) (700 mL) LiAlH$_4$ (30.0 g, 791 mmol) was added slowly at 0° C. The reaction mixture was stirred at 0° C. for 1 hr. The mixture was added to 30 mL water slowly then 30 mL 10% NaOH solution was added, then 90 mL water was added and stirred for 1 hr. Then the suspension was filtered and concentrated in vacuo to give the title compound (5-bromo-2-methylphenyl)methanol (130 g, 619 mmol, 94% yield) as yellow oil. LC-MS m/z 183.0/185.0 (M-17)$^+$, 1.75 min (ret. time). $^1$H NMR (500 MHz, CDCl3) δ 7.48 (d, J=2.0 Hz, 1H), 7.28 (dt, J=12.6, 6.3 Hz, 1H), 7.00 (d, J=8.0 Hz, 1H), 4.59 (s, 2H), 2.23 (s, 3H).

4-Bromo-2-(((4-methoxybenzyl)oxy)methyl)-1-methylbenzene

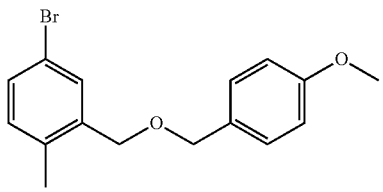 [SMILES: COc1ccc(COCc2cc(Br)ccc2C)cc1]

To a solution of (5-bromo-2-methylphenyl)methanol (130 g, 647 mmol) in N,N-dimethylformamide (DMF) (800 mL) at 0° C. under the protection of N$_2$, NaH (60%) (31.0 g, 776 mmol) was added in two portions and stirred for 30 mins. 1-(chloromethyl)-4-methoxybenzene (111 g, 711 mmol) was added to the mixture and stirred at 0° C. to 20° C. for 1 hr. Water (600 mL) was added slowly and the mixture was extracted by EtOAc (3×500 mL). The organic layers were combined and washed with the brine (2×500 mL), dried with Na$_2$SO$_4$, the solvent was removed in vacuo. The residue was purified by Combiflash chromatography (silica gel 330 g and eluted with petroleum ether:ethyl acetate=10:1 to give the title compound 4-bromo-2-(((4-methoxybenzyl)oxy) methyl)-1-methylbenzene (150 g, 429 mmol, 66.3% yield). LC-MS m/z 321.1/323.1 (M+H)$^+$, 1.75 min (ret. time). $^1$H NMR (400 MHz, CDCl3) δ 7.50 (d, J=2.0 Hz, 1H), 7.34-7.25 (m, 3H), 7.01 (d, J=8.1 Hz, 1H), 6.92-6.83 (m, 2H), 4.50 (s, 2H), 4.45 (s, 2H), 3.86-3.75 (m, 3H), 2.23 (s, 3H).

(R)-3-(((S)-3-(1-Ethyl-4-methyl-1H-benzo[d][1,2,3] triazol-5-yl)-3-(3-(((4-methoxybenzyl)oxy)methyl)-4-methylphenyl)propanoyl)-4-phenyloxazolidin-2-one

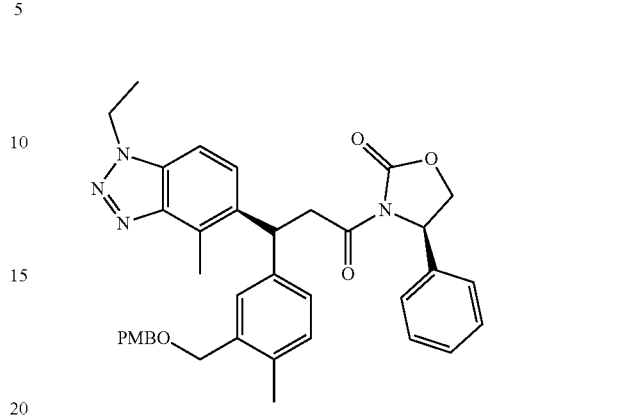

To an oven dried 100 mL three neck flask, cooled with N2 stream and equipped with a reflux condenser, was added magnesium (1.227 g, 50.5 mmol) and the flask was placed in an oil bath at 75° C., to which was added a solution of 4-bromo-2-(((4-methoxybenzyl)oxy)methyl)-1-methylbenzene (11.95 g, 37.2 mmol) in tetrahydrofuran (THF) (50 mL) and iodine (0.5 g). The reaction was stirred at 85° C. under N2 for 3 hrs.

To an oven dried 500 mL 3-neck flask, cooled with a N2 stream and equipped with an internal temperature probe, was added copper(I) bromide-dimethyl sulfide complex (3.82 g, 18.60 mmol), (R,E)-3-(3-(1-ethyl-4-methyl-1H-benzo[d][1,2,3]triazol-5-yl)acryloyl)-4-phenyloxazolidin-2-one (5 g, 13.28 mmol) and tetrahydrofuran (THF) (50 mL). The mixture was cooled to −40° C. then dimethylsulfane (8.25 g, 133 mmol) was added. The reaction mixture was stirred for 15 mins at −40° C. The cooled Grignard solution was added dropwise over ~40 min with an addition funnel, maintaining internal reaction temp below −40° C. After the addition, the reaction mixture was stirred at −40° C. for 1 hr. The reaction mixture was quenched with aqueous saturated NH$_4$Cl (~200 mL) and diluted with EtOAc (2×400 mL). The combined organic extracts were washed with water, brine, dried over Na$_2$SO$_4$, filtered and the solvent evaporated to afford an oil. The crude residue was dissolved in DCM, preabsorbed onto a silica gel precolumn and purified by Combiflash chromatography (silic gel; 120 g) eluting with 100% hexanes to 70% EtOAc gradient to afford the title compound (R)-3-((S)-3-(1-ethyl-4-methyl-1H-benzo[d][1,2,3]triazol-5-yl)-3-(3-(((4-methoxybenzyl)oxy)methyl)-4-methylphenyl)propanoyl)-4-phenyloxazolidin-2-one (6.9 g, 11.04 mmol, 83% yield) as a white foam solid. LC-MS m/z 619.3 (M+H)$^+$, 1.91 min (ret. time). $^1$H NMR (500 MHz, CDCl3) δ 7.41 (d, J=8.7 Hz, 1H), 7.24 (s, 1H), 7.22-7.17 (m, 5H), 7.15 (s, 1H), 7.11-7.05 (m, 2H), 7.05-7.00 (m, 2H), 6.88-6.80 (m, 2H), 5.29 (q, J=4.0 Hz, 1H), 5.10-5.03 (m, 1H), 4.62 (q, J=7.3 Hz, 2H), 4.54 (t, J=8.8 Hz, 1H), 4.40 (d, J=3.0 Hz, 4H), 4.18 (dd, J=8.9, 4.0 Hz, 1H), 3.85-3.74 (m, 5H), 2.82 (s, 3H), 2.24 (s, 3H), 1.58 (t, J=7.3 Hz, 3H).

(R)-3-((2R,3S)-3-(1-Ethyl-4-methyl-1H-benzo[d][1,2,3]triazol-5-yl)-3-(3-(((4-methoxybenzyl)oxy)methyl)-4-methylphenyl)-2-methylpropanoyl)-4-phenyloxazolidin-2-one

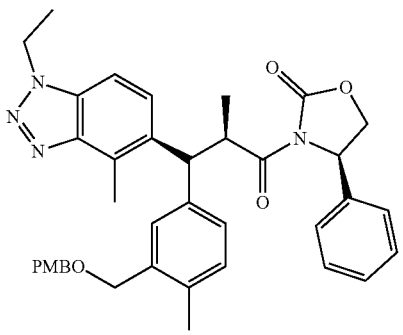

To a solution of (R)-3-((S)-3-(1-ethyl-4-methyl-1H-benzo[d][1,2,3]triazol-5-yl)-3-(3-(((4-methoxybenzyl)oxy)methyl)-4-methylphenyl)propanoyl)-4-phenyloxazolidin-2-one (12 g, 19.39 mmol) in dry THF (480 mL) was added NaHMDS in THF (23.27 mL, 23.27 mmol) under N2 protection at −78° C. The mixture was stirred at −78° C. for half an hour, then MeI (12.13 mL, 194 mmol) was added. The mixture was continuously stirred for an hour at −78° C. The reaction mixture was quenched with saturated aqueous NH₄Cl (50 mL) and extracted with ethyl acetate (2×200 mL). The organic layer was combined and washed with brine (200 mL), dried over Na₂SO₄ and concentrated. The residue was purified by combiflash chromatography (silica gel column 120 g, hexane:ethyl acetate=1:1) to obtain the title compound (R)-3-((2R,3S)-3-(1-ethyl-4-methyl-1H-benzo[d][1,2,3]triazol-5-yl)-3-(3-(((4-methoxybenzyl)oxy)methyl)-4-methylphenyl)-2-methylpropanoyl)-4-phenyloxazolidin-2-one (9.5 g, 12.43 mmol, 64.1% yield). LC-MS m/z 633.3 (M+H)⁺, 1.70 min (ret. time). ¹H NMR (500 MHz, CDCl₃) δ 7.65 (d, J=8.7 Hz, 1H), 7.32 (dd, J=20.9, 7.9 Hz, 5H), 7.25 (d, J=8.6 Hz, 2H), 7.20-7.17 (m, 3H), 7.08 (d, J=7.8 Hz, 1H), 6.88 (d, J=8.6 Hz, 2H), 5.06 (dd, J=8.5, 3.6 Hz, 2H), 4.64-4.58 (m, 3H), 4.44 (d, J=2.4 Hz, 4H), 4.25 (t, J=8.7 Hz, 1H), 3.81 (s, 3H), 2.86 (s, 3H), 2.23 (s, 3H), 1.61-1.52 (m, 4H), 1.11 (d, J=6.7 Hz, 3H).

(R)-3-((2R,3S)-3-(1-ethyl-4-methyl-1H-benzo[d][1,2,3]triazol-5-yl)-3-(3-(hydroxymethyl)-4-methylphenyl)-2-methylpropanoyl)-4-phenyloxazolidin-2-one

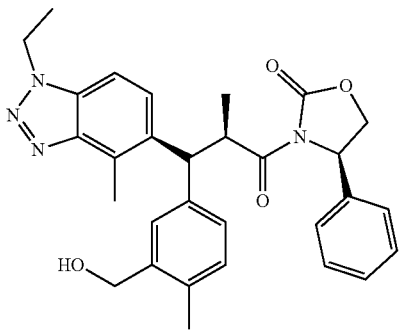

The solution of 4 N HCl in 1,4-dioxane (100 ml, 400 mmol) was added to (R)-3-((2R,3S)-3-(1-ethyl-4-methyl-1H-benzo[d][1,2,3]triazol-5-yl)-3-(3-(((4-methoxybenzyl)oxy)methyl)-4-methylphenyl)-2-methylpropanoyl)-4-phenyloxazolidin-2-one (5 g, 7.90 mmol) and stirred for 1 h. The reaction mixture was concentrated, purified via flash chromatography (EtOAc/hexanes) over silica gel column to give the titled compound (3.5 g, 6.83 mmol, 86% yield). LC-MS m/z 513.35 (M+H)⁺, 1.04 min (ret. time).

(2R,3S)-3-(1-ethyl-4-methyl-1H-benzo[d][1,2,3]triazol-5-yl)-2-methyl-3-(4-methyl-3-(((S)-4-methyl-1,1-dioxido-7-(trifluoromethyl)-4,5-dihydrobenzo[f][1,2]thiazepin-2(3H)-yl)methyl)phenyl)propanoic Acid

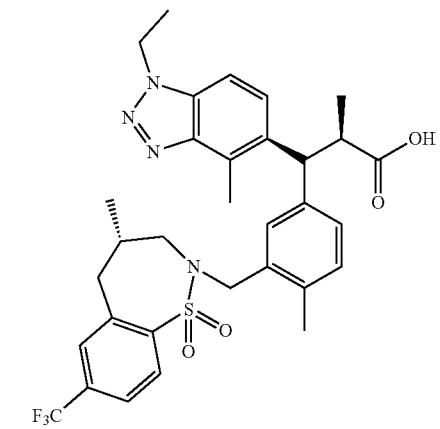

To a solution of (R)-3-((2R,3S)-3-(1-ethyl-4-methyl-1H-benzo[d][1,2,3]triazol-5-yl)-3-(3-(hydroxymethyl)-4-methylphenyl)-2-methylpropanoyl)-4-phenyloxazolidin-2-one (300 mg, 0.585 mmol), (S)-4-methyl-7-(trifluoromethyl)-2,3,4,5-tetrahydrobenzo[f][1,2]thiazepine 1,1-dioxide (196 mg, 0.702 mmol) and 1,1'-(Azodicarbonyl)dipiperidine (295 mg, 1.170 mmol) in tetrahydrofuran (11.823 ml) at ambient temperature was added tributylphosphane (0.292 ml, 1.170 mmol). The reaction mixture was stirred at ambient temperature for 4 h. It was quenched with water and extracted with ethyl acetate three times. The combined organic layer was washed with brine and concentrated. It was purified by flash chromatography (ethyl acetate/hexane) to give intermediate (R)-3-((2R,3S)-3-(1-ethyl-4-methyl-1H-benzo[d][1,2,3]triazol-5-yl)-2-methyl-3-(4-methyl-3-(((S)-4-methyl-1,1-dioxido-7-(trifluoromethyl)-4,5-dihydrobenzo[f][1,2]thiazepin-2(3H)-yl)methyl)phenyl)propanoyl)-4-phenyloxazolidin-2-one (450 mg, 0.581 mmol, 99% yield). This intermediate was dissolved in tetrahydrofuran (11.82 ml) and water (2.96 ml) (4:1) was added followed by 2M LiOH (0.878 ml, 1.756 mmol) and hydrogen peroxide (0.478 ml, 4.68 mmol). The resulting reaction mixture was stirred at ambient temperature for 21 h. To the reaction was added 1 M HCl to pH=2 and extracted with EtOAc three times. The combined organic layer was concentrated and purified with reverse phase HPLC (with 0.1% Formic acid as modifier) to give the title compound (152.4 mg, 0.242 mmol, 41.4% yield). LC-MS m/z 629.4 (M+H)⁺, 1.34 min (ret. time).

The compounds in Table 20 were prepared by a method similar to the one described for the preparation of (2R,3S)-

3-(1-ethyl-4-methyl-1H-benzo[d][1,2,3]triazol-5-yl)-2-methyl-3-(4-methyl-3-(((S)-4-methyl-1,1-dioxido-7-(trifluoromethyl)-4,5-dihydrobenzo[f][1,2]thiazepin-2(3H)-yl) methyl)phenyl)propanoic acid. As is appreciated by those skilled in the art, these analogous examples may involve variations in general reaction conditions.

TABLE 20

| Structure | Name | LCMS [M + 1] | Retention Time (min) |
|---|---|---|---|
| 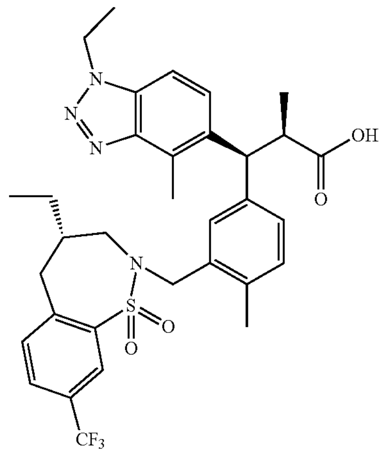 [SMILES: CC[C@H]1Cc2ccc(C(F)(F)F)cc2S(=O)(=O)N(Cc2cc([C@@H](c3ccc4c(nnn4CC)c3C)[C@@H](C)C(=O)O)ccc2C)C1] | (2R,3S)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2-methylpropanoic acid | 643.4 | 1.37 |
| 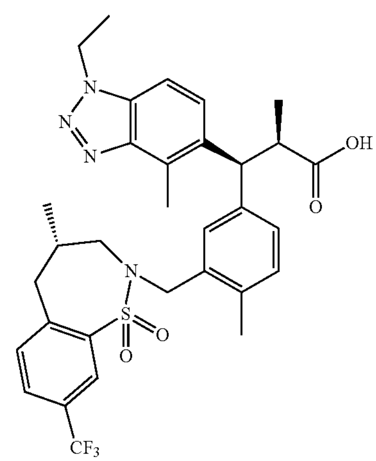 [SMILES: CCn1nnc2c(C)c([C@H](c3ccc(C)c(CN4C[C@@H](C)Cc5ccc(C(F)(F)F)cc5S4(=O)=O)c3)[C@@H](C)C(=O)O)ccc21] | (R)-3-((2R,3S)-3-(1-ethyl-4-methyl-1H-benzo[d][1,2,3]triazol-5-yl)-2-methyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)propanoyl)-4-phenyloxazolidin-2-one | 629.3 | 1.33 |
| 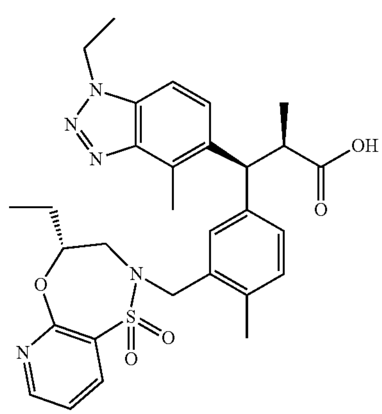 [SMILES: CC[C@@H]1CN(Cc2cc([C@@H](c3ccc4c(nnn4CC)c3C)[C@@H](C)C(=O)O)ccc2C)S(=O)(=O)c2cccnc2O1] | (2R,3S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2-methylpropanoic acid | 578.4 | 1.04 |

(S)-3-(1-ethyl-4-methyl-1H-benzo[d][1,2,3]triazol-5-yl)-3-(3-(((S)-8-fluoro-4-methyl-1,1-dioxido-4,5-dihydrobenzo[f][1,2]thiazepin-2(3H)-yl)methyl)-4-methylphenyl)propanoic Acid

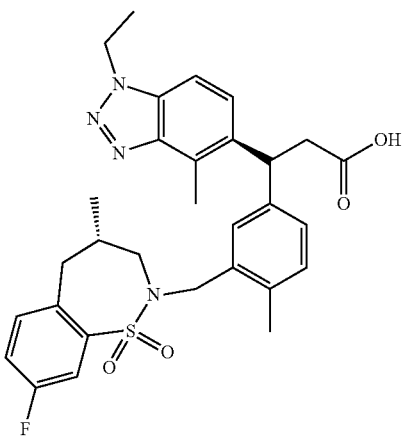

To a solution of ethyl (S)-3-(1-ethyl-4-methyl-1H-benzo[d][1,2,3]triazol-5-yl)-3-(3-(hydroxymethyl)-4-methylphenyl)propanoate (150 mg, 0.393 mmol), (S)-8-fluoro-4-methyl-2,3,4,5-tetrahydrobenzo[f][1,2]thiazepine 1,1-dioxide (108 mg, 0.472 mmol) and 1,1'-(Azodicarbonyl)dipiperidine (198 mg, 0.786 mmol) in tetrahydrofuran (5.243 ml) at ambient temperature was added tributylphosphine (0.196 ml, 0.786 mmol). The reaction mixture was stirred at ambient temperature for 23 h. It was quenched with water and extracted with ethyl acetate three times. The combined organic layer was washed with brine and concentrated. It was purified by flash chromatography (ethyl acetate/hexane) to give intermediate ethyl (S)-3-(1-ethyl-4-methyl-1H-benzo[d][1,2,3]triazol-5-yl)-3-(3-(((S)-8-fluoro-4-methyl-1,1-dioxido-4,5-dihydrobenzo[f][1,2]thiazepin-2(3H)-yl)methyl)-4-methylphenyl)propanoate as a colorless oil. This intermediate was dissolved in methanol (3.50 ml) and 2 M LiOH (1.180 ml, 2.359 mmol) was added and stirred at ambient temperature for 18 h. HCl (1M) was added until pH=2 and extracted with EtOAc (3×2 ml). The combined organic layer was concentrated and purified with reverse phase HPLC (with 0.1% Formic acid as modifier) to give the title compound (23.4 mg, 0.041 mmol, 10.54% yield). LC-MS m/z 565.5 (M+H)⁺, 1.20 min (ret. time).

Example 168

(S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-2-yl)propanamide

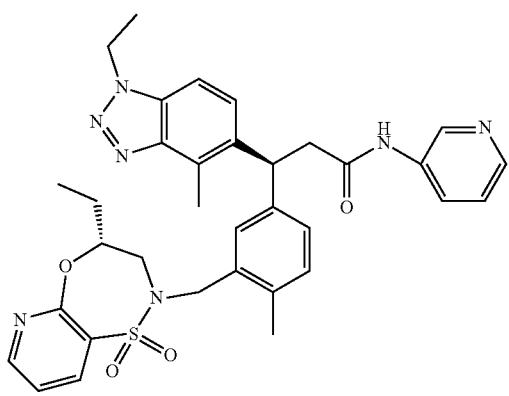 [SMILES: CC[C@@H]1CN(Cc2cc([C@H](CC(=O)Nc3cccnc3)c3ccc4c(nnn4CC)c3C)ccc2C)S(=O)(=O)c2cccnc2O1]

To a solution of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanoic acid (prepared as in WO 2015/092713, page 480, published Jun. 25, 2015) (80 mg, 0.142 mmol) in N,N-dimethylformamide (0.710 ml) was added DIPEA (0.074 ml, 0.426 mmol) and HATU (54.0 mg, 0.142 mmol). The reaction mixture was stirred at 25° C. for 3 min followed by addition of pyridin-2-amine (16.03 mg, 0.170 mmol). The mixture was stirred at 25° C. for 72 h then was diluted with water and extracted with ethyl acetate (3×2 mL). The combined organic layer was concentrated and then purified with neutral HPLC to give the title compound (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-2-yl)propanamide (19.8 mg, 0.031 mmol, 21.81% yield). LC-MS m/z 640.5 (M+H)⁺, 0.95 min (ret. time).

(S)-3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoic Acid

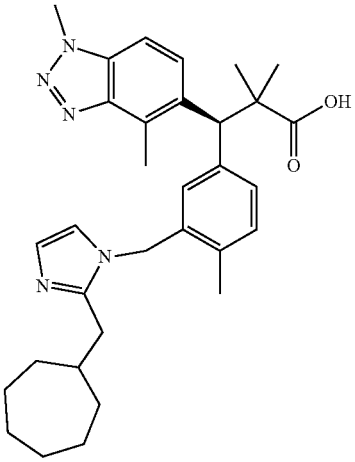 [SMILES: Cc1ccc([C@@H](c2ccc3c(nnn3C)c2C)C(C)(C)C(=O)O)cc1Cn1ccnc1CC1CCCCCC1]

(S)-3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethylpropanoic acid of the invention was made using compounds described in WO 2016/202253 on page 515, published Dec. 22, 2016, and incorporated herein by reference.

(S)-3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic Acid

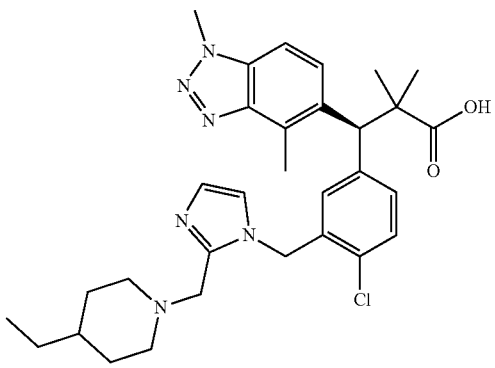 [SMILES: CCC1CCN(Cc2nccn2Cc2cc([C@@H](c3ccc4c(nnn4C)c3C)C(C)(C)C(=O)O)ccc2Cl)CC1]

(S)-3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethylpropanoic acid of the invention was made using compounds described in WO 2016/202253 on page 523, published Dec. 22, 2016, and incorporated herein by reference.

The compounds in Table 21 were prepared by a method similar to the one described for the preparation of (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(pyridin-2-yl)propanamide. As is appreciated by those skilled in the art, these analogous examples may involve variations in general reaction conditions.

TABLE 21

| Ex # | Structure | Name | LCMS [M + 1] | Retention Time (min) |
|---|---|---|---|---|
| Example 169 | 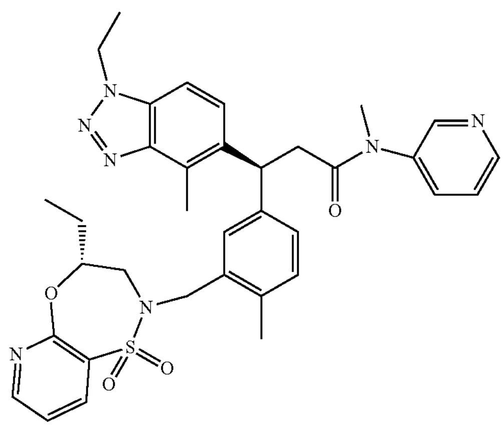 [SMILES: CC[C@@H]1CN(Cc2cc([C@H](CC(=O)N(C)c3cccnc3)c3ccc4c(nnn4CC)c3C)ccc2C)S(=O)(=O)c2cccnc2O1] | (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-methyl-N-(pyridin-3-yl)propanamide | 654.5 | 0.93 |
| Example 170 | 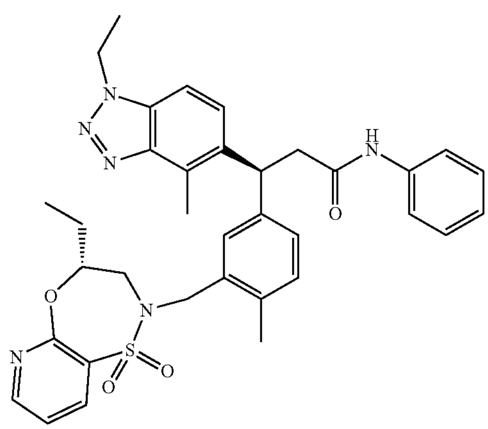 [SMILES: CC[C@@H]1CN(Cc2cc([C@H](CC(=O)Nc3ccccc3)c3ccc4c(nnn4CC)c3C)ccc2C)S(=O)(=O)c2cccnc2O1] | (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-phenylpropanamide | 639.5 | 1.15 |
| Example 171 | 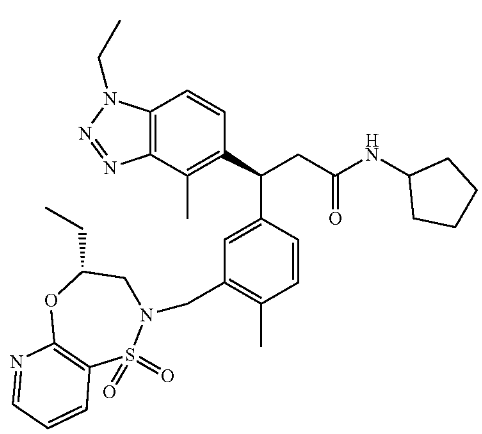 [SMILES: CC[C@@H]1CN(Cc2cc([C@H](CC(=O)NC3CCCC3)c3ccc4c(nnn4CC)c3C)ccc2C)S(=O)(=O)c2cccnc2O1] | (S)-N-cyclopentyl-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)propanamide | 631.5 | 1.08 |

TABLE 21-continued

| Ex # | Structure | Name | LCMS [M + 1] | Retention Time (min) |
|---|---|---|---|---|
| Example 172 | 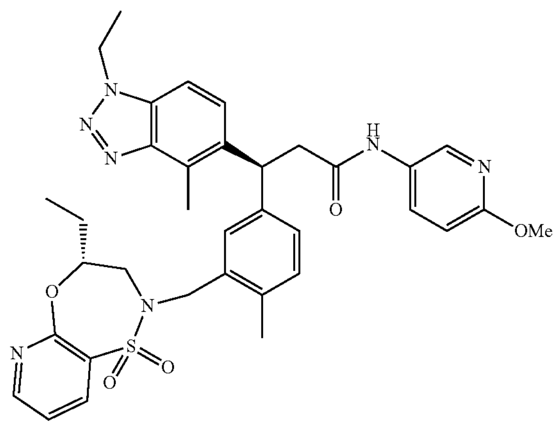 [SMILES: CC[C@@H]1CN(Cc2cc([C@H](CC(=O)Nc3ccc(OC)nc3)c3ccc4c(nnn4CC)c3C)ccc2C)S(=O)(=O)c2cccnc2O1] | (S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-N-(6-methoxypyridin-3-yl)propanamide | 670.6 | 1.05 |
| Example 173 | 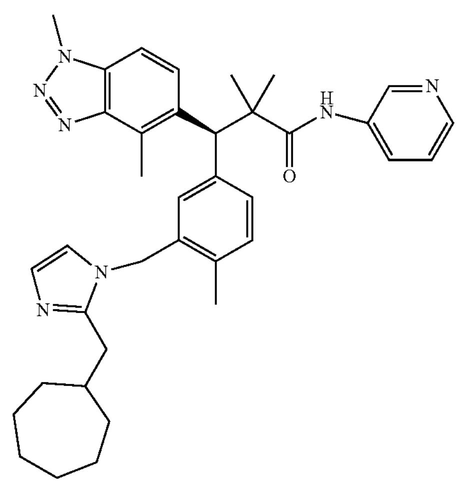 [SMILES: Cc1ccc([C@@H](c2ccc3c(nnn3C)c2C)C(C)(C)C(=O)Nc2cccnc2)cc1Cn1ccnc1CC1CCCCCC1] | (S)-3-(3-((2-(cycloheptylmethyl)-1H-imidazol-1-yl)methyl)-4-methylphenyl)-3-(1,4-dimethyl-1H-benzo[d][1,2,3]triazol-5-yl)-2,2-dimethyl-N-(pyridin-3-yl)propanamide | 604.6 | 0.67 |
| Example 174 | 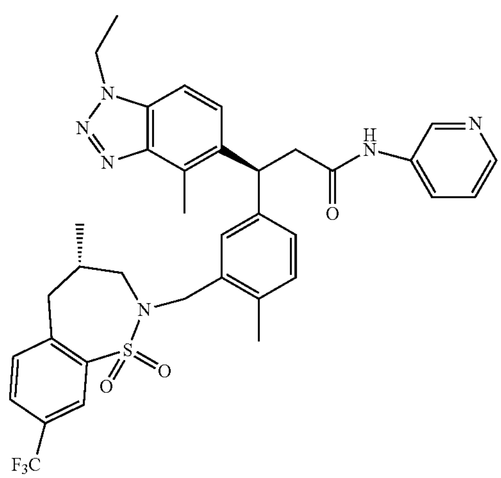 [SMILES: CCn1nnc2c(C)c([C@@H](CC(=O)Nc3cccnc3)c3ccc(C)c(CN4C[C@@H](C)Cc5ccc(C(F)(F)F)cc5S4(=O)=O)c3)ccc21] | (S)-3-(1-ethyl-4-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)-N-(pyridin-3-yl)propanamide | 691.5 | 1.02 |

TABLE 21-continued

| Ex # | Structure | Name | LCMS [M + 1] | Retention Time (min) |
|---|---|---|---|---|
| Example 175 | 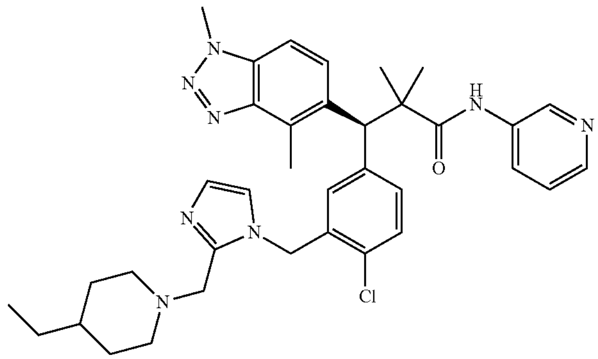 [SMILES: CCC1CCN(Cc2nccn2Cc2cc([C@@H](c3ccc4c(nnn4C)c3C)C(C)(C)C(=O)Nc3cccnc3)ccc2Cl)CC1] | (S)-3-(4-chloro-3-((2-((4-ethylpiperidin-1-yl)methyl)-1H-imidazol-1-yl)methyl)phenyl)-3-(1,4-dimethyl-1H-benzo[d][1,2,3]triazol-5-yl)-2,2-dimethyl-N-(pyridin-3-yl)propanamide | 639.5 | 0.61 |
| Example 176 | 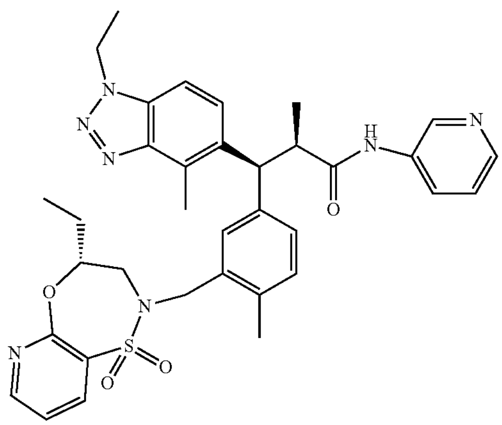 [SMILES: CC[C@@H]1CN(Cc2cc([C@@H](c3ccc4c(nnn4CC)c3C)[C@@H](C)C(=O)Nc3cccnc3)ccc2C)S(=O)(=O)c2cccnc2O1] | ((2R,3S)-3-(3-(((R)-4-ethyl-1,1-dioxido-3,4-dihydro-2H-pyrido[2,3-b][1,4,5]oxathiazepin-2-yl)methyl)-4-methylphenyl)-3-(1-ethyl-4-methyl-1H-benzo[d][1,2,3]triazol-5-yl)-2-methyl-N-(pyridin-3-yl)propanamide | 654.4 | 0.81 |
| Example 177 | 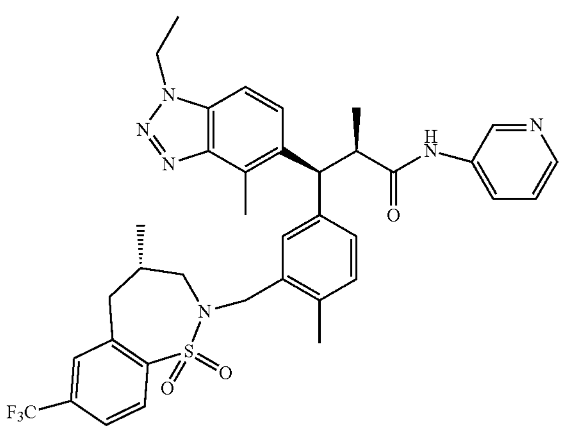 [SMILES: CCn1nnc2c(C)c([C@H](c3ccc(C)c(CN4C[C@@H](C)Cc5cc(C(F)(F)F)ccc5S4(=O)=O)c3)[C@@H](C)C(=O)Nc3cccnc3)ccc21] | (2R,3S)-3-(1-ethyl-4-methyl-1H-benzo[d][1,2,3]triazol-5-yl)-2-methyl-3-(4-methyl-3-(((S)-4-methyl-1,1-dioxido-7-(trifluoromethyl)-4,5-dihydrobenzo[f][1,2]thiazepin-2(3H)-yl)methyl)phenyl)-N-(pyridin-3-yl)propanamide | 705.5 | 1.03 |

TABLE 21-continued

| Ex # | Structure | Name | LCMS [M + 1] | Retention Time (min) |
|---|---|---|---|---|
| Example 178 | 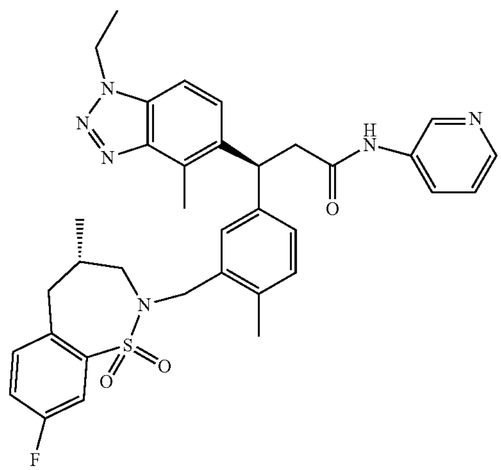 [SMILES: CCn1nnc2c(C)c([C@@H](CC(=O)Nc3cccnc3)c3ccc(C)c(CN4C[C@@H](C)Cc5ccc(F)cc5S4(=O)=O)c3)ccc21] | (S)-3-(1-ethyl-4-methyl-1H-benzo[d][1,2,3]triazol-5-yl)-3-(3-(((S)-8-fluoro-4-methyl-1,1-dioxido-4,5-dihydrobenzo[f][1,2]thiazepin-2(3H)-yl)methyl)-4-methylphenyl)-N-(pyridin-3-yl)propanamide | 641.5 | 0.94 |
| Example 179 | 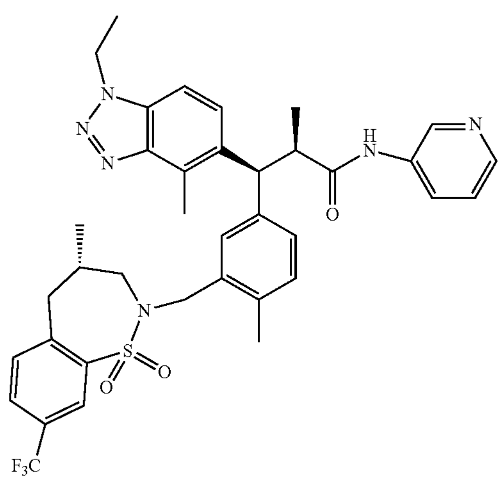 [SMILES: CC[C@H]1Cc2ccc(C(F)(F)F)cc2S(=O)(=O)N(Cc2cc([C@@H](c3ccc4c(nnn4CC)c3C)[C@@H](C)C(=O)Nc3cccnc3)ccc2C)C1] | (2R,3S)-3-(1-ethyl-4-methyl-1H-benzo[d][1,2,3]triazol-5-yl)-2-methyl-3-(4-methyl-3-(((S)-4-methyl-1,1-dioxido-8-(trifluoromethyl)-4,5-dihydrobenzo[f][1,2]thiazepin-2(3H)-yl)methyl)phenyl)-N-(pyridin-3-yl)propanamide | 705.8 | 1.06 |
| Example 180 | 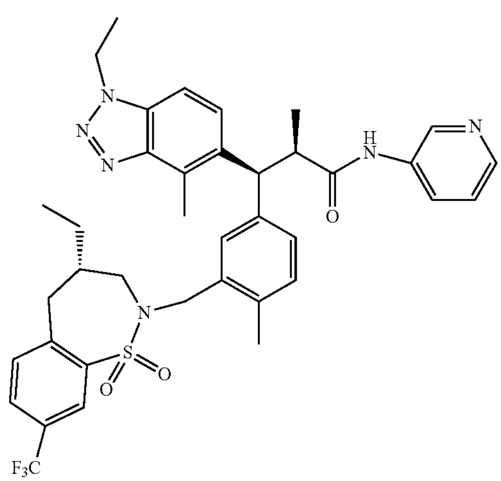 | (2R,3S)-3-(3-(((S)-4-ethyl-1,1-dioxido-8-(trifluoromethyl)-4,5-dihydrobenzo[f][1,2]thiazepin-2(3H)-yl)methyl)-4-methylphenyl)-3-(1-ethyl-4-methyl-1H-benzo[d][1,2,3]triazol-5-yl)-2-methyl-N-(pyridin-3-yl)propanamide | 719.5 | 1.11 |

TABLE 21-continued

| Ex # | Structure | Name | LCMS [M + 1] | Retention Time (min) |
|------|-----------|------|--------------|----------------------|
| Example 181 | 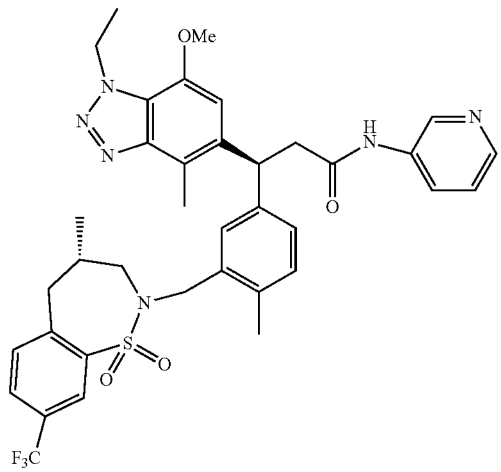 [SMILES: CCn1nnc2c(C)c([C@@H](CC(=O)Nc3cccnc3)c3ccc(C)c(CN4C[C@@H](C)Cc5ccc(C(F)(F)F)cc5S4(=O)=O)c3)cc(OC)c21] | (S)-3-(1-ethyl-7-methoxy-4-methyl-1H-benzo[d][1,2,3]triazol-5-yl)-3-(4-methyl-3-(((S)-4-methyl-1,1-dioxido-8-(trifluoromethyl)-4,5-dihydrobenzo[f][1,2]thiazepin-2(3H)-yl)methyl)phenyl)-N-(pyridin-3-yl)propanamide | 721.4 | 1.08 |

(S)-4-ethyl-9-(trifluoromethyl)-2,3,4,5-tetrahydro-1H-benzo[c]azepine hydrochloride

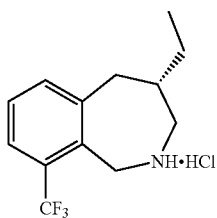

Methyl 2-fluoro-3-(trifluoromethyl)benzoate

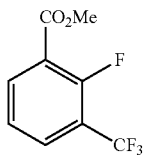

To a solution of 2-fluoro-3-(trifluoromethyl)benzoic acid (100 g, 481 mmol) in methanol (600 mL) was added SOCl₂ (42.1 mL, 577 mmol) and N,N-dimethylformamide (DMF) (10 mL) at 0° C. and the reaction mixture was stirred at reflux for 4 h under N2 atmosphere. The reaction mixture was concentrated under vacuum, quenched with saturated NaHCO₃ and extracted with (2×100 mL) EtOAc. The organic layer was dried over anhydrous Na₂SO₄ and filtered. The filtrate was evaporated under reduced pressure to afford the title compound (80 g, 358 mmol, 74.5% yield). GCMS m/z=222 (M+), 5.62 min (ret. time).

2-Cyano-3-(trifluoromethyl)benzoic Acid

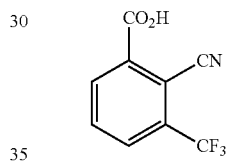

To a solution of methyl 2-fluoro-3-(trifluoromethyl)benzoate (80 g, 360 mmol) in dimethyl sulfoxide (DMSO) (200 mL) was added potassium cyanide (46.9 g, 720 mmol) and the reaction mixture was stirred at 150° C. for 8 h under N2 atmosphere. The reaction was cooled and the reaction was acidified to pH=6 with 1N HCl. The precipitate that formed was filtered and washed with water and n-Hexane. The filtrate was extracted with EtOAc (2×50 mL). The organic layer was dried over anhydrous Na₂SO₄ and filtered. The filtrate was evaporated under reduced pressure to afford the crude title compound, which was used without further purification. (50 g, 218 mmol, 60% yield). LCMS m/z=213 (M+), 1.37 min (ret. time).

2-(Hydroxymethyl)-6-(trifluoromethyl)benzonitrile

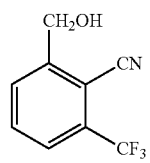

To a solution of 2-cyano-3-(trifluoromethyl)benzoic acid (20 g, 93 mmol) in tetrahydrofuran (THF) (200 mL) was added 2M borane-methyl sulfide complex (69.7 mL, 139 mmol) in THF at 0° C. The reaction mixture was stirred for 8 h under N2 atmosphere. The reaction mixture was cooled and slowly methanol was added into it and then concentrated under vacuum. The residue was quenched with 1N HCl and extracted with EtOAc (2×100 mL). The combined organic layers were dried over anhydrous Na$_2$SO$_4$ and filtered. The filtrate was evaporated under reduced pressure to afford the title compound which was carried on to the next step without further purification. (15 g, 40.1 mmol, 43.2% yield, 53% pure) LCMS m/z=202 (M+), 3.12 min (ret. time).

2-(Bromomethyl)-6-(trifluoromethyl)benzonitrile

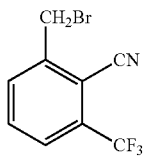

To a solution of 2-(hydroxymethyl)-6-(trifluoromethyl) benzonitrile (13 g, 64.6 mmol) in dichloromethane (DCM) (150 mL) was added triphenylphosphine (20.34 g, 78 mmol) and CBr$_4$ (25.7 g, 78 mmol) at 0° C. and the reaction mixture was stirred for 1 h under N$_2$ atmosphere. The reaction mixture was extracted with DCM (2×100 mL). The organic layer was dried over anhydrous Na$_2$SO$_4$ and filtered. The filtrate was evaporated under reduced pressure and purified by column chromatography eluting with EtOAc:n-Hexane (10:90) to provide the title compound (6 g, 17.82 mmol, 27.6% yield, 78% pure), GCMS m/z=262/264 (M/M+2), 7.72 min (ret. time).

Ethyl 2-(2-cyano-3-(trifluoromethyl)benzyl)butanoate

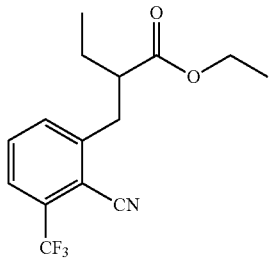 [SMILES: CCOC(=O)C(CC)Cc1cccc(C(F)(F)F)c1C#N]

To a solution of ethyl butyrate (9.00 mL, 68.2 mmol) in tetrahydrofuran (THF) (50 mL) was added 2M LDA in THF (22.72 mL, 45.4 mmol) at −78° C. The reaction mixture was stirred for 1 h under N2 atmosphere and 2-(bromomethyl)-6-(trifluoromethyl)benzonitrile (6 g, 22.72 mmol) was added to the reaction and stirred for 8 h. The reaction mixture was treated with 1N HCl and extracted with EtOAc (2×100 mL). The organic layer was dried over anhydrous Na$_2$SO$_4$ and filtered. The filtrate was evaporated under reduced pressure and purified by column chromatography eluting with EtOAc:n-Hexane (5:95) to afford the title compound (11 g, 7.70 mmol, 33.9% yield, 20% pure). LCMS m/z=300 (M+), 2.61 min (ret. time).

Tert-Butyl 2-(2-(hydroxymethyl)butyl)-6-(trifluoromethyl)benzylcarbamate

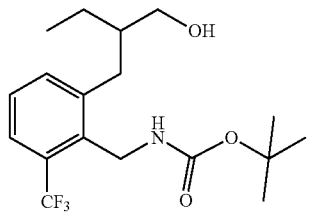 [SMILES: CCC(CO)Cc1cccc(C(F)(F)F)c1CNC(=O)OC(C)(C)C]

To a stirred solution of ethyl 2-(2-cyano-3-(trifluoromethyl)benzyl)butanoate (11 g, 7.70 mmol) in tetrahydrofuran (THF) (100 mL) was added LiAlH$_4$ (11.56 mL, 23.11 mmol) at 0° C. and the reaction mixture was stirred at ambient temperature for 4 hr under N$_2$ atmosphere. The reaction was quenched with wet Na$_2$SO$_4$, filtered through celite bed, dried over Na$_2$SO$_4$ and concentrated under reduced pressure to obtain the crude compound. The crude compound was dissolved in dichloromethane (DCM) (100 mL), cooled to 0° C., and treated with Et$_3$N (2.147 mL, 15.41 mmol) and Boc-anhydride (2.68 mL, 11.56 mmol). The reaction was stirred at ambient temperature for 2 hr under N$_2$ atmosphere. The crude compound was purified by column chromatography eluted with EtOAc:pet-ether (12:88) to afford the title compound (2.4 g, 5.93 mmol, 77% yield), LCMS m/z=362 (M+), 2.62 min (ret. time).

2-(2-(((tert-Butoxycarbonyl)amino)methyl)-3-(trifluoromethyl)benzyl)butyl methanesulfonate

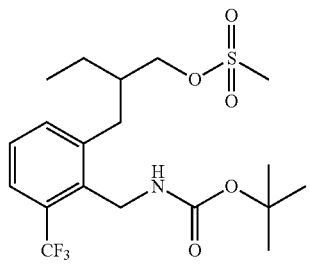 [SMILES: CCC(COS(C)(=O)=O)Cc1cccc(C(F)(F)F)c1CNC(=O)OC(C)(C)C]

To a solution of tert-butyl 2-(2-(hydroxymethyl)butyl)-6-(trifluoromethyl)benzylcarbamate (2.4 g, 5.25 mmol) in dichloromethane (DCM) (30 ml) was added triethylamine (1.462 ml, 10.49 mmol) and methanesulfonyl chloride (0.613 ml, 7.87 mmol) at 0° C. The reaction mixture was stirred for 2 h under N$_2$ atmosphere. The reaction mixture was quenched with saturated NaHCO$_3$ and extracted with DCM (2×30 mL). The organic layer was dried over anhydrous Na$_2$SO$_4$ and filtered. The filtrate was evaporated under reduced pressure to afford the title compound which carried on to next step without further purification. (2.5 g, 5.17 mmol, 99% yield, 90% pure) LCMS m/z=384 (M+H)$^+$, 2.70 min (ret. time).

359

Tert-Butyl 4-ethyl-9-(trifluoromethyl)-4,5-dihydro-1H-benzo[c]azepine-2(3H)-carboxylate

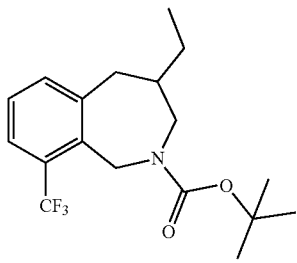 [SMILES: CCC1Cc2cccc(C(F)(F)F)c2CN(C(=O)OC(C)(C)C)C1]

To a solution of 2-(2-(((tert-butoxycarbonyl)amino)methyl)-3-(trifluoromethyl)benzyl)butyl methanesulfonate (2.5 g, 5.69 mmol) in N,N-dimethylformamide (DMF) (20 mL) was added potassium tert-butoxide (0.638 g, 5.69 mmol) at 0° C. and the reaction mixture was stirred for 2 h under $N_2$ atmosphere. The reaction mixture was quenched with ice-water and extracted with EtOAc (2×30 mL). The organic layer was dried over anhydrous $Na_2SO_4$ and filtered. The filtrate was evaporated under reduced pressure and was purified by column chromatography using neutral alumina by eluting with 2% EtOAc in petroleum-ether to the title compound (1.8 g, 4.99 mmol, 88% yield), LCMS m/z=288 (M+H)$^+$, 3.03 min (ret. time).

4-Ethyl-9-(trifluoromethyl)-2,3,4,5-tetrahydro-1H-benzo[c]azepine Hydrochloride

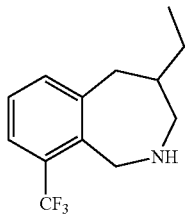 [SMILES: CCC1CNCc2c(cccc2C(F)(F)F)C1]

To a solution of tert-butyl 4-ethyl-9-(trifluoromethyl)-4,5-dihydro-1H-benzo[c]azepine-2(3H)-carboxylate (4 g, 11.65 mmol) in 1,4-dioxane (40 mL) was added 4M HCl in 1,4 dioxane (20.39 mL, 82 mmol) at 0° C. and the reaction mixture was stirred at ambient temperature for 8 h under $N_2$ atmosphere. The reaction mixture was concentrated under vacuum. The solid residue was washed with n-pentane (20 mL) and the solid was dried under reduced pressure to afford the title compound (3.3 g, 11.22 mmol, 96% yield). LCMS m/z=244 (M+H)$^+$, 1.71 min (ret. time).

360

(S)-4-Ethyl-9-(trifluoromethyl)-2,3,4,5-tetrahydro-1H-benzo[c]azepine and (R)-4-Ethyl-9-(trifluoromethyl)-2,3,4,5-tetrahydro-1H-benzo[c]azepine

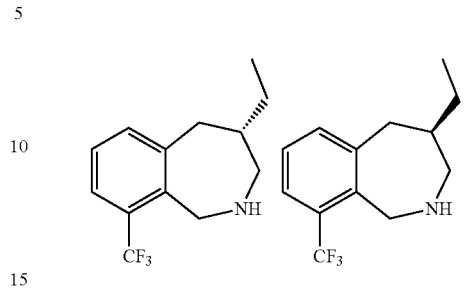

The compound 4-ethyl-9-(trifluoromethyl)-2,3,4,5-tetrahydro-1H-benzo[c]azepine hydrochloride (3.3 g) was made into the free base by treating with saturated aqueous solution of $NaHCO_3$, extracted with 10% MeOH in DCM and concentrated under reduced pressure to obtain the racemic 4-ethyl-9-(trifluoromethyl)-2,3,4,5-tetrahydro-1H-benzo[c]azepine (2.975 g, 12.23 mmol) as a free base. This compound was resolved by chiral SFC (Column: Lux Cellulose-2 30×250 mm, 5 u; Co-solvent: 10% (15 mM methanolic ammonia in methanol); 90% CO2, Flowrate: 90 g/min; Back pressure: 80Bar) to provide (S)-4-ethyl-9-(trifluoromethyl)-2,3,4,5-tetrahydro-1H-benzo[c]azepine (0.800 g, 25% yield, 93% pure). m/z=244 (M+H)$^+$, 1.32 min (ret. time) and (R)-4-ethyl-9-(trifluoromethyl)-2,3,4,5-tetrahydro-1H-benzo[c]azepine (0.640 g, 20% yield, 95% pure). LCMS m/z=244 (M+H)$^+$, 1.30 min (ret. time).

(S)-4-Ethyl-9-(trifluoromethyl)-2,3,4,5-tetrahydro-1H-benzo[c]azepine hydrochloride

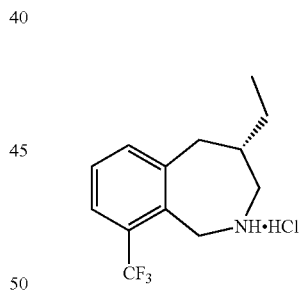

To a stirred solution of (S)-4-ethyl-9-(trifluoromethyl)-2,3,4,5-tetrahydro-1H-benzo[c]azepine (800 mg, 3.29 mmol) in 1,4-dioxane (10 ml) was added hydrochloric acid in 1,4-dioxane (0.822 ml, 3.29 mmol) at 0° C. and the reaction mixture was stirred for 3 hr under N2 atmosphere at ambient temperature. The reaction mixture was concentrated under vacuum to obtain a solid compound. The compound was washed with n-pentane (20 mL) and dried under vacuum. The obtained compound was dissolved in water and lyopholized to obtain (S)-4-ethyl-9-(trifluoromethyl)-2,3,4,5-tetrahydro-1H-benzo[c]azepine, hydrochloride (847 mg, 3.00 mmol, 91% yield, 99% pure) LCMS m/z=244 (M+H)$^+$, 2.31 min (ret. time).

(2R,3S)-3-(3-(((R)-2-ethyl-2,3-dihydropyrido[2,3-f]
[1,4]oxazepin-4(5H)-yl)methyl)-4-methylphenyl)-3-
(1-ethyl-4-methyl-1H-benzo[d][1,2,3]triazol-5-yl)-2-
methylpropanoic Acid

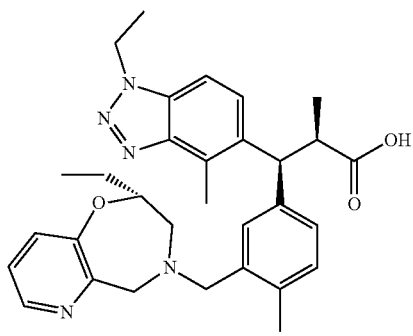 [SMILES: CC[C@@H]1CN(Cc2cc([C@@H](c3ccc4c(nnn4CC)c3C)[C@@H](C)C(=O)O)ccc2C)Cc2ncccc2O1]

(E)-3-(1-ethyl-4-methyl-1H-benzo[d][1,2,3]triazol-
5-yl)acrylic acid N61727-34-A1

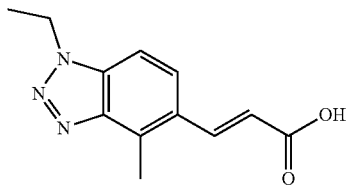 [SMILES: CCn1nnc2c(C)c(/C=C/C(=O)O)ccc21]

To a solution of (E)-ethyl 3-(1-ethyl-4-methyl-1H-benzo
[d][1,2,3]triazol-5-yl)acrylate (23 g, 89 mmol) (prepared as described in WO2016/202253, published Dec. 22, 2016) in ethanol (100 mL) was added lithium hydroxide (4.25 g, 177 mmol) in water (100 mL). The reaction mixture was stirred at 20° C. for 16 h. The organic solvent was removed. The residue was acidified with HCl (2M) and the solid was filtered and collected to give the product as a white solid. (E)-3-(1-ethyl-4-methyl-1H-benzo[d][1,2,3]triazol-5-yl) acrylic acid (20 g, 86 mmol, 98% yield). LC-MS m/z 232.2 (M+1)$^+$, 1.48 (ret. time)

(R,E)-3-(3-(1-ethyl-4-methyl-1H-benzo[d][1,2,3]
triazol-5-yl)acryloyl)-4-phenyloxazolidin-2-one

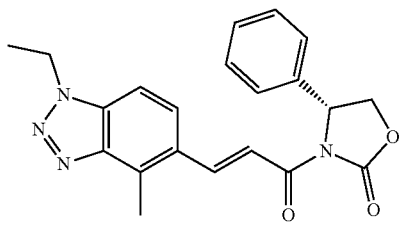 [SMILES: CCn1nnc2c(C)c(/C=C/C(=O)N3C(=O)OC[C@H]3c3ccccc3)ccc21]

Mixture A: To a solution of (E)-3-(1-ethyl-4-methyl-1H-benzo[d][1,2,3]triazol-5-yl)acrylic acid (8 g, 34.6 mmol) in tetrahydrofuran (THF) (180 mL) at −78° C., Et$_3$N (5.30 mL, 38.1 mmol) and PivCl (5.11 mL, 41.5 mmol) was added at −78° C. and stirred for 15 minutes warmed to 0° C. and stirred for 45 minutes.

Mixture B: To (R)-4-phenyloxazolidin-2-one (5.08 g, 31.1 mmol) in tetrahydrofuran (THF) (180 mL) at −78° C. was added 2.5M nBuLi in hexanes (12.45 mL, 31.1 mmol) and stirred for 20 minutes at −78° C.

Mixture A was added to Mixture B at −78° C. dropwise over 5 minutes at and the resulting mixture was warmed to 10° C. over 1 hour. The reaction mixture was quenched with saturated aqueous NH$_4$Cl (100 mL) and extracted with ethyl acetate (2×150 mL). The organic layers were combined and washed with brine (150 mL), dried over Na$_2$SO$_4$ and concentrated. The residue was purified by silica gel chromatography hexane:ethyl acetate=2:1 to afford (R,E)-3-(3-(1-ethyl-4-methyl-1H-benzo[d][1,2,3]triazol-5-yl)acryloyl)-4-phenyloxazolidin-2-one (9.1 g, 23.21 mmol, 67.1% yield) as a yellow solid. LC-MS m/z 377.2 (M+H)$^+$, 1.86 (ret. time)

(R)-3-(((S)-3-(1-ethyl-4-methyl-1H-benzo[d][1,2,3]
triazol-5-yl)-3-(3-(((4-methoxybenzyl)oxy)methyl)-
4-methylphenyl)propanoyl)-4-phenyloxazolidin-2-
one

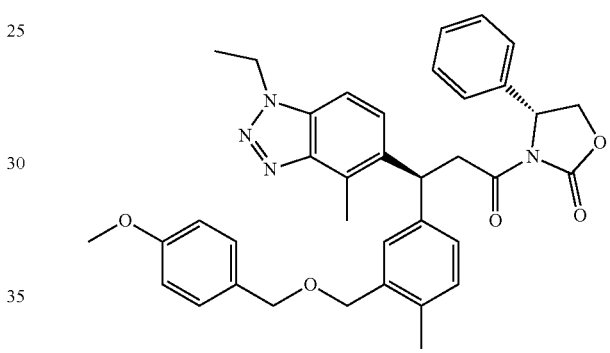

Mixture A: To an oven dried 100 mL flask, cooled under a N2 stream and equipped with a reflux condenser, was added magnesium (1.483 g, 61.0 mmol) and the flask was placed in an oil bath at 75° C., to which was added a solution 4-bromo-2-(((4-methoxybenzyl)oxy)methyl)-1-methylbenzene (15.24 g, 47.5 mmol) in tetrahydrofuran (THF) (50 mL), followed by iodine (0.103 g, 0.406 mmol). The reaction was stirred at 75° C. under N2 for 3 h, then was cooled to 25° C.

To an oven dried 250 mL 3-neck flask, under a N2 stream and equipped with N2 balloon and an internal temperature probe, was added copper(I) bromide-dimethyl sulfide complex (4.88 g, 23.73 mmol), (R,E)-3-(3-(1-ethyl-4-methyl-1H-benzo[d][1,2,3]triazol-5-yl)acryloyl)-4-phenyloxazolidin-2-one (6.38 g, 16.95 mmol) and tetrahydrofuran (THF) (50.0 mL). The mixture was cooled to −40° C. and then dimethyl sulfide (12.54 mL, 169 mmol) was added. The mixture was stirred for 20 mins at −40° C., then Mixture A was added dropwise. The mixture was stirred for half an hour and then quenched with aqueous saturated NH$_4$Cl (~200 mL) and diluted with EtOAc (2×400 mL). The combined organic extracts were washed with H$_2$O, brine, dried (Na$_2$SO$_4$) filtered and the solvent evaporated to afford an oil. The crude product was purified by silica gel chromatography with a gradient from hexanes to 80% EtOAc in hexanes to afford (R)-3-((S)-3-(1-ethyl-4-methyl-1H-benzo[d][1,2,3]triazol-5-yl)-3-(3-(((4-methoxybenzyl)oxy) methyl)-4-methylphenyl)propanoyl)-4-phenyloxazolidin-2- one (5.2 g, 6.39 mmol, 37.7% yield) as pale yellow oil. LC/MS m/z 619.3 (M+H)+, 2.09 min (ret.)

(R)-3-((2R,3S)-3-(1-ethyl-4-methyl-1H-benzo[d][1,2,3]triazol-5-yl)-3-(3-(((4-methoxybenzyl)oxy)methyl)-4-methylphenyl)-2-methylpropanoyl)-4-phenyloxazolidin-2-one

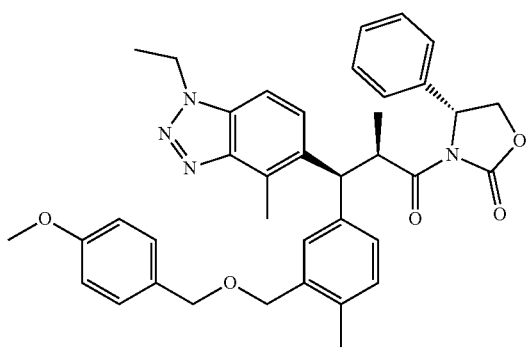 [SMILES: CCn1nnc2c(C)c([C@H](c3ccc(C)c(COCc4ccc(OC)cc4)c3)[C@@H](C)C(=O)N3C(=O)OC[C@H]3c3ccccc3)ccc21]

To a solution of (R)-3-((S)-3-(1-ethyl-4-methyl-1H-benzo[d][1,2,3]triazol-5-yl)-3-(3-(((4-methoxybenzyl)oxy)methyl)-4-methylphenyl)propanoyl)-4-phenyloxazolidin-2-one (6.1 g, 9.86 mmol) in dry tetrahydrofuran (THF) (120 mL) was added 1M NaHMDS (11.83 mL, 11.83 mmol) in THF under N2 at −78° C. The mixture was stirred at −78° C. for half an hour, then MeI (6.16 mL, 99 mmol) was added. The resulting mixture was stirred for an hour at −78° C. The reaction mixture was quenched with saturated aqueous NH4Cl (80 mL) and extracted with ethyl acetate (2×200 mL). The organic layer was combined and washed with brine (200 mL), dried over Na2SO4 and concentrated. The residue was purified by silica gel chromatography (hexane:ethyl acetate=1:1) to afford (R)-3-((2R,3S)-3-(1-ethyl-4-methyl-1H-benzo[d][1,2,3]triazol-5-yl)-3-(3-(((4-methoxybenzyl)oxy)methyl)-4-methylphenyl)-2-methylpropanoyl)-4-phenyloxazolidin-2-one (3.7 g, 5.85 mmol, 59.3% yield) as a yellow solid.

(R)-3-((2R,3S)-3-(1-ethyl-4-methyl-1H-benzo[d][1,2,3]triazol-5-yl)-3-(3-(hydroxymethyl)-4-methylphenyl)-2-methylpropanoyl)-4-phenyloxazolidin-2-one

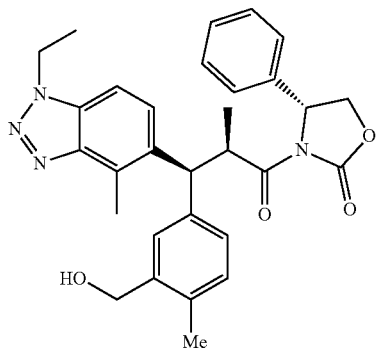 [SMILES: CCn1nnc2c(C)c([C@H](c3ccc(C)c(CO)c3)[C@@H](C)C(=O)N3C(=O)OC[C@H]3c3ccccc3)ccc21]

(R)-3-((2R,3S)-3-(1-ethyl-4-methyl-1H-benzo[d][1,2,3]triazol-5-yl)-3-(3-(((4-methoxybenzyl)oxy)methyl)-4-methylphenyl)-2-methylpropanoyl)-4-phenyloxazolidin-2-one (200 mg, 0.316 mmol), and ammonium cerium (IV) nitrate (347 mg, 0.632 mmol) in acetonitrile (2 mL) and water (0.2 mL) were stirred for 2 h. The reaction was combined with water 20 mL and EtOAc (75 mL) shaken and separated and the aqueous phase was extracted again with EtOAc (25 mL) and the combined EtOAc was washed with water (25 mL) and saturated aqueous NaCl (25 mL) dried (Na2SO4), concentrated, and the crude product was purified by silica gel chromatography (12 g) with a gradient running from DCM to 50% EtOAc/DCM over 25 min to elute (R)-3-((2R,3S)-3-(1-ethyl-4-methyl-1H-benzo[d][1,2,3]triazol-5-yl)-3-(3-(hydroxymethyl)-4-methylphenyl)-2-methylpropanoyl)-4-phenyloxazolidin-2-one (163 mg, 0.318 mmol, 101% yield)

(R)-3-((2R,3S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2-methylpropanoyl)-4-phenyloxazolidin-2-one

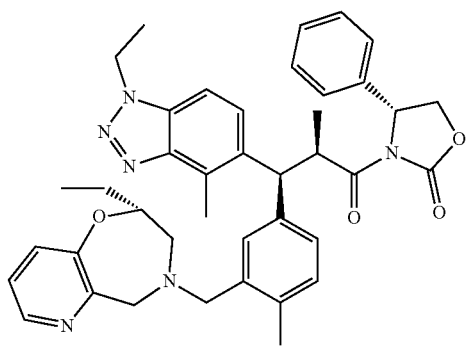 [SMILES: CC[C@@H]1CN(Cc2cc([C@@H](c3ccc4c(nnn4CC)c3C)[C@@H](C)C(=O)N3C(=O)OC[C@H]3c3ccccc3)ccc2C)Cc2ncccc2O1]

To a solution of (R)-3-((2R,3S)-3-(1-ethyl-4-methyl-1H-benzo[d][1,2,3]triazol-5-yl)-3-(3-(hydroxymethyl)-4-methylphenyl)-2-methylpropanoyl)-4-phenyloxazolidin-2-one (155 mg, 0.302 mmol) in dichloromethane (DCM) (5 mL) was added sulfurous dichloride (0.088 mL, 1.209 mmol) and the mixture was stirred at 23° C. for 20 min. The reaction was concentrated under a stream of nitrogen at 50° C., and the residue was dissolved in acetonitrile (2.5 mL). To this solution was added a solution of (R)-2-ethyl-2,3,4,5-tetrahydropyrido[2,3-f][1,4]oxazepine, hydrochloride (78 mg, 0.363 mmol) (prepared as described in WO2016/202253, published Dec. 22, 2016) and ethyldiisopropylamine (0.422 mL, 2.419 mmol) in acetonitrile (2.5 mL) and the reaction heated via microwave at 120° C. at the high setting for 1 h. The reaction was dissolved in EtOAc (100 mL) and washed with water (25 mL). The aqueous phase was extracted again with EtOAc (50 mL) and the combined EtOAc was washed with water (25 mL) and then saturated aqueous NaCl (25 mL). The EtOAc was dried (Na2SO4) filtered and concentrated to a light green oil. The residue was combined with DCM, filtered and purified by silica gel chromatography with a gradient running from DCM to 100% EtOAc to afford (R)-3-((2R,3S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2-methylpropanoyl)-4-phenyloxazolidin-2-one (163 mg, 0.242 mmol, 80% yield) LCMS (ES+) (M+H)+=673.6 (0.96 min).

365

(2R,3S)-3-(3-(((R)-2-ethyl-2,3-dihydropyrido[2,3-f]
[1,4]oxazepin-4(5H)-yl)methyl)-4-methylphenyl)-3-
(1-ethyl-4-methyl-1H-benzo[d][1,2,3]triazol-5-yl)-2-
methylpropanoic Acid

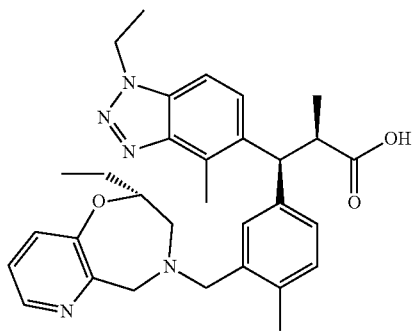 [SMILES: CC[C@@H]1CN(Cc2cc([C@@H](c3ccc4c(nnn4CC)c3C)[C@@H](C)C(=O)O)ccc2C)Cc2ncccc2O1]

(R)-3-((2R,3S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2-methylpropanoyl)-4-phenyloxazolidin-2-one (163 mg, 0.242 mmol) was dissolved in 1,4-dioxane (3 mL) and 6 M HCl (1.0 mL, 32.9 mmol) was added and the solution was sealed in a 20 mL vial with a pressure release cap and heated to 100° C. for 22 h. The reaction was concentrated in vacuo and the residue was dissolved in DMSO and purified by reverse-phase HPLC (YMC C18 S-5 mm/12 nm 50×20 mm preparatory column), with a linear gradient running from 10% CH$_3$CN/H$_2$O (0.1% HCO$_2$H) to 90% CH$_3$CN/H$_2$O (0.1% HCO$_2$H) to afford (2R,3S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2-methylpropanoic acid (59.2 mg, 0.112 mmol, 46.3% yield) LCMS (ES+)(M+H)$^+$=528.4 (0.72 min).

(S)-3-(1-ethyl-4-methyl-1H-benzo[d][1,2,3]triazol-5-
yl)-3-(3-(((S)-4-ethyl-9-(trifluoromethyl)-1,3,4,5-
tetrahydro-2H-benzo[c]azepin-2-yl)methyl)-4-meth-
ylphenyl)-2,2-dimethylpropanoic Acid

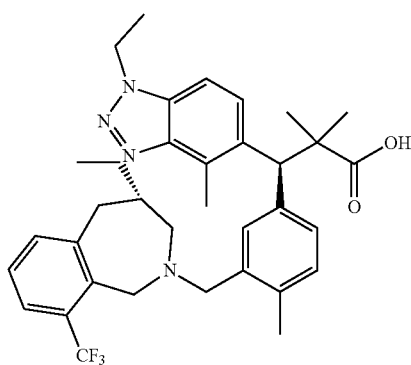 [SMILES: CC[C@H]1Cc2cccc(C(F)(F)F)c2CN(Cc2cc([C@@H](c3ccc4c(nnn4CC)c3C)C(C)(C)C(=O)O)ccc2C)C1]

366

Benzyl (S)-3-(1-ethyl-4-methyl-1H-benzo[d][1,2,3]
triazol-5-yl)-3-(3-(((S)-4-ethyl-9-(trifluoromethyl)-1,
3,4,5-tetrahydro-2H-benzo[c]azepin-2-yl)methyl)-4-
methylphenyl)-2,2-dimethylpropanoate

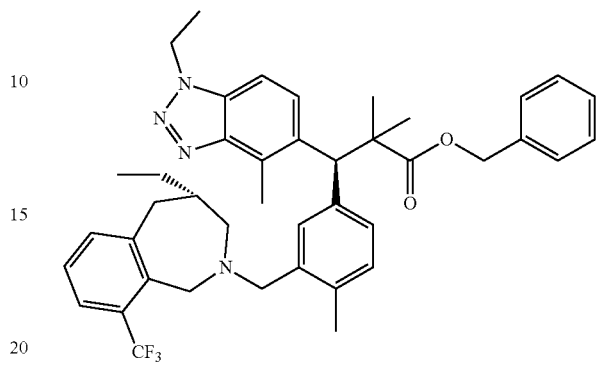

To a solution of benzyl (S)-3-(1-ethyl-4-methyl-1H-benzo[d][1,2,3]triazol-5-yl)-3-(3-(hydroxymethyl)-4-methylphenyl)-2,2-dimethylpropanoate (184 mg, 0.390 mmol) in dichloromethane (DCM) (6 mL) was added sulfurous dichloride (0.114 mL, 1.561 mmol) and the mixture was stirred at 23° C. for 20 min. The reaction was concentrated under a stream of nitrogen at 50° C., and the residue was dissolved in acetonitrile (3 mL). To this solution was added a solution of (S)-4-ethyl-9-(trifluoromethyl)-2,3,4,5-tetrahydro-1H-benzo[c]azepine, hydrochloride (131 mg, 0.468 mmol) and ethyldiisopropylamine (0.545 mL, 3.12 mmol) in acetonitrile (3 mL) and the resulting reaction heated via microwave at 120° C. at the high setting for 1 h. The reaction was concentrated in vacuo. Redissolved in EtOAc (100 mL) and washed with water (25 mL). The aqueous phase was extracted again with EtOAc (50 mL) and the combined EtOAc was washed with water (25 mL) and then saturated aqueous NaCl (25 mL). The EtOAc was dried (Na$_2$SO$_4$) and concentrated to afford a brown residue which was purified by silica gel chromatography with a gradient running from DCM to 20% EtOAc to afford benzyl (S)-3-(1-ethyl-4-methyl-1H-benzo[d][1,2,3]triazol-5-yl)-3-(3-(((S)-4-ethyl-9-(trifluoromethyl)-1,3,4,5-tetrahydro-2H-benzo[c]azepin-2-yl)methyl)-4-methylphenyl)-2,2-dimethylpropanoate (206 mg, 0.296 mmol, 76% yield). LCMS (ES+) (M+H)$^+$=697.8 (1.08 min).

(S)-3-(1-ethyl-4-methyl-1H-benzo[d][1,2,3]triazol-5-
yl)-3-(3-(((S)-4-ethyl-9-(trifluoromethyl)-1,3,4,5-
tetrahydro-2H-benzo[c]azepin-2-yl)methyl)-4-meth-
ylphenyl)-2,2-dimethylpropanoic Acid

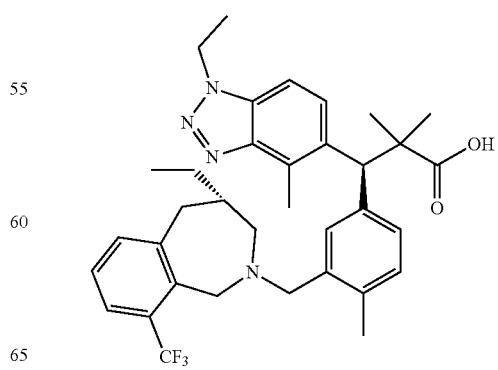

Benzyl (S)-3-(1-ethyl-4-methyl-1H-benzo[d][1,2,3]triazol-5-yl)-3-(3-(((S)-4-ethyl-9-(trifluoromethyl)-1,3,4,5-tetrahydro-2H-benzo[c]azepin-2-yl)methyl)-4-methylphenyl)-2,2-dimethylpropanoate (115 mg, 0.165 mmol) was combined with tetrahydrofuran (THF) (1.0 mL) and methanol (1.000 mL). Separately, lithium hydroxide (19.76 mg, 0.825 mmol) was dissolved in water (0.5 mL) and the two solutions were combined and heated in a microwave tube at high setting on the microwave at 120° C. for 7 h. The reaction was concentrated and the residue was added to 1 M HCl and extracted with EtOAc and the organic phase was concentrated and the residue was dissolved in DMSO 4 mL and purified by reverse-phase HPLC (YMC C18 S-5 mm/12 nm 50×20 mm preparatory column), with a linear gradient running from 10% CH$_3$CN/H$_2$O (0.1% HCO$_2$H) to 90% CH$_3$CN/H$_2$O (0.1% HCO$_2$H) which was dried in vacuo (0.1 mm) to afford as a white solid (S)-3-(1-ethyl-4-methyl-1H-benzo[d][1,2,3]triazol-5-yl)-3-(3-(((S)-4-ethyl-9-(trifluoromethyl)-1,3,4,5-tetrahydro-2H-benzo[c]azepin-2-yl)methyl)-4-methylphenyl)-2,2-dimethylpropanoic acid (43 mg, 0.071 mmol, 42.9% yield) LCMS (ES+) (M+H)$^+$=607.5 (0.85 min)

(S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic Acid

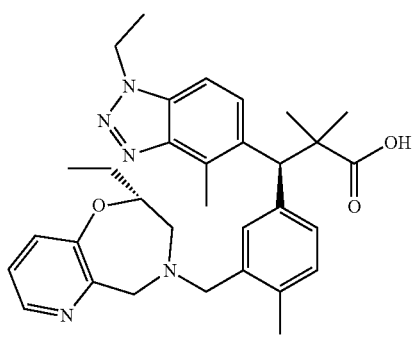 [SMILES: CC[C@@H]1CN(Cc2cc([C@@H](c3ccc4c(nnn4CC)c3C)C(C)(C)C(=O)O)ccc2C)Cc2ncccc2O1]

Benzyl (S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoate

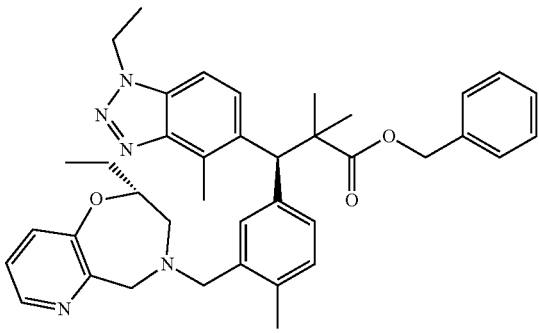 [SMILES: CC[C@@H]1CN(Cc2cc([C@@H](c3ccc4c(nnn4CC)c3C)C(C)(C)C(=O)OCc3ccccc3)ccc2C)Cc2ncccc2O1]

To a solution of benzyl (S)-3-(1-ethyl-4-methyl-1H-benzo[d][1,2,3]triazol-5-yl)-3-(3-(hydroxymethyl)-4-methylphenyl)-2,2-dimethylpropanoate (300 mg, 0.636 mmol) in dichloromethane (DCM) (10 mL) was added sulfurous dichloride (0.186 mL, 2.54 mmol) and the mixture was stirred at 23° C. for 20 min. The reaction was concentrated under a stream of nitrogen at 50° C., and the residue was dissolved in acetonitrile (5 mL). To this solution was added a solution of (R)-2-ethyl-2,3,4,5-tetrahydropyrido[2,3-f][1,4]oxazepine, hydrochloride (164 mg, 0.763 mmol) (prepared as described in WO2016/202253, published Dec. 22, 2016) and ethyldiisopropylamine (0.111 mL, 0.636 mmol) in acetonitrile (5 mL) and the resulting reaction heated via microwave at 120° C. at the high setting for 1 h. The reaction was concentrated, redissolved in EtOAc (100 mL) and washed with water (25 mL). The aqueous phase was extracted again with EtOAc (50 mL) and the combined EtOAc was washed with water (25 mL) and then saturated aqueous NaCl (25 mL). The EtOAc was dried (Na$_2$SO$_4$), filtered and concentrated to a brown oil which was combined with DCM, filtered and the product was purified by silica gel chromatography with a gradient running from DCM to 40% EtOAc to afford a light yellow oil, benzyl (S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoate (225 mg, 0.356 mmol, 56.0% yield). LCMS (ES+) (M+H)$^+$=632.4 (1.01 min)

(S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic Acid

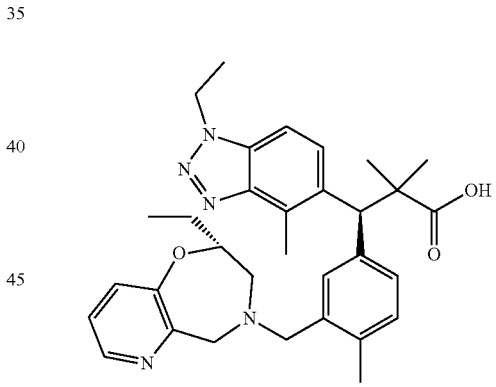

Benzyl (S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoate (165 mg, 0.261 mmol) was combined with tetrahydrofuran (THF) (2.5 mL) and methanol (2.5 mL). Separately, LiOH (125 mg, 5.22 mmol) was dissolved in water (1.2 mL) and the two solutions were combined and heated via microwave at high setting at 120° C. for 3 h. The volume of the crude product was adjusted to 9 mL with a combination of DMSO and acetonitrile and filtered through a 0.45 mm acrodisc syringe filter and the filtrate was purified by reverse phase chromatography (YMC C18 S-5 mm/12 nm 50×20 mm preparatory column), with a gradient running from 10% CH$_3$CN/H$_2$O (0.1% HCO$_2$H) to 90% CH$_3$CN/H$_2$O (0.1% HCO$_2$H). The desired fractions were concentrated and dried in vacuo at 0.15 mm for 20 h. to afford (S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2,2-dimethylpropanoic acid (121 mg, 0.223 mmol, 86% yield) as a white solid. LCMS (ES+) (M+H)$^+$=542.3 (0.78 min)

(R)-3-(4-chloro-3-(((R)-4-ethyl-1,1-dioxido-3,4-dihydro-2H-benzo[b][1,4,5]oxathiazepin-2-yl)methyl)phenyl)-5-(1-cyclobutyl-1H-1,2,3-triazol-4-yl)-2,2-dimethylpentanoic Acid

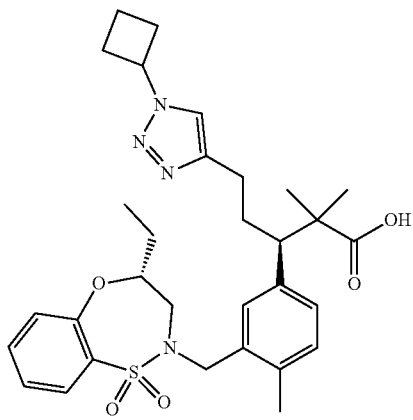 [SMILES: CC[C@@H]1CN(Cc2cc([C@@H](CCc3cn(C4CCC4)nn3)C(C)(C)C(=O)O)ccc2C)S(=O)(=O)c2ccccc2O1]

Benzyl (R)-3-(4-chloro-3-(((4-methoxybenzyl)oxy)methyl)phenyl)-5-(1-cyclobutyl-1H-1,2,3-triazol-4-yl)-2,2-dimethylpentanoate

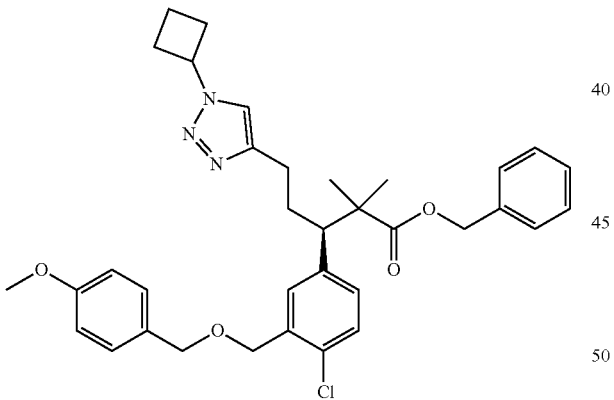

Benzyl 3-(4-chloro-3-(((4-methoxybenzyl)oxy)methyl)phenyl)-2,2-dimethylhept-6-ynoate (4.99 g, 9.88 mmol) (prepared as described in WO2016/202253, published Dec. 22, 2016) was dissolved in DCM and divided into 8 separate samples and each was placed in a separate vial and concentrated under a stream of N2 to afford 8 separate samples of approximately 624 mg, 1.24 mmol. Each was separately treated as follows:

Bromocyclobutane (834 mg, 6.18 mmol) in N,N-dimethylformamide (DMF) (3 mL) was treated with sodium azide (402 mg, 6.18 mmol) and heated to 80° C. for 2 h. Cooled on an ice bath and N-ethyl-N-isopropylpropan-2-amine (798 mg, 6.18 mmol) was added. The resulting mixture was added to a mixture of benzyl 3-(4-chloro-3-(((4-methoxybenzyl)oxy)methyl)phenyl)-2,2-dimethylhept-6-ynoate (624 mg, 1.236 mmol) and copper(I) iodide (235 mg, 1.236 mmol) in tert-butanol (5.000 mL) and water (5.000 mL) and was heated via microwave at high setting at 70° C. for 1 h. The reaction was diluted with water (25 mL) and EtOAc (75 mL) and the aqueous phase was extracted a second time with EtOAc (75 mL). The combined EtOAc was washed with water (25 mL) and saturated aqueous NaCl (25 mL), dried (Na$_2$SO$_4$) and concentrated. This was repeated until all 8 portions were reacted and the combined residue obtained by concentration of an EtOAc solution in vacuo was purified by silica gel chromatography with a gradient running from hexanes to 60% EtOAc/hexanes to afford benzyl 3-(4-chloro-3-(((4-methoxybenzyl)oxy)methyl)phenyl)-5-(1-cyclobutyl-1H-1,2,3-triazol-4-yl)-2,2-dimethylpentanoate (5.22 g, 8.67 mmol, 88%) as a light yellow oil. The compound was resolved by chiral SFC (Column: Chiralpak IA 20×250 mm, 5 u; Co-solvent: 35% EtOH; Flowrate: 50 g/min; Back pressure: 100Bar, 30° C.) to elute first benzyl (S)-3-(4-chloro-3-(((4-methoxybenzyl)oxy)methyl)phenyl)-5-(1-cyclobutyl-1H-1,2,3-triazol-4-yl)-2,2-dimethylpentanoate (2.14 g, 36%) LCMS (M+H)$^+$=602.4, 604.4 (1.50 min) and second benzyl (R)-3-(4-chloro-3-(((4-methoxybenzyl)oxy)methyl)phenyl)-5-(1-cyclobutyl-1H-1,2,3-triazol-4-yl)-2,2 dimethylpentanoate (2.28 g, 38%) LCMS (M+H)$^+$=602.4, 604.4 (1.50 min). The absolute stereochemistry was determined by VCD analysis.

Benzyl (R)-3-(4-chloro-3-(hydroxymethyl)phenyl)-5-(1-cyclobutyl-1H-1,2,3-triazol-4-yl)-2,2-dimethylpentanoate

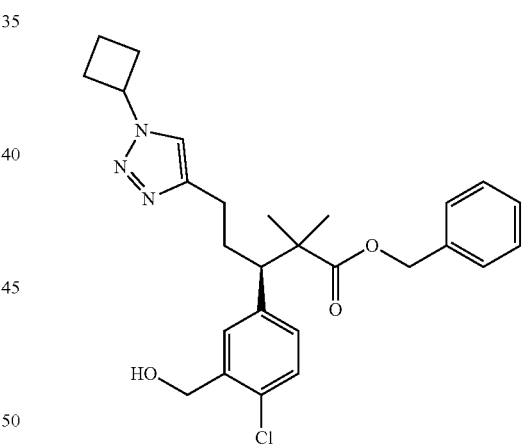

Benzyl (R)-3-(4-chloro-3-(((4-methoxybenzyl)oxy)methyl)phenyl)-5-(1-cyclobutyl-1H-1,2,3-triazol-4-yl)-2,2-dimethylpentanoate (2.19 g, 3.64 mmol) in acetonitrile (18 mL) was combined with ammonium cerium (IV) nitrate (1.994 g, 3.64 mmol) and water (1.8 mL) and stirred for 1 h 15 min and the reaction was partioned between EtOAc (2×) and water. The combined EtOAc was washed with water (2×) and saturated aqueous NaCl, dried (Na$_2$SO$_4$) and concentrated. The crude product was purified by silica gel chromatography with a gradient running from/hexanes to 70% EtOAc/hexanes to afford benzyl (R)-3-(4-chloro-3-(hydroxymethyl)phenyl)-5-(1-cyclobutyl-1H-1,2,3-triazol-4-yl)-2,2-dimethylpentanoate (1.56 g, 3.24 mmol, 89% yield) as a colorless oil. LCMS (M+H)$^+$=482.3, 484.3 (1.20 min).

Benzyl (R)-3-(4-chloro-3-(((R)-4-ethyl-1,1-dioxido-3,4-dihydro-2H-benzo[b][1,4,5]oxathiazepin-2-yl)methyl)phenyl)-5-(1-cyclobutyl-1H-1,2,3-triazol-4-yl)-2,2-dimethylpentanoate

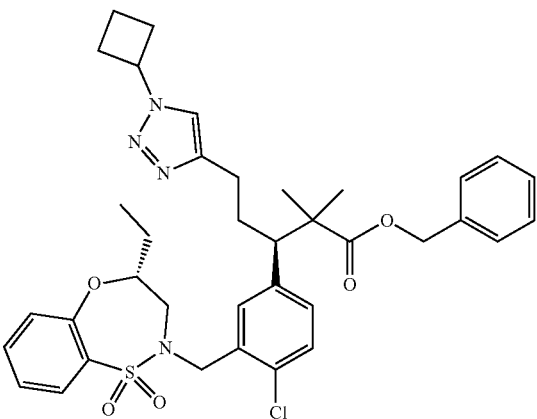 [SMILES: CC[C@@H]1CN(Cc2cc([C@@H](CCc3cn(C4CCC4)nn3)C(C)(C)C(=O)OCc3ccccc3)ccc2Cl)S(=O)(=O)c2ccccc2O1]

Benzyl (R)-3-(4-chloro-3-(hydroxymethyl)phenyl)-5-(1-cyclobutyl-1H-1,2,3-triazol-4-yl)-2,2-dimethylpentanoate (1.55 g, 3.22 mmol), (R)-4-ethyl-3,4-dihydro-2H-benzo[b][1,4,5]oxathiazepine 1,1-(0.877 g, 3.86 mmol) dioxide (prepared as described in WO2016/202253, published Dec. 22, 2016) and (E)-diazene-1,2-diylbis (piperidin-1-ylmethanone) (1.623 g, 6.43 mmol) in tetrahydrofuran (THF) (32 mL) was treated with tributylphosphane (1.606 mL, 6.43 mmol) and stirred for 3.5 h. Work-up with water (75 mL) and EtOAc (3×100 mL). The combined EtOAc was washed with water (2×) and saturated aqueous NaCl, dried (Na$_2$SO$_4$), concentrated and purified by silica chromatography with a gradient running from hexanes to 70% EtOAc/hexanes to afford benzyl (R)-3-(4-chloro-3-(((R)-4-ethyl-1,1-dioxido-3,4-dihydro-2H-benzo[b][1,4,5]oxathiazepin-2-yl)methyl)phenyl)-5-(1-cyclobutyl-1H-1,2,3-triazol-4-yl)-2,2-dimethylpentanoate (2.15 g, 3.11 mmol, 97% yield) as a clear colorless oil. LCMS (ES+) (M+H)$^+$=691.5, 693.5 (1.49 min).

(R)-3-(4-chloro-3-(((R)-4-ethyl-1,1-dioxido-3,4-dihydro-2H-benzo[b][1,4,5]oxathiazepin-2-yl)methyl)phenyl)-5-(1-cyclobutyl-1H-1,2,3-triazol-4-yl)-2,2-dimethylpentanoic Acid

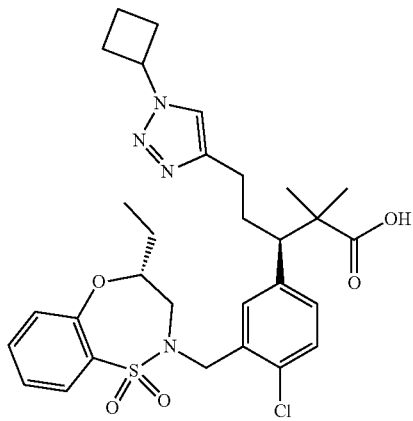 [SMILES: CC[C@@H]1CN(Cc2cc([C@@H](CCc3cn(C4CCC4)nn3)C(C)(C)C(=O)O)ccc2Cl)S(=O)(=O)c2ccccc2O1]

Benzyl (R)-3-(4-chloro-3-(((R)-4-ethyl-1,1-dioxido-3,4-dihydro-2H-benzo[b][1,4,5]oxathiazepin-2-yl)methyl)phenyl)-5-(1-cyclobutyl-1H-1,2,3-triazol-4-yl)-2,2-dimethylpentanoate (2.15 g, 3.11 mmol) was dissolved in THF (25 mL) and to this was added a solution of LiOH (420 mg, 18.3 mmol) in water (12 mL) and MeOH (18 mL) and this was divided into 4 portions which were separately heated at high setting in a microwave reactor at 120° C. for 3 h. The combined reactions were diluted with EtOAc (300 mL) and water (50 mL) containing 1 M HCl (25 ml). The phases were shaken together, separated and the aqueous phase was extracted again with EtOAc (100 mL) and the combined EtOAc was washed with water (50 mL) and saturated aqueous NaCl (50 mL) and the EtOAc was dried (Na$_2$SO$_4$) and concentrated. Purification by reverse-phase HPLC (Waters Atlantics T3 20×100 mm acetonitrile:Water 50-80%) afforded (R)-3-(4-chloro-3-(((R)-4-ethyl-1,1-dioxido-3,4-dihydro-2H-benzo[b][1,4,5]oxathiazepin-2-yl)methyl)phenyl)-5-(1-cyclobutyl-1H-1,2,3-triazol-4-yl)-2,2-dimethylpentanoic acid (1.21 g, 64% yield). LCMS (ES+) (M+H)$^+$= 601.3, 603.3 (1.27 min).

Example 182

(2R,3S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2-methylpropanamide

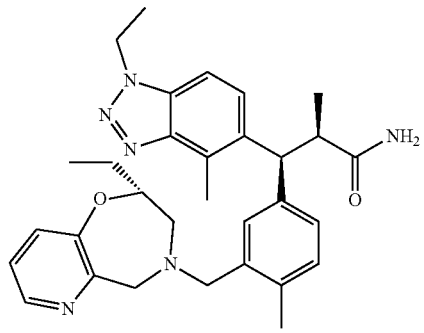 [SMILES: CC[C@@H]1CN(Cc2cc([C@@H](c3ccc4c(nnn4CC)c3C)[C@@H](C)C(N)=O)ccc2C)Cc2ncccc2O1]

(2R,3S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2-methylpropanoic acid (35 mg, 0.066 mmol) was combined with sulfurous dichloride (2 mL, 27.4 mmol) in a sealed vial and stirred for 45 min. The reaction was concentrated under a stream of nitrogen at 50° C., redissolved in THF (5 mL) and NH$_3$(g) was slowly bubbled through the mixture for 1 min. The white NH$_4$Cl precipitate formed rapidly and the reaction was stirred for 45 min. The reaction was concentrated under a stream of nitrogen at 50° C., and the crude product was dissolved in a mixture of DMSO and acetonitrile and water, filtered through a 0.45 mm acrodisc, and purified via preparative reverse phase HPLC (YMC C18 S-5 mm/12 nm 50×20 mm preparatory column), eluting at 20 mL/min with a linear gradient running from 10% CH$_3$CN/H$_2$O (0.1% HCO$_2$H) to 85% CH$_3$CN/H$_2$O (0.1% HCO$_2$H). The desired fractions were concentrated in vacuo pumped down to 0.1 mm for 16 h to afford (2R,3S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2-methylpropanamide (17 mg, 49%) LCMS (ES+) (M+H)$^+$=547.2 (0.63 min).

The compounds in Table 22 were prepared by a method similar to the one described for the preparation of (2R,3S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2-methylpropanamide from the appropriate acid. As is appreciated by those skilled in the art, these analogous examples may involve variations in general reaction conditions.

TABLE 22

| Ex # | Structure | Name | LCMS [M + 1] | Retention Time (min) |
|---|---|---|---|---|
| Example 183 | 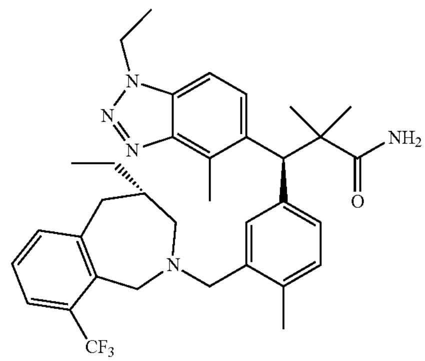 [SMILES: CC[C@H]1Cc2cccc(C(F)(F)F)c2CN(Cc2cc([C@@H](c3ccc4c(nnn4CC)c3C)C(C)(C)C(N)=O)ccc2C)C1] | (S)-3-(1-ethyl-4-methyl-1H-benzo[d][1,2,3]triazol-5-yl)-3-(3-(((S)-4-ethyl-9-(trifluoromethyl)-4,5-dihydro-1H-benzo[c]azepin-2(3H)-yl)methyl)-4-methylphenyl)-2,2-dimethylpropanamide | 606.5 | 0.78 min |
| Example 184 | 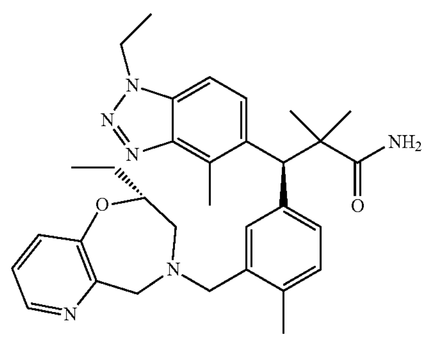 [SMILES: CC[C@@H]1CN(Cc2cc([C@@H](c3ccc4c(nnn4CC)c3C)C(C)(C)C(N)=O)ccc2C)Cc2ncccc2O1] | (S)-3-(3-(((R)-2-ethyl-2,3-dihydropyrido[2,3-f][1,4]oxazepin-4(5H)-yl)methyl)-4-methylphenyl)-3-(1-ethyl-4-methyl-1H-benzo[d][1,2,3]triazol-5-yl)-2,2-dimethylpropanamide | 547.2 | 0.63 min |
| Example 185 | 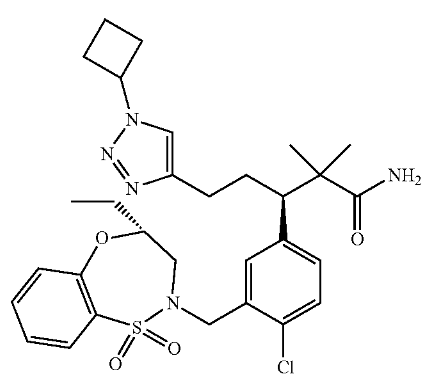 [SMILES: CC[C@@H]1CN(Cc2cc([C@@H](CCc3cn(C4CCC4)nn3)C(C)(C)C(N)=O)ccc2Cl)S(=O)(=O)c2ccccc2O1] | (R)-3-(4-chloro-3-(((R)-4-ethyl-1,1-dioxido-3,4-dihydro-2H-benzo[b][1,4,5]oxathiazepin-2-yl)methyl)phenyl)-5-(1-cyclobutyl-1H-1,2,3-triazol-4-yl)-2,2-dimethylpentanamide | 600.3 602.3 | 1.17 min |

5-Bromo-2-(((tert-butyldimethylsilyl)oxy)methyl)pyrimidine

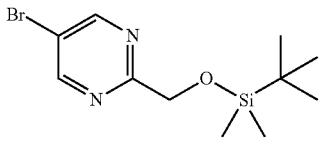 [SMILES: CC(C)(C)[Si](C)(C)OCc1ncc(Br)cn1]

A solution of (5-bromopyrimidin-2-yl)methanol (75 mg, 0.397 mmol) and 2,6-lutidine (131 uL, 0.992 mmol) in DCM (2 mL) was cooled to −78° C. tert-butyldimethylsilyl trifluoromethanesulfonate (131 uL, 0.595 mmol) was added and allowed to stir for 2 hours. The reaction was warmed to ambient temperature, diluted with a saturated solution of NaHCO₃ (2 mL), and extracted with DCM (3×5 mL). The organic layer was dried over MgSO₄, filtered, and concentrated. The filtrate was then adsorbed onto celite and purified by silica gel chromatography to provide the title compound as a colorless oil (95 mg, 0.313 mmol, 79% yield). LC-MS m/z 303.00 (M+H)$^+$, 1.40 min (ret. time).

5-Bromo-2-(2-((tert-butyldimethylsilyl)oxy)propan-2-yl)pyrimidine

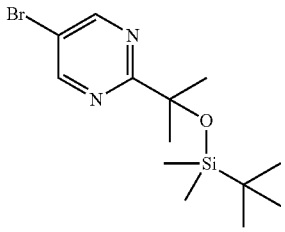 [SMILES: CC(C)(O[Si](C)(C)C(C)(C)C)c1ncc(Br)cn1]

A solution of 2-(5-bromopyrimidin-2-yl)propan-2-ol (86 mg, 0.397 mmol) and 2,6-lutidine (131 uL, 0.992 mmol) in DCM (2 mL) was cooled to −78° C. tert-Butyldimethylsilyl trifluoromethanesulfonate (131 uL, 0.595 mmol) was added and allowed to stir for 2 hours. The reaction was warmed to ambient temperature and stirred for 30 minutes before diluting with a saturated solution of NaHCO₃ (2 mL), and extracting with DCM (3×5 mL). The organic layer was dried over MgSO₄, filtered, and concentrated. The filtrate was then adsorbed on to celite and purified by silica gel chromatography to provide the title compound as a colorless oil (103 mg, 0.311 mmol, 78% yield). LC-MS m/z 331.11 (M+H)$^+$, 1.76 min (ret. time).

Tert-Butyl (2-((5-bromopyrimidin-2-yl)oxy)ethyl)carbamate

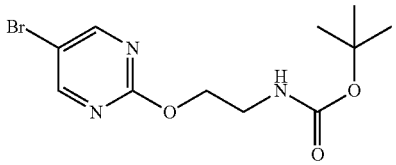 [SMILES: CC(C)(C)OC(=O)NCCOc1ncc(Br)cn1]

In a nitrogen purged glovebox, tert-butyl(2-hydroxyethyl)carbamate (83 mg, 0.517 mmol), 5-bromo-2-chloropyrimidine (100 mg, 0.517 mmol), {(R)-1-[(Sp)-2-(dicyclohexylphosphino)ferrocenyl]ethyldi-tert-butylphosphine}[2-(2'-amino-1,1'-biphenyl)]palladium(II) methanesulfonate (48.5 mg, 0.052 mmol), cesium carbonate (337 mg, 1.034 mmol), and DMA (2.6 mL) were combined in a 20 mL vial. The vial was capped, removed from the glovebox, and stirred at 80° C. for 6 hours. The reaction was cooled to ambient temperature and filtered over celite. The filtrate was then adsorbed onto celite and purified by silica gel chromatography to provide the title compound as a white solid (33 mg, 0.102 mmol, 20% yield). $^1$H NMR (400 MHz, CHLOROFORM-d) δ ppm 8.28 (s, 2H), 5.49 (m, 1H), 4.22 (m, 2H), 3.68 (m, 2H), 1.49 (s, 9H).

5-Bromo-2-(2-(tert-butoxy)ethoxy)pyrimidine

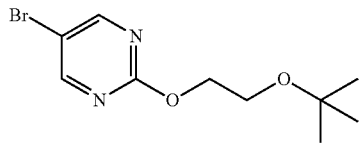

A solution of 2-(tert-butoxy)ethan-1-ol (92 mg, 0.775 mmol) and 5-bromo-2-chloropyrimidine (150 mg, 0.775 mmol) in THF (2.6 mL) was cooled to 0° C. Sodium hydride 60% in oil (33.5 mg, 0.8525 mmol) was added and the reaction was stirred for 1 hour at 0° C. before allowing to warm to ambient temperature overnight. The volatiles were removed in vacuo and the reaction mixture was diluted with H₂O (5 mL), and extracted with DCM (3×5 mL). The organic layer was dried over MgSO₄, filtered, and concentrated. The filtrate was then adsorbed onto celite and purified by silica gel chromatography to provide the title compound as a solid (61.2 mg, 0.222 mmol, 29% yield). $^1$H NMR (400 MHz, CHLOROFORM-d) δ ppm 8.52 (s, 2H), 4.45 (m, 2H), 3.73 (m, 2H), 1.22 (s, 9H).

5-Bromo-2-(2-methoxyethoxy)pyrimidine

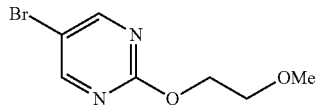 [SMILES: COCCOc1ncc(Br)cn1]

A solution of 2-methoxyethan-1-ol (59 mg, 0.775 mmol) and 5-bromo-2-chloropyrimidine (150 mg, 0.775 mmol) in THF (2.6 mL) was cooled to 0° C. Sodium hydride 60% in oil (33.5 mg, 0.8525 mmol) was added and the reaction was stirred for 1 hour at 0° C. before allowing to warm to ambient temperature overnight. The volatiles were removed in vacuo and the reaction mixture was diluted with H₂O (5 mL), and extracted with DCM (3×5 mL). The organic layer was dried over MgSO₄, filtered, and concentrated. The filtrate was then adsorbed onto celite and purified by flash chromatography to provide the title compound as a solid (32.4 mg, 0.139 mmol, 18% yield). $^1$H NMR (400 MHz, CHLOROFORM-d) δ ppm 8.53 (s, 2H), 4.44-4.54 (m, 2H), 3.70-3.81 (m, 2H), 3.43 (s, 3H).

Example 186

(S)—N-(2-(((tert-Butyldimethylsilyl)oxy)methyl)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

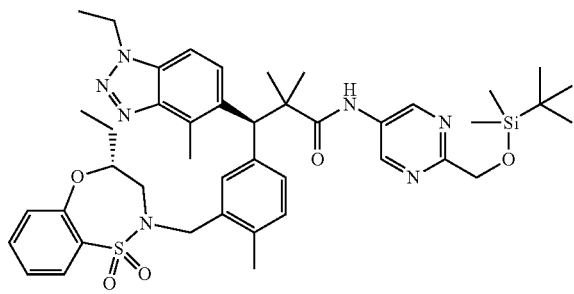 [SMILES: CC[C@@H]1CN(Cc2cc([C@@H](c3ccc4c(nnn4CC)c3C)C(C)(C)C(=O)Nc3cnc(CO[Si](C)(C)C(C)(C)C)nc3)ccc2C)S(=O)(=O)c2ccccc2O1]

In a nitrogen purged glovebox, (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide (70.8 mg, 0.120 mmol), [(4,5-bis(diphenylphosphino)-9,9-dimethylxanthene)-2-(2'-amino-1,1'-biphenyl)]palladium(II) methanesulfonate (11.2 mg, 0.0118 mmol), 5-bromo-2-(((tert-butyldimethylsilyl)oxy)methyl)pyrimidine (39.9 mg, 0.132 mmol), cesium carbonate (95.8 mg, 0.294 mmol), and dioxane (1 mL) were combined in a 4 mL vial. The vial was sealed and removed from the glovebox where it was stirred while heating at 100° C. for 6 hours. The reaction was cooled to ambient temperature and filtered over celite. The filtrate was then adsorbed onto celite and purified by silica gel chromatography (67 mg, 0.0825 mmol, 70% yield) LC-MS m/z 812.7 (M+H)+, 1.44 min (ret. time).

The compounds in Table 23 were prepared by a method similar to the one described for the preparation of (S)—N-(2-(((tert-butyldimethylsilyl)oxy)methyl)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide. As is appreciated by those skilled in the art, these analogous examples may involve variations in general reaction conditions.

TABLE 23

| Ex # | Structure | Name | LCMS [M + 1] | Retention Time (min) |
|---|---|---|---|---|
| Example 187 | 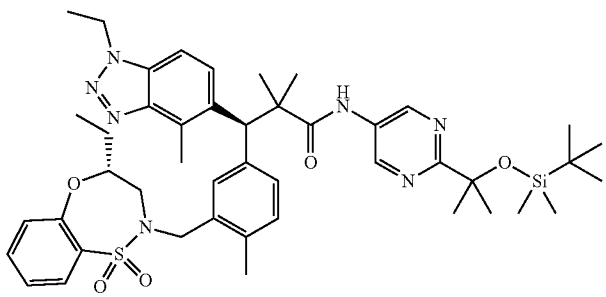 [SMILES: CC[C@@H]1CN(Cc2cc([C@@H](c3ccc4c(nnn4CC)c3C)C(C)(C)C(=O)Nc3cnc(C(C)(C)O[Si](C)(C)C(C)(C)C)nc3)ccc2C)S(=O)(=O)c2ccccc2O1] | (S)-N-(2-(2-((tert-Butyldimethylsilyl)oxy)propan-2-yl)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide | 840.7 | 1.63 |
| Example 188 | 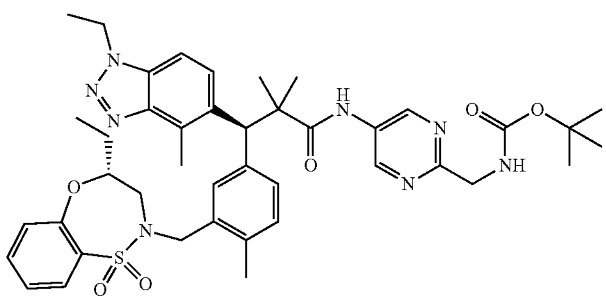 [SMILES: CC[C@@H]1CN(Cc2cc([C@@H](c3ccc4c(nnn4CC)c3C)C(C)(C)C(=O)Nc3cnc(CNC(=O)OC(C)(C)C)nc3)ccc2C)S(=O)(=O)c2ccccc2O1] | tert-Butyl ((5-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidin-2-yl)methyl)carbamate | 797.3 | 1.20 |
| Example 189 | 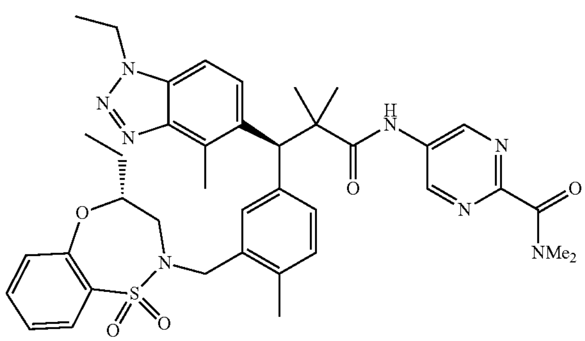 [SMILES: CC[C@@H]1CN(Cc2cc([C@@H](c3ccc4c(nnn4CC)c3C)C(C)(C)C(=O)Nc3cnc(C(=O)N(C)C)nc3)ccc2C)S(=O)(=O)c2ccccc2O1] | 5-((S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-N,N-dimethylpyrimidine-2-carboxamide | 739.7 | 1.08 |

TABLE 23-continued

| Ex # | Structure | Name | LCMS [M + 1] | Retention Time (min) |
|---|---|---|---|---|
| Example 190 | 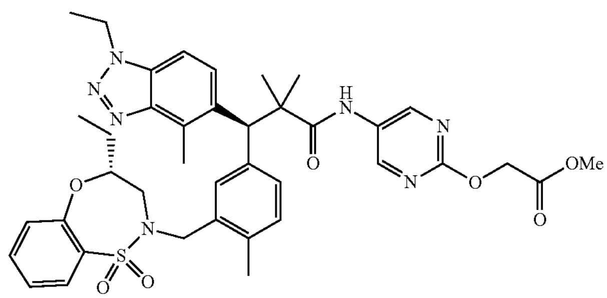 [SMILES: CC[C@@H]1CN(Cc2cc([C@@H](c3ccc4c(nnn4CC)c3C)C(C)(C)C(=O)Nc3cnc(OCC(=O)OC)nc3)ccc2C)S(=O)(=O)c2ccccc2O1] | Methyl 2-((5-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidin-2-yl)oxy)acetate | 756.7 | 1.14 |
| Example 191 | 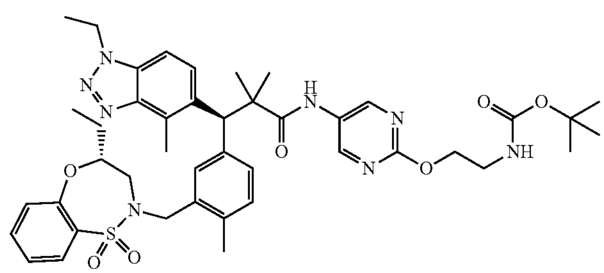 [SMILES: CC[C@@H]1CN(Cc2cc([C@@H](c3ccc4c(nnn4CC)c3C)C(C)(C)C(=O)Nc3cnc(OCCNC(=O)OC(C)(C)C)nc3)ccc2C)S(=O)(=O)c2ccccc2O1] | tert-Butyl (2-((5-((S)-3-(3-(((R)-4-ethyl-1,1-dioxido-3,4-dihydro-2H-benzo[b]-[1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidin-2-yl)oxy)ethyl)carbamate | 827.3 | 1.21 |
| Example 192 | 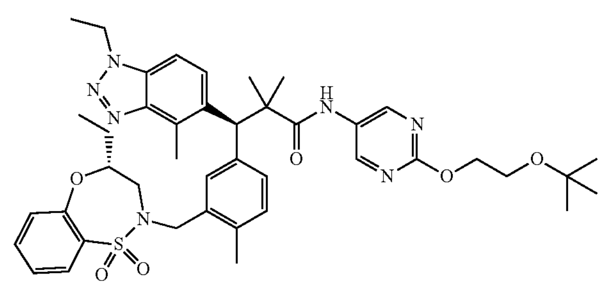 [SMILES: CC[C@@H]1CN(Cc2cc([C@@H](c3ccc4c(nnn4CC)c3C)C(C)(C)C(=O)Nc3cnc(OCCOC(C)(C)C)nc3)ccc2C)S(=O)(=O)c2ccccc2O1] | (S)-N-(2-(2-(tert-Butoxy)ethoxy)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide | 784.3 | 1.25 |
| Example 193 | 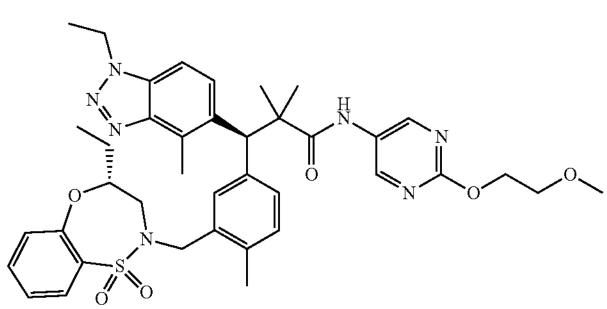 [SMILES: CC[C@@H]1CN(Cc2cc([C@@H](c3ccc4c(nnn4CC)c3C)C(C)(C)C(=O)Nc3cnc(OCCOC)nc3)ccc2C)S(=O)(=O)c2ccccc2O1] | (S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-N-(2-(2-methoxyethoxy)pyrimidin-5-yl)-2,2-dimethylpropanamide | 742.7 | 1.14 |

Example 194

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-N-(2-(hydroxymethyl)pyrimidin-5-yl)-2,2-dimethylpropanamide

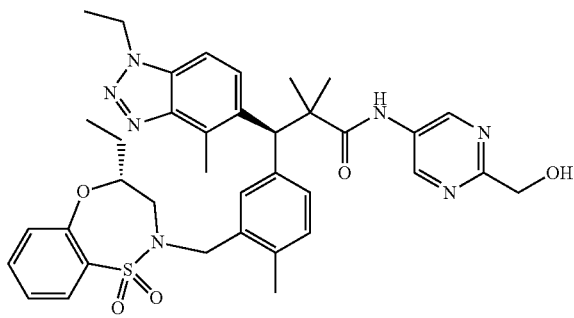 [SMILES: CC[C@@H]1CN(Cc2cc([C@@H](c3ccc4c(nnn4CC)c3C)C(C)(C)C(=O)Nc3cnc(CO)nc3)ccc2C)S(=O)(=O)c2ccccc2O1]

To a solution of (S)—N-(2-(((tert-butyldimethylsilyl)oxy)methyl)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide (60.6 mg, 0.0746 mmol) in THF (0.75 mL) was added 1 M TBAF in THF (0.082 mL, 0.0821 mmol). The mixture was stirred at ambient temperature overnight. The volatiles were removed and the reaction mixture was diluted with H$_2$O (0.5 mL), and extracted with DCM (3×0.5 mL). The organic layer was dried over MgSO$_4$, filtered, and concentrated. The residue was then dissolved in acetonitrile (1 mL) and washed with hexane (3×1 mL). The acetonitrile layer was concentrated to give the title compound as a solid (40 mg, 0.0573 mmol, 77% yield). LC-MS m/z 698.2 (M+H)$^+$, 1.04 min (ret. time).

Example 195

5-((S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidine-2-carboxylic Acid

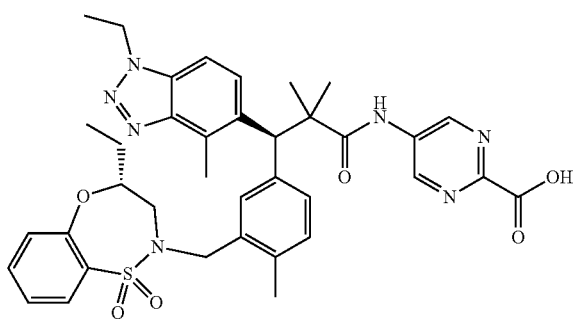 [SMILES: CC[C@@H]1CN(Cc2cc([C@@H](c3ccc4c(nnn4CC)c3C)C(C)(C)C(=O)Nc3cnc(C(=O)O)nc3)ccc2C)S(=O)(=O)c2ccccc2O1]

To a solution of ethyl 5-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidine-2-carboxylate (20 mg, 0.0270 mmol) (prepared by a method similar to the one described for the preparation of (S)—N-(2-(((tert-butyldimethylsilyl)oxy)methyl)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide) in THF (0.3 mL) was added LiOH (1.3 mg, 0.054 mmol) and water (1.3 uL, 0.081 mmol). The mixture was stirred at ambient temperature overnight. The volatiles were removed and the reaction mixture was diluted with 1M NH$_4$Cl (0.5 mL), and extracted with DCM (3×0.5 mL). The product precipitated from DCM and was filtered to give the title compound as a solid (7 mg, 0.00983 mmol, 36% yield). LC-MS m/z 712.3 (M+H)$^+$, 1.03 min (ret. time).

Example 196

(S)—N-(2-(Aminomethyl)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

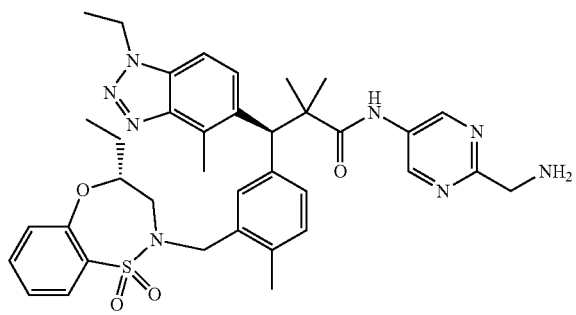 [SMILES: CC[C@@H]1CN(Cc2cc([C@@H](c3ccc4c(nnn4CC)c3C)C(C)(C)C(=O)Nc3cnc(CN)nc3)ccc2C)S(=O)(=O)c2ccccc2O1]

To a solution of tert-butyl ((5-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidin-2-yl)methyl)carbamate (63.1 mg, 0.0792 mmol) in DCM (0.8 mL) was added TFA (121 uL, 1.58 mmol). The mixture was stirred at ambient temperature overnight. The volatiles were removed and the reaction mixture was diluted with water (0.5 mL), and extracted with DCM (3×0.5 mL). The organic layer was dried over MgSO$_4$, filtered, and concentrated to give the title compound as a solid (49.7 mg, 0.0713 mmol, 90% yield). LC-MS m/z 697.0 (M+H)$^+$, 0.83 min (ret. time).

Example 197

2-((5-((S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidin-2-yl)oxy)acetic Acid

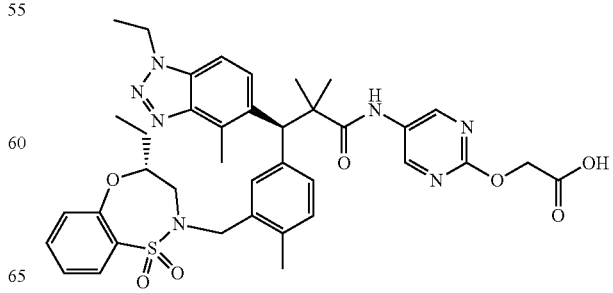

To a solution of methyl 2-((5-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidin-2-yl)oxy)acetate (31.7 mg, 0.0419 mmol) in THF (0.4 mL) was added LiOH (2 mg, 0.0838 mmol) and water (2 uL, 0.1257 mmol). The mixture was stirred at ambient temperature overnight. The volatiles were removed and the reaction mixture was diluted with 1M NH₄Cl (0.5 mL), and extracted with DCM (3×0.5 mL). The organic layer was dried over MgSO₄, filtered, and concentrated to give the title compound as a solid (18.5 mg, 0.0247 mmol, 59% yield). LC-MS m/z 742.3 (M+H)⁺, 1.06 min (ret. time).

Example 198

(S)—N-(2-(2-Aminoethoxy)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide

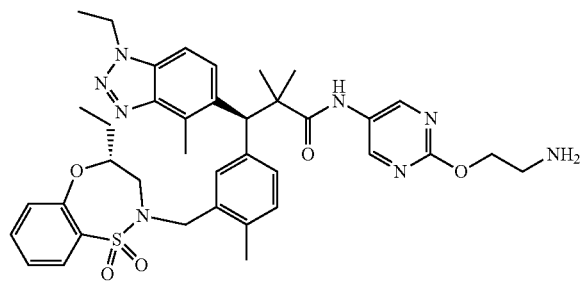 [SMILES: CC[C@@H]1CN(Cc2cc([C@@H](c3ccc4c(nnn4CC)c3C)C(C)(C)C(=O)Nc3cnc(OCCN)nc3)ccc2C)S(=O)(=O)c2ccccc2O1]

To a solution of tert-butyl (2-((5-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pyrimidin-2-yl)oxy)ethyl)carbamate (25.6 mg, 0.0310 mmol) in DCM (0.3 mL) was added TFA (47 uL, 6.2 mmol). The mixture was stirred at ambient temperature overnight. Volatiles were removed and methanol (0.3 mL) and KOtBu (16.8 mg, 0.15 mmol) were added and the reaction was allowed to stir at ambient temperature overnight. Volatiles were removed and the crude mixture was diluted with water (0.5 mL), and extracted with DCM (3×0.5 mL). The organic layer was dried over MgSO₄, filtered, and concentrated to give the title compound as a solid (23 mg, 0.03224 mmol, 104% yield). LC-MS m/z 727.2 (M+H)⁺, 1.01 min (ret. time).

Example 199

(S)-3-(3-(((R)-4-Ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-N-(2-(2-hydroxyethoxy)pyrimidin-5-yl)-2,2-dimethylpropanamide

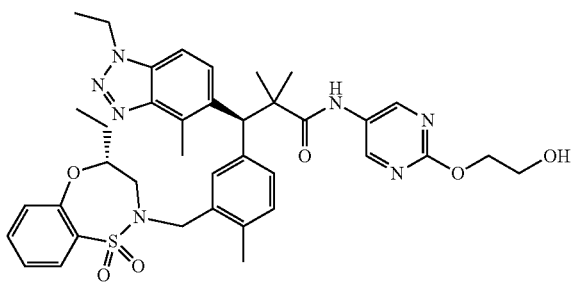 [SMILES: CC[C@@H]1CN(Cc2cc([C@@H](c3ccc4c(nnn4CC)c3C)C(C)(C)C(=O)Nc3cnc(OCCO)nc3)ccc2C)S(=O)(=O)c2ccccc2O1]

A solution (S)—N-(2-(2-(tert-butoxy)ethoxy)pyrimidin-5-yl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide (48.4 mg, 0.0617 mmol) in TFA (0.6 mL) was stirred at ambient temperature overnight. The volatiles were removed and methanol (0.3 mL) and KOtBu (34.6 mg, 0.309 mmol) were added and allowed to stir at ambient temperature overnight. Volatiles were removed and the crude mixture was diluted with water (0.5 mL), and extracted with DCM (3×0.5 mL). The organic layer was dried over MgSO₄, filtered, and concentrated to give the title compound as a solid (30.5 mg, 0.0420 mmol, 68% yield). LC-MS m/z 728.2 (M+H)⁺, 1.05 min (ret. time).

Example 200

2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)acetate

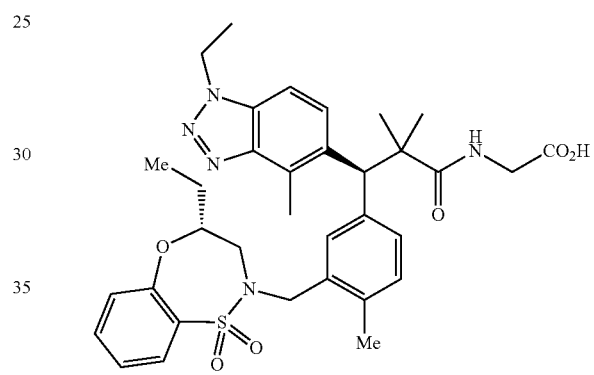

Methyl-2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)acetic acidyl)methyl)phenyl)propanoate

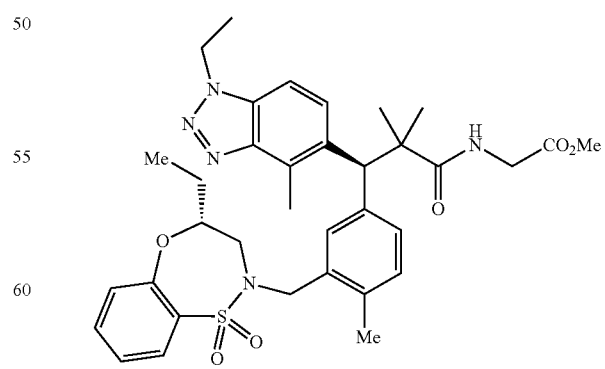

In a 4 mL vial, (S)-3-(3-(((R)-4-ethyl-1,1-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanoic acid (50.0 mg, 0.085 mmol) was dissolved in thionyl chloride (0.50 mL, 2.56 mmol) and stirred at ambient temperature. After 15 hr the reaction mixture concentrated in vacuo and azeotroped with 1,2-dichloroethane (3×1 mL). This residue was dissolved in NMP (0.5 mL), treated with glycine methyl ester hydrochloride (12.8 mg, 0.102 mmol) and triethylamine (18 µL, 0.128 mmol). After stirring for an additional 15 hr at ambient temperature, the reaction mixture was partitioned between EtOAc (1.5 mL) and water (0.50 mL). The organic layer was washed with water (3×0.50 mL) brine (0.50 mL), dried over MgSO$_4$, filtered, and concentrated in vacuo. This material was dissolved in acetonitrile (0.50 mL) and purified by solid phase extraction (SPE) using a C8+aminopropyl cartridge (500 mg) to remove any starting carboxylic acid to afford the title compound (11 mg, 0.017 mmol, 21% yield) as a white film. LC-MS m/z 662.2 (M+H)$^+$, 1.20 min (ret. time).

2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)acetate

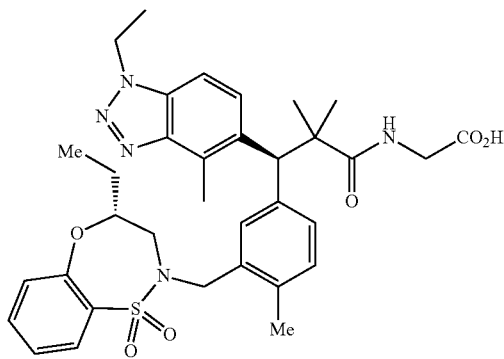 [SMILES: CC[C@@H]1CN(Cc2cc([C@@H](c3ccc4c(nnn4CC)c3C)C(C)(C)C(=O)NCC(=O)O)ccc2C)S(=O)(=O)c2ccccc2O1]

In a 4 mL vial, Methyl 2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)acetate was dissolved in tetrahydrofuran (0.5 mL) and water (0.15 mL). Lithium hydroxide (1.3 mg, 0.055 mmol) was added and the reaction mixture was stirred at ambient temperature. After 15 hr the reaction mixture was concentrated in vacuo and the residue was partitioned between EtOAc (1.5 mL) and 1.0 N HCl (0.50 mL). The organic layer was washed with water (0.50 mL) brine (0.50 mL), dried over MgSO$_4$, filtered, and concentrated in vacuo. The solvent was removed and the crude product purified with preparative HPLC under neutral conditions to give the title compound (7.0 mg, 0.011 mmol, 65.0% yield). LC-MS m/z 647.3 (M+H)$^+$, 1.11 min (ret. time). $^1$H NMR (400 MHz, CD$_3$OD): δ=7.83-7.79 (m, 2H), 7.63-7.58 (m, 1H), 7.53 (d, J=9.2 Hz, 1H), 7.33-7.29 (m, 1H), 7.25-7.21 (m, 2H), 7.15-7.11 (m, 2H), 4.71 (q, J=7.0 Hz, 2H), 4.54 (d, J=14.1 Hz, 1H), 3.92-3.85 (m, 1H), 3.81-3.74 (m, 2H), 3.86-3.59 (m, 1H), 2.77 (dd, J=15.1, 1.4 Hz, 1H), 2.70 (s, 3H), 2.32 (s, 3H), 1.60 (t, J=7.1 Hz, 2H), 1.45-1.38 (m, 1H), 1.37 (s, 3H), 1.30 (s, 3H), 1.12-1.02 (m, 1H), 0.89 (t, J=7.0 Hz, 3H).

The compounds in Table 24 were prepared by a method similar to the one described for the preparation of 2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)acetate As is appreciated by those skilled in the art, these analogous examples may involve variations in general reaction conditions.

TABLE 24

| Ex # | Structure | Name | LCMS [M + 1] | Retention Time (min) |
|---|---|---|---|---|
| Example 201 | 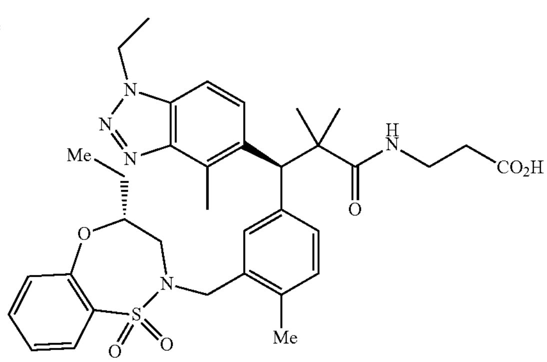 [SMILES: CC[C@@H]1CN(Cc2cc([C@@H](c3ccc4c(nnn4CC)c3C)C(C)(C)C(=O)NCCC(=O)O)ccc2C)S(=O)(=O)c2ccccc2O1] | 3-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido) propanoic acid | 662.3 | 1.11 |

TABLE 24-continued

| Ex # | Structure | Name | LCMS [M + 1] | Retention Time (min) |
|---|---|---|---|---|
| Example 202 | 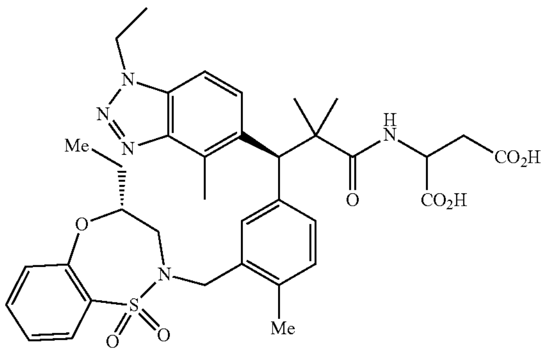 [SMILES: CC[C@@H]1CN(Cc2cc([C@@H](c3ccc4c(nnn4CC)c3C)C(C)(C)C(=O)NC(CC(=O)O)C(=O)O)ccc2C)S(=O)(=O)c2ccccc2O1] | 2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido) succinic acid | 706.3 | 1.07 |
| Example 203 | 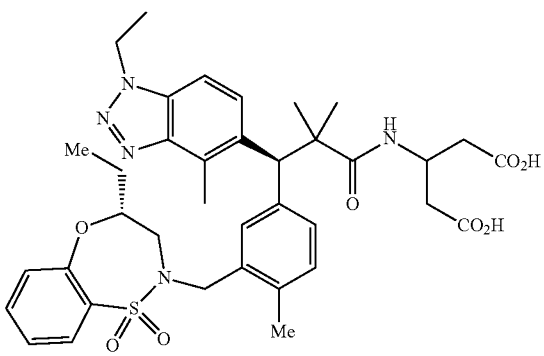 [SMILES: CC[C@@H]1CN(Cc2cc([C@@H](c3ccc4c(nnn4CC)c3C)C(C)(C)C(=O)NC(CC(=O)O)CC(=O)O)ccc2C)S(=O)(=O)c2ccccc2O1] | 3-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido) pentanedioic acid | 720.4 | 1.06 |
| Example 204 | 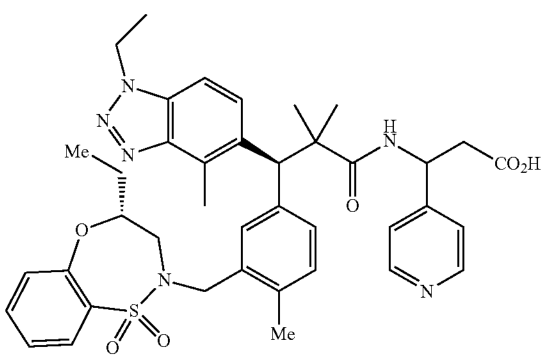 [SMILES: CC[C@@H]1CN(Cc2cc([C@@H](c3ccc4c(nnn4CC)c3C)C(C)(C)C(=O)NC(CC(=O)O)c3ccncc3)ccc2C)S(=O)(=O)c2ccccc2O1] | 3-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-3-(pyridin-4-yl)propanoic acid | 738.3 | 0.79 |
| Example 205 | 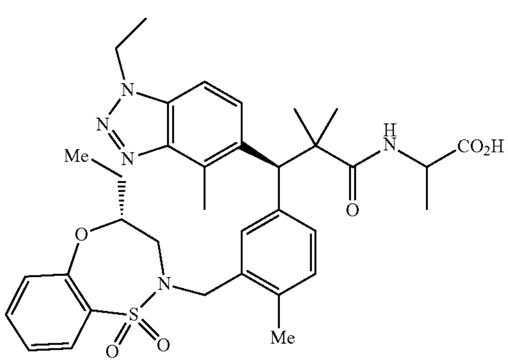 [SMILES: CC[C@@H]1CN(Cc2cc([C@@H](c3ccc4c(nnn4CC)c3C)C(C)(C)C(=O)NC(C)C(=O)O)ccc2C)S(=O)(=O)c2ccccc2O1] | 2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido) propanoic acid | 662.3 | 1.14 |

TABLE 24-continued

| Ex # | Structure | Name | LCMS [M + 1] | Retention Time (min) |
|---|---|---|---|---|
| Example 206 | 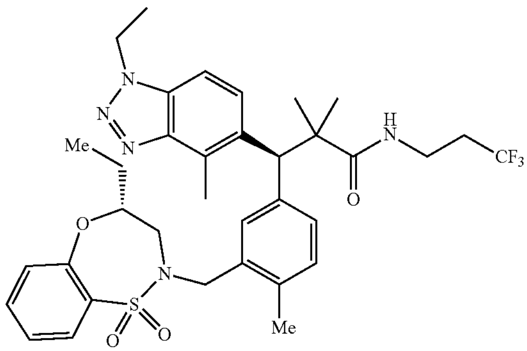 [SMILES: CC[C@@H]1CN(Cc2cc([C@@H](c3ccc4c(nnn4CC)c3C)C(C)(C)C(=O)NCCC(F)(F)F)ccc2C)S(=O)(=O)c2ccccc2O1] | (S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethyl-N-(3,3,3-trifluoropropyl)propanamide | 686.3 | 1.30 |
| Example 207 | 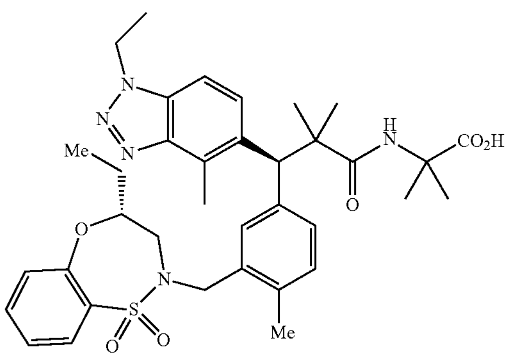 [SMILES: CC[C@@H]1CN(Cc2cc([C@@H](c3ccc4c(nnn4CC)c3C)C(C)(C)C(=O)NC(C)(C)C(=O)O)ccc2C)S(=O)(=O)c2ccccc2O1] | 2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-2-methylpropanoic acid | 676.3 | 1.16 |
| Example 208 | 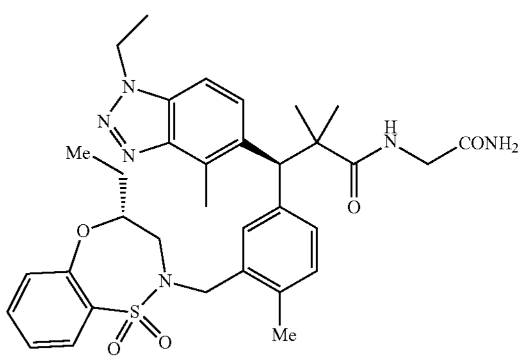 [SMILES: CC[C@@H]1CN(Cc2cc([C@@H](c3ccc4c(nnn4CC)c3C)C(C)(C)C(=O)NCC(N)=O)ccc2C)S(=O)(=O)c2ccccc2O1] | (S)-N-(2-amino-2-oxoethyl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamide | 647.3 | 1.06 |
| Example 209 | 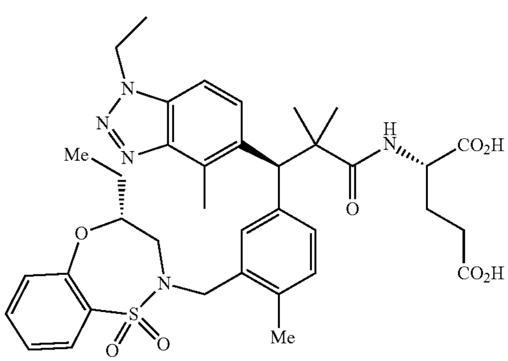 [SMILES: CC[C@@H]1CN(Cc2cc([C@@H](c3ccc4c(nnn4CC)c3C)C(C)(C)C(=O)N[C@@H](CCC(=O)O)C(=O)O)ccc2C)S(=O)(=O)c2ccccc2O1] | (S)-2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)pentanedioic acid | 720.3 | 1.06 |

TABLE 24-continued

| Ex # | Structure | Name | LCMS [M + 1] | Retention Time (min) |
|---|---|---|---|---|
| Example 210 | 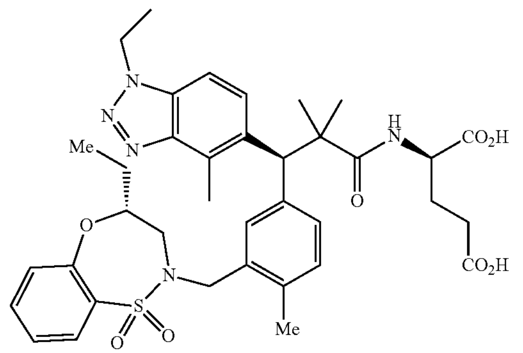 [SMILES: CC[C@@H]1CN(Cc2cc([C@@H](c3ccc4c(nnn4CC)c3C)C(C)(C)C(=O)N[C@H](CCC(=O)O)C(=O)O)ccc2C)S(=O)(=O)c2ccccc2O1] | (R)-2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido) pentanedioic acid | 720.3 | 1.06 |
| Example 211 | 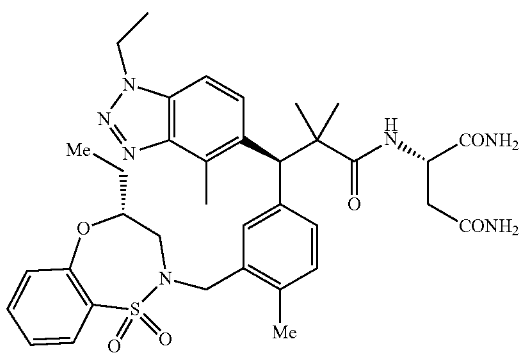 [SMILES: CC[C@@H]1CN(Cc2cc([C@@H](c3ccc4c(nnn4CC)c3C)C(C)(C)C(=O)N[C@@H](CC(N)=O)C(N)=O)ccc2C)S(=O)(=O)c2ccccc2O1] | (S)-4-amino-2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-4-oxobutanoic acid | 705.3 | 1.03 |
| Example 212 | 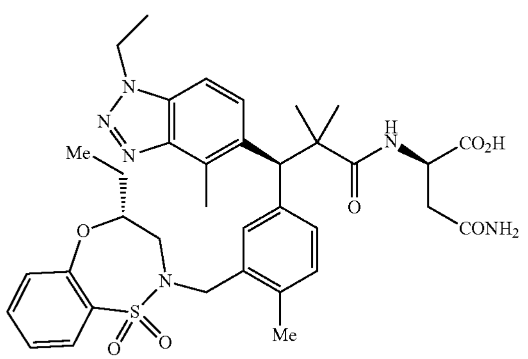 [SMILES: CC[C@@H]1CN(Cc2cc([C@@H](c3ccc4c(nnn4CC)c3C)C(C)(C)C(=O)N[C@H](CC(N)=O)C(=O)O)ccc2C)S(=O)(=O)c2ccccc2O1] | (R)-4-amino-2-((S)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido)-4-oxobutanoic acid | 705.3 | 1.03 |
| Example 213 | 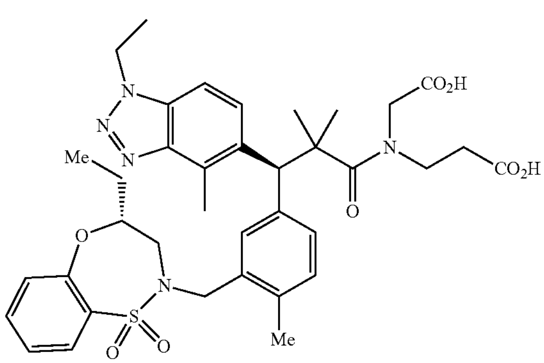 [SMILES: CC[C@@H]1CN(Cc2cc([C@@H](c3ccc4c(nnn4CC)c3C)C(C)(C)C(=O)N(CCC(=O)O)CC(=O)O)ccc2C)S(=O)(=O)c2ccccc2O1] | 3-((S)-N-(carboxymethyl)-3-(3-(((R)-4-ethyl-1,1-dioxido-3,4-dihydro-2H-benzo[b][1,4,5]oxathiazepin-2-yl)methyl)-4-methylphenyl)-3-(1-ethyl-4-methyl-1H-benzo[d][1,2,3]triazol-5-yl)-2,2-dimethylpropanamido) propanoic acid | 720.3 | 1.08 |

What is claimed is:

1. A compound of Formula (I)

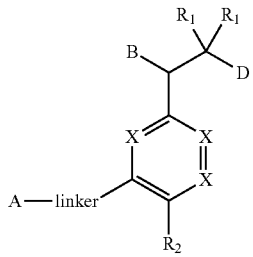

wherein:
B is benzotriazolyl, phenyl, triazolopyridinyl, —O—(CH$_2$)-triazolyl, or —(CH$_2$)$_2$-triazolyl, wherein each of benzotriazolyl, phenyl, triazolopyridinyl, —O—(CH$_2$)-triazolyl, or —(CH$_2$)$_2$-triazolyl is unsubstituted or substituted by 1, 2, or 3 substituents independently selected from —C$_{1-3}$alkyl, —C$_{3-7}$cycloalkyl, —O—C$_{1-3}$alkyl, —CN, —(CH$_2$)$_2$—O—(CH$_2$)$_2$—OR$_3$ and halo;
D is —C(O)—NR$_4$R$_5$, —NR$_4$—C(O)—R$_5$, —NR$_3$—C(O)—NR$_4$R$_5$, or —NR$_4$—C(O)—O—R$_5$;
R$_1$ is hydrogen, —C$_{1-3}$alkyl, F, oxetanyl, or the two R$_1$ groups together with the carbon to which they are attached form a cyclopropyl group;
R$_2$ is hydrogen, methyl, —CF$_3$, or halo;
R$_3$ is hydrogen or —C$_{1-5}$alkyl;
R$_4$ is hydrogen or —C$_{1-5}$alkyl;
R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_3$R$_4$, aryl, —C$_{1-5}$ alkylheteroaryl, or heteroaryl, wherein each of —C$_{1-5}$alkyl, —C$_{3-7}$cycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$alkylaryl, —C$_{1-3}$alkylheteroaryl, —C$_{1-3}$alkylC(O)R$_3$, —C$_{1-3}$alkylC(O)OH, —C$_{1-3}$alkylNHC(O)OR$_4$, —C$_{1-3}$alkylOSi(R$_3$)$_3$, —C$_{1-3}$alkylOH, —C$_{1-3}$alkylNH$_2$, —SCH$_3$, —C$_{4-8}$heterocycloalkyl (optionally substituted with R$_3$), —NH—(CH$_2$)n-CH—(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —NH—C(O)—C$_{1-3}$alkyl, F, Cl, —CN, —CH—F$_2$, —CF$_3$, —(CH$_2$)$_n$—O—(CH$_2$)$_m$—CH$_3$, —O(CH$_2$)$_n$—OH, —O(CH$_2$)$_n$C(O)OR$_3$, —O(CH$_2$)$_n$OR$_3$, —O(CH$_2$)$_n$NHC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S;
or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;
Linker is —CH$_2$—, —CH$_2$—N(-cyclopropyl)-CH$_2$—, —CH$_2$—N(CH$_3$)—CH$_2$— or —N—(CH$_3$)—CH$_2$—;
A is

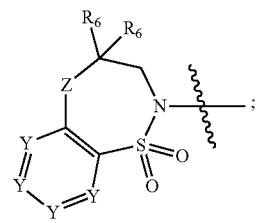

Y is independently selected from N or CH;
Z is O or CH$_2$;
R$_6$ is independently selected from hydrogen or —C$_{1-4}$alkyl;
wherein A is unsubstituted or substituted with one, two or three substituents independently selected from halo, —CF$_3$, —C$_{1-4}$alkyl, —CN, —OMe, —C(O)NH$_2$, —OCF$_3$, —C$_{1-4}$alkylNR$_8$R$_9$;
R$_8$ is hydrogen or —C$_{1-4}$alkyl;
R$_9$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkylheteroaryl or —C$_{1-3}$alkylaryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkylheteroaryl or —C$_{1-3}$alkylaryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;
X is independently CH or N;
m is 1, 2 or 3; and
n is 1, 2 or 3;
or a pharmaceutically acceptable salt thereof.

2. The compound of claim 1, wherein:
B is benzotriazolyl or —(CH$_2$)$_2$ triazolyl, wherein each of benzotriazolyl or —(CH$_2$)$_2$ triazolyl is unsubstituted or substituted by 1, 2, or 3 substituents independently selected from —C$_{1-3}$alkyl and halo;
D is —C(O)—NR$_4$R$_5$;
R$_1$ is hydrogen;
R$_2$ is methyl or halo;
R$_4$ is hydrogen;
R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_3$R$_4$, aryl, —C$_{1-5}$alkylheteroaryl, or heteroaryl, wherein each of —C$_{1-5}$alkyl, —C$_{3-7}$cycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$alkylaryl, —C$_{1-3}$alkylheteroaryl, aryl, —C$_{1-3}$alkylC(O)R$_3$, —C$_{1-3}$alkylC(O)OH, —C$_{1-3}$alkylNHC(O)OR$_4$, —C$_{1-3}$alkylOSi(R$_3$)$_3$, —C$_{1-3}$alkylOH, —C$_{1-3}$alkylNH$_2$, —SCH$_3$, —C$_{4-8}$heterocycloalkyl (optionally substituted with R$_3$), —NH—(CH$_2$)n—CH—(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —NH—C(O)—C$_{1-3}$alkyl, F, Cl, —CN, —CH—F$_2$, —CF$_3$, —(CH$_2$)$_n$—O—(CH$_2$)$_m$—CH$_3$, —O(CH$_2$)$_n$—OH, —O(CH$_2$)$_n$C(O)OR$_3$, —O(CH$_2$)$_n$OR$_3$, —O(CH$_2$)$_n$NHC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S;

or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—;

A is

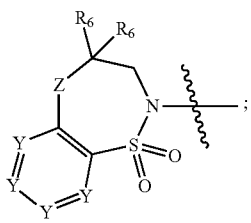

Y is independently selected from N or CH;
Z is O or CH$_2$;
R$_6$ is independently hydrogen or —C$_{1-4}$alkyl;
wherein A is unsubstituted or substituted with one, two or three substituents independently selected from halo, —CF$_3$, —C$_{1-4}$alkyl, —CN, —OMe, —C(O)NH$_2$, —OCF$_3$, —C$_{1-4}$alkylNR$_8$R$_9$;
R$_8$ is hydrogen or —C$_{1-4}$alkyl;
R$_9$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkylheteroaryl or —C$_{1-3}$alkylaryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkylheteroaryl or —C$_{1-3}$alkylaryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and O-heteroaryl;

X is independently CH or N;
m is 1, 2 or 3; and
n is 1, 2 or 3;
or a pharmaceutically acceptable salt thereof.

3. The compound of claim 1, wherein:
B is benzotriazolyl wherein benzotriazolyl is unsubstituted or substituted by 1, 2, or 3 substituents independently selected from —C$_{1-3}$alkyl and halo;
D is —C(O)—NR$_4$R$_5$;
R$_1$ is independently selected from hydrogen or methyl;
R$_2$ is methyl or halo;
R$_3$ is hydrogen, methyl or ethyl;
R$_4$ is hydrogen;
R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_3$R$_4$, aryl, —C$_{1-5}$ alkylheteroaryl, or heteroaryl, wherein each of —C$_{1-5}$alkyl, —C$_{3-7}$cycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$alkylaryl, —C$_{1-3}$alkylheteroaryl, aryl, —C$_{1-3}$alkylC(O)R$_3$, —C$_{1-3}$alkylC(O)OH, —C$_{1-3}$alkylNHC(O)OR$_4$, —C$_{1-3}$alkylOSi(R$_3$)$_3$, —C$_{1-3}$alkylOH, —C$_{1-3}$alkylNH$_2$, —SCH$_3$, —C$_{4-8}$heterocycloalkyl (optionally substituted with R$_3$), —NH—(CH$_2$)n—CH—(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, —NH—C(O)—C$_{1-3}$alkyl, F, Cl, —CN, —CH—F$_2$, —CF$_3$, —(CH$_2$)$_n$—O—(CH$_2$)$_m$—CH$_3$, —O(CH$_2$)$_n$—OH, —O(CH$_2$)$_n$C(O)OR$_3$, —O(CH$_2$)$_n$OR$_3$, —O(CH$_2$)$_n$NHC(O)OR$_3$, —O(CH$_2$)$_n$NH$_2$, —C$_{3-7}$cycloalkyl, and a 5-6-membered heteroaryl ring containing 1, 2 or 3 heteroatoms selected from O, N and S;

or R$_4$ and R$_5$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —S(O)$_2$, and wherein each 5-8-membered ring, 8-11-membered bicyclic ring, or 9-10-membered bridged bicyclic ring optionally independently contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —C$_{1-5}$alkyl, —C$_{3-7}$cycloalkyl, —C$_{4-7}$heterocycloalkyl, —(CH$_2$)phenyl, halogen, —NR$_3$R$_4$, —CHF$_2$, —CF$_3$, and —(CH$_2$)$_n$—O—(CH$_2$)$_m$—CH$_3$;

Linker is —CH$_2$—;

A is

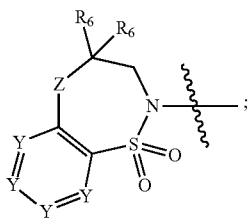

Y is independently selected from N or CH;
Z is O or CH$_2$;
R$_6$ is hydrogen or —C$_{1-4}$alkyl;
wherein A is unsubstituted or substituted with one, two or three substituents independently selected from halo, —CF$_3$, —C$_{1-4}$alkyl, —CN, —OMe, —C(O)NH$_2$, —OCF$_3$, —C$_{1-4}$alkylNR$_8$R$_9$;
R$_8$ is hydrogen or —C$_{1-4}$alkyl;
R$_9$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, wherein each of —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl is unsubstituted or substituted by 1, 2 or 3 substituents independently selected from halo, —CF$_3$, —OCF$_3$ and —OCH$_3$;
X is independently CH or N;
m is 1, 2 or 3; and
n is 1, 2 or 3;
or a pharmaceutically acceptable salt thereof.

4. The compound of claim 1, wherein:
B is benzotriazolyl wherein benzotriazolyl is unsubstituted or substituted by 1, 2, or 3 substituents independently selected from —C$_{1-3}$alkyl and halo;
D is —C(O)—NR$_4$R$_5$;
R$_1$ is independently selected from hydrogen or methyl;
R$_2$ is methyl or halo;
R$_3$ is hydrogen or —C$_{1-5}$alkyl;
R$_4$ is hydrogen;
R$_5$ is hydrogen, —C$_{1-5}$alkyl, —C$_{3-7}$cycloalkyl, —C$_{4-8}$heterocycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-NH—C(O)R$_3$, —C$_{1-3}$alkyl-SO$_2$C$_{1-3}$alkyl, —C$_{1-3}$alkyl-C$_{4-8}$heterocycloalkyl, —C$_{1-3}$alkyl-C(O)NR$_3$R$_4$, aryl, —C$_{1-5}$ alkylheteroaryl, or heteroaryl, wherein each of —C$_{1-5}$alkyl, —C$_{3-7}$cycloalkyl, —C$_{1-5}$alkoxy, —C$_{1-3}$alkyl-O—C$_{1-3}$alkyl, —C$_{1-3}$alkyl-NH—C$_{1-3}$alkyl, —C$_{1-3}$alkyl-C(O)NR$_3$R$_4$, aryl, —C$_{1-5}$alkylheteroaryl, or heteroaryl is unsubstituted or substituted by one or two substituents independently selected from —C$_{1-3}$alkyl, —C$_{1-3}$alkylheteroaryl, aryl, —C$_{1-3}$alkylC(O)R$_3$, —C$_{1-3}$alkylC(O)OH, —C$_{1-3}$alkylNHC(O)OR$_4$, —C$_{1-3}$alkylOSi(R$_3$)$_3$, —C$_{1-3}$alkylOH, —C$_{1-3}$alkylNH$_2$, —SCH$_3$, —C$_{4-8}$heterocycloalkyl (optionally substituted with R$_3$), —NH—(CH$_2$)n-CH—(OH)$_2$, —O—CH$_2$—CH—(NH$_2$)—CH$_2$—OH, —SO$_2$R$_3$, —SO$_2$NR$_3$R$_4$, —OH, —C$_{1-3}$alkoxy, oxo, —CO$_2$H, —C(O)NR$_3$R$_4$, —C(O)OR$_3$, C(O)—C$_{1-3}$alkyl, F, Cl, —CN, —CF$_3$, —(CH$_2$)$_n$—O—(CH$_2$)$_m$—CH$_3$, —O(CH$_2$)$_n$—OH, —O(CH$_2$)$_n$C(O)OR$_3$, —O(CH$_2$)$_n$OR$_3$, —O(CH$_2$)$_n$NHC(O)OR$_3$, —O(CH$_2$)$_n$NH$_2$, —C$_{3-7}$ cycloalkyl, and a 5-6-membered heteroaryl ring containing 1, 2 or 3 heteroatoms selected from O, N and S;
Linker is —CH$_2$—;
A is

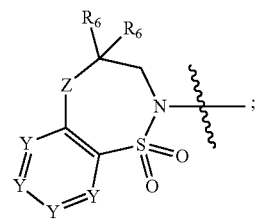

Y is independently selected from N or CH;
Z is O or CH$_2$;
R$_6$ is independently hydrogen or —C$_{1-4}$alkyl;
wherein A is unsubstituted or substituted with one, two or three substituents independently selected from halo, —CF$_3$, —C$_{1-4}$alkyl, —CN, —OMe, —C(O)NH$_2$, —OCF$_3$, —C$_{1-4}$alkylNR$_8$R$_9$;
R$_8$ is hydrogen or —C$_{1-4}$alkyl;
R$_9$ is —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, wherein each of —C$_{1-3}$alkyl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl is unsubstituted or substituted by 1, 2 or 3 substituents independently selected from halo, —CF$_3$, —OCF$_3$ and —OCH$_3$;
X is CH;
m is 1, 2 or 3; and
n is 1, 2 or 3;
or a pharmaceutically acceptable salt thereof.

5. The compound of claim 4 or a pharmaceutically acceptable salt thereof, wherein A is

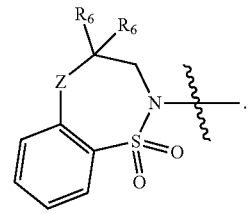

6. The compound of claim 5 or a pharmaceutically acceptable salt thereof, wherein Z is O.

7. The compound of claim 5 or a pharmaceutically acceptable salt thereof, wherein Z is CH$_2$.

8. The compound of claim 4 or a pharmaceutically acceptable salt thereof, wherein A is

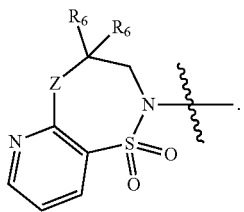

9. The compound of claim 8 or a pharmaceutically acceptable salt thereof, wherein Z is O.

10. The compound of claim 8 or a pharmaceutically acceptable salt thereof, wherein Z is $CH_2$.

11. A pharmaceutical composition comprising the compound of claim 1 and a pharmaceutically acceptable excipient.

12. A method of treating a respiratory disorder selected from COPD, asthma, ALI, ARDS, fibrosis, chronic asthma, acute asthma, lung disease secondary to environmental exposures, acute lung infection or chronic lung infection which comprises administering to a human in need thereof, a therapeutically effective amount of the compound of claim 1.

13. The method of claim 12 wherein the disorder is COPD.

14. The method of claim 13, wherein the compound is administered by inhalation.

15. A method of treating a disease or disorder selected from atherosclerosis, hypertension, heart failure, acute coronary syndrome, myocardial infarction, myocardial repair, cardiac remodeling, cardiac arrhythmias, heart failure with preserved ejection fraction, heart failure with reduced ejection fraction or diabetic cardiomyopathy which comprises administering to a human in need thereof, a therapeutically effective amount of the compound of claim 1.

16. The method of claim 15 wherein the disorder is heart failure.

17. The method of claim 16, wherein the compound is administered orally.

18. A method of treating a disease or disorder selected from Parkinson's disease, Alzheimer's disease, Friedreich's Ataxia, amyotrophic lateral sclerosis or multiple sclerosis which comprises administering to a human in need thereof, a therapeutically effective amount of the compound of claim 1.

* * * * *